US011884939B2

(12) United States Patent
Deng et al.

(10) Patent No.: US 11,884,939 B2
(45) Date of Patent: Jan. 30, 2024

(54) VACCINIA VIRUS MUTANTS USEFUL FOR CANCER IMMUNOTHERAPY

(71) Applicant: MEMORIAL SLOAN KETTERING CANCER CENTER, New York, NY (US)

(72) Inventors: Liang Deng, New York, NY (US); Stewart Shuman, New York, NY (US); Ning Yang, New York, NY (US); Taha Merghoub, New York, NY (US); Jedd Wolchok, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 35 days.

(21) Appl. No.: 17/565,332

(22) Filed: Dec. 29, 2021

(65) Prior Publication Data

US 2022/0186192 A1 Jun. 16, 2022

Related U.S. Application Data

(62) Division of application No. 16/612,127, filed as application No. PCT/US2018/032451 on May 11, 2018, now Pat. No. 11,242,509.

(60) Provisional application No. 62/505,713, filed on May 12, 2017.

(51) Int. Cl.

| | |
|---|---|
| ***C12N 15/86*** | (2006.01) |
| ***C12N 7/00*** | (2006.01) |
| ***C12N 15/63*** | (2006.01) |
| ***C12N 15/863*** | (2006.01) |
| ***A61K 39/285*** | (2006.01) |
| ***A61P 35/00*** | (2006.01) |
| *A61K 39/00* | (2006.01) |

(52) U.S. Cl.

CPC .............. *C12N 7/00* (2013.01); *A61K 39/285* (2013.01); *A61P 35/00* (2018.01); *C12N 15/86* (2013.01); *A61K 2039/525* (2013.01); *A61K 2039/54* (2013.01); *A61K 2039/55588* (2013.01); *C12N 2710/24121* (2013.01); *C12N 2710/24131* (2013.01); *C12N 2710/24143* (2013.01)

(58) Field of Classification Search

CPC .......... C12N 15/86; C12N 2710/24243; C12N 2710/24134; C12N 2710/24162; A61K 39/285

See application file for complete search history.

(56) References Cited

U.S. PATENT DOCUMENTS

| | | | |
|---|---|---|---|
| 5,494,807 | A | 2/1996 | Paoletti et al. |
| 5,762,938 | A | 6/1998 | Paoletti et al. |
| 5,766,882 | A | 6/1998 | Falkner et al. |
| 6,004,777 | A | 12/1999 | Tartaglia et al. |
| 6,265,189 | B1 | 7/2001 | Paoletti |
| 6,372,455 | B1 | 4/2002 | Jacobs et al. |
| 6,475,999 | B1 | 11/2002 | Mastrangelo et al. |
| 6,548,068 | B1 | 4/2003 | Schlom et al. |
| 6,750,043 | B2 | 6/2004 | Jacobs et al. |
| 6,761,893 | B2 | 7/2004 | Chaplin et al. |
| 6,846,652 | B2 | 1/2005 | Jacobs et al. |
| 6,942,855 | B2 | 9/2005 | Jacobs et al. |
| 7,001,718 | B2 | 2/2006 | Jacobs et al. |
| 7,049,145 | B2 | 5/2006 | Erfle et al. |
| 7,208,313 | B2 | 4/2007 | McCart et al. |
| 7,252,817 | B2 | 8/2007 | Coffey et al. |
| 7,256,037 | B2 | 8/2007 | Ellenhorn et al. |
| 7,306,902 | B2 | 12/2007 | Thompson et al. |
| 7,431,929 | B2 | 10/2008 | Jacobs et al. |
| 7,550,147 | B2 | 6/2009 | Howley et al. |
| 7,588,767 | B2 | 9/2009 | Szalay et al. |
| 7,807,146 | B2 | 10/2010 | Delcayre et al. |
| 8,052,968 | B2 | 11/2011 | Chen et al. |
| 8,105,578 | B2 | 1/2012 | Roberts et al. |
| 8,377,688 | B2 | 2/2013 | Delcayre et al. |
| 8,506,947 | B2 | 8/2013 | McCart et al. |
| 8,679,509 | B2 | 3/2014 | Evans et al. |
| 8,747,837 | B2 | 6/2014 | Kirn et al. |

(Continued)

FOREIGN PATENT DOCUMENTS

| | | | |
|---|---|---|---|
| CA | 2435967 | A1 | 1/2005 |
| CA | 2436196 | A1 | 1/2005 |

(Continued)

OTHER PUBLICATIONS

Liu Z, Zhou H, Wang W, Fu YX, Zhu M. A novel dendritic cell targeting HPV16 E7 synthetic vaccine in combination with PD-L 1 blockade elicits therapeutic antitumor immunity in mice. Oncoimmunology. Mar. 10, 2016;5(6):e1147641. doi: 10.1080/2162402X .2016.1147641. PMID: 27471615; PMCID: PMC4938372. (Year: 2016).

Terawaki S, Chikuma S, Shibayama S, Hayashi T, Yoshida T, Okazaki T, Honjo T. IFN-a directly promotes programmed cell death-1 transcription and limits the duration of T cell-mediated immunity. J Immunol. Mar. 1, 2011; 186(5):2772-9. (Year: 2011).

Yang, et al., "Vaccinia ES is a major inhibitor of the DNA sensor cGAS." BioRxiv, Oct. 26, 2021, 45 pages.

(Continued)

*Primary Examiner* — Barry A Chestnut

(74) *Attorney, Agent, or Firm* — Foley & Lardner LLP

(57) ABSTRACT

Disclosed herein are methods and compositions related to the treatment, prevention, and/or amelioration of cancer in a subject in need thereof. In particular aspects, the present technology relates to the use of poxviruses, including a recombinant modified vaccinia Ankara (MVA) virus or vaccinia virus with deletion of vaccinia host-range factor C7 (MVAΔC7L and VACVΔC7L, respectively), alone or in combination with immune checkpoint blocking agents, as an oncolytic and immunotherapeutic composition. In some embodiments, the technology of the present disclosure relates to a MVAΔC7L or VACVΔC7L virus further modified to express human Fms-like tyrosine kinase 3 ligand (Flt3L).

16 Claims, 44 Drawing Sheets

Specification includes a Sequence Listing.

(56) References Cited

U.S. PATENT DOCUMENTS

| | | | |
|---|---|---|---|
| 8,778,328 | B2 | 7/2014 | Erbs et al. |
| 8,852,927 | B2 | 10/2014 | Szalay et al. |
| 8,859,256 | B2 | 10/2014 | Szalay et al. |
| 8,865,153 | B2 | 10/2014 | Szalay et al. |
| 8,871,219 | B2 | 10/2014 | Heeney et al. |
| 9,101,658 | B2 | 8/2015 | Contag et al. |
| 9,175,057 | B2 | 11/2015 | Schlom et al. |
| 9,180,150 | B2 | 11/2015 | Erbs et al. |
| 9,234,197 | B2 | 1/2016 | Chaput et al. |
| 9,273,327 | B2 | 3/2016 | Cottingham |
| 9,670,506 | B2 | 6/2017 | Pantaleo et al. |
| 9,879,281 | B2 | 1/2018 | Son et al. |
| 9,919,062 | B2 | 3/2018 | Kirn |
| 10,548,930 | B2 | 2/2020 | Deng et al. |
| 10,736,962 | B2 | 8/2020 | Deng et al. |
| 2002/0061298 | A1 | 5/2002 | Coffey et al. |
| 2002/0155529 | A1 | 10/2002 | Jacobs et al. |
| 2003/0113919 | A1 | 6/2003 | Emtage et al. |
| 2004/0091995 | A1 | 5/2004 | Schlom et al. |
| 2004/0208850 | A1 | 10/2004 | Ellenhorn et al. |
| 2005/0287162 | A1 | 12/2005 | Baier et al. |
| 2006/0088909 | A1 | 4/2006 | Compans et al. |
| 2006/0099181 | A1 | 5/2006 | Jacobs et al. |
| 2006/0216312 | A1 | 9/2006 | Jacobs |
| 2007/0036758 | A1 | 2/2007 | Jacobs et al. |
| 2007/0178065 | A1 | 8/2007 | Lattime et al. |
| 2007/0275010 | A1 | 11/2007 | Feinberg et al. |
| 2008/0075694 | A1 | 3/2008 | Drexler et al. |
| 2008/0181870 | A1 | 7/2008 | Lowenstein et al. |
| 2009/0162288 | A1 | 6/2009 | Chen et al. |
| 2010/0247622 | A1 | 9/2010 | Coffey et al. |
| 2010/0316609 | A1 | 12/2010 | Dewhurst et al. |
| 2011/0064650 | A1 | 3/2011 | Szalay |
| 2011/0142874 | A1 | 6/2011 | Jacobs et al. |
| 2011/0206640 | A1 | 8/2011 | Bell et al. |
| 2012/0308484 | A1 | 12/2012 | Szalay et al. |
| 2012/0328649 | A1 | 12/2012 | Falkner et al. |
| 2013/0195912 | A1 | 8/2013 | Cottingham |
| 2013/0243813 | A1 | 9/2013 | Howley et al. |
| 2013/0295675 | A1 | 11/2013 | Jacobs et al. |
| 2014/0086976 | A1 | 3/2014 | Szalay et al. |
| 2014/0087362 | A1 | 3/2014 | Szalay et al. |
| 2014/0193859 | A1 | 7/2014 | Jacobs et al. |
| 2014/0271549 | A1 | 9/2014 | Szalay |
| 2014/0377870 | A1 | 12/2014 | Jacobs et al. |
| 2015/0037355 | A1 | 2/2015 | Kirn et al. |
| 2015/0202272 | A1 | 7/2015 | Lauterbach et al. |
| 2015/0240246 | A1 | 8/2015 | Jacobs et al. |
| 2015/0250837 | A1 | 9/2015 | Nolin et al. |
| 2015/0250869 | A1 | 9/2015 | Sene et al. |
| 2015/0283220 | A1 | 10/2015 | Mandl et al. |
| 2016/0130564 | A1 | 5/2016 | Marais et al. |
| 2016/0185875 | A1 | 6/2016 | Cheng et al. |
| 2016/0235793 | A1 | 8/2016 | Thorne |
| 2016/0271239 | A1 | 9/2016 | Foy et al. |
| 2016/0339090 | A1 | 11/2016 | Hacohen et al. |
| 2017/0020938 | A1 | 1/2017 | Wang et al. |
| 2017/0021009 | A1 | 1/2017 | Jacobs et al. |
| 2017/0106065 | A1 | 4/2017 | Foy et al. |
| 2017/0143780 | A1 | 5/2017 | Zitvogel et al. |
| 2017/0157188 | A1 | 6/2017 | Silvestre et al. |
| 2017/0246280 | A1 | 8/2017 | Pantaleo et al. |
| 2017/0266270 | A1 | 9/2017 | Foy et al. |
| 2017/0340687 | A1 | 11/2017 | Nakao et al. |

FOREIGN PATENT DOCUMENTS

| | | | |
|---|---|---|---|
| CN | 1842602 | A | 10/2006 |
| CN | 105039269 | A | 11/2015 |
| CN | 106456747 | A | 2/2017 |
| CN | 107735103 | A | 2/2018 |
| CN | 109152827 | A | 1/2019 |
| DE | 10144664.9 | A1 | 6/2005 |
| EP | 2 771 465 | A1 | 5/2013 |
| EP | 2 136 633 | B1 | 10/2015 |
| EP | 3 142 690 | A2 | 4/2017 |
| EP | 3 850 103 | A1 | 7/2021 |
| JP | 2006-512097 | A | 4/2006 |
| JP | 2010-521497 | A | 6/2010 |
| JP | 5690214 | B2 | 3/2015 |
| WO | WO-03/023040 | A2 | 3/2003 |
| WO | WO-2003/088994 | | 10/2003 |
| WO | WO-2004/024756 | A2 | 3/2004 |
| WO | WO-2004/058801 | A2 | 7/2004 |
| WO | WO-2004/003987 | A1 | 8/2004 |
| WO | WO-2006/120474 | A2 | 11/2006 |
| WO | WO-2007/119895 | A1 | 10/2007 |
| WO | WO-2008/045346 | A2 | 4/2008 |
| WO | WO-2008/113078 | A1 | 9/2008 |
| WO | WO-2009/152179 | A1 | 12/2009 |
| WO | WO-2011/156470 | A1 | 12/2011 |
| WO | WO-2012/009644 | A2 | 1/2012 |
| WO | WO-2013/038066 | A1 | 3/2013 |
| WO | WO-2014/036412 | A2 | 3/2014 |
| WO | WO-2014/081976 | A1 | 5/2014 |
| WO | WO-2015/066715 | A1 | 5/2015 |
| WO | WO-2015/069571 | A1 | 5/2015 |
| WO | WO-2015/084897 | A2 | 6/2015 |
| WO | WO-2015/138741 | A1 | 9/2015 |
| WO | WO-2016/008976 | A1 | 1/2016 |
| WO | WO-2016/046357 | A1 | 3/2016 |
| WO | WO-2016/128542 | A1 | 8/2016 |
| WO | WO-2016/144564 | A1 | 9/2016 |
| WO | WO-2016/144564 | A2 | 9/2016 |
| WO | WO-2016/168862 | A1 | 10/2016 |
| WO | WO-2016/205429 | A1 | 12/2016 |
| WO | WO-2017/024000 | A1 | 2/2017 |
| WO | WO-2017/037523 | A1 | 3/2017 |
| WO | WO-2017/043815 | A1 | 3/2017 |
| WO | WO-2017/044780 | A1 | 3/2017 |
| WO | WO-2017/075570 | A1 | 5/2017 |
| WO | WO-2017/103291 | A1 | 6/2017 |
| WO | WO-2017/129765 | A1 | 8/2017 |
| WO | WO-2017/147553 | A2 | 8/2017 |
| WO | WO-2017/147554 | A1 | 8/2017 |
| WO | WO-2017/147554 | A2 | 8/2017 |
| WO | WO-2017/156349 | A1 | 9/2017 |
| WO | WO-2017/205674 | A1 | 11/2017 |
| WO | WO-2018/015448 | A1 | 1/2018 |
| WO | WO-2018/016917 | A1 | 1/2018 |
| WO | WO-2018/017747 | A2 | 1/2018 |
| WO | WO-2018/031694 | A1 | 1/2018 |
| WO | WO-2018/049248 | A1 | 3/2018 |
| WO | WO-2018/057755 | A1 | 3/2018 |
| WO | WO-2018/058258 | A1 | 4/2018 |

OTHER PUBLICATIONS

Yang, et al., "Intratumoral delivery of engineered recombinant modified vaccinia virus Ankara expressing Flt3L and OX40L generates potent antitumor immunity through activating the cGAS/STING pathway and depleting tumor-infiltrating regulatory T cells." BioRxiv, Nov. 1, 2021, 53 pages.

Yang, et al., "Vaccinia virus E5 is a dominant inhibitor of the cytosolic DNA sensor cGAS." J. of Immunol., May 1, 2019, vol. 202, No. 1 Suppl., p. 197.8.

Carroll et al., "Highly attenuated modified vaccinia virus Ankara (MVA) as an effective recombinant vector: a Murine tumor model", Vaccine, 15(4), pp. 387-394, 31.

Greiner et al., "The blockade of immune checkpoints in cancer immunotherapy", Nat Rev Cancer, 12(4), pp. 252-264, Mar. 22, 2012 (Mar. 22, 2012).

Kwissa et al., "Adjuvanting a DNA vaccine with a TLR9 ligand plus Flt3 ligand results in enhanced cellular immunity against the simian immunodeficiency virus." J. Exp. Medicine. Oct. 29, 2007, vol. 204, No. 11, pp. 2733-2746.

Alharbi, et al., "ChAdOx1 and MVA based vaccine candidates against MERS-COV elicit neutralising antibodies and cellular immune responses in mice," Vaccine, vol. 35, pp. 3780-3788 (Jun. 27, 2017).

Angell et al., "From the immune contexture to the Immunoscore: the role of prognostic and predictive immune markers in cancer," Curr. Opin. Immunol., 25, pp. 261-267 (2013).

(56) References Cited

OTHER PUBLICATIONS

Antoine et al., "The complete genomic sequence of the modified vaccinia Ankara strain: comparison with other orthopoxviruses", Virology, 244, pp. 365-396 (1998).
Arsenio et al., "Antagonizing activity of vaccinia virus E3L against human interferons in Huh7 cells," Journal of Virology, vol. 377, No. 1, p. 124-132 (Jul. 20, 2008).
Backes et al., "Viral host-range factor C7 or K1 is essential for modified vaccinia virus Ankara late gene expression in human and murine cells, irrespective of their capacity to inhibit protein kinase R-mediated phosphorylation of eukaryotic translation initiation factor 2a," J. of General Virology, vol. 91, pp. 470-482 (Feb. 1, 2010).
Barber, "Innate immune DNA sensing pathways: STING, AIMII and the regulation of interferon production and inflammatory responses", Curr. Opin. Immunol., 23, pp. 10-20 (2011).
Bisht et al., "Severe acute respiratory syndrome coronavirus spike protein expressed by attenuated vaccinia virus protectively immunizes mice," PNAS, vol. 101, pp. 6641-6646 (Apr. 27, 2004).
Bommareddy et al., "MEK inhibition enhances oncolytic virus immunotherapy through increased tumor cell killing and T cell activation," Science Translational Medicine, vol. 10, Issue 471 (Dec. 12, 2018).
Brandler et al., "Preclinical studies of a modified vaccinia virus Ankara-based HIV candidate vaccine: antigen presentation and antiviral effect", J. Virol., vol. 84, No. 10, pp. 5314-5328 (2010).
Brandt et al., "The N-terminal domain of the vaccinia virus E3L-protein is required for neurovirulence" Virology, vol. 333, No. 2, pp. 263-270 (Mar. 15, 2005).
Breitbach et al., "Targeted and armed oncolytic poxviruses for cancer: the lead example of JX-594," Current Pharmaceutical Biotechnology, 13, pp. 1768-1772 (2012).
Brinkman et al., "Fingolimod (FTY720): discovery and development of an oral drug to treat multiple sclerosis," Nature Reviews | Drug Discovery, vol. 9, pp. 883-897 (Nov. 2010).
Caisova et al., "Innate immunity based cancer immunotherapy: B16-F10 murine melanoma model," BMC Cancer, 16:940, 11 pages (2016).
Cao et al., "Innate immune response of human plasmacytoid dendritic cells to poxvirus infection is subverted by vaccinia E3 via its Z-DNA/RNA binding domain," PLOS ONE, vol. 7, No. 5, p. e36823 (May 14, 2012).
Carina Riediger et al:Fms-like tyrosine kinase 3 receptor ligand (Flt3L)-based vaccination administered with an adenoviral vector prevents tumor growth of colorectal cancer in a BALB/c mouse model 11 , Journal of Cancer Research and Clinical Oncology., vol. 139, No. 12, Oct. 10, 2013 (Oct. 10, 2013), pp. 2097-2110, XP055672630, DE ISSN: 0171-5216, DOI: 10.1007/s00432-013-1532-z * Figures 6, 8 *.
Castle et al., "Exploiting the mutanome for tumor vaccination", Cancer Res., 72, pp. 1081-1091 (2012).
Chafekar, et al., "MERS-COV: Understanding the Latest Human Coronavirus Threat," Viruses, 10, 93, 22 pages (Feb. 24, 2018).
Chavan et al., "Expression of CCL20 and granulocyte-macrophage colony-stimulating factor, but not Flt3-L, from modified vaccinia virus Ankara enhances antiviral cellular and humoral immune responses," J. Virology, vol. 80, No. 15, pp. 7676-7687 (2006).
Chi et al., "DNA vaccine encoding Middle East respiratory syndrome coronavirus S1 protein induces protective immune responses in mice," Vaccine, vol. 35, pp. 2069-2075 (Apr. 11, 2017).
Coffey et al., "Reovirus therapy of tumors with activated Ras pathway," Science, 282, pp. 1332-1334 (1998).
Curran et al, Tumor Vaccines Expressing Flt2 Ligand Synergize with CTLA-4 Blockade to Reject Preimplanted Tumors, Cancer Research vol. 69 No. 19, Sep. 8, 2009, pp. 7747-7755.
Dai et al., "Abstract B031 : Heat-inactivated modified vaccinia virus Ankara induces type | IFN and antitumor immunity via the cytosolic DNA-sensing pathway," retrieved from: http://www.cancerimmunolrres.aacrjournals.org/content/4/1_Supplement/B031 (Jun. 15, 2018).
Dai et al., "Intratumoral delivery of inactivated modified vaccinia virus Ankara (iMVA) induces systemic antitumor immunity via STING and Batf3-dependent dendritic cells" Science Immunology, vol. 2, No. 11, pp. 1-34 (May 19, 2017).
Dai, P et al, Modified Vaccinia Virus Ankara Triggers Type 1 IFN Production In Murine Conventional Dendritic Cells Via A cGAS/STING-Mediated Cytosolic DNA-Sensing Pathway, PLOS Pathogens, Apr. 2014, vol. 10, pp. 1-13.
Dai, P et al, Myxoma Virus Induces Type 1 Interferon Production In Murine Plasmacytoid Dendritic Cells Via A TLR9/MyD88−, IRF5/IRF7−, and IFNAR-Dependent Pathway. Journal of Virology, Oct. 2011, pp. 10814-10825.
Deng et al., "STING-Dependent Cytosolic DNA Sensing Promotes Radiation-Induced Type I Interferon-Dependent Antitumor Immunity in Immunogenic Tumors", Immunity, vol. 41, No. 5, pp. 843-852 (2014).
Deng et al., "Vaccinia virus infection attenuates innate immune responses and antigen presentation by epidermal dendritic cells", J Virol., 80, pp. 9977-9987 (2006).
Diamond et al., "Type I interferon is selectively required by dendritic cells for immune rejection of tumors", J Exp Med., vol. 208, No. 10, pp. 1989-2003 (2011).
Drexler et al., "Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo1," Cancer Research, vol. 59, p. 4955-4963 (Oct. 1, 1999).
Drillien et al, Modified vaccination virus Ankara induces moderate activation of human dendritic cells, Journal of General Virology, Society for General Microbiology, vol. 85, No. Pt 8, Aug. 1, 2004, pp. 2167-2175.
Du et al., "The spike protein of SARS-CoV—a target for vaccine and therapeutic development," Microbiology, vol. 7, pp. 226-236 (Mar. 2009).
Engelmayer et al., "Vaccinia virus inhibits the maturation of human dendritic cells: a novel mechanism of immune evasion", J Immunol., 163, pp. 6762-6768 (1999).
Espenschied J et al, "CTL-4 blockade enhances the therapeutic effect of an attenuated poxvirus vaccine targeting p53 in in established murine tumor model", Journal of Immunology, vol. 170, Issue 6, pp. 3401-3407.
Extended European Search Report on App. No. 17757398.7 dated Aug. 19, 2019 (9 pages).
Fishcer et al., "Modified vaccinia virus Ankara protein F1L is a novel BH3-domain-binding protein and acts together with the early viral protein E3L to block virus-associated apoptosis" Cell Death Differ., 13, pp. 109-118 (2006).
Fuertes et al., "Host type I IFN signals are required for antitumor CD8 T-cell responses through CD8{alpha} dendritic cells", J. Exp. Med., vol. 208, No. 10, 2005-2016 (2011).
Fuertes et al., "Type I interferon response and innate immune sensing of cancer," Trends Immunol., vol. 34, No. 2, pp. 67-73 (Feb. 2013).
Fung et al., "Human Coronavirus: Host-Pathogen Interaction," Annual Review of Microbiology, 73, pp. 529-557 (Jun. 21, 2019).
Gao et al., "Structure-function analysis of STING activation by c[G(2',5')pA(3',5')p] and targeting by antiviral DMXAA", Cell, 154, pp. 748-762 (2013).
Garcia et al., "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)", Vaccine, 29, pp. 8309-8316 (2011).
Garrido et al., "The escape of cancer from T lymphocytes: immunoselection of MHC class I loss variants harboring structural-irreversible "hard" lesions," Cancer Immunol. Immunother., 59, pp. 1601-1606 (2010).
GenBank: U94848.1 "Vaccinia virus strain Ankara, complete genomic sequence" p. 1-3 (Apr. 13, 2003).
Gerlini et al., "Metastatic melanoma secreted IL-10 down-regulates CD1 molecules on dendritic cells in metastatic tumor lesions", Am J Pathol., 165, pp. 1853-1863 (2004).

(56) References Cited

OTHER PUBLICATIONS

Gitlin et al., "Essential role of mda-5 in type I IFN responses to polyriboinosinic:polyribocytidylic acid and encephalomyocarditis picornavirus", Proc. Natl. Acad. Sci. U S A., vol. 103, No. 22, pp. 8459-8464 (May 30, 2006).
Goepfert et al., "Phase 1 safety and immunogenicity testing of DNA and recombinant modified vaccinia Ankara vaccines expressing HIV-1 virus-like particles", J Infect Dis., 203, pp. 610-619 (2011).
Gomez et al., "MVA and NYVAC as vaccines against emergent infectious diseases and cancer," Current Gene Therapy, vol. 11, No. 3, p. 189-217 (Jun. 2011).
Gomez et al., "The poxvirus vectors MVA and NYVAC as gene delivery systems for vaccination against infectious diseases and cancer", Curr Gene Ther., 8, pp. 97-120 (2008).
Greiner et al. "The highly attenuated vaccinia virus strain modified virus Ankara induces apoptosis in melanoma cells and allows bystander dendritic cells to generate a potent anti tumoral immunity" Clinical and Experimental Immunology vol. 146. No. 2, Nov. 1, 2006 pp. 344-353.
Guerra et al., "Distinct gene expression profiling after infection of immature human monocyte-derived dendritic cells by the attenuated poxvirus vectors MVA and NYVAC," J. of Virology, vol. 61, No. 16, pp. 8701-8721 (May 30, 2007).
Guerra et al., "Host-Range Restriction in Vaccinia Virus E3L Deletion Mutant Can Be Overcome In Vitro, but Not In Vivo, by Expression of the Influenza Virus NS1 Protein," PLoS ONE. vol. 6 No. 12, p. e28677 (2011).
Haagmans, et al., "An orthopoxvirus-based vaccine reduces virus excretion after MERS-CoV infection in dromedary camels," Science, vol. 351, pp. 77-81 (Jan. 1, 2016).
Hamid et al., "Safety and Tumor Responses with Lambrolizumab (Anti-PD-1) in Melanoma", The New England journal of medicine, vol. 369, No. 2, pp. 134-144 (2013).
Hammerich et al., In situ vaccination for the treatment of cancer, Immunotherapy vol. 8, No. 3, Mar. 1, 2016, pp. 315-330.
Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial," Clinical Cancer Research, vol. 12, No. 11 Pt. 1, p. 3416-6424 (Jun. 1, 2006).
Hodge et al., "Modified Vaccinia Virus Ankara Recombinants Are as Potent as Vaccinia Recombinants in Diversified Prime and Boost Vaccine Regimens to Elicit Therapeutic Antitumor Responses," American Association for Cancer Research, vol. 63, No. 22, p. 7942-7949 (Nov. 15, 2003).
Hodi et al., "Improved survival with ipilimumab in patients with metastatic melanoma", The New England journal of medicine, 363, pp. 711-723 (2010).
Holshue et al., "First Case of 2019 Novel Coronavirus in the United States," New England Journal of Medicine, 9 pages (Jan. 31, 2020).
Hornemann et al., "Replication of Modified Vaccinia Virus Ankara in Primary Chicken Embryo Fibroblasts Requires Expression of the Interferon Resistance Gene E3L," Journal of Virology, vol. 77, No. 15, p. 8394-8407 (Aug. 2003).
Huber et al., "Regulation of effector and memory T-cell functions by type I interferon", Immunology, 132, pp. 466-474 (2011).
Inman, "Immunotherapy/Targeted Therapy Combinations Show Promise in BRAF-Mutated Melanoma," Targeted Oncology, retrieved from: https://www.targetedonc.com/conference/smr-esmo-melanoma/immunotherapytargeted-therapy-combinations-show-promise-in-brafmutated-melanoma (Oct. 20, 2017).
International Search Report and Written Opinion on PCT/US2016/028184, dated Sep. 9, 2016, 17 pages.
International Search Report and Written Opinion on PCT/US2017/019548, dated Aug. 8, 2017, 17 pages.
International Search Report and Written Opinion on PCT/US2017/019549, dated Aug. 14, 2017 (17 pages).
International Search Report and Written Opinion on PCT/US2018/032451, dated Aug. 23, 2018, 16 pages.
International Search Report and Written Opinion on PCT/US2018/059476, dated Feb. 14, 2019, 9 pages.
International Search Report and Written Opinion, PCT/US2019/021853, Memorial Sloan Kettering Cancer Center (dated Jul. 16, 2019).
International Search Report and Written Opinion, PCT/US2019/051343 (dated Feb. 7, 2020).
Ishikawa et al., "STING is an endoplasmic reticulum adaptor that facilitates innate immune signaling", Nature, 455, pp. 674-678 (2008).
Jacobs et al., Vaccinia virus vaccines: Past, present and future, Antiviral Research, Elsevier BV, NL vol. 84, No. 1, Oct. 1, 2009 pp. 1-13.
Jenne et al., "Poxvirus as a vector to transduce human dendritic cells for immunotherapy: abortive infection but reduced APC function", Gene therapy, 7, pp. 1575-1583 (2000).
Jochems et al., "Tumor-infiltrating immune cells and prognosis: the potential link between conventional cancer therapy and immunity", Exp Biol Med.(Maywood), 236, pp. 567-579 (2011).
Kibler et al., "Double-stranded RNA is a trigger for apoptosis in vaccinia virus-infected cells", J. Virol., vol. 71, No. 3, pp. 1992-2003 (1997).
Kirn et al., "Replication-selective virotherapy for cancer: Biological principles, risk management and future directions," Nat. Med., 7, pp. 781-787 (2001).
Kirn et al., "Targeted and armed oncolytic poxviruses: a novel multi-mechanistic therapeutic class for cancer," Nature Reviews—Cancer, 9, pp. 64-71 (2009).
Kirn et al., "Targeting of interferon-beta to produce a specific, multi-mechanistic oncolytic vaccinia virus", PLoS Med., vol. 4, No. 12, pp. 2001-2012 (2007).
Kreiter et al., "Mutant MHC class II epitopes drive therapeutic immune responses to cancer." Nature. Apr. 22, 2015, vol. 520, No. 7549, pp. 692-696.
Kuzu et al., "Current State of Animal (Mouse) Modeling in Melanoma Research," Cancer Growth and Metastasis, 8(S1):81-94 (2015).
Lacy et al., "Immunotherapy for Melanoma," Expert Rev. Dermatol., 7, pp. 51-68 (2012).
Langland et al., "Inhibition of PKR by vaccinia virus: role of the N- and C-terminal domains of E3L," Journal of Virology, vol. 324, No. 2, p. 419-429 (Jul. 1, 2004).
Leach et al., "Enhancement of antitumor immunity by CTLA-4 blockade," Science, 271, pp. 1734-1736 (1996).
Lee et al., "The interferon-induced double-stranded RNA-activated protein kinase induces apoptosis," Journal of Virology, vol. 199, No. 2, p. 491-496 (Mar. 1994).
Lee et al., "Effect of resveratrol on the metastasis of 4T1 mouse breast cancer cells in vitro and in vivo," Nutrition Res. and Practice, vol. 6, No. 4, pp. 294-300 (2012).
Li et al., "Angiotensin-converting enzyme 2 is a functional receptor for the SARS coronavirus," Nature, vol. 426, pp. 450-454 (Nov. 27, 2003).
Li et al., "Disruption of MHC class II-restricted antigen presentation by vaccinia virus," J. Immunol., 175, pp. 6481-6488 (2005).
Li et al., "Early Transmission Dynamics in Wuhan, China, of Novel Coronavirus—Infected Pneumonia," New England Journal of Medicine, 9 pages (Jan. 29, 2020).
Li et al., "Pivotal roles of cGAS-cGAMP signaling in antiviral defense and immune adjuvant effects", Science, 341, pp. 1390-1394 (2013).
Li et al., "Structure of SARS Coronavirus Spike Receptor-Binding Domain Complexed with Receptor," Science, vol. 309, pp. 1864-1868 (Sep. 16, 2005).
Liu et al., "Deletion of C7L and K1L genes leads to significantly decreased virulence of recombinant vaccinia cirus TianTian," PLoS One, vol. 8, No. 7:e68115, pp. 1-13 (Jul. 1, 2013).
Liu, "Cancer-killing virus plus PD-1 and MEK inhibitors make for a 3-pronged attack on melanoma," retrieved from: https://www.fiercebiotech.com/research/pd-1-mek-inhibitor-and-anti-cancer-virus-a-3-pronged-attack-melanoma, 2 pages (Dec. 12, 2018).
Ludwig et al., "Role of Viral Factor E3L in Modified Vaccinia Virus Ankara Infection of Human HeLa Cells: Regulation of the Virus

(56) References Cited

OTHER PUBLICATIONS

Life Cycle and Identification of Differentially Expressed Host Genes," Journal of Virology, vol. 79, No. 4, p. 2584-2596 (Feb. 2005).
Mandl, SJ et al, Immunotherapy With MVA-BN-HER2 Induces HER-2-specific Th1 Immunity And Alters The Intratumoral Balance Of Effector And Regulatory T cells. Cancer Immunol Immunother, 2012, vol. 61, pp. 19-29.
Mayr et al., English-language translation of Abstract of: "[The smallpox vaccination strain MVA: marker, genetic structure, experience gained with the parenteral vaccination and behavior in organisms with a debilitated defence mechanism (author's transl)]," Zentralbl Bakteriol, Orig. B, 167, pp. 375-390 (1978).
Mayr et al., English-language translation of Abstract of: "Passage history, properties, and applicability of the attenuated vaccinia virus strain MVA," Infection, 3, pp. 6-14 (1975).
McCart et al., "Systemic Cancer Therapy with a Tumor-selective Vaccinia Virus Mutant Lacking Thymidine Kinase and Vaccinia Growth Factor Genes.", Cancer Res., (2001), 61, [24], p. 8751-8757.
McIntyre et al., "Mouse models of colorectal cancer as preclinical models," Bioessays, 37(8), pp. 909-920 (Aug. 2015).
Mellman et al., "Cancer immunotherapy comes of age", Nature, 480, pp. 480-489 (2011).
Meng et al., "C7L Family of Poxvirus Host Range Genes Inhibits Antiviral Activities Induced by Type I Interferons and Interferon Regulatory Factor 1", J. Virol., vol. 86, No. 8, pp. 538-4547 (2012).
Meng et al., "Vaccinia Virus K1L and C7L Inhibit Antiviral Activities Induced by Type 1 Interferons," Journal of Virology, vol. 83, No. 20, p. 10627-10636 (Oct. 2009).
Meyer et al., "Mapping of deletions in the genome of the highly attenuated vaccinia virus MVA and their influence on virulence", J. Gen. Virol., 72 ( Pt 5), pp. 1031-1038 (1991).
Mlecnik et al., "Tumor immunosurveillance in human cancers", Cancer Metastasis Rev, 30, pp. 5-12 (2011).
Morales et al., Genome comparison of a nonpathogenic myoxma virus field strain with its ancestor, the virulent Lausanne strain, J. Virol, vol. 83, No. 5, pp. 2397-2403 Mar. 2009.
Moss, "Poxviridae: The viruses and their replication," In Fields Virology (Lippincott Williams & Wilkins), pp. 2905-2946 (2007).
Nagaria et al., "Combined targeting of RAF and MEK synergistically inhibits tumorigenesis in triple negative breast cancer model systems," Oncotarget, vol. 8, No. 46, pp. 80804-80819 (Aug. 24, 2017).
Nagorsen et al., "Transcriptional analysis of tumor-specific T-cell responses in cancer patients," Crit. Rev. Immunol., 22, pp. 449-462 (2002).
Nakayama et al., "In vitro comparison between mouse B16 and human melanoma cell lines of the expression of ICAM-1 induced by cytokines and/or hyperthermia," J. Dermatol., 24(6), pp. 351-360 (Jun. 1997).
Nemunaitis, J., "Oncolytic viruses,". Invest. New Drugs, 17, pp. 375-386 (1999).
Non-Final Office Action on U.S. Appl. No. 16/612,127 dated Apr. 23, 2021.
Notice of Allowance on U.S. Appl. No. 16/612,127 dated Sep. 17, 2021.
Oble et al., "Focus on TILs: prognostic significance of tumor infiltrating lymphocytes in human melanoma", Cancer immunity, 9, pp. 1-20 (2009).
Pardoll, "The blockade of immune checkpoints in cancer immunotherapy," Nat. Rev. Cancer, 12(4), pp. 252-264 (Mar. 22, 2012).
Park et al., "Use of a targeted oncolytic poxvirus, JX-594, in patients with refractory primary or metastatic liver cancer: a phase I trial," Lancet Oncol., 9, pp. 533-542 (May 19, 2008).
Peggs et al., "Blockade of CTLA-4 on both effector and regulatory T-cell compartments contributes to the antitumor activity of anti-CTLA-4 antibodies", J Exp Med., 206, pp. 1717-1725 (2009).
Peihong et al., "Modified Vaccinia Virus Ankara Triggers Type 1 IFN Production in Murine Conventional Dendritic Cells via a cGAS/STING-Mediated Cytosolic DNA-Sensing Pathway," PLOS Pathogens, vol. 10, No. 4, p. e1003989 (Apr. 17, 2014).
Peihong, "P339 Intratumoral delivery of modified vaccinia virus Ankara expressing human Flt3L as cancer immunotherapy," 31st Annual Meeting and Associated Programs of the Society for Immunotherapy of Cancer, Pt. 2, p. 1-241 (2016).
Peiris, et al., "The Severe Acute Respiratory Syndrome," New England Journal of Medicine, vol. 349, pp. 2431-2441 (Dec. 18, 2003).
Perkus et al., "Vaccinia virus host genes," Virology, 179(1), pp. 276-286 (1990).
Pramanick et al., "Excipient selection in parenteral formulation development", Pharma Times, vol. 45, No. 3, pp. 65-77 (2013).
Raj et al., "Dipeptidyl peptidase 4 is a functional receptor for the emerging human coronavirus—EMC," Nature, vol. 495, 6 pages (Mar. 13, 2013).
Reddy et al., "Influences of BRAF Inhibitors on the Immune Microenvironment and the Rationale for Combined Molecular and Immune Targeted Therapy," Curr. Oncol. Rep., 18(7)15 pages (Jul. 2016).
Rice et al. An H PV-E6/E7 immunotherapy plus PD-1 checkpoint inhibition results in tumor regression and reduction in PD-L 1 expression. Cancer Gene Therapy (2015) 22, 454-462.
Robert et al., "Ipilimumab plus dacarbazine for previously untreated metastatic melanoma", The New England journal of medicine, 364, pp. 2517-2526 (2011).
Sabbatino et al., "Antitumor activity of BRAF inhibitor and IFN combination in BRAF-mutant melanoma," J. Natl. Cancer Inst., 108(7), 11 pages (Feb. 5, 2016).
Sato et al., "Distinct and essential roles of transcription factors IRF-3 and IRF-7 in response to viruses for IFN-alpha/beta gene induction", Immunity, 13, pp. 539-548 (2000).
Sauer et al., "The N-ethyl-N-nitrosourea-induced Goldenticket mouse mutant reveals an essential function of Sting in the in vivo interferon response to Listeria monocytogenes and cyclic dinucleotides", Infection and immunity, vol. 79, No. 2, pp. 688-694 (2011).
Schaedler et al., "Sequential administration of a MVA-based MUC1 cancer vaccine and the TLR9 ligand Litenimod (Li28) improves local immune defense against tumors," Vaccine, vol. 35, No. 4, p. 577-585 (Jan. 23, 2017).
Schumacher et al., "Neoantigens in cancer immunotherapy", Science, 348, pp. 69-74 (2015).
Sharma et al., "The future of immune checkpoint therapy", Science, 348, pp. 56-61 (2015).
Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBio, vol. 6, No. 4, pp. 1-9 (2015).
Song, et al., "Middle East Respiratory Syndrome Coronavirus Spike Protein Delivered by Modified Vaccinia Virus Ankara Efficiently Induces Virus-Neutralizing Antibodies," Journal of Virology, vol. 87, pp. 11950-11954 (Nov. 2013).
Sun et al., "Cyclic GMP-AMP synthase is a cytosolic DNA sensor that activates the type I interferon pathway", Science, 339, pp. 786-791 (2013).
Sutter et al., "Vaccinia vectors as candidate vaccines: the development of modified vaccinia virus Ankara for antigen delivery," Current Drug Targets—Infectious Disorders 3, pp. 263-271 (2003).
Tagliamonte et al., "Antigen-specific vaccines for cancer treatment", Human vaccines & immunotherapeutics, 10, pp. 3332-3346 (2014).
Takaoka et al., "New aspects of IFN-alpha/beta signalling in immunity, oncogenesis and bone metabolism", Cancer Sci., vol. 94, No. 5, pp. 405-411 (2003).
Thorne et al., "Rational strain selection and engineering creates a broad-spectrum, systemically effective oncolytic poxvirus, JX-963", J Clin Invest., vol. 117, No. 11, pp. 3350-3358 (2007).
Topalian et al., "Immune checkpoint blockade: a common denominator approach to cancer therapy", Cancer Cell, vol. 27, No. 4, pp. 450-461 (2015).

(56) References Cited

OTHER PUBLICATIONS

Topalian et al., "Targeting the PD-1/B7-H1(PD-L1) pathway to activate anti-tumor immunity", Curr Opin Immunol., 24, pp. 207-212 (2012).
Tormo et al., "Targeted activation of innate immunity for therapeutic induction of autophagy and apoptosis in melanoma cells", Cancer Cell, vol. 16, No. 2, pp. 103-114 (2009).
Tumeh et al., "PD-1 blockade induces responses by inhibiting adaptive immune resistance", Nature, vol. 515, No. 7258, pp. 568-571 (2014).
U.S. Office Action on U.S. Appl. No. 16/612,127 dated Dec. 15, 2020.
Verardi et al., "A vaccinia virus renaissance: new vaccine and immunotherapeutic uses after smallpox eradication", Human vaccines & immunotherapeutics, 8, pp. 961-970 (2012).
Verheust et al., "Biosafety aspects of modified vaccinia virus Ankara (MVA)-based vectors used for gene therapy or vaccination," Vaccine, 30, pp. 2623-2632 (2012).
Vijaysri et al., "Vaccinia Viruses with Mutations in the E3L Gene as Potential Replication—Competent, Attenuated Vaccines: Intra-Nasal Vaccination," Vaccine, vol. 26, No. 5, p. 664-676 (Jan. 30, 2008).
Volz, et al., "Protective Efficacy of Recombinant Modified Vaccinia Virus Ankara Delivering Middle East Respiratory Syndrome Coronavirus Spike Glycoprotein," Journal of Virology, vol. 89, pp. 8651-8656 (Aug. 2015).
Waibler et al., "Modified Vaccinia Virus Ankara Induces Toll-Like Receptor-Independent Type I Interferon Responses," Journal of Virology, vol. 81, No. 22, p. 12101-12110 (Nov. 2007).
Wang et al., "034 recombinant replication competent attenuated vaccinia virus expressing human Flt3L for cancer immunotherapy," J. Invest. Derm., vol. 136, No. 5, p. S6 (May 2016).
Wang et al., Abstracts—Adaptive Immunity and Vaccination 034, Recombinant replication competent attenuated vaccinia virus expressing human Flt3L for cancer immunotherapy, Journal of Investigative Dermatology vol. 136, No. 5 May 2016 p. S6.
Weaver et al., "The identification and characterization of a monoclonal antibody to the vaccinia virus E3 protein", Virus Res., 130, pp. 269-274 (2007).
Wing et al., "CTLA-4 control over Foxp3 regulatory T-cell function", Science, 322, pp. 271-275 (2008).
Wolchok et al., "Ipilimumab monotherapy in patients with pretreated advanced melanoma: a randomised, double-blind, multicentre, phase 2, dose-ranging study," Lancet Oncol., 11, pp. 155-164 (2010).
Wolchok et al., "Nivolumab plus ipilimumab in advanced melanoma", The New England journal of medicine, 369, pp. 122-133 (2013).
Woo et al., "STING-dependent cytosolic DNA sensing mediates innate immune recognition of immunogenic tumors", Immunity, vol. 41, No. 5, pp. 830-842 (2014).
Wu et al., "Cyclic GMP-AMP is an endogenous second messenger in innate immune signaling by cytosolic DNA", Science, 339, pp. 826-830 (2013).
Wyatt et al., "Enhanced cell surface expression, immunogenicity and genetic stability resulting from a spontaneous truncation of HIV Env expressed by a recombinant MVA", Virology, 372, pp. 260-272 (2008).
Yong, et al., "Recent Advances in the Vaccine Development Against Middle East Respiratory Syndrome-Coronavirus," Frontiers in Microbiology, vol. 10, 18 pages (Aug. 2, 2019).
Zaki, et al., "Isolation of a Novel Coronavirus from a Man with Pneumonia in Saudi Arabia," The New England Journal of Medicine, vol. 367, pp. 1814-1820 (Nov. 8, 2012).
Zamarin et al., "Localized oncolytic virotherapy overcomes systemic tumor resistance to immune checkpoint blockade immunotherapy", Science translational medicine, vol. 6, No. 226, pp. 1-12 (2014).
Zhang, et al., "A DNA vaccine induces SARS coronavirus neutralization and protective immunity in mice," Nature, vol. 428, pp. 561-564 (Apr. 2004).
Zhou, et al., "A pneumonia outbreak associated with a new coronavirus of probable bat origin," Nature, 23 pages (Feb. 3, 2020).
Zurkova et al., "The expression of the soluble isoform of hFlt3 ligand by recombinant vaccinia virus enhances immunogenicity of the vector," vol. 21, No. 5, p. 1335-1343 (Apr. 6, 2009).
Foy et al., "Poxvirus immunotherapies in combination with immune checkpoint inhibitors synergize to eliminate tumors in a mouse tumor model." Journal for ImmunoTherapy of Cancer 2013, 1(Suppl 1):P72.
Wong et al. Oncolytic Viruses for Cancer Therapy: Overcoming the Obstacles. Viruses, 2010, 2: 78-106.
Fang J et al: "Stable antibody expression at therapeutic levels using the 2A peptide", Nature Biotechnology, Nature Publishing Group US, New York, vol. 23, No. 5, Apr. 17, 2005 (Apr. 17, 2005) , pp. 584-590.
T Du et al: "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.
Wang Weiyi et al: "LB-306: Oncolytic vaccinia virus expressing immune checkpoint blockade antibody as cancer immunotherapeutics", Cancer Research; Annual Meeting of the American-Association-for-Cancer-Research (AACR), American Association for Cancer Research, US; Chicago, IL, USA, vol. 78, No. 13, Suppl . S, Jun. 30, 2018 (Jun. 30, 2018), pp. LB-306.
Wu, et al., "Structure and function of vaccinia virus E3L protein." Journal of Biology, No. 2, pp. 64-83, (Apr. 13, 2013).
Lee SY et al. Intratumoral injection of therapeutic H PV vaccinia vaccine following cisplatin enhances H PV-specific anti tumor effects. Cancer Immunol Immunother (2013) 62: 1175-1185 (Year: 2013).
Reuschenbach M et al. High-risk human papillomavirus in non-melanoma skin lesions from renal allograft recipients and immunocompetent patients. British Journal of Cancer 2011 104, 1334-1341 (Year: 2011).

| Lane | Marker or PCR primer pair | Predicted band size (bp) |
|---|---|---|
| 1 | Fermentas 1kb Plus ladder | 20k, 10k, 7k, **5k**, 4k, 3k, 2k, **1.5k**, 1k, 700, **500** 400, 300, 200, 100, 75 |
| 2 | P500F1/P500R2 | 420 |
| 3 | P500F2/P500R1 | 407 |
| 4 | P501F1/P500R3 | 465 |
| 5 | P501F2/P501R2 | 2020 |
| 6 | P501R2/P500R3 | 321 |
| 7 | P501F3/P500R1 | 371 |
| 8 | P501F2/P500F3 | 1195 |

SEQUENCE LISTING

```
<160> NUMBER OF SEQ ID NOS: 6

<210> SEQ ID NO 1
<211> LENGTH: 194711
<212> TYPE: DNA
<213> ORGANISM: Vaccinia virus WR

<400> SEQUENCE: 1

atttaaaata taatattaat gtactaaaac ttatatatta ttaatttatc taactaaagt      60

tagtaaatta tatatataat tttataatta atttaatttt actaatttta tttagtgtct     120

agaaaaaaat gtgtgaccca tgactgtagg aaactctaga gtgtaagaaa gatcgatcgc     180

tttatagaga ccatcagaaa gaggtttaat atttttgtga gaccatcgaa gagagaaaga     240

gataaaactt ttttacgact ccatcagaaa gaggtttaat atttttgtga gaccatcgaa     300
```

-continued

```
gagagaaaga gataaaactt ttttacgact ccatcagaaa gaggtttaat atttttgtga    360
gaccatcgaa ggagaaagag ataaaacttt tttacgactc catcagaaag aggtttaata    420
tttttgtgag accatcgaag gagaaagaga taaaactttt ttacgactcc atcagaaaga    480
ggtttaatat ttttgtgaga ccatcgaaga gagaaagaga taaaactttt ttacgactcc    540
atcagaaaga ggtttaatat ttttgtgaga ccatcgaaga gagaaagaga taaaactttt    600
ttacgactcc atcagaaaga ggtttaatat ttttgtgaga ccatcgaagg agaaagagat    660
aaaacttttt tacgactcca tcagaaagag gtttaatatt tttgtgagac catcgaagag    720
agaaagagat aaaacttttt tacgactcca tcagaaagag gtttaatatt tttgtgagac    780
catcgaagag agaaagagat aaaacttttt tacgactcca tcagaaagag gtttaatatt    840
tttgtgagac catcgaagag agaaagagat aaaacttttt tacgactcca tcagaaagag    900
gtttaatatt tttgtgagac catcgaagag agaaagagat aaaacttttt tacgactcca    960
tcagaaagag gtttaatatt tttgtgagac catcgaagag agaaagagat aaaacttttt   1020
tacgactcca tcagaaagag gtttaatatt tttgtgagac catcgaagag agaaagagaa   1080
agagatagtt gatctagata tttttcttag tacaaaagtc aatgttttaa aatatatgga   1140
caagaatttg tctgtataaa aacttgtgtg aaattttgta ccaaagaaaa aatgtgagca   1200
gtatccccta catggatttt actagatcat ttatatacca aaaaatatta tacgatctac   1260
gttttattat atgattttaa cgtgtaaatt ataaacatta ttttatgata tacaattgtc   1320
tggtaaccta gatgggcata ggggatgttg ataagctcga cgagtatatg ttgttggacg   1380
ttattgttta agaaatagtt gatgcatcag aaagagaata aaaaatattt tagtgagacc   1440
atcgaagaga gaaagagata aaactttttt acgactccat cagaaagagg tttaatattt   1500
ttgtgagacc atcgaagaga gaaagagata aaactttttt acgactccat cagaaagagg   1560
tttaatattt ttgtgagacc atcgaagaga gaaagagata aaactttttt acgactccat   1620
cagaaagagg tttaatattt ttgtgagacc atcgaagaga gaaagagata aaactttttt   1680
acgactccat cagaaagagg tttaatattt ttgtgagacc atcgaagaga gaaagagata   1740
aaactttttt acgactccat cagaaagagg tttaatattt ttgtgagacc atcgaagaga   1800
gaaagagata aaactttttt acgactccat cagaaagagg tttaatattt ttgtgagacc   1860
atcgaagaga gaaagagata aaactttttt acgactccat cagaaagagg tttaatattt   1920
ttgtgagacc atcgaagaga gaaagagata aaactttttt acgactccat cagaaagagg   1980
tttaatattt ttgtgagacc atcgaagaga gaaagagata aaactttttt acgactccat   2040
cagaaagagg tttaatattt ttgtgagacc atcgaagaga gaaagagata aaactttttt   2100
acgactccat cagaaagagg tttaatattt ttgtgagacc atcgaagaga gaaagagata   2160
aaactttttt acgactccat cagaaagagg tttaatattt ttgtgagacc atcgaagaga   2220
gaaagagata aaactttttt acgactccat cagaaagagg tttaatattt ttgtgagacc   2280
atcgaagaga gaaagagata aaactttttt acgactccat cagaaagagg tttaatattt   2340
ttgtgagacc atcgaagaga gaaagagata aaactttttt acgactccat cagaaagagg   2400
tttaatattt ttgtgagacc atcgaagaga gaaagagata aaactttttt acgactccat   2460
cagaaagagg tttaatattt ttgtgagacc atcgaagaga gaaagagata aaactttttt   2520
acgactccat cagaaagagg tttaatattt ttgtgagacc atcgaagaga gaaagagata   2580
aaactttttt acgactccat cagaaagagg tttaatattt ttgtgagacc atcgaagaga   2640
```

-continued

```
gaaagagata aaactttttt acgactccat cagaaagagg tttaatattt ttgtgagacc   2700
atcgaagaga gaaagagaat aaaaatattt tatgactcca ttgaagagag aaagagaaaa   2760
tgagaatgag aataaaaata ttttagtgac accatcagaa agaggtttaa tatttttgtg   2820
agaccatcga agagagaaag agaataaaaa tattttatga ctccattgaa gagagaaaga   2880
gaaaatgaga atgagaataa aaatatttta gtgacaccat cagaaagagg tttaatattt   2940
tttatgagac catcaaagag agaaagagaa taaaaatatt tttgtaaaac tttttttatg   3000
agaccatcaa agagagaaag agaataaaaa tatttttgta aaactttttt tatgagacca   3060
tcaaagagag aaagagaata aaaatatttt tgtaaaactt tttttatgag accatcaaag   3120
agagaaagag aataaaaata tttttgtaaa acttttttta tgagaccatc aaagagagaa   3180
agagaataaa aatatttttg taaaactttt tttatgagac catcaaagag agaaagagaa   3240
taaaaatatt tttgtaaaac tttttttatg agaccatcaa agagagaaag agaataaaaa   3300
tatttttgta aaactttttt tatgagacca tcaaagagag aaagagaata aaaatatttt   3360
tgtaaaactt tttttatgag accatcagaa agaggtttaa tatttttgtg ataccctgaa   3420
aggaaatagg aataggaata ggaatagtgt cataatcgta tcacactatt gagacagaaa   3480
aagaagaagt cgcgagaggt aactttttgt gaatgtagtt aagaacattt ttgttttgca   3540
aaccggaata tagtgtccgg tacacttttt taattcgtgg tgtgcctgaa tcgttcgatt   3600
aaccctactc atccaatttc agatgaatag agttatcgat tcagacacac gctttgagtt   3660
ttgttgaatc gatgagtgaa gtatcatcgg ttgcaccttc agatgccgat ccgtcgacat   3720
acttaaatcc atccttgacc tcaagttcag atgattcctt gcacatgtct ccgatacgaa   3780
cgctaaactc tagattcttg acacattttg tatcgacgat cgttgaaccg atgatatctt   3840
cgtaactcac tttcttatga gagatgttag acccgagtac tggatgggtc ttgatgtcgc   3900
tgtctttctc ttcttcgcta catctgatgt cgatagacac ctcacagtct ttgatcatag   3960
ccagagcttc ttcatgagtg atcgcgggag agtccttacc ttgtcctggg gacacgctgg   4020
acaatctagc attcactgtg tttccatcag cggattctga gatggattta atctgaggac   4080
atttggtgaa tccaaagttc attctcagac ctccaccgat gatggagtaa taagtggtag   4140
gaggatctac atcctcgact gatgtggaat catcttctga ttccacctcg ggatctggat   4200
ctgactcgga ctctgtaatt tccgttacgg attggcaaat cttatcattg gtcggtgttt   4260
ggtcttgctt tgtgactttg ataataacat cgattcccat atgatgtttg ttttcttctt   4320
ccgtacacga ggaggaggat gaggatgatt gctgaagact ggcaggcaca tgcatgccag   4380
gacgatatat tgtttcatga ttgctattga ttgagtactg ttctttatga ttctacttcc   4440
ttaccgtgca ataaattaga atatattttc tacttttacg agaaattaat tattgtattt   4500
attatttatg ggtgaaaaac ttactataaa aagcgggtgg gtttggaatt agtgatcagt   4560
ttatgtatat cgcaactacc gggcatatgg ctatcgacat cgagaacatt acccacatga   4620
taagagattg tatcagtttc gtagtcttga gtattggtat tactatatag tatatagatg   4680
tcgacgctag atagacagtc tccgaatgcg gcatgatacc gtcatcattc tttgctttcg   4740
ttaactgttt ggaggaaaaa tttttgttat tgcatttaat ctcgaaattc agagtgcaca   4800
cctttctcct gtaaagaaac ctgaagttgc taccttatta aggacggaga agtattcctc   4860
acgaaatacg ggattacagt ctttatgatt catagtaata gttagttccg acgttgagat   4920
ggattcgctg agaccggtag tggtcgttaa ctggatacag attaatttcc acatcgatat   4980
agttaaaggt attactgggt acgggttcgc atttatctgc ggaagagacg gtgtgagaat   5040
```

-continued

```
atgttccgag accacacgga gaacagatga cgtctccgga tactccgtat cctattccac   5100
attttgtttg ggaaacacat gccttgcatc cggatgatcc tttgagaaga caataatatc   5160
cgggagagca ttcacagatt ctattgtgag tcgtgttaca cggtcgcgtc ttccgttaca   5220
acttagacaa gcgggtaaat gattattgcg agatgtgaag gtacccgaac cacacggcgt   5280
acattgtgtg ttagtcttgc tatcgcataa tctggaagcg tatgttcccg gacacaaatt   5340
atggcgtttg tattcgttgt ctttacactt tccatcggat ggtgcatgcg gtgctatatc   5400
tcttccgttt attattatac atgagagaaa caatatatac gagtataata cggacttcat   5460
gatttaataa tgtagtaatc gtcgtcttgt tcctgtttcc tacttctcca atcatataga   5520
tattttcttt ctatcatgga taatatttgt aatggttctt ttcgtacaac atactgttta   5580
gatgatattg cgcataattt ccggaggcaa atacgatagt ctagattgac cgatggtaga   5640
ctctaattta ttgagtgctt tgtcgacgag tttactttta cgctccatcg atagatggca   5700
ctgttctatg agatcgtcgt acatgggaaa tgaaatgtga ctgtctgaat gtatggcttt   5760
aagatagctg tgataccgta tacaggtcgg tgtcggagat tcgaatctct ttaaggcgac   5820
ttatgtcacg atgatggaat ctatcttatc gaatgatata tttttcataa atacactttt   5880
atagtcctcg tttaaacaga atttactatg tagttccgcg aatgactcgt cccttaatag   5940
gcagtaggct attatcttct ttacgtagta atcgtcgtag ggagagacat cttgtagaac   6000
aacgatttaa tcataggtag agatactttc agtctgtggt ggatgatgtc attcacaaca   6060
tccgccttgt atatgatgtt tctgttttca aacaccaagt cgaataccgt ctttagtcgg   6120
aaggttgatg tcgtatccga tgtatgaggc aacattgttg ttacaatttt gaaaggcggt   6180
attatagtat tcgtctttct gaatgtcgaa cctatctagt agataccgta gtatattgag   6240
agtgtatcct tgattatgtt ttatgaatag ataaagtaga tgttgtcctt cttccttttg   6300
ttcgtgccaa ttgagtaaca ttatgagaat atgacctgtt gcacaatcgt tccatgatgg   6360
gtgtacaatc aagattatta cgtatcctcg tatcggctcc tcgagataaa agagcataca   6420
ccacacgagg actatgtttg gtatactgtt gaaggtaagt gtgtaaccgc gttaatgttt   6480
gctccataat ctattatcgc gtagatgaat cgcttctcgg ctcgcatctt agtgtgactt   6540
aacttgtaat aattgctttt gtagaacgtg gatatgtgtt tacagtagta atgaagagaa   6600
gtgagttcat cctcgtcgga tcctttgtac agaacgtaat agtttaagct cccattgaat   6660
ttatatctaa gataacacag caatagatcg gatgatttac taaagtcatc aatggtgtcc   6720
gttagtatat caaagatctt gttatcgatt gatagtggtg tcctttttca tccttgctat   6780
caaagttacg catgccgtgg tgtaacaata tctttaatac agatggatta aatcgtgtat   6840
tcatcgtata gcaatgtaat ggagagttac ctcgtttatt cagatcgcag tgtttaataa   6900
ctagcttaaa cagatgagac gatgtatcca catcaaagaa cgtgaaatac atatgacaga   6960
cattgttgac agaaacgtga ccttcattct taccgtcgtc cataaatacg ttaggtatgt   7020
accacatact gtcgcgaacg atgcgtacaa tctcgtccat ctcataatga tttacttttt   7080
cataattaaa gatgtgaaag aaaaacagaa caatatattt ttttagtaat gtttatgcga   7140
gacatataaa ataaactccg tgtttatgat catttttaac agcaacacat tcaatattgt   7200
attgttattt ttatattatt tacacaatta acaatatatt attagtttat attactgaat   7260
taataatata aaattcccaa tcttgtcata aacacacact gagaaacagc ataaacacaa   7320
aatccatcaa aaatgtcgat gaaatatctg atgttgttgt tcgctgctat gataatcaga   7380
```

-continued

```
tcattcgccg atagtggtaa cgctatcgaa acgacatcgc cagaaattac aaacgctaca   7440
acagatattc cagctatcag attatgcggt ccagagggag atggatattg tttacacggt   7500
gactgtatcc acgctagaga tattgacggt atgtattgta gatgctctca tggttataca   7560
ggcattagat gtcagcatgt agtattagta gactatcaac gttcagaaaa cccaaacact   7620
acaacgtcat atatcccatc tcccggtatt atgcttgtat tagtaggcat tattattatt   7680
acgtgttgtc tattatctgt ttataggttc actcgacgaa ctaaactacc tatacaagat   7740
atggttgtgc cataattttt ataaattttt ttatgagtat ttttacaaaa aaaatgtata   7800
aagtgtatgt cttatgtata tttataaaaa tgctaagtat gcgatgtatc tatgttattt   7860
gtatttatct aaacaatacc tctacctcta gatattatac aaaaattttt tatttcggca   7920
tattaaagta aaatctagtt accttgaaaa tgaatacagt gggtggttcc gtatcaccag   7980
taagaacata atagtcgaat acagtatccg attgagattt tgcatacaat actagtctag   8040
aaagaaattt gtaatcatct tctgtgacgg gagtccatat atctgtatca tcgtctagtt   8100
tatcagtgtc ccatgctata ttcctgttat catcattagt taatgaaaat aactctcgtg   8160
cttcagaaaa gtcaaatatt gtatccatac atacatctcc aaaactatcg cttatacgtt   8220
tatctttaac gatacctata cctagatggt tatttactaa cagacatttt ccagatctat   8280
tgactataac tcctatagtt tccacatcaa ccaagtaatg atcatctatt gttatataac   8340
aataacataa ctcttttcca tttttatcag tatgtatatc tatatcaacg tcgtcgttgt   8400
agtgaatagt agtcattgat ctattatatg aaacggatat gtctagaacg gcaattgttt   8460
tacgtccagt taacactttc tttgatttaa agtctagagt ctttgcaaac ataatatcct   8520
tatccgactt tatatttcct gtagggtggt ataattttat tttgcctcca catatcggtg   8580
tttccaaata tattactaga caatattcca tatagttatt agttaagggt acccaattag   8640
aacacgtacg cttattatca tcatttggat cgtatttcat aaaagttatt gtactatcga   8700
tgtcaacaca ttctacattt tttaatcgtc tatatagtat ttttctgata ttttctataa   8760
tatcagaatt gtcttccatc ggaagttgta tactatcgga atcagttaca tgtttaaata   8820
attctctgat gtcattcctt atacaatcaa attcattatt aaacagttta atagtctgta   8880
gacctttatc gtcgtaaata tccattgtct tattagttac gcttattttt atgtgtttta   8940
cgttgcttta ttatatttta taagaatgat tgtttgacga atcacgagaa ctattaagac   9000
acattattag gtatatatta taaaaaagtt tttgattacg atgttataag aggaaagagg   9060
acacattaac atcatacatc aattaactac attcttataa catcgtaatc aaaagaattg   9120
caattttgat gtataacaac tgtcaatggg ttatggaatt gtatattaca tattatacgg   9180
tatgttggta acgacaaata ccgatcggta attgtctgcc ggtgtaatag aattatatat   9240
atctatctat tacaccggct gagtatgcat aataataagt tgtggtagta tgatctccat   9300
atttataatt taggactttg tattcagtat ttttggaatc ataaaaaata aaaaaaagtt   9360
ttactaattt aaaatttaaa aagtatttac attttttca ctgtttagtc gcggatatgg   9420
aattcgatcc tgccaaaatc aatacatcat ctatagatca tgtaacaata ttacaataca   9480
tagatgaacc aaatgatata agactaacag tatgcattat ccgaaatatt aataacatta   9540
catattatat caatatcaca aaaataaata cacatttggc taatcaattt cgggcttgga   9600
aaaaacgtat cgccggaagg gactatatga ctaacttatc tagagataca ggaatacaac   9660
aatcaaaact tactgaaact atacgtaact gtcaaaaaaa tagaaacata tatggtctat   9720
atatacacta caatttagtt attaatgtgg ttattgattg gataaccgat gtgattgttc   9780
```

-continued

```
aatcaatatt aagagggttg gtaaattggt acatagctaa taatacctat acacccaata   9840
atacaacaac catttctgag ttggatatca tcaaaatact ggataaatac gaggacgtgt   9900
atagagtaag taaagaaaaa gaatgtggaa tttgctatga agttgtttac tcaaaacgat   9960
agatactttg gtttattgga ttcgtgtact catatatttt gcataacatg catcaatata  10020
tggcataaaa cacgaagaga aaccggtgcg tcggataatt gtcctatatg tcgtacccgt  10080
tttagaaaca taacaatgag caagttctat aagctagtta actaataaat aaaaagttta  10140
atttgttgac gacgtatgtc gttatttttc tcgtatgaaa gattaaattc aattcaattc  10200
gttgtttcta atataatctg ccgtattgga tggattctca agacaattgc atttagatta  10260
tattatcatg aataaaaata gtagcacgca ctacttcagc caaatattct tttttgaaac  10320
gccatctatc gtagtgagga cacaagtgaa cctataatta tcaaatttat tagtatcagt  10380
cacatgaagg actttctgta gagtgacgat tctaccatct atggtactaa cggtttcatc  10440
ctccttgata ccctcaccca aatgttctat aaatttagca tcctcgtccg atctcatatc  10500
ctttgccaac caatacatgt agctaaaatt aggcataaat ttcacacatc cagtgcaacg  10560
aaattctcca gaagatgtta cgatgtttag gttaggacat ttgatttcgt cggcattaac  10620
atatgggtga acacacccat acatgaaagc gatgagaaat aggattctca tcttgccaaa  10680
atatcactag aaaaaattta tttatcaatt ttaaaggtat aaaaaatact tattgttgct  10740
cgaatatttt gtatttgatg gtatacggaa gattagaaat gtaggtatta tcatcaactg  10800
attctatggt tttatgtatt ctatcatgtt tcactattgc gtcggaaata atatcatatg  10860
cttccacata tattttattt tgttttaact cataatactc acgtaattct ggattattgg  10920
catatctatg aataatttta gctccatgat cagtaaatat taatgagaac atagtattac  10980
cacctaccat tatttttttc atttcgttca attcttgatt gcaaagatct atataatcat  11040
tatagcgttg acttatggac tctggaatct tagacgatgt acagtcatct ataatcatgg  11100
catatttaat acattgtttt atagcatagt agttatctac gatgttagat atttctctca  11160
atgaatcaat cacacaatct aatgtaggtt tatgacataa tagcattttc agcagttcaa  11220
tgtttctaga ttcgttgatg gcaatggcta tacatgtata tccgttattt gatctaatgt  11280
tgacatctga accggattct agcagtaaag atactagaga ttgtttatta tatctaacag  11340
ccttgtgaag aagtgtttct cctcgtttgt caatcatgtt aatgtcttta agataaggta  11400
ggcaaatgtt tatagtacta agaattgggc aagcataaga catgtcacaa agaccctttt  11460
tgtatgtata agtgtaaaaa ttataacatt catagttgga tttacatagg tgtccaatcg  11520
ggatctctcc atcatcgaga taattgatgg catctccctt cctttttag tagatatttc  11580
atcgtgtaag aatcaatatt aatatttcta aagtattcgt gtatagcctc tttatttacc  11640
acagttccat attccactag agggatatcg ccgaatgtca tatactcaat tagtatatgt  11700
tggaggacat ccgagttcat tgttttcaat atcaaaaaga tggtttcctt atcatttctc  11760
catagtggta caatactaca cattattccg tgcggctttc cattttccaa aaacaatttg  11820
accaaatcta aatctacatc tttattgtat ctataatcac tatttagata atcagccata  11880
attactcgag tgcaacatgt tagatcgtct atatatgaat aagcagtgtt atctattcct  11940
ttcattaaca atttaacgat gtctatatct atatgagatg acttaatata atattgaaga  12000
gctgtacaat agtttttatc tatagaagac ggcttgattc cgtgattaat tagacattta  12060
acaacttccg gacgcacata tgctctcgta tccgactttg aatacagatg agagatgata  12120
```

-continued

```
tacagatgca atacggtacc gcaatttcgt agttgataat catcatacgc gtatcagtac  12180
tcgtcctcat aaagaacact gcagccattt tctatgaaca aatcaataat tttaggaaca  12240
ggatcattgt cattacataa ttttctataa ctgaacgatg gttttcacat ttaacactca  12300
agtcaaatcc atgttctacc aacaccttta tcaagtcaac gtctacattt ttggatttca  12360
tatagctgaa tatattaaag tcatttatgt tgctaaatcc agtggcttct agtagagcca  12420
tcgctatatc ctttaacttt aacatgtcta ctatttgtgt attcttctaa tggggtagct  12480
gtctccaatt tttgcgtaat ggattagtgc cactgtctag tagtagtttg acgacctcga  12540
cattattaca atgctcatta aaaaggtatg cgtgtaaagc attattcttg aattggttcc  12600
tggtatcatt aggatctctg tctctcaaca tctgtttaag ttcatcgaga gccacctcct  12660
cattttccag atagtcaaac attttgactg aatgagctac tgtgaactct atacacccac  12720
acaactaatg tcattaaata ttattttttt gaatgtattt ataccatgtc aaaaacttgt  12780
acaattatta ataaaaataa tttagtgttt aaattttacc agttccagat tttacacctc  12840
cgttaacccc actttttaca ccactggacg atcctcctcc ccacattcca ccgccaccag  12900
atgtataagt tttagatcct ttattactac catcatgtcc atggataaag acactccaca  12960
tgccgccact actacccccct ttagaagaca tattaataag acttaaggac aagtttaaca  13020
ataaaattaa tcacgagtac cctactacca acctacacta ttatatgatt atagtttcta  13080
tttttacagt accttaacta aagtctctag tcacaagagc aatactacca acctacacta  13140
ttatatgatt atagtttcta tttttatagg aacgcgtacg agaaaatcaa atgtctaatt  13200
tctaacggta gtgttgataa acgattatcg tcaatggata cctcctctat catgtcgtct  13260
atttcttac tttgttctat taacttatta gcattatata ttatttgatt ataaaactta  13320
tattgcttat tagcccaatc tgtaaatatc ggattattaa catatcgttt ctttgtaggt  13380
ttatttaaca tgtacatcac tgtaagcatg tccgtaccat ttattttaat ttgacgcata  13440
tccgcaattt ctttttcgca gtcggttata aattctatat atgatggata catgctacat  13500
gtgtacttat aatcgactaa tatgaagtac ttgatacata ttttcagtaa cgatttatta  13560
ttaccaccta tgaataagta cctgtgatcg tctaggtaat caactgtttt cttaatacat  13620
tcgatggttg gtaatttact cagaataatt tccaatatct taatatataa ttctgctatt  13680
tctgggatat atttatctgc cagtataaca caaatagtaa tacatgtaaa cccatatttt  13740
gttattatat taatgtctgc gccattatct attaaccatt ctactaggct gacactatgc  13800
gacttaatac aatgataaag tatactacat ccatgtttat ctattttgtt tatatcatca  13860
atatacggct tacaaagttt tagtatcgat aacacatcca actcacgcat agagaaggta  13920
gggaataatg gcataatatt tattaggtta tcatcattgt cattatctac aactaagttt  13980
ccatttttta aaatatactc gacaacttta ggatctctat tgccaaattt ttgaaaatat  14040
ttatttatat gcttaaatct atataatgta gctccttcat caatcataca tttaataaca  14100
ttgatgtata ctgtatgata agatacatat tctaacaata gatcttgtat agaatctgta  14160
tatcttttaa gaattgtgga tattaggata ttattacgta aactattaca caattctaaa  14220
atataaaacg tatcacggtc gaataatagt tgatcaacta tataattatc gattttgtga  14280
tttttcttcc taaactgttt acgtaaatag ttagatagaa tattcattag ttcatgacca  14340
ctatagttac tatcgaataa cgcgtcaaat atttcccgtt taatatcgca tttgtcaaga  14400
taataataga gtgtggtatg ttcacgataa gtataataac gcatctcttt tttgtgtgaa  14460
attaaatagt ttatcacgtc caaagatgta gcataaccat cttgtgacct agtaataata  14520
```

taataataga gaactgtttt acccattcta tcatcataat cagtggtgta gtcgtaatcg 14580
taatcgtcta attcatcatc ccaattataa tattcaccag cacgtctaat ctgttctatt 14640
ttgatcttgt atccatactg tatgttgcta catgtaggta ttcctttatc caataatagt 14700
ttaaacacat ctacattggg atttgatgtt gtagcgtatt tctctacaat attaatacca 14760
tttttgatac tatttatttc tataccctttc gaaattagta atttcaataa gtctatatcg 14820
atgttatcag aacatagata ttcgaatata tcaaaatcat tgatattttt atagtcgact 14880
gacgacaata acaaaatcac aacatcgttt ttgatattat tatttttctt ggtaacgtat 14940
gcctttaatg gagtttcacc atcatactca tataatggat ttgcaccact ttctatcaat 15000
gattgtgcac tgctggcatc gatgttaaat gttttacaac tatcatagag tatcttatcg 15060
ttaaccatga ttggttgttg atgctatcgc attttttggt ttctttcatt tcagttatgt 15120
atggatttag cacgtttggg aagcatgagc tcatatgatt tcagtactgt agtgtcagta 15180
ctattagttt cgatcagatc aatgtctaga tctatagaat caaaacacga taggtcagaa 15240
gataatgaat atctgtacgc ttctttttgt actgtaactt ctggttttgt tagatggttg 15300
catcgtgctt taacatcaat ggtacaaatt ttatcctcgc tttgtgtatc atattcgtct 15360
ctagtataaa attctatatt cagattatca tgcgatgtgt atacgctaac ggtatcaata 15420
aacggagcac accatttagt cataacagta atccaaaatt ttttaaagta tatcttaacg 15480
aaagaagttg tgtcattgtc tacggtgtat ggtactagat cctcataagt gtatatatct 15540
agagtaatgt ttaatttatt aaatggttga taatatggat cctcatgaca atttccgaag 15600
atggaaatga gatatagaca tgcaataaat ctaatcgaag acatggttac tccttaaaaa 15660
aatacgaata atcaccttgg ctatttagta agtgtcattt aacactatac tcatattaat 15720
ccatggactc ataatctcta tacgggatta acggatgttc tatatacggg gatgagtagt 15780
tttcttcttt aactttatac tttttactaa tcatatttag actgatgtat gggtaatagt 15840
gtttaaagag ttcgttctca tcatcagaat aaatcaatat ctctgttttt ttgttataca 15900
gatgtattac agcctcatat attacgtaat agaacgtgtc atctacctta ttaactttca 15960
ccgcatagtt gtttgcaaat acggttaatc ctttgacctc gtcgatttcc gaccaatctg 16020
ggcgtataat gaatctaaac tttaatttct tgtaatcatt cgaaataatt tttagtttgc 16080
atccgtagtt atcccctta tgtaactgta aatttctcaa cgcgatatct ccattaataa 16140
tgatgtcgaa ttcgtgctgt atacccatac tgaatggatg aactaacgaa tatcaacggc 16200
gttaatagta atttactttt tcatctttac atattgggta ctagttttac tatcataagt 16260
ttataaattc cacaagctac tatggaataa gccaaccatc ttagtatacc acacatgtct 16320
taaagtttat taattaatta catgttgttt tatatatatc gctacgaatt taaagagaaa 16380
tcagtttagg aagaaaaaaa ttatctatct acatcatcac gtctctgtat tctacgatag 16440
agtgctactt taagatgaga catatccgtg tcatcaaaaa tatactccat taaaatgatt 16500
attccggcag cgaacttgat attggatata tcacaacctt tgttaatatc tacgacaata 16560
gacagcagtc ccatggttcc ataaacagtg agtttatctt tctttgaagc gatagtttgt 16620
agagatctta taaaaccgtc aaacgacatc gcatttatat ctttagctaa ttcatatatg 16680
ttaccatcgt aatatctaac cgcgtctatc ttaaacgttt ccatcgcttt aaagacgttt 16740
ccgatagatg gtctcatttc atcagtcata ctgagccaac aaatataatc gtgtataaca 16800
tctttgatag aatcagactc taaagaaaac gaatcggctt tattatacgc attcatgata 16860

-continued

```
aacttaatga aaaatgtttt tcgttgttta agttggatga atagtatgtc ttaataattg  16920
ttattatttc attaattaat atttagtaac gagtacactc tataaaaacg agaatgacat  16980
aactagttat caaagtgtct aggacgcgta attttcatat ggtatagatc ctgtaagcat  17040
tgtctgtatt ctggagctat tttctttatc gcattagtaa gttcagaata tgttataaat  17100
ttaaatcgaa taacgaacat gactttagta aagtcgtcta tattaactct tttattttct  17160
agccatcgta ataccatgtt taagatagta tattctctag ttactacgat ctcatcgttg  17220
tctagaatat cacatactga atctacatcc aattttagaa attggtctgt gttacatatc  17280
tcttctatat tattgttgat gtattgtcgt agaaaactat tacgtagacc attttcttta  17340
taaaacgaat atatagtact ccaattatct ttaccgatat atttgcacac ataatccatt  17400
ctctcaatca ctacatcttt aagattttcg ttgttaagat atttggctaa actatataat  17460
tctattagat catcaacaga atcagtatat atttttctag atccaaagac gaactctttg  17520
gcgtcctcta taatattccc agaaaagata ttttcgtgtt ttagtttatc gagatctgat  17580
ctgttcatat acgccatgat tgtacggtac gttatgataa ccgcataaaa taaaaatcca  17640
ttttcatttt taaccaatac tattcataat tgagattgat gtaatacttt gttactttga  17700
acgtaaagac agtacacgga tccgtatctc caacaagcac gtagtaatca aatttggtgt  17760
tgttaaactt cgcaatattc atcaatttag atagaaactt atactcatca tctgttttag  17820
gaatccatgt attattacca ctttccaact tatcattatc ccaggctatg tttcgtccat  17880
catcgttgcg cagagtgaat aattcttttg tattcggtag ttcaaatata tgatccatgc  17940
atagatcggc aaagctattg tagatgtgat tttcctaaa tctaatataa aactcgttta  18000
ctagcaaaca ctttcctgat ttatcgacca agacacatat ggtttctaaa tctatcaagt  18060
ggtggggatc catagttatg acgcagtaac atagattatt acattcttga ctgtcgctaa  18120
tatctaaata tttattgtta tcgtattgga ttctgcatat agatggcttg tatgtcaaag  18180
atatagaaca cataaccaat ttatagtcgc gctttacatt ctcgaatcta aagttaagag  18240
atttagaaaa cattatatcc tcggatgatg ttatcactgt ttctggagta ggatatatta  18300
aagtctttac agatttcgtc cgattcaaat aaatcactaa ataatatccc acattatcat  18360
ctgttagagt agtatcatta aatctattat attttatgaa agatatatca ctgctcacct  18420
ctatatttcg tacattttta aactgtttgt ataatatctc tctgatacaa tcagatatat  18480
ctattgtgtc ggtagacgat accgttacat ttgaattaat ggtgttccat tttacaactt  18540
ttaacaagtt gaccaattca tttctaatag tatcaaactc tccatgatta aatattttaa  18600
tagtatccat tttatatcac tacggacaca aagtagctga cataaaccat tgtataattt  18660
ttatgtttta tgtttattag cgtacacatt ttggaagttc cggcttccat gtatttcctg  18720
gagagcaagt agatgatgag gaaccagata gtttatatcc gtacttgcac ttaaagtcta  18780
cattgtcgtt gtatgagtat gatcttttaa acccgctaga caagtatccg tttgatattg  18840
taggatgtgg acatttaaca atctgacacg tgggtggatc ggaccattct cctcctgaac  18900
acaggacacc agagttacca atcaacgaat atccactatt gcaactataa gttacaacgc  18960
tcccatcggt ataaaaatcc tcgtatccgt tatgtcttcc gttggatata gatggagggg  19020
attggcattt aacagattca caaataggtg cctcgggatt ccataccata gatccagtag  19080
atcctaattc acaatacgat ttagattcac cgatcaaatg atatccgcta ttacaagagt  19140
acgttatact agagccaaag tctactccac caatatcaag ttggccatta tcgatatctc  19200
gaggcgatgg gcatctccgt ttaatacatt gattaaagag tgtccatcca gtacctgtac  19260
```

atttagcata tataggtccc attttttgct ttctgtatcc aggtagacat agatattcta 19320
tagtgtctcc tatgttgtaa ttagcattag catcagtctc cacactattc ttaaatttca 19380
tattaatggg tcgtgacgga atagtacagc atgatagaac gcatcctatt cccaacaatg 19440
tcaggaacgt cacgctctcc accttcatat ttatttatcc gtaaaaatgt tatcctggac 19500
atcgtacaaa taataaaaag cccatatatg ttcgctattg tagaaattgt ttttcacagt 19560
tgctcaaaaa cgatggcagt gacttatgag ttacgttaca ctttggagtc tcatctttag 19620
taaacatatc ataatattcg atattacgag ttgacatatc gaacaaattc caagtatttg 19680
attttggata atattcgtat tttgcatctg ctataattaa gatataatca ccgcaagaac 19740
acacgaacat ctttcctaca tggttaaagt acatgtataa ttctatccat ttgtcttcct 19800
taactatata tttgtataga taattacgag tctcgtgagt aattccagta attacataga 19860
tgtcgccgtc gtactctaca gcataaacta tactatgatg tctaggcatg ggagactttt 19920
ttatccaacg atttttagtg aaacattcca catcgtttaa tactacatat ttttcatacg 19980
tggtataaac tccacccatt acatatatat catcgtttac gaataccgac gcgcctgaat 20040
atctaggagt aattaagttt ggaagtctta tccatttcga agtgccgtgt ttcaaatatt 20100
ctgccacacc cgttgaaata gaaaattcta atcctcctat tacatataac tttccatcgt 20160
taacacaagt actaacttct gattttaacg acgacatatt agtaaccgtt ttccattttt 20220
tcgtttcaag atctacccgc gatacggaat aaacatgtct attgttaatc atgccgccaa 20280
taatgtatag acaattatgt aaaacatttg cattatagaa ttgtctatct gtattaccga 20340
ctatcgtcca atattctgtt ctaggagagt aatgggttat tgtggatata taatcagagt 20400
ttttaatgac tactatatta tgttttatac catttcgtgt cactggcttt gtagatttgg 20460
atatagttaa tcccaacaat gatatagcat tgcgcatagt attagtcata aacttgggat 20520
gtaaaatgtt gatgatatct acatcgtttg gatttttatg tatccacttt aataaatatca 20580
tagctgtaac atcctcatga tttacgttaa cgttttcgtg ggataagata gttgtcagtt 20640
catcctttga taattttcca aattctggat cggatgtcac cgcagtaata ttgttgatta 20700
tttctgacat cgacgcatta tatagttttt taattccata tcttttagaa aagttaaaca 20760
tccttataca atttgtggaa ttaatattat gaatcatagt ttttacacat agatctacta 20820
caggcggaac atcaattatt atggcagcaa ctagtatcat ttctacattg tttatggtga 20880
tgtttatctt cttccagcgt atatagtcta atagcgattc aaacgcgtga tagtttatac 20940
cattcaatat aatcgcttca tcctttagat ggtgatcctg aattcgttta aaaaaattat 21000
acggagatgc cgtaataatt tccttattca cttgtataat ttccccattg atagaaaata 21060
tcacgctttc cattcttgaa gtactataag taattatagt ataatgtaaa ggtttatata 21120
ttcaatattt tttataaaaa aatcattttg acattaattc ctttttaaat ttccgtctat 21180
catctataga aacgtattct atgaatttat aaaatgcttt tacgtgtcct atcgtaggcg 21240
atagaaccgc taaaaagcct atcgaatttc tacaaaagaa tctgttatat ggtataggga 21300
gagtataaaa cattaaatgt ccgtacttat taaagtattc agtagccaat cctaactctt 21360
tcgaatactt attaatggct cttgttctgt acgaatctat ttttttgaac aacggaccta 21420
gtggtatatc ttgttctatg tatctaaaat aatgtctgac tagatccgtt agtttaatat 21480
cctcagtcat cttgtctaga atggcaaatc taactgcggg tttaggcttt agtttagttt 21540
ttatatctac atctatgtct ttatctaaca ccaaaaatat aatagctaat attttattac 21600

-continued

```
aatcatccgg atattcttct acgatctcac taactaatgt ttctttggtt atactagtat  21660
agtcactatc ggacaaataa agaaaatcag atgatcgatg aataatacat ttaaattcat  21720
catctgtaag atttttgaga tgtctcatta aaatattatt agggtcagta ctcattatca  21780
ttcggcagct attacttatt ttatttttct gtattttatt atttttcacc atatagatca  21840
atcattagat catcaaaata tgtttcaatc atcctaaaga gtatggtgaa tgactcttcc  21900
catctaattt ctgaacgttc accaatgtct ctagccactt tggcactaat agcgatcatt  21960
cgcttagcgt cttctatatt attaactggt tgattcaatc tatctagcaa tggaccgtcg  22020
gacagcgtca ttctcatgtt cttaatcaat gtacatacat cgccgtcatc taccaattca  22080
tccaacaaca taagcttttt aaaatcatca ttataatagg tttgatcgtt gtcatttctc  22140
caaagaatat atctaataag tagagtcctc atgcttagta atttaactat tttagttaac  22200
aactattttt tatgttaaat caattagtac accgctatgt ttaatactta ttcatatttt  22260
agtttttagg attgagaatc aatacaaaaa attaatgcat cattaatttt agaaatactt  22320
agtttccacg tagttaatga aacatttgaa ctcatcgtac aggacgttct cgtacaggac  22380
gtaactataa accggtttat atttgttcaa gatagataca aatccgataa cttttttttac  22440
gaattctacg ggatccactt taaaagtgtc ataccgggtt ctttttattc ttttaaacag  22500
atcaatggtg tgatgttgat taggtctttt acgaatttga tatagaatag cgttcacata  22560
tcctccataa tggtcaatcg ccatttgttc gtatgtcata aattctttaa ttatatgaca  22620
ctgtgtatta tttagttcat ccttgttcat cattaggaat ctatccaaaa tggcaattat  22680
actagaacta taggtgcgtt gtatacacat attgatgtgt ctgtttatac aatccatgat  22740
atttggatcc atgctactac cttcgggtaa aattgtagca tcatatacca tttctagtac  22800
tttaggttca ttattatcca ttgcagagga cgtcatgatc gaatcctaaa aaaatatatt  22860
atttttatgt tattttgtta aaaataatca tcgaatactt cgtaagatac tccttcatga  22920
acataatcag ttacaaaacg tttatatgaa gtaaagtatc tacgattttt acaaaagtcc  22980
ggatgcataa gtacaaagta cgcgataaac ggaataataa tagatttatc tagtctatct  23040
ttttctatag ctttcatagt tagatacatg gtctcagaag taggattatg taacatcagc  23100
ttcgataaaa tgactgggtt atttagtctt acacattcgc tcatacatgt atgaccgtta  23160
actacaaagt ctacactaaa atgattgaac aatagatagt ctaccattgt ttcgtattca  23220
gatagtacag cgtagtacat agcatcttca caaattatat cattgtctaa tagatatttg  23280
acgcatctta tggatcccac ttcaacagcc atcttaaaat cggtagaatc atattgcttt  23340
cctttatcat taataatttc taaaacatca tctctatcat aaaagataca aatattaact  23400
gtttgatccg taataacatt gctagtcgat agcaatttgt taataagatg cgctgggctc  23460
aatgtcttaa taagaagtgt aagaggacta tctccgaatt tgttttgttt attaacatcc  23520
gttgatggaa gtaaaagatc tataatgtct acattcttga ctgttttaga gcatacaata  23580
tggagaggtg tatttccatc atgatctggt tttgagggac taattcctag tttcatcatc  23640
catgagattg tagaagcttt tggattgtct gacataagat gtctatgaat atgatttttg  23700
ccaaatttat ccactatcct ggcttcgaat ccgatggaca ttattttttt aaacactctt  23760
tctgaaggat ctgtacacgc caacaacgga ccacatcctt cttcatcaac cgagttgtta  23820
atcttggctc catactgtac caataaattt attctctcta tgacttcatc atctgttccc  23880
gagagataat atagaggtgt tttattatgt ttatcacacg cgtttggatc tgcgccgtgc  23940
gtcagcagca tcgcgactat tctattatta ttaattttag aagctatatg caatggataa  24000
```

```
tttccatcat catccgtctc atttggagag tatcctctat gaagaagttc ttcgacaaat  24060
cgttcatcta gtcctttaat tccacaatac gcatgtagaa tgtgataatt atttccagaa  24120
ggttcgatag cttgtagcat attcctaaat acatctaaat ttttactatt atatttggca  24180
taaagagata gataatactc ggccgacata atgttgtcca ttgtagtata aaaattaata  24240
tttctatttc tatttctgta tatttgcaac aatttactct ctataacaaa tatcataact  24300
tagttctttt atgtcaagaa ggcactggtt tagttcatct ataaatgtca cgccataact  24360
accacgcatg ctatactcag aattatgata aagatattta tccttggggt gtaggtaatg  24420
gggattaatc tttgttggat cagtctctaa gttaacacat gtcacacatg atccatttat  24480
agttatatca cacgatgatg atttatgaat tgattccgga agatcgctat cgtattttgt  24540
ggttccacaa ttcatttcca tacatgttat tgtcacacta atattatgat gaactttatc  24600
tagccgctga gtggtaaaca acagaacaga tagtttatta tctttaccaa caccctcagc  24660
cgctgccaca aatctctgat ccgtatccat gatggtcatg tttatttcta gtccgtatcc  24720
agtcaacact atgttagcat ttctgtcgat atagctttca ctcatatgac actcaccaat  24780
aatagtagaa ttaatgtcgt aatttacacc aatagtgagt tcggcggcaa agtaccaata  24840
ccggtaatct tgtcgaggag gacatatagt attcttgtat tctaccgaat acccgagaga  24900
tgcgatacaa aagagtaaga ctaatttgta aaccatctta ctcaaaatat gtaacaatag  24960
tacgatgcaa tgagtaagac aataggaaat ctatcttata tacacataat tattctatca  25020
attttaccaa ttagttagtg taatgttaac aaaaatgtgg gagaatctaa ttagtttttc  25080
tttacacaat tgacgtacat gagtctgagt tccttgtttt tgctaattat ttcatccaat  25140
ttattattct tgactatatc gagatctttt gtataggagt cagacttgta ttcaacatgc  25200
ttttctataa tcattttagc tatttcggca tcatccaata gtacattttc cagattagca  25260
gaatagatat taatgtcgta tttgaacaga gcctgtaaca tctcaatgtc tttattatct  25320
atagccaatt taatgtccgg aatgaagaga agggaattat tggtgtttgt cgacgtcata  25380
tagtcgagca agagaatcat catatccacg tgtccatttt ttatagtgat gtgaatacaa  25440
ctaaggagaa tagccagatc aaaagtagat ggtatctctg aaagaaagta ggaaacaata  25500
cttacatcat taagcatgac ggcatgataa aatgaagttt tccatccagt tttcccatag  25560
aacatcagtc tccaattttt cttaacaaac agttttaccg tttgcatgtt accactatca  25620
accgcataat acaatgcggt gtttcccttg tcatcaaatt gtgaatcatc cagtccactg  25680
aatagcaaaa tctttactat tttggtatct tccaatgtgg ctgcctgatg taatggaaat  25740
tcattctcta gaagattttt caatgctcca gcgttcaaca acgtacatac tagacgcacg  25800
ttattatcag ctattgcata atacaaggca ctatgtccat ggacatccgc cttaaatgca  25860
tctttgctag agagaaagct tttcagctgc ttagacttcc aagtattaat tcgtgacaga  25920
tccatgtctg aaacgagacg ctaattagtg tatatttttt catttttat aattttgtca  25980
tattgcacca gaattaataa tatctctaat agatctgatt agtagataca tggctatcgc  26040
aaaacaacat atacacattt aataaaaata atatttatta agaaaattca gatttcacgt  26100
acccatcaat ataaataaaa taatgattcc ttacaccgta cccatattaa ggagattcca  26160
ccttacccat aaacaatata aatccagtaa tatcatgtct gatgatgaac acaaatggtg  26220
tattaaattc cagtttttca ggagatgatc tcgccgtagc taccataata gtagatgcct  26280
ctgctacagt tccttgttcg tcgacatcta tctttgcatt ctgaaacatt ttataaatat  26340
```

-continued

```
ataatgggtc cctagtcata tgtttaaacg acgcattatc tggattaaac atactaggag  26400
ccatcatttc ggctatcgac ttaatatccc tcttattttc gatagaaaat ttagggagtt  26460
taagattgta cactttattc cctaattgaa acgaccaata gtctaatttt gcagccgtaa  26520
tagaatctgt gaaatgggtc atattatcac ctattgccag gtacatacta atattagcat  26580
ccttatacgg aaggcgtacc atatcatatt cttcgtcatc gattgtgatt gtatttcctt  26640
gcaatttagt aactacgttc atcatgggaa ccgttttcgt accgtactta ttagtaaaac  26700
tagcattgcg tgttttagtg atatcaaacg gatattgcca tataccttta aaatatatag  26760
tattaatgat tgcccataga gtattattgt cgagcatatt agaatctact acattagaca  26820
taccggatct acgttctact atagaattaa ttttattaac cgcatctcgt ctaaagttta  26880
atctatatag gccgaatcta tgatattgtt gataatacga cggtttaatg cacacagtat  26940
tatctacgaa actttgataa gttagatcag tgtacgtata tttagatgtt ttcagcttag  27000
ctaatcctga tattaattct gtaaatgctg gacccagatc tctttttctc aaatccatag  27060
tcttcaataa ttctattcta gtattacctg atgcaggcaa tagcgacata aacatagaaa  27120
acgaataacc aaacggtgag aagacaatat tatcatcttg aatattttta tacgctacta  27180
taccggcatt ggtaaatcct tgcagacgat aggtagacac tgaacacgtt aacgatagta  27240
tcaataacgc aatcatgatt ttatggtatt aataattaac cttattttta tgttcggtat  27300
aaaaattatt gatgtctaca catccttttg taattgacat ctatatatcc ttttgtataa  27360
tcaactctaa tcactttaac ttttacagtt ttccctacca gtttatccct atattcaaca  27420
tatctatcca tatgcatctt aacactctct gccaagatag cttcaaagtg aggatagtca  27480
aaaagataaa tatatagagc ataatccttc tcgtatactc tgccctttat tacatcaccc  27540
gcattgggca acgaataaca aaatgcaagc atcttgttaa cgggctcgta aattgggata  27600
aaaattatgt ttttatatct attttattca agagaatatt caggaatttc tttttccggt  27660
tgtatctcat cgcagtatat atcatttgta cattgtttca tattttttaa tagtctacac  27720
cttttagtag gactagtatc gtacaattca tagctgtatt ttgaattcca atcacgcata  27780
aaaatatctt ccaattgttg acgaagacct aatccatcat ccggtgtaat attaatagat  27840
gctccacatg tatccgtaaa gtaatttcct gtccaatttg aggtacctat atacgccgtt  27900
ttatcggtta ccatatattt ggcatggttt accctagaat acggaatggg aggatcagca  27960
tctggtacaa taaatagctt tacttctata tttatgtttt tagattttag catagcgata  28020
gatcttaaaa agtttctcat gataaacgaa gatcgttgcc agcaactaat caatagctta  28080
actgacactt gtctgtctat agcggctctt cttaattcat cttctatata aggccaaaac  28140
aaaatattgc ctgccttcga ataaataata gggataaagt tcataacaga tacataaacg  28200
aatttactcg catttctgat acatgacaat aaagcggtta aatcattggt tctttccata  28260
gtacatagtt gttgcggtgc agaagcaata aatacagagt gtggaacgcc gcttacgtta  28320
atactaagag gatgatctgt attatataatac gacggataaa agtttttcca attatatggt  28380
agattgttaa ctccaagata ccagtatacc tcaaaaattt gagtgagatc cgctgccaag  28440
ttcctattat tgaagatcgc aatacccaat tctttgacct gagttagtga tctccaatcc  28500
atgttagcgc ttcctaaata aatatgtgta ttatcagata tccaaaattt tgtatgaaga  28560
actcctccta ggatatttgt aatatctatg tatcgtactt caactccggc catttgtagt  28620
ctttcaacat cctttaatgg tttgttagat ttattgacgg ctactctaac tcgtactcct  28680
cttttgggta attgtacaat cttgtttaat attatcgtgc cgaaattcgt acccacttca  28740
```

tccgataaac tccaataaaa agatgatata tctagtgttt ttgtggtatt ggatagaatt 28800
tccctccaca tgttaaatgt agacaaatat actttatcaa attgcatacc tataggaata 28860
gtctctgtaa tcactgcgat tgtattatcc ggattcattt tatttgttaa aagaataatc 28920
ctatatcact tcactctatt aaaaatccaa gtttctattt ctttcatgac tgattttttta 28980 acttcatccg tttccttatg aagatgatgt ttggcacctt cataaatttt tatttctcta 29040
ttacaatttg catgttgcat gaaataatat gcacctaaaa catcgctaat cttattgttt 29100
gttccctgga gtatgagagt cggggggtgt taatcttgga aattattttt ctaaccttgt 29160
tggtagcctt caagacctga ctagcaaatc cagccttaat tttttcatga ttgattaatg 29220
ggtcgtattg gtatttataa actttatcca tatctctaga tactgattct ggacatagct 29280
ttccgactgg cgcatttagt gtgatggttc ccataagttt ggcagctagc agattcagtt 29340
ttgaaacagc atctgcatta actagaggag acattagaat cattgctgta aacaagtttg 29400
gattatcgta agaggctagc tcccatggaa tgacccaata agtagattta atagttacca 29460
cgtgctgtac caaagtcatc aatcatcatt ttttcaccat tacttcttcc atgtccaata 29520
tgatcatgtg agaatactaa aattcctaac gatgatatgt tttcagctag ttcgtcataa 29580
cgtccagaat gtttaccagc tccatgactt atgaatacta atgccttagg atatgtaata 29640
ggtttccaat atatgtaatc attgtccaga ttgaacatac agtttgcact catgattcac 29700
gttatataac tatcaatatt aacagttcgt ttgatgatca tattattttt atgttttatt 29760
gataattgta aaaacataca attaaatcaa tatagaggaa ggagacggct actgtctttt 29820
gtgagatagt catggcgact aaattagatt atgaggatgc tgttttttac tttgtggatg 29880
atgataaaat atgtagtcgc gactccatca tcgatctaat agatgaatat attacgtgga 29940
gaaatcatgt tatagtgttt aacaaagata ttaccagttg tggaagactg tacaaggaat 30000
tgatgaagtt cgatgatgtc gctatacggt actatggtat tgataaaatt aatgagattg 30060
tcgaagctat gagcgaagga gaccactaca tcaattttac aaaagtccat gatcaggaaa 30120
gtttattcgc taccatagga atatgtgcta aaatcactga acattgggga tacaaaaaga 30180
tttcagaatc tagattccaa tcattgggaa acattacaga tctgatgacc gacgataata 30240
taaacatctt gatacttttt ctagaaaaaa aattgaattg atgatatagg ggtcttcata 30300
acgcataatt attacgttag cattctatat ccgtgttaaa aaaaattatc ctatcatgta 30360
tttgagagtt ttatatgtag caaacatgat agctgtgatg ccaataagct ttagatattc 30420
acgcgtgcta gtgttaggga tggtattatc tggtggtgaa atgtccgtta tataatctac 30480
aaaataatca tcgcatatag tatgcgatag tagagtaaac atttttatcg tttctactgg 30540
gttcatacat cgtctaccca attcggttat aaatgaaatt gtcgccaatc ttacacccaa 30600
ccccttgtta tccattagta tagtattaac ttcgttattt atgtcataaa ctgtaaatga 30660
ttttgtagat gccatatcat acatgatatt catgtcccta ttataatcat tactaacttt 30720
atcacaatat atgttgataa tatctatata tgatctagtc tttgtgggca actgtctata 30780
caagtcgtct aaacgttgtt tactcatata gtatcgaaca gccatcatta catggtcccg 30840
ttccgttgat agataatcga gtatgttagt ggacttgtca aatctatata ccatattttc 30900
tggaagtgga tatacatagt cgtgatcaac attattgcta gcctcatctt ctatatcctg 30960
tactatacca ttatctatat catctacata atctacgata ttattacaca taaacatcga 31020
caacatacta ttgtttatta tctaagtcct gttgatccaa acccttgatc tcctctattt 31080

-continued

```
gtactatcta gagattgtac ttcttccagt tctggataat atatacgttg atagattagc  31140
tgagctattc tatctccagt atttacatta aacgtacatt ttccattatt aataagaatg  31200
actcctatgt ttcccctata atcttcgtct attacaccgc ctcctatatc aatgcctttt  31260
agggacagac cagacctagg agctattcta ccatagcaga acttaggcat ggacatacta  31320
atatctgtct taattaactg tcgttctcct ggagggatag tataatcgta agcgctatat  31380
aaatcatatc cggcggcgta aggtgattgc ctagtaggag atttagctct gttagtttcc  31440
ttaacaaatc taactggtga gttaatattc atgttgaaca taaaactaat attttatttc  31500
aaaattattt accatcccat atattccatg aataagtgtg atgattgtac acttctatag  31560
tatctatata cgattcacga taaaatcctc ctatcaatag cagtttatta tccactatga  31620
tcaattctgg attatccctc ggataaatag gatcatctat cagagtccat gtattgctgg  31680
attcacaata aaattccgca tttctaccaa ccaagaataa ccttctaccg aacactaacg  31740
cgcatgattt ataatgagga taataagtgg atggtccaaa ctgccactga tcatgattgg  31800
gtagcaaata ttctgtagtt gtatcagttt cagaatgtcc tcccattacg tatataacat  31860
tgtttatgga tgccactgct ggattacatc taggtttcag aagactcggc atattaaccc  31920
aagcagcatc cccgtggaac caacgctcaa cagatgtggg atttggtaga cctcctacta  31980
cgtataattt attgttagcg ggtatcccgc tagcatacag tctggggcta ttcatcggag  32040
gaattggaat ccaattgttt gatatataat ttaccgctat agcattgtta tgtatttcat  32100
tgttcatcca tccaccgatg agatatacta cttctccaac atgagtactt gtacacatat  32160
ggaatatatc tataatttga tccatgttca taggatactc tatgaatgga tacttgtatg  32220
atttgcgtgg ttgtttatca caatgaaata ttttggtaca gtctagtatc cattttacat  32280
tatttatacc tctgggagaa agataatttg acctgattac atttttgata aggagtagca  32340
gatttcctaa tttatttctt cgctttatat accacttaat gacaaaatca actacataat  32400
cctcatctgg aacatttagt tcatcgcttt ctagaataag tttcatagat agataatcaa  32460
aattgtctat gatgtcatct tccagttcca aaaagtgttt ggcaataaag tttttagtat  32520
gacataagag attggatagt ccgtattcta tacccatcat gtaacactcg acacaatatt  32580
cctttctaaa atctcgtaag ataaagttta tacaagtgta gatgataaat tctacagagg  32640
ttaatataga agcacgtaat aaattgacga cgttatgact atctatatat acctttccag  32700
tatacgagta aataactata gaagttaaac tgtgaatgtc aaggtctaga caaacccttg  32760
taactggatc tttatttttc gtgtattttt gacgtaaatg tgtgcgaaag taaggagata  32820
actttttcaa tatcgtagaa ttgactatta tattgccacc tatagcatca ataattgttt  32880
tgaatttctt agtcatagac aatgctaata tattcttaca gtacacagta ttaacaaata  32940
tcggcattta tgtttcttta aaagtcaaca tctaaagaaa aatgattatc ttcttgagac  33000
ataactccca ttttttggta ttcacccaca cgtttttcga aaaaattagt ttttccttcc  33060
aatgatatat tttccatgaa atcaaacgga ttggtaacat tataaatttt tttaaatccc  33120
aattcagaaa tcaatctatc cgcgacgaat tctatatatg ttttcatcat ttcacaattc  33180
attcctataa gtttaactgg aagagccgca gtaagaaatt cttgttcaat ggataccgca  33240
tctgttataa tagatctaac ggtttcttca ctcggtggat gcaataaatg tttaaacatc  33300
aaacatgcga aatcgcagtg cagaccctcg tctctactaa ttagttcgtt ggaaaacgtg  33360
agtccgggca ttaggccacg ctttttaagc caaaatatgg aagcgaatga tccagaaaag  33420
aagattcctt ctactgcagc aaaggcaata agtctctctc cataaccggc gctgtcatgt  33480
```

-continued atccactttt gagcccaatc ggccttcttt tttacacaag gcatcgtttc tatggcatta 33540
aagagatagt ttttttcatt actatcttta acataagtat cgatcaaaag actatacatt 33600
tccgaatgaa tgttttcaat ggccatctga aatccgtaga aacatctagc ctcggtaatc 33660
tgtacttctg tacaaaatcg ttccgccaaa ttttcattca ctattccgtc actggctgca 33720
aaaaacgcca atacatgttt tataaaatat ttttcgtctg gtgttagttt attccaatca 33780
ttgatatctt tagatatatc tacttcttcc actgtccaaa atgatgcctc tgccttttta 33840
tacatgttcc agatgtcata atattggatt gggaaaataa caaatctatt tggatttggt 33900
gcaaggatgg gttccataac taaattaaca ataacaataa atttttttc agttatctat 33960
atgcctgtac ttggatcttt tgtacatcga tatcgccgca atcactacaa taattacaag 34020
tattattgat agcattgtta ttagtactat cataattaaa ttatcgacat tcatgggtgc 34080
tgaataatcg ttattatcat cattatcatt ttgtaattgt gacatcatac tagataaatc 34140
gtttgcgaga ttgttgtggg aagcgggcat ggaggatgaa ttatcgttat tattatttaa 34200
cgcctcccat tcggattcac aaatgttacg cacattcaac attttatgga aactataatt 34260
ttgtgaaaac agataacaag aaaactcgtc atcgttcaaa tttttaacga tagtaaaccg 34320
attaaacgtc gagctaattt ctaacgctag cgactctgtt ggatatgggt ttccagatat 34380
atatcttttc agttccccta cgtatctata atcatctgta ggaaatggaa gatatttcca 34440
tttatctact gttcctaata tcatatgtgg tggtgtagta gaaccattaa gcgcgaaaga 34500
tgttatttcg catcgtattt taacttcgca ataatttctg gttagataac gcactctacc 34560
agtcaagtca atgatattag cctttacaga tatattcata gtagttgtaa cgatgactcc 34620
atcttttaga tgcgatactc ctttgtatgt accagaatct tcgtaccgca aactcgatat 34680
atttaaacaa gttaatgaga tattaacgcg ttttatgaat gatgatatat aaccagaagt 34740
tttatcctcg gtggctagcg ctataacctt atcattataa taccaactag tgtgattaat 34800
atgtgacacg ttagtgtggg tacaaatatg tacattatcg tctacgtcgt attcgataca 34860
tccgcataca gccaacaaat ataaaatgac aaatactcta acgccgttcg tacccatctt 34920
gatgcggttt aataaatgtt ttgatttcaa tttattgtaa aaaaagattc ggttttatac 34980
tgttcgatat tctcattgct tatattttca tctatcatct ccacacagtc aaatccgtgg 35040
ttagcatgca cctcatcaac cggtaaaaga ctatcggact cttctatcat tataactcta 35100
gaatatttaa tttggtcatt attaatcaag tcaattatct tatttttaac aaacgtgagt 35160
atttactca tttttataa aaacttttag aaatatacag actctatcgt gtgtctatat 35220
cttcttttta tatccaatgt atttatgtct gatttttctt catttatcat atataatggt 35280
ccaaattcta cacgtgcttc ggattcatcc agatcattaa ggttcttata attgtaacat 35340
ccttctcttc cctcttctac atcttccttc ttattcttat tcttagcgtc acagaatcta 35400
ccacagcagg atcccatgac gagcgtcata ttaaactaat ccattttcaa ttataatata 35460
cgattagtaa tgaccattaa aataaaaaat attcttcata accggcaaga aagtgaaaag 35520
ttcacattga aactatgtca gtagtataca tcatgaaatg atgatatata tatactctat 35580
tttggtggag gattatatga tataattcgt ggataatcat tcttaagaca catttcttca 35640
ttcgtaaatc ttttcacgtt aaatgagtgt ccatattttg caatttcttc atatgatggc 35700
ggtgtacgtg gacgaagctg ctcctgttct tgttgtagtc gccgactgtc gtgtttgcgt 35760
ttagatccct ccattatcgc gattgcgtag atggagtact attatatacc ttgtaattaa 35820

-continued

```
atttttttat taattaaacg tataaaaacg ttccgtatct gtatttaaga gccagatttc  35880
gtctaataga acaaatagct acagtaaaaa taactagaat aattgctaca cccactagaa  35940
accacggatc gtaatacggc aatcggtttt cgataatagg tggaacgtat attttattta  36000
aggacttaac aattgtctgt aaaccacaat ttgcttccgc ggatcctgta ttaactatct  36060
gtaaaagcat atgttgaccg ggcggagccg aacattctcc gatatctaat ttctgtatat  36120
ctataatatt attaacctcc gcatacgcat tacagttctt ttctagcttg gataccgcac  36180
taggtacatc gtctagatct attcctattt cttcagcgat agctcttcta tccttttccg  36240
gaagcaatga aatcacttca ataaatgatt caaccatgag tgtgaaacta agtcgagaat  36300
tactcatgca tttgttagtt attcggagcg cgcaattttt aaactgtcct ataacctctc  36360
ctatatgaat agcacaagtg acattagtag ggatagaatg ttgagctaat ttttgtaaat  36420
aactatctat aaaaagatta tacaaagttt taaactcttt agtttccgcc atttatccag  36480
tctgagaaaa tgtctctcat aataaatttt tccaagaaac taattgggtg aagaatggaa  36540
acctttaatc tatatttatc acagtctgtt ttggtacaca tgatgaattc ttctaatgct  36600
gtactaaatt cgatatcttt ttcgatttct ggatatgttt ttaataaagt atgaacaaag  36660
aaatggaaat cgtaatacca gttatgttca actttgaaat tgttttttat tttcttgtta  36720
atgattccag ccacttggga aaagtcaaag tcgtttaatg ccgatttaat acgttcatta  36780
aaaacaaact ttttatcctt tagatgaatt attattggtt cattggaatc aaaaagtaag  36840
atattatcgg gtttaagatc tgcgtgtaaa aagttgtcgc aacagggtag ttcgtagatt  36900
ttaatgtata acagagccat ctgtaaaaag ataaacttta tgtattgtac caaagattta  36960
aatcctaatt tgatagctaa ctcggtatct actttatctg ccgaatacag tgctagggga  37020
aaaattataa tatttcctct ttcgtattcg tagttagttc tcttttcatg ttcgaaaaag  37080
tgaaacatgc ggttaaaata gtttataaca ttaatattac tgttaataac tgccggataa  37140
aagtgggata gtaatttcac gaatttgata ctgtcctttc tctcgttaaa cgcctttaaa  37200
aaaactttag aagaatatct caatgagagt tcctgaccat ccatagtttg tatcaataat  37260
agcaacatat gaagaacccg tttatacaga gtatgtaaaa atgttaattt atagtttaat  37320
cccatggccc acgcacacac gattaatttt ttttcatctc cctttagatt gttgtataga  37380
aatttgggta ctgtgaactc cgccgtagtt tccatgggac tatataattt tgtggcctcg  37440
aatacaaatt ttactacata gttatctatc ttaaagacta taccatatcc tcctgtagat  37500
atgtgataaa aatcgtcgtt tataggataa aatcgtttat ccttttgttg gaaaaaggat  37560
gaattaatgt aatcattctc ttctatcttt agtagtgttt ccttattaaa attcttaaaa  37620
taatttaaca atctaactga cggagcccaa ttttggtgta aatctaattg ggacattatg  37680
ttgttaaaat acaaacagtc tcctaatata acagtatctg ataatctatg gggagacatc  37740
cattgatatt caggggatga atcattggca acacccattt attgtacaaa aagccccaat  37800
ttacaaacga aagtccaggt ttgatagaga caaacaatta actattttgt ctctgttttt  37860
aatttctttg gtaatgaaat tattcacaat atcagtatct tctttatcta ccagagattt  37920
tactaacttg ataaccttgg ctgtctcatt caatagggta gtaatatttg tatgtgtgat  37980
attgatatct ttttgaattg tttcttttag aagtgattct ttgatggtgc cagcatacga  38040
attacaataa tgcagaaact cagttaacat gcaggaatta tagtaagcca attccaattg  38100
ttgcctgtat tgtattagag tattaatatg cgcaatggtg tccttgcgtt tctctgatag  38160
aatgcgagca gcgattttgg cgttatcatt tgacgatatt tctggaatga cgaatcctgt  38220
```

ttctactaac tttttggtag gacaaagtga aacaatcaag aagatagctt ctcctcctat 38280
ttgtggaaga aattgaactc ctctagatga tctactgacg atagtatctc cttgacagat 38340
attggaccga attacagaag tacctggaat gtaaagccct gaaaccccct catttttttaa 38400
gcagattgtt gccgtaaatc ctgcactgtg accaagatag agagctcctt tggtgaatcc 38460
atctctatgt ttcagtttaa ccaagaaaca gtcagctggt ctaaaatttc catctctatc 38520
taatacagca tctaacttga tgtcaggaac tatgaccggt ttaatgttat atgtaacatt 38580
gagtaaatcc ttaagttcat aatcatcact gtcatcagtt atgtacgatc caaacaatgt 38640
ttctactggc atagtggata cgaagatgct atccatcaga atgtttccct gattagtatt 38700
ttctatatag ctattcttct ttaaacgatt ttccaaatca gtaactatgt tcattttttt 38760
aggagtagga cgcctagcca gtatggaaga ggattttcta gatcctctct tcaacatctt 38820
tgatctcgat ggaatgcaaa accccatagt gaaacaacca acgataaaaa taatattgtt 38880
tttcactttt tataatttta ccatctgact catggattca ttaatatctt tataagagct 38940
actaacgtat aattctttat aactgaactg agatatatac accggatcta tggtttccat 39000
aattgagtaa atgaatgctc ggcaataact aatggcaaat gtatagaaca acgaaattat 39060
actagagttg ttaaagttaa tattttctat gagctgttcc aataaattat ttgttgtaac 39120
tgcgttcaag tcataaatca tcttgatact atccagtaaa ccgtgtttaa gttctggaat 39180
attatcatcc cattgtaaag cccctaattc gactatcgaa tatcctgctc tgatagcagt 39240
ttcaatatcg acggacgtca atactgtaat aaaggtggta gtattgtcat catcgtgata 39300
aactacggga atatggtcgt tagtaggtac ggtgacttta cacaacgcga tatataactt 39360
tccttttgta ccatttttaa cgtagttggg acgtcctgca gggtattgtt ttgaagaaat 39420
gatatcgaga acagatttga tacgatattt gttggattcc tgattattca ctataatata 39480
atctagacag atagatgatt cgataaatag agaaggtata tcgttggtag gataatacat 39540
ccccattcca gtattctcgg atactctatt gatgacacta gttaagaaca tgtcttctat 39600
tctagaaaac gaaaacatcc tacatggact cattaaaact tctaacgctc ctgattgtgt 39660
ctcgaatgcc tcgtacaagg atttcaagga tgccatagat tctttgacca acgatttaga 39720
attgcgttta gcatctgatt tttttattaa atcgaatggt cggctctctg gtttgctacc 39780
ccaatgataa caatagtctt gtaaagataa accgcaagaa aatttatacg catccatcca 39840
aataacccta gcaccatcgg atgatattaa tgtattatta tagattttcc atccacaatt 39900
attgggccag tatactgtta gcaacggtat atcgaataga ttactcatgt aacctactag 39960
aatgatagtt cgtgtactag tcataatatc tttaatccaa tctaagaaat ttaaaattag 40020
attttttaca ctgttaaagt taacaaaggt attacccgga tacgtggata tcatatatgg 40080
cattggtcca ttatcagtaa tagctccata aactgatacg gcgatggttt ttatatgtgt 40140
ttgatctaac gaggaagaaa ttcgcgccca caattcatct ctagatatgt atttaatatc 40200
aaacggtaac acatcaattt cgggacgcgt atatgtttct aaatttttaa tccaaatata 40260
atgatgacct atatgcccta ttatcatact gtcaactata gtacacctag agaacttacg 40320
atacatctgt ttcctataat cgttaaattt tacaaatcta taacatgcta aacctttttga 40380
cgacagccat tcattaattt ctgatatgga atctgtattc tcgataccgt attgttctaa 40440
agccagtgct atatctccct gttcgtggga acgctttcgt ataatatcga tcaacggata 40500
atctgaagtt tttggagaat aatatgactc atgatctatt tcgtccataa acaatctaga 40560

-continued cataggaatt ggaggcgatg atcttaattt tgtgcaatga gtcgtcaatc ctataacttc 40620
taatcttgta atattcatca tcgacataat actatctatg ttatcatcgt atattagtat 40680
accacggcct tcttcatttc gtgccaaaat aatatacagt cttaaataat tacgcaatat 40740
ctcaatagtt tcataattgt tagctgtttt catcaagatt tgtaccctgt ttaacatgat 40800
ggcgttctat acgtctctat tttctttttt ttaaattttt aacgatttac tgtggctaga 40860
tacccaatct ctctcaaata ttttttagc ctcgcttaca agctgtttat ctatactatt 40920
aaaactgacg aatccgtgat tttggtaatg ggttccgtcg aaatttgccg aagtgatatg 40980
aacatattcg tcgtcgacta tcaacaattt tgtattattc tgaatagtga aaaccttcac 41040
agatagatca ttttgaacac acaacgcgtc tagacttctg gcggttgcca tagaatatac 41100
gtcgttctta tcccaattac caactagaag tctgatctta actcctctat taatggctgc 41160
ttctataatg gagttgtaaa tgtcgggcca atagtagcta ttaccgtcga cacgtgtagt 41220
gggaactatg gccaaatgtt caatatctat actagtctta gccgacttga gtttatcaat 41280
aactacatcg gtatctagat ctctagaata tcccaatagg tgttccggag aatcagtaaa 41340
gaacactcca cctataggat tcttaatatg atacgcagtg ctaactggca aacaacaagc 41400
cgcagagcat aaattcaacc atgaattttt tgcgctatta aaggctttaa aagtatcaaa 41460
tcttctacga agatctgtgg ccagcggggg ataatcagaa tatacaccta acgttttaat 41520
cgtatgtata gatcctccag taaatgacgc gtttcctaca taacatcttt catcatctga 41580
cacccaaaaa caaccgagta gtagtcccac attatttttt ttatctatat taacggttat 41640
aaaatttata tccgggcagt gactttgtag ctctcccaga tttcttttcc ctcgttcatc 41700
tagcaaaact attattttaa tcccttttc agatgcctct tttagtttat caaaaataag 41760
cgctccccta gtcgtactca gaggattaca acaaaaagat gctatgtata tatatttctt 41820
agctagagtg ataatttcgt taaaacattc aaatgttgtt aaatgatcgg atctaaaatc 41880
catattttct ggtagtgttt ctaccagcct acattttgct cccgcaggta ccgatgcaaa 41940
tggccacatt tagttaacat aaaaacttat acatcctgtt ctatcaacga ttctagaata 42000
tcatcggcta tatcgctaaa attttcatca aagtcgacat cacaacctaa ctcagtcaat 42060
atattaagaa gttccatgat gtcatcttcg tctatttcta tatccgtatc cattgtagat 42120
tgttgaccga ttatcgagtt taaatcatta ctaatactca atccttcaga atacaatctg 42180
tgtttcattg taaatttata ggcggtgtat ttaagttggt agattttcaa ttatgtatca 42240
atatagcaac agtagttctt gctcctcctt gattctagca tcctcttcat tattttcttc 42300
tacgtacata agcatgtcca atacgttaga caacacaccg acgatggcgg ccgccacaga 42360
cacgaatatg actagaccga tgaccattta aaaacccctc tctagctttc acttaaactg 42420
tatcgattat tcttttagaa catgtataat ataaaaacat tattctattt cgaatttagg 42480
cttccaaaaa tttttcatcc gtaaaccgat aataatatat atagacttgt taatagtcgg 42540
aataaataga ttaatgctta aactatcatc atctccacga ttagagatac aatatttaca 42600
ttttttttgc tgtttcgaaa ctttatcaat acacgttaat acaaacccag gaaggagata 42660
ttgaaactga ggctgttgaa aatgaaacgg tgaatacaat aattcagata atgtaaaatc 42720
atgattccgt attctgatga tattagaact gctaatggat gtcgatggta tgtatctagg 42780
agtatctatt ttaacaaagc atcgatttgc taatatacaa ttatcctttt gattaattgt 42840
tattttattc atattcttaa aaggtttcat atttatcaat tcttctacat taaaaatttc 42900
catttttaat ttatgtagcc cccgcaatac tcctcattac gtttcatttt ttgtctataa 42960
tatccatttt gttcatctcg gtacatagat tatccaattg agaagcgcat ttagtagttt 43020
tgtacatttt aagtttattg acgaatcgtc gaaaactagt tatagttaac attttattat 43080
ttgataccct gatattaata cccctgccgt tactattatt tataactgat gtaatccacg 43140
taacattaga attaattatc gatagtaatg catcgacgct tccaaaattg tctattataa 43200
actcaccgat aattttttta ttgcatgttt tcatattcat taggattatc aaatctttaa 43260
tcttactacg attgtatgcg ttgatattgc aagacgtcat tctaaaagac ggaggatctc 43320
catcaaatgc cagacaatca cgtacaaagt acatggaaat aggttttgtt ctattgcgca 43380
tcatagattt atatagaaca cccgtagaaa tactaatttg ttttactcta taaaatacta 43440
atgcatctat ttcatcgttt tgtataacgt ctttccaagt gtcaaattcc aaattttttt 43500
cattgatagt accaaattct tctatctctt taactacttg catagatagg taattacagt 43560
gatgcctaca tgccgttttt tgaaactgaa tagatgcgtc tagaagcgat gctacgctag 43620
tcacaatcac cactttcata tttagaatat atgtatgtaa aaatatagta gaatttcatt 43680
ttgttttttt ctatgctata aatgaattct cattttgcat ctgctcatac tccgttttat 43740
atcaatacca aagaaggaag atatctggtt ctaaaagccg ttaaagtatg cgatgttaga 43800
actgtagaat gcgaaggaag taaagcttcc tgcgtactca aagtagataa accctcatcg 43860
cccgcgtgtg agagaagacc ttcgtccccg tccagatgcg agagaatgaa taaccctgga 43920
aaacaagttc cgtttatgag gacggacatg ctacaaaata tgttcgcggc taatcgcgac 43980
aacgtggcgt cgagactttt gaactaaaat acaattatat ccttttcgat attaataaat 44040
ccgtgtcgtc caggtttttt atctctttca gtatgtgaat agataggtat tttatctcta 44100
ttcatcatcg aatttaagag atccgataaa cattgtttgt attctccaga tgtcagcatc 44160
tgatacaaca atatatgtgc acataaacct ctggcactta tttcatgtac cttcccctta 44220
tcactaagga gaatagtatt tgagaaatat gtatacatga tattatcatg aattagatat 44280
acagaatttg taacactctc gaaatcacac gatgtgtcgg cgttaagatc taatatatca 44340
ctcgataaca cattttcatc tagatacact agacattttt taaagctaaa atagtcttta 44400
gtagtgacag taactatgcg attattttca tcgatgatac atttcatcgg catattatta 44460
cgcttaccat caaagactat accatgtgta tatctaacgt attctagcat ggttgccata 44520
cgcgcattaa acttttcagg atctttggat agatcttcca atctatctat ttgagaaaac 44580
atttttatca tgttcaatag ttgaaacgtc ggatccacta tatagatatt atctataaag 44640
attttaggaa ctacgttcat ggtatcctgg cgaatattaa aactatcaat gatatgatta 44700
tcgttttcat cttttatcac catatagttt ctaagatatg ggattttact taatataata 44760
ttatttcccg tgataaattt tattagaaag gccaaatcta taagaaaagt tctagaatta 44820
gtctgaagaa tatctatatc gccgtaccgt atatttggat taattagata tagagaatat 44880
gatccgtaac atatacaact tttattatgg cgtctaagat attcttccat caacttatta 44940
acatttttga ctagggaaga tacattatga cgtcccatta cttttgcctt gtctattact 45000
gcgacgttca tagaatttag catatctctt gccaattctt ccattgatgt tacattataa 45060
gaaattttag atgaaattac atttggagct ttaatagtaa gaactcctaa tatgtccgtg 45120
tatgtggtca ctaatacaga ttgtagttct ataatcgtaa ataatttacc tatattatat 45180
gtttgagtct gtttagaaaa gtagctaagt atacgatctt ttatttctga tgcagatgta 45240
ttaacatcgg aaaaaaatct ttttttattc ttttttacta aagatacaaa tatgtctttg 45300

-continued ttaaaaacag ttatttttg aatatttcta gcttgtaatt ttaacatatg atattcgttc 45360
acactaggta ctctgcctaa ataggtttct ataatcttta atgtaatatt aggaagagta 45420
ttctgatcag gattcctatt cattttgagg atttaaaact ctgattattg tctaatatgg 45480
tctctacgca aactttttca cagagcgata gagtttttga taactcgttt ttcttaagaa 45540
atataaaact actgtctcca gagctcgctc tatcttttat tttatttaat tcgatacaaa 45600
ctcctgatac tggttcagaa agtaattcat taattttcag tcctttatag aagatattta 45660
atatagataa tacaaaattt tcagttcttg atatcgatct gattgatcct agaactagat 45720
atattaataa cgtgctcatt aggcagttta tggcagcttg ataattagat atagtatatt 45780
ccagttcata tttattagat accgcattgc ccagattttg atattctatg aattcctctg 45840
aaaataaatc caaaataact aaacattcta ttttttgtgg attagtgtac tctcttccct 45900
ctatcatgtt cactactggt gtccacgatg ataaatatct agagggaata taatatagtc 45960
cataggatgc caatctagca atgtcgaata actgtaattt gattcttcgt tcttcattat 46020
gaattgattc ttgaggtata aacctaacac aaattatatt attagacttt tcgtatgtaa 46080
tgtctttcat gttataagtt tttaatcctg gaatagaatc tattttaatg aggcttttaa 46140
acgcagagtt ctccaacgag tcaaagcata atactctgtt gtttttctta tatacgatgt 46200
tacgattttc ttctttgaat ggaataggtt tttgaattag tttataatta caacataata 46260
gataaggaag tgtgcaaata gtacgcggaa aaaacataat agctcccctg ttttcatcca 46320
tggttttaag taaatgatca ctggcttctt tagtcaatgg atattcgaac attaaccgtt 46380
tcatcatcat tggacagaat ccatatttct taatgtaaag agtgatcaaa tcattgtgtt 46440
tattgtacca tcttgttgta aatgtgtatt cggttatcgg atctgctcct ttttctatta 46500
aagtatcgat gtcgatctcg tctaagaatt caactatatc gacatatttc atttgtatac 46560
acataaccat tactaacgta gaatgtatag gaagagatgt aacgggaaca gggtttgttg 46620
attcgcaaac tattctaata cataattctt ctgttaatac gtcttgcacg taatctatta 46680
tagatgccaa gatatctata taattatttt gtaagatgat gttaactatg tgatctatat 46740
aagtagtgta ataattcatg tatttcgata tatgttccaa ctctgtcttt gtgatgtcta 46800
gtttcgtaat atctatagca tcctcaaaaa atatattcgc atatattccc aagtcttcag 46860
ttctatcttc taaaaaatct tcaacgtatg gaatataata atctatttta cctcttctga 46920
tatcattaat gatatagttt ttgacactat cttctgtcaa ttgattctta ttcactatat 46980
ctaagaaacg gatagcgtcc ctaggacgaa ctactgccat taatatctct attatagctt 47040
ctggacataa ttcatctatt ataccagaat taatgggaac tattccgtat ctatctaaca 47100
tagttttaag aaagtcagaa tctaagacct gatgttcata tattggttca tacatgaaat 47160
gatctctatt gatgatagtg actatttcat tctctgaaaa ttggtaactc attctatata 47220
tgctttcctt gttgatgaag gatagaatat actcaataga atttgtacca acaaactgtt 47280
ctcttatgaa tcgtatatca tcatctgaaa taatcatgta aggcatacat ttaacaatta 47340
gagacttgtc tcctgttatc aatatactat tcttgtgata atttatgtgt gaggcaaatt 47400
tgtccacgtt ctttaatttt gttatagtag atatcaaatc caatggagct acagttcttg 47460
gcttaaacag atatagtttt tctggaacga attctacaac attattataa aggactttgg 47520
gtagataagt gggatgaaat cctattttaa ttaatgcgat agccttgtcc tcgtgcagat 47580
atccaaacgc ttttgtgata gtatggcatt cattgtctag aaacgctcta cgaatatctg 47640
tgacagatat catctttaga gaatatacta gtcgcgttaa tagtactaca atttgtattt 47700

```
tttaatctat ctcaataaaa aaattaatat gtatgattca atgtataact aaactactaa  47760
ctgttattga taactagaat cagaatctaa tgatgacgta accaagaagt ttatctactg  47820
ccaatttagc tgcattattt ttagcatctc gtttagattt tccatctgcc ttatcgaata  47880
ctcttccgtc gatgtctaca caggcataaa atgtaggaga gttactaggc cccactgatt  47940
caatacgaaa agaccaatct ctcctagtaa tttggcagta ctcattaata acggtgacag  48000
ggttagcacc tttccaatca ataatttttt tagccggaat aacatcatca aaagacttat  48060
gatcctctct cattgatttt tcgcgggata catcatctat tatgacgtca gccatagcat  48120
cagcatccgg cttatccgcc tccgttgtca taaaccaacg aggaggaata tcgtcggagc  48180
tgtacaccat agcactacgt tgaagatcgt acagagcttt attaacttct cgcttctcca  48240
tattaagttg tctagttagt tgtgcagcag tagctccttc gattccaatg gttttaatag  48300
cctcacacac aatctctgcg ttagaacgct cgtcgatata gattttagac atttttagag  48360
agaactaacg caatcagtaa taaaactaat ttattttatc atttttttta ttcatcatcc  48420
tctggtggtt cgtcgtttct atcgaatgta gctctgatta acccgtcatc tataggtgat  48480
gctggttctg gagattctgg aggagatgga ttattatctg gaagaatctc tgttatttcc  48540
ttgttttcat gtatcgattg cgttgtaaca ttaagattgc gaaatgctct aaatttggga  48600
ggcttaaagt gttgtttgca atctctacac gcgtgtctaa ctagtggagg ttcgtcagcg  48660
gctctagttt gaatcatcat cggcgtagta ttcctacttt tacagttagg acacggtgta  48720
ttgtatttct cgtcgagaac gttaaaataa tcgttgtaac tcacatcctt tattttatct  48780
atattgtatt ctactccttt cttaatgcat tttataccga ataagagata gcgaaggaat  48840
tctttttcgg tgccgctagt acccttaatc atatcacata gtgttttata ttccaaattt  48900
gtggcaatag acggtttatt tctatacgat agtttgtttc tggaatcctt tgagtattct  48960
ataccaatat tattctttga ttcgaattta gtttcttcga tattagattt tgtattacct  49020
atattcttga tgtagtactt tgatgatttt tccatggccc attctattaa gtcttccaag  49080
ttggcatcat ccacatattg tgatagtaat tctcggatat cagtagcggt taccgccatt  49140
gatgtttgtt cattggatga gtaactacta atgtatacat tttccattta taacacttat  49200
gtattaactt tgttcattta tattttttca ttattatgtt gatattaaca aaagtgaata  49260
tatatatgtt aataattgta ttgtggttat acggctacaa ttttataatt agtgaaagtc  49320
agtgtccgat gatcaatgac gatagcttta ctctgaaaag aaagtatcaa atcgatagtg  49380
cggagtcaac aataaaaatg gataagaaga ggacaaagtt tcagaataga gccaaaatgg  49440
taaaagaaat aaatcagaca ataagagcag cacaaactca ttacgagaca ttgaaactag  49500
gatacataaa atttaagaga atgattagga ctactactct agaagatata gcaccatcta  49560
ttccaaataa tcagaaaact tataaactat tctcggacat ttcagccatc ggcaaagcat  49620
cacggaatcc aagtaagatg gtatatgctc tgctgcttta catgtttccc aatttgtttg  49680
gagatgatca tagattcatt cgttatagaa tgcatccaat gagtaaaatc aaacacaaga  49740
tcttctctcc tttcaaactt aatcttatta gaatattagt ggaagaaaga ttctataata  49800
atgaatgcag atctaataaa tggagaataa ttggaacaca agttgataaa atgttgatag  49860
ctgaatctga taaatataca atagatgcaa ggtataacct aaaacccatg tatagaatca  49920
agggaaaatc tgaagaagat accctcttta tcaaacagat ggtagaacaa tgtgtgacat  49980
cccaggaatt ggtggaaaaa gtgttgaaga tactgtttag agatttgttc aagagtggag  50040
```

-continued

```
aatacaaagc gtacagatac gatgatgatg tagaaaatgg atttattgga ttggatacac  50100
taaaattaaa cattgttcat gatatagttg aaccatgtat gcctgttcgt aggccagtgg  50160
ctaagatact gtgtaaagaa atggtaaata aatactttga gaatccgcta catattattg  50220
gtaaaaatct tcaagagtgc attgactttg ttagtgaata ggcatttcat ctttctccaa  50280
tactaattca aattgttaaa ttaataatgg atagtataaa tagttattag tgataaaata  50340
gtaaaaataa ttattagaat aagagtgtag tatcatagat aactctcttc tataaaaatg  50400
gattttattc gtagaaagta tcttatatac acagtagaaa ataatataga tttttttaaag  50460
gatgatacat taagtaaagt aaacaatttt accctcaatc atgtactagc tctcaagtat  50520
ctagttagca attttcctca acatgttatt actaaggatg tattagctaa taccaatttt  50580
tttgttttca tacatatggt acgatgttgt aaagtgtacg aagcggtttt acgacacgca  50640
tttgatgcac ccacgttgta cgttaaagca ttgactaaga attatttatc gtttagtaac  50700
acaatacaat cgtacaagga aaccgtgcat aaactaacac aagatgaaaa atttttagag  50760
gttgccaaat acatggacga attaggagaa cttataggcg taaattatga cttagttctt  50820
aatccattat ttcacggagg ggaacccatc aaagatatgg aaatcatttt tttaaaactg  50880
tttaagaaaa cagacttcaa agttgttaaa aaattaagtg ttataagatt acttatttgg  50940
gcttacctaa gcaagaaaga tacaggcata gagtttgcgg ataatgatag acaagatata  51000
tatactctat ttcaacaaac tggtagaatc gtccatagca atctaacaga aacgtttaga  51060
gattatatct ttcccggaga taagactagc tattgggtgt ggttaaacga aagtatagct  51120
aatgatgcgg atattgttct taatagacac gccattacca tgtatgataa aattcttagt  51180
tatatatact ctgagataaa acaaggacgc gttaataaaa acatgcttaa gttagtttat  51240
atctttgagc ctgaaaaaga tatcagagaa cttctgctag aaatcatata tgatattcct  51300
ggagatatcc tatctattat tgatgcaaaa aacgacgatt ggaaaaaata ttttattagt  51360
ttttataaag ctaattttat taacggtaat acatttatta gtgatagaac gtttaacgag  51420
gacttattca gagttgttgt tcaaatagat cccgaatatt tcgataatga acgaattatg  51480
tctttattct ctacgagtgc tgcggacatt aaacgatttg atgagttaga tattaataac  51540
agttatatat ctaatataat ttatgaggtg aacgatatca cattagatac aatggatgat  51600
atgaagaagt gtcaaatctt taacgaggat acgtcgtatt atgttaagga atacaataca  51660
tacctgtttt tgcacgagtc ggatcccatg gtcatagaga acggaatact aaagaaactg  51720
tcatctataa aatccaagag tagacggctg aacttgttta gcaaaaacat tttaaaatat  51780
tatttagacg gacaattggc tcgtctaggt cttgtgttag atgattataa aggagacttg  51840
ttagttaaaa tgataaacca tcttaagtct gtggaggatg tatccgcatt cgttcgattt  51900
tctacagata aaaaccctag tattcttcca tcgctaatca aaactatttt agctagttat  51960
aatatttcca tcatcgtctt atttcaaagg tttttaagag ataatctata tcatgtagaa  52020
gaattcttgg ataaaagcat ccatctaacc aagacggata agaaatatat acttcaattg  52080
ataagacacg gtagatcata gaacagacca aatatattat taataatttg tatatacata  52140
gatataatta tcacatatta aaaattcaca catttttgat aaatgggaac tgctgcaaca  52200
attcagactc ccaccaaatt aatgaataaa gaaaatgcag aaatgatttt ggaaaaaatt  52260
gttgatcata tagttatgta tattagtgac gaatcaagtg attcagaaaa taatcctgaa  52320
tatattgatt ttcgtaacag atacgaagac tatagatctc tcattataaa aagtgatcac  52380
gagtttgtaa agctatgtaa aaatcatgca gagaaaagtt ctccagaaac gcaacaaatg  52440
```

attatcaaac acatatacga acaatatctt attccagtat ctgaagtact attaaaacct 52500
ataatgtcca tgggtgacat aattacatat aacggatgta aagacaatga atggatgcta 52560
gaacaactct ctaccctaaa ctttaacaat ctccgcacat ggaactcatg tagcataggc 52620
aatgtaacgc gtctgtttta tacatttttt agttatctga tgaaagataa actaaatata 52680
taagtataat cccattctaa tactttaacc tgatgtatta gcatcttatt agaatattaa 52740
cctaactaaa agacataaca taaaaactca ttacatagtt gataaaaagc ggtaggatat 52800
aaatattatg gctgccaccg ttccgcgttt tgacgacgtg tacaaaaatg cacaaagaag 52860
aattctagat caagaaacat tttttagtag aggtctaagt agaccgttaa tgaaaaacac 52920
atatctattt gataattacg cgtatggatg gataccagaa actgcaattt ggagtagtag 52980
atacgcaaac ttagatgcaa gtgactatta tcccatttcg ttgggattac ttaaaaagtt 53040
cgagtttctc atgtctctat ataaaggtcc tattccagta tacgaagaaa aagtaaatac 53100
tgaattcatt gctaatggat cgttctctgg tagatacgta tcatatcttc gaaagttttc 53160
tgctcttcca acaaacgagt ttattagttt tttgttactg acttccattc caatctataa 53220
tatcttgttc tggtttaaaa atactcagtt tgatattact aaacacacat tattcagata 53280
cgtctataca gataatgcca aacacctggc gttggctagg tatatgcatc aaacaggaga 53340
ctataagcct ttgtttagtc gtctcaaaga gaattatata tttaccggtc ccgttccaat 53400
aggtatcaaa gatataaatc accctaatct tagtagagca agaagtccat ccgattatga 53460
gacattagct aatattagta ctatattgta ctttaccaag tatgatccgg tattaatgtt 53520
tttattgttt tacgtacctg ggtattcaat tactacaaaa attactccag ccgtagaata 53580
tctaatggat aaactgaatc taacaaagag cgacgtacaa ctgttgtaaa ttattttatg 53640
cttcgtaaaa tgtaggtttt gaaccaaaca ttctttcaaa gaatgagatg cataaaactt 53700
tattatccaa tagattgact atttcggacg tcaatcgttt aaagtaaact tcgtaaaata 53760
ttctttgatc actgccgagt ttaaaacttc tatcgataat tgtttcatat gttttaatat 53820
ttacaagttt tttggtccat ggtacattag ccggacaaat atatgcaaaa taatatcgtt 53880
ctccaagttc tatagtttct ggattatttt tattatattc agtaaccaaa tacatattag 53940
ggttatctgc ggatttataa tttgagtgat gcattcgact caacataaat aattctagag 54000
gagacgatct actatcaaat tcggatcgta aatctgtttc taaagaacgg agaatatcta 54060
tacatacctg attagaattc atccgtcctt cagacaacat ctcagacagt ctggtcttgt 54120
atgtcttaat catattctta tgaaacttgg aaacatctct tctagtttca ctagtacctt 54180
tattaattct ctcaggtaca gattttgaat tcgacgatgc cgagtatttc atcgttgtat 54240
atttcttctt cgattgcata atcagattct tatataccgc ctcaaactct attttaaaat 54300
tattaaacaa tactctatta ttaatcagtc gttctaactc ctttgctatt tctatggact 54360
tatctacatc ttgactgtct atctctgtaa acacggagtc ggtatctcca tacacgctac 54420
gaaaacgaaa tctgtaatct ataggcaacg atgttttcac aatcggatta atatctctat 54480
cgtccatata aaatggatta cttaatggat tggcaaaccg taacataccg ttagataact 54540
ctgctccatt tagtaccgat tctagataca agatcattct acgtcctatg gatgtgcaac 54600
tcttagccga agcgtatgag tatagagcac tatttctaaa tcccatcaga ccatatactg 54660
agttggctac tatcttgtac gtatattgca tggaatcata gatggccttt tcagttgaac 54720
tggtagcctg ttttaacatc tttttatatc tggctctctc tgccaaaaat gttcttaata 54780

```
gtctaggaat ggttccttct atcgatctat cgaaaattgc tatttcagag atgaggttcg  54840
gtagtctagg ttcacaatga accgtaatat atctaggagg tggatatttc tgaagcaaga  54900
gctgattatt tatttcttct tccaatctat tggtactaac aacgacaccg actaatgttt  54960
ccggagatag atttccaaag atacacacat taggatacag actgttataa tcaaagatta  55020
atacattatt actaaacatt ttttgttttg gagcaaatac cttaccgcct tcataaggaa  55080
acttttgttt tgtttctgat ctaactaaga tagttttagt ttccaacaat agctttaaca  55140
gtggaccctt gatgactgta ctcgctctat attcgaatac catggattga ggaagcacat  55200
atgttgacgc acccgcgtct gtttttgttt ctactccata atactcccac aaatactgac  55260
acaaacaagc atcatgaata cagtatctag ccatatctaa agctatgttt agattataat  55320
ccttatacat ctgagctaaa tcaacgtcat cctttccgaa agataattta tatgtatcat  55380
taggtaaagt aggacataat agtacgactt taaatccatt ttcccaaata tctttacgaa  55440
ttactttaca tataatatcc tcatcaacag tcacataatt acctgtggtt aaaacctttg  55500
caaatgcagc ggctttgcct ttcgcgtccg tagtatcgtc accgatgaac gtcatttctc  55560
taactcctct atttaatact ttacccatgc aactgaacgc gttcttggat atagaatcca  55620
atttgtacga atccaatttt tcagattttt gaatgaatga atatagatcg aaaaatatag  55680
ttccattatt gttattaacg tgaaacgtag tattggccat gccgcctact cccttatgac  55740
tagactgatt tctctcataa atacagagat gtacagcttc ctttttgtcc ggagatctaa  55800
agataatctt ctctcctgtt aataactcta gacgattagt aatatatctc agatcaaagt  55860
tatgtccgtt aaaggtaacg acatagtcga acgttagttc caacaattgt ttagctattc  55920
gtaacaaaac tatttcagaa cataaaacta gttctcgttc gtaatccatt tccattagtg  55980
actgtatcct caaacatcct ctatcgacgg cttcttgtat ttcctgttcc gttaacatct  56040
cttcattaat gagcgtaaac aataatcgtt taccacttaa atcgatataa cagtaacttg  56100
tatgcgagat tgggttaata aatacagaag gaaacttctt atcgaagtga cactctatat  56160
ctagaaataa gtacgatctt gggatatcga atctaggtat ttttttagcg aaacagttac  56220
gtggatcgtc acaatgataa catccattgt taatctttgt caaatattgc tcgtccaacg  56280
agtaacatcc gtctggagat atcccgttag aaatataaaa ccaactaata ttgagaaatt  56340
catccatggt ggcattttgt atgctgcgtt tctttggctc ttctatcaac cacatatctg  56400
cgacggagca ttttctatct ttaatatcta gattataact tattgtctcg tcaatgtcta  56460
tagttctcat ctttcccaac ggcctcgcat taaatggagg aggagacaat gactgatata  56520
tttcgtccgt cactacgtaa taaaagtaat gaggaaatcg tataaatacg gtctcaccat  56580
ttcgacatct ggatttcaga tataaaaatc tgttttcacc gtgactttca aaccaattaa  56640
tgcaccgaac atccatttat agaatttaga aatatatttt catttaaatg aatcccaaac  56700
attggggaag agccgtatgg accattattt ttatagtact ttcgcaagcg ggtttagacg  56760
gcaacataga agcgtgtaaa cgaaaactat atactatagt tagcactctt ccatgtcctg  56820
catgtagacg gcacgcgact atcgctatag aggacaataa tgtcatgtct agcgatgatc  56880
tgaattatat ttattatttt ttcatcagat tatttaacaa tttggcatct gatcccaaat  56940
acgcgatcga tgtgacaaag gttaaccctt tataaactta acccattata aaacttatga  57000
ttagtcacga ctgaaataac cgcgtgatta ttttttggta taattctaca cggcatggtt  57060
tctgtgacta tgaattcaac cccgttaca ttagtgaaat ctttaacaaa cagcaagggt  57120
tcgtcaaaga cataaaactc attgtttaca atcgaaatag accccctatc acacttaaaa  57180
```

-continued taaaaaatat ccttatcctt taccaccaaa taaaattctg attggtcaat gtgaatgtat 57240
tcacttaaca gttccacaaa tttatttatt aactccgagg cacatacatc gtcggtattt 57300
tttatggcaa actttactct tccagcatcc gtttctaaaa aaatattaac gagttccatt 57360
tatatcatcc aatattattg aaatgacgtt gatggacaaa tgatacaaat aagaaggtac 57420
ggtacctttg tccaccatct cctccaattc atgctctatt ttgtcattaa ctttaatgta 57480
tgaaaacagt acgccacatg cttccatgac agtgtgtaac actttggata caaaatgttt 57540
gacattagta taattgttca agactgtcaa tctataatag atagtagcta taatatattc 57600
tatgatggta ttgaagaaga tgacaacctt ggcatattga tcatttaaca cagacatggt 57660
atcaacagat agcttgaatg aaagagaatc agtaattgga ataagcgtct tctcgatgga 57720
gtgtccgtat accaacatgt ctgatatttt gatgtattcc attaaattat ttagtttttt 57780
ctttttattc tcgttaaaca gcatttctgt caacggaccc caacatcgtt gaccgattaa 57840
gttttgattg atttttccgt gtaaggcgta tctagtcaga tcgtatagcc tatccaataa 57900
tccatcgtct gtgtgtagat cacatcgtac actttttaat tctctataga agagcgacag 57960
acatctggag caattacaga cagcaatttc tttattctct acagatgtaa gatacttgaa 58020
gacattccta tgatgatgca gaattttgga taacacggta ttgatggtat ctgttaccat 58080
aattcctttg atggctgata gtgtcagagc acaagatttc caatctttga caatttttag 58140
caccattatc tttgttttga tatctatatc agacagcatg gtgcgtctga caacacaagg 58200
attaagacgg aaagatgaaa tgattctctc aacatcttca atggatacct tgctattttt 58260
tctggcatta tctatatgtg cgagaatatc ctctagagaa tcagtatcct ttttgatgat 58320
agtggatctc aatgacatgg gacgtctaaa ccttcttatt ctatcaccag attgcatggt 58380
gatttgtctt ctttctttta tcataatgta atctctaaat tcatcggcaa attgtctata 58440
tctaaaatca taatatgaga tgtttacctc tacaaatatc tgttcgtcca atgttagagt 58500
atttacatca gttttgtatt ccaaattaaa catggcaacg gatttaattt tatattcctc 58560
tattaagtcc tcgtcgataa taacagaatg tagataatca tttaatccat cgtacatggt 58620
tggaagatgc tcgttgacaa aatctttaat tgtcttgatg aaggtgggac tatatctaac 58680
atcttgatta ataaaattta taacattgtc cataggatac tttgtaacta gttttataca 58740
catctcttca tcggtaagtt tagacagaat atcgtgaaca ggtggtatat tatattcatc 58800
agatatacga agaacaatgt ccaaatctat attgtttaat atattatata gatgtagtgt 58860
agctcctaca ggaatatctt taactaagtc aatgatttca tcaaccgtta gatctatttt 58920
aaagttaatc atataggcat tgatttttaa aaggtatgta gccttgacta cattctcatt 58980
aattaaccat tccaagtcac tgtgtgtaag aagattatat tctatcataa gcttgactac 59040
atttggtccc gataccatta aagaattctt atgatataag gaaacagatt ttaggtactc 59100
atctactcta caagaatttt ggagagcctt aacgatatca gtgacgttta ttatttcagg 59160
aggaaaaaac ctaacattga gaatatcgga attaatagct tccagataca gtgattttgg 59220
caatagtccg tgtaatccat aatccagtaa cacgagctgg tgcttgctag acaccttttc 59280
aatgtttaat ttttttgaaa taagctttga taaagccttc ctcgcaaatt ccggatacat 59340
gaacatgtcg gcgacatgat taagtattgt tttttcatta tttttatatt ttctcaacaa 59400
gttctcaata ccccaataga tgatagaata tcacccaatg cgtccatgtt gtctatttcc 59460
aacaggtcgc tatatccacc aatagaagtt ttcccaaaaa agattctagg aacagttcta 59520

-continued ccaccagtaa tttgttcaaa atagtcacgc aattcatttt cgggtttaaa ttctttaata 59580
tcgacaattt catacgctcc tcttttgaaa ctaaacttat ttagaatatc cagtgcattt 59640
ctacaaaaag gacatgtata cttgacaaaa attgtcactt tgttattggc caacctttgt 59700
tgtacaaatt cctcggccat tttaatattt aagtgatata aaactatctc gacttattta 59760
actctttagt cgagatatat ggacgcagat agctatatga tagccaacta cagaaggcaa 59820
acgctataaa aaacataatt acgacgagca tatttataaa tatttttatt cagcattact 59880
tgatatagta atattaggca cagtcaaaca ttcaaccact ctcgatacat taactctctc 59940
attttcttta acaaattctg caatatcttc gtaaaaagat tcttgaaact ttttagaata 60000
tctatcgact ctagatgaaa tagcgttcgt caacatacta tgttttgtat acataaaggc 60060
gcccatttta acagtttcta gtgacaaaat gctagcgatc ctaggatcct ttagaatcac 60120
atagattgac gattcgtctc tcttagtaac tctagtaaaa taatcataca atctagtacg 60180
cgaaataata ttatccttga cttgaggaga tctaaacaat ctagttttga gaacatcgat 60240
aagttcatcg ggaatgacat acatactatc tttaatagaa ctcttttcat ccagttgaat 60300
ggattcgtcc ttaaccaact gattaatgag atcttctatt ttatcatttt ccagatgata 60360
tgtatgtcca ttaaagttaa attgtgtagc gcttcttttt agtctagcag ccaatacttt 60420
aacatcacta atatcgatat acaaaggaga tgatttatct atggtattaa gaattcgttt 60480
ttcgacatct gtcaaaacca attccttttt gcctgtatca tccagttttc catcctttgt 60540
aaagaaatta ttttctacta gactattaat aagactgata aggattcctc cataattgca 60600
caatccaaac tttttcacaa aactagactt tacaagatct acaggaatgc gtacttcagg 60660
tttcttagct tgtgattttt tcttttgtgg acattttctt gtgaccaact catctaccat 60720
ttcattgatt ttagcagtga aataagcttt caatgcacgg gcactgatac tattgaaaac 60780
gagttgatct tcaaattccg ccatttaagt tcaccaaaca acttttaaat acaaatatat 60840
caatagtagt agaataagaa ctataaaaaa aataataatt aaccaatacc aaccccaaca 60900
accggtatta ttagttgatg tgactgtttt ctcatcactt agaacagatt taacaatttc 60960
tataaagtct gtcaaatcat cttccggaga ccccataaat acaccaaata tagcggcgta 61020
caacttatcc atttatacat tgaatattgg cttttcttta tcgctatctt catcatattc 61080
atcatcaata tcaacaagtc ccagattacg agccagatct tcttctacat tttcagtcat 61140
tgatacacgt tcactatctc cagagagtcc gataacgtta gccaccactt ctctatcaat 61200
gattagtttc ttgagtgcga atgtaatttt tgtttccgtt ccggatctat agaaaactac 61260
aggtgtgata attgccttgg ccaattgtct ttctctttta ctgagtgatt ctagttcacc 61320
ttctatagat ctgagaatgg atgattctcc agtcgaaaca tattctacca tggctccgtt 61380
taatttgttg atgaagatgg attcatcctt aaatgttttc tctgtaatag tttccaccga 61440
aagactatgc aaagaatttg gaatgcgttc cttgtgctta atgtttccat agacggcttc 61500
tagaagttga tacaacatag gactagccgc ggtaactttt atttttagaa agtatccatc 61560
gcttctatct tgtttagatt tatttttata aagtttagtc tctccttcca acataataaa 61620
agtggaagtc atttgactag ataaactatc agtaagtttt atagagatag acgaacaatt 61680
agcgtattga gaagcattta gtgtaacgta ttcgatacat tttgcattag atttactaat 61740
cgattttgca tactctataa cacccgcaca agtctgtaga gaatcgctag atgcagtagg 61800
tcttggtgaa gtttcaactc tcttcttgat taccttactc atgattaaac ctaaataatt 61860
gtactttgta atataatgat atatattttc actttatctc atttgagaat aaaaatgttt 61920

-continued ttgtttaacc actgcatgat gtacagattt cggaatcaca aaccaccggt ggttttattt 61980
tatccttgtc caatgtgaat tgaatgggag cggatgcggg tttcgtacgt agatagtaca 62040
ttcccgtttt tagaccgaga ctccatccgt aaaaatgcat actcgttagt ttggaataac 62100
tcggatctgc tatatggata ttcatagatt gactttgatc gatgaaggct cccctgtctg 62160
cagccatttt tatgatcgtc ttttgtggaa tttcccaaat agttttataa actcgcttaa 62220
tatcttctgg aaggtttgta ttctgaatgg atccaccatc tgccataatc ctattcttga 62280
tctcatcatt ccataatttt ctctcggtta aaactctaag gagatgcgga ttaactactt 62340
gaaattctcc agacaatact ctccgagtgt aaatattact ggtatacggt tccaccgact 62400
cattatttcc caaaatttga gcagttgatg cagtcggcat aggtgccacc aataaactat 62460
ttctaagacc gtatgttctg attttatctt ttagaggttc ccaattccaa agatccgacg 62520
gtacaacatt ccaaagatca tattgtagaa taccgttact ggcgtacgat cctacatatg 62580
tatcgtatgg tccttccttc tcagctagtt cacaactcgc ctctaatgca ccgtaataaa 62640
tggtttcgaa gatcttctta tttagatctt gtgcttccag gctatcaaat ggataattta 62700
agagaataaa cgcgtccgct aatccttgaa caccaatacc gataggtcta tgtctcttat 62760
tagagatttc agcttctgga ataggataat aattaatatc tataatttta ttgagatttc 62820
tgacaattac tttgaccaca tccttcagtt tgagaaaatc aaatcgccca tctattacaa 62880
acatgttcaa ggcaacagat gccagattac aaacggctac ctcattagca tccgcatatt 62940
gtattatctc agtgcaaaga ttactacact tgatagttcc taaattttgt tgattactct 63000
ttttgttaca cgcatcctta taaagaatga atggagtacc agtttcaatc tgagattcta 63060
taatcgcttt ccagacgact cgagccttta ttatagattt gtatctcctt tctctttcgt 63120
atagtgtata caatcgttcg aactcgtctc cccaaacatt gtccaatcca ggacattcat 63180
ccggacacat caacgaccac tctccgtcat ccttcactcg tttcataaag agatcaggaa 63240
tccaaagagc tataaataga tctctggttc tatgttcctc gtttcctgta ttctttttaa 63300
gatcgaggaa cgccataata tcagaatgcc acggttccaa gtatatggcc ataactccag 63360
gccgtttgtt tcctccctga tctatgtatc tagcggtgtt attataaact ctcaacattg 63420
gaataatacc gtttgatata ccattggtac cggagatata gcttccactg gcacgaatat 63480
tactaattga tagacctatt ccccctgcca ttttagagat taatgcgcat cgttttaacg 63540
tgtcatagat accctctatg ctatcatcga tcatgttaag tagaaaacag ctagacattt 63600
ggtgacgact agttcccgca ttaaataagg taggagaagc gtgcgtaaac catttttcag 63660
aaagtagatt gtacgtctca atagctgagt ctatatccca ttgatgaatt cctactgcga 63720
cacgcattaa catgtgctga ggtctttcaa cgatcttgtt gtttattttc aacaagtagg 63780
atttttccaa agttttaaaa ccaaaatagt tgtatgaaaa gtctcgttcg taaataataa 63840
ccgagttgag tttatcctta tatttgttaa ctatatccat ggtgatactt gaaataatcg 63900
gagaatgttt cccattttta ggattaacat agttgaataa atcctccatc acttcactaa 63960
atagtttttt tgtttccttg tgtagatttg atacggctat tctggcggct agaatggcat 64020
aatccggatg ttgtgtagta caagtggctg ctatttcggc tgccagagtg tccaattcta 64080
ccgttgttac tccattatat attccttgaa taaccttcat agctatttta ataggatcta 64140
tatgatccgt gtttaagcca taacataatt ttctaatacg agacgtgatt ttatcaaaca 64200
tgacattttc cttgtatcca tttcgtttaa tgacaaacat ttttgttggt gtaataaaaa 64260

-continued

```
aattatttaa cttttcatta atagggattt gacgtacgta gcgtacaaaa tgattgttcc  64320
tggtatatag ataaagagtc ctatatattt gaaaatcgtt acggctcgat taaactttaa  64380
tgattgcata gtgaatatat cattaggatt taactccttg actatcaggg cggcaccaga  64440
aattaccatc aaaagcatta atacagttat gcctatcgca gttagaacgg ttatagcatc  64500
caccatttat atctaaaaat tagatcaaag aatatgtgac aaagtcctag ttgtatattg  64560
agaattgaca aaacaatgtt tcttacatat ttttttttta ttagtaaccg acttaatagt  64620
aggaactgga aaactagact tgattattct ataagtatag atacccttcc aaataatatt  64680
ctctttgata aaagttccag aaaatgtaga atttttaaa aagttatctt ttgctattac  64740
caagattgtg tttagacgct tattattaat atgagtgatg aaatccacac cgcctctaga  64800
tatcgccttt atttccacat tagatggtaa atccaatagt gaaactatct ttttaggaat  64860
gtatggactc gcgtttagag gagtgaacgt cttgggcgtc ggaaaggatg attcgtcaaa  64920
cgaataaaca atttcacaaa tggatgttaa tgtattagta ggaaattttt tgacgctagt  64980
ggaattgaaa attctaatgg atgatgttct acctatttca tccgataaca tgttaatttc  65040
cgacaccaac ggttttaata tttcgatgat atacggtagt ctctctttcg gacttatata  65100
gcttattcca caatacgagt cattatatac tccaaaaaac aaaataacta gtataaaatc  65160
tgtatcgaat gggaaaaacg aaattatcga cataggtata gaatccggaa cattgaacgt  65220
attaatactt aattcttttt ctgtggtaag taccgatagg ttattgacat tgtatggttt  65280
taaatattct ataacttgag acttgataga tattagtgat gaattgaaaa ttatttttat  65340
caccacgtgt gtttcaggat catcgtcgac gcccgtcaac caaccgaacg gagtaaaata  65400
aatatcatta atatatgctc tagatattag tatttttatc aatcctttga ttatcatctt  65460
ctcgtaggcg aatgattcca tgatcaagag tgatttaaga acatcctccg gagtattaat  65520
gggcttagta aacagtccat cgttgcaata ataaaagtta tccaagttaa aggatattat  65580
gcattcgttt aaagatatca cctcatctga cggagacaat tttttggtag gttttagaga  65640
ctttgaagct acttgtttaa caaagttatt catcgtcgtt tactattcta tttaattttg  65700
tagttaattt atcacatatc acattaattg actttttggt ccatttttcc atacgtttat  65760
attcttttaa tcctgcgtta tccgtttccg ttatatccag tgatagatcg tgcaggttaa  65820
atagaatgct cttaaataat gtcatttttt tatccgctaa aaatttaaag aatgtataaa  65880
ctttttttcaa agatttaaaa cttttaggtg gtgtcctagt acacaatatc ataaacaaac  65940
taataaacat cccgcattca gattccaaca gctgattaac ttccacatta atacagccta  66000
ttttcgctcc aaatgtacat tcgaaaaatc tgaataaaac atcaatgtcg caatttgtat  66060
tatccaatac agaatgtttg tgattcgtgt taaaaccatc ggagaaggaa tagaaataaa  66120
aattattata gtggtggaat tcagttggaa tattgcctcc ggagtcataa aaggatacta  66180
aacattgttt tttatcataa attacacatt tccaatgaga caaataacaa aatccaaaca  66240
ttacaaatct agaggtagaa cttttaattt tgtctttaag tatatacgat aagatatgtt  66300
tattcataaa cgcgtcaaat ttttcatgaa tcgctaagga gtttaagaat ctcatgtcaa  66360
attgtcctat ataatccact tcggatccat aagcaaactg agagactaag ttcttaatac  66420
ttcgattgct catccaggct cctctctcag gctctatttt catcttgacg acctttggat  66480
tttcaccagt atgtattcct ttacgtgata aatcatcgat tttcaaatcc atttgtgaga  66540
agtctatcgc cttagatact ttttcccgta gtcgaggttt aaagaaatac gctaacggta  66600
tactagtagg taactcaaaa acatcatata tagaatggta acgcgtcttt aactcgtcgg  66660
```

ttaactcttt cttttgatcg agttcgtcgc tactattggg tctgctcagg tgccccgact 66720
ctactagttc caacatcata ccgataggaa tacaagacac tttgccggcg gttgtagatt 66780
tatcatattt ttccactaca tatccgttac aatttgttaa aaatttagat acatctatat 66840
tgctacataa tccagctagt gaatatatat gacataataa attggtaaat cctagttctg 66900
gtattttact aattactaaa tctgtatatc tttccattta tcatggaaaa gaatttacca 66960
gatatcttct tttttccaaa ctgcgttaat gtattctctt acaaatattc acaagatgaa 67020
ttcagtaata tgagtaaaac ggaacgtgat agtttctcat tggccgtgtt tccagttata 67080
aaacatagat ggcataacgc acacgttgta aaacataaag gaatatacaa agttagtaca 67140
gaagcacgtg gaaaaaaagt atctcctcca tcactaggaa aacccgcaca cataaaccta 67200
accgcgaagc aatatatata cagtgaacac acaataagct ttgaatgtta tagttttcta 67260
aaatgtataa caaatacaga aatcaattcg ttcgatgagt atatattaag aggactatta 67320
gaagctggta atagtttaca gatattttcc aattccgtag gtaaacgaac agatactata 67380
ggtgtactag ggaataagta tccatttagc aaaattccat tggcctcatt aactcctaaa 67440
gcacaacgag agatattttc agcgtggatt tctcatagac ctgtagtttt aactggagga 67500
actggagtgg gtaagacgtc acaggtaccc aagttattgc tttggtttaa ttatttattt 67560
ggtggattct ctactctaga taaaatcact aactttcacg aaagaccagt cattctatct 67620
cttcctagga tagctttagt tagattgcat agcaatacca ttttaaaatc attgggattt 67680
aaggtactag atggatctcc tatttcttta cggtacggat ctataccgga agaattaata 67740
aacaaacaac caaaaaaata tggaattgta ttttctaccc ataagttatc tctaacaaaa 67800
ctatttagtt atggcactct tattatagac gaagttcatg agcatgatca aataggagat 67860
attattatag cagtagcgag aaagcatcat acgaaaatag attctatgtt tttaatgact 67920
gccacgttag aggatgaccg agaacggcta aaagtatttt tacctaatcc cgcatttata 67980
catattcctg gagatacact gtttaaaatt agcgaggtat ttattcataa taagataaat 68040
ccatcttcca gaatggcata catagaagaa gaaaagagaa atttagttac tgctatacag 68100
atgtatactc ctcctgatgg atcatccggt atagtctttg tggcatccgt tgcacagtgt 68160
cacgaatata aatcatattt agaaaaaaga ttaccgtatg atatgtatat tattcatggt 68220
aaggtcttag atatagacga aatattagaa aaagtgtatt catcacctaa tgtatcgata 68280
attatttcta ctccttattt ggaatccagc gttactatac gcaatgttac acacatttat 68340
gatatgggta aagtttttgt ccccgctcct tttggaggat cgcaagaatt tatttctaaa 68400
tctatgagag atcaacgaaa aggaagagta ggaagagtta atcctggtac atacgtctat 68460
ttctatgatc tgtcttatat gaagtctata cagcgaatag attcagaatt tctacataat 68520
tatatattgt acgctaataa gtttaatcta acactccccg aagatttgtt tataatccct 68580
acaaatttgg atattctatg gcgtacaaag gaatatatag actcgttcga tattagtaca 68640
gaaacatgga ataaattatt atccaattat tatatgaaga tgatagagta tgctaaactt 68700
tatgtactaa gtcctattct cgctgaggag ttggataact ttgagaggac gggagaatta 68760
actagtattg tacgagaagc cattttatct ctaaatttac gaattaagat tttaaatttt 68820
aaacataaag atgatgatac gtatatacac ttttgtaaaa tattattcgg tgtctataac 68880
ggaacaaacg ctactatata ttatcataga cctctaacgg gatatatgaa tatgatttca 68940
gatactatat ttgttcctgt agataataac taaaaatcaa actctaatga ccacatcttt 69000

-continued

```
ttttagagat gaaaaatttt ctacatctcc ttttgtagac acgactaaac attttgcaaa  69060
aaaaagttta ttagtgttta gataatcgta tacttcatca gtgtagatag taaatgtgaa  69120
caaataaaag gtattcttac tcaatagatt ggtaaattcc atagaatata ttaatccttt  69180
cttcttgaga tcccacatca tttcaaccag agacgtttta tccaatgatt tacctcgtac  69240
tataccacat acaaaactag attttgcagt gacgtcgtac ctggtattcc taccaaacaa  69300
aattttactt ttagttcttt tagaaaattc taaggtagaa tctctatttg ccaatatgtc  69360
atctatggaa ttaccactag caaaaaatga tagaaatata tattgataca tcgcagctgg  69420
ttttgatcta ctatacttta aaaacgaatc agattccata attgcctgta tatcatcagc  69480
tgaaaaacta tgttttacac gtattccttc ggcatttctt tttaatgata tatcttgttt  69540
agacaatgat aaagttatca tgtccatgag agacgcgtct ccgtatcgta taaatatttc  69600
attagatgtt agacgcttca ttaggggtat acttctataa ggtttcttaa tcagtccatc  69660
attggttgcg tcaagaacta ctatcggatg ttgttgggta tctctagtgt tacacatggc  69720
cttactaaag tttgggtaaa taactatgat atctctatta attatagatg catatatttc  69780
attcgtcaag gatattagta tcgacttgct atcgtcatta atacgtgtaa tgtaatcata  69840
taaatcatgc gatagccaag gaaaattcaa atagatgttc atcatataat cgtcgctata  69900
attcatatta atacgttgac attgactaat ttgtaatata gcctcgccac gaagaaagct  69960
ctcgtattca gtttcatcga taaaggatac cgttaaatat aactggttgc cgatagtctc  70020
atagtctatt aagtggtaag tttcgtacaa atacagaatc cctaaaatat tatctaatgt  70080
tggattaatc tttaccataa ctgtataaaa tggagacgga gtcataacta ttttaccgtt  70140
tgtacttact ggaatagacg aaggaataat ctccggacat gctggtaaag acccaaatgt  70200
ctgtttgaag aaatccaatg ttccaggtcc taatctctta acaaaaaatta cgatattcga  70260
tcccgatatc ctttgcattc tatttaccag catatcacga actatattaa gattatctat  70320
catgtctatt ctcccaccgt tatataaatc gcctccgcta agaaacgtta gtatatccat  70380
acaatggaat acttcatttc taaaatagta ttcgttttct aattctttaa tgtgaaatcg  70440
tatactagaa agggaaaaat tatctttgag ttttccgtta gaaaagaacc acgaaactaa  70500
tgttctgatt gcgtccgatt ccgttgctga attaatggat ttacaccaaa aactcatata  70560
acttctagat gtagaagcat tcgctaaaaa attagtagaa tcaaaggata taagtagatg  70620
ttccaacaag tgagcaattc ccaagatttc atctatatca ttctcgaatc cgaaattaga  70680
aattcccaag tagatatcct ttttcatccg atcgttgatg aaaatacgaa ctttattcgg  70740
taagacaatc atttactaag gagtaaaata ggaagtaatg ttcgtatgtc gttatcatcg  70800
tataaattaa aggtgtgttt tttaccatta agtgacatta taattttacc aatattggaa  70860
ttataatata ggtgtatttg cgcactcgcg acggttgatg catcggtaaa tatagctgta  70920
tctaatgttc tagtcggtat ttcatcattt cgctgtctaa taatagcgtt ttctctatct  70980
gtttccatta cagctgcctg aagtttattg gtcggataat atgtaaaata ataagaaata  71040
catacgaata acaaaaataa aataagatat aataaagatg ccatttagag atctaatttt  71100
gttcaacttg tccaaattcc tacttacaga agatgaggaa tcgttggaga tagtgtcttc  71160
cttatgtaga ggatttgaaa tatcttatga tgacttgata acttactttc cagataggaa  71220
ataccataaa tatatttcta aagtatttga acatgtagat ttatcggagg aattaagtat  71280
ggaattccat gatacaactt tgcgagattt agtctatctt agattgtaca agtattccaa  71340
gtgtatacgg ccgtgttata aattaggaga taatctaaaa ggcatagttg ttataaagga  71400
```

caggaatatt tatattaggg aagcaaatga tgacttgata gaatatctcc tcaaggaata 71460
cactcctcag atttatacat attctaatga gcgcgtcccc ataactggtt caaaattaat 71520
tctttgtgga ttttctcaag ttacatttat ggcgtataca acgtcgcata taacaacaaa 71580
taaaaaggta gatgttctcg tttccaaaaa atgtatagat gaactagtcg atccaataaa 71640
ttatcaaata cttcaaaatt tatttgataa aggaagcgga acaataaaca aaatactcag 71700
gaagatattt tattcggtaa caggtggcca aactccatag gtagcttttt ctatttcgga 71760
ttttagaatt tccaaattca ccagcgattt atctgttttg gtgaaatcca aggatttatt 71820
aatgtccaca aatgccattt gttttgtctg tggattgtat ttgaaaatgg aaacgatgta 71880
gttagataga tgcgctgcga agtttcctat tagggttccg cgcttcacgt cacccagcat 71940
acttgaatca ccatccttta aaaaaaatga taagatatca acatggagta tatcatactc 72000
ggattttaat tcttctactg catcactgac attttcacaa atactacaat acggtttacc 72060
gaaaataatc agtacgttct tcatttatgg gtatcaaaaa cttaaaatcg ttactgctgg 72120
aaaataaatc actgacgata ttagatgata atttatacaa agtatacaat ggaatatttg 72180
tggatacaat gagtatttat atagccgtcg ccaattgtgt cagaaactta gaagagttaa 72240
ctacggtatt cataaaatac gtaaacggat gggtaaaaaa gggagggcat gtaacccttt 72300
ttatcgatag aggaagtata aaaattaaac aagacgttag agacaagaga cgtaaatatt 72360
ctaaattaac caaggacaga aaaatgctag aattagaaaa gtgtacatcc gaaatacaaa 72420
atgttaccgg atttatggaa gaagaaataa aggcagaaat gcaattaaaa atcgataaac 72480
tcacatttca aatatattta tctgattctg ataacataaa aatatcattg aatgagatac 72540
taacacattt caacaataat gagaatgtta cattatttta ttgtgatgaa cgagacgcag 72600
aattcgttat gtgtctcgag gctaaaacac atttctctac cacaggagaa tggccgttga 72660
taataagtac cgatcaggat actatgctat ttgcatctgc tgataatcat cctaagatga 72720
taaaaaactt aactcaactg tttaaatatg ttccatctgc agaggataac tatttagcaa 72780
aattaacggc gttagtgaat ggatgtgatt tctttcctgg actctatggg gcatctataa 72840
cacccaacaa cttaaacaaa atacaattgt ttagtgattt tacaatcgat aatatagtca 72900
ctagtttggc aattaaaaat tattatagaa agactaactc taccgtagac gtgcgtaata 72960
ttgttacgtt tataaacgat tacgctaatt tagacgatgt ctactcgtat attcctcctt 73020
gtcaatgcac tgttcaagaa tttatatttt ccgcattaga tgaaaaatgg aatgaattta 73080
aatcatctta tttagaaagc gtgccgttac cctgccaatt aatgtatgcg ttagaaccac 73140
gcaaggagat tgatgtttca gaagttaaaa ctttatcatc ttatatagat ttcgaaaata 73200
ctaaatcaga tatcgatgtt ataaaatcta tatcctcgat cttcggatat tctaacgaaa 73260
actgtaacac gatagtattc ggcatctata aggataattt actactgagt ataaatagtt 73320
cattttactt taacgatagt ctgttaataa ccaatactaa aagtgataat ataataaata 73380
taggttacta gattaaaaat ggtgttccaa ctcgtgtgct ctacgtgcgg caaagatatt 73440
tctcacgaac gatataaatt gattatacga aaaaaatcat taaaggatgt actcgtcagt 73500
gtaaagaacg aatgttgtag gttaaaatta tctacacaaa tagaacctca acgtaactta 73560
acagtgcaac ctctattgga tataaactaa tatggatccg gttaatttta tcaagacata 73620
tgcgcctaga ggttctatta tttttattaa ttataccatg tcattaacaa gtcatttgaa 73680
tccatcgata gaaaaacatg tgggtattta ttatggtacg ttattatcgg aacacttggt 73740
agttgaatca acatatagaa aaggagttcg aatagtccca ttggatagtt tttttgaagg 73800
atatcttagt gcaaaagtat acatgttaga gaatattcaa gttatgaaaa tagcagctga 73860
tacgtcatta actttattgg gtattccgta tggatttggt catgatagaa tgtattgttt 73920
taaattggta gctgactgtt ataaaaatgc cggtattgat acatcgtcta aacgaatatt 73980
aggtaaagat atttttctga gccaaaactt cacagacgat aatagatgga taaagatata 74040
tgattctaat aatttaacat tttggcaaat tgattacctt aaagggtgag ttaatatgca 74100
taactactcc tccgttgttt tttccctcgt tctttttctt aacgttgttt gccatcactc 74160
tcataatgta aagatattct aaaatggtaa acttttgcat atcggacgca gaaattggta 74220
taaatgttgt aattgtatta tttcccgtca atggactagt cacagctcca tcagttttat 74280
atcctttaga gtatttctca ctcgtgtcta acattctaga gcattccatg atctgtttat 74340
cgttgatatt ggccggaaag atagattttt tattttttat tatattacta ttggcaattg 74400
tagatataac ttctggtaaa tatttttcta ccttttcaat ctcttctatt ttcaagccgg 74460
ctatatattc tgctatattg ttgctagtat caataccttt tctggctaag aagtcatatg 74520
tggtattcac tatatcagtt ttaactggta gttccattag cctttccact tctgcagaat 74580
aatcagaaat tggttcttta ccagaaaatc cagctactat aataggctca ccgatgatca 74640
ttggcaaaat cctatattgt accagattaa tgagagcata tttcatttcc aataattctg 74700
ctagttcttg agacattgat ttatttgatg aatctagttg gttctctaga tactctacca 74760
tttctgccgc atacaataac ttgttagata aaatcagggt tatcaaagtg tttagcgtgg 74820
ctagaatagt gggcttgcat gtattaaaga atgcggtagt atgagtaaac cgttttaacg 74880
aattatatag tctccagaaa tctgtggcgt tacatacatg agccgaatga catcgaagat 74940
tgtccaatat ttttaatagc tgctctttgt ccattatttc tatatttgac tcgcaacaat 75000
tgtagatacc attaatcacc gattcctttt tcgatgccgg acaatagcac aattgtttag 75060
ctttggactc tatgtattca gaattaatag atatatctct taatacagat tgcactatac 75120
attttgaaac tatgtcaaaa attgtagaac gacgctgttc tgcagccatt taactttaaa 75180
taatttacaa aaatttaaaa tgagcatccg tataaaaatc gataaactgc gccaaattgt 75240
ggcatatttt tcagagttca gtgaagaagt atctataaat gtagactcga cggatgagtt 75300
aatgtatatt tttgccgcct tgggcggatc tgtaaacatt tgggccatta tacctctcag 75360
tgcatcagtg ttctaccgcg gagccgaaaa tattgtgttt aatcttcctg tgtccaaggt 75420
aaaatcgtgt ttgtgtagtt ttcacaatga tgccatcata gatatagaac ctgatctgga 75480
aaataatcta gtaaaacttt ctagttatca tgtagtaagt gtcgattgta ataaggaact 75540
gatgcctatt aggacagata ctactatttg tctaagtata gatcaaaaga aatcttacgt 75600
gtttaatttt cacaagtatg aagaaaaatg ttgtggtaga accgtcattc atttagaatg 75660
gttgttgggc tttatcaagt gtattagtca gcatcagcat ttggctatta tgtttaaaga 75720
tgacaatatt attatgaaga ctcctggtaa tactgatgca ttttccaggg aatattctat 75780
gactgaatgt tctcaagaac tacaaaagtt ttctttcaaa atagctatct cgtctctcaa 75840
caaactacga ggattcaaaa agagagtcaa tgtttttgaa actagaatcg taatggataa 75900
tgacgataac attttaggaa tgttgttttc ggatagagtt caatccttta agatcaacat 75960
ctttatggcg tttttagatt aatactttca atgagataaa tatgggtggc ggagtaagtg 76020
ttgagctccc taaacgggat ccgcctccgg gagtacccac tgatgagatg ttattaaacg 76080
tggataaaat gcatgacgtg atagctcccg ctaagctttt agaatatgtg catataggac 76140
cactagcaaa agataaagag gataaagtaa agaaaagata tccagagttt agattagtca 76200
acacaggacc cggtggtctt tcggcattgt taagacaatc gtataatgga accgcaccca 76260
attgctgtcg cacttttaat cgtactcatt attggaagaa ggatggaaag atatcagata 76320
agtatgaaga gggtgcagta ttagaatcgt gttggccaga cgttcacgac accggaaaat 76380
gcgatgttga tttattcgac tggtgtcagg gggatacgtt cgatagaaac atatgccatc 76440
agtggatcgg ttcagccttt aataggagta atagaactgt agagggtcaa caatcgttaa 76500
taaatctgta taataagatg caaacattat gtagtaaaga tgctagtgta ccaatatgtg 76560
aatcattttt gcatcattta cgcgcacaca atacagaaga tagcaaagag atgatcgatt 76620
atattctaag acaacagtct gcggacttta aacagaaata tatgagatgt agttatccca 76680
ctagagataa gttagaagag tcattaaaat atgcggaacc tcgagaatgt tgggatccag 76740
agtgttcgaa tgccaatgtt aatttcttgc taacacgtaa ttataataat ttaggacttt 76800
gcaatattgt acgatgtaat actagcgtga acaacttaca gatggataaa acttcctcat 76860
taagattgtc atgtggatta agcaatagtg atagattttc tactgttccc gtcaatagag 76920
caaaagtagt tcaacataat attaaacact cgttcgacct aaaattgcat ttgatcagtt 76980
tattatctct cttggtaata tggatactaa ttgtagctat ttaaatgggt gccgcggcaa 77040
gcatacagac gacggtgaat acactcagcg aacgtatctc gtctaaatta gaacaagaag 77100
cgaatgctag tgctcaaaca aaatgtgata tagaaatcgg aaatttttat atccgacaaa 77160
accatggatg taacctcact gttaaaaata tgtgctctgc ggacgcggat gctcagttgg 77220
atgctgtgtt atcagccgct acagaaacat atagtggatt aacaccggaa caaaaagcat 77280
acgtgccagc tatgtttact gctgcgttaa acattcagac gagtgtaaac actgttgtta 77340
gagattttga aaattatgtg aaacagactt gtaattctag cgcggtcgtc gataacaaat 77400
taaagataca aaacgtaatc atagatgaat gttacggagc cccaggatct ccaacaaatt 77460
tggaatttat taatacagga tctagcaaag gaaattgtgc cattaaggcg ttgatgcaat 77520
tgacgactaa ggccactact caaatagcac ctaaacaagt tgctggtaca ggagttcagt 77580
tttatatgat tgttatcggt gttataatat tggcagcgtt gtttatgtac tatgccaagc 77640
gtatgttgtt cacatccacc aatgataaaa tcaaacttat tttagccaat aaggaaaacg 77700
tccattggac tacttacatg gacacattct ttagaacttc tccgatggtt attgctacca 77760
cggatatgca aaactgaaaa tatattgata atattttaat agattaacat ggaagttatc 77820
actgatcgtc tagacgatat agtgaaacaa aatatagcgg atgaaaaatt tgtagatttt 77880
gttatacacg gtctagagca tcaatgtcct gctatacttc gaccattaat taggttgttt 77940
attgatatac tattatttgt tatagtaatt tatattttta cggtacgtct agtaagtaga 78000
aattatcaaa tgttgttggc gttggtggcg ctagtcatca cattaactat tttttattac 78060
tttatactat aatagtacta gactgacttc taacaaacat ctcacctgcc ataaataaat 78120
gcttgatatt aaagtcttct atttctaaca ctattccatc tgtggaaaat aatactctga 78180
cattatcgct aattgacaca tcggtgagtg atatgcctat aaagtaataa tcttctttgg 78240
gcacatatac cagtgtacca ggttctaaca acctatttac tggtgctcct atagcatact 78300
ttttctttac cttgagaata tccatcgttt gcttggtcaa tagcgatatg tgattttttta 78360
tcaaccactc gaaaaagtaa ttggagtgtt catatcctct acgggctatt gtctcatggc 78420
cgtgtatgaa atttaagtaa cacgactgtg gtagatttgt tctatagagc cggttgccgc 78480
aaatagatag aactaccaat atgtctgtac aaatgttaaa cattaattga ttaacagaaa 78540
aaacaatgtt cgttctggga atagaaacca gatcaaaaca aaattcgtta gaatatatgc 78600
cacgtttata cattgaatat aaaataacta cagtttgaaa aataacagta tcatttaaac 78660
atttaacttg cggggttaat ctcacaactt tactgttttt gaactgttca aaatatagca 78720
tagatccgtg agaaatacgt ttagccgcct ttaatagagg aaatcccacc gcctttctgg 78780
atctcaccaa cgacgatagt tctgaccagc aactcatttc ttcatcatcc acctgtttta 78840
acatataata ggcaggagat agatatccgt cattgcaata ttccttctcg taggcacaca 78900
atctaatatt gataaaatct ccattctctt ctctgcattt attatcttgt ttcggtggct 78960
gattaggctg tagtcttggt ttaggctttg gtatatcgtt gttgaatcta ttttggtcat 79020
taaatctttc atttcttcct ggtatatttt tatcacctcg tttggttgga tttttgtcta 79080
tattatcgtt tgtaacatcg gtacgggtat tcatttatca caaaaaaaac ttctctaaat 79140
gagtctactg ctagaaaacc tcatcgaaga agataccata ttttttgcag gaagtatatc 79200
tgagtatgat gatttacaaa tggttattgc cggcgcaaaa tccaaatttc caagatctat 79260
gctttctatt tttaatatag tacctagaac gatgtcaaaa tatgagttgg agttgattca 79320
taacgaaaat atcacaggag caatgtttac cacaatgtat aatataagaa acaatttggg 79380
tctaggagat gataaactaa ctattgaagc cattgaaaac tatttcttgg atcctaacaa 79440
tgaagttatg cctcttatta ttaataatac ggatatgact gccgtcattc ctaaaaaaag 79500
tggtaggaga aagaataaga acatggttat cttccgtcaa ggatcatcac ctatcttgtg 79560
tattttcgaa actcgtaaaa agattaatat ttataaagaa aatatggaat ccgcgtcgac 79620
tgagtataca cctatcggag acaacaaggc tttgatatct aaatatgcgg gaattaatat 79680
cctaaatgtg tattctcctt ccacatccat aagattgaat gccatttacg gattcaccaa 79740
taaaaataaa ctagagaaac ttagtactaa taaggaacta gaatcgtata gttctagccc 79800
tcttcaagaa cccattaggt taaatgattt tctgggacta ttggaatgtg ttaaaaagaa 79860
tattcctcta acagatattc cgacaaagga ttgattacta taaatggaga atgttcctaa 79920
tgtatacttt aatcctgtgt ttatagagcc cacgtttaaa cattctttat taagtgttta 79980
taaacacaga ttaatagttt tatttgaagt attcgttgta ttcattctaa tatatgtatt 80040
ttttagatct gaattaaata tgttcttcat gcctaaacga aaaatacccg atcctattga 80100
tagattacga cgtgctaatc tagcgtgtga agacgataaa ttaatgatct atggattacc 80160
atggatgaca actcaaacat ctgcgttatc aataaatagt aaaccgatag tgtataaaga 80220
ttgtgcaaag cttttgcgat caataaatgg atcacaacca gtatctctta acgatgttct 80280
tcgcagatga tgattcattt tttaagtatt tggctagtca agatgatgaa tcttcattat 80340
ctgatatatt gcaaatcact caatatctag actttctgtt attattattg atccaatcaa 80400
aaaataaatt agaagccgtg ggtcattgtt atgaatctct ttcagaggaa tacagacaat 80460
tgacaaaatt cacagacttt caagatttta aaaaactgtt taacaaggtc cctattgtta 80520
cagatggaag ggtcaaactt aataaaggat atttgttcga ctttgtgatt agtttgatgc 80580
gattcaaaaa agaatcctct ctagctacca ccgcaataga tcctgttaga tacatagatc 80640
ctcgtcgcaa tatcgcattt tctaacgtga tggatatatt aaagtcgaat aaagtgaaca 80700
ataattaatt ctttattgtc atcatgaacg gcggacatat tcagttgata atcggcccca 80760
tgttttcagg taaaagtaca gaattaatta gacgagttag acgttatcaa atagctcaat 80820
ataaatgcgt gactataaaa tattctaacg ataatagata cggaacggga ctatggacgc 80880

-continued

```
atgataagaa taattttgaa gcattggaag caactaaact atgtgatgtc ttggaatcaa  80940
ttacagattt ctccgtgata ggtatcgatg aaggacagtt ctttccagac attgttgaat  81000
tctgtgagcg tatggcaaac gaaggaaaaa tagttatagt agccgcactc gatgggacat  81060
ttcaacgtaa accgtttaat aatattttga atcttattcc attatctgaa atggtggtaa  81120
aactaactgc tgtgtgtatg aaatgcttta aggaggcttc cttttctaaa cgattgggtg  81180
aggaaaccga gatagaaata ataggaggta atgatatgta tcaatcggtg tgtagaaagt  81240
gttacatcga ctcataatat tatatttttt atctaaaaaa ctaaaaataa acattgatta  81300
aattttaata taatacttaa aaatggatgt tgtgtcgtta gataaaccgt ttatgtattt  81360
tgaggaaatt gataatgagt tagattacga accagaaagt gcaaatgagg tcgcaaaaaa  81420
actgccgtat caaggacagt taaaactatt actaggagaa ttattttttc ttagtaagtt  81480
acagcgacac ggtatattag atggtgccac cgtagtgtat ataggatctg ctcccggtac  81540
acatatacgt tatttgagag atcatttcta taatttagga gtgatcatca aatggatgct  81600
aattgacggc cgccatcatg atcctatttt aaatggattg cgtgatgtga ctctagtgac  81660
tcggttcgtt gatgaggaat atctacgatc catcaaaaaa caactgcatc cttctaagat  81720
tattttaatt tctgatgtga gatccaaacg aggaggaaat gaacctagta cggcggattt  81780
actaagtaat tacgctctac aaaatgtcat gattagtatt ttaaaccccg tggcgtctag  81840
tcttaaatgg agatgcccgt ttccagatca atggatcaag gacttttata tcccacacgg  81900
taataaaatg ttacaacctt ttgctccttc atattcagct gaaatgagat tattaagtat  81960
ttataccggt gagaacatga gactgactcg agttaccaaa tcagacgctg taaattatga  82020
aaaaaagatg tactacctta ataagatcgt ccgtaacaaa gtagttgtta actttgatta  82080
tcctaatcag gaatatgact attttcacat gtactttatg ctgaggaccg tgtactgcaa  82140
taaaacattt cctactacta aagcaaaggt actatttcta caacaatcta tatttcgttt  82200
cttaaatatt ccaacaacat caactgaaaa agttagtcat gaaccaatac aacgtaaaat  82260
atctagcaaa aattctatgt ctaaaaacag aaatagcaag agatccgtac gcagtaataa  82320
atagaaacgt actactgaga tatactaccg atatagagta taatgattta gttactttaa  82380
taaccgttag acataaaatt gattctatga aaactgtgtt tcaggtattt aacgaatcat  82440
ccataaatta tactccggtt gatgatgatt atggagaacc aatcattata acatcgtatc  82500
ttcaaaaagg tcataacaag tttcctgtaa attttctata catagatgtg gtaatatctg  82560
acttatttcc tagctttgtt agactagata ctacagaaac taatatagtt aatagtgtac  82620
tacaaacagg cgatggtaaa aagactcttc gtcttcccaa aatgttagag acggaaatag  82680
ttgtcaagat tctctatcgc cctaatatac cattaaaaat tgttagattt ttccgcaata  82740
acatggtaac tggagtagag atagccgata gatctgttat ttcagtcgct gattaatcaa  82800
ttagtagaga tgagataaga acattataat aatcaataat atatcttata tctcgtttag  82860
aaaaatgcta atattaaaat agctaacgct agtaatccaa tcggaagcca tttgatatct  82920
ataatagggt atctaatttc ctgattcaga tagcggacag ctatattctc ggtagctact  82980
cgtttggaat cacaaacatt atttacatct aatttactat ctgtaatgga aacgtttccc  83040
aatgaaatgg tacaatccga tacattgcat tttgttatat ttttttttaa agaggctggt  83100
aacaacgcat cgcttcgttt acatggctcg taccaacaat aatagggtaa tcttgtatct  83160
attcctatcc gtactatgct tttatcagga taaatacatt tacatcgtat atcgtctttg  83220
```

-continued

```
ttagcatcac agaatgcata aatttgttcg tccgtcatga taaaaattta aagtgtaaat  83280
ataactatta tttttatagt tgtaataaaa agggaaattt gattgtatac cttcggttct  83340
ttaaaagaaa ctgacttgat aaaaatggct gtaatctcta aggttacgta tagtctatat  83400
gatcaaaaag agattaatgc tacagatatt atcattagtc atgttaaaaa tgacgacgat  83460
atcggtaccg ttaaagatgg tagactaggt gctatggatg gggcattatg taagacttgt  83520
gggaaaacgg aattggaatg tttcggtcac tggggtaaag taagtattta taaaactcat  83580
atagttaagc ctgaatttat ttcagaaatt attcgtttac tgaatcatat atgtattcac  83640
tgcggattat tgcgttcacg agaaccgtat tccgacgata ttaacctaaa agagttatcg  83700
ggacacgctc ttaggagatt aaaggataaa atattatcca agaaaaagtc atgttggaac  83760
agtgaatgta tgcaaccgta tcaaaaaatt actttttcaa agaaaaaggt ttgtttcgtc  83820
aacaagttgg atgatattaa cgttcctaat tctctcatct atcaaaagtt aatttctatt  83880
catgaaaagt tttggccatt attagaaatt catcaatatc cagctaactt attttataca  83940
gactactttc ccatccctcc gttgattatt agaccggcta ttagtttttg gatagatagt  84000
atacccaaag aaaccaatga attaacttac ttattaggta tgatcgttaa gaattgtaac  84060
ttgaatgctg atgaacaggt tatccagaag gcggtaatag aatacgatga tattaaaatt  84120
atttctaata acacttccag tatcaattta tcatatatta catccggcaa aaataatatg  84180
attagaagtt atatcgtcgc ccgacgaaaa gatcagacgg ctagatctgt aattggtccc  84240
agtacatcta tcaccgttaa tgaggtagga atgcccgcat atattagaaa tacacttaca  84300
gaaaagatat ttgttaatgc ctttacagtg gataaagtta aacaactatt agcatcaaac  84360
caagttaaat tttactttaa taaacgatta aaccaattaa caagaatacg ccaaggaaag  84420
tttatcaaaa ataaaataca tttattgcct ggtgattggg tagaagtagc tgttcaagaa  84480
tatacaagta ttatttttgg aagacagccg tctctacata gatacaacgt catcgcttca  84540
tctatcagag ctaccgaagg agatactatc aaaatatctc ccggaattgc caactctcaa  84600
aatgctgatt tcgacggaga tgaagaatgg atgatattag aacaaaatcc taaagctgta  84660
attgaacaaa gtattcttat gtatccgacg acgttactca aacacgatat tcatggagcc  84720
cccgtttatg gatctattca agatgaaatc gtagcagcgt attcattgtt taggatacaa  84780
gatctttgtt tagatgaagt attgaacatc ttggggaaat atggaagaga gttcgatcct  84840
aaaggtaaat gtaaattcag cggtaaagat atctatactt acttgatagg tgaaaagatt  84900
aattatccgg gtctcttaaa ggatggtgaa attattgcaa acgacgtaga tagtaatttt  84960
gttgtggcta tgaggcatct gtcattggct ggactcttat ccgatcataa gtcgaacgtg  85020
gaaggtatca actttattat caagtcatct tatgttttta agagatatct atctatttac  85080
ggttttgggg tgacattcaa agatctgaga ccaaattcga cgttcactaa taaattggag  85140
gccatcaacg tagaaaaaat agaacttatc aaagaagcat acgccaaata tctcaacgat  85200
gtaagagacg ggaaaatagt tccattatct aaagctttag aggcggacta tgtggaatcc  85260
atgttatcca acttgacaaa tcttaatatc cgagagatag aagaacatat gagacaaacg  85320
ctgatagatg atccagataa taacctcctg aaaatggcca aagcgggtta taaagtaaat  85380
cctacagaac taatgtatat tctaggtacg tatggacaac aaaggattga tggtgaacca  85440
gcagagactc gagtattggg tagagtctta ccttactatc ttccagactc taaggatcca  85500
gaaggaagag gttacattct taattcttta acaaaaggat taacaggttc tcaatattac  85560
ttttcgatgc tggttgcaag atctcaatct actgatatcg tctgtgaaac atcacgtacc  85620
```

ggaacactgg ctagaaaaat cattaaaaag atggaggata tggtggtcga cggatacgga 85680
caagtagtta taggtaatac gctcatcaag tacgccgcca attataccaa aattctaggc 85740
tcagtatgta aacctgtaga tcttatctat ccagatgagt ccatgacttg gtatttggaa 85800
attagtgctc tgtggaataa aataaaacag ggattcgttt actctcagaa acagaaactt 85860
gcaaagaaga cattggcgcc gtttaatttc ctagtattcg tcaaacccac cactgaggat 85920
aatgctatta aggttaagga tctgtacgat atgattcata acgtcattga tgatgtgaga 85980
gagaaatact tctttacggt atctaatata gattttatgg agtatatatt cttgacgcat 86040
cttaatcctt ctagaattag aattacaaaa gaaacggcta tcactatctt tgaaaagttc 86100
tatgaaaaac tcaattatac tctaggtggt ggaactccta ttggaattat ttctgcacag 86160
gtattgtctg agaagtttac acaacaagcc ctgtccagtt ttcacactac tgaaaaaagt 86220
ggtgccgtca aacaaaaact tggtttcaac gagtttaata acttgactaa tttgagtaag 86280
aataagaccg aaattatcac tctggtatcc gatgatatct ctaaacttca atctgttaag 86340
attaatttcg aatttgtatg tttgggagaa ttaaatccag acatcactct tcgaaaagaa 86400
acagataggt atgtagtaga tataatagtc aatagattat acatcaagag agcagaaatt 86460
accgaattag tcgtcgaata tatgattgaa cgattcatct cctttagcgt cattgtaaag 86520
gaatggggta tggaaacatt cattgaggac gaggataata ttagatttac tgtctatcta 86580
aatttcgttg aaccagagga attgaatctt agtaagttta tgatggttct tccgggggca 86640
gccaacaagg gaaagattag taaattcaag attcctatct ctgattatac gggttatgac 86700
gacttcaatc aaacaaaaaa gctcaataag atgactgtag aactcatgaa tctaaaagaa 86760
ttaggttctt tcgatttgga aaacgtcaac gtgtatcctg gagtatggaa tacatacgat 86820
atcttcggta tcgaggccgc tcgtgaatac ttgtgcgaag ccatgttaaa cacctatgga 86880
gaagggttcg attatctgta tcagccttgt gatcttctcg ctagtttact atgtgctagt 86940
tacgaaccag aatcagtgaa taaattcaag ttcggcgcag ctagtactct taagagagct 87000
acgttcggag acaataaagc attgttaaac gcggctcttc ataaaaagtc agaacctatt 87060
aacgataata gtagctgcca ctttttagc aaggtcccta atataggaac tggatattac 87120
aaatacttta tcgacttggg tcttctcatg agaatggaaa ggaaactatc tgataagata 87180
tcttctcaaa agatcaagga aatggaagaa acagaagact tttaattctt atcaataaca 87240
tatttttcta tgatctgtct tttaaacgat ggattttcca caaatgcgcc tctcaagtcc 87300
ctcatagaat gatacacgta taaaaaatat agcataggca atgactcctt atttttagac 87360
attagatatg ccaaaatcat agccccgctt ctatttactc ccgcagcaca atgaaccaac 87420
acgggctcgt ttcgttgatc acatttagat aaaaaggcgg ttacgtcgtc aaaatattta 87480
ctaatatcgg tagttgtatc atctaccaac ggtatatgaa taatattaat attagagtta 87540
ggtaatgtat atttatccat cgtcaaattt aaaacatatt tgaacttaac ttcagatgat 87600
ggtgcatcca tagcattttt ataatttccc aaatacacat tattggttac ccttgtcatt 87660
atagtgggag atttggctct gtgcatatct ccagttgaac gtagtagtaa gtatttatac 87720
aaacttttct tatccattta taacgtacaa atggataaaa ctactttatc ggtaaacgcg 87780
tgtaatttag aatacgttag agaaaaggct atagtaggcg tacaagcagc caaaacatca 87840
acacttatat tctttgttat tatattggca attagtgcgc tattactctg gtttcagacg 87900
tctgataatc cagtctttaa tgaattaacg agatatatgc gaattaaaaa tacggttaac 87960

-continued gattggaaat cattaacgga tagcaaaaca aaattagaaa gtgatagagg tagacttcta 88020
gccgctggta aggatgatat attcgaattc aaatgtgtgg atttcggcgc ctattttata 88080
gctatgcgat tggataagaa aacatatctg ccgcaagcta ttaggcgagg tactggagac 88140
gcgtggatgg ttaaaaaggc ggcaaaggtc gatccatctg ctcaacaatt ttgtcagtat 88200
ttgataaaac acaagtctaa taatgttatt acttgtggta atgagatgtt aaatgaatta 88260
ggttatagcg gttattttat gtcaccgcat tggtgttccg attttagtaa tatggaatag 88320
tgttagataa atgcggtaac gaatgttcct gtaaggaacc ataacagttt agatttaacg 88380
ttaaagatga gcataaacat aataaacaaa attacaatca aacctataac attaatatca 88440
aacaatccaa aaaatgaaat cagtggagta gtaaacgcgt acataactcc tggataacgt 88500
ttagtagctg ccgttcctat tctagaccaa aaattcggtt tcatgttttc gaaacggtgt 88560
tctgcaacaa gtcggggatc gtgttctaca tatttggcgg cattatccag tatctgccta 88620
ttgatcttca tttcgttttc aattctggct atttcaaaat aaaatcccga tgatagacct 88680
ccagacttta taatttcatc tacgatgttc agcgccgtag taactctaat aatataggct 88740
gataagctaa catcataccc tcctgtatat gtgaatatgg catgattttt gtccattaca 88800
agctcggttt taactttatt gcctgtaata atttctctca tctgtaggat atctattttt 88860
ttgtcatgca ttgccttcaa gacgggacga agaaacgtaa tatcctcaat aacgttatcg 88920
ttttctacaa taactacata ttctaccttt ttattttcta actcggtaaa aaaattagaa 88980
tcccataggg ctaaatgtct agcgatattt cttttcgttt cctctgtaca catagtgtta 89040
caaaaccctg aaaagaagtg agtatacttg tcatcatttc taatgtttcc tccagtccac 89100
tgtataaacg cataatcctt gtaatgatct ggatcatcct tgactaccac aacatttctt 89160
ttttctggca taacttcgtt gtcctttaca tcatcgaact tctgatcatt aatatgctca 89220
tgaacattag gaaatgtttc tgatggaagt ctatcaataa ctggcacaac aataacagga 89280
gttttcgccg ccgccattta gttattgaaa ttaatcatat acaactcttt aatacgagtt 89340
atattttcgt ctatccattg tttcacattt acatatttcg acaaaaagat ataaaatgcg 89400
tattccaatg cttctctgtt taatgaatta ctaaaatata caaacacgtc actgtctggc 89460
aataaatgat atcttagaat attgtaacaa tttattttgt attgcacatg ttcgtgatct 89520
atgagttctt cttcgaatgg cataggatct ccgaatctga aaacgtataa ataggagtta 89580
gaataataat atttgagagt attggtaata tataaactct ttagcggtat aattagtttt 89640
tttctctcaa tttctatttt tagatgtgat ggaaaaatga ctaattttgt agcattagta 89700
tcatgaactc taatcaaaat cttaatatct tcgtcacacg ttagctcttt gaagttttta 89760
agagatgcat cagttggttc gaccgatgga gtaggtgcaa caattttttg ttcgatgtat 89820
gtatgtactg gagccattgt tttaactata atggtgcttg tatcgaaaaa ctttaatgca 89880
gatagcggaa gctcttcgcc gcgactttct acatcgtaat tgggttctaa cgccgatctc 89940
tgaatggata ctagttttct aagttctaat gtgattctct gaaaatgtaa atccaattcc 90000
tccggcatta tagatgtgta tacatcggta aataaaacta tagtatccaa cgatcccttc 90060
tcgcaaattc tagtcttaac caaaaaatcg tatataacca cggagatggc gtatttaaga 90120
gtggattctt ctaccgtttt gttcttggat gtcatatagg aaactataaa gtccgcacta 90180
ctgttaagaa tgattactaa cgcaactata tagttcaaat taagcatttt ggaaacataa 90240
aataactctg tagacgatac ttgactttcg aataagtttg cagacaaacg aagaaagaac 90300
agacctctct taatttcaga agaaaacttt ttttcgtatt cctgacgtct agagtttata 90360

-continued

```
tcaataagaa agttaagaat tagtcggtta atgttgtatt tcattaccca agtttgagat  90420
ttcataatat tatcaaaaga catgataata ttaaagataa agcgctgact atgaacgaaa  90480
tagctatatg gttcgctcaa aaatatagtc ttgttaaacg tggaaacgat aactgtattt  90540
ttaatcacgt cagcggcatc taaattaaat ataggtatat ttattccaca cactctacaa  90600
tatgccacac catcttcata ataaataaat tcgttagcaa aattattaat tttagtgaaa  90660
tagttagcgt caactttcat agcttccttc aatctaattt gatgctcaca cggtgcgaat  90720
tccactctaa catccctttt ccatgcctca ggttcatcga tctctataat atctagtttt  90780
ttgcgtttca caaacacagg ctcgtctctc gcgatgagat ctgtatagta actatgtaaa  90840
tgataactag atagaaagat gtagctatat agatgacgat cctttaagag aggtataata  90900
actttacccc aatcagatag actgttgtta tggtcttcgg aaaaagaatt tttataaatt  90960
tttccagtat tttccaaata tacgtactta acatctaaaa aatccttaat gataatagga  91020
atggataatc cgtctatttt ataaagaaat acatatcgca cattatactt tttttggaa  91080
atgggaatac cgatgtgtct acataaatat gcaaagtcta aatatttttt agagaatctt  91140
aattggtcca aattcttttc caagtacggt aatagatttt tcatattgaa cggtatcttc  91200
ttaatctctg gttctagttc cgcattaaat gatgaaacta agtcactatt tttataacta  91260
acgattacat cacctctaac atcatcattt accagaatac tgatcttctt ttgtcgtaaa  91320
tacatgtcta atgtgttaaa aaaaagatca tacaagttat acgtcatttc atctgtggta  91380
ttcttgtcat tgaaggataa actcgtacta atctcttctt taacagcctg ttcaaattta  91440
tatcctatat acgaaaaaat agcaaccagt gtttgatcat ccgcgtcaat attctgttct  91500
atcgtagtgt ataacaatcg tatatcttct tctgtgatag tcgatacgtt ataaaggttg  91560
ataacgaaaa tatttttatt tcgtgaaata aagtcatcgt aggattttgg acttatattc  91620
gcgtctagta gatatgcttt tatttttgga atgatctcaa ttagaatagt ctctttagag  91680
tccatttaaa gttacaaaca actaggaaat tggtttatga tgtataattt ttttagtttt  91740
tatagattct ttattctata cttaaaaaat gaaaataaat acaaaggttc ttgagggttg  91800
tgttaaattg aaagcgagaa ataatcataa attatttcat tatcgcgata tccgttaagt  91860
ttgtatcgta atggcgtggt caattacaaa taaagcggat actagtagct tcacaaagat  91920
ggctgaaatc agagctcatc taaaaaatag cgctgaaaat aaagataaaa acgaggatat  91980
tttcccggaa gatgtaataa ttccatctac taagcccaaa accaaacgag ccactactcc  92040
tcgtaaacca gcggctacta aaagatcaac caaaaaggag gaagtggaag aagaagtagt  92100
tatagaggaa tatcatcaaa caactgaaaa aaattctcca tctcctggag tcagcgacat  92160
tgtagaaagc gtggccgctg tagagctcga tgatagcgac ggggatgatg aacctatggt  92220
acaagttgaa gctggtaaag taaatcatag tgctagaagc gatctctctg acctaaaggt  92280
ggctaccgac aatatcgtta aagatcttaa gaaaattatt actagaatct ctgcagtatc  92340
gacggttcta gaggatgttc aagcagctgg tatctctaga caatttactt ctatgactaa  92400
agctattaca acactatctg atctagtcac cgagggaaaa tctaaagttg ttcgtaaaaa  92460
agttaaaact tgtaagaagt aaatgcgtgc actttttat aaagatggta aactctttac  92520
cgataataat tttttaaatc ctgtatcaga cgataatcca gcgtatgagg ttttgcaaca  92580
tgttaaaatt cctactcatt taacagatgt agtagtatat gaacaaacgt gggaggaggc  92640
gttaactaga ttaattttg tgggaagtga ttcaaaagga cgtagacaat acttttacgg  92700
```

aaaaatgcat gtacagaatc gcaacgctaa aagagatcgt atttttgtta gagtatataa 92760
cgttatgaaa cgaattaatt gttttataaa caaaaatata aagaaatcgt ccacagattc 92820
caattatcag ttggcggttt ttatgttaat ggaaactatg tttttatta gatttggtaa 92880 aatgaaatat cttaaggaga atgaaacagt agggttatta acactaaaaa ataaacacat 92940
agaaataagt cccgatgaaa tagttatcaa gtttgtagga aaggacaaag tttcacatga 93000
atttgttgtt cataagtcta atagactata taagccgcta ttgaaactga cggatgattc 93060
tagtcccgaa gaatttctgt tcaacaaact aagtgaacga aaggtatatg aatgtatcaa 93120
acagtttggt attagaatca aggatctccg aacgtatgga gtcaattata cgtttttata 93180
taatttttgg acaaatgtaa agtccatatc tcctcttcca tcaccaaaaa agttaatagc 93240
gttaactatc aaacaaactg ctgaagtggt aggtcatact ccatcaattt caaaaagagc 93300
ttatatggca acgactattt tagaaatggt aaaggataaa aatttttag atgtagtatc 93360 taaaactacg ttcgatgaat tcctatctat agtcgtagat cacgttaaat catctacgga 93420
tggatgatat agatctttac acaaataatt acaaaaccga taaatggaaa tggataagcg 93480
tatgaaatct ctcgcaatga ccgctttctt tggggagcta agcacattag atattatggc 93540
attgataatg tctatattta aacgccatcc aaacaatacc atttttcag tggataagga 93600 tggtcagttt atgattgatt tcgaatacga taattataag gcttctcaat atttggatct 93660
gaccctcact ccgatatctg gagatgaatg caagactcac gcatcgagta tagccgaaca 93720
attggcgtgt gtggatatta ttaaagagga tattagcgaa tatatcaaaa ctactccccg 93780
tcttaaacga tttataaaaa aataccgcaa tagatcagat actcgcatca gtcgagatac 93840
agaaaagctt aaaatagctc tagctaaagg catagattac gaatatataa aagacgcttg 93900
ttaataagta aatgaaaaaa aactagtcgt ttataataaa acacgatatg gatgccaacg 93960
tagtatcatc ttctactatt gcgacgtata tagacgcttt agcgaagaat gcttcggaat 94020
tagaacagag gtctaccgca tacgaaataa ataatgaatt ggaactagta tttattaagc 94080
cgccattgat tactttgaca aatgtagtga atatctctac gattcaggaa tcgtttattc 94140
gatttaccgt tactaataag gaaggtgtta aaattagaac taagattcca ttatctaagg 94200
tacatggtct agatgtaaaa aatgtacagt tagtagatgc tatagataac atagtttggg 94260
aaaagaaatc attagtgacg gaaaatcgtc ttcacaaaga atgcttgttg agactatcga 94320
cagaggaacg tcatatattt ttggattaca agaaatatgg atcctctatc cgactagaat 94380
tagtcaatct tattcaagca aaaacaaaaa actttacgat agactttaag ctaaaatatt 94440
ttctaggatc cggtgcccag tctaaaagtt ctttattaca cgctattaat catccaaagt 94500
caaggcctaa tacatctctg gaaatagaat ttacacctag agacaatgaa acagttccat 94560
atgatgaact aataaaggaa ttgacgactc tctcgcgtca tatatttatg gcttctccag 94620
agaatgtaat tctttctccg cctattaacg cgcctataaa aacctttatg ttgcctaaac 94680
aagatatagt aggtttggat ctggaaaatc tatatgccgt aactaagact gacggcattc 94740
ctataactat cagagttaca tcaaacgggt tgtattgtta ttttacacat cttggttata 94800
ttattagata tcctgttaag agaataatag attccgaagt agtagtcttt ggtgaggcag 94860
ttaaggataa gaactggacc gtatatctca ttaagctaat agagcctgtg aatgcaatca 94920
atgatagact agaagaaagt aagtatgttg aatctaaact agtggatatt tgtgatcgga 94980
tagtattcaa gtcaaagaaa tacgaaggtc cgtttactac aactagtgaa gtcgtcgata 95040
tgttatctac atatttacca aagcaaccag aaggtgttat tctgttctat tcaaagggac 95100
ctaaatctaa cattgatttt aaaattaaaa aggaaaatac tatagaccaa actgcaaatg 95160
tagtatttag gtacatgtcc agtgaaccaa ttatctttgg agagtcgtct atctttgtag 95220
agtataagaa atttagcaac gataaaggct ttcctaaaga atatggttct ggtaagattg 95280
tgttatataa cggcgttaat tatctaaata atatctattg tttggaatat attaatacac 95340
ataatgaagt gggtattaag tccgtggttg tacctattaa gtttatagca gaattcttag 95400
ttaatggaga aatacttaaa cctagaattg ataaaaccat gaaatatatt aactcagaag 95460
attattatgg aaatcaacat aatatcatag tcgaacattt aagagatcaa agcatcaaaa 95520
taggagatat ctttaacgag gataaactat cggatgtggg acatcaatac gccaataatg 95580
ataaatttag attaaatcca gaagttagtt attttacgaa taaacgaact agaggaccgt 95640
tgggaatttt atcaaactac gtcaagactc ttcttatttc tatgtattgt tccaaaacat 95700
ttttagacga ttccaacaaa cgaaaggtat tggcgattga ttttggaaac ggtgctgacc 95760
tggaaaaata cttttatgga gagattgcgt tattggtagc gacggatccg gatgctgatg 95820
ctatagctag aggaaatgaa agatacaaca aattaaactc tggaattaaa accaagtact 95880
acaaatttga ctacattcag gaaactattc gatccgatac atttgtctct agtgtcagag 95940
aagtattcta ttttggaaag tttaatatca tcgactggca gtttgctatc cattattctt 96000
ttcatccgag acattatgct accgtcatga ataacttatc cgaactaact gcttctggag 96060
gcaaggtatt aatcactacc atggacggag acaaattatc aaaattaaca gataaaaaga 96120
cttttataat tcataagaat ttacctagta gcgaaaacta tatgtctgta gaaaaaatag 96180
ctgatgatag aatagtggta tataatccat caacaatgtc tactccaatg actgaataca 96240
ttatcaaaaa gaacgatata gtcagagtgt ttaacgaata cggatttgtt cttgtagata 96300
acgttgattt cgctacaatt atagaacgaa gtaaaaagtt tattaatggc gcatctacaa 96360
tggaagatag accatctaca agaaactttt tcgaactaaa tagaggagcc attaaatgtg 96420
aaggtttaga tgtcgaagac ttacttagtt actatgttgt ttatgtcttt tctaagcggt 96480
aaataataat atggtatggg ttctgatctc ccagttctaa atgcattaaa taattccaat 96540
agagcgattt ttgttcctat aggaccttcc aactgtggat actctgtatt gttaatagat 96600
atattaatac ttttgtcggg taacagaggt tctacgtctt ttaaaaataa aagtttgata 96660
acatctggcc tgttcataaa taaaaacttg gcgattctat atatactctt attatcaaat 96720
ctagccattg tcttatagat gtgagctact gtaggtgtac catttgattt tctttctaat 96780
actatatatt tctctcgaag aagttcttgc acatcatctg ggaataaaat actactgttg 96840
agtaaatcag ttattttttt tatatcgata ttgatggaca tttttatagt taaggataat 96900
aagtatccca aagtagataa cgacgataac gaagtattta tacttttagg aaatcacaat 96960
gactttatca gattaaaatt aacaaaatta aaggagcatg tatttttttc tgaatatatt 97020
gtgactccag atacatatgg atctttatgc gtcgaattaa atgggtctag ttttcagcac 97080
ggcggtagat atatagaggt ggaggaattt atagatgctg gaagacaagt tagatggtgt 97140
tctacatcca atcatatatc taaagatata cccgaagata tgcacactga taaatttgtc 97200
atttatgata tatacacttt tgacgctttc aagaataaac gattggtatt cgtacaggta 97260
cctccgtcgt taggagatga tagtcatttg actaatccgt tattgtctcc gtattatcgt 97320
aattcagtag ccagacaaat ggtcaatgat atgattttta atcaagattc atttttaaaa 97380
tatttattag aacatctgat tagaagccac tatagagttt ctaaacatat aacaatagtt 97440
agatacaagg ataccgaaga attaaatcta acgagaatat gttataatag agataagttt 97500
aaggcgtttg tattcgcttg gtttaacggc gtttcggaaa atgaaaaggt actagatacg 97560
tataaaaagg tatctaattt gatataatga attcagtgac tgtatcacac gcgccatata 97620
ctattactta tcacgatgat tgggaaccag taatgagtca attggtagag ttttataacg 97680
aagtagccag ttggctgcta cgagacgaga cgtcgcctat tcctgataag ttctttatac 97740
agttgaaaca accgcttaga aataaacgag tatgtgtgtg cggtatagat ccgtatccga 97800
aagatggaac tggtgtaccg ttcgaatcac caaattttac aaaaaaatca attaaggaga 97860
tagcttcatc tatatctaga ttaaccggag taattgatta taaaggttat aaccttaata 97920
taatagacgg ggttataccc tggaattatt acttaagttg taaattagga gaaacaaaaa 97980
gtcacgcgat ctactgggat aagatttcca agttactgct gcagcatata actaaacacg 98040
ttagtgttct ttattgtttg ggtaaaacag atttctcgaa tatacgggcc aagttagaat 98100
ccccggtaac taccatagtc ggatatcatc cagcggctag agaccgccaa ttcgagaaag 98160
atagatcatt tgaaattatc aacgttttac tggaattaga caacaaggca cctataaatt 98220
gggctcaagg gtttatttat taatgcttta gtgaaatttt aacttgtgtt ctaaatggat 98280
gcggctatta gaggtaatga tgttatcttt gttcttaaga ctataggtgt cccgtcagcg 98340
tgcagacaaa atgaagatcc aagatttgta gaagcattta aatgcgacga gttagaaaga 98400
tatattgaga ataatccaga atgtacacta ttcgaaagtc ttagggatga ggaagcatac 98460
tctatagtca gaattttcat ggatgtagat ttagacgcgt gtctagacga aatagattat 98520
ttaacggcta ttcaagattt tattatcgag gtgtcaaact gtgtagctag attcgcgttt 98580
acagaatgcg gcgccattca tgaaaatgta ataaaatcca tgagatctaa tttttcattg 98640
actaagtcta caaatagaga taaaacaagt tttcatatta tctttttaga cacgtatacc 98700
actatggata cattgatagc tatgaaacga acactattag aattaagtag atcatctgaa 98760
aatccactaa caagatcgat agacactgcc gtatatagga gaaaaacaac tcttcgggtt 98820
gtaggtacta ggaaaaatcc aaattgcgac actattcatg taatgcaacc accgcatgat 98880
aatatagaag attacctatt cacttacgtg gatatgaaca acaatagtta ttacttttct 98940
ctacaacaac gattggagga tttagttcct gataagttat gggaaccagg gtttatttca 99000
ttcgaagacg ctataaaaag agtttcaaaa atattcatta attctataat aaactttaat 99060
gatctcgatg aaaataattt tacaacggta ccactggtca tagattacgt aacaccttgt 99120
gcattatgta aaaaacgatc gcataaacat ccgcatcaac tatcgttgga aaatggtgct 99180
attagaattt acaaaactgg taatccacat agttgtaaag ttaaaattgt tccgttggat 99240
ggtaataaac tgtttaatat tgcacaaaga attttagaca ctaactctgt tttattaacc 99300
gaacgaggag accatatagt ttggattaat aattcatgga aatttaacag cgaagaaccc 99360
ttgataacaa aactaatttt gtcaataaga catcaactac ctaaggaata ttcaagcgaa 99420
ttactctgtc caagaaaacg aaagactgta gaagctaaca tacgagacat gttagtagat 99480
tcagtagaga ccgataccta tccggataaa cttccgttta aaaatggtgt attggacctg 99540
gtagacggaa tgttttactc tggagatgat gctaaaaaat atacgtgtac tgtatcaacc 99600
ggatttaaat ttgacgatac aaagttcgtc gaagacagtc cagaaatgga agagttaatg 99660
aatatcatta acgatatcca accattaacg gatgaaaata agaaaaatag agagctatat 99720
gaaaaaacat tatctagttg tttatgcggt gctaccaaag gatgtttaac attctttttt 99780
ggagaaactg caactggaaa gtcgacaacc aaacgtttgt taaagtctgc tatcggtgac 99840
ctgtttgttg agacgggtca aacaatttta acagatgtat tggataaagg acctaatcca 99900
tttatcgcta acatgcattt gaaaagatct gtattctgta gcgaactacc tgattttgcc 99960
tgtagtggat caaagaaaat tagatctgac aatattaaaa agttgacaga accttgtgtc 100020
attggaagac cgtgtttctc caataaaatt aataatagaa accatgcgac aatcattatc 100080
gatactaatt acaaacctgt ttttgatagg atagataacg cattaatgag aagaattgcc 100140
gtcgtgcgat tcagaacaca cttttctcaa ccttctggta gagaggctgc tgaaaataat 100200
gacgcgtacg ataaagtcaa actattagac gaggggttag atggtaaaat acaaaataat 100260
agatatagat tcgcatttct atacttgttg gtgaaatggt acagaaaata tcatgttcct 100320
attatgaaac tatatcctac acccgaagag attcctgact ttgcattcta tctcaaaata 100380
ggtactctgt tagtatctag ctctgtaaag catattccat taatgacgga cctctccaaa 100440
aagggatata tattgtacga taatgtggtc actcttccgt tgactacttt ccaacagaaa 100500
atatccaagt attttaattc tagactattt ggacacgata tagagagctt catcaataga 100560
cataagaaat ttgccaatgt tagtgatgaa tatctgcaat atatattcat agaggatatt 100620
tcatctccgt aaatatatgc tcatatattt atagaagata tcacatatct aaatgaatac 100680
cggaatcata gatttatttg ataatcatgt tgatagtata ccaactatat tacctcatca 100740
gttagctact ctagattatc tagttagaac tatcatagat gagaacagaa gcgtgttatt 100800
gttccatatt atgggatcag gtaaaacaat aatcgctttg ttgttcgcct tggtagcttc 100860
cagatttaaa aaggtttaca ttctagtgcc taatatcaac attttgaaaa tttttaatta 100920
taatatgggt gtagctatga acttgtttaa tgacgaattc atagctgaga atatctttat 100980
tcattccaca acaagttttt attctcttaa ttataacgat aacgtcatta attataacgg 101040
attatctcgc tacaataact ctatttttat cgttgatgag gcacataata tctttgggaa 101100
taatactgga gaacttatga ccgtgataaa aaataaaaac aagattcctt ttctactatt 101160
gtctggatct cccattacta acacacctaa tactctgggt catattatag atttaatgtc 101220
cgaagagacg atagatttgg gtgagattat tagtcgtggt aagaaagtaa ttcagacact 101280
tcttaacgaa cgcggtgtga atgtacttaa ggatttgctt aaaggaagaa tatcatatta 101340
cgaaatgcct gataaagatc taccaacgat aagatatcac ggacgtaagt ttctagatac 101400
tagagtagta tattgtcaca tgtctaaact tcaagagaga gattatatga ttactagacg 101460
acagctatgt tatcatgaaa tgtttgataa aaatatgtat aacgtgtcaa tggcagtatt 101520
gggacaactt aatctgatga ataatttaga tactttattt caggaacagg ataaggaatt 101580
gtacccaaat ctgaaaataa ataatggcgt gttatacgga gaagaattgg taacgttaaa 101640
cattagttcc aaatttaaat actttattaa tcggatacag acactcaacg gaaaacattt 101700
tatatacttt tctaattcta catatggcgg attggtaatt aaatatatca tgctcagtaa 101760
tggatattct gaatataatg gttctcaggg aactaatcca catatgataa acggcaaacc 101820
aaaaacattt gctatcgtta ctagtaaaat gaaatcgtct ttagaggatc tattagatgt 101880
gtataattct cctgaaaacg atgatggtag tcaattgatg tttttgtttt cgtcaaacat 101940
tatgtccgaa tcctatactc tgaaagaggt aaggcatatt tggtttatga ctatcccaga 102000
tacttttttct caatacaacc aaattcttgg acgatctatt agaaaattct cttacgccga 102060
tatttctgaa ccagttaatg tatatctttt agccgccgta tattccgatt tcaatgacga 102120
agtaacgtca ttaaacgatt acacacagga tgaattgatt aatgttttac catttgacat 102180

-continued

```
caaaaagctg ttatatctaa aatttaagac taaagaaacg aatagaatat actctattct 102240
tcaagagatg tctgaaacgt attctcttcc accacatcca tcaattgtaa aagttttatt 102300
gggagaattg gtcagacaat ttttttataa taattctcgt attaagtata acgactccaa 102360
gttacttaaa atggttacat cagttataaa aaataaagaa gacgctagga attacataga 102420
tgatattgta aacggtcact tctttgtatc gaataaagta tttgataaat ctcttttata 102480
caaatacgaa aacgatatta ttacagtacc gtttagactt tcctacgaac catttgtttg 102540
gggagttaac tttcgtaaag aatataacgt ggtatcttct ccataaaact gatgaaatat 102600
ataaagaaat aaatgtcgag ctttgttacc aatggatacc ttccagttac attggaacca 102660
cacgagctga cgttagacat aaaaactaat attaggaatg ccgtatataa gacgtatctc 102720
catagagaaa ttagtggtaa aatggccaag aaaatagaaa ttcgtgaaga cgtggaatta 102780
cctctcggcg aaatagttaa taattctgta gttataaacg ttccgtgtgt aataacctac 102840
gcgtattatc acgttgggga tatagtcaga ggaacattaa acatcgaaga tgaatcaaat 102900
gtaactattc aatgtggaga tttaatctgt aaactaagta gagattcggg tactgtatca 102960
tttagcgatt caaagtactg ctttttttcga aatggtaatg cgtatgacaa tggcagcgaa 103020
gtcactgccg ttctaatgga ggctcaacaa ggtatcgaat ctagttttgt ttttctcgcg 103080
aatatcgtcg actcataaaa aagagaatag cggtaagtat aaacacgaat actatggcaa 103140
taattgcgaa tgttttattc tcttcgatat atttttgata atatgaaaaa catgtctctc 103200
tcaaatcgga caaccatctc ataaaatagt tctcgcgcgc tggagaggta gttgctgctc 103260
gtataatctc cccagaataa tatacttgcg tgtcgtcgtt caatttatac ggatttctat 103320
agttctctgt tatataatgc ggttttccat catgattaga cgacgacaat agtgttctga 103380
atttagatag ttgatcagaa tgaatgttta ttggcgttgg aaaaattatc catacagcgt 103440
ctgcagagtg gttgatagtt gttcctagat atgtaaaata atccaactta ctaggcagca 103500
aattgtctag ataaaatact gaatcaaacg gtgcagacgt attggcggat ctaatggaat 103560
ccaattgatt aactatcttt tgaaaatata catttttatg atccaatact tgtaagaata 103620
tagaaataat gataagtcca tcatcgtgtt tttttgcctc ttcataagaa ctatattttt 103680
tcttattcca atgaacaaga ttaatctctc cagagtattt gtacacatct atcaagtgat 103740
tggatccata atcgtcttcc tttccccaat atatatgtag tgatgataac acatattcat 103800
tggggagaaa ccctccactt atatatcctc ctttaaaatt aatccttact agttttccag 103860
tgttctggat agtggttggt ttcgactcat tataatgtat gtctaacggc ttcaatcgcg 103920
cgttagaaat tgcttttttta gtttctatat taataggaga tagttgttgc ggcatagtaa 103980
aaatgaaatg ataactgttt aaaaatagct cttagtatgg gaattacaat ggatgaggaa 104040
gtgatatttg aaactcctag agaattaata tctattaaac gaataaaaga tattccaaga 104100
tcaaaagaca cgcacgtgtt tgctgcgtgt ataacaagtg acggatatcc gttaatagga 104160
gctagaagaa cttcattcgc gttccaggcg atattatctc aacaaaattc agattctatc 104220
tttagagtat ccactaaact attacggttt atgtactaca atgaactaag agaaatcttt 104280
agacggttga gaaaaggttc tatcaacaat atcgatcctc actttgaaga gttaatatta 104340
ttgggtggta aactagataa aaaggaatct attaaagatt gtttaagaag agaattaaaa 104400
gaggaaagtg atgaacgtat aacagtaaaa gaattcggaa atgtaattct aaaacttaca 104460
acgcgcgata aattatttaa taaagtatat ataggttatt gcatggcgtg ttttattaat 104520
caatcgttgg aggatttatc gcatactagt atttacaatg tagaaattag aaagattaaa 104580
```

-continued tcattaaatg attgtattaa cgacgataaa tacgaatatc tgtcttatat ttataatatg 104640
ctagttaata gtaaatgaac ttttacagat ctagtataat tagtcagatt attaagtata 104700
atagacgact agctaagtct attatttgcg aggatgactc tcaaattatt acactcacgg 104760
cattcgttaa ccaatgccta tggtgtcata aacgagtatc cgtgtccgct attttattaa 104820
ctactgataa caaaatatta gtatgtaaca gacgagatag ttttctctat tctgaaataa 104880
ttagaactag aaacatgttt agaaagaaac gattatttct gaattattcc aattatttga 104940
acaaacagga aagaagtata ctatcgtcat ttttttctct agatccagct actgctgata 105000
atgatagaat agacgctatt tatccgggtg gcatacccaa aaggggtgag aatgttccag 105060
agtgtttatc cagggaaatt aaagaagaag ttaatataga caattctttt gtattcatag 105120
acactcggtt ttttattcat ggcatcatag aagataccat tattaataaa ttttttgagg 105180
taatcttctt tgtcggaaga atatctctaa cgagtgatca aatcattgat acatttaaaa 105240
gtaatcatga aatcaaggat ctaatatttt tagatccgaa ttcaggtaat ggactccaat 105300
acgaaattgc aaaatatgct ctagatactg caaaactcaa atgttatggc catagaggat 105360
gttattacga atcattaaaa aaattaactg aggatgattg attagaaaat ataaattaat 105420
ttaccatcgt gtatttttat aacgggattg tccggcatat catgtagata gttaccgtct 105480
acatcgtata ctcgaccatc tacgccttta aatcctctat ttattgacat taatctatta 105540
gaattggaat accaaatatt agtaccctca attagtttat tggtaatatt tttgttagac 105600
gatagatcga tggctcttga aaccaaggtt ttccaaccgg actcattgtc gatcggtgag 105660
aagtcttttt cattagcatg aatccattct aatgatgtat gtttaaacac tctaaacaat 105720
tggacaaatt cttttgattt gctttgaatg atttcaaata ggtcttcgtc tacagtaggc 105780
ataccattag ataatctagc cattataaag tgcacgttta catatctacg ttctggagga 105840
gtaagaacgt gactattgag acgaatggct cttcctacta tctgacgaag agacgcctcg 105900
ttccatgtca tatctaaaat gaagatatca ttgattgaga agaagctaat accctcgcct 105960
ccactagaag agaatacgca tgttttaatg cattctccgt tagtgtttga ttcttggtta 106020
aactcagcca ccgccttgat tctagtatct tttgttctag atgagaactc tatattagag 106080
ataccaaaga ctttgaaata tagtaataag atttctattc ctgactgatt aacaaatggt 106140
tcaaagacta gacatttacc atgggatgct aatattccca aacatacatc tataaatttg 106200
acgcttttct cttttaattc agtaaataga gagatatcag ccgcactagc atcccctccc 106260
aatagttctc cccttttaaa ggtatctaat gcagatttag aaaattctct atctcttaat 106320
gaatttttaa aatcattata tagtgttgct atctcttgcg cgtattcgcc cggatcacga 106380
ttttgtcttt caggaaagct atcgaacgta aacgtagtag ccatacgtct cagaattcta 106440
aatgatgata tacctgtttt tatttcagcg agtttagcct tttgataaat ttcttcttgc 106500
tttttcgaca tattaacgta tcgcattaat actgttttct tagcgaatga tgcagaccct 106560
tctacgtcat caaaaataga aaactcgtta ttaactatgt acgaacatag gcctcctagt 106620
ttggagacta attctttttc atcaactaga cgtttattct caaatagcga ttggtgttgt 106680
aaggatcctg gtcgtagtaa gttaaccaac atggtgaatt cttgcacact attgacgata 106740
ggtgtagccg ataaacaaat catcttatgg ttttttaatg cgatggtctt agataaaaaa 106800
ttatatactg aacgagtagg acggatctta ccatcttctt tgattaatga tttagaaatg 106860
aagttatgac attcatcaat aatgacgcat attctactct tggaattaat agttttgata 106920

-continued ttagtaaaaa atttatttct aaaattttga tcatcgtaat taataaaaat acaatccttc 106980
gttatctctg gagcgtatct gagtatagtg ttcatccaag gatcttctat caaagccttt 107040
ttcaccaata agataatagc ccaattcgta taaatatcct taagatgttt gagaatatat 107100
acagtagtca ttgttttacc gacacccgtt tcatggaaca ataaaagaga atgcatactg 107160
tctaatccta agaaaactct tgctacaaaa tgttgataat ccttgaggcg tactacgtcc 107220
gaccccatca tttcaacagg catattagta gttctgcgca atgcataatc gatataggcc 107280
gcgtgtgatt tactcattta tgagtgataa gtaataacta tgttttaaaa atcacagcag 107340
tagtttaact agtcttctct gatgtttgtt ttcgatactt tttgaatcag aagtcatact 107400
agaataaagc aacgagtgaa cgtaatagag agcttcgtat actctattcg aaaactctaa 107460
gaacttatta atgaattccg tatccactgg attgtttaaa atactaaatt gaacactgtt 107520
cacatccttc caagaagaag acttagtgac ggacttaaca tgagacataa ataaatccaa 107580
atttttttta caaacatcac tagccaccat aatggcgcta tcttttaacc agctatcgct 107640
tacgcatttt agcagtctaa catttttaaa gagactacaa tatattctca tagtatcgat 107700
tacacctcta ccgaataaag ttggaagttt aataatacaa tatttttcgt ttacaaaatc 107760
aaataatggt cgaaacacgt cgaaggttaa catcttataa tcgctaatgt atagattgtt 107820
ttcagtgaga tgattattag atttaatagc atctcgttca cgtttgaaca gtttattgcg 107880
tgcgctgagg tcggcaacta cggcgtccgc tttagtactc ctcccataat actttacgct 107940
attaatcttt aaaatttcat agactttatc tagatcgctt tctggtaaca tgatatcatg 108000
tgtaaaaagt tttaacatgt cggtcggcat tctatttaga tcattaactc tagaaatctg 108060
aagaaagtaa ttagctccgt attccagact aggtaatggg cttttaccta gagacagatt 108120
aagttctggc aatgtttcat aaaatggaag aaggacatgc gttccctccc ggatattttt 108180
tacaatttca tccatttaca actctatagt ttgttttcat tattattagt tattatctcc 108240
cataatcttg gtaatactta ccccttgatc gtaagatacc ttatacaggt cattacatac 108300
aactaccaat tgtttttgta cataatagat tggatggttg acatccatgg tggaataaac 108360
tactcgaaca gatagtttat ctttcccccct agatacatta gccgtaatag ttgtcggcct 108420
aaagaatatc tttggtgtaa agttaaaagt tagggttctt gttccattat tgctttttgt 108480
cagtagttca ttataaattc tcgagatggg tccgttctct gaatatagaa catcatttcc 108540
aaatctaact tctagtctag aaataatatc ggtcttattc ttaaaatcta ttcccttgat 108600
gaagggatcg ttaatgaaca aatccttggc ctttgattcg gctgatctat tatctccgtt 108660
atagacgtta cgttgactag tccaaagact tacaggaata gatgtatcga tgatgttgat 108720
actatgtgat atgtgagcaa agattgttct cttagtggca tcactatatg ttccagtaat 108780
ggcggaaaac tttttagaaa tgttatatat aaaagaattt tttcgtgttc caaacattag 108840
cagattagta tgaagataaa cactcatatt atcaggaaca ttatcaattt ttacatacac 108900
atcagcatct tgaatagaaa cgataccatc ttctggaacc tctacgatct cggcagactc 108960
cggataacca gtcggtggac catcgctaac aataactaga tcatccaaca atctactcac 109020
atatgcatct atataatctt tttcatcttg tgagtaccct ggatacgaaa taaatttatt 109080
atccgtattt ccataataag gtttagtata aacagagagc gatgttgccg catgaacttc 109140
agttacagtc gccgttggtt ggtttatttg acctattact ctcctaggtt tctctataaa 109200
tgatggttta atttgtacat tcttaaccat atatccaata aagctcaatt caggaacata 109260
aacaaattct ttgttgaacg tttcaaagtc gaacgaagag tcacgaataa cgatatcgga 109320
tactggattg aaggttaccg ttacggtaat ttttgaatcg gatagtttaa gactgctgaa 109380
tgtatcttcc acatcaaacg gagttttaat ataaacgtat actgtagatg gttctttaat 109440
agtgtcatta ggagttaggc caatagaaat atcattaagt tcactagaat atccagagtg 109500
tttcaaagca attgtattat tgatacaatt attatataat tcttcgccct caatttccca 109560
aataacaccg ttacacgaag agatagatac gtgattaata catttatatc caacatatgg 109620
tacgtaaccg aatcttccca tacctttaac ttctggaagt tccaaactca gaaccaaatg 109680
attaagcgca gtaatatact gatccctaat ttcgaagcta gcgatagcct gattgtctgg 109740
accatcgttt gtcataactc cggatagaga aatatattgc ggcatatata aagttggaat 109800
ttgactatcg actgcgaaga cattagaccg tttaatagag tcatccccac cgatcaaaga 109860
attaatgata gtattattca ttttctattt aaaatggaaa aagcttacaa taaactccgt 109920
agagaaatat ctataatttg tgagttttcc ttaaagtaac agcttccgta aacgccgtct 109980
ttatctctta gtaagtttat tgtatttata accttttcct tatcttcata gaatactaaa 110040
ggcaacaaag aaatttttgg ttcttctcta agagctacgt gagacttaac catagacgcc 110100
aacgaatccc tacatatttt agaacagaaa tacccaactt caccaccctt gaatgtctca 110160
atactaatag gtttaaaaac caaatcttga ttacaaaacc aacacttatc aattacacta 110220
tttgtcttaa tagacacatc tgccatagat ttataatact ttggtagtat acaagcgagt 110280
gcttcttctt tagcgggctt aaagactgct ttaggtgctg aaataaccac atctggaagg 110340
cttactcgct tagccattta attacggaac tattttttta tacttctaat gagcaagtag 110400
aaaacctctc atctacaaaa acatactcgt gtccataatc ctctaccata gttacacgtt 110460
ttttagatct catatgtgct aaaaagtttt cccatactaa ttggttacta ttatttttcg 110520
tataattttt aacagtttga ggttttagat ttttagttac agaagtgata tcgaatattt 110580
tatccaaaaa gaatgaataa ttaattgtct tagaaggagt gttttcttgg caaaagaata 110640
ccaagtgctt aaatatttct actacttcat taatcttttc tgtactcaga ttcagtttct 110700
catcttttac ttgattgatt atttcaaaga ctaacttata atccttttta tttattctct 110760
cgttagcctt aagaaaacta gatacaaaat ttgcatctac atcatccgtg gatatttgat 110820
ttttttccat gatatccaag agttccgaga taatttctcc agaacattga tgagacaata 110880
atctccgcaa tacatttctc aaatgaataa gtttattaga cacatggaag tttgactttt 110940
tttgtacctt tgtacatttt tgaaataccg actcgcaaaa aatacaatat tcatatcctt 111000
gttcagatac tataccgttg tgtctacaac cgctacataa tcgtagattc atgttaacac 111060
tctacgtatc tcgtcgtcca atattttata taaaaacatt ttatttctag acgttgccag 111120
aaaatcctgt aatattttta gttttttggg ctgtgaataa agtatcgccc taatattgtt 111180
accgtcttcc gccaatatag tagttaaatt atccgcacat gcaaaagaac accgcttagg 111240
cggattcagt acaatgttat atttttcgta ccaactcatt taaatatcat aatctaaaat 111300
agttctgtaa tatgtctagc gctaatatat tgatcataat cctgtgcata aattaagata 111360
caacaatgtc tcgaaatcat cgacatggct tcttccatag ttagaagatc gtcgtcaaag 111420
ttagcaacgt gattcatcaa catttgctgt tttgaggcag caaatactga accgtcgcca 111480
ttcaaccatt cataaaaacc atcgtctgaa tccattgata atttcttgta ctggtttttg 111540
agagctcgca tcaatctagc atttctagct cccggattga aaacagaaag aggatcgtac 111600
atccagggtc cattttctgt aaatagaatc gtataatgtc ccttcaagaa gatatcagac 111660

-continued gatccacaat caaagaattg gtctccgagt ttgtaacaaa ctgcggactt taacctatac 111720
atgataccgt ttagcatgat ttctggtgat acgtcaatcg gagtatcatc tattagagat 111780
ctaaagccgg tgtaacattc tccaccaaac atattcttat tctgacgtcg ttctacataa 111840
aacatcattg ctccattaac gataacaggg gaatgaacag cactacccat cacattagtt 111900
cccaatggat caatgtgtgt aactccagaa catcttccat atcctatgtt aggaggagcg 111960
aacaccactc ttccactatt gccatcgaat gccatagaat aaatatcctt ggaattgata 112020
gaaatcggac tgtcggatgt tgtgatcatc ttcataggat taacaactat gtatggtgcc 112080
gcctgaagtt tcatatcgta actgatgccg tttataggtc tagccacaga aaccaacgta 112140
ggtctaaatc caactataga caaaatagaa gccaatatct gttcctcatc tgtcataact 112200
tgagagcatc cagtatgaat aatcttcatt agatggggat ctaccgcatc atcatcgtta 112260
caataaaaaa ttcccattct aatgttcata attgcttttc taatcatggt atgcatgttt 112320
gctctctgaa tctctgtgga aattagatct gatacacctg taatcactat cggattatcc 112380
tccgtaagac gattaaccaa caacatataa ttataagact ttacttttct aaattcataa 112440
agttgctgga ttaggctata ggtgtctcca tgtacatacg cgttctcgag cgcaggaagt 112500
ttaataccga atagtgccat cagaatagga tgaatatagt aattagtttc tggttttcta 112560
taaataaaag acaaatcttg tgaactagac atatcggtaa aatgcatgga ttggaatcgt 112620
gtagtcgaca gaagaatatg atgattagat ggagagtata ttttatctaa ctctttgagt 112680
tggtcaccga ttctaggact agctcgagaa tgaataagta ctaaaggatg agtacatttc 112740
acagaaacac tagcattgtt caatgtgctc tttacatggg taaggagttg aaatagctcg 112800
tttctatttg ttctgacaat atttagttta ttcataatgt taagcatatc ctgaatagta 112860
aagttagatg tgtcatactt gttagtagtt agatatttag caattgcatt cccatcattt 112920
ctcaatctcg tactccaatc atgtgtagat gctacttcgt cgatggaaac catacaatcc 112980
tttttgatag gctgttgaga ttgattattt cctgcacgtt taggtttggt acgttgattt 113040
ctagcccctg cggatataaa gtcatcgtct acaatttggg acaatgaatt gcatacacta 113100
caagacaaag atttatcaga agtgtgaata tgatcttcat ctaccaaaga aagagtttga 113160
ttagtataac tagattttag tcctgcgtta gatgttaaaa aaacatcgct attgaccacg 113220
gcttccatta tttatattcg tagtttttac tcgaaagcgt gattttaata tccaatctta 113280
ttacttttgg aatcgttcaa aacctttgac tagttgtaga atttgatcta ttgccctacg 113340
cgtatactcc cttgcatcat atacgttcgt caccagatcg tttgtttcgg cctgaagttg 113400
gtgcatatct ctttcaacat tcgacatgag atccttaagg gccatatcgt ctagattttg 113460
ttgagatgct gctcctggat ttggattttg ttgtgctgtt gtacatactg taccaccagt 113520
aggtgtagga gtacatacag tggccacaat aggaggttga ggaggtgtaa ccgttggagt 113580
agtacaagaa atatttccat ccgattgttg tgtacatgta gttgttggta acgtctgaga 113640
aggttgggta gatggcggtg tcgtcgtctt ttgatcttta ttaaatttag agataatatc 113700
ctgaacagca ttgctcggcg tcaacgctgg aaggagtgaa ctcgccggcg catcagtatc 113760
ttcagacagc caatcaaaaa gattagacat atcagatgat gtattagttt gttgtcgtgg 113820
ttttggtgta ggaacagtac tactaggtag aagaatagga gccggtgtag ctgttggaac 113880
cggctgtgga gttatatgaa tagttggttg tagcggttgg ataggctgtc tgctggcgac 113940
cgtcatatta tctctagcta gttgttctcg caactgtctt tgataatacg actcttgaga 114000
ctttagtcct atttcaatcg cttcatcctt tttcgtatcc ggatcctttt cttcagaata 114060
atagattgac gactttggtg tagaggattc tgccagcccc tgtgagaact tgttaaagaa 114120
gtccatttaa ggctttaaaa ttgaattgcg attataagat taaatggcag acacagacga 114180
tattatcgac tatgaatccg atgatctcac cgaatacgag gatgatgaag aagaggaaga 114240
agatggagag tcactagaaa ctagtgatat agatcccaaa tcttcttata agattgtaga 114300
atcagcatcc actcatatag aagatgcgca ttccaatctt aaacatatag ggaatcatat 114360
atctgctctt aaacgacgct atactagacg tataagtcta tttgaaatag cgggtataat 114420
agcagaaagc tataacttgc ttcaacgagg aagattacct ctagtttcag aattttctga 114480
cgaaacgatg aagcaaaata tgctacatgt aattatacaa gagatagagg agggttcttg 114540
tcctatagtc atcgaaaaga acggagaatt gttgtcggta aacgattttg acaaagatgg 114600
tctaaaattc catctagact atattatcaa aatttggaaa cttcaaaaac gatattagaa 114660
tttatacgaa tatcgttctc taaatgtcac aatcaagtct cgcatgttca gcaatttatt 114720
gtcgtacttt atatcgtgtt cattaacgat atcttgcaaa atagtaatga ttctatcttc 114780
cttcgataga tattcttcag agattattgt cttatatttt ttcttgttat ccgatatgaa 114840
tttgataaga ctttgaacat tattgatacc cgtctgttta atttttttcta cagatatttt 114900
agttttggca gattctatcg tatctgtcaa tagacatcca acatcgacat tcgacgtcaa 114960
ttgtctataa atcaacgtat aaattttaga aataacatta gcgaattgtt gtgcattgat 115020
gtcgttattc tgaaacagta tgattttagg tagcattttc ttaacaaaga gaacgtattt 115080
attgttactc agttgaacag atgatatatc cagattacta acgcatctga ttccgtatac 115140
caaactttca gaagaaatgg tgtacaattg tttgtattca ttcaatgtct ctttttcaga 115200
aattagttta gagtcgaata ctgcaataat tttcaagaga tagttttcat cagataagat 115260
tttatttagt gtagatatga taaaactatt gttttgttgg agaacttgat acgccgcgtt 115320
ctctgtagtc gacgctctca aatgggaaac aatctccatt atttttttgg aatcggatac 115380
tatatcttcg gtatcttgac gcagtctagt atacatagag ttaagagaga ttagagtttg 115440
tacattaagc aacatgtctc taaatgtggc tacaaacttt tcctttttca cataatctag 115500
tttattatat accgatttca caacggcacc agatttaagg aaccagaatg aaaaactctg 115560
ataactacaa tatttcatca tagttacgat tttatcatct tctatagttg gtgtaatagc 115620
gcataccttt ttctccaaga ctggaaccaa cgtcataaaa atgtttaaat caaaatccat 115680
atcaacatct gatgcgctaa gaccagtctc gcgttcaaga ttatctttac taatggtgac 115740
gaactcatca tatagaactc taagtttgtc cattatttat ttacagattt agttgtttaa 115800
tttatttgtg ctcttccaga gttgggatag tatttttcta acgtcggtat tatattatta 115860
ggatctacgt tcatatgtat cataatatta atcatccacg ttttgataaa tctatcttta 115920
gcttctgaaa taacgtattt aaacaaagga gaaaaatatt tagctacggc atcagacgca 115980
ataacatttt ttgtaaatgt aacgtattta gacgacagat cttcgttaaa aagttttcca 116040
tctatgtaga atccatcggt tgttaacacc attcccgcgt cagattgaat aggagtttga 116100
atagtttgtt ttggaaatag atccttcaat aacttatagt tgggtgggaa aaaatcgatt 116160
ttatcactag actctttctt ttttactatc attacctcat gaactatttc ttgaatgagt 116220
atatgtattt tctttcctat atcggacgcg ttcattggaa aatataccat gtcgttaact 116280
ataagaatat ttttatcctc gtttacaaac tgaataatat cagatgtagt tcgtaaacga 116340
actatatcat caccagcaca acatctaact atatgatatc cactagtttc ctttagccgt 116400

-continued ttattatctt gttccatatt agcagtcatt ccatcattta agaaggcgtc aaagataata 116460
gggagaaatg acattttgga ttctgttacg actttaccaa aattaaggat atacggactt 116520
actatctttt tctcaacgtc gatttgatga acacacgatg aaaatgtgct tctatgagat 116580
tgatcatgta gaaaacaaca agggatacaa tatttccgca tatcatgaaa tatattaaga 116640
aatcccacct tattatattt ccccaaagga tccatgcatg taaacattat gccgttatca 116700
ttaataaaga cttctttctc atcggatttg taaaagttgt tactgatttt tttcattcca 116760
ggatctagat aattaataat gatgggtttt ctattcttat tctttgtatt ttggcatatc 116820
ctagaccagt aaacagtttc cactttggta aaatcagcag acttttgaac gctattaaac 116880
atggcattaa tggcaataac taaaaatgta aaatattttt ctatgttagg aatatggttt 116940
ttcactttaa tagatatatg gtttttggcc aaaatgatag atattttttt atccgaggat 117000
agtaaaatat tattagtcgc cgtctctata aaaatgaagc tagtctcgat atccaatttt 117060
attctagaat tgataggagt cgccaaatgt accttatacg ttatatctcc cttgatgcgt 117120
tccatttgtg tatctatatc ggacacaaga tctgtaaata gttttacgtt attaatcatc 117180
acggtatcgc cgtcgctaga taacgctaat gtaccatcca agtcccaaat ggagagattt 117240
aactgttcat cgtttagaat aaaatgatta ccggtcatat taataaagtg ttcatcgtat 117300
ctagataaca acgacttata attaatgtcc aagtcttgaa ctcgctgaat gatctttttt 117360
aacccagtta gttttagatt ggtacgaaat atattgttaa actttgattc tacagtaatg 117420
tccaaatcta gttgtggaaa tacttccatc aacattgttt caaacttgat aatattatta 117480
tctacatctt catacgatcc aaattccgga atagatgtat cacatgctct tgccacccag 117540
ataaccaaaa agtcacacgc tccaggatat acattgtata aaaagctatc gttttttagt 117600
agtgtttttt tctgagtata tacgaaggga ttaaaaatag tattatcaac gtaactatat 117660
tccaaattat tcttatgaga atagataata atatcgtcct taatatctaa caaatttcct 117720
aaatatccct ttaattgagt cattcgaagc gtcaatagaa tatgtctctt aactatttcc 117780
ggctgttgta tatttaaatg acttcgtaaa aaataatata tgggcgactt ctcatctatg 117840
taatcatatg gagtgagata tagggctcgt tctacctcct gccccttacc cacctgtaat 117900
accaattgcg gacttactat atatcgcata tttatatcgt ggggtaaagt gaaaatctac 117960
taccgatgat gtaagtctta caatgttcga accagtacca gatcttaatt tggaggcctc 118020
cgtagaacta ggggaggtaa atatagatca aacaacacct atgataaagg aaaatagcgg 118080
ttttatatcc cgtagtagac gtctattcgc ccatagatct aaggatgatg agagaaaact 118140
agcactacga ttctttttac aaagacttta ttttttagat catagagaga ttcattattt 118200
gttcagatgc gttgacgctg taaaagacgt cactattacc aaaaaaaata acattatcgt 118260
ggcgccttat atagcacttt taactatcgc atcaaaagga tgcaaactta cagaaacaat 118320
gattgaagca ttttttccag aactatataa tgaacatagt aagaaattta aattcaactc 118380
tcaagtatcc atcatccaag aaaaactcgg ataccagttt ggaaactatc acgtttatga 118440
ttttgaaccg tattactcta cagtagctct ggctattcga gatgaacatt catctggcat 118500
ttttaatatc cgtcaagaga gttatctggt aagttcatta tctgaaataa catatagatt 118560
ttatctaatt aatctaaaat ctgatcttgt tcaatggagt gctagtacgg gcgctgtaat 118620
taatcaaatg gtaaatactg tattgattac agtgtatgaa aagttacaac tggtcataga 118680
aaatgattca caatttacat gttcattggc tgtggaatca aaacttccaa taaaattact 118740
taaagataga aatgaattat ttacaaaatt cattaacgag ttaaaaaaga ccagttcatt 118800

-continued caagataagc aaacgcgata aggatacgct actaaaatat tttacttagg actggagtta 118860
gaatttatag acgactcatt tcgtttatca ttgttactat tattactatt actatcatta 118920
ttagtgttgg cattattagt attcttcttg tcatcttgtt cagaaatata cagcaatgct 118980
atacctaata ctaaatacat tatcatgctc gcaatggctc taacaacaac gaaccaaaat 119040
gaatttggtc gtagcttttg ttcacaaaaa tacataaaga aatgtctaca taaatctatg 119100
gcgccattgg ctacttgaaa tagcgccagt cctcctacag attttaatat agctgtataa 119160
catgacattt attcatcatc aaaagagaca gagtcaccat ctgtcatatt tagatttttt 119220
ttcatgtgtt caaagtatcc tctactcatt tcattataat agtttatcat acttagaatt 119280
ttaggacgga tcaatgagta agacttgact agatcgtcag tagtaatttg tgcatcgtct 119340
attctgcatc cgcttcgtcg aataatgtat agcatcgctt tgagattctc catagctatc 119400
aagtctttat acaatgacat ggaaatatct gtgaatactt tatacttctc caacatcgat 119460
gccttaacat catcgcctac tttagcattg aaaatacgtt ctattgtgta gatggatgta 119520
gcaagatttt taaacaacaa tgccatctta cacgatgatt gcctcaagtc tccaatcttt 119580
tgtttagaac gattagctac agagttcaac gcttggctga ctagcatatt attatcttta 119640
gaaattgtat tcttcaatga ggcgtttatc atatctgtga tttcgttagt catattacag 119700
tctgactggg ttgtaatgtt atccaacata tcacctatgg atacggtaca cgtaccagca 119760
tttgtaataa tcctatctaa gatgttgtat ggcattgcgc agaaaaatatc ttctcctgta 119820
atatctccac tctcgataaa tctactcaga ttattcttaa atgccttatt ctctggagaa 119880
aagatatcag tgtccatcat ttcattaata gtatacgcag aaaagatacc acgagtatca 119940
attctatcca agatacttat cggttccgag tcacagataa tggtttcctc tccttcggga 120000
gatcctgcat agaaatatct aggacaatag tttctatact gtctgtaact ctgataatct 120060
ctaaagtcac taactgatac catgaaattg agaagatcaa acgctgaagt aatcaatttt 120120
tctgcctcgt ttttactaca actagttttc atcaatgtag cgacgatgta ttgtttagtt 120180
actcttggtc taatactgat gatagagata ttattgcttc ccataatgga tcttctagta 120240
gtcaccttaa agcccattga tgcgaatagc agatagataa agtcttggta tgactccttt 120300
ctaatatagt acggactacc tttgtcaccc aactttatac ccacataagc cataacaacc 120360
tctttaatag ccgtttcatg aggtttatca gccatgagcc tgagtagttg gaagaatctc 120420
atgaatcccg tctcagaaag tcctatatgc atgatagatt tatctttcct gggaaactct 120480
cgtatagtca tagatgaaat actcttcaaa gtttctgaaa taagattagt aacagtctta 120540
cctccgacta ctctgggtaa caaacatact ctaataggtg ttttctctgc ggagataata 120600
tcagaaagga tagagcaata agtagtatta ttgtgattat aaagaccgaa tacataacag 120660
gtagaattta taaacatcat gtcctgaagg tttttagact tgtattcctc gtaatccata 120720
ccgtcccaaa acatggattt ggtaactttg atagccgtag atctttgttc cttcgccaac 120780
aggttaaaga aattaataaa gaatttgttg tttctattta tgtccacaaa ttgcacgttt 120840
ggaagcgcca cggttacatt cactgcagca ttttgaggat cgcgagtatg aagtacgatg 120900
ttattgttta ctggtatatc tggaaagaaa tctaccagtc taggaataag agattgatat 120960
cgcatagaaa tagtaaagtt tataatctca tcatcgaaga gcattttgtt accattgtaa 121020
taaatatcca ctctgtcata tgtataaatg aagtactgtt caaacatgat gagatgttta 121080
tatgttggca tagtagtgag atcgacgttt ggtaatggca atgtattaag attaactcca 121140
taatgtctag cagcatctgc gatgttataa gcgtcgtcaa agcggggtcg atcttgtatt 121200
gttatatatt gtctaacacc tataagatta tcaaaatctt gtctgcttaa tacaccgtta 121260
acaatttttg ccttgaattc ttttattggt gcattaataa catccttata gaggatgtta 121320
aacaaataag tgttatcaaa gttaagatct ggatatttct tttctgctag aacatccatt 121380
gagtcggagc catctggttt aatataacca ccgataaatc tagctctgta ttctgtatcc 121440
gtcaatctaa tattaagaag gtgttgagtg aaaggtggaa gatcgtaaaa gctgtgagta 121500
ttaatgatag gattagtttc cgaactaatg ttaattgggg tattaataat atctatattt 121560
ccagcgttaa gtgtaacatt aaacagtttt aattcacgtg acgtggtatc aattaaataa 121620
ttaatgccca atttggatat agcagcctga agctcatctt gtttagttac ggatcctaat 121680
gagttattaa gcaatatatc gaacggatga acgaaggttg ttttaagttg gtcacatact 121740
ttgtaatcta gacatagatg cggaagaacg gtagaaacta tacgaaataa atattcagag 121800
tcctctaatt gatcaagagt aactattgac ttaataggca tcatttattt agtattaaat 121860
gacgaccgta ccagtgacgg atatacaaaa cgatttaatt acagagtttt cagaagataa 121920
ttatccatct aacaaaaatt atgaaataac tcttcgtcaa atgtctattc taactcacgt 121980
taacaacgtg gtagatagag aacataatgc cgccgtagtg tcatctccag aggaaatatc 122040
ctcacaactt aatgaagatc tatttccaga tgatgattca ccggccacta ttatcgaacg 122100
agtacaacct catactacta ttattgacga tactccacct cctacttttc gtagagagtt 122160
attgatatcg gaacaacgtc aacaacgaga aaaaagattt aatattacag tatcgaaaaa 122220
tgctgaagca ataatggaat ctagatctat gataacttct atgccaacac aaacaccatc 122280
cttgggagta gtttatgata aagataaaag aattcagatg ttggaggatg aagtggttaa 122340
tcttagaaat caacgatcta atacaaaatc atctgataat ttagataatt ttaccaaaat 122400
actatttggt aagactccgt ataaatcaac agaagttaat aagcgtatag ccatcgttaa 122460
ttatgcaaat ttgaacgggt ctcccttatc agtcgaggac ttggatgttt gttcagagga 122520
tgaaatagat agaatctata aaacgattaa acaatatcac gaaagtagaa aacaaaaaat 122580
tatcgtcact aacgtgatta ttattgtcat aaacattatc gagcaagcat tgctaaaact 122640
cggatttgaa gaaatcaaag gactgagtac cgatatcact tcagaaatta tcgatgtgga 122700
gatcggagat gactgcgatg ctgtagcatc aaaactagga atcggtaaca gtccggttct 122760
taatattgta ttgtttatac tcaagatatt cgttaaacga attaaaatta tttaatttaa 122820
tacattccca tatccagaca acaatcgtct ggattaatct gttcctgtcg tctcataccg 122880
gacgacatat taatcttttt attagtaggc atctttttag atggtttctt tttcccagca 122940
ttaactgagt cgatacctag aagatcgtga ttgatctctc cgaccattcc acgaacttct 123000
aattggccgt ctctaacggt accataaact attttaccag cattagtaac agcttggaca 123060
atctgaccat ccatcgcatt gtacgatgta gtagtaactg ttgttctacg tctaggagca 123120
ccagaagtat ttttggagcc cttggaggct gatgtagaag aagacgagga ttttgatttt 123180
ggtttacatg taatacattt tgaactcttt gattttgtat cacatgcgcc ggcagtcaca 123240
tctgtttgag aattaagatt attgttgcct cctttgacgg ctgcatctcc accgatttgc 123300
gctagtagat ttttaagctg tggtgtaatc ttattaactg tttcgatata atcatcgtaa 123360
ctgcttctaa cggctaaatt ttttttatcc gccatttaga agctaaaaat atttttattt 123420
atacagaaga tttaactaga ttatacaatg aactaatatg atccttttcc agattattta 123480
caaacttggt atttttttggt tctggaggag gcgaatttaa attcggactt ggattcggat 123540

-continued tttgtgagtt cttgatctta ttatacatcg agtataggat ggcgacggta actgctacac 123600
aaataccgat caacaaaaga ataccaatca tttattgaca ataacttcac tattgatcaa 123660
gtatgcaata tatcatcttt tcactaaata agtagtaata atgattcaac aatgtcgaga 123720
tatatggacg ataataattt agttcatgga aatatcgcta tgattggtat gaatgactcc 123780
gctaactctg tggggcgcgc agtgctttcc ccacatagaa taaattagca ttccgactgt 123840
gataataata ccaagtataa acgccataat actcaatact ttccatgtac gagtgggact 123900
ggtagactta ctaaagtcaa taaaggcgaa gatacacgaa agaatcaaaa gaatgattcc 123960
agcgattagc acgccggaaa aataatttcc aatcataagc atcatgtcca tttaactaat 124020
aaaaatttta aatcgccgaa tgaacaaagt ggaatataaa ccatataaaa acaatagttt 124080
gtactgcaaa aataatatct atttttgttt tcgaagatat ggtaaaatta aatagtagta 124140
cacagcatgt tataactaac agcagcaacg gctcgtaatt acttatcatt tactagacga 124200
aaaggtggtg ggatattttc ttgctcaaat aatacgaata tatcacccat ccattttatg 124260
cgatgtttat atactctaat ctttaataga tctatagacg acgggtttac caacaatata 124320
gattttatcg attcatctaa tttaaaccct tccttaaacg tgaatgatct attatctggc 124380
ataacgatga ccctacctga tgaatcggac aatgtactgg gccatgtaga ataaattatc 124440
aacgaattat cgtctacgaa catttatatc atttgtttta attttaggac gcgaataaat 124500
agatataaaa tagaaaataa cagatattac aaccagtgtt atggccgcgc ccaaccaggt 124560
aggcagtttt attttatctt ttactacagg ttctcctgga tgtacgtcac caacggcgga 124620
cgtagttcta gtacaattag acgtaagttc cgcttgggaa ttttttaacg ctaaagagtt 124680
aacgttaatc gtgcacccaa cgtatttaca tctagttctt tgaacatctt gattataata 124740
taaccatttt ctatctctag attcgtcggt gcactcatgt aaccaacata ccctaggtcc 124800
taaatattta tctccggaat tagattttgg ataattcgcg caccaacaat ttctatttcc 124860
tttatgatcg ttacaaaaga cgtataatgc cgtatcccca aaagtaaaat aatcaggacg 124920
aataattcta ataaactcag aacaatatct cgcatccata tgtttggagc aaatatcgga 124980
ataagtagac atagccggtt tccgttttgc acgtaaccat tctaaacaat tggggtttcc 125040
aggatcgttt ctacaaaatc cagtcatgaa atcgtcacaa tgttctgtct tgtaattatt 125100
attaaatatt tttggacagt gtttggtatt tgtcttagaa caacattttg ccacgctatc 125160
actatcgccc aggagataat cctttttttat aaaatgacat cgttgcccgg atgctatata 125220
atcagtagcg tgttttaaat ccttaatata ttcaggagtt acctcgttct gataatagat 125280
taatgatcca ggacgaaatt tgaaagaact acatggttct ccatgaatta atacatattg 125340
tttagcaaat tcaggaacta taaaactact acaatgatct atcgacatac catctatcaa 125400
acaaaacttg ggtttaattt ctcccggaga tgtttcataa tagtacgtat aactttcttc 125460
tgcaaactta acagctctat tatattcagg ataattaaaa cctaattcca tatatttgtc 125520
tcgtatatct gctattcctg gtgctatttt gattctatta agagtaacag ctgccccccat 125580 tcttaataat cgtcagtatt taaactgtta aatgttggta tatcaacatc taccttattt 125640
cccgcagtat aaggtttgtt gcaggtatac tgttcaggaa tggttacatt tatacttctt 125700
ctatagtcct gtctttcgat gttcatcaca tatgcaaaga acagaataaa caaaataatg 125760
taagaaataa tattaaatat ctgtgaattc gtaaatacat tgattgccat aataattaca 125820
gcagctacaa tacacacaat agacattccc acagtgttgc cattacctcc acgatacatt 125880

-continued

```
tgagttacta agcaataggt aataactaag ctagtaagag gcaatagaaa agatgagata 125940
aatatcatca atatagagat tagaggaggg ctatatagag ccaagacgaa caaaatcaaa 126000
ccgagtaacg ttctaacatc attatttttg aagattccca aataatcatt cattcctcca 126060
taatcgtttt gcatcatacc tccatcttta ggcataaacg attgctgctg ttcctctgta 126120
aataaatctt tatcaagcac tccagcaccc gcagagaagt cgtcaagcat attgtaatat 126180
cttaaataac tcatttatat attaaaaaat gtcactatta aagatggagt ataatcttta 126240
tgccgaacta aaaaaaatga cttgtggtca accccctaagt cttttttaacg aagacgggga 126300
tttcgtagaa gttgaaccgg gatcatcctt taagtttctg atacctaagg gattttacgc 126360
ctctccttcc gtaaagacga gtctagtatt tgaaacatta acaacgaccg ataataaaat 126420
cactagtatc aatccaacaa atgcgccaaa gttatatcct cttcaacgca aagtcgtatc 126480
tgaagtagtt tctaatatga ggaaaatgat cgaatcaaaa cgtcctctat acattactct 126540
tcacttggcg tgtggatttg gtaagactat taccacgtgt tatcttatgg ctacacacgg 126600
tagaaaaacc gtcatttgcg tacccaataa aatgttaata catcaatgga agacacaggt 126660
agaggcagtc ggattggaac ataagatatc catagatgga gtaagtagtc tattaaagga 126720
actaaagact caaagtccgg atgtattaat agtagtcagt agacatctga caaacgatgc 126780
cttttgtaaa tatatcaata agcattatga tttgttcatc ttggatgaat cacatacgta 126840
taatctgatg aacaatacag cagttacaag atttttagcg tattatcctc cgatgatgtg 126900
ttatttttta actgctacac ctagaccagc taaccgaatt tattgtaaca gtattattaa 126960
tattgccaag ttatccgatc taaaaaaaac tatctatgcg gtagatagtt tttttgagcc 127020
atattccaca gacaatatta gacatatggt aaaacgacta gatggaccat ctaataaata 127080
tcatatatat accgagaagt tattatctgt agacgagcct agaaatcaac ttattcttaa 127140
taccctggta gaagaattca agtcaggaac tattaatcgc attttagtta ttactaaact 127200
acgtgaacat atggtattat tctacaaacg attattagat cttttcggac cagaggttgt 127260
atttatagga gacgcccaaa atagacgtac tccagatatg gtcaaatcaa tcaaggaact 127320
aaatagattt atattcgtat ccaccttatt ttattccggt actggtttag atattcctag 127380
tttggattcg ttgttcattt gctcggcagt aatcaacaat atgcaaatag agcaattact 127440
agggagggta tgtcgagaaa cagaactatt agataggacg gtatatgtat ttcctaacac 127500
atccatcaaa gaaataaagt acatgatagg aaatttcatg caacgaatta ttagtctgtc 127560
tgtagataaa ctaggattta aacaagaaag ttatcggaaa catcaagaat ccgatcccac 127620
ttctgtatgt acaacatcct ccagagaaga acgtgtatta aatagaatat ttaactcgca 127680
aaatcgttaa gaagtttaag cgacgatccg catgctgcgc aggccagtgt attacccctc 127740
atagtattaa tataatccaa tgatactttt gtgatgtcgg aaatcttaac caatttagac 127800
tgacaggcag aacacgtcat gcaatcatca tcgtcatcga taactgtagt cttgggcttc 127860
tttttgcggc tcttcattcc ggaacgcaca ttggtgctat ccatttaggt agtaaaaaat 127920
aagtcagaat atgccctata acacgatcgt gcaaaacctg gtatatcgtc tctatcttta 127980
tcacaatata gtgtatcgac atctttatta ttattgacct cgtttatctt ggaacatgga 128040
atgggaacat ttttgttatc aacggccacc tttgccttaa ttccagatgt tgtaaaatta 128100
taactaaaca gtctatcatc gacacaaatg aaattcttgt ttagacgttt gtagtttacg 128160
tatgcggctc gttcgcgtct catttttttca gatattgcag gtactataat attaaaaata 128220
agaatgaaat aacataggat taaaaataaa gttatcatga cttctagcgc tgatttaact 128280
```

aacttaaaag aattacttag tctgtacaaa agtttgaaat tttcagattc tgcggctata 128340
gaaaagtata attctttggt agaatgggga acatctactt actggaaaat aggcgtgcaa 128400
aaggtagcta atgtcgagac gtcaatatct gattattatg atgaggtaaa aaataaaccg 128460
tttaatattg atccgggcta ttacattttc ttaccggtat attttgggag cgtctttatt 128520
tattcgaagg gtaaaaatat ggtagaactt ggatctggaa actcttttca aataccagat 128580
gatatgcgaa gtgcgtgtaa caaagtatta gacagcgata acggaataga ctttctgaga 128640
tttgttttgt taaacaatag atggataatg gaagatgcta tatcaaaata tcagtctcca 128700
gttaatatat ttaaactagc tagtgagtac ggattaaaca tacccaaata tttagaaatt 128760
gaaatagagg aagacacatt atttgacgac gagttatact ctattataga acgctctttt 128820
gatgataaat ttccaaaaat atccatatcg tatattaagt tgggagaact taggcggcaa 128880
gttgtagact ttttcaaatt ctcgttcatg tatattgagt ccatcaaggt agatcgtata 128940
ggagataata tttttattcc tagcgttata acaaaatcag gaaaaaagat attagtaaaa 129000
gatgtagacc atttaatacg atctaaggtt agagaacata catttgtaaa agtaaaaaag 129060
aaaaacacat tttccatttt atacgactat gatgggaacg gaacagaaac tagaggagaa 129120
gtaataaaac gaattataga cactatagga cgagactatt atgttaacgg aaagtatttc 129180
tctaaggttg gtagtgcagg cttaaagcaa ttgactaata aattagatat taatgagtgc 129240
gcaactgtcg atgagttagt tgatgagatt aataaatccg gaactgtaaa acgaaaaata 129300
aaaaaccaat cagcatttga tttaagcaga gaatgtttgg gatatccaga agcagatttt 129360
ataacgttag ttaataacat gcggttcaaa atagaaaatt gtaaggttgt aaatttcaat 129420
attgaaaata ctaattgttt aaataacccg agtattgaaa ctatatatgg aaactttaac 129480
cagttcgtct caatctttaa tatcgtcacc gatgtcaaaa aaagattatt cgagtgaaat 129540
aatatgcgcc tttgatatag gtgcaaaaaa tcctgccaga actgttttag aagtcaagga 129600
taactccgtt agggtattgg atatatcaaa attagactgg agttctgatt gggaaaggcg 129660
catagctaaa gatttgtcac aatatgaata cactacagtt cttctagaac gtcagcctag 129720
aaggtcgccg tatgttaaat ttatctattt tattaaaggc tttttatatc atacatcggc 129780
tgccaaagtt atttgcgtct cgcctgtcat gtctggtaat tcatatagag atcgaaaaaa 129840
gagatcggtc gaagcatttc ttgattggat ggacacattc ggattgcgag actccgttcc 129900
ggatagacgc aaattagacg atgtagcgga tagtttcaat ttggctatga gatacgtatt 129960
agataaatgg aatactaatt atacacctta taataggtgt aaatctagaa attacataaa 130020
aaaaatgtaa taacgttagt aacgccatta tggataatct atttaccttt ctacatgaaa 130080
tagaagatag atatgccaga actattttta actttcatct aataagttgc gatgaaatag 130140
gagatatata tggtcttatg aaagaacgca tttcctcaga ggatatgttt gataatatag 130200
tatataataa agatatacat cctgccatta agaaactagt gtattgcgac atccaactta 130260
ctaaacacat tattaatcag aatacgtatc cggtatttaa cgattcttca caagtgaaat 130320
gttgtcatta tttcgacata aactcagata atagcaatat tagctctcgt acagtagaga 130380
tatttgagag ggaaaagtca tctcttgtat catatattaa aactaccaat aagaagagaa 130440
aggtcaatta cggcgaaata aagaaaactg ttcatggagg cactaatgca aattactttt 130500
ccggtaaaaa gtctgacgag tatctgagta ctacagttag atccaacatt aatcaacctt 130560
ggatcaaaac catttctaag agaatgagag tagatatcat taatcactct atagtaacgc 130620

-continued

```
gtggaaaaag ctctatatta caaactatag aaattatttt tactaataga acatgtgtga 130680
aaatattcaa ggattctact atgcacatta ttctatccaa ggacaaggat gaaaaggggt 130740
gtatacacat gattgacaaa ttattctatg tctattataa tttatttctg ttgttcgaag 130800
atatcatcca aaacgagtac tttaaagaag tagctaatgt tgtaaaccac gtacttacgg 130860
ctacggcatt agatgagaaa ttattcctaa ttaagaaaat ggctgaacac gatgtttatg 130920
gagttagcaa tttcaaaata gggatgttta acctgacatt tattaagtcg ttggatcata 130980
ccgttttccc ctctctgtta gatgaggata gcaaaataaa gtttttaag gggaaaaagc 131040
tcaatattgt agcattacga tctctggagg attgtataaa ttacgtgact aaatccgaga 131100
atatgataga aatgatgaag gaaagatcga ctattttaaa tagcatagat atagaaacgg 131160
aatcggtaga tcgtctaaaa gaattgcttc taaaatgaaa aaaaacactg attcagaaat 131220
ggatcaacga ctagggtata agtttttggt gcctgatcct aaagccggag tttttatag 131280
accgttacat ttccaatatg tatcgtattc taattttata ttgcatcgat tgcatgaaat 131340
cttgaccgtc aagcggccac tcttatcgtt taagaataat acagaacgaa ttatgataga 131400
aattagcaat gttaaagtga ctcctccaga ttactcacct ataatcgcga gtattaaagg 131460
taagagttat gatgcattag ccacgttcac tgtaaatatc tttaaagagg taatgaccaa 131520
agagggtata tccatcacta aaataagtag ttatgaggga aaagattctc atttgataaa 131580
aattccgcta ctaataggat acgggaataa aaatccactt gatacagcca agtatcttgt 131640
tcctaatgtc ataggtggag tctttatcaa taaacaatct gtcgaaaaag taggaattaa 131700
tctagtagaa aagattacaa catggccaaa atttagggtt gttaagccaa actcattcac 131760
tttctcgttt tcctccgtat cccctcctaa tgtattaccg acaagatatc gccattacaa 131820
gatatctctg gatatatcac aattggaagc gttgaatata tcatcgacaa agacatttat 131880
aacggtcaat attgttttgc tgtctcaata tttatctaga gtgagtctag aattcattag 131940
acgtagttta tcatacgata tgcctccaga agttgtctat ctagtaaacg cgataataga 132000
tagtgctaaa cgaattactg aatctattac tgactttaat attgatacat acattaatga 132060
cctggtggaa gctgaacaca ttaaacaaaa atctcagtta acgatcaacg agttcaaata 132120
tgaaatgctg cataactttt tacctcatat gaactataca cccgatcaac taaagggatt 132180
ttatatgata tctttactaa gaaagtttct ctactgtatc taccacactt ctagatatcc 132240
agatagagat tcgatggttt gtcatcgcat cctaacgtac ggcaaatatt ttgagacgtt 132300
ggcacatgat gaattagaga attacatagg caacatccga aacgatatca tgaacaatca 132360
caagaacaga ggcacttacg cggtaaacat tcatgtacta acaactcccg gacttaatca 132420
cgcgttttct agcttattga gtggaaagtt caaaaagtca gacggtagtt atcgaacaca 132480
tcctcactat tcatggatgc agaatatttc tattcctagg agtgttggat tttatccgga 132540
tcaagtaaag atttcaaaga tgttttctgt cagaaaatac catccaagtc aatatcttta 132600
cttttgttca tcggacgttc cggaaagagg tcctcaggta ggtttagtat ctcaattgtc 132660
tgtcttgagt tccattacaa atatactaac gtctgagtat ttggatttgg aaaagaaaat 132720
ttgtgagtat atcagatcat attataaaga tgatataagt tactttgaaa caggatttcc 132780
aatcactata gaaaatgctc tagtcgcatc tcttaatcca aatatgatat gtgattttgt 132840
aactgacttt agacgtagaa aacggatggg attcttcggt aacttggagg taggtattac 132900
tttagttagg gatcacatga atgaaattcg cattaatatt ggagcgggaa gattagtcag 132960
accattcttg gttgtggata acggagagct catgatggat gtgtgtccgg agttagaaag 133020
```

cagattagac gacatgacat tctctgacat tcagaaagag tttccgcatg tcatcgaaat 133080
ggtagatata gaacaattta cttttagtaa cgtatgtgaa tcggttcaaa aatttagaat 133140
gatgtcaaag gatgaaagaa agcaatacga tttatgtgac tttcctgccg aatttagaga 133200
tggatatgtg gcatcttcat tagtgggaat caatcacaat tctggaccca gagctattct 133260
tggatgtgct caagctaaac aagctatctc ttgtctgagt tcggatatac gaaataaaat 133320
agacaatgga attcatttga tgtatccaga gaggccaatc gtgattagta aggctttaga 133380
aacttcaaag attgcggcta attgcttcgg ccaacatgtt actatagcat taatgtcgta 133440
caaaggtatc aatcaagagg atggaattat catcaaaaaa caatttattc agagaggcgg 133500
tctcgatata gttaccgcaa agaaacatca agtagaaatt ccgttggaaa actttaataa 133560
caaagaaaga gataggtcta acgcctattc aaaattagaa agtaatggat tagttagact 133620
gaatgctttc ttggaatccg gagacgctat ggcacgaaat atctcatcaa gaactcttga 133680
agatgatttt gctagagata atcagattag cttcgatgtt tccgagaaat ataccgatat 133740
gtacaaatct cgcgttgaac gagtacaagt agaacttact gacaaagtta aggtacgagt 133800
attaaccatg aaagaaagaa gacccattct aggagataaa tttaccacta gaacgagtca 133860
aaagggaaca gtcgcgtatg tcgcggatga aacggaactt ccatacgacg aaaatggtat 133920
cacaccagat gtcattatta attctacatc catcttctct agaaaaacta tatctatgtt 133980
gatagaggtt attttaacag ccgcatattc tgctaagccg tacaacaata agggagaaaa 134040
ccgacctgtc tgttttccta gtagtaacga aacatccatc gatacatata tgcaattcgc 134100
taaacaatgt tatgagcatt caaatccgaa attgtccgat gaagaattat cggataaaat 134160
cttttgtgaa aagattctct atgatcctga aacggataag ccttatgcat ccaaagtatt 134220
ttttggacca atttattact tgcgtctgag gcatttaact caggacaagg caaccgttag 134280
atgtagaggt aaaaagacga agctcattag acaggcgaat gagggacgaa aacgtggagg 134340
aggtatcaag ttcggagaaa tggagagaga ctgtttaata gcgcatggcg cagccaatac 134400
tattacagaa gttttaaaag actcagaaga ggattatcaa gatgtgtatg tttgtgaaaa 134460
ttgtggagac atagcagcac aaatcaaggg tattaataca tgtcttagat gttcaaaact 134520
taatctctct cctctcttaa caaaaattga taccacgcac gtatctaaag tatttcttac 134580
tcaaatgaac gccagaggcg taaaagtcaa attagatttc gaacgaaggc ctccttcgtt 134640
ttataaacca ttagataaag ttgatctcaa gccgtctttt ctggtgtaat attctagttt 134700
ggtagtagat acatatcaat atcatcaaat tcgagatccg aattataaaa tgggcgtgga 134760
ttgttaacta tagaatcgga cgtctgatat tcgaaaatct gtggagtttt aggttttggt 134820
ggaggtgtaa ctgctacttg ggatactgaa gtctgatatt cagaaagctg ggggatgttc 134880
tggttcgaca tccaccgatg gtgtcacatc actaatcggt tcggtaacgt ctgtggatgg 134940
aggtgctact tctacagaac ctgtagcctc agttgtcaac ggagatacat ttttaatgcg 135000
aggaaatgta taatttggta atggtttctc atgtggatct gaagaagagg taagatatct 135060
actagaaaga taccgatcac gttctagttc tcttttgtag aacttaactt tttctttctc 135120
agcatctagt tgatattcca acctcttcac gttactacgt tcagattcca attcacgttc 135180
gcatgggtta cctccgcagt ttttacgagc gatttcacgt tcagccttca tgcgtctctc 135240
cttctctcta tcgagtttat cagagcagtc tttctgaagg cgatcgaact ccataaattt 135300
ctccaacgct ttgattgttt ccatagattt ccgaagttca gcttttagga ctgtgattct 135360

-continued ttttctttcg aattcacagc tggatgtgca accgtttcca ttaccgccat ctctaagttt 135420
cttttctaga tcggcaacat ttcatcccca tgccttttac attcctcgag tctactgtcg 135480
tcgaaatatc gttccagctc cttttcgaca tcaataactt tagcacgttg tctctcaagc 135540
tctcttttgt agttatctga ttccctggca cgtttaagat cttcatgcaa ttgagtcagc 135600
tcttaacaca atctcttgct tcttcgtcat agtacttaca atcactatgg gatccattgt 135660
taccacgtct acactcggcg agctcgcgtt taagagattc aatttcccgt ttgtattggt 135720
ccatgtttcc attgctacca ccattagatt tacaggctgc tagttgtcgt tcgagatcag 135780
aaatacgggt tttcttggaa ttgatttcgt cgatgtactt ggcatcgaaa cacttattaa 135840
gttctttttc caattctacg attttatttc tttcgcgagt caattccctc ctgtagtaac 135900
tatctgtttt gtcagattca cgctctctac gtagactttc ttgcaagtta ctaatttgtt 135960
ccctagcacg tccgagttta gttttatatg ctgaatagag ttctgattca tcctttgagc 136020
agatctctag cgatcgttta agattcctga ttctagtctt tagcctattt acctcctcag 136080
aagatgttcc gttaccgttg cgtttacact cgttaagctg tctatcaaga tccatgattc 136140
tatctctaag acgttgcatc tctctttcca tatcagcatt gctttcatta ttacgtctgc 136200
agtcactcaa ctgtctttca atatctgaga ttctatctct aagacgtcgc atctctctct 136260
gtttcggcat tggtttcatt attacgtcta cagtcgttca actgtctttc aagatctgat 136320
attctagatt ggagtctgct aatctctgta gcattttcac ggcattcact cagttgtctt 136380
tcaagatctg agattttaga ttggagtctg ctaatctctg taagatttcc tcctccgctc 136440
tcgatgcagt cggtcaactt attctctagt tctctaatac gcgaacgcag tgcatcaact 136500
tcttgcgtgt cttcctggtt gcgtgtacat tcatcgagtc tagattcgag atctctaacg 136560
cgtcgtcgtt cttcctcaag ttctctgcgt actacagaaa gcgtgtccct atcttgttga 136620
tatttagcaa tttctgattc tagagtactg attttgctta cgtagttact aatagttgtc 136680
ttggccttat caagatcctc cttgtatttg tcgcattcct tgatatccct acgaagtctg 136740
gacagttccc attcgacatt acgacgttta tcgatttcag ctcggagatc gtcatcgcgt 136800
tgttttagcc acatacgact gagttcaagt tctcgttgac aagatccatc tacttttcca 136860
ttcctaatag tatccagttc cttttctagt tctgaacgca tttctcgttc cctatcaagc 136920
gattctctca attctcggat agtcttctta tcaatttcta ataaatctga accatcatct 136980
gtcccatttt gaatatccct gtgttctttg atctcttttg taagtcggtc gattctttcg 137040
gttttataaa cagaatccct ttccaaagtc ctaatcttac tgagtttatc actaagttct 137100
gcattcaatt cggtgagttt tctcttggct tcttccaact ctgttttaaa ctctccacta 137160
tttccgcatt cttcctcgca tttatctaac cattcaatta gtttattaat aactagttgg 137220
taatcagcga ttcctatagc cgttcttgta attgtgggaa cataattagg atcttctaat 137280
ggattgtatg gcttgatagc atcatcttta tcattattag ggggatggac aaccttaatt 137340
ggttggtcct catctcctcc agtagcgtgt ggttcttcaa taccagtgtt agtaataggc 137400
ttaggcaaat gcttgtcgta cgcgggcact tcctcatcca tcaagtattt ataatcgggt 137460
tctacgtctg aatattcttt tctaagagac gcgacttcgg gagttagtag aagaactctg 137520
tttctgtatc tatcaacgct ggaatcaata ctcaagttaa ggatagcgaa tacctcatcg 137580
tcatcatccg tatcttctga aacaccatca tatgacattt catgaagtct aacgtattga 137640
taaatagaat cagatttagt attaaacaga tccttaacct ttttagtaaa cgcatatgta 137700
tattttagat ctccagattt cataatatga tcacatgcct taaatgtcag tgcttccatg 137760
atataatctg gaacactaat gggtgacgaa aaagatacag caccatatgc tacgttgata 137820
aataaatctg aaccactaag tagataatga ttaatgttaa ggaagaggaa atattcagta 137880
tatagatatg ccttagcatc atatcttgta ctaaacacgc taaacagttt attgatgtga 137940
tcaatttcca acagaataat tagagcagcg ggaataccaa caaacatatt accacatccg 138000
tattttctat gaatatcaca tatcatgtta aaaaatcttg atagaagagc gaatatctcg 138060
tctgacttaa tgagtcgtag ttcagcagca acataagtca taactgtaaa tagaacatac 138120
tttcctgtag tgttgattct agactccaca tcaacaccat tattaaaaat agttttatat 138180
acatctttaa tctgctctcc gttaatcgtc gaacgttcta gtatacggaa acactttgat 138240
ttcttatctg tagttaatga cttagtgata tcacgaagaa tattacgaat tacatttctt 138300
gtttttcttg agagacctga ttcagaactc aactcatcgt tccatagttt ttttacctca 138360
gtggcgaaat ctttggagtg cttggtacat ttttcaataa ggttcgtgac ctccatttat 138420
tataaaaaat tttattcaaa acttaactac aatcgggtaa ttataaaatc gtagatctcc 138480
catgtggtgg aatactacca tctatcgcat gtggatggac agtaggtaat ggccatggga 138540
acagtaatgt ttgcatattt atctttcttg ccagtattac tgcatattgt cccaatgttt 138600
cgatgtgatg ttctaaccta tcaactgccg ctgtatcaca acaatagtgt ccgatgaaat 138660
taagattatg atccaatgtg tttaatatat gattatcaag tcttatacga tccgcgtctt 138720
ttttgacagg atcaggttct tctacaggaa gaagtttcgg cctcttatga tattcatgtc 138780
tgggaaacgg tggtctaggg tgaggctccg gtatcggagt gggttttgga ttataatcat 138840
catcgtctat gacatcatct tcgacttcga tatttatttt gctatcttga tgatgtcctg 138900
tatcagttgc attttcagca ctcgactgaa tattagcgca ttcattgtct attattacca 138960
tatttctaaa cccaaaatgt atgtgttgaa catcagtact atcgttgatg agtcttatag 139020
catgaattcg cttatcgtta tcgggtttat cttctgtcac cttagcaatt cctttttttat 139080 taaactctac ataatcatat ccatttctat tgtttgttct aatataaacg agtatagcat 139140
cattgctaaa tttttcaata gtatcgaaaa cagaatatcc taaaccatat aatatatatt 139200
cagggacact caaactaaat gtccaggatt ctcctaaata cgtaaacttt aatagtgcga 139260
aatcattcaa aaatctacca cttatagata gatagtacat aaatgcgtat agtagtctac 139320
ctatctcttt attatgaaaa ccggcattac gatcatatat gtcgtgatat acctgtgatc 139380
cgtttacgtt aaaccataaa tacatgggtg atcctataaa catgaattta tttctaattc 139440
tcagagctat agttaattga ccgtgtaata tttgcttaca tgcatacttg atacgctcat 139500
taataaaatt tttatcattg ctcgttatct cagaatcgta tatataagga gtaccatcgt 139560
gattcttacc agatattata caaaatacta tatataaaat atattgacca acgttagtaa 139620
tcatataaat gtttaacgtt ttaaattttg tattcaatga tccattatca tacgctagca 139680
tggtcttatg atattcattc tttaaaatat aatattgtgt tagccattgc attggggctc 139740
ctaatggaga tttttttattc tcatccattt taggataggc tttcataaag tccctaataa 139800
cttcgtgaat aatgtttcta tgttttctac tgatgcatgt atttgcttcg atttttttat 139860
cccatgtttc atctatcata gatttaaacg cagtaatgct cgcaacatta acatcttgaa 139920
ccgttggtac aattccgttc cataaattta taatgttcgc catttatata actcattttt 139980
tgaatatact tttaattaac aaaagagtta agttactcat atgggcgccg tccagtctga 140040
acatcaatct ttttagccag agatatcata gccgctctta gagtttcagc gtgattttcc 140100

-continued aacctaaata gaacttcatc gttgcgttta caacactttt ctatttgttc aaactttgtt 140160
gttacattag taatcttttt ttccaaatta gttagccgtt gtttgagagt ttcctcattg 140220
tcgtcttcat cggctttaac aattgcttcg cgtttagcct ctggcttttt agcagccttt 140280
gtagaaaaaa attcagttgc tggaattgca agatcgtcat ctccggggaa aagagttccg 140340
tccatttaaa gtacagattt tagaaactga cactctgcgt tatttatatt tggtacaaca 140400
catggattat aaatatcgat gttaataaca tcagaaaatg taaagtctat acattgttgc 140460
atcgtgttaa attttctaat ggatctagta ttattgggtc caacttctgc ctgaaatcca 140520
aatatggaag cggatacaaa accgtttcct ggataaacca cacatctcca cttttgcttt 140580
acatcagaaa ttgtgtcgtt gacatcttga actctcctat ctaatgccgg tgttccacct 140640
atagattttg aatattcgaa tgctgcatga gtagcattaa attccttaat attgccataa 140700
ttttcatata ttgagtaacc ctggataaaa agtaaacaca ccgcagccgt cgctaccaca 140760
ataaaaaaaa ttgatagaga gttcatttat aatctattag aagctgacaa aattttttta 140820
cacgcatcag acaatgcttt aataaatagt tcaacatcta cttttgtcat atcgaaccga 140880
tggtatgatt ctaacctaga attacatccg aaaaagttga ctatgttcat agtcattaag 140940
tcattaacaa acaacattcc agactctgga ttataagacg atactgtttc gtcacaatta 141000
cctaccttaa tcatgtgatt atgaatattg gctattagag caccttctaa gaaatctata 141060
atatctttga aacacgattt aaaatcaaac cacgaatata cttctacgaa gaaagttagt 141120
ttacccatag gagaaataac tataaatgga gatctaaata caaaatccgg atctatgata 141180
gttttaacat tattatattc tctattaaat acctccacat ctaaaaatgt taattttgaa 141240
actatgtctt cgtttattac cgtacctgaa ctaaacgcta taagctctat tgtttgagaa 141300
ctctttaaac gatattcttg aaatacatgt aacaaagttt cctttaactc ggtcggttta 141360
tctaccatag ttacagaatt tgtatcctta tctataaatat aataatcaaa atcgtataaa 141420
gttatataat tatcgcgttc agattgggat cttttcaaat agactaaaaa ccccatttct 141480
ctagtaagta tcttatgtat atgtttgtaa aatatcttca tggtgggaat atgctctacc 141540
gcagttagcc attcctcatt gacagcggta gatgtattag acaaaactat tccaatgttt 141600
aacaagggcc attttacgag attattaaat ccttgtttga taaatgtagc caatgagggt 141660
tcgagttcaa cgacgattga attctcttcc cgcggatgct gcatgatgaa cgacgggatg 141720
ttgttcgatt gatttggaat tctttttcga ctttttgttt atattaaata ttttaaaatt 141780
tatagcggat agcaattcat gtaccacgga taatgtagac gcgtattgcg catcgatatc 141840
tttattatta gataaattta tcaataaatg tgagaagttt gcctcgttaa ggtcttccat 141900
ttaaatatta tataaacatt tgtgtttgta tcttattcgt cttttatgga atagtttttt 141960
actagtaaag ctgcaattac acactttgtc cgtaaaacat aaatataaac accagctttt 142020
atcaatcgtt ccaaaaagtc gacggcggac atttttaaca tggcatctat tttaaataca 142080
cttaggtttt tggaaaaaac atcattttat aattgtaacg attcaataac taaagaaaag 142140
attaagatta aacataaggg aatgtcattt gtattttata agccaaagca ttctaccgtt 142200
gttaaatact tgtctggagg aggtatatat catgatgatt tggttgtatt ggggaaggta 142260
acaattaata atctaaagat gatgctattt tacatggatt tatcatatca tggagtgaca 142320
agtagtggag caatttacaa attgggatcg tctatcgata gactttctct aaataggact 142380
attgttacaa aagttaataa ttatgatgat acattttttg acgacgatga ttgatcgcta 142440
ttgcacaatt ttgttttttt actttctaat atagcgttta gattcttttt catgtgcgaa 142500
tattgattta ctaaaatatc gatgtttaac ttttgttcta tgacgtcctt atcagcggta 142560
tcggtacata tacgtaattc accttcacaa aatacggagt cttcgataat aatagccaat 142620
cgattattgg atctagctgt ctgtatcata ttcaacatgt ttaatatatc ctttcgtttc 142680
ccctttacag gcatcgatcg tagcatattt tccgcgtctg agatggaaat gttaaaacta 142740
caaaaatgcg taatgttagc ccgtcctaat attggtacgt gtctataagt ttggcatagt 142800
agaataatag acgtgtttaa atgccttcca aagtttaaga attctattag agtattgcat 142860
tttgatagtt tatcacctac atcatcaaaa ataagtaaaa agtgtgctga tttttttatga 142920 ttttgtgcga cagcaataca tttttctatg ttacttttag ttcgtatcag attatattct 142980
agagattcct gactactaac gaaattaata tgatttggcc aaatgtatcc atcataatct 143040
gggttataaa cgggtgtaaa caagaatata tgtttatatt ttttaactag tgtagaaaac 143100
agagatagta aatagatagt ttttccagat ccagatcctc ccgttaaaac cattctaaac 143160
ggcattttta ataaatttc tcttgaaaat tgtttttctt ggaaacaatt cataattata 143220
tttacagtta ctaaattaat ttgataataa atcaaaatat ggaaaactaa ggtcgttagt 143280
agggaggaga acaaagaagg cacatcgtga cataaataac atttattatc atgatgacac 143340
cagaaaacga cgaagagcag acatctgtgt tctccgctac tgtttacgga gacaaaattc 143400
aaggaaagaa taaacgcaaa cgcgtgattg gtctatgtat tagaatatct atggttattt 143460
cactactatc tatgattacc atgtccgcgt ttctcatagt gcgcctaaat caatgcatgt 143520
ctgctaacga ggctgctatt actgacgccg ctgttgccgt tgctgctgca tcatctactc 143580
atagaaaggt tgcgtctagc actacacaat atgatcacaa agaaagctgt aatggtttat 143640
attaccaggg ttcttgttat atattacatt cagactacca gttattctcg gatgctaaag 143700
caaattgcac tgcggaatca tcaacactac ccaataaatc cgatgtcttg attacctggc 143760
tcattgatta tgttgaggat acatggggat ctgatggtaa tccaattaca aaaactacat 143820
ccgattatca agattctgat gtatcacaag aagttagaaa gtatttttgt gttaaaacaa 143880
tgaactaata tttatttttg tacattaata aatgaaatcg cttaatagac aaactgtaag 143940
taggtttaag aagttgtcgg tgccggccgc tataatgatg atactctcaa ccattattag 144000
tggcatagga acatttctgc attacaaaga agaactgatg cctagtgctt gcgccaatgg 144060
atggatacaa tacgataaac attgttattt agatactaac attaaaatgt ctacagataa 144120
tgcggtttat cagtgtcgta aattacgagc cagattgcct agaccggata ctagacatct 144180
gagagtattg tttagtattt tttataaaga ttattgggta agtttaaaaa agaccaatga 144240
taaatggtta gatattaata atgataaaga tatagatatt agtaaattaa caaattttaa 144300
acaactaaac agtacgacgg atgctgaagc gtgttatata tacaagtctg gaaaactggt 144360
taaaacagta tgtaaaagta ctcaatctgt actatgtgtt aaaaaattct acaagtgaca 144420
acaaaaaatg aattaataat aagtcgttaa cgtacgccgc catggacgcc gcgtttgtta 144480
ttactccaat gggtgtgttg actataacag atacattgta tgatgatctc gatatctcaa 144540
tcatggactt tataggacca tacattatag gtaacataaa aactgtccaa atagatgtac 144600
gggatataaa atattccgac atgcaaaaat gctactttag ctataagggt aaaatagttc 144660
ctcaggattc taatgatttg gctagattca acatttatag catttgtgcc gcatacagat 144720
caaaaaatac catcatcata gcatgcgact atgatatcat gttagatata gaagataaac 144780
atcagccatt ttatctattc ccatctattg atgtttttaa cgctacaatc atagaagcgt 144840
ataacctgta tacagctgga gattatcatc taatcatcaa tccttcagat aatctgaaaa 144900
tgaaattgtt gtttaattct tcattctgca tatcagacgg caatggatgg atcataattg 144960
atgggaaatg caatagtaat tttttatcat aaaagttgta aagtaaataa taaaacaata 145020
aatattgaac tagtagtacg tatattgagc aatcagaaat gatgctggta cctcttatca 145080
cggtgaccgt agttgcggga acaatattag tatgttatat attatatatt tgtaggaaaa 145140
agatacgtac tgtctataat gacaataaaa ttatcatgac aaaattaaaa aagataaaga 145200
gttctaattc cagcaaatct agtaaatcaa ctgatagcga atcagactgg gaggatcact 145260
gtagtgctat ggaacaaaac aatgacgtag ataatatttc taggaatgag atattggacg 145320
atgatagctt cgctggtagt ttaatatggg ataacgaatc caatgtcatg gcgcctagca 145380
cagaacacat ttacgatagt gttgctggaa gcacgctgct aataaataat gatcgtaatg 145440
aacagactat ttatcagaac actacagtag taattaatga gacggagact gttgaagtac 145500
ttaatgaaga taccaaacag aatcctaact attcatccaa tcctttcgta aattataata 145560
aaaccagtat ttgtagcaag tcaaatccgt tcattacaga actcaacaat aaatttagtg 145620
agaataatcc gtttagacga gcacatagcg atgattatct taataagcaa gaacaagatc 145680
atgaacacga tgatatagaa tcatcggtcg tatcattggt gtgattagtt tccttttat 145740
aaaattgaag taatatttag tattattgct gccgtcacgt tgtacaaatg gagatattcc 145800
ctgtattcgg catttctaaa attagcaatt ttattgctaa taatgactgt agatattata 145860
tagatacaga acatcaaaaa attatatctg atgagatcaa tagacagatg gatgaaacgg 145920
tacttcttac caacatctta agcgtagaag ttgtaaatga caatgagatg taccatctta 145980
ttccccatag actatcgact attatactct gtattagttc tgtcggagga tgtgttatct 146040
ctatagataa tgacatcaat gacaaaaata ttctaacatt tcccattgat catgctgtaa 146100
tcatatcccc actgagtaaa tgtgtcgtag ttagcaaggg tcctacaacc atattggttg 146160
ttaaagcgga tatacccagc aaacgattgg taacatcgtt tacaaacgac atactgtatg 146220
taaacaatct gtcactgatt aattatttgc cgttgtctgt attcattatt agacgagtca 146280
ccgactattt ggatagacac atatgcgatc agatatttgc gaataataag tggtattcca 146340
ttataaccat cgacgataag caatatccta ttccatcaaa ctgtataggt atgtcctctg 146400
ccaagtacat aaattctagc atcgagcaag atactttaat acatgtttgt aacctcgagc 146460
atccattcga cttagtatac aaaaaaatgc agtcgtacaa ttctgtacct atcaaggaac 146520
aaatattgta cggtagaatt gataatataa atatgagcat tagtatttct gtggattaat 146580
agatttctag tatggggatc attaatcatc tctaatctct aaatacctca taaaacgaaa 146640
aaaaagctat tatcaaatac tgtacggaat ggattcattc tcttctcttt ttatgaaact 146700
ctgttgtata tctactgata aaactggaag caaaaaatct gataaaaaga ataagaataa 146760
gatcaaggat tatatggaac acgattatta taaaataaca atagttcctg gttcctcttc 146820
cacgtctact agctcgtggt attatacaca tgcctagtaa tagtctcttt gcgttgacgg 146880
aaagcagact agaaataaca ggctaaaatg ttcagacacc ataatagttc ccaacccaga 146940
taataacaga gtaccatcaa cacattcctt taaactcaat cccaaaccca aaaccgttaa 147000
aatgtatccg gccaattgat agtagataat gaggtgtaca gcgcatgata atttacacag 147060
taaccaaaat gaaaatactt tagtaattat aagaaatata gatggtaacg tcatcatcaa 147120
caatccaata atatgccgga gagtaaacat tgacggataa aacaaaaatg ctccgcataa 147180
ctctatcatg gcaataacac aaccaaatac ttgtaagatt cctaaattag tagaaaatac 147240
aacggatatc gatgtataag tgatctcgag aaataataag aataaagtaa tgcccgtaaa 147300
gataaacatc aacattgttt ggtaatcatt aaaccaatta gtatgaagtt gaactaattt 147360
cacagtagat tttattccag tgttatcctc gcatgtatac gtacctggta agatatcttt 147420
atattctata atcaatgaga catcactatc cgataacgaa tgaagtctag cactagtatg 147480
ccatttactt aatatggtcg tcttggaagt tttattataa gttaaaatat catggttgtc 147540
caatttccat ctaatatact ttgtcggatt atctatagta cacggaataa tgatggtatt 147600
attacatgct gtatactcta tagtctttgt agatgttata atcataaaag tacagaggta 147660
tatcaacgat attctaactc ttgacatttt ttatttattt aaaatgatac ctttgttatt 147720
tattttattc tattttgcta acggtatcga atggcataag tttgaaacga gtgaagaaat 147780
aatttctact tacttattag acgacgtatt atacacgggt gttaatgggg cggtatacac 147840
attttcaaat aataaactaa acaaaactgg tttagctaat actaattata tcacaacatc 147900
tataaaagta gaggatgcgg ataaggatac attagtatgc ggaaccaata acggaaatcc 147960
caaatgttgg aaaatagacg gttcagacga cccaaaacat agaggtagag gatacgctcc 148020
ttatcaaaat agcaaagtaa cgataatcag tcacaacgga tgtgtactat ctgacataaa 148080
catatcaaaa gaaggaatta aacgatggag aagatttgac ggaccatgtg gttatgattt 148140
atacacggcg gataacgtaa ttccaaaaga tggtttacga ggagcattcg tcgataaaga 148200
tggtacttat gacaaagttt acattctttt cactgatact atcggctcaa agagaattgt 148260
caaaattccg tatatagcac aaatgtgcct aaacgacgaa ggtggtccat catcattgtc 148320
tagtcataga tggtcgacgt ttctcaaagt cgaattagaa tgtgatatcg acggaagaag 148380
ttatagacaa attattcatt ctagaactat aaaaacagat aatgatacga tactatatgt 148440
attcttcgat agtccgcatt atgtacctat tctatgaata ccattaaaca atctttttct 148500
acgtcaaaat tggaaggata tacaaagcaa ttgccgtctc cagctcctgg tatatgtcta 148560
ccagctggaa aagttgttcc acataccacg tttgaagtca tagaaaaata taatgtacta 148620
gatgatatta taaagccttt atctaaccaa cctatcttcg aaggaccgtc tggtgttaaa 148680
tggttcgata taaaggagaa ggaaaatgaa catcgggaat atagaatata cttcataaaa 148740
gaaaattcta tatattcgtt cgatacaaaa tctaaacaaa ctcgtagctc gcaagtcgat 148800
gcgcgactat tttcagtaat ggtaacttcg aaaccgttat ttatagcaga tatagggata 148860
ggagtaggaa tgccacaaat gaaaaaaata cttaaaatgt aatcttaatc gagtacacca 148920
cacgacaatg aacaaacata agacagatta tgctggttat gcttgctgcg taatatgcgg 148980
tctaattgtt ggaattattt ttacagcgac actattaaaa gttgtagaac gtaaattagt 149040
tcatacacca tcaatagata aaacgataaa agatgcatat attagagaag attgtcctac 149100
tgactggata agctataata ataaatgtat ccatttatct actgatcgaa aaacctggga 149160
ggaaggacgt aatgcatgca aagctctaaa tccaaattcg gatctaatta agatagagac 149220
tccaaacgag ttaagttttt taagaagcat tagacgcgga tattgggtag gagaatccga 149280
aatattaaac cagacaaccc catataattt tatagctaag aatgccacga agaatggaac 149340
taaaaaacgg aaatatattt gtagcacaac gaatactccc aaactgcatt cgtgttacac 149400
tatataacaa ttacactaca tttttatcat accactactt cggttagatg ttttagaaaa 149460
aaataaatat cgccgtaccg ttcttgtttt tataaaaata acaattaaca attatcaaat 149520
tttttcttta atattttacg tggttgacca ttcttggtgg taaaataatc tcttagtgtt 149580

-continued ggaatggaat gctgtttaat gtttccacac tcatcgtata ttttgacgta tgtagtcaca 149640
tcgtttacgc aatagtcaga ctgtagttct atcatgcttc ctacattaga aggaggaaca 149700
gttttaaagt ctcttggttt taatctatta ccgttagttt tcatgaaatc ctttgtttta 149760
tccacttcac attttaaata aatgtccact atacattctt ctgttaattt tactagatcg 149820
tcatgggtca tagaatttat aggttccgta gtccatggat ccaaactagc aaacttcgcg 149880
tatacggtat cgcgattagt gtatacacca actgtatgaa aattaagaaa acagtttaat 149940
agatcaacag aaatatttaa tcctccgttt gatacagatg caccatattt atggattttg 150000
gattcacacg ttgtttgtct gaggggttcg tctagcgttg cttctacata aacttctatt 150060
cccatatatt ctttattgtc agaatcgcat accgatttat catcatacac tgtttgaaaa 150120
ctaaatggta tacacatcaa aataacaaat actaacgagt acattctgca atattgttat 150180
cgtaattgga aaaatagtgt tcgagtgagt tggattatgt gagtattgga ttgtatattt 150240
tattttatat tttgtaataa gaataaaatg ctaatgtcaa gtttattcca atagatgtct 150300
tattaaaaac atatataata aataacaatg gctgaatggc ataaaattat cgaggatatc 150360
tcaaaaaata ataagttcga ggatgccgcc atcgttgatt acaagactac aaagaatgtt 150420
ctagctgcta ttcctaacag aacatttgcc aagattaatc cgggtgaaat tattcctctc 150480
atcactaatc gtaatattct aaaacctctt attggtcaga aatattgtat tgtatatact 150540
aactctctaa tggatgagaa cacgtatgct atggagttgc ttactgggta cgcccctgta 150600
tctccgatcg ttatagcgag aactcatacc gcacttatat ttttgatggg taagccaaca 150660
acatccagac gtgacgtgta tagaacgtgt agagatcacg ctacccgtgt acgcgcaact 150720
ggtaattaaa ataaaaagta atattcatat gtagtgtcaa ttttaaatga tgatgatgaa 150780
atggataata tccatattga cgatgtcaat aatgccggta ttggcataca gctcatcgat 150840
ttttagattt cattcagagg atgtggaatt atgttatggg catttgtatt ttgataggat 150900
ctataatgta gtaaatataa aatataatcc gcatattcca tatagatata attttattaa 150960
tcgcacgtta accgtagatg aactagacga taatgtcttt tttacacatg gttatttttt 151020
aaaacacaaa tatggttcac ttaatcctag tttgattgtc tcattatcag gaaacttaaa 151080
atataatgat atacaatgct cagtaaatgt atcgtgtctc attaaaaatt tggcaacgag 151140
tacatctact atattaacat ctaaacataa gacttattct ctacatcggt ccacgtgtat 151200
tactataata ggatacgatt ctattatatg gtataaagat ataaatgaca agtataatgg 151260
catctatgat tttactgcaa tatgtatgct aatagcgtct acattgatag tgaccatata 151320
cgtgtttaaa aaaataaaaa tgaactctta attatgctat gctattagaa atggataaaa 151380
tcaaaattac ggttgattca aaaattggta atgttgttac catatcgtat aacttggaaa 151440
agataactat tgatgtcaca cctaaaaaga aaaaagaaaa ggatgtatta ttagcgcaat 151500
cagttgctgt cgaagaggca aaagatgtca aggtagaaga aaaaaatatt atcgatattg 151560
aagatgacga tgatatggat gtagaaagcg cataatacga tctataaaaa taagtatata 151620
aatacttttt atttactgta ctcttactgt gtagtggtga taccctactc gattattttt 151680
ttaaaaaaat acttattctg attcttctag ccatttccgt gttcgttcga atgccacatc 151740
gacgttaaag ataggggagt agttgaaatc tagttctgca ttgttggtac gcacctcaaa 151800
tgtagtgttg gatatcttca acgtatagtt gttgagtagt gatggttttc taaatagaat 151860
tctcttcata tcattcttgc acgcgtacat ttttagcatc catcttggaa ttctagatcc 151920
ttgttctatt cccaatggtt tcatcaatag aagattaaac atatcgtacg aacacgatgg 151980

-continued agagtaatcg tagcaaaagt aagcatttcc tttaatctca gatcccggat actggatata 152040
ttttgcagcc aacacgtgca tccatgcaac atttcctaca tatacccggc tatgcaccgc 152100
gtcatcatcg actgtacgat acataatgtt accgtgttgc ttacattgct cgtaaaagac 152160
tttcgtcaat ttgtctcctt ctccgtaaat tccagtgggt cttaggcaac aagtatacaa 152220
ttttgctcca ttcatgatta cggaattatt ggctttcata accagttgct cggccatacg 152280
tttacttttt gcgtatacat gtcctggtga tatatcataa agggtatgct catggccgat 152340
gaatggatca ccgtgtttat ttggtcctat tgcttccatg ctactagtat agatcaaata 152400
cttgattcct aggtccacac aagctgccaa tatagtctgt gttccataat agtttacttt 152460
catgatttca ttatcggtgt attttccaaa tacatccact agagcagccg tatgaataat 152520
cagatttacc ccatctagcg cttctctcac cttatcaaag tcgtttatat cacattgtat 152580
atagtttata accttaactt tcgaggttat tggttgtgga tcttctacaa tatctatgac 152640
tctgatttct tgaacatcat ctgcactaat taacagtttt actatatacc tgcctagaaa 152700
tccggcacca ccagtaaccg cgtacacggc cattgctgcc actcataata tcagactact 152760
tattctattt tactaaataa tggctgtttg tataatagac cacgataata tcagaggagt 152820
tatttacttt gaaccagtcc atggaaaaga taaagtttta ggatcagtta ttggattaaa 152880
atccggaacg tatagtttga taattcatcg ttacggagat attagtcaag gatgtgattc 152940
cataggcagt ccagaaatat ttatcggtaa catctttgta aacagatatg gtgtagcata 153000
tgtttattta gatacagatg taaatatatc tacaattatt ggaaaggcgt tatctatttc 153060
aaaaaatgat cagagattag cgtgtggagt tattggtatt tcttacataa atgaaaagat 153120
aatacatttt cttacaatta acgagaatgg cgtttgatat atcagttaat gcgtctaaaa 153180
caataaatgc attagtttac ttttctactc agcaaaataa attagtcata cgtaatgaag 153240
ttaatgatac acactacact gtcgaatttg atagggacaa agtagttgac acgtttattt 153300
catataatag acataatgac accatagaga taagaggggt gcttccagag gaaactaata 153360
ttggttgcgc ggttaatacg ccggttagta tgacttactt gtataataag tatagtttta 153420
aactgatttt agcagaatat ataagacaca gaaatactat atccggcaat atttattcgg 153480
cattgatgac actagatgat ttggctatta aacagtatgg agacattgat ctattattta 153540
atgagaaact taaagtagac tccgattcgg gactatttga ctttgtcaac tttgtaaagg 153600
atatgatatg ttgtgattct agaatagtag tagctctatc tagtctagta tctaaacatt 153660
gggaattgac aaataaaaag tataggtgta tggcattagc cgaacatata tctgatagta 153720
ttccaatatc tgagctatct agactacgat acaatctatg taagtatcta cgcggacaca 153780
ctgagagcat agaggataaa tttgattatt ttgaagacga tgattcgtct acatgttctg 153840
ccgtaaccga cagggaaacg gatgtataat ttttttata gcgtgaagga tatgataaaa 153900
aatataattg ttgtatttat cccattccaa tcaccttata tgattctgta acacaatgaa 153960
ggagtctcat agatgtatag aggtcagata ctggtttgat aaactgttta ttccacatga 154020
gtatgtttga ctttatggtt agacccgcat actttaacaa atcactgaaa attggagtta 154080
ggtattgacc tctcagaatc agttgccgtt ctggaacatt aaatgtattt tttatgatat 154140
actccaacgc atttatgtgg gcatacaaca agtcattact aatggagtat tccaagagtt 154200
ttagttgtct agtatttaac aagagaagag atttcaacag actgtttatg aactcgaatg 154260
ccgcctcatt gtcgcttata ttgatgatgt cgaattctcc caatatcatc accgatgagt 154320

-continued agctcatctt gttatcggga tccaagtttt ctaaagatgt cattaaaccc tcgatcatga 154380
atggatttat catcatcgtt tttatgttgg acatgagctt agtccgtttg tccacatcta 154440
tagacgacga tttctgaatt attttatata tccctctctt taactccagg aacttgtcag 154500
gatggtctac tttaatatgt tctcgtctaa gagatgaaaa tctttggatg gttgcacgcg 154560
acttttctct aaaggatgac gttgcccaag atcctctctt aaatgaatcc atcttatcct 154620
tggacaagat ggacagtcta ttttccttag atggtttaat atttttgtta cccatgatct 154680
ataaaggtag acctaatcgt ctcggatgac ctatatattt attttcagtt ttattatacg 154740
cataaattgt aaaaaatatg ttaggtttac aaaaatgtct cgtggggcat taatcgtttt 154800
tgaaggattg gacaaatctg gaaaaacaac acaatgtatg aacatcatgg aatctatacc 154860
ggcaaacacg ataaaatatc ttaactttcc tcagagatcc actgtcactg gaaagatgat 154920
agatgactat ctaactcgta aaaaaaccta taatgatcat atagttaatc tattattttg 154980
tgcaaataga tgggagtttg catcttttat acaagaacaa ctagaacagg gaattacttt 155040
aatagttgat agatacgcgt tctctggagt agcgtatgcc gccgctaaag gcgcgtcaat 155100
gactctcagt aagagttatg aatctggatt gcctaaaccc gacttagtta tattcttgga 155160
atctggtagc aaagaaatta atagaaacgt cggcgaggaa atttatgaag atgttacatt 155220
ccaacaaaag gtattacaag aatataaaaa aatgattgaa gaaggagata ttcattggca 155280
aattatttct tctgaattcg aggaagatgt aaagaaggag ttgattaaga atatagttat 155340
agaggctata cacacggtta ctggaccagt ggggcaactg tggatgtaat agtgaaatta 155400 catttttat aaatagatgt tagtacagtg ttataaatgg atgaagcata ttactctggc 155460
aacttggaat cagtactcgg atacgtgtcc gatatgcata ccgaactcgc atcaatatct 155520
caattagtta ttgccaagat agaaactata gataatgata tattaaacaa ggacattgta 155580
aattttatca tgtgtagatc aaacttggat aatccattta tctctttcct agatactgta 155640
tatactatta tagatcaaga gaactatcag accgaattga ttaattcatt agacgacaat 155700
gaaattatcg attgtatagt taataagttt atgagctttt ataaggataa cctagaaaat 155760
atagtagatg ctatcattac tctaaaatat ataatgaata atccagattt taaaactacg 155820
tatgccgaag tactcggttc cagaatagcc gatatagata ttaaacaagt gatacgtgag 155880
aatatactac aattgtctaa tgatatccgc gaacgatatt tgtgaaaaat attaaaaaaa 155940
aatacttttt ttattaaatg acgtcgcttc gcgaatttag aaaattatgc tgtgatatat 156000
atcacgcatc aggatataaa gaaaaatcta aattaattag agactttata acagataggg 156060
atgataaata tttgatcatt aagctattgc ttcccggatt agacgataga atttataaca 156120
tgaacgataa acaaattata aaattatata gtataatatt taaacaatct caggaagata 156180
tgctacaaga tttaggatac ggatatatag gagacactat taggactttc ttcaaagaga 156240
acacagaaat ccgtccacga gataaaagca ttttaacttt agaagacgtg gatagtttct 156300
taactacgtt atcatccgta actaaagaat cgcatcaaat aaaattattg actgatatcg 156360
catccgtttg tacatgtaat gatttaaaat gtgtagtcat gcttattgat aaagatctaa 156420
aaattaaagc gggtcctcgg tacgtactta acgctattag tcctaatgcc tatgatgtgt 156480
ttagaaaatc taataacttg aaagagataa tagaaaatgc atctaaacaa aatctagact 156540
ctatatctat ttctgttatg actccaatta atcccatgtt agcggaatcg tgtgattctg 156600
tcaataaggc gtttaaaaaa tttccatcag gaatgtttgc ggaagtcaaa tacgatggtg 156660
aaagagtaca agttcataaa aataataacg agtttgcctt ctttagtaga aacatgaaac 156720
cagtactctc tcataaagtg gattatctca aagaatacat accgaaagca tttaaaaaag 156780
ctacgtctat cgtattggat tctgaaattg ttcttgtaga cgaacataat gtaccgctcc 156840
cgtttggaag tttaggaata cacaaaaaga aagaatataa aaactctaac atgtgtttgt 156900
tcgtgtttga ctgtttgtac tttgatggat tcgatatgac ggacattcca ttgtacgaac 156960
gaagatcttt tctcaaagat gttatggttg aaatacccaa tagaatagta ttctcagagt 157020
tgacgaatat tagtaacgag tctcagttaa ctgacgtatt ggatgatgca ctaacgagaa 157080
aattagaagg attggtctta aaagatatta atggagtata cgaaccggga aagagaagat 157140
ggttaaaaat aaagcgagac tatttgaacg agggttccat ggcagattct gccgatttag 157200
tagtactagg tgcttactat ggtaaaggag caaagggtgg tatcatggca gtctttctaa 157260
tgggttgtta cgacgatgaa tccggtaaat ggaagacggt taccaagtgt tcaggacacg 157320
atgataatac gttaagggtt ttgcaagacc aattaacgat ggttaaaatt aacaaggatc 157380
ccaaaaaaat tccagagtgg ttggtagtta ataaaatcta tattcccgat tttgtagtag 157440
aggatccgaa acaatctcag atatgggaaa tttcaggagc agagtttaca tcttccaagt 157500
cccataccgc aaatggaata tccattagat ttcctagatt tactaggatt agagaagata 157560
aaacgtggaa agaatctact catctaaacg atttagtaaa cttgactaaa tcttaatagt 157620
tacatacaaa ctgaaaatta aaataacact atttagttgg tggtcgccat ggatggtgtt 157680
attgtatact gtctaaacgc gttagtaaaa catggcgagg aaataaatca tataaaaaat 157740
gatttcatga ttaaaccatg ttgtgaaaga gtttgtgaaa aagtcaagaa cgttcacatt 157800
ggcggacaat ctaaaaacaa tacagtgatt gcagatttgc catatatgga taatgcggta 157860
tccgatgtat gcaattcact gtataaaaag aatgtatcaa gaatatccag atttgctaat 157920
ttgataaaga tagatgacga tgacaagact cctactggtg tatataatta ttttaaacct 157980
aaagatgtta ttcctgttat catatctata ggaaaggata aagatgtctg tgaactatta 158040
atctcatcag acatatcgtg tgcatgcgtg gagttaaatt catatcacgt agccattctt 158100
cccatggatg tttccttttt taccaaagga aatgcatcat tgattattct cctgtttgat 158160
ttctctatcg atgcagcacc tctcttaaga agtgtaaccg ataataatgt tattatatct 158220
agacaccagc gtctacatga cgagcttccg agttccaatt ggttcaagtt ttacataagt 158280
ataaagtccg actattgttc tatattatat atggttgttg atggatctgt gatgcatgcg 158340
atagctgata atagaactca cgcaattatt agcaaaaata tattagacaa tactacgatt 158400
aacgatgagt gtagatgctg ttattttgaa ccacagatta ggattcttga tagagatgag 158460
atgctcaatg gatcatcgtg tgatatgaac agacattgta ttatgatgaa tttacctgat 158520
gtaggcaaat ttggatctag tatgttgggg aaatatgaac ctgacatgat taagattgct 158580
ctttcggtgg ctggtaattt aataagaaat cgagactaca ttcccgggag acgaggatat 158640
agctactacg tttacggtat agcctctaga taattttttt aagcacgaaa taaaaaacat 158700
aattttaaac caatctattt catactattt tgtgtgatca ccatggacat aaagatagat 158760
attagtattt ctggtgataa atttacggtg actactagga gggaaaatga agaaagaaaa 158820
aaatatctac ctctccaaaa agaaaaaact actgatgtta tcaaacctga ttatcttgag 158880
tacgatgact tgttagatag agatgagatg tttactattc tagaggaata ttttatgtac 158940
agaggtctat taggcctcag aataaaatat ggacgactct ttaacgaaat taaaaaattc 159000
gacaatgatg cggaagaaca attcggtact atagaagaac tcaagcagaa acttagatta 159060
aattctgaag agggagcaga taactttata gattatataa aggtacaaaa acaggatatc 159120
gtcaaactta ctgtatacga ttgcatatct atgataggat tgtgtgcatg cgtggtagat 159180
gtttggagaa atgagaaact gttttctaga tggaaatatt gtttacgagc tattaaactg 159240
tttattaatg atcacatgct tgataagata aaatctatac tgcagaatag actagtatat 159300
gtggaaatgt catagaaagt taaaagttaa tgagagcaaa aatatataag gttgtattcc 159360
atatttgtta ttttttctgt aatagttaga aaaatacatt cgatggtcta tctaccagat 159420
tattatgtgt tataaggtac tttttctcat aataaactag agtatgagta agatagtgtt 159480
tttcaaaaca tataaatcta aaattgatgg atgagatata cagctattaa tttcgaaaat 159540
atattttaat ctgataactt taaacatgga tttttgatgg tggtttaacg ttttaaaaaa 159600
agattttgtt attgtagtat atgataatat taaaagatgg atataaagaa tttgctgact 159660
gcatgtacta ttttttacat tactacattg gctacggcag atatacctac tccgccacca 159720
acgggtcatg tgacaaggga gaatatcttg ataagaggca taatcaatgt tgtaatcggt 159780
gtccacctgg agaatttgcc aaggttagat gtaatggtaa cgataacaca aaatgtgaac 159840
gctgcccacc tcatacatat accacaatcc caattattct aatggatgtc atcaatgtag 159900
aaaatgccca accggatcat ttgataaggt aaagtgtacc ggaacacaga acagtaaatg 159960
ttcgtgtctt cctggttggt attgtgctac tgattcttca cagactgaag attgttgaaa 160020
ttgtgtacca aaaaggagat gtccatgcgg atactttggt ggaatagatg aacaaggaaa 160080
tcctatttgt aaatcgtgtt gtgttggtga atattgcgac tacctacgta attatagact 160140
tgatccattt cctccatgca aactatctaa atgtaattaa ttatgatttt gatgataatg 160200
ttaccataca ttatatcgct acttggttag tgtattattc agtatgaaga cctattaata 160260
attacttatc ttttgacgat cttgttataa ttataatata aaaatactta tggcatagta 160320
actcataatt gctgacgcga taaattcgta ataatctgtt ttgttcaaat ttttataagg 160380
aatctacagg cataaaaata aaaatataat ttataatata ctcttacagc gcgccatcat 160440
gaataacagc agtgaattga ttgctgttat taatggattt agaaatagtg gacgattttg 160500
tgatattagt atagttatta atgatgaaag gataaacgct cataaactca tcctatctgg 160560
agcctccgaa tatttttcca ttctgttttc caataatttt atcgattcta atgaatacga 160620
agttaatcta agtcatttag attatcaaag cgttaacgat ttgatcgatt acatttatgg 160680
gataccttttg agcctaacta acgataacgt gaaatatatt ctttcaaccg ctgatttttt 160740
acaaattgga tctgctatta cggagtgtga aaattacata cttaaaaatc tttgttctaa 160800
aaactgtatc gatttctaca tatacgctga taaatataat aacaagaaaa tagaatcagc 160860
gtcgtttaac acaatattac aaaatatttt gagactcatc aacgatgaaa actttaaata 160920
cttaacagag gaatcaatga taaaaatttt aagcgatgat atgttaaata taaaaaatga 160980
ggattttgca ccactaattc tcattaaatg gttagagagt actcaacaat catgcaccgt 161040
cgagttactt agatgcctca gaatatcatt gctttcccca caagttataa aatcacttta 161100
tagtcatcaa ctggttagtt caatctacga atgtataaca ttcttaaaca atatagcatt 161160
cttggatgaa tcatttccta gataccatag catcgagttg atatctatcg gtataagtaa 161220
ttcgcatgat aagatttcca taaactgcta caatcataaa aaaaatacat gggaaatgat 161280
atcttcacgt agatataggt gtagtttcgc agtggccgtc ctggataata ttatctatat 161340
gatgggtgga tatgatcagt ccccgtatag aagttcaaag gttatagcgt acaatacatg 161400
tacaaattct tggatatatg atataccaga gctaaaatat cctcgttcta attgtggggg 161460
actggctgat gacgaataca tttattgtat aggcggcata cgcgatcagg attcatcgtt 161520
gacatctagt attgataaat ggaagccatc aaaaccatat tggcagaagt atgctaaaat 161580
gcgcgaacca aaatgtgata tgggggttgc gatgttaaac ggattaatat atgtcatggg 161640
tggaatcgtt aaaggtgaca cgtgtaccga cgcactagag agtttatcag aagatggatg 161700
gatgaagcat caacgtcttc caataaaaat gtccaatatg tcgacgattg ttcatgatgg 161760
caagatttat atatctggag gttacaacaa tagtagtgta gttaatgtaa tatcgaatct 161820
agtccttagc tataatccga tatatgatga atggaccaaa ttatcatcat taaacattcc 161880
tagaattaat cccgctctat ggtcagcgca taataaatta tatgtaggag gaggaatatc 161940
tgatgatgtt cgaactaata catctgaaac atacgataaa gaaaaagatt gttggacatt 162000
ggataatggt cacgtgttac cacgcaatta tataatgtat aaatgcgaac cgattaaaca 162060
taaatatcca ttggaaaaaa cacagtacac gaatgatttt ctaaagtatt tggaaagttt 162120
tataggtagt tgatagaaca aaatacataa ttttgtaaaa ataaatcact ttttatacta 162180
atatgacacg attaccaata cttttgttac taatatcatt agtatacgct acaccttttc 162240
ctcagacatc taaaaaaata ggtgatgatg caactctatc atgtaatcga aataatacaa 162300
atgactacgt tgttatgagt gcttggtata aggagcccaa ttccattatt cttttagctg 162360
ctaaaagcga cgtcttgtat tttgataatt ataccaagga taaaatatct tacgactctc 162420
catacgatga tctagttaca actatcacaa ttaaatcatt gactgctaga gatgccggta 162480
cttatgtatg tgcattcttt atgacatcaa ctacaaatga cactgataaa gtagattatg 162540
aagaatactc cacagagttg attgtaaata cagatagtga atcgactata gacataatac 162600
tatctggatc tacacattca ccggaaacta gttctaagaa acctgattat atagataatt 162660
ctaattgctc gtcggtattc gaaatcgcga ctccggaacc aattactgat aatgtagaag 162720
atcatacaga caccgtcaca tacactagtg atagcattaa tacagtaagt gcatcatctg 162780
gagaatccac aacagacgag actccggaac caattactga taaagaagat catacagtta 162840
cagacactgt ctcatacact acagtaagta catcatctgg aattgtcact actaaatcaa 162900
ccaccgatga tgcggatctt tatgatacgt acaatgataa tgatacagta ccaccaacta 162960
ctgtaggcgg tagtacaacc tctattagca attataaaac caaggacttt gtagaaatat 163020
ttggtattac cgcattaatt atattgtcgg ccgtggcaat tttctgtatt acatattata 163080
tatataataa acgttcacgt aaatacaaaa cagagaacaa agtctagatt tttgacttac 163140
ataaatgtct gggatagtaa aatctatcat attgagcgga ccatctggtt taggaaagac 163200
agccatagcc aaaagactat gggaatatat ttggatttgt ggtgtcccat accactagat 163260
ttcctcgtcc tatggaacga gaaggtgttg attaccatta cgttaacaga gaggccatct 163320
ggaagggaat agccgccgga aactttctag aacatactga gtttttagga aatatttacg 163380
gaacttctaa aacagctgtg aatacagcgg ctattaataa tcgtatttgt gtgatggatc 163440
taaacatcga cggtgttaga agtcttaaaa atacgtacct aatgccttac tcggtgtata 163500
taagacctac ctctcttaaa atggttgaga ccaagcttcg ttgtagaaac actgaagcta 163560
acgatgagat tcatcgtcgc gtgatattgg caaaaacgga tatggatgag gccaacgaag 163620
caggtctatt cgacactatt atcattgaag atgatgtgaa tttagcatat agtaagttaa 163680
ttcagatact acaggaccgt attagaatgt attttaacac taattagaga cttaagactt 163740
aaaacttgat aattaataat ataactcgtt tttatatgtg gctatttcaa cgtctaatgt 163800

-continued attagttaaa tattaaaact taccacgtaa aacttaaaat ttaaaatgat atttcattga 163860
cagatagatc acacattatg aactttcaag gacttgtgtt aactgacaat tgcaaaaatc 163920
aatgggtcgt tggaccatta ataggaaaag gtggattcgg tagtatttat actactaatg 163980
acaataatta tgtagtaaaa atagagccca aagctaacgg atcattattt accgaacagg 164040
cattttatac tagagtactt aaaccatccg ttatcgaaga atggaaaaaa tctcacaata 164100
taaagcacgt aggtcttatc acgtgcaagg catttggtct atacaaatcc attaatgtgg 164160
aatatcgatt cttggtaatt aatagattag gtgcagatct agatgcggtg atcagagcca 164220
ataataatag attaccaaaa aggtcggtga tgttgatcgg aatcgaaatc ttaaatacca 164280
tacaatttat gcacgagcaa ggatattctc acggagatat taaagcgagt aatatagtct 164340
tggatcaaat agataagaat aaattatatc tagtggatta cggattggtt tctaaattca 164400
tgtctaatgg agaacatgtt ccatttataa gaaatccaaa taaaatggat aacggtactc 164460
tagaatttac acctatagat tcgcataaag gatacgttgt atctagacgt ggagatctag 164520
aaacacttgg atattgtatg attagatggt tgggaggtat cttgccatgg actaagatat 164580
ctgaaacaaa gaattgtgca ttagtaagtg ccacaaaaca gaaatatgtt aacaatactg 164640
cgactttgtt aatgaccagt ttgcaatatg cacctagaga attgctgcaa tatattacca 164700
tggtaaactc tttgacatat tttgaggaac ccaattatga cgagtttcgg cacatattaa 164760
tgcagggtgt atattattaa gtgtggtgtt tggtcgatgt aaaatttttg tcgataaaaa 164820
ttaaaaaata acttaattta ttattgatct cgtgtgtaca accgaaatca tggcgatgtt 164880
ttacgcacac gctctcggtg ggtacgacga gaatcttcat gcctttcctg gaatatcatc 164940
gactgttgcc aatgatgtca ggaaatattc tgttgtgtca gtttataata acaagtatga 165000
cattgtaaaa gacaaatata tgtggtgtta cagtcaggtg aacaagagat atattggagc 165060
actgctgcct atgtttgagt gcaatgaata tctacaaatt ggagatccga tccatgatca 165120
agaaggaaat caaatctcta tcatcacata tcgccacaaa aactactatg ctctaagcgg 165180
aatcgggtac gagagtctag acttgtgttt ggaaggagta gggattcatc atcacgtact 165240
tgaaacagga aacgctgtat atggaaaagt tcaacatgat tattctacta tcaaagagaa 165300
ggccaaagaa atgaatgcac ttagtccagg acctatcatt gattaccacg tctggatagg 165360
agattgtatc tgtcaagtta ctgctgtgga cgtacatgga aaggaaatta tgagaatgag 165420
attcaaaaag ggtgcggtgc ttccgatccc aaatctggta aaagttaaac ttggggagaa 165480
tgatacagaa aatctttctt ctactatatc ggcggcacca tcgaggtaac cacctctctg 165540
gaagacagcg tgaataatgt actcatgaaa cgtttggaaa ctatacgcca tatgtggtct 165600
gtcgtatatg atcattttga tattgtgaat ggtaaagaat gctgttatgt gcatacgcat 165660
ttgtctaatc aaaatcttat accgagtact gtaaaaacaa atttgtacat gaagactatg 165720
ggatcatgca ttcaaatgga ttccatggaa gctctagagt atcttagcga actgaaggaa 165780
tcaggtggat ggagtcccag accagaaatg caggaatttg aatatccaga tggagtggaa 165840
gacactgaat caattgagag attggtagag gagttcttca atagatcaga acttcaggct 165900
ggtgaatcag tcaaatttgg taattctatt aatgttaaac atacatctgt ttcagctaag 165960
caactaagaa cacgtatacg gcagcagctt cctttatact ctcatctttt accaacacaa 166020
agggtggata tttgttcatt ggagttgata ataatacaca caaagtaatt ggattcacgg 166080
tgggtcatga ctacctcaga ctggtagaga atgatataga aaagcatatc aaaagacttc 166140
gtgttgtgca tttctgtgag aagaaagagg acatcaagta cacgtgtcga ttcatcaagg 166200
tatataaacc tggggatgag gctacctcga catacgtgtg cgctatcaaa gtggaaagat 166260
gctgttgtgc tgtgtttgca gattggccag aatcatggta tatggatact aatggtatca 166320
agaagtattc tccagatgaa tgggtgtcac atataaaatt ttaattaatg taatagagaa 166380
caaataataa ggttgtaata tcatatagac aataactaac aattaattag taactgttat 166440
ctctttttta actaaccaac taactatata cctattaata catcgtaatt atagttctta 166500
acatctatta atcattaatt cgcttcttta attttttata aactaacatt gttaattgaa 166560
aagggataac atgttacaga atataaatta tatatggatt tttttaaaaa ggaaatactt 166620
gactggagta tatatttatc tcttcattat atagcacgcg tgttttccaa tttttccaca 166680
tcccatataa tacaggatta taatctcgtt cgaacatacg agaaagtgga taaaacaata 166740
gttgattttt tatctaggtt gccaaattta ttccatattt tagaatatgg ggaaaatatt 166800
ctacatattt attctatgga tgatgctaat acgaatatta taattttttt tctagataga 166860
gtattaaata ttaataagaa cgggtcattt atacacaatc tcaggttatc atcatccatt 166920
aatataaaag aatatgtata tcaattagtt aataatgatc atccagataa taggataaga 166980
ctaatgcttg aaaatggacg tagaacaaga catttttgt cctatatatc agatacagtt 167040
aatatctata tatgtatttt aataaatcat ggattttata tagatgccga agacagttac 167100
ggttgtacat tattacatag atgtatatat cactataaga aatcagaatc agaatcatac 167160
aatgaattaa ttaagatatt gttaaataat ggatcagatg tagataaaaa agatacgtac 167220
ggaaacacac cttttatcct attatgtaaa cacgatatca acaacgtgga attgtttgag 167280
atatgtttag agaatgctaa tatagactct gtagacttta atagatatac acctcttcat 167340
tatgtctcat gtcgtaataa atatgatttt gtaaagttat taatttctaa aggagcaaat 167400
gttaatgcgc gtaatagatt cggaactact ccattttatt gtggaattat acacggtatc 167460
tcgcttataa aactatattt ggaatcagac acagagttag aaatagataa tgaacatata 167520
gttcgtcatt taataatttt tgatgctgtt gaatctttag attatctatt atccagagga 167580
gttattgata ttaactatcg tactatatac aacgaaacat ctatttacga cgctgtcagt 167640
tataatgcgt ataatacgtt ggtctatcta ttaaacagaa atggtgattt tgagacgatt 167700
actactagtg gatgtacatg tatttcggaa gcagtcgcaa acaacaacaa aataataatg 167760
gaagtactat tgtctaaacg accatctttg aaaattatga tacagtctat gatagcaatt 167820
actaaacata aacagcataa tgcagattta ttgaaaatgt gtataaaata tactgcgtgt 167880
atgaccgatt atgatactct tatagatgta cagtcgctac agcaatataa atggtatatt 167940
ttaaaatgtt tcgatgaaat agatatcatg aagagatgtt atataaaaaa taaaactgta 168000
ttccaattag ttttttgtat caaagacatt aatactttaa tgagatacgg taaacatcct 168060
tctttcgtga aatgcactag tctcgacgta tacggaagtc gtgtacgtaa tatcatagca 168120
tctattagat atcgtcagag attaattagt ctattatcca agaagctgga tcctggagat 168180
aaatggtcgt gttttcctaa cgaaataaaa tataaaatat tggaaaactt taacgataac 168240
gaactatcca catatctaaa aatcttataa acactattaa aatataaaat ctaagtagga 168300
taaaatcaca ctacatcatt gtttcctttt agtgctcgac agtgtatact atttttaaca 168360
ctcataaata aaaatgaaaa cgatttccgt tgttacgttg ttatgcgtac tacctgctgt 168420
tgtttattca acatgtactg tacccactat gaataacgct aaattaacgt ctaccgaaac 168480
atcgtttaat gataaacaga aagttacgtt tacatgtgat cagggatatc attcttcgga 168540
tccaaatgct gtctgcgaaa cagataaatg gaaatacgaa aatccatgca aaaaaatgtg 168600
cacagtttct gattacatct ctgaattata taataaaccg ctatacgaag tgaattccac 168660
catgacacta agttgcaacg gcgaaacaaa atattttcgt tgcgaagaaa aaaatggaaa 168720
tacttcttgg aatgatactg ttacgtgtcc taatgcggaa tgtcaacctc ttcaattaga 168780
acacggatcg tgtcaaccag ttaaagaaaa atactcattt ggggaatata tgactatcaa 168840
ctgtgatgtt ggatatgagg ttattggtgc ttcgtacata agttgtacag ctaattcttg 168900
gaatgttatt ccatcatgtc aacaaaaatg tgatatgccg tctctatcta atggattaat 168960
ttccggatct acattttcta tcggtggcgt tatacatctt agttgtaaaa gtggttttac 169020
actaacgggg tctccatcat ccacatgtat cgacggtaaa tggaatcccg tactcccaat 169080
atgtgtacga actaacgaag aatttgatcc agtggatgat ggtcccgacg atgagacaga 169140
tttgagcaaa ctctcgaaag acgttgtaca atatgaacaa gaaatagaat cgttagaagc 169200
aacttatcat ataatcatag tggcgttaac aattatgggc gtcatatttt taatctccgt 169260
tatagtatta gtttgttcct gtgacaaaaa taatgaccaa tataagttcc ataaattgct 169320
accgtaaata taaatccgtt aaaataatga ataattaata acgaacaagt atcaaaagat 169380
taaagaatta tagctagaat caattgagat gtcttcttca gtggatgttg atatctacga 169440
tgccgttaga gcatttttac tcaggcacta ttataacaag agatttattg tgtatggaag 169500
aagtaacgcc atattacata atatatacag gctatttaca agatgcgccg ttataccgtt 169560
cgatgatata gtacgtacta tgccaaatga atcacgtgtt aaacaatggg tgatggatac 169620
acttaatggt ataatgatga atgaacgcga tgtttctgta agcgttggca ccggaatact 169680
attcatggaa atgtttttcg attacaataa aaatagtatc aacaatcaac taatgtatga 169740
tataattaat agcgtatcta taattctagc taatgagaga tatagaagcg cttttaacga 169800
cgatggtata tacatccgta gaaatatgat taacaagttg tacggatacg catctctaac 169860
tactattggc acgatcgctg gaggtgtttg ttattatctg ttgatgcatc tagttagttt 169920
gtataaataa ttatttcaat atactagtta aaattttaag attttaaatg tataaaaaac 169980
taataacgtt tttatttgta ataggtgcat tagcatccta ttcgaataat gagtacactc 170040
cgtttaataa actgagtgta aaactctata tagatggagt agataatata gaaaattcat 170100
atactgatga taataatgaa ttggtgttaa attttaaaga gtacacaatt tctattatta 170160
cagagtcatg cgacgtcgga tttgattcca tagatataga tgttataaac gactataaaa 170220
ttattgatat gtataccatt gactcgtcta ctattcaacg cagaggtcac acgtgtagaa 170280
tatctaccaa attatcatgc cattatgata agtaccctta tattcacaaa tatgatggtg 170340
atgagcgaca atattctatt actgcagagg gaaaatgcta taaaggaata aaatatgaaa 170400
taagtatgat caacgatgat actctattga gaaaacatac tcttaaaatt ggatctactt 170460
atatatttga tcgtcatgga catagtaata catattattc aaaatatgat ttttaaaaat 170520
ttaaaatata ttatcacttc agtgacagta gtcaaataac aaacaacacc atgagatata 170580
ttataattct cgcagttttg ttcattaata gtatacacgc taaaataact agttataagt 170640
ttgaatccgt caattttgat tccaaaattg aatggactgg ggatggtcta tacaatatat 170700
cccttaaaaa ttatggcatc aagacgtggc aaacaatgta tacaaatgta ccagaaggaa 170760
catacgacat atccgcattt ccaaagaatg atttcgtatc tttctgggtt aaatttgaac 170820
aaggcgatta taaagtggaa gagtattgta cgggactatg cgtcgaagta aaaattggac 170880
caccgactgt aacattgact gaatacgacg accatatcaa tttgtacatc gagcatccgt 170940
atgctactag aggtagcaaa aagattccta tttacaaacg cggtgacatg tgtgatatct 171000
acttgttgta tacggctaac ttcacattcg gagattctaa agaaccagta ccatatgata 171060
tcgatgacta cgattgcacg tctacaggtt gcagcataga ctttgtcaca acagaaaaag 171120
tgtgcgtgac agcacaggga gccacagaag ggtttctcga aaaaattact ccatggagtt 171180
cgaaagtatg tctgacacct aaaaagagtg tatatacatg cgcaattaga tccaaagaag 171240
atgttcccaa tttcaaggac aaaatggcca gagttatcaa gagaaaattt aataaacagt 171300
ctcaatctta tttaactaaa tttctcggta gcacatcaaa tgatgttacc acttttctta 171360
gcatgcttaa cttgactaaa tattcataac taatttttat taatgataca aaaacgaaat 171420
aaaactgcat attatacact ggttaacgcc cttataggct ctaaccattt tcaagatgag 171480
gtccctgatt atagtccttc tgttcccctc tatcatctac tccatgtcta ttagacaatg 171540
tgagaagact gaagaggaaa catggggatt gaaaataggg ttgtgtataa ttgccaaaga 171600
tttctatccc gaaagaactg attgcagtgt tcatctccca actgcaagtg aaggattgat 171660
aactgaaggc aatggattca gggatatacg aaacaccgat aaattataaa aaaagcaatg 171720
tgtccgctgt ttccgttaat aatactattt tcgtaactgg cggattattc ataaataact 171780
ctaatagcac gatcgtggtt aacaatatgg aaaaacttga catttataaa gacaaacaat 171840
ggtcgattat agaaatgcct atggctaggg tatatcacgg catcgactcg acatttggaa 171900
tgttatattt tgccggaggt ctatccgtta ccgaacaata tggtaattta gagaaaaaca 171960
acgagatatc ttgttacaat cctagaacga ataagtggtt tgatatttca tatactattt 172020
ataagatatc catatcatca ttgtgtaaac taaataacgt cttctatgta tttagtaagg 172080
acattggata tgtggaaaag tatgatggtg catggaagtt agtacatgat cgtctccccg 172140
ctataaaggc attatcaact tctccttatt gattgaaaat gaaaatataa atagttttta 172200
tgtatagcag tattacccta tagttttatt gcttactact aacatggata cagatgttac 172260
aaatgtagaa gatatcataa atgaaataga tagagagaaa gaagaaatac taaaaaatgt 172320
agaaattgaa aataataaaa acattaacaa gaatcatcca agtggatata ttagagaagc 172380
actcgttatt aataccagta gtaatagtga ttccattgat aaagaagtta tagaatgtat 172440
ctgtcacgat gtaggaatat agatcatatc tactaatttt tataatcgat acaaaacata 172500
aaaaacaact cgttattaca tagcaggcat ggaatccttc aagtattgtt ttgataacga 172560
tggcaagaaa tggattatcg gaaatacttt atattctggt aattcaatac tatataaggt 172620
cagaaaaaat ttcactagtt cgttctacaa ttacgtaatg aagatagatc acaaatcaca 172680
caagccattg ttgtctgaaa tacgattcta tatatctgta ttggatcctt tgactatcga 172740
caactggaca cgggaacgtg gtataaagta tttggctatt ccagatctgt atggaattgg 172800
agaaaccgat gattatatgt tcttcgttat aaagaatttg ggaagagtat tcgccccaaa 172860
ggatactgaa tcagtcttcg aagcatgcgt cactatgata aacacgttag agtttataca 172920
ctctcaagga tttacccatg gaaaaataga accgaggaat atactgatta gaaataaacg 172980
tctttcacta attgactatt ctagaactaa caaactatac aagagtggaa actcacatat 173040
agattacaac gaggacatga taacttcagg aaatatcaat tatatgtgtg tagacaatca 173100
tcttggagca acagtttcaa gacgaggaga tttagaaatg ttgggatatt gcatgataga 173160
atggttcggt ggcaaacttc catggaaaaa cgaaagtagt ataaaagtaa taaaacaaaa 173220
aaaagaatat aaaaaattta tagctacttt ctttgaggac tgttttcctg aaggaaatga 173280

-continued acctctggaa ttagttagat atatagaatt agtatacacg ttagattatt ctcaaactcc 173340
taattatgac agactacgta aactgtttat acaagattga aattatattc ttttttttat 173400
agagtgtggt agtgttacgg atatttaata ttagactatc tctatcgcgc tacacgacca 173460
atatcgatta ctatggatat cttcagggaa atcgcatctt ctatgaaagg agagaatgta 173520
ttcatttctc cagcgtcaat ctcgtcagta ttgacaatac tgtattatgg agctaatgga 173580
tccactgctg aacagctatc aaaatatgta gaaaaggagg agaacatgga taaggttagc 173640
gctcaaaata tctcattcaa atccataaat aaagtatatg ggcgatattc tgccgtgttt 173700
aaagattcct ttttgagaaa aattggcgat aagtttcaaa ctgttgactt cactgattgt 173760
cgcactatag atgcaatcaa caagtgtgta gatatcttta ctgaggggaa aatcaatcca 173820
ctattggatg aaccattgtc tcctgatacc tgtctcctag caattagtgc cgtatacttt 173880
aaagcaaaat ggttgacgcc attcgaaaag gaatttacca gtgattatcc cttttacgta 173940
tctccgacgg aaatggtaga tgtaagtatg atgtctatgt acggcaaggc atttaatcac 174000
gcatctgtaa aggaatcatt cggcaacttt tcaatcatag aactgccata tgttggagat 174060
actagtatga tggtcattct tccagacaag attgatggat tagaatccat agaacaaaat 174120
ctaacagata caaattttaa gaaatggtgt aactctctgg aagctacgtt tatcgatgtt 174180
cacattccca agtttaaggt aacaggctcg tataatctgg tggatactct agtaaagtca 174240
ggactgacag aggtgttcgg ttcaactgga gattatagca atatgtgtaa ttcagatgtg 174300
agtgtcgacg ctatgatcca caaaacgtat atagatgtca atgaagagta tacagaagca 174360
gctgcagcaa cttgtgcact ggtgtcagac tgtgcatcaa caattacaaa tgagttctgt 174420
gtagatcatc cgttcatcta tgtgattagg catgttgatg gaaaaattct tttcgttggt 174480
agatattgct ctccgacaac taattgttaa ccattttttt taaaaaatag aaaaaacatg 174540
tggtattagt gcaggtcgtt attcttccaa ttgcaattgg taagatgacg gccaacttta 174600
gtacccacgt cttttcacca cagcactgtg gatgtgacag actgaccagt attgatgacg 174660
tcagacaatg tttgactgaa tatatttatt ggtcgtccta tgcataccgc aacaggcaat 174720
gcgctggaca attgtattcc acactcctct cttttagaga tgatgcggaa ttagtgttca 174780
tcgacattcg cgagctggta aaaaatatgc cgtgggatga tgtcaaagat tgtgcagaaa 174840
tcatccgttg ttatataccg gatgagcaaa aaaccatcag agagatttcg gccatcatcg 174900
gactttgtgc atatgctgct acttactggg gaggtgaaga ccatcccact agtaacagtc 174960
tgaacgcatt gtttgtgatg cttgagatgc tcaattacgt ggattataac atcatattcc 175020
ggcgtatgaa ttgatgagtt gtacatcttg acattttctt ctttcttctc ttctcccttt 175080
cccagaaaca aactttttt acccactata aaataaaatg agtatactac ctgttatatt 175140
tctttctata ttttttatt cttcattcgt tcagactttt aacgcgcctg aatgtatcga 175200
caaagggcaa tattttgcat cattcatgga gttagaaaac gagccagtaa tcttaccatg 175260
tcctcaaata aatacgctat catccggata taatatatta gatattttat gggaaaaacg 175320
aggagcggat aatgatagaa ttataccgat agataatggt agcaatatgc taattctgaa 175380
cccgacacaa tcagactctg gtatttatat atgcattacc acgaacgaaa cctactgtga 175440
catgatgtcg ttaaatttga caatcgtgtc tgtctcagaa tcaaatatag atcttatctc 175500
gtatccacaa atagtaaatg agagatctac tggcgaaatg gtatgtccca atattaatgc 175560
atttattgct agtaacgtaa acgcagatat tatatggagc gggcatcgac gccttagaaa 175620
taagagactt aaacaacgga cacctggaat tattaccata gaagatgtta gaaaaaatga 175680
tgctggttat tatacatgtg ttttagaata tatatacggt ggcaaaacat ataacgtaac 175740
cagaattgta aaattagagg tacgggataa aataatacct tctactatgc aattaccaga 175800
tggcattgta acttcaatag gtagtaattt gactattgca tgcagagtat cgttgagacc 175860
tcccacaacg gatgcagacg tcttttggat aagtaatggt atgtattacg aagaagatga 175920
tggggacgga aacggtagaa taagtgtagc aaataaaatc tatatgaccg ataagagacg 175980
tgttattaca tcccggttaa acattaatcc tgtcaaggaa gaagatgcta caacgtttac 176040
gtgtatggcg tttactattc ctagcatcag taaaacagtt actgttagta taacgtgaat 176100
gtatgttgtt acatttccat gtcaattgag tttataagaa tttttataca ttatcttcca 176160
acaagcaatt gacgaacgta ttgctatgat taactcccac gatactatgc atattattaa 176220
tcattaactt gcagactata cctagagcta ttttgacata ctcgtgttct tgtgtaattg 176280
cagtatctat attattaaag tacgtaaatc tagctatagt tttattattt aattttagat 176340
aatataccgt ctccttattt ttaaaaattg ccacatcctt tattaaatca tgaatgggaa 176400
tttctatgtc atagttaata tattgtgaac aacaagagca gatatctata ggaaagggtg 176460
gaatgcgata cattgatcta tgtagtttta aaacacacgc aaactttgaa gaatttatat 176520
aaatcattcc atcgatacat ccttctatgt tgagatgtat atatccagga attcgtttat 176580
taatatcggg aaatgtataa actaaaacat tgcccggaag cggagcttct accggagtta 176640
tatcagtttt taacttacaa aatgtaacca ataccttttgc atgacttgtt ttgttcggca 176700
acgttagttt aaacttgacg aatggattaa ttacaatagc atgatccgcg catctattaa 176760 gttttttttac tttaacgccc ttgtatgttt ttacagagac tttatctaaa tttctagtgc 176820
ttgtatgtgt tataaatata acgggatata gaactgaatc acctacctta gatacccaat 176880
tacattttat cagatccaga taataaacaa attttgtcgc cctaactaat tctatattgt 176940
tatatatttt acaattggtt atgatatcat gtaataactt ggaatctaac gcacatcgtc 177000
gtacgtttat acaattgtga tttagtgtag tatatctaca catgtatttt tccgcgctat 177060
agtattctgg actagtgata aaactatcgt tatatctgtc ttcaatgaac tcatcgagat 177120
attgctctct gtcatattca tacacctgca taaactttct agacatctta caatccgtgt 177180
tattttagga tcatatttac atatttacgg gtatatcaaa gatgttagat tagttaatgg 177240
gaatcgtcta taataatgaa tattaaacaa ttatatgagg acttttacca caaagcatca 177300
taaaaatgag tcgtcgtctg atttatgttt taaatatcaa ccgcgaatca actcataaaa 177360
tacaagagaa tgaaatatat acatatttta gtcattgcaa tatagaccat acttctacag 177420
aacttgattt tgtagttaaa aactatgatc taaacagacg acaacctgta actgggtata 177480
ctgcactaca ctgctatttg tataataatt actttacaaa cgatgtactg aagatattat 177540
taaatcatgg agtggatgta acgatgaaaa ccagtagcgg acgtatgcct gtttatatat 177600
tgcttactag atgttgcaat atttcacatg atgtagtgat agatatgata gacaaagata 177660
aaaaccactt attacataga gactattcca acctattact agagtatata aaatctcgtt 177720
acatgttatt aaaggaagag gatatcgatg agaacatagt atccacttta ttagataagg 177780
gaatcgatcc taactttaaa caagacggat atacagcgtt acattattat tatttgtgtc 177840
tcgcacacgt ttataaacca ggtgagtgta gaaaaccgat aacgataaaa aaggccaagc 177900
gaattatttc tttgtttata caacatggag ctaatctaaa cgcgttagat aattgtggta 177960
atacaccatt ccatttgtat cttagtattg aaatgtgtaa taatattcat atgactaaaa 178020
tgctgttgac ttttaatccg aatttcgaaa tatgtaataa tcatggatta acgcctatac 178080
tatgttatat aacttccgac tacatacaac acgatattct tgttatgtta atacatcact 178140
atgaaacaaa tgttggagaa atgccgatag atgagcgtcg tataatcgta ttcgagttta 178200
tcaaaacata ttctacacgt cctgcagatt cgataactta tttgatgaat aggtttaaaa 178260
atatagatat ttatacccgc tatgaaggaa agacattatt acacgtagca tgtgaatata 178320
ataatacaca cgtaatagat tatcttatac gtatcaacgg agatataaat gcgttaaccg 178380
acaataacaa acacgctaca caactcatta tagataacaa agaaaattcc ccatatacca 178440
ttaattgttt actgtatata cttagatata ttgtagataa gaatgtgata agatcgttgg 178500
tggatcaact tccatctcta cctatcttcg atataaaatc atttgagaaa ttcatatcct 178560
actgtatact tttagatgac acattttaca atagacacgt taggaatcgc gattctaaaa 178620
cgtatcgata cgcattttca aaatacatgt cgtttgataa atacgatggt ataataacta 178680
aatgtcataa agaaacaata ttgctcaaac tatccactgt tctagacact acactatatg 178740
cagttttaag atgccataat tcgaaaaagt taagaagata cctcaccgag ttaaaaaaat 178800
ataataacga taagtccttt aaaatatatt ctaatattat gaatgagaga taccttaatg 178860
tatattataa agatatgtac gtgtcaaagg tatatgataa actatttcct gttttcacag 178920
ataaaaattg tctactaaca ttactacctt cagaaattat atacgaaata ttatacatgc 178980
tgacaattaa cgatctttat aatatatcgt atccacctac caaagtatag ttgtattttt 179040
ctcatgcgat gtgtgtaaaa aaactgatat tatataaata ttttagtgcc gtataataaa 179100
gatgacgatg aaaatgatgg tacatatata tttcgtatca ttattgttat tgctattcca 179160
cagttacgcc atagacatcg aaaatgaaat cacagaattc ttcaataaaa tgagagatac 179220
tctaccagct aaagactcta aatggttgaa tccagcatgt atgttcggag gcacaatgaa 179280
tgatatagcc gctctaggag agccattcag cgcaaagtgt cctcctattg aagacagtct 179340
tttatcgcac agatataaag actatgtggt taaatgggaa aggctagaaa aaaatagacg 179400
gcgacaggtt tctaataaac gtgttaaaca tggtgattta tggatagcca actatacatc 179460
taaattcagt aaccgtaggt atttgtgcac cgtaactaca aagaatggtg actgtgttca 179520
gggtatagtt agatctcata ttagaaaacc tccttcatgc attccaaaaa catatgaact 179580
aggtactcat gataagtatg gcatagactt atactgtgga attctttacg caaaacatta 179640
taataatata acttggtata aagataataa ggaaattaat atcgacgaca ttaagtattc 179700
acaaacggga aaggaattaa ttattcataa tccagagtta gaagatagcg gaagatacga 179760
ctgttacgtt cattacgacg acgttagaat caagaatgat atcgtagtat caagatgtaa 179820
aatacttacg gttataccgt cacaagacca caggtttaaa ctaatactag atccaaaaat 179880
caacgtaacg ataggagaac ctgccaatat aacatgcact gctgtgtcaa cgtcattatt 179940
gattgacgat gtactgattg aatgggaaaa tccatccgga tggcttatag gattcgattt 180000
tgatgtatac tctgttttaa ctagtagagg cggtattacc gaggcgacct tgtactttga 180060
aaatgttact gaagaatata taggtaatac atataaatgt cgtggacaca actattattt 180120
tgaaaaaacc cttacaacta cagtagtatt ggagtaaata tacaatgcat tttatatac 180180
attactgaat aattattatt attatttata tcgtatttgt gctataacgc gactatctag 180240
gtatttgtat ctcaccgata gagaacatat aaatgtagac tctattaaac agttgtgtaa 180300
aatatcagat cctaatgcat gttatagatg tggatgtacg gctttacatg agtactttta 180360
taattataga tcagtcaacg gaaaatacaa gtatagatac aacggttact atcaatatta 180420
tttatctagc gattatgaaa attataatga atattattat gatgattatg atagaactgg 180480
tatgaacagt gagagtgata atatatcaat caaaacagaa tatgaattct atgatgaaac 180540
acaagatcaa agtacacaac tagtaggtta cgacattaaa ctcaaaacca atgaggatga 180600
ttttatggct atgatagatc agtgggtgtc catgattata tagatgaatc aattaataaa 180660
gtagtatatg gaagagagtc tcacgtaaga tggcgggata tatggcaaga acataatgat 180720
ggcgtataca gtataggaaa ggagtgcata gataatatat acgaagacaa ccataccgta 180780
gacgaattct acaagataga cagcgtatca gatgtagatg acgcggaaca catatctccg 180840
ataactaatg atgtatctac acaaacatgg gaaaagaaat cagagttaga tagatacatg 180900
gaaatgtatc ctcgtcatag atatagtaag cattctgtct ttaagggatt ttctgacaaa 180960
gttagaaaaa atgatttaga catgaatgtg gtaaaagaat tactttctaa cggtgcatct 181020
ctaacaatta aggatagcag taataaggat ccaataaccg tttattttcg aagaacgata 181080
atgaatttag aaatgattga tgaacgaaag tatatagtac actcctatct aaaaaattat 181140
aaaaatttcg attatccatt tttcaggaag ttagttttga ctaataaaca ttgtctcaac 181200
aattattata atataagcga cagcaaatat ggaacaccgc tacatatatt ggcgtctaat 181260
aaaaaattaa taactcctaa ttacatgaag ttattagtgt ataacggaaa tgatataaac 181320
gcacgaggtg aagatacaca aatgcgaact ccattacaca aatatttgtg taaatttgta 181380
tatcataata ttgaatatgg tatccgatac tataatgaaa agattataga cgcatttata 181440
gagttaggag ccgatctaac tattccaaat gacgatggaa tgataccagt agtttactgt 181500
atacactcaa atgccgaata tggttataac aatattacta acataaagat aatacgtaaa 181560
ctacttaatc ttagtagacg tgcgtcacat aatctattta gagatcgagt catgcacgat 181620
tatataagta atacatatat tgatcttgag tgtttagata ttattagatc gttggatgga 181680
ttcgatatca atggttactt tgaaggacgt acaccacttc attgcgctat acaacataac 181740
ttcactcaga ttgctaagta cttattagat cgaggagctg atatagtcgt acccaacaca 181800
ttgattatac atcagtacat acagtaaata gcatagatat ggaggaggat acaaatattt 181860
caaataaagt tataaggtac aacactgtca ataatatatg ggaaacatta cctaacttct 181920
ggactggaac tataaatcca ggcgtggtct cgcataaaga tgatatatat gttgtatgcg 181980
acatcaaaga tgaaaaaaat gttaaaactt gtatatttag atataacacg aatacgtata 182040
acggatggga attggtcacg acgacagaaa gcagattatc agctctgcat actattcttt 182100
ataacaatac cataatgatg ttacattgtt atgaatcgta tatgttacaa gatacattta 182160
atgtgtacac tcgcgaatgg aatcatatgt gtcatcaaca ttcgaatagt tatatcatgt 182220
acaatatact acccatctac taaatataat agaataaaat aaatgagtat gatcatttta 182280
gataacgatt gattttatca ttaccgcttc attcttatat tctttgctta cggaacctat 182340
atttagaaac atctactaac gattttttat gcttgcatta ttaatggtat gtaatatgat 182400
tgattgtgta cgcaatacca atttgttaag tatgaatacg gggtacaaac ataaactgaa 182460
gtttaacatt atttatttat gatatatatc gttattgttt ggtctatacc atggatatct 182520
ttaaagaact aatcttaaaa cacacggatg aaaatgtttt gatttctcca gtttctattt 182580
tatctacttt atctattcta aatcatggag cagctggttc tacagctgaa caactatcaa 182640
aatatataga gaatatgaat gagaatacac ccgatgacaa taatgacatg gacgtagata 182700
ttccgtattg tgcgacacta gctaccgcaa ataaaatata cggtagcgat agtatcgagt 182760

-continued tccacgcctc cttcctacaa aaaataaaag acgattttca aactgtaaac tttaataatg 182820
ctaaccaaac aaaggaacta atcaacgaat gggttaagac aatgacaaat ggtaaaatta 182880
attccttatt gactagtccg ctatccatta atactcgtat gacagttgtt agcgccgtcc 182940
attttaaagc aatgtggaaa tatccatttt ctaaacatct tacatataca gacaagtttt 183000
atatttctaa gaatatagtt accagtgttg atatgatggt gagcactgag aataacttgc 183060
aatatgtaca tattaatgaa ttattcggag gattctctat tatcgatatt ccatacgagg 183120
gaaactctag tatggtaatt atactaccgg acgacataga aggtatatat aacatagaaa 183180
aaaatataac agatgaaaaa tttaaaaaat ggtgtggtat gttatctact aaaagtatag 183240
acttgtatat gccaaagttt aaagtggaaa tgacagaacc gtataatctg gtaccgattt 183300
tagaaaattt aggacttact aatatattcg gatattatgc agattttagc aagatgtgta 183360
atgaaactat cactgtagaa aaatttctac atacgacgtt tatagatgtt aatgaggagt 183420
atacagaagc atcggccgtt acaggagtat ttatgactaa cttttcgatg gtatatcgta 183480
cgaaggtcta cataaaccat ccattcatgt acatgattaa agacaacaca ggacgtatac 183540
tttttatagg gaaatactgc tatccgcaat aaatataaac aaatagactt ttatcacgtt 183600
tatctatgtc taaatattac aaatagtaat agtataaact aaagctgata atacttaaaa 183660
aaataataat atcatttaca attaatagta taaactaaaa attaaacaaa tcgttattat 183720
aagtaatatc aaaatgatga tatacggatt aatagcgtgt cttatattcg tgacttcatc 183780
catcgctagt ccactttata ttcccgttat tccacccatt tcggaagata aatcgttcaa 183840
tagtgtagag gtattagttt ccttgtttag agatgaccaa aaagactata cggtaacttc 183900
tcagttcaat aactacacta tcgataccaa agactggact atcggcgtac tatccacacc 183960
tgatggtttg gatataccat tgactaatat aacttattgg tcacggttta ctataggtcg 184020
tgcattgttc aaatcagagt ctgaggatat tttccaaaag aaaatgagta ttctaggtgt 184080
ttctatagaa tgtaagaagt cgtcgacatt acttactttt ttgaccgtgc gtaaaatgac 184140
tcgagtattt aataaatttc cagatatggc ttattatcga ggagactgtt taaaagccgt 184200
ttatgtaaca atgacttata aaaatactaa aactggagag actgattaca cgtacctctc 184260
taatgggggg ttgcctgcat actatcgtaa tggggtcgat ggttgattat tgattagtat 184320
attccttatt ctttttattc acacaaaaag aacattttta taaacatgaa accactgtct 184380
aaatgtaatt atgatcttga tttatagatg aagatcagcc tttagaggat tttaaccagt 184440
atgtttaata tgaaaaaaat aaacataaca tattttgaga ttaagcgcta ttgtgcaaga 184500
ttatattaga atcaaattaa tctttcatac gagaaaaata acgacatacg tcgtcaacaa 184560
attaaacttt ttatttatta gttaactagc ttatagaact tgctcattgt tatgtttcta 184620
aaacgggtac gacatatagg acaattatcc gacgcaccgg tttctcttcg tgttttatgc 184680
catatattga tgcatgttat gcaaaatata tgagtacacg aatccaataa accaaagtat 184740
ctatcgtttt gagtaaacaa cttcatagca aattccacat tctttttctt tacttactct 184800
atacacgtcc tcgtatttat ccagtatttt gatgatatcc aactcagaaa tggttgttgt 184860
attattgggt gtattgggag tataggtatt attagctatg taccaattta ccaaccctct 184920
taatattgat tgaacaatca catcggttat ccaatcaata accacattaa taactaaatt 184980
gtagtgtata tatagaccat atatgtttct attttttgga cagttacgta tagtttcagt 185040
aagttttgat tgttgtattc ctgtatctct agataagtta gtcatatagt cccttccggc 185100
gatacgtttt ttccaagccc gaaattgatt agccaaatgt gtatttattt ttgtgatatt 185160

-continued gatataatat gtaatgttat taatatttcg gataatgcat actgttagtc ttatatcatt 185220
tggttcatct atgtattgta atattgttac atgatctata gatgatgtat tgattttggc 185280
aggatcgaat tccatatccg cgactaaaca gtgaaaaaaa tgtaaatact ttttaaattt 185340
taaattagta aaactttttt ttattttttta tgattccaaa aatactgaat acaaagtcct 185400
aaattataaa tatggagatc atactaccac aacttattat tatgcatact cagccggtgt 185460
aatagataga tatatataat tctattacac cggcagacaa ttaccgatcg gtatttgtcg 185520
ttaccaacat accgtataat atgtaatata caattccata acccattgac agttgttata 185580
catcaaaatt gcaattcttt tgattacgat gttataagaa tgtagttaat tgatgtatga 185640
tgttaatgtg tcctctttcc tcttataaca tcgtaatcaa aaactttttt ataatatata 185700
cctaataatg tgtcttaata gttctcgtga ttcgtcaaac aatcattctt ataaaatata 185760
ataaagcaac gtaaaacaca taaaaataag cgtaactaat aagacaatgg atatttacga 185820
cgataaaggt ctacagacta ttaaactgtt taataatgaa tttgattgta taaggaatga 185880
catcagagaa ttatttaaac atgtaactga ttccgatagt atacaacttc cgatggaaga 185940
caattctgat attatagaaa atatcagaaa aatactatat agacgattaa aaaatgtaga 186000
atgtgttgac atcgatagta caataacttt tatgaaatac gatccaaatg atgataataa 186060
gcgtacgtgt tctaattggg taccccttaac taataactat atggaatatt gtctagtaat 186120
atatttggaa acaccgatat gtggaggcaa aataaaatta taccaccccta caggaaatat 186180
aaagtcggat aaggatatta tgtttgcaaa gactctagac tttaaatcaa agaaagtgtt 186240
aactggacgt aaaacaattg ccgttctaga catatccgtt tcatataata gatcaatgac 186300
tactattcac tacaacgacg acgttgatat agatatacat actgataaaa atggaaaaga 186360
gttatgttat tgttatataa caatagatga tcattacttg gttgatgtgg aaactatagg 186420
agttatagtc aatagatctg gaaaatgtct gttagtaaat aaccatctag gtataggtat 186480
cgttaaagat aaacgtataa gcgatagttt tggagatgta tgtatggata caatatttga 186540
cttttctgaa gcacgagagt tattttcatt aactaatgat gataacagga atatagcatg 186600
ggacactgat aaactagacg atgatacaga tatatggact cccgtcacag aagatgatta 186660
caaatttctt tctagactag tattgtatgc aaaatctcaa tcggatactg tattcgacta 186720
ttatgttctt actggtgata cggaaccacc cactgtattc attttcaagg taactagatt 186780
ttactttaat atgccgaaat aaaaaatttt tgtataaatat ctagaggtag aggtattgtt 186840
tagataaata caaataacat agatacatcg catacttagc atttttataa atatacataa 186900
gacatacact ttatacattt tttttgtaaa aatactcata aaaaaattta taaaaattat 186960
ggcacaacca tatcttgtat aggtagttta gttcgtcgag tgaacctata aacagataat 187020
agacaacacg taataataat aatgcctact aatacaagca taataccggg agatgggata 187080
tatgacgttg tagtgtttgg gttttctgaa cgttgatagt ctactaatac tacatgctga 187140
catctaatgc ctgtataacc atgagagcat ctacaataca taccgtcaat atctctagcg 187200
tggatacagt caccgtgtaa acaatatcca tctccctctg gaccgcataa tctgatagct 187260
ggaatatctg ttgtagcgtt tgtaatttct ggcgatgtcg tttcgatagc gttaccacta 187320
tcggcgaatg atctgattat catagcagcg aacaacaaca tcagatattt catcgacatt 187380
tttgatggat tttgtgttta tgctgtttct cagtgtgtgt ttatgacaag attgggaatt 187440
ttatattatt aattcagtaa tataaactaa taatatattg ttaattgtgt aaataatata 187500

-continued aaaataacaa tacaatattg aatgtgttgc tgttaaaaat gatcataaac acggagttta 187560
ttttatatgt ctcgcataaa cattactaaa aaaatatatt gttctgtttt tctttcacat 187620
ctttaattat gaaaaagtaa atcattatga gatggacgag attgtacgca tcgttcgcga 187680
cagtatgtgg tacataccta acgtatttat ggacgacggt aagaatgaag gtcacgtttc 187740
tgtcaacaat gtctgtcata tgtatttcac gttctttgat gtggatacat cgtctcatct 187800
gtttaagcta gttattaaac actgcgatct gaataaacga ggtaactctc cattacattg 187860
ctatacgatg aatacacgat ttaatccatc tgtattaaag atattgttac accacggcat 187920
gcgtaacttt gatagcaagg atgaaaaagg acaccactat caatcgataa caagatcttt 187980
gatatactaa cggacaccat tgatgacttt agtaaatcat ccgatctatt gctgtgttat 188040
cttagatata aattcaatgg gagcttaaac tattacgttc tgtacaaagg atccgacgag 188100
gatgaactca cttctcttca ttactactgt aaacacatat ccacgttcta caaaagcaat 188160
tattacaagt taagtcacac taagatgcga gccgagaagc gattcatcta cgcgataata 188220
gattatggag caaacattaa cgcggttaca cacttacctt caacagtata ccaaacatag 188280
tcctcgtgtg gtgtatgctc ttttatctcg aggagccgat acgaggatac gtaataatct 188340
tgattgtaca cccatcatgg aacgattgtg caacaggtca tattctcata atgttactca 188400
attggcacga acaaaaggaa gaaggacaac atctacttta tctattcata aaacataatc 188460
aaggatacac tctcaatata ctacggtatc tactagatag gttcgacatt cagaaagacg 188520
aatactataa taccgccttt caaaattgta acaacaatgt tgcctcatac atcggatacg 188580
acatcaacct tccgactaaa gacggtattc gacttggtgt ttgaaaacag aaacatcata 188640
tacaaggcgg atgttgtgaa tgacatcatc caccacagac tgaaagtatc tctacctatg 188700
attaaatcgt tgttctacaa gatgtctctc cctacgacga ttactacgta aagaagataa 188760
tagcctactg cctattaagg gacgagtcat tcgcggaact acatagtaaa ttctgtttaa 188820
acgaggacta taaaagtgta tttatgaaaa atatatcatt cgataagata gattccatca 188880
tcgtgacata agtcgcctta aagagattcg aatctccgac accgacctgt atacggtatc 188940
acagctatct taaagccata cattcagaca gtcacatttc atttcccatg tacgacgatc 189000
tcatagaaca gtgccatcta tcgatggagc gtaaaagtaa actcgtcgac aaagcactca 189060
ataaattaga gtctaccatc ggtcaatcta gactatcgta tttgcctccg gaaattatgc 189120
gcaatatcat ctaaacagta tgttgtacga aaagaaccat tacaaatatt atccatgata 189180
gaaagaaaat atctatatga ttggagaagt aggaaacagg aacaagacga cgattactac 189240
attattaaat catgaagtcc gtattatact cgtatatatt gtttctctca tgtataataa 189300
taaacggaag agatatagca ccgcatgcac catccgatgg aaagtgtaaa gacaacgaat 189360
acaaacgcca taatttgtgt ccgggaacat acgcttccag attatgcgat agcaagacta 189420
acacacaatg tacgccgtgt ggttcgggta ccttcacatc tcgcaataat catttacccg 189480
cttgtctaag ttgtaacgga agacgcgacc gtgtaacacg actcacaata gaatctgtga 189540
atgctctccc ggatattatt gtcttctcaa aggatcatcc ggatgcaagg catgtgtttc 189600
ccaaacaaaa tgtggaatag gatacggagt atccggagac gtcatctgtt ctccgtgtgg 189660
tctcggaaca tattctcaca ccgtctcttc cgcagataaa tgcgaacccg tacccagtaa 189720
tacctttaac tatatcgatg tggaaattaa tctgtatcca gttaacgacc actaccggtc 189780
tcagcgaatc catctcaacg tcggaactaa ctattactat gaatcataaa gactgtaatc 189840
ccgtatttcg tgaggaatac ttctccgtcc ttaataaggt agcaacttca ggtttcttta 189900
caggagaaag gtgtgcactc tgaatttcga gattaaatgc aataacaaaa atttttcctc 189960
caaacagtta acgaaagcaa agaatgatga cggtatcatg ccgcattcgg agactgtcta 190020
tctagcgtcg acatctatat actatatagt aataccaata ctcaagacta cgaaactgat 190080
acaatctctt atcatgtggg taatgttctc gatgtcgata gccatatgcc cggtagttgc 190140
gatatacata aactgatcac taattccaaa cccacccgct ttttatagta agtttttcac 190200
ccataaataa taaatacaat aattaatttc tcgtaaaagt agaaaatata ttctaattta 190260
ttgcacggta aggaagtaga atcataaaga acagtactca atcaatagca atcatgaaac 190320
aatatatcgt cctggcatgc atgtgcctgc cagtcttcag caatcatcct catcctcctc 190380
ctcgtgtacg gaagaagaaa acaaacatca tatgggaatc gatgttatta tcaaagtcac 190440
aaagcaagac caaacaccga ccaatgataa gatttgccaa tccgtaacgg aaattacaga 190500
gtccgagtca gatccagatc ccgaggtgga atcagaagat gattccacat cagtcgagga 190560
tgtagatcct cctaccactt attactccat catcggtgga ggtctgagaa tgaactttgg 190620
attcaccaaa tgtcctcaga ttaaatccat ctcagaatcc gctgatggaa acacagtgaa 190680
tgctagattg tccagcgtgt ccccaggaca aggtaaggac tctcccgcga tcactcatga 190740
agaagctctg gctatgatca aagactgtga ggtgtctatc gacatcagat gtagcgaaga 190800
agagaaagac agcgacatca agacccatcc agtactcggg tctaacatct ctcataagaa 190860
agtgagttac gaagatatca tcggttcaac gatcgtcgat acaaaatgtg tcaagaatct 190920
agagtttagc gttcgtatcg gagacatgtg caaggaatca tctgaacttg aggtcaagga 190980
tggatttaag tatgtcgacg gatcggcatc tgaaggtgca accgatgata cttcactcat 191040
cgattcaaca aaactcaaag cgtgtgtctg aatcgataac tctattcatc tgaaattgga 191100
tgagtagggt taatcgaacg attcaggcac accacgaatt aaaaaagtgt accggacact 191160
atattccggt ttgcaaaaca aaaatgttct taactacatt cacaaaaagt tacctctcgc 191220
gacttcttct ttttctgtct caatagtgtg atacgattat gacactattc ctattcctat 191280
tcctatttcc tttcagggta tcacaaaaat attaaacctc tttctgatgg tctcataaaa 191340
aaagttttac aaaaatattt ttattctctt tctctctttg atggtctcat aaaaaaagtt 191400
ttacaaaaat atttttattc tctttctctc tttgatggtc tcataaaaaa agttttacaa 191460
aaatattttt attctctttc tctctttgat ggtctcataa aaaaagtttt acaaaaatat 191520
ttttattctc tttctctctt tgatggtctc ataaaaaaag ttttacaaaa atatttttat 191580
tctctttctc tctttgatgg tctcataaaa aaagttttac aaaaatattt ttattctctt 191640
tctctctttg atggtctcat aaaaaaagtt ttacaaaaat atttttattc tctttctctc 191700
tttgatggtc tcataaaaaa agttttacaa aaatattttt attctctttc tctctttgat 191760
ggtctcataa aaaatattaa acctctttct gatggtgtca ctaaaatatt tttattctca 191820
ttctcatttt ctctttctct cttcaatgga gtcataaaat atttttattc tctttctctc 191880
ttcgatggtc tcacaaaaat attaaacctc tttctgatgg tgtcactaaa atatttttat 191940
tctcattctc attttctctt tctctcttca atggagtcat aaaatatttt tattctcttt 192000
ctctcttcga tggtctcaca aaaatattaa acctctttct gatggagtcg taaaaaagtt 192060
ttatctcttt ctctcttcga tggtctcaca aaaatattaa acctctttct gatggagtcg 192120
taaaaaagtt ttatctcttt ctctcttcga tggtctcaca aaaatattaa acctctttct 192180
gatggagtcg taaaaaagtt ttatctcttt ctctcttcga tggtctcaca aaaatattaa 192240

-continued acctctttct gatggagtcg taaaaaagtt ttatctcttt ctctcttcga tggtctcaca 192300
aaaatattaa acctctttct gatggagtcg taaaaaagtt ttatctcttt ctctcttcga 192360
tggtctcaca aaaatattaa acctctttct gatggagtcg taaaaaagtt ttatctcttt 192420
ctctcttcga tggtctcaca aaaatattaa acctctttct gatggagtcg taaaaaagtt 192480
ttatctcttt ctctcttcga tggtctcaca aaaatattaa acctctttct gatggagtcg 192540
taaaaaagtt ttatctcttt ctctcttcga tggtctcaca aaaatattaa acctctttct 192600
gatggagtcg taaaaaagtt ttatctcttt ctctcttcga tggtctcaca aaaatattaa 192660
acctctttct gatggagtcg taaaaaagtt ttatctcttt ctctcttcga tggtctcaca 192720
aaaatattaa acctctttct gatggagtcg taaaaaagtt ttatctcttt ctctcttcga 192780
tggtctcaca aaaatattaa acctctttct gatggagtcg taaaaaagtt ttatctcttt 192840
ctctcttcga tggtctcaca aaaatattaa acctctttct gatggagtcg taaaaaagtt 192900
ttatctcttt ctctcttcga tggtctcaca aaaatattaa acctctttct gatggagtcg 192960
taaaaaagtt ttatctcttt ctctcttcga tggtctcaca aaaatattaa acctctttct 193020
gatggagtcg taaaaaagtt ttatctcttt ctctcttcga tggtctcaca aaaatattaa 193080
acctctttct gatggagtcg taaaaaagtt ttatctcttt ctctcttcga tggtctcaca 193140
aaaatattaa acctctttct gatggagtcg taaaaaagtt ttatctcttt ctctcttcga 193200
tggtctcaca aaaatattaa acctctttct gatggagtcg taaaaaagtt ttatctcttt 193260
ctctcttcga tggtctcact aaaatatttt ttattctctt tctgatgcat caactatttc 193320
ttaaacaata acgtccaaca acatatactc gtcgagctta tcaacatccc ctatgcccat 193380
ctaggttacc agacaattgt atatcataaa ataatgttta taatttacac gttaaaatca 193440
tataataaaa cgtagatcgt ataatatttt ttggtatata aatgatctag taaaatccat 193500
gtaggggata ctgctcacat tttttctttg gtacaaaatt tcacacaagt ttttatacag 193560
acaaattctt gtccatatat tttaaaacat tgacttttgt actaagaaaa atatctagat 193620
caactatctc tttctctttc tctcttcgat ggtctcacaa aaatattaaa cctctttctg 193680
atggagtcgt aaaaaagttt tatctctttc tctcttcgat ggtctcacaa aaatattaaa 193740
cctctttctg atggagtcgt aaaaaagttt tatctctttc tctcttcgat ggtctcacaa 193800
aaatattaaa cctctttctg atggagtcgt aaaaaagttt tatctctttc tctcttcgat 193860
ggtctcacaa aaatattaaa cctctttctg atggagtcgt aaaaaagttt tatctctttc 193920
tctcttcgat ggtctcacaa aaatattaaa cctctttctg atggagtcgt aaaaaagttt 193980
tatctctttc tctcttcgat ggtctcacaa aaatattaaa cctctttctg atggagtcgt 194040
aaaaaagttt tatctctttc tccttcgatg gtctcacaaa aatattaaac ctctttctga 194100
tggagtcgta aaaaagtttt atctctttct ctcttcgatg gtctcacaaa aatattaaac 194160
ctctttctga tggagtcgta aaaaagtttt atctctttct ctcttcgatg gtctcacaaa 194220
aatattaaac ctctttctga tggagtcgta aaaaagtttt atctctttct ccttcgatgg 194280
tctcacaaaa atattaaacc tctttctgat ggagtcgtaa aaaagtttta tctctttctc 194340
cttcgatggt ctcacaaaaa tattaaacct ctttctgatg gagtcgtaaa aaagttttat 194400
ctctttctct cttcgatggt ctcacaaaaa tattaaacct ctttctgatg gagtcgtaaa 194460
aaagttttat ctctttctct cttcgatggt ctcacaaaaa tattaaacct ctttctgatg 194520
gtctctataa agcgatcgat ctttcttaca ctctagagtt tcctacagtc atgggtcaca 194580
catttttttc tagacactaa ataaaattag taaaattaaa ttaattataa aattatatat 194640
ataatttact aactttagtt agataaatta ataatatata agttttagta cattaatatt 194700
atattttaaa t 194711

<210> SEQ ID NO 2
<211> LENGTH: 177923
<212> TYPE: DNA
<213> ORGANISM: Vaccinia virus

<400> SEQUENCE: 2
gtaagattaa attaattata aaattatgta tataatatta attataaaat tatgtatatg 60
atttactaac tttagttaga taaattaata atacataaat tttagtatat taatattata 120
aattaataat acataaattt tagtatatta atattatatt ttaaatattt atttagtgtc 180
tagaaaaaaa tgtgtgacca acgaccgtag gaaactctag agggtaagaa aaatcaatcg 240
ctttatagag accatcagaa agaggtttaa tatttttgtg agaccatcga aggagaaaga 300
gataaaactt ttttacgact ccatcagaaa gaggtttaat atttttgtga gaccatcgaa 360
gagagaaaga gataaaactt ttttacgact ccatcagaaa gaggtttaat atttttgtga 420
gaccatcgaa gagagaaaga gataaaactt ttttacgact ccatcagaaa gaggtttaat 480
atttttgtga gaccatcgaa ggagaaagag ataaaacttt tttacgactc catcagaaag 540
aggtttaata tttttgtgag accatcgaag gagaaagaga taaaactttt ttacgactcc 600
atcagaaaga ggtttaatat ttttgtgaga ccatcgaagg agaaagagat aaaacttttt 660
tacgactcca tcagaaagag gtttaatatt tttgtgagac catcgaagag agaaagagat 720
aaaacttttt tacgactcca tcagaaagag gtttaatatt tttgtgagac catcgaagga 780
gaaagagata aaactttttt acgactccat cagaaagagg tttaatattt ttgtgagacc 840
atcgaagaga gaaagagaat aaaaatattt tagtgacacc atcagaaaga ggtttaatat 900
ttttgtgaga ccatcgaaga gagaaagaga taaaactttt ttacgactcc atcagaaaga 960
ggtttaatat ttttgtgaga ccatcgaagg agaaagagat aaaacttttt tacgactcca 1020
tcagaaagag gtttaatatt tttgtgagac catcgaagag agaaagagat aaaacttttt 1080
tacgactcca tcagaaagag gtttaatatt tttgtgagac catcgaagag agaaagagat 1140
aaaacttttt tacgactcca tcagaaagac catcgaagag agaaagagaa agagatagtt 1200
agtctagata tttttcttag tacaaaagtc aatgttttaa aatatatgga caagaatttg 1260
tctgtataaa aacttgtgtg aaattttgta ccaaagaaaa aatgtgagca gtatccccta 1320
catggatttt actagatcat ttatatacca aaaaatatta tacgatctac gttttattat 1380
atgattttaa cgtgtaaatt ataaacatta ttttatgata tacaattgtc tggtaaccta 1440
gatgggcata ggggatgagt atatgttgtt ggacgttatt gtttaagaaa tagttgatgc 1500
atcagaaaga ggtttaatat ttttgtgaga ccatcgaaga gagaaagaga taaaactttt 1560
ttacgactcc atcagaaaga ggtttaatat ttttgtgaga ccatcgaaga gagaaagaga 1620
taaaactttt ttatgactcc attgaagaga gaatgagaat aaaaatattt tagtgacacc 1680
atcagaaaga ggtttaatat tttttatgag accatcaaag agagaaagag aataaaaata 1740
ttttatgact ccattgaaga gagaaagaga aaatgagaat aaaaatattt tagtgacacc 1800
atcagaaaga ggtttaatat tttttatgag accatcaaag agagaaagag aataaaaata 1860
tttttgtaaa actttttta tgagaccatc aaagagagaa agagaataaa aatatttttg 1920
taaaactttt tttatgagac catcaaagag agaaagagaa taaaaatatt tttgtaaaac 1980

-continued

```
tttttttatg agaccatcaa agagagaaag agaataaaaa tatttttgta aaactttttt   2040
tatgagacca tcaaagagag aaagagaata aaaatatttt tgtaaaactt tttttatgag   2100
accatcaaag agagaaagag aataaaaata tttttgtaaa acttttttta tgagaccatc   2160
aaagagagaa agagaataaa aatatttttg taaaactttt tttatgagac catcaaagag   2220
agaaagagaa taaaaatatt ttatgactcc attgaagaga gaaagagaat aaaaatattt   2280
tagtgacacc atcagaaaga ggtttaatat ttttgtgaga ccatcgaaga gagaaagaga   2340
ataaaaatat tttatgactc cattgaagag agaaagagaa taaaaatatt ttagtgacac   2400
catcagaaag aggtttaata ttttttatga gaccatcaaa gagagaaaga gaataaaaat   2460
atttttgtaa aacttttttt atgagaccat caaagagaga aagagaataa aaatattttt   2520
gtaaaacttt ttttatgaga ccatcaaaga gagaaagaga ataaaaatat ttttgtaaaa   2580
cttttttat gagaccatca aagagagaaa gagaataaaa atatttttgt aaaacttttt   2640
ttatgagacc atcaaagaga gaaagagaat aaaaatattt ttgtaaaact tttttttatga   2700
gaccatcaaa gagagaaaga gaataaaaat attttatgac tccattgaag agagaatgag   2760
aataaaaata ttttagtgac accatcagaa agaggtttaa tatttttgtg agaccatcga   2820
agagagaaag agaataaaaa tattttatga ctccattgaa gagagaaaga gaataaaaat   2880
attttagtga caccatcaga aagaggttta atattttta tgagaccatc aaagagagaa   2940
agagaataaa aatatttttg taaaactttt tttatgagac catcaaagag agaaagagaa   3000
taaaaatatt tttgtaaaac tttttttatg agaccatcaa agagagaaag agaataaaaa   3060
tatttttgta aaactttttt tatgagacca tcaaagagag aaagagaata aaaatatttt   3120
tgtaaaactt tttttatgag accatcaaag agagaaagag aataaaaata tttttgtaaa   3180
acttttttta tgagaccatc aaagagagaa agagaataaa aatatttttg taaaactttt   3240
tttatgagac catcaaagag agaaagagaa taaaaatatt tttgtaaaac tttttttatg   3300
agaccatcaa agagagaaag agaataaaaa tattttatga ctccattgaa gagagaatga   3360
gaataaaaat attttagtga caccatcaga aagaggttta atatttttgt gagaccatcg   3420
aagagagaaa gagaataaaa atattttatg actccattga agagagaatg agaataaaaa   3480
tattttagtg acaccatcag aaagaggttt aatattttt atgagaccat caaagagaga   3540
aagagaataa aaatattttt gtaaaacttt ttttatgaga ccatcaaaga gagaaagaga   3600
ataaaaatat ttttgtaaaa attataaaca ttattttatg atatacaatt gtctggtaac   3660
ctagatgggc ataggggatg ttgataagct cgacgagtat atgttgttgg acgttattgt   3720
ttaagaaata gttgatgcat cagaaagaga ataaaaaata ttttagtgag accatcgaag   3780
agagaaagag ataaaacttt tttacgactc catcagaaag aggtttaata tttttgtgag   3840
accatcgaag agagaaagag ataaaacttt tttacgactc catcagaaag aggtttaata   3900
tttttgtgag accatcgaag gagaaagaga taaaactttt ttacgactcc atcagaaaga   3960
ggtttaatat ttttgtgaga ccatcaaaga gagaaagaga ataaaaatat ttttgtaaaa   4020
cttttttat gagaccatca aagagagaaa gagaataaaa atatttttgt aaaacttttt   4080
ttatgagacc atcaaagaga gaaagagaat aaaaatattt ttgtaaaact tttttttatga   4140
gaccatcaaa gagagaaaga gaataaaaat atttttgtaa aacttttttt atgagaccat   4200
caaagagaga aagagaataa aaatatttta tgactccatt gaagagagaa tgagaataaa   4260
aatattttag tgacaccatc agaaagaggt ttaatatttt tgtgagacca tcgaagagag   4320
aaagagaata aaaatatttt atgactccat tgaagagaga atgagaataa aaatatttta   4380
```

gtgacaccat cagaaagagg tttaatattt tttatgagac catcaaagag agaaagagaa 4440
taaaaatatt tttgtaaaac ttttttatg agaccatcaa agagagaaag agaataaaaa 4500
tatttttgta aaactttttt tatgagacca tcaaagagag aaagagaata aaaatatttt 4560
tgtaaaactt tttttatgag accatcaaag agagaaagag aataaaaata tttttgtaaa 4620
acttttttta tgagaccatc aaagagagaa agagaataaa aatattttat gactccattg 4680
aagagagaat gagaataaaa atattttagt gacaccatca gaaagaggtt taatattttt 4740
gtgagaccat cgaagagaga aagagaataa aaatatttta tgactccatt gaagagagaa 4800
agagaataaa aatattttag tgacaccatc agaaagaggt ttaatatttt ttatgagacc 4860
atcaaagaga gaaagagaat aaaaatattt ttgtaaaact ttttttatga gaccatcaaa 4920
gagagaaaga gaataaaaat attttatgac tccattgaag agagaatgag aataaaaata 4980
ttttagtgac accatcagaa agaggtttaa tatttttgtg agaccatcga agagagaaag 5040
agaataaaaa tattttatga ctccattgaa gagagaatga gaataaaaat attttagtga 5100
caccatcaga aagaggttta atatttttgt gagaccatcg aagagagaaa gagaataaaa 5160
atattttatg actccattga agagagaatg agaataaaaa tattttagtg acaccatcag 5220
aaagaggttt aatatttttt atgagaccat caaagagaga aagagaataa aaatattttt 5280
gtaaaacttt ttttatgaga ccatcaaaga gagaaagaga ataaaaatat ttttgtaaaa 5340 cttttttat gagaccatca aagagagaaa gagaataaaa atatttttgt aaaacttttt 5400
ttatgagacc atcaaagaga gaaagagaat aaaaatattt ttgtgagacc atcaaagaga 5460
gaaagagaat aaaaatattt ttgtgagacc atcaaagaga gaaagagaat aaaaatattt 5520
ttgtgagacc atcaaagaga gaaagagaat aaaaatattt tatgactcca ttgaagagag 5580
aaagagaata aaaatatttt agtgacacca tcagaaagag gtttaatatt tttgtgagac 5640
catcgaagag agaaagagaa taaaaatatt ttatgactcc attgaagaga gaaagagaat 5700
aaaaatattt tagtgacacc atcagaaaga ggtttaatat tttttatgag accatcaaag 5760
agagaaagag aataaaaata ttttttatga gaccatcaaa gagagaaaga gaataaaaat 5820
attttatgag accatcaaag agagaaagag aataaaaata ttttttatga gaccatcaaa 5880
gagagaaaga gaataaaaat attttatgag accatcaaag agagaaagag aataaaaata 5940
ttttttatga gaccatcaaa gagagaaaga gaataaaaat atttttgtat gagaccatca 6000
gaaagaggtt taatattttt gtgataccct gaaaggaaat aggaatagtg tcataatcgt 6060
atcacactat tgagacagaa aaagaagaag tcgcgagagg taactttttg ttttgcaaac 6120
cggaatatag tgtccggtac actttttttaa ttcgtggtgt gcctgaatcg ttcgattaac 6180
cctactcatc caatttcaga tgaatagagt tatcgattca gacacacgct ttgagttttg 6240
ttgaatcgat gagtgaagta tcatcggttg caccttcaga tgccgatccg tcgacatact 6300
tgacctcaag ttcagatgat tccttgcaca tgtctccgat acgaacgcta aactctagat 6360
tcttgacaca ttttgtatcg acgatcgttg aaccgatgat atcttcgtaa ctcactttct 6420
tatgagagat gttagacccg agtactggat gggtcttgat gtcgctgtct ttctcttctt 6480
cgctacatct gatgtcgata gacacctcac agtctttcca tcagcggatt ctgagatgga 6540
tttaatctga ggacatttgg tgaatccaaa gttcattctc agacctccac cgatgatgga 6600
gtaataagtg gtaggaggat ctacatcctc gactgattcc acctcgggat ctggatctga 6660
ctcggactct gtaatttccg ttacggattg gcaaatctta tcatcggtcg gtgtttggtc 6720

-continued

```
ttgctttgtg actttgataa taacatcgat tcccatatga tgtttgtttt cttcttccgt   6780
acacgatgag gatgattgct gaagactggc aggcacatgc atgccagtac gatatattgt   6840
ttcatgattg ctattgattg agtactgttc tttatgattc tacttcctta ccgtgcaata   6900
aattagaata tattttctac ttttacgaga aattaattat tgtatttatg ggtgaaaaac   6960
ttactataaa aagcgggtgg gtttggaatt agtgatcagt ttatgtatat cgcaactacc   7020
gggcatatgg ctacattacc cacatgataa gagattgtat cagtttcgta gtcttgagta   7080
ttggtattac tatatagtat atagatgtcg acgctagagt tactgtctcc gaatgcggca   7140
tgatagtatc attctttgct ttcgttaact gtttggagga agaatctttg ttattgcatt   7200
taatctcgaa attcagagtg cacacctttc tcctgtaaag aaacctgaag tcgctacctt   7260
attaagaaga cgggatcgca gtctttatga ttcatagtaa tagttagttc cgacgttgag   7320
atggattcgc tgagaccggt agtggtcgtc cgagtacacg atgtgtcgtt aactggatac   7380
aggttaattt ccacatcgat atagttaaag gtatttctgg gtacgggttc gcatttatct   7440
gcggaagaga cggtgtgaga atatgttccg agaccacacg gagaacagat gacgtctccg   7500
gatactccgt atcctattcc acattttgtt tgggaaacac atgccttgca tccatgatcg   7560
ggagagcatt cacagattct attgtgagtc gtgttacacg atcgcgtcga cattgttgac   7620
agaaacgtga ccttcattct taccgtcgtc cataaatacg ttaggtatgt accacatact   7680
gtcgcgaacg atgcgtccat ctcataatga tttacttttt cataattaaa gatgtgaaag   7740
aaaaccgaac aatatatttt tttagtaatg tttatgcgag acatataaaa taaactccgt   7800
gtttatgatg ccggtaaatg tttttatcat cttggacgga atcgattttg taatatgcca   7860
tggaaacagg acattatcac tccatgataa attatttaat ggagtcgatc ctctcattgt   7920
tctttgcgta tctcaatctg tggcgtttgc ttcgtttaaa taatatatca aacatggaga   7980
cgcctgatat gtaggcattc ttcattctat taatgtctgc tctatagcgc tttagttcct   8040
tatgacgacc ggcgatatca tacttacttt agaaggaaaa tcatcatcta ggattaaggc   8100
gtatctgata caggcgaata atggttcagg atatagatag cgtatatctc tattaaatgc   8160
gtcaatcata gtctctagag tgggatggta actcagtaat aaatcaacta gcttctcttt   8220
ggtaactgct tttctggatg gccgtattga ttatcgagcg tgacactcgc tccatattcc   8280
aataaccgct ttgcaaattg tatattattg acatcgaccg cgtaatatag tagagttatc   8340
gatcatatct atatcatcca tgtacttgct tagtatatca aatacatctt cataacagtg   8400
atacccgcaa ttattaaatc tcgataatat cagaccgtac atacatagac ggccattgtt   8460
agatatgtga tttacagccg cgtgtccata ttttccacga taaaccttac gacgtttaca   8520
tcgacgagat tattattaac aaagttgttg tccgtcgtct tatccaacat gcattgaatg   8580
ataggtatac ttaccatatc gccgtaatgt aagtagttta tcagtatggc ttgtacgatg   8640
gattcatcct gttgtctaaa tctctttaga atgttatcga tgatgtagtg gttatattct   8700
ctggaatcgt acgaagtaat actacgcatt acgtcgacaa gagtatgacg tctctcaata   8760
agaagattaa cgatttccat gtctacatta tatggggtta ctctaaatcg cttgtttaga   8820
taatacgcct ctaatatagg gctgacgtcg tatactctac acgtgtccac atcctttatt   8880
aataatctct atatctatgg ttgagcaaga ccagtagtat tggatggaaa cattgttatc   8940
gatcaaacat ttaattacat ccttggatag agattctcta tgagacgata tatagtaatg   9000
aagagagttc ttacacatat cactgttgta catacaggta cgaaatacgt aaccggtgct   9060
gtaacattct gatttaagaa gccatagcaa tacttctggt ctcggattag gcgtcgttac   9120
```

-continued gtatatatcc accaatccga gaccattgat tgcataattc gtattcttgg acggacgtat 9180
ccgtttatcc acaattaggt attttagcag acgtaagtcg aaatcattta tattcgactt 9240
gagttcgtta gaggaattcg aatagctgga tatcagtaga tgcacaatct gagattttac 9300
gtatctatgc ttactgtatg ctcctagcgg agttaatcct tcgttgtttc tacaaagtct 9360
ctcgactccg cgagagagta acagtcgaac aatcttaatg tctgtatcgc atttattgga 9420
gacgtaacaa tgtagcgcat tgtttcctcg tctatctata tgttttgata agttgtgaca 9480
cgtttcaatt tctagtttta ttttttgta cgtcacatct tcatccagta gacgacatag 9540
aatacatgtg caatccatag ctattctggt gctaattatt cctcataaga tgataaaaag 9600
tgtagtgaga gagcatgaag gagatttagt atttagcagt gcggatatga tccaagaggg 9660
tgagatagtc gttctcgttc agaatctttc gcagcataag tagtatgtcg atatacttat 9720
cgttgaagac tcttccagag acgatagctg attgagtaca aagtccaatg attgcacgaa 9780
gttcttcggc ggttttcatg gagtcatttc tgatgaaaca tttaatgatc taaatttcag 9840
tttatgtttg taccccgtat tcatacttaa caaattggta ttacatacca ttaataatgc 9900
aagcataaaa aatcgttagt agatgtttct aaatataggt tccgtaagca aagaatataa 9960
gaatgaagcg gtaatgataa aatcaatcgt tatctaaaat gatcatactc atttatttta 10020
ttctattata ttaacacata catttttaac agcaacacat tcaatattgt attgttattt 10080
ttatattatt tacacaatta acaatatatt attagtttat attactgaat taataatata 10140
aaattcccaa tcttgtcata aacacacact gagaaacagc ataaacacaa aatccatcaa 10200
aaatgttgat aaattatctg atgttgttgt tcgctgctat gataatcaga tcattcgccg 10260
atagtggtaa cgctatcgaa acgacatcgc cagaaattac aaacgctaca acagatattc 10320
cagctatcag attatgcggt ccagagggag atggatattg tttacacggt gactgtatcc 10380
acgctagaga tatcgacggt atgtattgta gatgctctca tggttataca ggcattagat 10440
gtcagcatgt agtattagta gactatcaac gttcagaaaa accaaacact acaacgtcat 10500
atatcccatc tcccggtatt atgcttgtat tagtaggcat tattattatt acgtgttgtc 10560
tattatctgt ttataggttc actcgacgaa ctaaactacc tatacaagat atggttgtgc 10620
cataattttt ataaattttt tttatgagta tttttacaaa aatgtataaa gtgtatgtct 10680
tatgtatatt tataaaaatg ctaaatatgc gatgtatcta tgttatttgt atttatctaa 10740
acaatacctc tacctctaga tattatacaa aaatttttta tttcggcata ttaaagtaaa 10800
atctagttac cttgaaaatg aatacagtgg gtggttccgt atcaccagta agaacataat 10860
agtcgaatac agtatccgat tgagattttg catacaatac tagtctagaa agaaatttgt 10920
aatcatcttc tgtgacggga gtccatatat ctgtatcatc gtcccatgct atattcctgt 10980
tatcatcatt agttaatgaa aataactctc gtgcttcaga aaagtcaaat attgtatcca 11040
tacatacatc tccaaaacta tcgcttatac gtttatcttt aacgatacct atacctagat 11100
ggttatttac taacagacat tttccagatc tattgactat aactcctata gtttccacat 11160
caaccaagta atgatcatct attgttatat aacaataaca taactctttt ccgtttttat 11220
cagtatgtat atctatatca acgtcgtcgt tgtagtgaat agtagtcatt gatctattat 11280
atgaaacgga tatgtctaga acggcaattg ttttacgtcc agttaacact ttcgttgatt 11340
taaagtctag agtctttgca aacataatat ccttatccga ctttatattt cctgtagggt 11400
ggtataattt tattttgcct ccacatatcg gtgtttccaa atatattact agacaatatt 11460
ccatatagtt attagttaag ggtacccaat tagaacacgt acgcttatta tcatcatttg 11520
gatcgtattt cataaaagtt attgtactat cgatgtcaac acattctaca ttttttaatc 11580
gtctatatag tatttttctg atattttcta taatatcaga attgtcttcc atcggaagtt 11640
gtatactatc ggaatcagtt acatgtttaa ataattctct gatgtcattc cttatacaat 11700
caaattcatt attaaacagt ttaatagtct gtagaccttt atcgtcgtaa atatccattg 11760
tcttattagt tacgcttatt tttatgtgtt tttacgttgc tttattatat tttataagaa 11820
tgattgtttg acgaatcacg agaactatta agacacatta ttaggtatat attataaaaa 11880
agtttttgat tacgatgtta taagaggaaa gaggacacat taacatcata catcaattaa 11940
ctacattctt ataacatcgt aatcaaaaga attgcaattt tgatgtataa caactgtcaa 12000
tgggttatgg aattgtatat tacatattat acggtatgtt ggtaacgaca aataccgatc 12060
ggtaattgtc tgccggtgta atagaattat atatatctat ctattacacc ggccttgtat 12120
acataataat aagttgtggt agtatgatct ccatatttat aatttaggac tttgtattca 12180
gttttttgg aatcataaaa aataaaaaaa agttttacta atttaaaatt atttacattt 12240
ttttcactgt ttagtcgcgg atatggaatt cgatcctgcc aaaatcaata catcatctat 12300
agatcatgta acaatattac aatacataga tgaaccaaat gatataagac taacagtatg 12360
cattatcaca aaaataaatc cacatttggc taatcaattt cgggcttgga aaaaacgtat 12420
cgccggaagg gactatatga ctaacttatc tagagataca ggaatacaac aatcaaaact 12480
tactgaaact gtcaaaaaaa tagaaacata tatggtctat atatacacta caatttagtt 12540
attaattgga taaccgatgt gattatcaat caatattaag aaggttggta aattggtaca 12600
tagctaataa tacctataca cccaataata caacaaccat ttctgagttg gatatcatca 12660
aaatactgga taaatacgag gacgtgtata gagtaagtaa agaaaaagaa tgtgaaattt 12720
gctatgaagt tgtttactca aaacgataga tactttggtt tattggattc gtgtaatcat 12780
atattttgca taacatgcat caatatatgg catagaacac gaagagaaac cggtgcgtcg 12840
gataattgtc ctatatgtcg tacccgtttt agaaacataa caatgagcaa gttaactaat 12900
aaataaaaag tttaatttgt tgacgacgta tgtcgttatt ttttctcgta taaaagatta 12960
atttgattct aatataatct ttagtattgg ataaatatca attcaaatta attccattag 13020
attatatcat aaataaaaat agtagcacgc actacttcag ccaaatattc tttttgaaa 13080
cgccatctat cgtagtgagg acacaagtga acctataatg agcaaattta ttagtatcgg 13140
ttacatgaag gactttacgt agagtggtga ttccactatc tgtggtacga acggtttcat 13200
cttctttgat gccatcaccc agatgttcta taaacttggt atcctttgcc aaccaataca 13260
tatagctaaa ctcaggcata tgttccacac atcctgaaca atgaaattct ccagaagatg 13320
ttacaatgtc tagatttgga catttggttt caaccgcgtt aacatatgag tgaacacacc 13380
catacatgaa agcgatgaga aataggattt tcatcttgcc aaaatatcac tagaaaaaat 13440
ttatttatca attttaaagg tataaaaaat acttattgtt gctcgaatat tttgtatttg 13500
atggtatacg gaagattaga aatgtaggta ttatcatcaa ctgattctat ggttttatgt 13560
attctatcat gtttcactat tgcgttggaa ataatatcat atgcttccac atatatttta 13620
ttttgtttta actcataata ctcacgtaat tctggattat tgacatatct atgaataatt 13680
ttagctccat gatcagtaaa tattaatgag aacatagtat taccacctac cattattttt 13740
ttcatctcat tcaattctta attgcaaaga tctatataat cattatagcg ttgacttatg 13800
gactctggaa tcttagacga tgtacagtca tctataatca tggcatattt aatacattgt 13860

-continued

```
tttatagcat agtcgttatc tacgatgtta gatatttctc tcaatgaatc aatcacacaa  13920
tctaatgtag gtttatgaca taatagcatt ttcagcagtt caatgttttt agattcgttg  13980
atggcaatgg ctatacatgt atatccgtta tttgatctaa tgttgacatc tgaaccggat  14040
tctagcagta aagatactag agattgttta ttatatctaa cagccttgtg aagaagtgtt  14100
tctcctcgtt tgtcaatcat gttaatgtct ttaagataag gtaggcaaat gtttatagta  14160
ctaagaattg ggcaagcata agacatgtca caaagaccct ttttgtatgt ataagtgtaa  14220
aaattataac attcatagtt ggatttacat aggtgtccaa tcgggatctc tccatcatcg  14280
agataattga tggcatctcc cttccttttt tagtagatat ttcatcgtgt aagaatcaat  14340
attaatattt ctaaagtatc cgtgtatagc ctctttattt accacagttc catattccac  14400
tagagggata tcgccgaatg tcatatactc aattagtata tgttggagga catccgagtt  14460
cattgttttc aatatcaaaa agatggtttc cttatcattt ctccatagtg gtacaatact  14520
acacattatt ccgtgcggct ttccattttc caaaaacaat ttgaccaaat ctacatcttt  14580
attgtatcta taatcactat ttagataatc agccataatt actcgagtgc aacatgttag  14640
atcgtctata tatgaataag ccgtgttatc tattcctttc attaacaatt taacgatgtc  14700
tatatctata tgagatgact taatataata ttgaagagct gtacaatagt ttttatctat  14760
aaaagacggc ttgattccgt gattaattag acatttaaca acttccggac gcacatatgc  14820
tctcgtatcc gactctgaat acagatgaga gatgatatac agatgcaata cggtaccgca  14880
atttcgtagt tgataatcat catacgcgta tcagtactcg tcctcataaa gaacactgca  14940
gccattttct atgaacaaat caataatttc aggaacagga tcatctgtca ttacataatt  15000
ttctataact gaacgatggt tttcacattt aacactcaag tcaaatccat gttctaccaa  15060
cacctttatc aagtcaacgt ctacattttt ggatttcata tagctgaata tattaaagtc  15120
atttatgttg ctaaatccag tggcttctag tagagccatc gctatatcct ttaactttaa  15180
catgtctact atttgtgtat tcttctaatg gggtagctgt ctccaatttt tgcgtaatgg  15240
attagtgcca ctgtctagta gtagtttgac gacctcgaca ttattacaat gctcattaaa  15300
aaggtatgcg tgtaaagcat tattcttgaa ttggttcctg gtatcattag gatctctgtc  15360
tctcaacatc tgtttaagtt catcgagagc cacctcctca ttttccaaat agtcaaacat  15420
tttgactgaa tgagctactg tgaactctat acacccacac aactaatgtc attaaatatc  15480
atgtcaaaaa cttgtacaat tattaataaa aataatttag tgtttaaatt ttaccagttc  15540
cagattttac acctccgtta accccacttt ttacaccact ggacgatcct cctccccaca  15600
ttccaccgcc accagatgta taagttttag atcctttatt actaccatca tgtccatgga  15660
taaagacact ccacatgccg ccactacccc ctttagaaga catattaata agacttaagg  15720
acaagtttaa caataaaatt aatcacgagt accctactac caacctacac tattatatga  15780
ttatagtttc tatttttaca gtaccttaac taaagtctct agtcacaaga gcaatactac  15840
caacctacac tattatatga ttatagtttc tatttttata ggaacgcgta cgagaaaatc  15900
aaatgtctaa tttctaacgg tagtgttgat aaacgattat cgtcaatgga tacctcctct  15960
atcatgtcgt ctattttctt actttgttct attaacttat tagcattata tattatttga  16020
ttataaaact tatattgctt attagcccaa tctgtaaata tcggattatt aacatatcgt  16080
ttctttgtag gtttatttaa catgtacatc actgtaagca tgtccgtacc atttatttta  16140
atttgacgca tatccgcaat ttctttttcg cagtcggtta taaattctat atatgatgga  16200
```

tacatgctac atgtgtactt ataatcgact aatatgaagt acttgataca tattttcagt 16260
aacgatttat tattaccacc tatgaataag tacctgtgat cgtctaggta atcaactgtt 16320
ttcttaatac attcgatggt tggtaattta ctcagaataa tttccaatat cttaatatat 16380
aattctgcta tttctgggat atatttatct gccagtataa cacaaatagt aatacatgta 16440
aacccatatt ttgttattat attaatgtct gcgccattat ctattaacca ttctactagg 16500
ctgacactat gcgacttaat acaatgataa agtatactac atccatgttt atatcatcaa 16560
tatacggctt acaaagtttt agtatcgata acacatccaa ctcacgcata gagaaggtag 16620
ggaataatgg cataaatatt attaggttat catcattgtc attatctaca actaagtttc 16680
catttttttaa aatatactcg acaactttag gatctctatt gccaaatttt tgaaaatatt 16740
tatttatatg cttaaatcta tataatgtag ctccttcatc aatcatacat ttaataacat 16800
tgatgtatac tgtatgataa gatacatatt ctaacaatag atcttgtata gaatctgtat 16860
atcttttaag aattgtggat attattacgt aaactattac acaattctaa aatataaaac 16920
gtatcacggt cgaataatag ttgatcaact atataattat cgattttgtg atttttcttc 16980
ctaaactgtt tacgtaaata gttagataga atattcatta gttcatgacc actatagtta 17040
ctatcgaata acgcgtcaaa tatttcccgt ttaatatcgc atttgtcaag ataataatag 17100
agtgtggtat gttcacgata agtataataa cgcatctctt tttcgtgtga aattaaatag 17160
tttattacgt ccaaagatgt agcataacca tcttgtgacc tagtaataat ataataatag 17220
agaactgttt tacccattct atcatcataa tcagtggtgt agtcgtaatc gtaattgtct 17280
aattcatcat cccaattata atattcacca gcacgtctaa tctgttctat tttgatcttg 17340
tatccatact gtatgttgct acatgtaggt attcctttat ccaataatag tttaaacaca 17400
tctacattgg gatttgatgt tgtagcgtat ttttctacaa tattaatacc atttttgata 17460
ctatttattt ctataccttt cgaaattagt aatttcaata agtctatatc gatgttatca 17520
gaacatagat attcgagtat atcaaaatca ttgatatttt tatagtcgac tgacgacaat 17580
aacaaaatca caacatcgtt tttgatatta ttatttttct tggtaacgta tgcctttaat 17640
ggagtttcac catcatactc atataatgga tttgcaccac tttctatcaa tgattgtgca 17700
ctgctggcat cgatgttaaa tgttttacaa ctatcataga gtatcttatc gttaaccatg 17760
attggttgtt gatgctatcg catttttttgg tttctttcat ttcagttatg tatggattta 17820
gcacgtttgg gaagcatgag ctcatatgat ttcagtactg tagtgtcagt actattagtt 17880
tcaataagat caatctctag atctatagaa tcaaaacacg ataggtcaga agataatgaa 17940
tatctgtagg cttcttgttg tactgtaact tctcgttttg ttagatgttt gcatcgtgct 18000
ttaacatcaa tggtacaaat tttatcctcg ctttgtgtat catattcgtc cctactataa 18060
aattgtatat tcagattatc atgagatgtg tatacgctaa cggtatcaat aaacggagca 18120
caccatttag tcataaccgt aatccaaaaa tttttaaagt atatcttaac gaaagaagtt 18180
gtgtcattgt ctacggtgta tggtactaga tcctcataag tgtatatatc tagagtaatg 18240
tttaatttat caaatggttg ataatatgga tcctcatgac aatttccgaa gatggaaatg 18300
agatatagac atgcaataaa tctaattgcg gacatggtta ctccttaaaa aaatacgaat 18360
aatcaccttg gctatttagt aagtgtcatt taacactata ctcatattaa tccatggact 18420
cataatctct atacgggatt aacggatgtt ctatatacgg ggatgagtag ttttcttctt 18480
taactttata ctttttacta atcatattta gactgatgta tgggtaatag tgtttaaaga 18540
gttcgttctc atcatcagaa taaatcaata tctctgtttt tttgttatac agatgtatta 18600

```
cagcctcata tattacgtaa tagaacgtgt catctacctt attaactttc accgcatagt  18660
tgtttgcaaa tacggttaat cctttgacct cgtcgatttc cgaccaatct gggcgtataa  18720
tgaatctaaa ctttaatttc ttgtaatcat tcgaaataat ttttagtttg catccgtagt  18780
tatccccttt atgtaactgt aaatttctca acgcgatatc tccattaata atgatgtcga  18840
attcgtgctg tatacccata ctgaatggat gaacgaatac cgacggcgtt aatagtaatt  18900
tactttttca tctttacata ttgggtacta gttttactat cataagttta taaattccac  18960
aagctactat ggaataagcc aaccatctta gtataacaca catgtcttaa agtttattaa  19020
ttaattacat gttgttttat atatcgctac gaatttaaac agagaaatca gtttaggaaa  19080
aaaaaatatc tatctacatc atcacgtctc tgtattctac gatagagtgc tactttaaga  19140
tgagacatat ccgtgtcatc aaaaatatac tccattaaaa tgattattcc ggcagcgaac  19200
ttgatattgg atatatcaca acctttgtta atatctacga caatagacag cagtcccatg  19260
gttccataaa cagtgagttt atctttcttt gaagagatat tttgtagaga tcttataaaa  19320
ctgtcgaatg acatcgcatt tatatcttta gctaaatcgt atatgttacc atcgtaatat  19380
ctaaccgcgt ctatcttaaa cgtttccatc gctttaaaga cgtttccgat agatggtctc  19440
atttcatcag tcatactgag ccaacaaata taatcgtgta taacatcttt gatagaatca  19500
gactctaaag aaaacgaatc ggctttatta tacgcattca tgataaactt aatgaaaaat  19560
gtttttcgtt gtttaagttg gatgaatagt atgtcttaat aattgttatt atttcattaa  19620
ttaatattta gtaacgagta cactctataa aaacgagaat gacataacta gttatcaaag  19680
tgtctaggac gcgtaatttt catatggtat agatcctgta agcattgtct gtattctgga  19740
gctattttct ctatatctaa tttctgaacg ttcaccaatg tctctagcca ctttggcact  19800
aatagcgatc attcgcttag cgtcttctat attattaact ggttgattca atctatctag  19860
caatggaccg tcggacagcg tcattctcat gttcttaatc aatgtacata catcgccgtc  19920
atctaccaat tcatccaaca acataagctt tttaaaatca tcattataat aggtttgatc  19980
gttgtcattt ctccaaagaa tatatctaat aagtagagtc ctcatgatta gttaacaact  20040
atttttatg ttaaatcaat tagtacaccg ctatgtttaa tacttattca tattttagtt  20100
tttaggattg agaatcaata caaaaattaa tgcatcatta attttagaaa tacttagttt  20160
ccacgtagtc aatgaaacat ttgaactcat cgtacaggac gttctcgtac aggacgtaac  20220
tataaaccgg tttatatttg ttcaagatag atacaaatcc gataactttt tttacgaatt  20280
ctacgggatc cactttaaaa gtgtcatacc gggttctttt tattttttta aacagattaa  20340
tggtgtgatg ttgattaggt cttttacgaa tttgatatag aatagcgttt acatattctc  20400
cataatggtc aatcgccatt tgttcgtatg tcataaattc tttaattata tgacactgtg  20460
tattatttag ttcatccttg ttcatcatta ggaatctatc caatatggca attatactag  20520
aactataggt gcgttgtata cacatattga tgtgtctgtt tatacaatcc atgctactac  20580
cttcgggtaa aattgtagca tcatatacca tttctagtac tttaggttca ttgttatcca  20640
ttgcagagga cgtcatgatc gcatcctaaa aaaatatatt atttttatgt tattttgtta  20700
aaaataatca tcgaatacga atcatccagt ccactgaata gcaaaatctt tactattttg  20760
gtatcttcca atgtggctgc ctgatgtaat ggaaattcat tctctagaag atttttcaat  20820
gctccagcgt tcaacaacgt acatactaga cgcacgttat tatcagctat tgcataatac  20880
aaggcactat gtccatggac atccgcctta aatgcatctt tgctagagag aaagcttttc  20940
```

```
agctgcttag acttccaagt attaattcgt gacagatcca tgtctgaaac gagacgctaa  21000
ttagtgtata atttttgtca tattgcacca gaattaataa tatctctaat agatctgatt  21060
agtagataca tggctatcgc aaaacaacat atacacattt aataaaaata atatttatta  21120
agaaaattca gatttcacgt acccatcaat ataaataaaa taatgattcc ttacaccgta  21180
cccatattaa ggagattcta ccttacccat aaacaatata aatccagtaa tatcatgtct  21240
gatgatgaac acaaatggtg tattaaattc cagtttttca ggagatgatc tcgccgtagc  21300
taccataata gtagatgcct ctgctacagt tccttgttcg tcgacatcta tctttgcatt  21360
ctgaaacatt ttataaatat ataatgggtc cctagtcata tgtttaaacg acgcattatc  21420
tggattaaac atactaggag ccatcatttc ggctatcgac ttaatatccc tcttattttc  21480
gatagaaaat ttagggagtt taagattgta cactttattc cctaattgaa acgaccaata  21540
gtctaatttt gcagccgtaa tagaatctgt gaaatgggtc atattatcac ctattgccag  21600
gtacatacta atattagcat ccttatacgg aaggcgtacc atgtcatatt ctttgtcatc  21660
gattgtgatt gtatttcctt gcaatttagt aactacgttc atcatgggaa ccgttttcgt  21720
accgtactta ttagtaaaac tagcattgcg tgttttagtg atatcaaacg gatattgcca  21780
tatacctttta aaatatatag tattaatgat tgcccataga gtattattgt cgagcatatt  21840
agaatctact acattagaca taccggatct acgttctact atagaattaa ttttattaac  21900
cgcatctcgt ctaaagttta atctatatag gccgaatcta tgatattgtt gataatacga  21960
cggtttaata cacacagtat tatctacgaa actttgataa gttagatcag tgtacgtata  22020
tttagatgtt ttcagcttag ctaatcctga tattaattct gtaaatgctg gacccagatc  22080
tctttttctc aaatccatag tcttcaataa ttctattcta gtattacctg atgcaggcaa  22140
tagcgacata aacatagaaa acgaataacc aaacggtgag aagacaatat tatcatcttg  22200
aatattttta tacgctacta taccggcatt ggtaaatcct tgtagacgat aggtagacgc  22260
tgaacacgtt aacgatagta tcaataacgc aatcatgatt ttatggtatt aataattaac  22320
cttattttta tgttcggtat aaaaaattatt gatgtctaca catccttttg taattgacat  22380
ctatatatcc ttttgtataa tcaactctaa tcactttaac ttttacagtt ttccctacca  22440
gtttatccct atattcaaca tatctatcca tatgcatctt aacactctct gccaagatag  22500
cttcagagtg aggatagtca aaaagataaa tatatagagc ataatcattc tcgtatactc  22560
tgccctttat tacatcgccc gcattgggca acgaataaca aaatgcaagc atcttgttaa  22620
cgggctcgta aattgggata aaaattatgt ttttatatct attttattca agagaatatt  22680
caggaatttc tttttccggt tgtatctcat cgcagtatat atcatttgta cattgtttca  22740
tattttttaa tagtttacac cttttagtag gactagtatc gtacaattca tagctgtatt  22800
ttgaattcca atcacgcata aaaatatctt ctaattgttg acgaagacct aatccatcat  22860
ccggtgtaat attaatagat gctccacatg tatccgtaaa gtaatttcct gtccaatttg  22920
aggtacctat ataggccgtt ttatcggtta ccatatattt ggcatggttt accctagaat  22980
acggaatggg aggatcagca tctggtacaa taaatagctt tacttctata tttatgtttt  23040
tagattttag catagcgata gatcttaaaa agtttctcat gataaacgaa gatcgttgcc  23100
agcaactaat caatagctta acggatactt gtctgtctat agcggatctt cttaattcat  23160
cttctatata aggccaaaac aaaattttac ccgccttcga ataaataata gggataaagt  23220
tcataacaga tacataaacg aatttactcg catttctaat acatgacaat aaagcggtta  23280
aatcattggt tctttccata gtacatagtt gttgcggtgc agaagcaata aatacagagt  23340
```

gtggaacacc acttacgtta atactaagag gatgatctgt attataatac gacggataaa 23400
agtttttcca attatatggt agattgttaa ctccaagata ccagtatacc tcaaaaattt 23460
gagtgagatc cgctgccaag ttcctattat tgaagatcgc aatacccaat tctttgacct 23520
gagttagtga tctccaatcc atgttagcgc ttcctaaata aatatgtgta ttatcagata 23580
tccaaaattt tgtatgaaga actcctccta ggatatttgt aatatctatg tatcgtactt 23640
caactccggc catttgtagt ctttcaacat cctttaatgg tttgttagat ttattgacgg 23700
ctactctaac tcgtactcct cttttgggta attgtacaat ctcgtttaat attatcgtgc 23760
cgaaattcgt acccacttca tccgataaac tccaataaaa agatgatata tctagtgttt 23820
ttgtggtatt ggatagaatt tccctccaca tgttaaatgt agacaaatat actttatcaa 23880
attgcatacc tataggaata gtctctgtaa tcactgcgat tgtattatcc ggattcattt 23940
tatttgttaa aagaataatc ctatatcact tcactctatt aaaaatccaa gtttctattt 24000
ctttcatgac tgatttttta acttcatccg tttccttatg aagatgatgt ttggcacctt 24060
cataaatttt tatttctcta ttacaatttg catgttgcat gaaataatat gcacctaaaa 24120
catcgctaat ctcattgttt gttccctgga gtatgagagt cggggtgtta atcttggaaa 24180
ttatttttct aaccttgttg gtagccttca agacctgact agcaaatcca gccttaattt 24240
tttcatgatt gattaatggg tcgtattggt atttataaac tttatccata tctctagata 24300
ctgattctgg acatagcttt ccgactggcg catttggtgt gatggttccc ataagtttgg 24360
cagctagcag attcagtctt gaaacagcat ctgcattaac tagaggagac attagaatca 24420
ttgctgtaaa caagtttgga ttatcgtaag aggctagtat agaaattgtt gctcccatgg 24480
aatgacccaa taagtagatt taatagttac cacgtgctgt accaaagtca tcaatcatca 24540
ttttttcacc attacttctt ccatgtccaa tatgatcatg tgagaatact aaaattccta 24600
acgatgatat gttttcagct agttcgtcat aacgtccaga atgtttacca gctccatgac 24660
ttatgaatac taatgcctta ggatatgtaa tcattgtcca gattgaacat acagtttgca 24720
ctcatgattc acgttatata actatcaata ttaacagttc gtttgatgat catattattt 24780
ttatgtttta ttgataattg taaaaacata caattaaatc aatatagagg aaggagacgg 24840
ctactgtctt ttgtgagata gtcatggcga ctaaattaga ttatgaggat gctgtttttt 24900
actttgtgga tgatgataaa atatgtagtc gcgactccat catcgatcta atagatgaat 24960
atattacgtg gagaaatcat gttatagtgt ttaacaaaga tattaccagt tgtggaagac 25020
tgtacaagga attgatgaag ttcgatgatg tcgctatacg gtactatggt attgataaaa 25080
ttaatgagat tgtcgaagct atgagcgaag gagaccacta catcaatttt acaaaagtcc 25140
atgatcagga aagtttattc gctaccatag gaatatgtgc taaaatcact gaacattggg 25200
gatacaaaaa gatttcagaa tctagattcc aatcattggg aaacattaca gatctgatga 25260
ccgacgataa tataaacatc ttgatacttt ttctagaaaa aaaattgaat tgatgatata 25320
ggggtcttca taacgcataa ttattacgtt agcattctat atccgtgtta aaaaaaatta 25380
tcctatcatg tatttgagag ttttatatgt agcaaacatg atagctgtga tgccaataag 25440
ctttagatat tcacgcgtgc tagtgttagg gatggtatta tctggtggtg aaatgtccgt 25500
tatataatct acaaaacaat catcgcatat agtatgcgat agtagagtaa acatttttat 25560
agtttttact ggattcatac atcgtctacc caattcggtt atgaatgaaa ttgtcgccaa 25620
tcttacaccc aacccccttgt tatccattag tatagtatta acttcgttat ttatgtcata 25680

-continued aactgtaaat gattttgtag atgccatatc atacatgata ttcatgtccc tattataatc 25740
attactaact ttatcacaat atatgttgat aatatctata tatgatctag tctttgtggg 25800
caactgtcta tacaagtcgt ctaaacgttg tttactcata tagtatcgaa cagccatcat 25860
tacatggtcc cgttccgttg atagataatc gagtatgtta gtggacttgt caaatctata 25920
taccatattt tctggaagtg gatatacata gtcgtgatca acattattgc tagcctcatc 25980
ttctatatcc tgtactatac catctacata atctacgata ttattacaca taaacatcga 26040
caacatacta ttgtttatta tctaagtcct gttgatccaa acccttgatc tcctctattt 26100
gtactatcta gagattgtac ttcttccagt tctggataat atatacgttg atagattagc 26160
tgagctattc tatctccagt atttacatta aacgtacatt ttccattatt aataagaatg 26220
actcctatgt ttcccctata atcttcgtct attacaccac ctcctatatc aatgcctttt 26280
agtgacagac cagacctagg agctattcta ccatagcaaa tcttaggcat ggacatacta 26340
atatctgtct taattaactg tctttctcct ggagggatag tataatcgta agcgctatac 26400
aaatcatatc cggcagcacc cggcgattgc ctagtaggag atttagctct gttagtttcc 26460
ttaacaaatc taactggtga gttaatattc atgttgaaca taaaactaat attttatttc 26520
aaaattattt accatcccat atattccatg aataagtgtg atgattgtac acttctatag 26580
tatctatata cgattcacga taaaatcctc ctatcaatag cagtttatta tccactatga 26640
tcaattctgg attatccctc ggataaatag gatcatctat cagagtccat gtattgctgg 26700
attcacaata aaattccgca tttctaccaa ccaagaataa ccttctaccg aacactaacg 26760
cgcatgattt ataatgagga taataagtgg atggtccaaa ctgccactga tcatgattgg 26820
gtagcaaata ttctgtagtt gtatcagttt cagaatgtcc tcccattacg tatataacat 26880
tgtttatgga tgccactgct ggattacatc taggtttcag aagactcggc atattaaccc 26940
aagcagcatc cccgtggaac caacgctcaa cagatgtggg atttggtaga cctcctacta 27000
cgtataattt attgttagcg ggtatcccgc tagcatacag tctggggcta ttcatcggag 27060
gaattggaat ccaattgttt gatatataat ttacagctat agcattgtta tgtatttcat 27120
tgttcatcca tccaccgatg agatatacta cttctccaac atgagtactt gtacacatat 27180
ggaatatatc tataatttga tccatgttca taggatactc tatgaatgga tacttgtatg 27240
atttgcgtgg ttgtttatca caatgaaata ttttggtaca gtctagtatc cattttacat 27300
tatttatacc tctgggagaa agataatttg acctgattac atttttgata aggagtagca 27360
gatttcctaa tttatttctt cgctttatat accacttaat gacaaaatcc tcatctggaa 27420
catttagttc atcgctttct agaataagtt tcatagatag ataatcaaaa ttgtctatga 27480
tgtcatcttc cagttccaaa aagtgtttgg caataaagtt tttagtatga cataagagat 27540
tggatagtcc gtattctata cccatcatgt aacactcgac acaatattcc tttctaaaat 27600
ctcgtaggat aaagtttata caagtgtaga tgataaattc tacagaggtt aatatagaag 27660
cacgtaataa attgacgacg ttatgactat ctatatatac ctttccagta tatgagtaaa 27720
taactataga agttagactg tgaatgtcaa ggtctagaca aaccctcgta actggatctt 27780
tatttttcgt gtatttttga cgtaaatgtg tgcgaaagta aggagataac tttttcaata 27840
tcgtagaatt gactattata ttgcctccta tggcatcaat aattgttttg aatttcttag 27900
tcatagacaa tgctaatata ttcttacagt acacagtatt gacaaatatc ggcatttatg 27960
tttctttaaa agtcaacatc taaagaaaaa tgattatctt cttgagacat aactcccatt 28020
ttttggtatt cacccacacg tttttcgaaa aaattagttt taccttctaa tgatatattt 28080

-continued tccatgaaat caaacggatt ggtaacatta taaatttttt taaatcccaa ttcagaaatc 28140
aatctatccg cgacgaattc tatatatgtt ttcatcattt cacaattcat tcctataagt 28200
ttaactggaa gagccgcagt aagaaattct tgttcaatgg ataccgcatc tgttataata 28260
gatctaacgg tttcttcact cggtggatgc aataaatgtt taaacatcaa acatgcgaag 28320
tcgcagtgta gaccctcgtc tctactaatc aattcgttgg aaaacgtgag tccgggcatt 28380
aggccacgct ttttaagcca aaatatggaa gcgaatgatc cggaaaagaa gattccttct 28440
actgcagcaa aggcaataag tctctctcca taaccggcgc tgtcatgtat ccacttttga 28500
gcccaatcgg ccttcttttt tacacaaggc atcgtttcta tggcattaaa gagatagttt 28560
ttttcattac tatctttaac ataagtatcg atcaaaagac tatacatttc cgaatgaatg 28620
ttttcaatgg ccatctgaaa tccgtagaaa catctagcct cggtaatctg tacttctgta 28680
caaaatcgtt ccgccaaatt ttcattcact attccgtcac tggctgcaaa aaacgccaat 28740
acatgtttta taaaatattt ttcgtctggt gttagtttat tccaatcatt gatatcttta 28800
gatatatcta cttcttccac tgtccaaaat gatgcctctg ccttttttata catgttccag 28860
atgtcatgat attggattgg gaaaataaca aatctatttg gatttggtgc aaggatgggt 28920
tccataacta aattaacaat aacaataaat ttttttcag ttatctatat gcctgtactt 28980
ggatcttttg tacatcgata tcgccgcaat cactacaata attacaagta ttattgatag 29040
cattgttatt agtactatca taattaaatt atcgttatta tcattttgta attgtgacat 29100
catactagat aaatcgtttg cgagattgtt gtgggaagcg ggcatggagg atgaattatc 29160
gttattatta tttaaagcct cccattcgga ttcacaaata tggcgcgcgt tcaacatttt 29220
atggaaacag ataacaagaa aactcgtcat cgttcaaatt tttaacgata gtaaaccgat 29280
taaacgtcga gctaatttct aacgctagcg actctgttgg atatgggttt ccagatatat 29340
atcttttcag ttcccctacg tatctataat catctgtagg aaatggaaga tatttccatt 29400
tatctactgt tcctaatatc atatgtggtg gtgtagtaga accattaagc gcgaaagatg 29460
ttatttcgca tcgtatttta acttcgcaat aatttctggt tagataacgc actctaccag 29520
tcaagtcaat gatattagcc tttacagata tattcatagt agtcgtaacg atgactccat 29580
cttttagatg cgatactcct ttgtatgtac cagaatcttc gtacctcaaa ctcgatatat 29640
ttaaacaagt taatgagata ttaacgcgtt ttatgaatga tgatatataa ccagaagttt 29700
tatcctcggt ggctagcgct ataaccttat cattataata ccaactagtg tgattaatat 29760
gtgacacgtt agtgtgggta caaatatgta cattatcgtc tacgtcgtat tcgatacatc 29820
cgcatacagc caacaaatat aaaatgacaa atactctaac gccgttcgta cccatcttga 29880
tgcggtttaa taaatgtttt gatttcaatt tattgtaaaa aaagattcgg ttttatactg 29940
ttcgatattc tcattgctta tattttcatc tatcatctcc acacagtcaa atccgtggtt 30000
agcatgcacc tcatcaaccg gtaaaagact atcggactct tctatcatta taactctaga 30060
atatttaatt tggtcattat taatcaagtc aattatctta tttttaacaa acgtgagtat 30120
tttactcatt ttttataaaa acttttagaa atatacagac tctatcgtgt gtctatatct 30180
tctttttata tccaatgtat ttatgtctga tttttcttca tttatcatat ataatggtcc 30240
aaattctaca cgtgcttcgg attcatccag atcattaagg ttcttataat tgtaacatcc 30300
ttctcttccc tcttctacat cttccttctt attcttattc ttagcgtcac agaatctacc 30360
acagcaggat cccatgacga gcgtcatatt aaactaatcc attttcaatt ataatatacg 30420

-continued

```
attagtaatg accattaaaa taaaaatatt cttcataacc ggcaagaaag tgaaaagttc  30480
acattgaaac tatgtcagta gtatacatca tgaaatgatg atatatatat actctatttt  30540
ggtggaggat tatatgatat aattcgtgga taatcattct taagacacat ttcttcattc  30600
gtaaatcttt tcacgttaaa tgagtgtcca tattttgcaa tttcttcata tgatggcggt  30660
gtacgtggac gaggctgctc ctgttcttgt tgtagtcgcc gactgtcgtg tctgcgttta  30720
gatccctcca ttatcgcgat tgcgtagatg gagtactatt ttataccttg taattaaatt  30780
tttttattaa ttaaacgtat aaaaacgttc cgtatctgta tttaagagcc agatttcgtc  30840
taatagaaca aatagctaca gtaaaaataa ctagaataat tgctacaccc actagaaacc  30900
acggatcgta atacggcaat cggttttcga taataggtgg aacgtatatt ttatttaagg  30960
acttaacaat tgtctgtaaa ccacaatttg cttccgcgga tcctgtatta actatctgta  31020
aaagcatatg ttgaccgggc ggagccgaac attctccgat atccaatttc tgtatatcta  31080
taatattatt aacctccgca tacgcattac agttcttttc tagcttggat accgcactag  31140
gtacatcgtc tagatctatt cctatttcct cagcgatagc tcttctatcc ttttccggaa  31200
gcaatgaaat cacttcaata aatgattcaa ccatgagtgt gaaactaagt cgagaattac  31260
tcatgcattt gttagttatt cggagcgcgc aatttttaaa ctgtcctata acctctccta  31320
tatgaatagc acaagtgaca ttagtaggga tagaatgttg agctaatttt tgtaaataac  31380
tatctataaa aagattatac aaagttttaa actctttagt ttccgccatt tatccagtct  31440
gagaaaatgt ctctcataat aaatttttcc aagaaactaa ttgggtgaag aatggaaacc  31500
tttaatctat atttatcaca gtctgttttg gtacacatga tgaattcttc caatgccgta  31560
ctaaattcga tatctttttc gatttctgga tatgttttta ataaagtatg aacaaagaaa  31620
tggaaatcgt aataccagtt atgtttaact ttgaaattgt tttttatttt cttgttaatg  31680
attccagcca cttgggaaaa gtcaaagtcg tttaatgccg atttaatacg ttcattaaaa  31740
acaaactttt tatcctttag atgaattatt attggttcat tggaatcaaa aagtaagata  31800
ttatcgggtt taagatctgc gtgtaaaaag ttgtcgcagc atggtagttc gtaaatttta  31860
atgtataaca gagccatctg taaaaagata aactttatgt attgtaccaa agatttaaat  31920
cctaatttga tagctagctc ggtatctact ttatctgccg aatacagtgc taggggaaaa  31980
attataatat ttcctctttc gtattcgtag ttagttctct tttcatgttc gaaaaagtga  32040
aacatgcggt taaaatagtt tataacatta atattactgt taataactgc cggataaaag  32100
tgggatagta atttcacgaa tttgatactg tcctttctct cgttaaacgc ctttaaaaaa  32160
actttagaag aatatctcaa tgatagttcc tgaccatcca tagtttgtat caataatagc  32220
aacatatgaa gaacacgttt atacagagta tgtaaaaatg ttaatttata gtttaatccc  32280
atggcccacg cacacacgat taattttttt tcatctccct ttagattgtt gtatagaaat  32340
ttgggtactg tgaactccgc cgtagtttcc atgggactat ataattttgt ggcctcgaat  32400
acaaatttta ctacatagtt atctatctta aagactatac catatcctcc tgtagatatg  32460
tgataaaaat cgtcgtttat aggataaaat cgtttatcct tttgttggaa aaaggatgaa  32520
ttaatgtaat cattctcttc tatctttagt agtgtttcct tattaaaatt cttaaaataa  32580
tttaacaatc taactgatgg agcccaattt tggtgtaaat ctaattggga cattatattg  32640
ttaaaataca aacagtctcc taatataaca gtatctgata atctatgggg agacatccat  32700
tgatattcag gggatgaatc attggcaaca cccatttatt gtacaaaaag ccccaattta  32760
caaacgaaag tccaggtttg atagagacaa actattaact attttgtctc tgtttttaat  32820
```

ttctttggta atgaaattat tcacaatatc agtatcttct ttatctacca gagattttac 32880
taacttgata accttggctg tctcattcaa tagggtagta atatttgtat gtgtgatatt 32940
gatatctttt agaagtgatt ctttgatggt gccagcatac gaattacaat aatgcagaaa 33000
ctcggttaac atgcaggaat tatagtaagc caattccaat tgttgcctgt gttgtattag 33060
agtgtcaata tgagcaatgg tgtccttgcg tttctctgat agaatgcgag cagcgatttt 33120
ggcgttatca tttgacgata tttctggaat gacgaatcct gtttctacta actttttggt 33180
aggacaaagt gaaacaatca agaagatagc ttctcctcct atttgtggaa gaaattgaac 33240
tcctctagat gatctccttg acagatattg gaccgaatta cagaagtacc tggaatgtaa 33300
agccctgaaa ccccctcatt ttttaagcag attgttgccg taaatcctgc actatgccca 33360
agatagagag ctcctttggt gaatccatct ctatgtttca gtttaaccaa gaaacagtca 33420
gctggtctaa aatttccatc tctatctaat acagcatcta acttgatgtc aggaactatg 33480
accggttatg ttatatgtaa cattgagtaa atccttaagt tcataatcat cactgtcatc 33540
agttatgtac gatccaaaca atgtttctac tggcatagtg gatacgaaga tgctatccat 33600
cagaatgttt ccctgattag tattttctat atagctattc ttctttaaac gattttccaa 33660
atcagtaact atgttcattt ttttaggagt aggacgccta gccagtatgg aagaggattt 33720
tctagatcct ctcttcaaca tctttgatct caatggaatg caaaaccccca tagtgtaaca 33780
accaacgata aaaataatat tgtttttcac tttttataat tttaccatct gactcatgga 33840
ttcattaata tctttataag agctactaac gtataattct ttataactga actgagatat 33900
atacaccgga tctatggttt ccataattga gtaaatgaat gctcggcaat aactaatggc 33960
aaatgtataa aacaacgaaa ttatactaga gttgttaaag ttaatatttt ctatgagctg 34020
ttccaataaa ttatttgttg taactgcgtt caagtcataa atcatcttga tactatccag 34080
taaaccgttt ttaagttctg gaatattatt atcccattgt aaagccccta attcgactat 34140
cgaatatcct gctctgatag cagtttcaat atcgacggac gtcaatactg taataaaggt 34200
ggtagtattg tcatcatcgt gataaactac tggaatatgg tcgttagtag gtacggtaac 34260
tttacacaac gcgatatata actttccttt tgtaccattt ttaacgtagt tgggacgtcc 34320
tgcagggtat tgttttgaag aaatgatatc gagaacagat ttgatacgat atttgttgga 34380
ttcctgatta tttactataa tataatctag acagatagat gattcgataa atagagaagg 34440
tatatcgttg gtaggataat acatccccat tccagtattc tcggatactc tattaatgac 34500
actagttaag aacatgtctt ctattctaga aaacgaaaac atcctacatg gactcattaa 34560
aacttctaac gctcctgatt gtgtctcgaa tgcctcgtac aaggatttca aggatgccat 34620
agattctttg accaacgatt tagaattgcg tttagcatct gatttttttta ttaaatcgaa 34680
tggtcggctc tctggtttgc taccccaatg ataacaatag tcttgtaaag ataaaccgca 34740
agaaaattta tacgcatcca tccaaataac cctagcacca tcggatgata ttaatgtatt 34800
attatagatt ttccatccac agttattggg ccagtatact gttagcaacg gtatatcgaa 34860
tagattactc atgtaaccta ctagaatgat agttcgtgta ctagtcataa tatctttaat 34920
ccaatctaag aaatttaaaa ttagattttt tacactgtta aagttaacaa aggtattacc 34980
cggatacgtg gatatcatat atggtattgg tccattatca gtaatagctc cataaactga 35040
tacggcgatg gtttttatat gtgtttgatc taacgaggaa gaaattcgcg cccacaattc 35100
atctctagat atgtatttaa tatcaaacgg taacacatca atttcgggac gcgtatatgt 35160
ttctaaattt ttaatccaaa tataatgatg acctatatgc cctattatca tactgtcaac 35220
tatagtacac ctagagaact tacgatacat ctgtttccta taatcgttaa attttacaaa 35280
tctataacat gctaaacctt ttgacgacaa ccattcatta atttctgata tggaatctgt 35340
attctcaata ccgtatcgtt ctaaagccag tgctatatct ccctgttcgt gagaacgctt 35400
tcgtataata tcgatcaacg gataatctga agtttttgga gaataatatg actcatgatc 35460
tatttcgtcc ataaacaatc tagacatagg aattggaggc gatgatctta attttgtgca 35520
atgagtcgtc aatcctataa cttctaatat tgtaatattc atcatcgaca taacactatc 35580
tatgttatca tcgtatatta gtataccatg accttcttca tttcgtgcca aaatgatata 35640
cagtcttaaa tagttacgca atatctcaat agtttcataa ttgttagctg ttttcatcaa 35700
ggtttgtatc ctgtttaaca tgatggcgtt ctatacgttt ctattttta aatttttaac 35760
gatttactgt ggctagatac ccaatctctc tcaaatattt ttttagcctc gcttacaagc 35820
tgtttatcta tactattaaa actgacgaat ccgtgatttt ggtaatgggt tccgtcgaaa 35880
tttgccgaag tgatatgaac atattcgtcg tcgactatca acaattttgt attattctga 35940
atagtgaaaa ccttcacaga tagatcattt tgaacacaca acgcgtctag acttctggcg 36000
gttgccatag aatatacgtc gttcttatcc caattaccaa ctagaagtct gatcttaact 36060
cctctattaa tggctgcttc tataatggag ttgtaaatgt cgggccaata gtagctatta 36120
ccgtcgacac gtgtagtggg aactatggcc aaatgttcaa tatctatact agtcttagcc 36180
gacttgagtt tatcaataac tacatcagtg tctagatctc tagaatatcc caataggtgt 36240
tccggagaat cagtaaagaa cactccacct ataggattct taatatgata cgcagtgcta 36300
actggcagac aacaagccgc agagcataaa ttcaaccatg aatttttgc gctattaaag 36360
gctttaaaag tatcaaatct tctacgaaga tctgtggcca gcgggggata atcagaatat 36420
acacctaacg ttttaatcgt atgtatagat cctccagtaa atgacgcgtt tcctacataa 36480
catctttcat tatctgacac ccaaaaacaa ccgagtagta gtcccacatt atttttttta 36540
tctatattaa cggttataaa atttatatcc gggcagtgac tttgtagctc tcccagattt 36600
cttttccctc gttcatctag caaaactatt attttaatcc ctttttcaga tgcctctttt 36660
agtttatcaa aaataagcgc tcccctagtc gtactcagag gattacaaca aaaagatgct 36720
atgtatatat atttcttagc tagagtgata atttcgttaa aacattcaaa tgttgttaaa 36780
tgatcggatc taaaatccat attttctggt agtgtttcta ccagcctaca ttttgctccc 36840
gcaggtaccg gtgcaaatgg ccacatttag ttaacataaa aacttataca tcctgttcta 36900
tcaacgattc tagaatatca tcggctatat cgctaaaatt ttcatcaaag tcgacatcac 36960
aacctaactc agtcaatata ttaagaagtt ccatgatgtc atcttcgtct atttctatat 37020
ccgtatccat tgtagattgt tgaccgatta tcgagtttaa atcattacta atactcaatc 37080
cttcagaata caatctgtgt ttcattgtaa atttataggc ggtgtattta agttggtaga 37140
ttttcaatta tgtatcaata tagcaacagt agttcttgct cctccttgat tctagcatcc 37200
tcttcattat tttcttctac gtacataaac atgtccaata cgttagacaa cacaccgacg 37260
atggcggccg ccacagacac gaatatgact aaaccgatga ccatttaaaa acccctctct 37320
agctttcact taaactgtat cgattattct tttagaacat gtataatata aaaacattat 37380
tctatttcga atttaggctt ccaaaaattt ttcatccgta aaccgataat aatatatata 37440
gacttgttaa tagtcggaat aaatagatta atgcttaaac tatcatcatc tccacgatta 37500
gagatacaat atttacattt tttttgctgt ttcgaaactt tatcaataca cgttaataca 37560

-continued

```
aacccaggaa ggagatattg aaactgaggc tgttgaaaat gaaacggtga atacaataat  37620
tcagataatg taaaatcatg attccgtatt ctgatgatat tagaactgct aatggatgtc  37680
gatggtatgt atctaggagt atctatttta acaaagcatc gatttgctaa tatacaatta  37740
tcattttgat taattgttat tttattcata ttcttaaaag gtttcatatt tatcaattct  37800
tctacattaa aaatttccat ttttaattta tgtagccccg caatactcct cattacgttt  37860
catttttgt ctataatatc cattttgttc atctcggtac atagattatc caattgagaa  37920
gcgcatttag tagttttgta cattttaagt ttattgacga atcgtcgaaa actagttata  37980
gttaacattt tattatttga taccctgata ttaatacccc tgccgttact attatttata  38040
actgatgtaa tccacgtaac attggaatta actatcgata gtaatgcatc gacgcttcca  38100
aaattgtcta ttataaactc accgataatt tttttattac atgttttcat attcattagg  38160
attattaaat ctttaatctt actacgattg tatgcgttga tattgcaaga cgtcattcta  38220
aaagacggag gatctccatc aaatgccaga caatcacgta caaagtacat ggaaataggt  38280
tttgttctat tgcgcatcat agatttatat agaacacccg tagaaatact aatttgtttt  38340
actctataaa atactaatgc atctatttca tcgttttgta taacgtcttt ccaagtgtca  38400
aattccaaat ttttttcatt gatagtacca aattcttcta tctctttaac tacttgcata  38460
gataggtaat tacagtgatg cctacatgcc gtttttttgaa actgaataga tgcgtctaga  38520
agcgatgcta cgctagtcac aatcaccact ttcatattta gaatatatat atgtaaaaat  38580
atagtagaat ttcattttgt ttttttttcta tgctataaat gaattctcat tttgcatctg  38640
ctcatactcc gttttatatc aataccaaag aaggaagata tctggttcta aaagccgtta  38700
aagtatgcga tgttagaact gtagaatgcg aaggaagtaa agcttcctgc gtactcaaag  38760
tagataaacc ctcatcaccc gcgtgtgaga gaagaccttc gtccccttcc agatgcgaga  38820
gaatgaataa cccaggaaaa caagttccgt ttatgaggac ggacatgcta caaaatatgt  38880
tcgcggctaa tcgcgataat gtagcttcta gacttttgtc ctaaaataca attatatcct  38940
tttcgatatt aataaatccg tgtcgtccag gtttttttatc tctttcagta tgtgaataga  39000
taggtatttt atctctattc atcatcgaat ttaagagatc cgataaacat tgtttgtatt  39060
ctccagatgt cagcatctga tacaacaata tatgtgcaca taaacctctg gcacttattt  39120
catgtacctt cccccttatca ctaaggagaa tagtatttga gaaatatgta tacatgatat  39180
tatcatgaat tagatataca gaatttgtaa cactctcgaa atcacacgat gtgtcggcgt  39240
taagatctaa tatatcactc gataacacat tttcatctag atacactaga catttttttaa  39300
agctaaaata gtctttagta gtaacagtaa ctatgcgatt attttcatcg atgatacatt  39360
tcatcggcat attattacgc ttaccatcaa agactatacc atgtgtatat ctaacgtatt  39420
ctagcatggt tgccatacgc gcattaaact tttcaggatc tttggataga tcttccaatc  39480
tatctatttg agaaaacatt tttatcatgt tcaatagttg aaacgtcgga tccactatat  39540
agatattatc tataaagatt ttaggaacta cgttcatggt atcctggcga atattaaaac  39600
tatcaatgat atgattatcg ttttcatctt ttatcaccat atagtttcta agatatggga  39660
ttttacttaa tataatatta tttcccgtaa taaattttat tagaaatgcc aaatctataa  39720
gaaaagtcct cgaattagtt tgaagaatat ctatatcgcc gtaccgtata tttggattaa  39780
ttagatatag agaatatgat ccgtaacata tacaactttt attatggcgt ctaagatatt  39840
cttccatcaa cttattaaca tttttgacta gggaagatac attatgacgt cccattactt  39900
```

ttgccttgtc tattactgcg acgttcatag aatttagcat atctcttgcc aattcttcca 39960
ttgatgttac attataagaa attttagatg aaattacatt tggagcttta atagtaagaa 40020
ctcctaatat gtccgtgtat gtggtcacta atacagattg tagttctata atcgtaaata 40080
atttacctat attatatgtt tgagtctgtt tagaaaagta gctaagtata cgatctttta 40140
tttctgatgc agatgtatca acatcggaaa aaaatctttt tttattcttt tttactaaag 40200
atacaaatat gtctttgtta aaaacagtta ttttctgaat atttctagct tgtaatttta 40260
acatatgata ttcgttcaca ctaggtactc tgcctaaata ggtttctata atctttaatg 40320
taatattagg aaaagtattc tgatcaggat tcctattcat tttgaggatt taaaactctg 40380
attattgtct aatatggtct caacacaaac tttttcacag agcgatagag tttttgataa 40440
ctcgtttttc ttaagaaata taaaactact gtctccagag ctcgctctat cttttatttt 40500
atttaattcg atacaaactc ctgatactgg ttcagaaagt aattcattaa ttttcagtcc 40560
tttatagaag atatttaata tagataatac aaaatcttca gtttttgata tcgatctgat 40620
tgatcctaga actagatata ttaataacgt gctcattagg cagtttatgg cagcttgata 40680
attagatata gtatattcca gttcatattt attagatacc gcattgccca gattttgata 40740
ttctatgaat tcctctgaaa ataaatccaa aataactaga cattctattt tttgtggatt 40800
agtgtactct cttccctcta tcatgttcac tactggtgtc cacgatgata aatatctaga 40860
gggaatataa tatagtccat aggatgccaa tctagcaatg tcgaataact gtaattttat 40920
tcttcgctct tcattatgaa ttgattcttg aggtataaac ctaacacaaa ttatattatt 40980
agacttttcg tatgtaatgt ctttcatgtt ataagttttt aatcctggaa tagaatctat 41040
tttaatgagg cttttaaacg cagagttctc caacgagtca aagcataata ctctgttggt 41100
tttcttatat acgatgttac gatttcttc tttgaatgga ataggttttt gaattagttt 41160
ataattacaa cataatagat aaggaagtgt gcaaatagta cgcggaaaaa acataatagc 41220
tcccctgttt tcatccatgg ttttaagtaa atgatcactg gcttctttag tcaatggata 41280
ttcgaacatt aaccgtttca tcatcattgg acagaatcca tatttcttaa tgtaaagagt 41340
gatcaaatca ttgtgtttat tgtaccatct tgttgtaaat gtgtattcgg ttatcggatc 41400
tgctcctttt tctattaaag tatcgatgtc gatctcgtct aagaattcaa ctatatcgac 41460
atatttcatt tgtatacaca taaccattac taacgtagaa tgtataggaa gagatgtaac 41520
gggaacaggg tttgttgatt cgcaaactat tctaatacat aattcttctg ttaatacgtc 41580
ttgcacgtaa tctattatag atgccaagat atctatataa ttattttgta agatgatgtt 41640
aactatgtga tctatataag tagtgtaata attcatgtat ttcgatatat gttccaactc 41700
tgtctttgtg atgtctagtt tcgtaatatc tatagcatcc tcaaaaaata tattcgcata 41760
tattcccaag tcttcagttc tatcttctaa aaaatcttca acgtatggaa tataataatc 41820
tattttacct cttctgatat cattaatgat atagtttttg acactatctt ctgtcaattg 41880
attcttattc actatatcta agaaacggat agcgtcccta ggacgaacta ctgccattaa 41940
tatctctatt atagcttctg gacataattc atctattata ccagaattaa tgggaactat 42000
tccgtatcta tctaacatag ttttaagaaa gtcagaatct aagacctgat gttcatatat 42060
tggttcatac atgaaatgat ctctattgat gatagtgact atttcattct ctgaaaattg 42120
gtaactcatt ctatatatgc tttccttgtt gatgaaggat agaatatact caatagaatt 42180
tgtaccaaca aactgttctc ttatgaatcg tatatcatca tctgaaataa tcatgtaagg 42240
catacattta acaattagag acttgtctcc tgttatcaat atactattct tgtgataatt 42300
tatgtgtgag gcaaatttgt ccacgttctt taattttgtt atagtagata tcaaatccaa 42360
tggagctaca gttcttggct taaacagata tagtttttct ggaacgaatt ctacaacatt 42420
attataaagg actttgggta gataagtggg atgaaatcct attttaatta atgcgatagc 42480
cttgtcctcg tgcagatatc caaacgcttt tgtgatagta tggcattcat tgtctagaaa 42540
cgctctacga atatctgtga cagatatcat ctttagagaa tatactagtc gcgttaatag 42600
tactacaatt tgtatttttt aatctatctc aataaaaaaa ttaatatgta tgattcaatg 42660
tataactaaa ctactaactg ttattgataa ctagaatcag aatctaatga tgacgtaacc 42720
aagaagttta tctactgcca atttagctgc attattttta gcatctcgtt tagattttcc 42780
atctgcctta tcgaatactc ttccgtcgat atctacacag gcataaaatg taggagagtt 42840
actaggcccc actgattcaa tacgaaaaga ccaatctctc ttagttattt ggcagtactc 42900
attaataatg gtgacagggt tagcatcttt ccaatcaata atttttttag ccggaataac 42960
atcatcaaaa gacttatgat cctctctcat tgatttttcg cgggatacat catctattat 43020
ggcgtcagcc ataacatcag catccggctt atccgcctcc gttgtcataa accaacgagg 43080
aggaatatcg tcggagctgt acaccatagc actacgttga agatcgtaca gagctttatt 43140
aacttctcgc ttctccatat taagttgtct agttagttgt gcagcagtag ctccttcgat 43200
tccaatgttt ttaatagccg cacacacaat ctctgcgtca gaacgctcgt caatatagat 43260
cttagacatt tttagagaga actaacacaa ccagcaataa aactaattta ttttatcatt 43320
tttttattca tcatcctctg gtggttcgtc gtttctatcg aatgtggatc tgattaaccc 43380
gtcatctata ggtgatgctg gttctggaga ttctggagga gatggattat tatctggaag 43440
aatctctgtt atttccttgt tttcatgtat cgattgcgtt gtaacattaa gattgcgaaa 43500
tgctctaaat ttgggaggct taaagtgttg tttgcaatct ctacacgcat gtctaactag 43560
tggaggttcg tcagcggctc tagtttgaat catcatcggc gtagtattcc tacttttaca 43620
gttaggacac ggtgtattgt atttctcgtc gagaacgtta aaataatcgt tgtaactcac 43680
atcctttatt ttatctatat tgtattctac tcctttctta atgcatttta taccgaataa 43740
gagatagcga aggaattctt tttcggtgcc gctagtaccc ttaatcatat cacatagtgt 43800
tttatattcc aaatttgtgg caatagacgg tttatttcta tacgatagtt tgtttctgga 43860
atcctttgag tattctatac caatattatt ctttgattcg aatttagttt cttcgatatt 43920
agattttgta ttacctatat tcttgatgta gtactttgat gatttttcca tggcccattc 43980
tattaagtct tccaagttgg catcatccac atattgtgat agtaattctc ggatatcagt 44040
agcggctacc gccattgatg tttgttcatt ggatgagtaa ctactaatgt atacattttc 44100
catttataac acttatgtat taactttgtt catttatatt ttttcattat tatgttgata 44160
ttaacaaaag tgaatatata tgttaataat tgtattgtgg ttatacggct acaatttcat 44220
aatgagtgga agtcagtgtc cgatgatcaa tgacgatagc tttactctga aaagaaagta 44280
tcaaatcgat agtgcggagt caacaataaa aatggataag aagaggataa agtttcagaa 44340
tagagccaaa atggtaaaag aaataaatca gacaataaga gcagcacaaa ctcattacga 44400
gacattgaaa ctaggataca taaaatttaa gagaatgatt aggactacta ctctagaaga 44460
tatagcacca tctattccaa ataatcagaa aacttataaa ctattctcgg acatttcagc 44520
catcggcaaa gcatcacaga atccgagtaa gatggtatat gctctgctgc tttacatgtt 44580
tcccaatttg tttggagatg atcatagatt cattcgttat agaatgcatc caatgagtaa 44640
aatcaaacac aagatcttct ctcctttcaa acttaatctt attagaatat tagtggaaga 44700
aagattctat aataatgaat gcagatctaa taaatggaga ataattggaa cacaagttga 44760
taaaatgttg atagctgaat ctgataaata tacaatagat gcaaggtata acctaaaacc 44820
catgtataga atcaagggaa aatctgaaga agataccctc tttatcaaac agatggtaga 44880
acaatgtgtg acatcccagg aattggtgga aaaagtgttg aagatactgt ttagagattt 44940
gttcaagagt ggagaataca aagcgtacag atacgatgat gatgtagaaa atggatttat 45000
tggattggat acactaaaat taaacattgt tcatgatata gttgaaccat gtatgcctgt 45060
tcgtaggcca gtggctaaga tactgtgtaa agaaatggta aataaatact ttgagaatcc 45120
gctacatatt attggtaaaa atcttcaaga gtgcattgac tttgttagtg aataggcatt 45180
tcatctttct ccaatactaa ttcaaattgt taaattaata atggatagta taaatagtta 45240
ttagtgataa aatagtaaaa ataattatta gaataagagt gtagtatcat agataactct 45300
cttctataaa aatggatttt attcgtagaa agtatcttat atacacagta gaaaataata 45360
tagatttttt aaaggatgat acattaagta aagtaaacaa ttttaccctc aatcatgtac 45420
tagctctcaa gtatctagtt agcaattttc ctcaacacgt tattactaag gatgtattag 45480
ctaataccaa ttttttgtt ttcatacata tggtacgatg ttgtaaagtg tacgaagcgg 45540
ttttacgaca cgcatttgat gcacccacgt tgtacgttaa agcattgact aagaattatt 45600
tatcgtttag taacgcaata caatcgtaca aggaaaccgt gcataaacta acacaagatg 45660 aaaaatttt agaggttgcc gaatacatgg acgaattagg agaacttata ggcgtaaatt 45720
atgacttagt tcttaatcca ttatttcacg gaggggaacc catcaaagat atggaaatca 45780 ttttttaaa actgtttaag aaaacagact tcaaagttgt taaaaaatta agtgttataa 45840
gattacttat ttgggcttac ctaagcaaga aagatacagg catagagttt gcggataatg 45900
atagacaaga tatatacact ctatttcaac aaactggtag aatagtccat agcaatctaa 45960
cagaaacgtt tagagattat atctttcccg gagataagac tagctattgg gtgtggttaa 46020
acgaaagtat agctaatgat gcggatattg ttcttaatag acacgccatt accatgtatg 46080
ataaaattct tagttatata tactctgaga taaaacaagg acgcgttaat aaaaacatgc 46140
ttaagttagt ttatatcttt gagcctgaaa aagatatcag agaacttctg ctagaaatca 46200
tatatgatat tcctggagat atcctatcta ttattgatgc aaaaaacgac gattggaaaa 46260
aatattttat tagtttttat aaagctaatt ttattaacgg taatacattt attagtgata 46320
gaacgtttaa cgaggactta ttcagagttg ttgttcaaat agatcccgaa tatttcgata 46380
atgaacgaat tatgtcttta ttctctacga gtgctgcgga cattaaacga tttgatgagt 46440
tagatattaa taacagttat atatctaata taatttatga ggtgaacgat atcacattag 46500
atacaatgga tgatatgaag aagtgtcaaa tctttaacga ggatacgtcg tattatgtta 46560
aggaatacaa tacatacctg tttttgcacg agtcggatcc catggtcata gagaacggaa 46620
tactaaagaa actgtcatct ataaaatcca agagtagacg gctgaacttg tttagcaaaa 46680
acattttaaa atattattta gacggacaat tggctcgtct aggtcttgtg ttagatgatt 46740
ataaaggaga cttgttagtt aaaatgataa accatcttaa gtctgtggag gatgtatccg 46800
cattcgttcg attttctaca gataaaaacc ctagtattct tccatcgcta atcaaaacta 46860
ttttagctag ttataatatt tccatcatcg tcttatttca aaggtttttg agagataatc 46920
tatatcatgt agaagaattc ttggataaaa gcatccatct aaccaagacg gataagaaat 46980
atatacttca attgataaga cacggtagat catagaacag accaaatata ttattaataa 47040
tttgtatata catagatata attatcacac atttttgata aatgggaact gctgcaacaa 47100
ttcagactcc caccaaatta atgaataaag aaaatgcaga aatgattttg gaaaaaattg 47160
ttgatcatat agttatgtat attagtgacg aatcaagtga ttcagaaaat aatcctgaat 47220
atattgattt tcgtaacaga tacgaagact atagatctct cattataaaa agtgatcacg 47280
agtttgtaaa gctatgtaaa aatcatgcag agaaaagttc tccagaaacg caacaaatga 47340
ttatcaaaca catatacgaa caatatctta ttccagtatc tgaagtacta ttaaaaccta 47400
taatgtccat gggtgacata attacatata acggatgtaa agacaatgaa tggatgctag 47460
aacaactctc taccctaaac tttaacaatc tccgcacatg gaactcatgt agcataggca 47520
atgtaacgcg tctgttttat acattttta gttatctgat gaaagataaa ctaaatatat 47580
aagtataatc ccattctaat actttaacct gatgtattac ctgcatctta ttagaatatt 47640
aacctaacta aaagacataa catagttgat aaaaagcggt aggatataaa tattatggct 47700
gccaccgttc cgcgttttga cgacgtgtac aaaaatgcac aaagaagaat tctagatcaa 47760
gaaacatttt ttagtagagg tctaagtaga ccgttaatga aaaacacata tctatttgat 47820
aattacgcgt atggatggat accagaaact gcaatttgga gtagtagata cgcaaactta 47880
gatgcaagtg actattatcc catttcgttg ggattactta aaaagttcga gtttctcatg 47940
tctctatata aaggtcctat tcccgtatat gaagaaaaag taaatactga attcattgct 48000
aatggatcgt tctctggtag atacgtatca tatcttcgaa agttttctgc ccttccaaca 48060
aacgagttta ttagtttttt gttactgact tccattccaa tctataatat cttgttctgg 48120
tttaaaaata ctcagtttga tattactaaa cacacattat tcagatacgt ctatacagat 48180
aatgccaaac acctggcgtt ggctaggtat atgcatcaaa caggagacta taagcctttg 48240
tttagtcgtc tcaaagagaa ttatatattt accggtcccg ttccaataag tatcaaagat 48300
atagatcacc ctaatcttag tagagcaaga agtccatccg attatgagac attagctaat 48360
attagtacta tattgtactt taccaagtat gatccggtat taatgttttt attgttttac 48420
gtacctgggt attcaattac tacaaaaatt actccagccg tagaatatct aatggataaa 48480
ctgaatctaa caaagagcga cgtacaactg ttgtaaatta ttttatgctt cgtaaaatgt 48540
aggttttgaa ccaaacattc tttcaaagaa tgagatgcat aaaactttat tatccaatag 48600
attgactatt tcggacgtca atcgtttaaa gtaaacttcg taaaatattc tttgatcact 48660
gccgagttta aaacttctat cgataattgt ttcatatgtt ttaatattta caagtttttt 48720
ggtccatggt acattagccg gacaaatata tgcaaaataa tatcgttctc caagttctat 48780
agtttctgga ttatttttat tatattcagt aaccaaatac atattagggt tatctgcgga 48840
tttataattt gagtgatgca ttcgactcaa cataaataat tctagaggag acgatctact 48900
atcaaattcg gatcgtaaat ctgtttctaa agaacggaga atatctatac atacctgatt 48960
agaattcatc cgtccttcag acaacatctc agacagtctg gtcttgtatg tcttaatcat 49020
attcttatga aacttggaaa catctcttct agtttcacta gtacctttat taattctctc 49080
aggtacagat tttgaattcg acgatgctga gtatttcatc gttgtatatt tcttcttcga 49140
ttgcataatc agattcttat ataccgcctc aaactctatt ttaaaattat taaacaatac 49200
tctattatta atcagtcgtt ctaactcttt cgctatttct atagacttat cgacatcttg 49260
actgtctatc tctgtaaaca cggagtcggt atctccatac acgctacgaa aacgaaatct 49320
gtaatctata ggcaacgatg ttttcacaat cggattaata tctctatcgt ccatataaaa 49380

-continued

```
tggattactt aatggattgg caaaccgtaa cataccgtta gataactctg ctccatttag  49440
taccgattct agatacaaga tcattctacg tcctatggat gtgcaactct tagccgaagc  49500
gtatgagtat agagcactat ttctaaatcc catcagacca tatactgagt tggctactat  49560
cttgtacgta tattgcatgg aatcatagat ggccttttca gttgaactgg tagcctgttt  49620
tagcatcttt ttatatctgg ctctctctgc caaaaatgtt cttaatagtc taggaatggt  49680
tccttctatc gatctatcga aaattgctat ttcagagatg aggttcggta gtctaggttc  49740
acaatgaacc gtaatatatc taggaggtgg atatttctga agcaagagct gattatttat  49800
ttcttcttcc aatctattgg tactaacaac gacaccgact aatgtttccg gagatagatt  49860
tccaaagata cacacattag gatacagact gttataatca aagattaata cattattact  49920
aaacattttt tgttttggag caaataccttaccgccttca taaggaaact tttgttttgt  49980
ttctgatcta actaagatag ttttagtttc caacaatagc tttaacagtg gacccttgat  50040
gactgtactc gctctatatt cgaataccat ggattgagga agcacatatg ttgacgcacc  50100
cgcgtctgtt tttgtttcta ctccataata ctcccacaaa tactgacaca aacaagcatc  50160
atgaatacag tatctagcca tatctaaagc tatgtttaga ttataatcct tatacatctg  50220
agctaaatca acgtcatcct ttccgaaaga taatttatat gtatcattag gtaaagtagg  50280
acatgatagt acgactttaa atccattttc ccaaatatct ttacgaatta ctttacatat  50340
aatatcctca tcaacagtca cataattacc tgtggttaaa acctttgcaa atgcagcggc  50400
tttgcctttc gcgtccgtag tatcgtcacc gatgaacgtc atttctctaa ctcctctatt  50460
taatacttta cccatgcaac tgaacgcgtt cttggatata gaatccaatt tgtacgaatc  50520
caatttttca gatttttgaa tgaatgaata tagatcgaaa aatatagttc cattattgtt  50580
attaacgtga aacgtagtat tggccatgcc gcctactccc ttatgactag actgatttct  50640
ctcataaata cagagatgta cagcttcctt tttgtccgga gatctaaaga taatcttctc  50700
tcctgttaat aactctagac gattagtaat atatctcaga tcaaagttat gtccgttaaa  50760
ggtaacgacg tagtcgaacg ttagttccaa caattgttta gctattcgta acaaaactat  50820
ttcagaacat agaactagtt ctcgttcgta atccatttcc attagtgact gtatcctcaa  50880
acatcctcta tcgacggctt cttgtatttc ctgttccgtt aacatctctt cattaatgag  50940
cgtaaacaat aatcgtttac cacttaaatc gatataacag taacttgtat gcgagattgg  51000
gttaataaat acagaaggaa acttcttatc gaagtgacac tctatatcta gaaataagta  51060
cgatcttggg atatcgaatc taggtatttt tttagcgaaa cagttacgtg gatcgtcaca  51120
atgataacat ccattgttaa tctttgtcaa atattgctcg tccaacgagt aacatccgtc  51180
tggagatatc ccgttagaaa tataaaacca actaatattg agaaattcat ccatggtggc  51240
attttgtatg ctgcgtttct ttggctcttc tatcaaccac atatctgcga cggagcattt  51300
tctatcttta atatctagat tataacttat tgtctcgtca atgtctatag ttctcatctt  51360
tcccaacggc ctcgcattaa atggaggagg agacaatgac tgatatattt cgtccgtaac  51420
tacgtaataa aagtaatgag gaaatcgtat aaatacggtc tcgccatttc gacatctgga  51480
tttcagatat aaaaatctgt tttcaccgtg actttcaaac caattaatgc accgaacatc  51540
catttataga atttagaaat atattttcat ttaaatgaat cccaaacatt ggggaagagc  51600
cgtatggacc attattttta tagtactttc gcaagcgggt ttagacggca acatagaagc  51660
gtgtaaacga aaactatata ctatagtcag cactcttcca tgtcctgcat gtagacggca  51720
cgcgactatc gctatagagg acaataatgt catgtctagc gatgatctga attatattta  51780
```

ttattttttc atcagattat ttaacaattt ggcatctgat cccaaatacg cgatcgatgt 51840
gacaaaggtt aaccctttat aaacttaacc cattataaaa cttatgatta gtcacgactg 51900
aaataaccgc gtgattattt tttggtataa ttctacacgg catggtttct gtaactatga 51960
attcaacccc cgttacatta gtgaaatctt taacaaacag caagggttcg tcaaagacat 52020
aaaactcatt gtttacaatc gaaatagacc ccctatcaca cttaaaataa aaaatatcct 52080
tatcctttac caccaaataa aattctgatt ggtcaatgtg aatgtattca cttaacagtt 52140
ccacaaattt atttattaac tccgaggcac atacatcgtc ggtatttttt atggcaaact 52200
ttactcttcc agcatccgtt tctaaaaaaa tattaacgag ttccatttat atcatccaat 52260
attattgaaa tgacgttgat ggacagatga tacaaataag aaggtacggt acctttgtcc 52320
accatctcct ccaattcatg ctctattttg tcattaactt taatgtatga aaacagtacg 52380
ccacatgctt ccatgacagt gtgtaacact ttggatacaa aatgtttgac attagtataa 52440
ttgtccaaga ctgtcaatct ataatagata gtagctataa tatattctat gatggtattg 52500
aagaagatga caatcttggc atattgatca tttaacacag acatggtatc aacagatagc 52560
ttgaatgaaa gagaatcagt aattggaata agcgtcttct cgatagagtg tccgtatacc 52620
aacatgtctg atattttgat gtattccatt aaattattta gtttttcttt tttattctcg 52680
ttaaacagca tttctgtcaa cggaccccaa catcgttgac cgattaagtt ttgattgatt 52740
tttccgtgta aggcgtatct agtcagatcg tatagcctat ccaataatcc atcatctgtg 52800
cgtagatcac atcgtacact ttttaattct ctatagaaga gcgacagaca gcaatttctt 52860
tattctctac agatgtaaga tacttgaaga cattcctatg atgatgcaga attttggata 52920
acacggtatt gatggtatct gttaccataa ttcctttgat ggctgatagt gtcagagcac 52980
aagatttcca atctttgttt tgatatctat atcagacagc atggtgcgtc tgacaacaca 53040
aggattaaga cggaaagatg aaatgattct ctcaacatct tcaatggata ccttgctatt 53100
ttttctggca ttatctatat gtgcgagaat atcctctaga gaatcagtat ccttttttgat 53160
gatagtggat ctcaatgaca tgggacgtct aaaccttctt attctatcac cagattgcat 53220
ggtgatttgt cttctttctt ttatcataat gtaatctcta aattcatcgg caaattgtct 53280
atatctaaaa tcataatatg agatgtttac ctctacaaat atctgttcgt ccaatgttag 53340
agtatctaca tcagttttgt attccaaatt aaacatggca acggatttaa ttttatattc 53400
ctctattaag tcctcgtcga taataacaga atgtagataa tcatttaatc catcgtacat 53460
ggttggaaga tgcttgttga caaaatcttt aattgtcttg atgaaggtgg gactatatct 53520
aacatcttga ttaataaaat ttataacatt gtccatagga tactttgtaa ctagttttat 53580
acacatctct tcatcggtaa gtttagacag aatatcgtga acaggtggta tattatattc 53640
atcagatata cgaagaacaa tgtccaaatc tatattgttt aatatattat atagatgtag 53700
cgtagctcct acaggaatat ctttaactaa gtcaatgatt tcatcaaccg ttagatctat 53760
tttaaagtta atcatatagg cattgatttt taaaaggtat gtagccttga ctacattctc 53820
attaattaac cattccaagt cactgtgtgt aagaagatta tattctatca taagcttgac 53880
tacatttggt cccgatacca ttaaagaatt cttatgatat aaggaaacag attttaggta 53940
ctcatctact ctacaagaat tttggagagc cttaacgata tcagtgacgt ttattatttc 54000
aggaggaaag aatctaacat tgagaatatc ggaattaata gcttccagat acagtgattt 54060
tggcaatagt ccgtgtaatc cataatccag taacacgagc tggtgcttgc tagacacctt 54120
ttcaatgttt aattttttg aaataagctt tgataaagcc ttcctcgcaa attccggata 54180
catgaacatg tcggcgacat gattaagtat tgttttttca ttattttctc aacaagttct 54240
caatacccca atagatgata gaatatcacc caatgcgtcc atgttgtcta tttccaacag 54300
gtcgctatat ccaccaatag aagtttttcc aaaaaagatt ctaggaacag ttctaccacc 54360
agtaatttgt tcaaaatagt cacgcaattc attttcgggt ttaaattctt taatatcgac 54420
aatttcatac gctcctcttt tgaaactaaa cttatttaga atatccagtg catttctaca 54480
aaaaggacat gtatacttga caaaaattgt cactttgtta ttggccaacc tttgttgtac 54540
aaattcctcg gccattttaa tatttaagtg atataaaact atctcgactt atttaactct 54600
ttagtcgaga tatatggacg cagatagcta tatgatagcc aactacagaa ggcaaacgct 54660
ataaaaaaca taattacgac gagcatattt ataaatattt ttattcagca ttacttgata 54720
tagtaatatt aggcacagtc aaacattcaa ccactctcga tacattaact ctctcatttt 54780
ctttaacaaa ttctacaata tcttcgtaaa aagattcttg aaacttttta gaatatctat 54840
cgactctaga tgaaatagcg ttcgtcaaca tactatgttt tgtatacata aaggcgccca 54900
ttttaacagt ttctagtgac aaaatgctag cgatcctagg atcctttaga atcacataga 54960
ttgacgattc gtctctctta gtaactctag taaaataatc atacaatcta gtacgcgaaa 55020
taatattatc cttgacttga ggagatctaa acaatctagt tttgagaaca tcgataagtt 55080
catcgggaat gacatacata ctatctttaa tagaactctt ttcatccagt tgaatggatt 55140
cgtccttaac caactgatta atgagatctt ctattttatc attttccaga tgatatgtat 55200
gtccattaaa gttaaattgt gtagcgcttc tttttagtct agcagccaat actttaacat 55260
cactaatatc gatatacaaa ggagatgatt tatctatggt attaagaatt cgtttttcga 55320
catctgtcaa aaccaattcc tttttgcctg tatcatccag ttttccatcc tttgtaaaga 55380
aattattttc tactagacta ttaataagac tgataaggat tcctccataa ttgcacaatc 55440
caaacttttt aacaaaacta gactttacaa gatctacagg aatgcgtaat tcaggtttct 55500
tagcttgtga ttttttcttt tgtggacatt ttcttgtgac caactcatct accatttcat 55560
tgattttagc agtgaaataa gctttcaatg cacgggcact gatactattg aaaacgagtt 55620
gatcttcaaa ttccgccatt taagttcacc aaacaacttt taaatacaaa tatatcaata 55680
gtagtagaat aagaactata aaaaaaataa taattaacca ataccaaccc caacaaccgg 55740
tattattagt tgatgtgact gttttctcat cacttagaac agatttaaca atttctataa 55800
agtctgtcaa atcatcttcc ggagacccca taaatacacc aaatatagcg gcgtacaact 55860
tatccattta tacattgaat attggctttt ctttatcgct atcttcatca tattcatcat 55920
caatatcaac aagtcccaga ttacgagcca gatcttcttc tacattttca gtcattgata 55980
cacgttcact atctccagag agtccgataa cgttagccac cacttctcta tcaatgatta 56040
gtttcttgag tgcgaatgta atttttgttt ccgttccgga tctatagaag acgataggtg 56100
tgataattgc cttggccaat tgtctttctc ttttactgag tgattctagt tcaccttcta 56160
tagatctgag aatggatgat tctccagtcg aaacatattc taccatggat ccgtttaatt 56220
tgttgatgaa gatggattca tccttaaatg ttttctctgt aatagtttcc accgaaagac 56280
tatgcaaaga atttggaatg cgttccttgt gcttaatgtt tccatagacg gcttctagaa 56340
gttgatacaa cataggacta gccgcggtaa cttttatttt tagaaagtat ccatcgcttc 56400
tatcttgttt agatttattt ttataaagtt tagtctctcc ttccaacata ataaaagtgg 56460
aagtcatttg actagataaa ctatcagtaa gttttataga gatagacgaa caattagcgt 56520

```
attgagaagc atttagtgta acgtattcga tacattttgc attagattta ctaatcgatt  56580
ttgcatactc tataacaccc gcacaagtct gtagagaatc gctagatgca gtaggtcttg  56640
gtgaagtttc aactctcttc ttgattacct tactcatgat taaacctaaa taattgtact  56700
ttgtaatata atgatatata ttttcacttt atctcatttg agaataaaaa tgtttttgtt  56760
taaccactgc atgatgtaca gatttcggaa tcgcaaacca ccagtggttt tattttatcc  56820
ttgtccaatg tgaattgaat gggagcggat gcgggtttcg tacgtagata gtacattccc  56880
gtttttagac cgagactcca tccgtaaaaa tgcatactcg ttagtttgga ataactcgga  56940
tctgctatat ggatattcat agattgactt tgatcgatga aggctcccct gtctgcagcc  57000
atttttatga tcgtcttttg tggaatttcc caaatagttt tataaactcg cttaatatct  57060
tctggaaggt ttgtattctg aatggatcca ccatctgcca taatcctatt cttgatctca  57120
tcattccata attttctctc ggttaaaact ctaaggagat gcggattaac tacttgaaat  57180
tctccagaca atactctccg agtgtaaata ttactggtat acggttccac cgactcatta  57240
tttcccaaaa tttgagcagt tgatgcagtc ggcataggtg ccaccaataa actatttcta  57300
agaccgtatg ttctgatttt atcttttaga ggttcccaat tccaaagatc cgacggtaca  57360
acattccaaa gatcatattg tagaataccg ttactggcgt acgatcctac atatgtatcg  57420
tatggtcctt ccttctcagc tagttcacaa ctcgcctcta atgcaccgta ataaatggtt  57480
tcgaagatct tcttatttag atcttgtgct tccaggctat caaatggata atttaagaga  57540
ataaacgcgt ccgctaatcc ttgaacacca ataccgatag gtctatgtct cttattagag  57600
atttcagctt ctggaatagg ataataatta atatctataa ttttattgag atttctgaca  57660
attactttga ccacatcctt cagtttgaga aaatcaaatc gcccatctat tacaaacatg  57720
ttcaaggcaa cagatgccag attacaaacg gctacctcat tagcatccgc atattgtatt  57780
atctcagtgc aaagattact acacttgata gttcctaaat tttgttgatt actctttttg  57840
ttacacgcat ccttataaag aatgaatgga gtaccagttt caatctgaga ttctataatc  57900
gctttccaga cgactcgagc ctttattata gatttgtatc tcctttctct ttcgtatagt  57960
gtatacaatc gttcgaactc gtctccccaa acattgtcca atccaggaca ttcatccgga  58020
cacatcaacg accactctcc gtcatccttc actcgtttca taaagagatc aggaatccaa  58080
agagctataa atagatctct ggttctatgt tcctcgtttc ctgtattctt tttaagatcg  58140
aggaacgcca taatatcaga atgccacggt tccaagtata tggccataac tccaggccgt  58200
ttgtttcctc cctgatctat gtatctagcg gtgttattat aaactctcaa cattggaata  58260
ataccgtttg atataccatt ggtaccggag atatagcttc cactggcacg aatattacta  58320
attgatagac ctattccccc tgccatttta gagattaatg cgcatcgttt taacgtgtca  58380
tagataccct ctatgctatc atcgatcatg ttaagtagaa aacagctaga catttggtga  58440
cgactagttc ccgcattaaa taaggtagga gaagcgtgcg taaaccattt ttcagaaagt  58500
agattgtacg tctcaatagc tgagtctata tcccattgat gaattcctac tgcgacacgc  58560
attaacatgt gctgaggtct ttcaacgatc ttgttgttta ttttcaacaa gtaggatttt  58620
tccaaagttt taaaaccaaa atagttgtat gaaaagtctc gttcgtaaat aataaccgag  58680
ttgagtttat ccttatattt gttaactata tccatggtga tacttgaaat aatcggagaa  58740
tgtttcccat ttttaggatt aacatagttg aataaatcct ccatcacttc actaaatagt  58800
tttttgttt ccttgtgtag atttgatacg gctattctgg cggctagaat ggcataatcc  58860
```

```
ggatgttgtg tagtacaagt ggctgctatt tcggctgcca gagtgtccaa ttctaccgtt  58920
gttactccat tatatattcc ttgaataacc ttcatagcta ttttaatagg atctatatga  58980
tccgtgttta agccataaca taattttcta atacgagacg tgattttatc aaacatgaca  59040
ttttccttgt atccatttcg tttaatgaca aacatttttg ttggtgtaat aaaaaaaatt  59100
atttaacttt tcattaatag ggatttgacg tatgtagcgt acaaaattat cgttcctggt  59160
atatagataa agagtcctat atatttgaaa atcgttacgg ctcgattaaa ctttaatgat  59220
tgcatagtga atatatcatt aggatttaac tccttgacta tcatggcggc gccagaaatt  59280
accatcaaaa gcattaatac agttatgccg atcgcagtta gaacggttat agcatccacc  59340
atttatatct aaaaattaga tcaaagaata tgtgacaaag tcctagttgt atactgagaa  59400
ttgacgaaac aatgtttctt acatattttt tttttattag taaccgactt aatagtagga  59460
actggaaaac tagacttgat tattctataa gtatagatac ccttccaaat aatattctct  59520
ttgataaaag ttccagaaaa tgtagaattt tttaaaaagt tatcttttgc tattaccaag  59580
attgtgttta gacgcttatt attaatatga gtgatgaaat ccacaccgcc tctagatatc  59640
gcttttattt ccacattaga tggtaaatcc aatagtgaaa ctatcttttt aggaatgtat  59700
ggactcgcgt ttagaggagt gaacgtctta ggcgtcggaa aggatgattc atcaaacgaa  59760
taaacaattt cacaaatgga tgttaatgta ttagtaggaa attttttgac gctagtggaa  59820
ttgaagattc taatggatga tgttctacct atttcatccg ataacatgtt aatttccgac  59880
accaacggtt ttaatatttc gatgatatac ggtagtctct ctttcggact tatatagctt  59940
attccacaat acgagtcatt atatactcca aaaaacaaaa taactagtat aaaatctgta  60000
tcgaatggga aaaacgaaat tatcgacata ggtatagaat ctggaacatt gaacgtatta  60060
atacttaatt ctttttctgt ggtaagtacc gataggttat tgacattgta tggttttaaa  60120
tattctataa cttgagactt gatagatatt agtgatgaat tgaaaattat ttttatcacc  60180
acgtgtgttt caggatcatc gtcgacgccc gtcaaccaac cgaatggagt aaaataaata  60240
tcattaatat atgctctaga tattagtatt tttatcaatc ctttgattat catcttctcg  60300
taggcgaatg attccatgat caagagtgat ttaagaacat cctccggagt attaatgggc  60360
ttagtaaaca gtccatcgtt gcaataataa aagttatcca agttaaagga tattatgcat  60420
tcgtttaaag atatcacctc atctgacgga gacaattttt tggtaggttt tagagacttt  60480
gaagctactt gtttaacaaa gttattcatc gtcgtttact attctattta attttgtagt  60540
taatttatca catatcacat taattgactt tttggtccat ttttccatac gtttatattc  60600
ttttaatcct gcgttatccg tttccgttat atccagggat agatcttgca agttaaatag  60660
aatgctctta aataatgtca ttttcttatc cgctaaaaat ttaaagaatg tataaacctt  60720
tttcagagat ttgaaactct taggtggtgt cctagtacac aatatcataa acaaactaat  60780
aaacattcca cattcagatt ccaacagctg attaacttct acattaatac agcctatttt  60840
cgctccaaat gtacattcga aaaatctgaa taaaacatcg atgtcacaat ttgtattatc  60900
caatacagaa tgtttgtgat tcgtgttaaa accatcggag aaggaataaa aataaaaatt  60960
attatagtgg tggaattcag ttggaatatt gcctccggag tcataaaagg atactaaaca  61020
ttgtttttta tcataaatta cacatttcca atgagacaaa taacaaaatc caaacattac  61080
aaatctagag gtagaacttt taattttgtc tttaagtata tacgataaga tatgtttatt  61140
cataaacgcg tcaaattttt catgaatcgc taaggagttt aagaatctca tgtcaaattg  61200
tcctatataa tccacttcgg atccataagc aaactgagag actaagttct taatacttcg  61260
```

attgctcatc caggctcctc tctcaggctc tattttcatc ttgacgacct ttggattttc 61320
accagtatgt attcctttac gtgataaatc atcgattttc aaatccattt gtgagaagtc 61380
tatcgcctta gatacttttt cccgtagtcg aggtttaaag aaatacgcta acggtatact 61440
agtaggtaac tcaaagacat catatataga atggtaacgc gtctttaact cgtcggttaa 61500
ctctttcttt tgatcgagtt cgtcgctact attgggtctg ctcaggtgcc ccgactctac 61560
tagttccaac atcataccga taggaataca agacactttg ccggcggttg tagatttatc 61620
atatttctcc actacatatc cgttacaatt tgttaaaaat ttagatacat ctatattgct 61680
acataatcca gctagtgaat atatatgaca taataaattg gtaaatccta gttctggtat 61740
tttactaatt actaaatctg tatatctttc catttatcat ggaaaagaat ttaccagata 61800
tcttcttttt tccaaactgc gttaatgtat tctcttacaa atattcacaa gatgaattca 61860
gtaatatgag taaaacggaa cgtgatagtt tctcattggc ggtgtttcca gttataaaac 61920
atagatggca taacgcacac gttgtaaaac ataaaggaat atacaaagtt agtacagaag 61980
cacgtggaaa aaaagtatct cctccatcac taggaaaacc cgcacacata aacctaaccg 62040
cgaagcaata tatatacagt gaacacacaa taagctttga atgttatagt tttctaaaat 62100
gtataacaaa tacagaaatc aattcgttcg atgagtatat attaagagga ctattagaag 62160
ctggtaatag tttacagata ttttccaatt ccgtaggtaa acgaacagat actataggtg 62220
tactagggaa taagtatcca tttagcaaaa ttccattggc ctcattaact cctaaagcac 62280
aacgagagat attttcagcg tggatttctc atagacctgt agttttaact ggaggaactg 62340
gagtgggtaa gacgtcacag gtacccaagt tattgctttg gtttaattat ttatttggtg 62400
gattctctac tctagataaa atcactgact ttcacgaaag accagtcatt ctatctcttc 62460
ctaggatagc tttagttaga ttgcatagca ataccatttt aaaatcattg ggatttaagg 62520
tactagatgg atctcctatt tctttacggt acggatctat accggaagaa ttaataaaca 62580
aacaaccaaa aaaatatgga attgtatttt ctacccataa gttatctcta acaaaactat 62640
ttagttatgg cactcttatt atagacgaag ttcatgagca tgatcaaata ggagatatta 62700
ttatagcagt agcgagaaag catcatacga aaatagattc tatgttttta atgactgcca 62760
cgttagagga tgacagggaa cggctaaaag tatttttacc taatcccgca tttatacata 62820
ttcctggaga tacactgttt aaaattagcg aggtatttat tcataataag ataaatccat 62880
cttccagaat ggcatacata gaagaagaaa agagaaattt agttactgct atacagatgt 62940
atactcctcc tgatggatca tccggtatag tctttgtggc atccgttgca cagtgtcacg 63000
aatataaatc atatttagaa aaaagattac cgtatgatat gtatattatt catggtaagg 63060
tcttagatat agacgaaata ttagaaaaag tgtattcatc acctaatgta tcgataatta 63120
tttctactcc ttatttggaa tccagcgtta ctatacgcaa tgttacacac atttatgata 63180
tgggtagagt ttttgtcccc gctccttttg gaggatcgca agaatttatt tctaaatcta 63240
tgagagatca acgaaaagga agagtaggaa gagttaatcc tgggacatac gtatatttct 63300
atgatctgtc ttatatgaag tctatacagc gaatagattc agaatttcta cataattata 63360
tattgtacgc taataagttt aatctaacac tccccgaaga tttgtttata atccctacaa 63420
atttggatat tctatggcgt acaaaggaat atatagactc gttcgatatt agtacagaaa 63480
catggaataa attattatcc aattattata tgaagatgat agagtatgct aaactttatg 63540
tactaagtcc tattctcgct gaggagttgg ataattttga gaggacggga gaattaacta 63600

-continued

```
gtattgtaca agaagccatt ttatctctaa atttacgaat taagatttta aattttaaac  63660
ataaagatga tgatacgtat atacactttt gtaaaatatt attcggtgtc tataacggaa  63720
caaacgctac tatatattat catagacctc taacgggata tatgaatatg atttcagata  63780
ctatatttgt tcctgtagat aataactaaa aatcaaactc taatgaccac atcttttttt  63840
agagatgaaa aattttccac atctcctttt gtagacacga ctaaacattt tgcagaaaaa  63900
agtttattag tgtttagata atcgtatact tcatcagtgt agatagtaaa tgtgaacaga  63960
taaaaggtat tcttgctcaa tagattggta aattccatag aatatattaa tcctttcttc  64020
ttgagatccc acatcatttc aaccagagac gttttatcca atgatttacc tcgtactata  64080
ccacatacaa aactagattt tgcagtgacg tcgtatctgg tattcctacc aaacaaaatt  64140
ttacttttag ttcttttaga aaattctaag gtagaatctc tatttgccaa tatgtcatct  64200
atggaattac cactagcaaa aaatgataga aatatatatt gatacatcgc agctggtttt  64260
gatctactat actttaaaaa cgaatcagat tccataattg cctgtatatc atcagctgaa  64320
aaactatgtt ttacacgtat tccttcggca tttcttttta atgatatatc ttgtttagac  64380
aatgataaag ttatcatgtc catgagagac gcgtctccgt atcgtataaa tatttcatta  64440
gatgttagac gcttcattag gggtatactt ctataaggtt tcttaatcag tccatcattg  64500
gttgcgtcaa gaactactat cggatgttgt tgggtatctc tagtgttaca catggcctta  64560
ctaaagtttg ggtaaataac tatgatatct ctattaatta tagatgcata tatttcattt  64620
gtcaaggata ttagtatcga cttgctatcg tcattaatac gtgtaatgta atcatataaa  64680
tcatgcgata gccaaggaaa atttaaatag atgttcatca tataatcgtc gctataattc  64740
atattaatac gttgacattg actaatttgt aatatagcct cgccacgaag aaagctctcg  64800
tattcagttt catcgataaa ggataccgtt aaatataact ggttgccgat agtctcatag  64860
tctattaagt ggtaagtttc gtacaaatac agaatcccta aaatattatc taatgttgga  64920
ttaatcttta ccataactgt ataaaatgga gacggagtca taactatttt accgtttgta  64980
cttactggaa tagacgaagg aataatctcc ggacatgctg gtaaagaccc aaatgtctgt  65040
ttgaagaaat ccaatgttcc aggtcctaat ctcttaacaa aaattacgat attcgatccc  65100
gatatccttt gcattctatt taccagcata tcacgaacta tattaagatt atctatcatg  65160
tctattctcc caccgttata taaatcgcct ccgctaagaa acgttagtat atccatacaa  65220
tggaatactt catttctaaa atagtattcg ttttctaatt ctttaatgtg aaatcgtata  65280
ctagaaaggg aaaaattatc tttgagtttt ccgttagaaa agaaccacga aactaatgtt  65340
ctgattgcgt ccgattccgt tgctgaatta atggatttac accaaaaact catataactt  65400
ctagatgtag aagcattcgc taaaaaatta gtagaatcaa aggatataag tagatgttcc  65460
aacaagtgag caattcccaa gatttcatct atatcattct cgaatccgaa attagaaatt  65520
cccaagtaga tatccttttt catccgatcg ttgatgaaaa tacgaacttt attcggtaag  65580
acaatcattt actaaggagt aaaataggaa gtaatgttcg tatgtcgtta tcatcgtata  65640
aattaaaggt gtgtttttta ccattaagtg acattataat tttaccaata ttggaattat  65700
aatataggtg tatttgcgca ctcgcgacgg ttgatgcatc ggtaaatata gctgtatcta  65760
atgttctagt cggtatttca tcatttcgct gtctaataat agcgttttct ctatctgttt  65820
ccattacagc tgcctgaagt ttattggtcg gataatatgt aaaataataa gaaatacata  65880
cgaataacaa aaataaaata agatataata aagatgccat ttagagatct aattttgttt  65940
aacttgtcca aattcctact tacagaagat gaggaatcgt tggagatagt gtcttcctta  66000
```

tgtagaggat ttgaaatatc ttatgatgac ttgataactt actttccaga taggaaatac 66060
cataaatata tttctaaagt atttgaacat gtagatttat cggaggaatt aagtatggaa 66120
ttccatgata caactctgag agatttagtc tatcttagat tgtacaagta ttccaagtgt 66180
atacggccgt gttataaatt aggagataat ctaaaaggca tagttgttat aaaggacagg 66240
aatatttata ttagagaagc aaatgatgac ttgatagaat atctcctcaa ggaatacact 66300
cctcagattt atacatattc taatgagcgc gtccccataa ctggttcaaa attaattctt 66360
tgtggatttt ctcaagttac atttatggcg tatacaacgt cgcatataac aacaaataaa 66420
aaggtagatg ttctcgtttc caaaaaatgt atagatgaac tagtcgatcc aataaattat 66480
caaatacttc aaaatttatt tgataaagga agcggaacaa taaacaaaat actcaggaag 66540
atattttatt cggtaaccgg tggccaaact ccataatttg ctttttctat ttcggatttt 66600
agaatttcca aattcaccag cgatttatcg gttttggtga aatccaagga tttattaatg 66660
tccacaaatg ccatttgttt tgtctgtgga ttgtatttga aaatggaaac gatgtagtta 66720
gatagatgcg ctgcaaagtt tcctattagg gttccgcgct ttacgtcacc cagcatactt 66780
gaatcaccat cctttaaaaa aaatgataag atatcaacat ggagtatatc atactcggat 66840
tttaattctt ctactgcatc actgacattt tcacaaatac tacaatacgg tttaccgaaa 66900
ataatcagta cgttcttcat ttatgggtat caaaaactta aaatcgttac tgctggaaaa 66960
taaatcactg acgatattag atgataattt atacaaagta tacaatggaa tatttgtgga 67020
tacaatgagt atttatatag ccgtcgccaa ttgtgtcaga aacttagaag agttaactac 67080
ggtattcata aaatacgtaa acggatgggt aaaaaaggga gggcatgtaa cccttttat 67140
cgatagagga agtataaaaa ttaaacaaga cgttagagac aagagacgta aatattctaa 67200
attaaccaag gacagaaaaa tgctagaatt agaaaagtgt acatccgaaa tacaaaatgt 67260
taccggattt atggaagaag aaataaaggc agaaatgcaa ttaaaaatcg ataaactcac 67320
atttcaaata tatttatctg attctgataa cataaaaata tcattgaatg agatactaac 67380
acatttcaac aataatgaga atgttacatt attttattgt gatgaacgag acgcagaatt 67440
cgttatgtgt ctcgaggcta aaacacattt ctctaccaca ggagaatggc cgttgataat 67500
aagtaccgat caggatacta tgctatttgc atctactgat aatcatccta agatgataaa 67560
aaacttaact caactgttta aatttgttcc ctcggcagag gataactatt tagcaaaatt 67620
aacggcgtta gtgaatggat gtgatttctt tcctggactc tatggggcat ctataacacc 67680
caccaactta aacaaaatac aattgtttag tgattttaca atcgataata tagtcactag 67740
tttggcaatt aaaaattatt atagaaagac taactctacc gtagacgtgc gtaatattgt 67800
tacgtttata aacgattacg ctaatttaga cgatgtctac tcgtatgttc ctccttgtca 67860
atgcactgtt caagaattta tattttccgc attagatgaa aaatggaaca attttaaatc 67920
atcttattta gagaccgttc cgttaccctg ccaattaatg tatgcattag aaccacgcaa 67980
ggagattgat gtttcagaag ttaaaacttt atcatcttat atagatttcg aaaatactaa 68040
atcagatatc gatgttataa aatctatatc ttcgatcttc ggatattcta acgaaaactg 68100
taacactata gtgttcggca tctataagga taatttacta ctgagtataa atagttcatt 68160
ttactttaac gatagtctgt taataaccaa tactaaaagt gataatataa taaatatagg 68220
ttactagatt aaaaatggtg ttccaactcg tgtgctctac gtgcggcaaa gatatttctc 68280
acgaacgata taaattgatt atacgaaaaa aatcattaaa ggatgtactc gtcagtgtaa 68340
agaacgaatg ttgtaggtta aaattatcta cacaaataga acctcaacgt aacttaacag 68400
tgcaacctct attggatata aactaatatg gatccggtta attttatcaa gacatatgcg 68460
cctagaggtt ctattatttt tattaattat accatgtcat taacaagtca tttgaatcca 68520
tcgatagaaa aacatgtggg tatttattat ggtacgttat tatcggaaca cttggtagtt 68580
gaatctacct atagaaaagg agttcgaata gtcccattgg atagtttttt tgaaggatat 68640
cttagtgcaa aagtatacat gttagagaat attcaagtta tgaaaatagc agctgatacg 68700
tcattaactt tattgggtat tccgtatgga tttggtcata atagaatgta ttgttttaaa 68760
ttggtagctg aatgttataa aaatgccggt attgatacat cgtctaaacg aatattaggt 68820
aaagatattt ttctgagcca aaacttcaca gatgataata gatggataaa gatatatgat 68880
tctaataatt taacattttg gcaaattgat taccttaaag ggtgagttaa tatgcataac 68940
tactcctccg ttgtttttc cctcgttctt tttcttaacg ttgtttgcca tcactctcat 69000
aatgtaaaga tattctaaaa tggtaaactt ttgcatatcg gacgcagaaa ttggtataaa 69060
tgttgtaatt gtattatttc ccgtcaatgg actagtcaca gctccatcag ttttatatcc 69120
tttagagtat ttctcactcg tgtctaacat tctagagcat tccatgatct gtttatcgtt 69180
gatattggcc ggaaagatag attttttatt ttttattata ttactattgg caattgtaga 69240
tataacttct ggtaaatatt tttctacctt ttcaatctct tctattttca agccggctat 69300
atattctgct atattgttgc tagtatcaat accttttctg gctaagaagt catatgtggt 69360
attcactata tcagttttaa ctggtagttc cattagcctt tccacttctg cagaataatc 69420
agaaattggt tctttaccag aaaatccagc tactataata ggctcaccga tgatcattgg 69480
caaaatccta tattgtacca gattaatgag agcatatttc atttccaata attctgctag 69540
ttcttgagac attgatttat ttgatgaatc tagttggttc tctagatact ctaccatttc 69600
tgccgcatac aataacttgt tagataaaat cagggttatc aaagtgttta gcgtggctag 69660
aatagtgggc ttgcatgtat taaagaatgc ggtagtatga gtaaaccgtt ttaacgaatt 69720
atatagtctc cagaaatctg tggcgttaca tacatgagcc gaatgacatc gaagattgtc 69780
caatattttt aatagctgct ctttgtccat tatttctata tttgactcgc aacaattgta 69840
gataccatta atcactgatt cctttttcga tgccggacaa tagcacaatt gtttagcttt 69900
ggactctatg tattcagaat taatagatat atctctcaat acagattgca ctatacattt 69960
tgaaactatg tcaaaaattg tagaacgacg ctgttctgca gccatttaac tttaaataat 70020
ttacaaaaat ttaaaatgag catccgtata aaaatcgata aactgcgcca aattgtggca 70080
tatttttcag agttcagtga agaagtatct ataaatgtag actcgacgga tgagttaatg 70140
tatattttg ccgccttggg cggatctgta aacatttggg ccattatacc tctcagtgca 70200
tcagtgttct accgcggagc cgaaaacatt gtgtttaatc ttcctgtgtc caaggtaaaa 70260
tcgtgtttgt gtagttttca caatgatgcc atcatagata tagaacctga tctggaaaat 70320
aatctagtaa aactttctag ttatcatgta gtaagtgtcg attgtaacaa ggaactgatg 70380
cctattagga cagatactac tatttgtcta agtatagatc aaaagaaatc ttacgtgttt 70440
aattttcaca agtatgaaga aaaatgttgt ggtagaaccg tcattcattt agaatggttg 70500
ttgggcttta tcaagtgtat tagtcagcat cagcatttgg ctattatgtt taaagatgac 70560
aatattatta tgaagactcc tggtaatact gatgcgtttt ccagggaata ttctatgact 70620
gaatgttctc aagaactaca aaagttttct ttcaaaatag ctatctcgtc tctcaacaaa 70680
ctacgaggat tcaaaaagag agtcaatgtt tttgaaacta gaatcgtaat ggataatgac 70740

```
gataacattc taggaatgtt gttttcggat agagttcaat cctttaagat caacatcttt  70800
atgacgtttt tagattaata ctttcaatga gataaatatg ggtggcagag taagtgttga  70860
gctccctaaa cgggatccgc ctccgggagt acccactgat gagatgttat taaacgtgga  70920
taaaatgcat gacgtgatag ctcccgctaa gcttttagaa tatgtgcata taggaccact  70980
agcaaaagat aaagaggata aagtaaagaa aagatatcca gagtttagat tagtcaacac  71040
aggacccggt ggtctttcgg cattgttaag acaatcgtat aatggaaccg cacccaattg  71100
ctgtcgcact tttaatcgta ctcattattg gaaaaaggat ggaaagatat cagataagta  71160
tgaagagggt gcagtattag aatcgtgttg gccagacgtt cacgacactg gaaaatgcga  71220
tgttgattta ttcgactggt gtcaggggga tacgttcgat agaaacatat gccatcagtg  71280
gatcggttca gcctttaata ggagtgatag aactgtagag ggtcaacaat cgttaataaa  71340
tctgtataat aagatgcaaa cattatgtag taaagatgct agtgtaccaa tatgtgaatc  71400
atttttgcat catttacgcg cacacaatac agaagatagc aaagagatga tcgattatat  71460
tctaagacaa cagtctgcgg actttaaaca gaaatatatg agatgtagtt atcccactag  71520
agataagtta gaagagtcat taaaatatgc ggaacctcga gaatgttggg atccagagtg  71580
ttcgaatgcc aatgttaatt tcttactaac acgtaattat aataatttag gactttgcaa  71640
tattgtacga tgtaatacta gcgtgaacaa cttacagatg gataaaactt cctcattaag  71700
attgtcatgt ggattaagca atagtgatag attttctact gttcccgtca atagagcaaa  71760
agtagttcaa cataatatta aacattcgtt cgacctaaaa ttgcatttga tcagtttatt  71820
atctctcttg gtaatatgga tactaattgt agctatttaa atgggtgccg cggcaagcat  71880
acagacgacg gtgaatacac tcagcgaacg tatctcgtct aaattagaac aagaagcgaa  71940
cgctagtgct caaacaaaat gtgatataga aatcggaaat ttttatatcc gacaaaacca  72000
tggatgtaac ctcactgtta aaaatatgtg ctctgcggac gcggatgctc agttggatgc  72060
tgtgttatca gccgctacag aaacatatag tggattaaca ccggaacaaa aagcatacgt  72120
accagctatg tttactgctg cgttaaacat tcagacgagt gtaaacactg ttgttagaga  72180
ttttgaaaat tatgtgaaac agacttgtaa ttctagcgcg gtcgtcgata acaaattaaa  72240
gatacaaaac gtaatcatag atgaatgtta cggagcccca ggatctccaa caaatttgga  72300
atttattaat acaggatcta gcaaaggaaa ttgtgccatt aaagcgttga tgcaattgac  72360
gactaaggcc actactcaaa tagcacctag acaagttgct ggtacaggag ttcagtttta  72420
tatgattgtt atcggtgtta taatattggc agcgttgttt atgtactatg ccaagcgtat  72480
gttgttcaca tccaccaatg ataaaatcaa acttatttta gccaataagg aaaacgtcca  72540
ttggactact tacatggaca cattctttag aacttctccg atggttattg ctaccacgga  72600
tatgcaaaac tgaaaatata ttgataatat tttaatagat taacatggaa gttatcgctg  72660
atcgtctaga cgatatagtg aaacaaaata tagcggatga aaaatttgta gattttgtta  72720
tacacggtct agagcatcaa tgtcctgcta tacttcgacc attaattagg ttgtttattg  72780
atatactatt atttgttata gtaatttata tttttacggt acgtctagta agtagaaatt  72840
atcaaatgtt gttggcgttg gtggcgctag tcatcacatt aactattttt tattacttta  72900
tactataata gtactagact gacttctaac aaacatctca cctgccataa ataaatgctt  72960
gatattaaag tcttctattt ctaacactat tccatctgtg gaaaataata ctctgacatt  73020
atcgctaatt gacacatcgg tgagtgatat gcctataaag taataatctt ctttgggcac  73080
```

-continued atataccagt gtaccaggtt ctaacaacct atttactggt gctcctgtag catacttttt 73140
ctttaccttg agaatatcca tcgtttgctt ggtcaatagc gatatgtgat tttttatcaa 73200
ccactcaaaa aagtaattgg agtgttcata tcctctacgg gctattgtct catggccgtg 73260
tatgaaattt aagtaacacg actgtggtag atttgttcta tagagccggt tgccgcaaat 73320
agatagaact accaatatgt ctgtacaaat gttaaacatt aattgattaa cagaaaaaac 73380
aatgttcgtt ctgggaatag aaaccagatc aaaacaaaat tcgttagaat atatgccacg 73440
tttatacatg gaatataaaa taactacagt ttgaaaaata acagtatcat ttaaacattt 73500
aacttgcggg gttaatttca caactttact gtttttaaac tgttcaaaat atagcatcga 73560
tccatgagaa atacgtttag ccgcctttaa tagaggaaat cccaccgcct ttctggatct 73620
caccaacgac gatagttctg accagcaact tatttcttca tcatccacct gttttaacat 73680
ataataggca ggagatagat atccgtcatt gcaatattcc ttttcgtagg cacacaatct 73740
aatattgata aaatctccat tctcttctct gcatttatta tcttgtttcg gtggctgatt 73800
aggctgtagt cttggtttag gctttggtat atcgttgttg aatctatttt ggtcattaaa 73860
tctttcattt cttcctggta tatttctatc acctcgtttg gttggatttt tgtctatatt 73920
atcgtttgta acatcggtac gggtattcat ttatcacaaa aaaaacttct ctaaatgagt 73980
ctactgctag aaaacctcat cgaagaagat accatatttt ttgcaggaag tatatctgag 74040
tatgatgatt tacaaatggt tattgccggc gcaaaatcca aatttccaag atctatgctt 74100
tctattttta atatagtacc tagaacgatg tcaaaatatg agttggagtt gattcataac 74160
gagaatatca caggggcaat gtttaccaca atgtataata taagaaacaa tttgggtcta 74220
ggagatgata aactaactat tgaagccatt gaaaactatt tcttggatcc taacaatgag 74280
gttatgcctc ttatcattaa taatacggat atgactgccg tcattcctaa aaaaagtggt 74340
aggagaaaga ataagaacat ggttatttc cgtcaaggat catcacctat cttgtgtatt 74400
ttcgaaactc gtaaaaagat taatatttat aaagaaaata tggaatccgc gtcgactgag 74460
tatacaccta tcggagacaa caaggctttg atatctaaat atgcgggaat taatgtcctg 74520
aatgtgtatt ctccttccac atccatgaga ttgaatgcca tttacggatt caccaataaa 74580
aataaactag agaaacttag tactaataag gaactagaat cgtatagttc tagccctctt 74640
caagaaccca ttaggttaaa tgattttctg ggactattgg aatgtgttaa aaagaatatt 74700
cctctaacag atattccgac aaaggattga ttactataaa tggagaatgt tcctaatgta 74760
tactttaatc ctgtgtttat agagcccacg tttaaacatt ctttattaag tgtttataaa 74820
cacagattaa tagttttatt tgaagtattc attgtattca ttctaatata tgtatttttt 74880
agatctgaat taaatatgtt cttcatgcct aaacgaaaaa tacccgatcc tattgataga 74940
ttacgacgtg ctaatctagc gtgtgaagac gataaattaa tgatctatgg attaccatgg 75000
atgacaactc aaacatctgc gttatcaata aatagtaaac cgatagtgta taaagattgt 75060
gcaaagcttt tgcgatcaat aaatggatca caaccagtat ctcttaacga tgttcttcgc 75120
agatgatgat tcattttttta agtatttggc tagtcaagat gatgaatctt cattatctga 75180
tatattgcaa atcactcaat atctagactt tctgttatta ttattgatcc aatcaaaaaa 75240
taaattagaa gccgtgggtc attgttatga atctctttca gaggaataca gacaattgac 75300
aaaattcaca gactttcaag attttaaaaa actgtttaac aaggtcccta ttgttacaga 75360
tggaagggtc aaacttaata aaggatattt gttcgacttt gtgattagtt tgatgcgatt 75420
caaaaaagaa tcctctctag ctaccaccgc aatagatcct attagataca tagatcctcg 75480
tcgcgatatc gcattttcta acgtgatgga tatattaaag tcgaataaag tgaacaataa 75540
ttaattcttt attgtcatca tgaacggcgg acatattcag ttgataatcg gccccatgtt 75600
ttcaggtaaa agtacagaat taattagacg agttagacgt tatcaaatag ctcaatataa 75660
atgcgtgact ataaaatatt ctaacgataa tagatacgga acgggactat ggacgcatga 75720
taagaataat tttgaagcat tggaagcaac taaactatgt gatgtcttgg aatcaattac 75780
agatttctcc gtgataggta tcgatgaagg acagttcttt ccagacattg ttgaattctg 75840
tgagcgtatg gcaaacgaag gaaaaatagt tatagtagcc gcactcgatg ggacatttca 75900
acgtaaaccg tttaataata ttttgaatct tattccatta tctgaaatgg tggtaaaact 75960
aactgctgtg tgtatgaaat gctttaagga ggcttccttt tctaaacgat tgggtgagga 76020
aaccgagata gagataatag gaggtaatga tatgtatcaa tcggtgtgta gaaagtgtta 76080
cgtcggctca taatattata tttttatct aaaaaactaa aaataaacat tgattaaatt 76140
ttaatataat acttaaaaat ggatgttgtg tcgttagata aaccgtttat gtattttgag 76200
gaaattgata atgagttaga ttacgaacca gaaagtgcaa atgaggtcgc aaaaaaactg 76260
ccgtatcaag gacagttaaa actattacta ggagaattat tttttcttag taagttacag 76320
cgacacggta tattagatgg tgccaccgta gtgtatatag gatctgctcc cggtacacat 76380
atacgttatt tgagagatca tttctataat ttaggagtga tcatcaaatg gatgctaatt 76440
gacggccgcc atcatgatcc tattttaaat ggattgcgtg atgtgactct agtgactcgg 76500
ttcgttgatg aggaatatct acgatccatc aaaaaacaac tgcatccttc taagattatt 76560
ttaatttctg atgtgagatc caaacgagga ggaaatgaac ctagtacggc ggatttacta 76620
agtaattacg ctctacaaaa tgtcatgatt agtattttaa accccgtggc gtctagtctt 76680
aaatggagat gcccgtttcc agatcaatgg atcaaggact tttatatccc acacggtaat 76740
aaaatgttac aaccttttgc tccttcatat tcagctgaaa tgagattatt aagtatttat 76800
accggtgaga acatgagact gactcgagtt accaaatcag acgctgtaaa ttatgaaaaa 76860
aagatgtact accttaataa gatcgtccgt aacaaagtag ttgttaactt tgattatcct 76920
aatcaggaat atgactattt tcacatgtac tttatgctga ggaccgtgta ctgcaataaa 76980
acatttccta ctactaaagc aaaggtacta tttctacaac aatctatatt tcgtttctta 77040
aatattccaa caacatcaac tgaaaaagtt agtcatgaac caatacaacg taaaatatct 77100
agcaaaaatt ctatgtctaa aaacagaaat agcaagagat ccgtacgcag taataaatag 77160
aaacgtacta ctgagatata ctaccgatat agagtataat gatttagtta ctttaataac 77220
cgttagacat aaaattgatt ctatgaaaac tgtgtttcag gtatttaacg aatcatccat 77280
aaattatact ccggttgatg atgattatgg agaaccaatc attataacat cgtatcttca 77340
aaaaggtcat aacaagtttc ctgtaaattt tctatacata gatgtggtaa tatctgactt 77400
atttcctagc tttgttagac tagatactac agaaactaat atagttaata gtgtactaca 77460
aacaggcgat ggtaaaaaga ctcttcgtct tcccaaaatg ttagagacgg aaatagttgt 77520
caagattctc taccgtccta atataccatt aaaaattgtt agatttttcc gcaataacat 77580
ggtaactgga gtagagatag ccgatagatc tgttatttca gtcgctgatt aatcaattag 77640
tagagatgag ataagaacat tataataatc aataaatatat tttatatctt atatcttgtt 77700
tagaaaaatg ctaatattaa aatagctaac gctagtaatc caatcggaag ccatttgata 77760
tctataatag ggtatctaat ttcctgattc agatagcgga cagctatatt ctcggtagct 77820

-continued

```
actcgtttgg aatcacaaac attatttaca tctaatttac tatctgtaat ggaaacgttt  77880
cccaatgaaa tggtacaatc cgatacattg cattttgtta tattttttt taaagaggct  77940
ggtaacaacg catcgcttcg tttacatggc tcgtaccaac aataataggg taatcttgta  78000
tctattccta tccgtactat gcttttatca ggataaatac atttacatcg tatatcgtct  78060
ttgttagcat cacagaatgc ataaatttgt tcgtccgtca tgataaaaat ttaaagtgta  78120
aatataacta ttattttata gttgtaataa aaagggaaat ttgattgtat actttcggtt  78180
ctttaaaaga aactgacttg ataaaaatgg ctgtaatctc taaggttacg tatagtctat  78240
atgatcaaaa agagattaat gctacagata ttatcattag tcatgttaaa aatgacgacg  78300
atatcggtac cgttaaagat ggtagactag gtgctatgga tggggcatta tgtaaaactt  78360
gtgggaaaac ggaattggaa tgtttcggtc actggggtaa agtaagtatt tataaaactc  78420
atatagttaa gcctgaattt atttcagaaa ttattcgttt actgaattat atatgtattc  78480
actgcggatt attgcgttca cgagaaccgt attccgacga tattaaccta aaagagttat  78540
cgggacacgc tcttaggaga ttaaaggata aaatattatc caagaaaaag tcatgttgga  78600
acagtgaatg tatgcaaccg tatcaaaaaa ttactttttc aaagaaaaag gtttgtttcg  78660
tcaacaagtt ggatgatatt aacgttccta attctctcat ctatcaaaag ttaatttcta  78720
ttcatgaaaa gttttggcca ttattagaaa ttcatcaata tccagctaac ttattttata  78780
cagactactt tcccatccct ccgttgatta ttagaccggc tattagtttt tggatagata  78840
gtatacccaa agaaaccaat gaattaactt acttattagg tatgatcgtt aagaattgta  78900
acttgaatgc tgatgaacag gttatccaga aggcggtaat agaatacgat gatattaaaa  78960
ttatttctaa taacacttcc agtatcaatt tatcatatat cacatccggc aaaaataata  79020
tgattagaag ttatatcgtc gcccggcgaa aagatcagac cgctagatct gtaattggtc  79080
ccagtacatc tatcaccgtt aatgaggtag gaatgcccgc atatattaga aatacactta  79140
cagaaaagat atttgttaat gcctttacag tggataaagt taaacaacta ttagcgtcaa  79200
accaagttaa attttacttt aataaacgat taaaccaatt aacaagaata cgccaaggaa  79260
agtttatcaa aaataaaata catttattgc ctggtgattg ggtagaagta gctgttcaag  79320
aatatacaag tattattttt ggaagacagc cgtctctaca tagatacaac gtcatcgctt  79380
catctatcag agctaccgaa ggagatacta tcaaaatatc tcccggaatt gtcaactctc  79440
aaaatgctga tttcgacgga gatgaagaat ggatgatatt ggagcaaaat cctaaagccg  79500
taattgaaca aagtattctt atgtatccga cgacgttact caaacacgat attcatggag  79560
cccccgttta tggatctatt caagatgaaa tcgtagcagc gtattcattg tttaggatac  79620
aagatctttg tttagatgaa gtattgaaca tcttggggaa atatggaaga gagttcgatc  79680
ctaaaggtaa atgtaaattc agcggtaaag atatctatac ttacttgata ggtgaaaaga  79740
ttaattatcc gggtctctta aaggatggtg aaattattgc aaacgacgta gatagtaatt  79800
ttgttgtggc tatgaggcat ctgtcattgg ctggactctt atccgatcat aagtcgaacg  79860
tggaaggtat caactttatt atcaagtcat cttatgtttt taagagatat ctatctattt  79920
acggttttgg ggtgacattc aaagatctga gaccaaattc gacgttcact aataaattgg  79980
aggccatcaa cgtagaaaaa atagaactta tcaaagaagc atacgccaaa tatctcaacg  80040
atgtaagaga cgggaaaata gttccattat ctaaagcttt agaggcggac tatgtggaat  80100
ccatgttatc caacttgaca aatcttaata tccgagagat agaagaacat atgagacaaa  80160
cgctgataga tgatccagat aataacctcc tgaaaatggc caaagcgggt tataaagtaa  80220
```

atcccacaga actaatgtat attctaggta cttatggaca acagaggatt gatggtgaac 80280
cagcagagac tcgagtattg ggtagagtct taccttacta tcttccagac tctaaggatc 80340
cagaaggaag aggttacatt cttaattctt taacaaaagg attaacgggt tctcaatatt 80400
acttttcgat gctggttgca agatctcaat ctactgatat cgtctgtgaa acatcacgta 80460
ccggaacact ggctagaaaa atcattaaaa agatggagga tatggtggtc gacggatacg 80520
gacaagtagt tataggtaat acgctcatca agtacgccgc caattatacc aaaattctag 80580
gctcagtatg taaacctgta gatcttatct atccagatga gtccatgact tggtatttgg 80640
aaattagtgc tctgtggaat aaaataaaac agggattcgt ttactctcag aaacagaaac 80700
ttgcaaaaaa gacattggcg ccgtttaatt tcctagtatt cgtcaaaccc accactgagg 80760
ataatgctat taaggttaag gatctgtacg atatgattca taacgtcatt gatgatgtga 80820
gagagaaata cttctttacg gtatctaata tagattttat ggagtatata ttcttgacgc 80880
atcttaatcc ttctagaatt agaattacaa aagaaacggc tatcactatc tttgaaaagt 80940
tctatgaaaa actcaattat actctaggtg gtggaactcc tattggaatt atttctgcac 81000
aggtattgtc tgagaagttt acacaacaag ccctgtccag ttttcacact actgaaaaaa 81060
gtggtgccgt caaacaaaaa cttggtttca acgagtttaa taacttgact aatttgagta 81120
agaataagac cgaaattatc actctggtat ccgatgatat ctctaaactt caatctgtta 81180
agattaattt cgaatttgta tgtttgggag aattaaatcc aaacatcact cttcgaaaag 81240
aaacagatag gtatgtagta gatataatag tcaatagatt atacatcaag agagcagaaa 81300
ttaccgaatt agtcgtcgaa tatatgattg aacgattcat ctcctttagc gtcattgtaa 81360
aggaatgggg tatggaaaca ttcattgagg atgaggataa tattagattt actgtctacc 81420
taaatttcgt tgaaccggaa gaattgaatc ttagtaagtt tatgatggtt cttccgggtg 81480
ccgccaacaa gggcaagatt agtaaattca agattcctat ctctgattat acgggatatg 81540
acgacttcaa tcaaacaaaa aagctcaata agatgactgt agaactcatg aatctaaaag 81600
aattgggttc tttcgatttg gaaaacgtca acgtgtatcc tggagtatgg aatacatacg 81660
atatcttcgg tatcgaggcc gctcgtgaat acttgtgcga agccatgtta aacacctatg 81720
gagaagggtt cgattatctg tatcagcctt gtgatcttct cgctagttta ctatgtgcta 81780
gttacgaacc agaatcagtg aataaattca agttcggcgc agctagtact cttaagagag 81840
ctacgttcgg agacaataaa gcattgttaa acgcggctct tcataaaaag tcagaaccta 81900
ttaacgataa tagtagctgc cactttttta gcaaggtccc taatatagga actggatatt 81960
acaaatactt tatcgacttg ggtcttctca tgagaatgga aaggaaacta tctgataaga 82020
tatcttctca aaagatcaag gaaatggaag aaacagaaga cttttaattc ttatcaataa 82080
catatttttc tatgatctgt cttttaaacg atggattttc cacaaatgcg cctctcaagt 82140
ccctcataga atgatacacg tataaaaaat atagcatagg caatgactcc ttatttttag 82200
acattagata tgccaaaatc atagccccgc ttctatttac tcccgcagca caatgaacca 82260
acacgggctc gtttcgttga tcacatttag ataaaaaggc ggttacgtcg tcaaaatatt 82320
tactaatatc ggtagttgta tcatctacca acggtatatg aataatatta atattagagt 82380
taggtaatgt atatttatcc atcgtcaaat ttaaaacata tttgaactta acttcagatg 82440
atggtgcatc catagcattt ttataatttc ccaaatacac attattggtt actcttgtca 82500
ttatagtggg agatttggct ttgtgcatat ctccagttga acgtagtagt aagtatttat 82560

-continued

```
acaaactttt cttatccatt tataacgtac aaatggataa aactacttta tcggtaaacg  82620
cgtgtaattt agaatacgtt agagaaaagg ctatagtagg cgtacaagca gccaaaacat  82680
caacacttat attctttgtt attatattgg caattagtgc gctattactc tggtttcaga  82740
cgtctgataa tccagtcttt aatgaattaa cgagatatat gcgaattaaa aatacggtta  82800
acgattggaa atcattaacg gatagcaaaa caaaattaga aagtgataga ggtagacttc  82860
tagccgctgg taaggatgat atattcgaat tcaaatgtgt ggatttcggc gcctatttta  82920
tagctatgcg attggataag aaaacatatc tgccgcaagc tattaggcga ggtactggag  82980
acgcgtggat ggttaaaaag gcggcaaagg tcgatccatc tgctcaacaa ttttgtcagt  83040
atttgataaa acacaagtct aataatgtta ttacttgtgg taatgagatg ttaaatgaat  83100
taggttatag cggttatttt atgtcaccgc attggtgttc cgattttagt aatatggaat  83160
agtgttagat aaatgcggta acgaatgttc ctgtaaggaa ccataacagc ttagatttaa  83220
cgttaaagat gagcataaac ataataaaca aaattacaat caaacctata acattaatat  83280
caaacaatcc aaaaaatgaa atcagtggag tagtaaacgc gtacataact cctggataac  83340
gtttagcagc tgccgttcct attctagacc aaaaattcgg tttcatgttt tcgaaacggt  83400
attctgcaac aagtcgagga tcgtgttcta catatttggc ggcgttatcc agtatctgcc  83460
tattgatctt catttcgttt tcgattctgg ctatttcaaa ataaaatccc gatgatagac  83520
ctccagactt tataatttca tctacgatgt tcagcgccgt agtaactcta ataatatagg  83580
ctgataagct aacatcatac cctcctgtat atgtgaatat ggcatgattt ttgtccatta  83640
caagctcggt tttaacttta ttgcctgtaa taatttctct catctgtagg atatctattt  83700
ttttgtcatg cattgccttc aagacgggac gaagaaacgt aatatcctca ataacgttat  83760
cgttttctac aataactaca tattctacct ttttattttc taactcggta aaaaaattag  83820
aatcccatag ggctaaatgt ctagcgatat ttcttttcgt ttcctctgta cacatagtgt  83880
tacaaaaccc tgaaaagaag tgagtatact tgtcatcatt tctaatgttt cctccagtcc  83940
actgtataaa cgcataatcc ttgtaatgat ctggatcatc cttgactacc acaacatttc  84000
ttttttctgg cataacttca ttgtccttta catcatcgaa cttctgatca ttaatatgct  84060
catgaacatt aggaaatgtt tctgatggag gtctatcaat aactggcaca acaataacag  84120
gagttttcac cgccgccatt tagttattga aattaatcat atacaactct ttaatacgag  84180
ttatattttc gtctatccat tgtttcacat ttacatattt cgacaaaaag atataaaatg  84240
cgtattccaa tgcttctctg tttaatgaat tactaaaata tacaaacacg tcactgtctg  84300
gcaataaatg atatcttaga atattgtaac aatttatttt gtattgcaca tgttcgtgat  84360
ctatgagttc ttcttcgaat ggcataggat ctccgaatct gaaaacgtat aaataggagt  84420
tagaataata atatttgaga gtattggtaa tatataaact ctttagcggt ataattagtt  84480
tttttctctc gatttctatt tttagatgtg atggaaaaat gactaatttt gtagcattag  84540
tatcatgaac tctaatcgag atcttaatat cttcgtcaca cgttagttct ttgaagtttt  84600
taagagatgc atcagttggt tcgaccgatg gagtaggtgc aacaattttt tgttcgatgt  84660
atgtatgtac tggagccatt gtcttaacta taatggtgct tgtatcgaaa aactttaatg  84720
cagataatgg aagctcttcg ccgcgacttt ctacatcgta attgggtttct aacgccgatc  84780
tctgaatgga tactagtttt ctaagttcta atgtgattct ctgaaaatgt aaatccaatt  84840
cctccggcat tatagatgtg tatacatcgg taaataaaac tatagtatcc aacgatccct  84900
tctcgcaaat tctagtctta accaaaaaat cgtatataac cacggagatg gcgtatttaa  84960
```

gagtggattc ttctaccgtt ttgttcttgg atttcatata agaaactata aagtccgcac 85020
tactgttaag aatgattact aacgcaacta tatagtttaa attaagcatc ttggaaacat 85080
aaaataactc tgtagacgat acttgacttt cgaataagtt tgcagacaaa cgaagaaaga 85140
acagacctct cttaatttca gaagaaaact ttttttcgta ttcctgacgt ctagagttta 85200
tatcaataag aaagttaaga attagtcggt taatgttgta tttcattacc caagtttgag 85260
atttcataat attatcaaaa gacatgataa tattaaagat aaagcgctga ctatgaacga 85320
aatagctata tggttcgctc aagaatatag tcttgttaaa cgtggaaacg ataactgtat 85380
ttttaatcac gtcagcggca tctaaattaa atataggtat atttattcca cacactctac 85440
aatatgccac accatcttca taataaataa attcgttagc aaaattatta attttagtga 85500
aatagttagc gtcaactttc atagcttcct tcaatctaat ttgatgctca cacggtgcga 85560
attccactct aacatccctt ttccatgcct caggttcatc gatctctata atatctagtt 85620
ttttgcgttt cacaaacaca ggctcgtctc tcgcgatgag atctgtatag taactatgta 85680
aatgataact agatagaaag atgtagctat atagatgacg atcctttaag agaggtatga 85740
tgactttacc ccaatcagat agactgttgt tatggtcttc ggaaaaagaa tttttataaa 85800
tttttccagt attttccaaa tatacgtact taacatctaa aaaatcctta atgataatag 85860
gaatggataa tccgtctatt ttataaagaa atacatatcg cacattatac ttttttttgg 85920
aaatgggaat accgatgtgt ctacataaat atgcaaagtc taaatatttt ttagagaatc 85980
ttagttggtc caaattcttt tccaagtacg gtaatagatt tttcatattg aacggtatct 86040
tcttaatctc tggttctagt tccgcattaa atgatgaaac taagtcacta tttttataac 86100
taacgattac atcacctcta acatcatcat ttaccagaat actgatcttc ttttgtcgta 86160
aatacatgtc taatgtgtta aaaaaaagat catacaagtt atacgtcatt tcatctgtgg 86220
tattcttgtc attgaaggat aaactcgtac taatctcttc tttaacagcc tgttcaaatt 86280
tatatcctat atacgaaaaa atagcaacca gtgtttgatc atccgcgtca atattctgtt 86340
ctatcgtagt gtataacaat cgtatatctt cttctgtgat agtcgatacg ttataaaggt 86400
tgataacgaa aatattttta tttcgtgaga taaagtcatc gtaggatttt ggacttatat 86460
tcgcgtctag tagatatgct tttatttttg gaatgatctc aattagaata gtctctttag 86520
agtccattta aagttacaaa caactaggaa attggtttat gatgtataat ttttttagtt 86580
tttatagatt ctttattcta tacttaaaaa atgaaaataa atacaaaggt tcttgagggt 86640
tgtgttaaat tgaaagcgag aaataatcat aaattatttc attatcgcga tatccgttaa 86700
gtttgtatcg taatggcgtg gtcaattaca aataaagcgg atactagtag cttcacaaag 86760
atggctgaaa tcagagctca tctaaaaaat agcgctgaaa ataaagataa aaacgaggat 86820
attttcccgg aagatgtaat aattccatct actaagccca aaaccaaacg agccactact 86880
cctcgtaaac cagcggctac taaaagatca accaaaaagg aggaagtgga agaagaagta 86940
gttatagagg aatatcatca aacaactgaa aaaaattctc catctcctgg agtcagcgac 87000
attgtagaaa gcgtggctgc tgtagagctc gatgatagcg acggggatga tgaacctatg 87060
gtacaagttg aagctggtaa agtaaatcat agtgctagaa gcgatctttc tgacctaaag 87120
gtggctaccg acaatatcgt taaagatctt aagaaaatta ttactagaat ctctgcagta 87180
tcgacggttc tagaggatgt tcaagcagct ggtatctcta gacaatttac ttctatgact 87240
aaagctatta caacactatc tgatctagtc accgagggaa aatctaaagt tgttcgtaaa 87300

```
aaagttaaaa cttgtaagaa gtaaatgcgt gcactttttt ataaagatgg taaactcttt  87360
accgataata attttttaaa tcctgtatca gacgataatc cagcgtatga ggttttgcaa  87420
catgttaaaa ttcctactca tttaacagat gtagtagtat atgaacaaac gtgggaggag  87480
gcgttaacta gattaatttt tgtgggaagt gattcaaaag gacgtagaca atacttttac  87540
ggaaaaatgc atgtacagaa tcgcaacgct aaaagagatc gtatttttgt tagagtatat  87600
aacgttatga aacgaattaa ttgttttata aacaaaaata taaagaaatc gtccacagat  87660
tccaattatc agttggcggt tttatgtta atggaaacta tgttttttat tagatttggt  87720
aaaatgaaat atcttaagga gaatgaaaca gtagggttat taacactaaa aaataaacac  87780
atagaaataa gtcccgatga aatagttatc aagtttgtag gaaaggacaa agtttcacat  87840
gaatttgttg ttcataagtc taatagacta tataaaccgc tattgaaact gacggatgat  87900
tctagtcccg aagaatttct gttcaacaaa ctaagtgaac gaaaggtata cgaatgtatc  87960
aaacagtttg gtattagaat caaggatctc cgaacgtatg gagtcaatta tacgttttta  88020
tataattttt ggacaaatgt aaagtccata tctcctcttc cgtcaccaaa aaagttaata  88080
gcgttaacta tcaaacaaac tgctgaagtg gtaggtcata ctccatcaat ttcaaaaaga  88140
gcttatatgg caacgactat tttagaaatg gtaaaggata aaaatttttt agatgtagta  88200
tctaaaacta cgttcgatga attcctatct atagtcgtag atcacgttaa atcatctacg  88260
gatggatgat atagatcttt acacaaataa ttacaagacc gataaatgga aatggataag  88320
cgtatgaaat ctctcgcaat gacagctttc ttcggagagc taaacacatt agatattatg  88380
gcattgataa tgtctatatt taaacgccat ccaaacaata ccattttttc agtggataag  88440
gatggtcagt ttatgattga tttcgaatac gataattata aggcttctca atatttggat  88500
ctgaccctca ctccgatatc tggagatgaa tgcaagactc acgcatcgag tatagccgaa  88560
caattggcgt gtgtggatat tattaaagag gatattagcg aatatatcaa aactactccc  88620
cgtcttaaac gatttataaa aaaataccgc aatagatcag atactcgtat cagtcgagat  88680
acagaaaagc ttaaaatagc tctagctaaa ggcatagatt acgaatatat aaaagacgct  88740
tgttaataag taaatgaaaa aaaactagtc gtttataata aaacacaata tggatgccaa  88800
catagtatca tcttctacta ttgcaacgta tatagacgct ttagcgaaga atgcttcaga  88860
attagaacag aggtctaccg catacgaaat aaataatgaa ttggaactag tatttattaa  88920
gccgccatta attactttga caaatgtagt gaatatctct acgattcagg aatcgtttat  88980
tcgatttacc gttactaata aggaaggtgt taaaattaga actaagattc cattatctaa  89040
ggtacatggt ctagatgtaa aaaatgtaca gttagtagat gctatagata acatagtttg  89100
ggaaaagaaa tcattagtga cggaaaatcg tcttcacaaa gaatgcttgt tgagactatc  89160
gacagaggaa cgtcatatat ttttggatta caagaaatat ggatcctcta tccgactaga  89220
attagtcaat cttattcaag caaaaacaaa aaactttacg atagacttta agctaaaata  89280
ttttctagga tccggtgccc agtctaaaag ttctttatta cacgctatta atcatccaaa  89340
gtcaaggcct aatacatctc tggaaataga attcacacct agagacaatg aaaaagttcc  89400
atatgatgaa ctaataaagg aattgacgac tctatcacgt catatattta tggcttctcc  89460
agagaatgta attctttctc cgcctattaa cgcgcctata aaaaccttta tgttgcctaa  89520
acaagatata gtaggtttgg atctggaaaa tctatatgcc gtaactaaga ctgacggaat  89580
tcctataact atcagagtta catcaaaagg gttgtattgt tattttacac atcttggtta  89640
tattattaga tatcctgtta agagaataat agattccgaa gtagtagtct ttggtgaggc  89700
```

```
agttaaggat aagaactgga ccgtatatct cattaagcta atagagcctg tgaatgcaat  89760
caatgataga ctagaagaaa gtaagtatgt tgaatctaaa ctagtggata tttgtgatcg  89820
gatagtattc aagtcaaaga aatacgaagg tccgtttact acaactagtg aagtcgtcga  89880
tatgttatct acatatttac caaagcaacc agaaggtgtt attctgttct attcaaaggg  89940
acctaaatct aacattgatt ttaaaattaa aaaggaaaat actatagacc aaactgcaaa  90000
tgtagtattt aggtacatgt ccagtgaacc aattatcttt ggagaatcgt ctatctttgt  90060
agagtataag aaatttagca acgataaagg ctttcctaaa gaatatggtt ctggtaagat  90120
tgtgttatat aacggcgtta attatctaaa taatatctat tgtttggaat atattaatac  90180
acataatgaa gtgggtatta agtccgtggt tgtacctatt aagtttatag cagaattctt  90240
agttaatgga gaaatactta aacctagaat tgataaaacc atgaaatata ttaactcaga  90300
agattattat ggaaatcaac ataatatcat agtcgaacat ttaagagatc aaagcatcaa  90360
aataggagat atctttaacg aggataaact atcggatgtg ggacatcaat acgccaataa  90420
tgataaattt agattaaatc cagaagttag ttattttacg aataaacgaa ctagaggacc  90480
gttgggaatt ttatcaaact acgtcaagac tcttcttatt tctatgtatt gttccaaaac  90540
atttttagac gattccaaca aacgaaaggt attggcgatt gattttggaa acggtgcgga  90600
cctggaaaaa tacttttatg gagagattgc gttattggta gcgacggatc cggatgctga  90660
tgctatagct agaggaaatg aaagatacaa caaattaaac tctggaatta aaaccaagta  90720
ctacaaattt gactacattc aggaaactat tcgatccgat acatttgtct ctagtgtcag  90780
agaagtattc tattttggaa agtttaatat catcgactgg cagtttgcta tccattattc  90840
ttttcatccg agacattatg ctaccgtcat gaataactta tccgaactaa ctgcttctgg  90900
aggcaaggta ttaatcacta ccatggacgg agacaaatta tcaaaattaa cagataaaaa  90960
gacttttata attcataaga atttacctag tagcgaaaac tatatgtctg tagaaaaaat  91020
agctgatgat agaatagtgg tatataatcc atcaacaatg tctactccaa tgactgaata  91080
cattatcaaa aagaacgata tagtcagagt gtttaacgaa tacggatttg ttcttgtaga  91140
taacgttgat ttcgctacaa ttatagaacg aagtaaaaag tttattaatg gcgcatctac  91200
aatggaagat agaccgtcta caaaaaactt tttcgaacta aatagaggag ccattaaatg  91260
tgaaggttta gatgtcgaag acttacttag ttactatgtt gtttatgtct tttctaagcg  91320
gtaaataata atatggtatg ggttctgata tccccgttct aaatgcatta aataattcca  91380
atagagcgat ttttgttcct ataggacctt ccaactgtgg atactctgta ttgttaatag  91440
atatattaat acttttgtcg ggtaacagag gttctacgtc ttctaaaaat aaaagtttga  91500
taacatctgg cctgttcata aataaaaact tggcgattct atatatactc ttattatcaa  91560
atctagccat tgtcttatag atgtgagcta ctgtaggtgt accatttgat tttctttcta  91620
atactatata tttctctcga agaagttctt gcacatcatc tgggaataaa atactactgt  91680
tgagtaaatc agttattttt tttatatcga tattgatgga catttttata gttaaggata  91740
ataagtatcc caaagtcgat aacgacgata acgaagtatt tatactttta ggaaatcaca  91800
atgactttat cagatcaaaa ttaacaaaat taaaggagca tgtatttttt tctgaatata  91860
ttgtgactcc agatacatat ggatctttat gcgtcgaatt aaatgggtct agttttcagc  91920
acggtggtag atatatagag gtggaggaat ttatagatgc tggaagacaa gttagatggt  91980
gttctacatc caatcatata tctgaagata tgcacactga taaatttgtc atttatgata  92040
```

```
tttatacgtt tgattcgttc aagaataaac gattggtatt tgtacaggtg cctccatcat  92100
taggagatga tagctatttg actaatccgt tattgtctcc gtattatcgt aattcagtag  92160
ccagacaaat ggtcaatgat atgattttta atcaagattc atttttaaaa tatttattag  92220
aacatctgat tagaagccac tatagagttt ctaaacatat aacaatagtt agatacaagg  92280
ataccgaaga attaaatcta acgagaatat gttataatag agataagttt aaggcgtttg  92340
tattcgcttg gtttaacggc gtttcggaaa atgaaaaggt actagatacg tataaaaagg  92400
tatctaattt gatataatga attcagtgac tgtatcacac gcgccatata ctattactta  92460
tcacgatgat tgggaaccag taatgagtca attggtagag ttttataacg aagtagccag  92520
ttggctgcta cgagacgaga cgtcgcctat tcctgataag ttctttatac agttgaaaca  92580
accgcttaga aataaacgag tatgtgtgtg tggtatagat ccgtatccga aagatggaac  92640
tggtgtaccg ttcgaatcac caaattttac aaaaaaatca attaaggaga tagcttcatc  92700
tatatctaga ttaaccggag taattgatta taaaggttat aaccttaata taatagacgg  92760
ggttataccc tggaattatt acttaagttg taaattagga gaaacaaaaa gtcacgcgat  92820
ctactgggat aagatttcca agttactgct gcagcatata actaaacacg ttagtgttct  92880
ttattgtttg ggtaaaacag atttctcgaa tatacgggca aagttagaat ccccggtaac  92940
taccatagtc ggatatcatc cagcggctag agaccgccaa ttcgagaaag atagatcatt  93000
tgaaattatc aacgttttac tggaattaga caacaaggca cctataaatt gggctcaagg  93060
gtttatttat taatgcttta gtgaaatttt aacttgtgtt ctaaatggat gcaactatta  93120
gaggtaatga tgttatcttt gttcttaaga ctataggtgt cccgtcagcg tgcagacaaa  93180
atgaagatcc aagatttgta gaagcattta aatgcgacga gttagaaaga tatattgaga  93240
ataatccaga atgtacacta ttcgaaagtc ttagggatga ggaagcatac tctatagtca  93300
gaattttcat ggatgtagat ttagacgcgt gtctagacga aatagattat ttaacggcta  93360
ttcaagattt tattatcgag gtgtcaaact gtgtagctag attcgcgttt acagaatgcg  93420
gtgccattca tgaaaatgta ataaaatcca tgagatctaa tttttcattg actaagtcta  93480
caaatagaga taaaacaagt tttcatatta tctttttaga cacgtatacc actatggata  93540
cattgatagc tatgaaacga acactattag aattaagtag atcatctgaa aatccactaa  93600
ccagatcgat agacactgcc gtatatagga gaaaaacaac tcttcgggtt gtaggtacta  93660
ggaaaaatcc aaattgcgac actattcatg taatgcaacc accgcatgat aatatagaag  93720
attacctatt cacttacgtg gatatgaaca acaatagtta ttacttttct ctacaacgac  93780
gattggagga tttagttcct gataagttat gggaaccagg gtttatttca ttcgaagacg  93840
ctataaaaag agtttcaaaa atattcatta attctataat aaactttaat gatctcgatg  93900
aaaataattt tacaacggta ccactggtca tagattacgt aacaccttgt gcattatgta  93960
aaaaacgatc gcataaacat ccgcatcaac tatcgttgga aaatggtgct attagaattt  94020
acaaaactgg taatccacat agttgtaaag ttaaaattgt tccgttggat ggtaataaac  94080
tgtttaatat tgcacaaaga attttagaca ctaactctgt tttattaacc gaacgaggag  94140
accatatagt ttggattaat aattcatgga aatttaacag cgaagaaccc ttgataacaa  94200
aactaattct gtcaataaga catcaactac ctaaggaata ttcaagcgaa ttactctgtc  94260
cgaggaaacg aaagactgta gaagctaaca tacgagacat gttaatagat tcagtggaga  94320
ccgataccta tccggataaa cttccgttta aaaatggtgt attggacctg gtagacggaa  94380
tgttttactc tggagatgat gctaaaaaat atacgtgtac tgtatcaacc ggatttaaat  94440
```

```
ttgacgatac aaagttcgtc gaagacagtc cagaaatgga agagttaatg aatatcatta  94500
acgatatcca accattaacg gatgaaaata agaaaaatag agagttgtac gaaaaaactt  94560
tatctagttg tttatgcggt gctaccaaag gatgtttaac attctttttt ggagaaactg  94620
caactggaaa gtcgacaacc aaacgtttgt taaagtctgc tatcggtgac ctgtttgttg  94680
agacgggtca aacaatttta acagatgtat tggataaagg acctaatcca tttatcgcta  94740
acatgcattt gaaaagatct gtattctgta gcgaactacc tgattttgcc tgtagtggat  94800
caaagaaaat tagatctgac aatattaaaa agttgacaga accttgtgtc attggaagac  94860
cgtgtttctc caataaaatt aataatagaa accatgcgac aatcattatc gatactaatt  94920
acaaacctgt ctttgatagg atagataacg cattaatgag aagaattgcc gtcgtgcgat  94980
tcagaacaca cttttctcaa ccttctggta gagaggctgc tgaaaataat gacgcgtacg  95040
ataaagtcaa actattagac gaggggttag atggtaaaat acaaaataat agatatagat  95100
tcgcatttct atacttgttg gtgaaatggt acaaaaaata tcatgttcct attatgaaac  95160
tatatcctac accggaagag attccggact ttgcattcta tctcaaaata ggtactctgt  95220
tagtatctag ctctgtaaag catattccat taatgacgga cctctccaaa aagggatata  95280
tattgtacga taatgtggtt actcttccgt tgactacttt ccaacagaaa atatccaagt  95340
attttaattc tagactattt ggacacgata tagagagctt catcaataga cataagaaat  95400
ttgccaatgt tagtgatgaa tatctgcaat atatattcat agaggatatt tcatctccgt  95460
aaatatatgc tcatatattt atagaagata tcacatatct aaatgaatac cggaatcata  95520
gatttatttg ataatcatgt tgatagtata ccaactatat tacctcatca gttagctact  95580
ctagattatc tagttagaac tatcatagat gagaacagaa gcgtgttatt gttccatatt  95640
atgggatcag gtaaaacaat aatcgctttg ttgttcgcct tggtagcttc cagatttaaa  95700
aaggtttaca ttctagtgcc taatattaac attttgaaaa tttttaatta taatatgggt  95760
gtagctatga acttgtttaa tgacgaattc atagctgaga atatctttat tcattccaca  95820
acaagttttt attctcttaa ttataacgat aacgtcatta attataacgg attatctcgc  95880
tacaataact ctatttttat cgttgatgag gcacataata tctttgggaa taatactgga  95940
gaacttatga ccgtgataaa aaataaaaac aagattcctt ttttactatt gtctggatct  96000
cccattacta acacacctaa tactctgggt catattatag atttaatgtc cgaagagacg  96060
atagattttg gtgaaattat tagtcgtggt aagaaagtaa ttcagacact tcttaacgaa  96120
cgaggtgtga atgtacttaa ggatttgctt aaaggaagaa tatcatatta cgaaatgcct  96180
gataaagatc taccaacgat aagatatcac ggacgtaagt ttctagatac tagagtagta  96240
tattgtcaca tgtctaaact tcaagagaga gattatatga ttactagacg acagctatgt  96300
tatcatgaaa tgtttgataa aaatatgtat aacgtgtcaa tggcagtatt gggacaactt  96360
aatctgatga ataatttaga tactttattt caggaacagg ataaggaatt gtacccaaat  96420
ctgaaaataa ataatggcgt gttatacgga gaagaattgg taacgttaaa cattagttcc  96480
aaatttaaat actttattaa tcggatacag acactcaacg gaaaacattt tatatacttt  96540
tctaattcta catatggcgg attggtaatt aaatatatca tgctcagtaa tggatattct  96600
gaatataatg gttctcaggg aactaatcca catatgataa acggcaaacc aaaaacattt  96660
gctatcgtta ctagtaaaat gaaatcgtct ttagaggatc tattagatgt gtataattct  96720
cctgaaaacg atgatggcag tcaattgatg tttttgtttt cgtcaaacat tatgtccgaa  96780
```

```
tcctatactc tgaaagaggt aaggcatatt tggtttatga ctatcccaga tactttttct  96840
caatacaacc aaattcttgg acgatctatt agaaaattct cttacgccga tatttctgaa  96900
ccagttaatg tatatctttt agccgccgta tattccgatt tcaatgacga agtgacgtca  96960
ttaaacgatt acacacagga tgaattaatt aatgttttac catttgacat caaaaagctg  97020
ttgtatctaa aatttaagac taaagaaacg aatagaatat actctattct tcaagagatg  97080
tctgaaacgt attctcttcc accacatcca tcaattgtaa aagttttatt gggagaattg  97140
gtcagacaat ttttttataa taattctcgt attaagtata acgataccaa gttacttaaa  97200
atggttacat cagttataaa aaataaagaa gacgctagga attacataga tgatattgta  97260
aacggtcact tctttgtatc gaataaagta tttgataaat ctcttttata caaatacgaa  97320
aacgatatta ttacagtacc gtttagactt tcctacgaac catttgtttg gggagttaac  97380
tttcgtaaag aatataacgt ggtatcttct ccataaaact gatgagatat ataaagaaat  97440
aaatgtcgag ctttgttacc aatggatacc ttccagttac attggagcca cacgagctga  97500
cgttagacat aaaaactaat attaggaatg ccgtatataa gacgtatctc catagagaaa  97560
ttagtggtaa aatggccaag aaaatagaaa ttcgtgaaga cgtggaatta cctctcggcg  97620
aaatagttaa taattctgta gttataaacg ttccgtgtgt aataacctac gcgtattatc  97680
acgttgggga tatagtcaga ggaacattaa acatcgaaga tgaatcaaat gtaactattc  97740
aatgtggaga tttaatctgt aaactaagta gagattcggg tactgtatca tttagcgatt  97800
caaagtactg ctttttcga aatggtaatg cgtatgacaa tggcagcgaa gtcactgccg  97860
ttctaatgga ggctcaacaa ggtatcgaat ctagttttgt ttttctcgcg aatatcgttg  97920
actcataaaa aagagaatag cggtaagtat aaacacgaat actatggcaa taattgcgaa  97980
tgttttattc ccttcgatat atttttgata atatgaaaaa catgtctctc tcaaatcgga  98040
caaccatctc ataaaatagt tctcgcgcgc tggagaggta gttgctgctc gtataatctc  98100
cccagaataa tatacttgcg tgtcgtcgtt caatttatac ggatttctat agttctctgt  98160
tatataatgc ggttttccat catgattaga cgacgacaat agtgttctaa atttagatag  98220
ttgatcagaa tgaatgttta ttggcgttgg aaaaattatc catacagcgt ctgcagagtg  98280
gttgatagtt gttcctagat atgtaaaata atccaactta ctaggcagca aattgtctag  98340
ataaaatact gaatcaaacg gtgcagacgt attggtggat ctaatggaat ccaattgatt  98400
aactatcttt tgaaaatata catttttatg atccgatact tgtaagaata tagaaataat  98460
gataagtcca tcatcgtgtt tttttgcctc ttcataagaa ctatattttt tcttattcca  98520
atgaacaaga ttaatctctc cagagtattt gtacacatct atcaagtgat tggatccata  98580
atcgtcttcc tttccccaat atatacgtag tgatgataac acatattcat tggggagaaa  98640
ccctccactt atatatcctc ctttaaaatt aatccttact agttttccag tgttctggat  98700
agtggttggt ttcgactcat tataatgtat gtctaacggc ttcaatcgcg cgttagaaat  98760
tgctttttta gtttctatat taataggaga tagttgttgc ggcatagtaa aaatgaaatg  98820
ataactgttt aaaaatagct cttagtatgg gaattacaat ggatgaggaa gtgatatttg  98880
aaactcctag agaattaata tctattaaac gaataaaaga tattccaaga tcaaaagaca  98940
cgcatgtgtt tgctgcgtgt ataacaagtg acggatatcc gttaatagga gctagaagaa  99000
cttcattcgc attccaagcg atattatctc aacaaaattc agattctatc tttagagtat  99060
ccactaaact attacggttt atgtactaca atgaactaag agaaatcttt agacggttga  99120
gaaaaggttc tatcaacgat atcgatcctc actttgaaga gttaatatta ttgggtggta  99180
```

aactagataa aaaggaatct attaaagatt gtttaagaag agaattaaaa gaggaaagtg 99240
atgaacgtat aacagtaaaa gaatttggaa atgtaattct aaaacttaca acacgggata 99300
aattatttaa taaagtatat ataagttatt gcatggcgtg ttttattaat caatcgttgg 99360
aggatttatc gcatactagt atttacaatg tagaaattag aaagattaaa tcattaaatg 99420
attgtattaa cgacgataaa tacgaatatc tgtcttatat ttataatatg ctagttaata 99480
gtaaatgaac ttttacagat ctagtataat tagtcagatt attaagtata atagacgact 99540
agctaagtct attatttgcg aggatgactc tcaaattatt acactcacgg cattcgttaa 99600
ccaatgccta tggtgtcata aacgagtatc cgtgtccgct attttattaa ctactgataa 99660
caaaatatta gtatgtaaca gacgagatag ttttctctat tctgaaataa ttagaactag 99720
aaacatgtct agaaagaaac gattatttct gaattattcc aattatttgt ccaaacagga 99780
aagaagtata ctatcgtcat ttttttctct agatccagct actactgata atgatagaat 99840
agatgctatt tatccgggtg gcatacccaa aaggggtgag aatgttccag agtgtttatc 99900
cagggaaatt aaagaagaag ttaatataga caattctttt gtattcatag acactcggtt 99960
ttttattcat ggcatcatag aagataccat tattaataaa ttttttgagg taatcttctt 100020
tgtcggaaga atatctttaa cgagtgatca aatcattgat acatttaaaa gtaatcatga 100080
aatcaaggat ctaatatttt tagatccgaa ttcaggtaat ggactccaat acgaaattgc 100140
aaaatatgct ctagatactg caaaactcaa atgttatggc catagaggat gttattacga 100200
atcattaaaa aaattaactg aggatgattg attagaaaat ataaattaat ttaccatcgt 100260
gtatttttat aacgggattg tccggcatat catgtagata gttaccgtct acatcgtata 100320
ctcgaccatc tacgccttta aatcctctat ttattgacat taatctatta gaattggaat 100380
accaaatatt agtaccctca attagtttat tggtaatatt ttttttagac gatagatcga 100440
tggctcttga aaccaaggtt ttccaaccgg actcattgtc gatcggtgag aagtcttttt 100500
cattagcatg aatccattct aatgatgtat gtttaaacac tctaaacaat tggacaaatt 100560
cttttgattt gctttgaatg atttcaaata ggtcttcgtc tacagtaggc ataccattag 100620
ataatctagc cattataaag tgcacgttta catatctacg ttctggagga gtaagaacgt 100680
gactattgag acgaatggct cttcctacta tctgacgaag agacgcctcg ttccatgtca 100740
tatctaaaat gaagatatca ttaattgaga aaaaactaat accctcgcct ccactagaag 100800
agaatacgca tgttttaatg cattctccgt tagtgtttga ttcttggtta aactcagcca 100860
ccgccttgat tctagtatct tttgttctag atgagaactc tatattagag ataccaaaga 100920
ctttgaaata tagtaataag atttctattc ctgactgatt aacaaatggt tcaaagacta 100980
gacatttacc atgggatgct aatattccca aacatacatc tataaatttg acgcttttct 101040
cttttaattc agtaaataga gagatatcag ccgcactagc atccccttc aatagttctc 101100
ccttttttaaa ggtatctaat gcggatttag aaaactctct atctcttaat gaatttttaa 101160
aatcattata tagtgttgct atctcttgcg cgtattcgcc cggatcacga ttttgtcttt 101220
caggaaagct atcgaacgta aacgtagtag ccatacgtct cagaattcta aatgatgata 101280
tacctgtttt tatttcagcg agtttagcct tttgataaat ttcttcttgc tttttcgaca 101340
tattaacgta tcgcattaat actgttttct tagcgaatga tgcagaccct tctacgtcat 101400
caaaaataga aaactcgtta ttaactatgt acgaacatag gcctcctagt ttggagacta 101460
attctttctc atcaactaga cgtttattct caaatagcga ttggtgttgt aaggatcctg 101520
gtcgtagtaa gttaaccaac atggtgaatt cttgcacact attaacgata ggtgtagccg 101580
ataaacaaat catcttatgg ttttttaatg cgatggtctt agataaaaaa ttatatactg 101640
aacgagtagg acggatctta ccatcttctt tgattaatga tttagaaatg aagttatgac 101700
attcatcaat aatgacgcat attctactct tggaattaat agttttgata ttagtaaaaa 101760
atttatttct aaaattttga tcatcgtaat taataaaaat acaatccttc gttatctctg 101820
gagcgtatct gagtatagtg ttcatccaag gatcttctat caaagccttt ttcaccaata 101880
agataatagc ccaattcgta taaatatcct taagatgttt gagaatatat acagtagtca 101940
ttgttttacc aacacccgtt tcatggaaca ataaaagaga atgcatactg tctaatccta 102000
agaaaactct tgctacaaaa tgttgataat ccttgaggcg tactacgtct gttcccatca 102060
tttcaacagg catattagta gttctgcgca atgcataatc gatataggcc gcgtgtgatt 102120
tactcattta tgagtgataa gtaataacta tgttttaaaa atcacagcag tagtttaact 102180
agtcttctct gatgtttgtt ttcgatactt tttgaatcag aagtcatact agaataaagc 102240
aacgagtgaa cgtaatagag agcttcgtat actctattcg aaaactctaa gaacttatta 102300
atgaattccg tatccactgg attgtttaaa atactaaatt gaacactgtt cacatccttc 102360
caagaagaag acttagtgac ggacttaaca tgagacataa ataaatccaa atttttttta 102420
caaacatcac tagccaccat aatggcgcta tctttcaacc agctatcgct tacgcatttt 102480
agcagtctaa catttttaaa gagactacaa tatattctca tagtatcgat tacacctcta 102540
ccgaataaag ttggaagttt aataatacaa tatttttcgt ttacaaaatc aaataatggt 102600
cgaaacacgt cgaaggttaa catcttataa tcgctaatgt atagattgtt ttcagtgaga 102660
tgattattag atttaatagc atctcgttca cgtttgaaca gtttattgtg tgcgctgagg 102720
tcggcaacta cggcgtccgc tttagtactc ctcccataat actttacgct attaatcttt 102780
aaaatttcat agactttatc tagatcgctt tctggtaaca tgatatcatg tgtaaaaagt 102840
tttaacatgt cggtcggcat tctatttaga tcattaactc tagaaatctg aagaaagtaa 102900
ttagctccgt attccagact aggtaatggg cttttaccta aagacaagtt aagttctggc 102960
aatgtttcat aaaatggaag aaggacatgc gttccctccc ggatattttt tacaatttca 103020
tccatttaca actctatagt ttgttttcat tattattagt tattatctcc cataatcttg 103080
gtaatactta ccccttgatc gtaagatacc ttatacaggt cattacatac aactaccaat 103140
tgtttttgta cataatagat tggatggttg acatccatgg tggaataaac tactcgaaca 103200
gatagtttat ctttcccccct agatacattg gccgtaatag ttgtcggcct aaagaatatc 103260
tttggtgtaa agttaaaagt tagggttctt gttccattat tgctttttgt cagtagttca 103320
ttataaattc tcgagatggg tccgttctct gaatatagaa catcatttcc aaatctaact 103380
tctagtctag aaataatatc ggtcttattc ttaaaatcta ttcccttgat gaagggatcg 103440
ttaatgaaca aatccttggc ctttgattcg gctgatctat tatctccgtt atagacgtta 103500
cgttgactag tccaaagact tacaggaata gatgtatcga tgatgttgat actatgtgat 103560
atgtgagcaa agattgttct cttagtggca tcactatatg ttccagtaat ggcggaaaac 103620
tttttagaaa tgttatatat aaaagaattt tttcgtgttc caaacattag cagattagta 103680
tgaagataaa cactcatatt atcaggaaca ttatcaattt ttacatacac atcagcatct 103740
tgaatagaaa cgataccatc ttctggaacc tcaacaatct cggcagactc cggataacca 103800
gtcggtgggc catcactaac aataactaga tcatccaaca atctactcac atatgcatct 103860
atataatctt tttcatcttg tgagtaccct ggatacgaaa taaatttatt atccgtattt 103920
ccataataag gtttagtata aacagagagc gatgttgccg catgaacttc agttacagtc 103980
gccgttggtt ggtttatttg acctattact ctcctaggtt tctctataaa cgatggttta 104040
atttgtacat tcttaaccat atatccaata aagctcaatt caggaacata aacaaattct 104100
ttgttgaacg tttcaaagtc gaacgaagag tcacgaataa cgatatcgga tactggattg 104160
aaggttaccg ttacggtaat ttttgaatcg gatagtttaa gactgctgaa tgtatcttcc 104220
acatcaaacg gagttttaat ataaacgtat actgtagatg gttctttaat agtgtcatta 104280
ggagttaggc caatagaaat atcattaagt tcactagaat atccagagtg tttcaaagca 104340
attgtattat tgatacaatt attatataat tcttcgccct caatttccca aataacaccg 104400
ttacacgaag agatagatac gtgattaata catttatatc caacatatgg tacgtaaccg 104460
aatcttccca tacctttaac ttctggaagt tccaaactca gaaccaaatg attaagcgca 104520
gtaatatact gatccctaat ttcgaagcta gcgatagcct gattgtctgg accatcgttt 104580
gtcataactc cggatagaga aatatattgc ggcatataca aagttggaat ttgactatcg 104640
actgcgaaga cattagaccg tttaatagag tcatccccac cgatcaaaga attaatgata 104700
gtattattca ttttctattt aaaatggaaa aagcttacaa taaactccgt agagaaatat 104760
ctataatttg tgagttttcc ttaaagtaac agcttccgta aacgccgtct ttatctctta 104820
gtaggtttat tgtatttatg accttttcct tatcttcata gaatactaaa ggcaacaaag 104880
aaatttttgg ttcttctcta agagctacgt gagacttaac catagaagcc aacgaatccc 104940
tacatatttt agaacagaaa tacccaactt caccaccctt gaatgtctca atactaatag 105000
gtctaaaaac caaatcttga ttacaaaacc aacacttatc aattacacta tttgtcttaa 105060
tagacacatc tgccatagat ttataatact ttggtagtat acaagcgagt gcttcttctt 105120
tagcgggctt aaagactgct ttaggtgctg aaataaccac atctggaagg cttactcgct 105180
tagccattta attacggaac tatttttta tacttctaat gagcaagtag aaaacctctc 105240
atctacaaaa acatactcgt gtccataatc ctctaccata gttacacgtt ttttagatct 105300
catatgtgct aaaaagtttt cccatactaa ttggttacta ttatttttcg tataattttt 105360
aacagtttga ggttttagat ttttagttac agaagtgata tcgaatattt tatccaaaaa 105420
gaatgaataa ttaattgtct tagaaggagt gttttcttgg caaaagaata ccaagtgctt 105480
aaatatttct actacttcat taatcttttc tgtactcaga ttcagtttct catcttttac 105540
ttgattgatt atttcaaaga ctaacttata atccttttta tttattctct cgttagcctt 105600
aagaaaacta gatacaaaat ttgcatctac atcatccgtg gatatttgat ttttttccat 105660
gatatccaag agttccgaga taatttctcc agaacattga tgagacaata atctccgcaa 105720
tacatttctc aaatgaataa gtttattaga cacatggaag tttgactttt tttgtacctt 105780
tgtacatttt tgaaatacag actcgcaaaa aatacaatat tcatatcctt gttcagatac 105840
tataccgttg tgtctacaac cgctacataa tcgtagattc atgttaacac tctacgtatc 105900
tcgtcgtcca atattttata taaaaacatt ttatttctag acgttgccag aaaatcctgt 105960
aatattttta gtttttttggg ctgtgaataa agtatcgccc taatatggtt accgtcctcc 106020
gccaatatag tagttaaatt atccgcacat gcagaagaac accgcttagg cggattcagt 106080
acaatgttat atttttcgta ccaactcatt taaatatcat aatctaaaat agttctgtaa 106140
tatgtctagc gctaatatat tgatcataat cctgtgcata aattaagata caacaatgtc 106200
tcgaaatcat cgacatggct tcttccatag ttagaagatc gtcgtcaaag ttagcaacgt 106260

-continued

```
gattcatcaa catttgctgt tttgaggcag caaatactga accgtcgcca ttcaaccatt 106320
cataaaaacc atcgtctgaa tccattgata atttcttgta ctggtttttg agagctcgca 106380
tcaatctagc atttctagct cccggattga aaacagaaag aggatcgtac atccagggtc 106440
cattttctgt aaatagaatc gtataatgtc ccttcaagaa gatatcagac gatccacaat 106500
caaagaattg gtctccgagt ttgtaacaaa ctgcggactt taacctatac atgataccgt 106560
ttagcatgat ttctggtgat acgtcaatcg gagtatcatc tattagagat ctaaagccgg 106620
tgtaacattc tccaccaaac atattcttat tctgacgtcg ttctacataa aacatcattg 106680
ctccattaac gataacaggg gaatgaacag cactacccat cacattagtt cccaatggat 106740
caatgtgtgt aactccagaa catcttccat atcctatgtt aggaggagcg aacaccactc 106800
ttccactatt gccatcgaat gccatagaat aaatatcctt ggaattgata gaaatcggac 106860
tgtcggatgt tgtgatcatc ttcataggat taacaactat gtatggtgcc gcctgaagtt 106920
tcatatcgta actgatgccg tttataggtc tagccacaga aaccaacgta ggtctaaatc 106980
caactataga caaaatagaa gccaatatct gttcttcatc tgtcataact tgagagcatc 107040
cagtatgaat aatcttcatt agatggggat ctaccgcatc atcatcgtta caataaaaaa 107100
ttcccattct aatgttcata attgcttttc taatcatggt atgcatgttt gctctctgaa 107160
tctctgtgga aattagatct gatacacctg taatcactat cggattatcc tccgtaagac 107220
gattaaccaa caacatataa ttataagact ttacttttct aaattcataa agttgctgga 107280
ttaggctata ggtgtctcca tgtacatacg cgttctcgag cgcaggaagt ttaataccga 107340
atagtgccat cagaatagga tgaatatagt aattagtttc tggttttcta taaataaaag 107400
acaaatcttg tgaactagac atatcggtaa aatgcatgga ttggaatcgt gtagtcgaca 107460
gaagaatatg atgattagat ggagagtata ttttatctaa ctctttgagt tggtcaccga 107520
ttctaggact agctcgagaa tgaataagta ctaaaggatg agtacatttc acagaaacac 107580
tagcattgtt caatgtgctc tttacatggg taaggagttg aaatagctcg tttctatttg 107640
ttctgacaat atttagttta ttcataatgt taagcatatc ctgaatagta aagttagatg 107700
tgtcatactt gttagtagtt agatatttag caattgcatt cccatcattt ctcaatctcg 107760
tactccaatc atgcgtggat gctacttcgt cgatggaaac catacaatcc tttttgatag 107820
gctgttgaga ttgattattt cctgcacgtt taggtttggt acgttgattt ctagcccctg 107880
cggatataaa gtcatcgtct acaattttgg ataatgaatt gcatacacta caagacaaag 107940
atttatcaga agtgtgaata tgatcttcat ctaccaaaga aagagtttga ttagtataac 108000
tagattttag tcctgcgtta gatgttaaaa aaacatcgct attgaccacg gcttccatta 108060
tttatattcg tagtttttac tcgaaagcgt gattttaata ttcaatctta ttacttttgg 108120
aatcgttcaa aacctttgac taattgtaga atttgatcta ttgccctacg cgtatactcc 108180
cttgcatcat atacgttcgt caccagatcg tttgtttcgg cctgaagttg gtgcatatct 108240
ctttcaacat tcgacatgag atccttaagg gccatatcgt ctagattttg ttgagatgct 108300
gctcctggat ttggattttg ttgtgctgtt gtacatactg taccaccagt aggtgtagga 108360
gtacatacag tggccacaat aggaggttga ggaggtgtaa ccgttggagt agtacaagaa 108420
atacttccat ccgattgttg tgtacatgta gttgttggta acgtctgaga aggttgggta 108480
gatggcggcg tcgtcgtctt ttgatcttta ttaaatttag agataatatc ctgaacagca 108540
ttgctcggcg tcaacgctgg aaggagtgaa ctcgccggcg catcagtatc tgcagacagc 108600
caatcaaaaa gattagacat atcagatgat gtattagttt gttgtcgtgg ttttggtgta 108660
```

ggagccggtg tagctgttgg aaccggctgt ggagttatat gaatagttgg ttgtagcggt 108720
tggataggct gtctgctggc ggccatcata ttatctctag ctagttgttc tcgcaactgt 108780
ctttgataat acgactcttg agactttagt cctatttcaa tcgcttcatc ctttttcgta 108840
tccggatcct tttcttcaga ataatagatt gacgactttg gtgtagagga ttctgccagc 108900
ccctgtgaga acttgttaaa gaagtccatt taaggcttta aaattgaatt gcgattataa 108960
gattaaatgg cagacacaga cgatattatc gactatgaat ccgatgatct caccgaatac 109020
gaggatgatg aagaagagga agaagatgga gagtcactag aaactagtga tatagatccc 109080
aaatcttctt ataagattgt agaatcagca tccactcata tagaagatgc gcattccaat 109140
cttaaacata tagggaatca tatatctgct cttaaacgac gctatactag acgtataagt 109200
ctatttgaaa tagcgggtat aatagcagaa agctataact tgcttcaacg aggaagatta 109260
cctctagttt cagaattttc tgacgaaacg atgaagcaaa atatgctaca tgtaattata 109320
caagagatag aggagggttc ttgtcctata gtcatcgaaa agaacggaga attgttgtcg 109380
gtaaacgatt ttgacaaaga tggtctaaaa ttccatctag actatattat caaaatttgg 109440
aaacttcaaa aacgatatta gaatttatac gaatatcgtt ctctaaatgt cacaatcaag 109500
tctcgcatgt tcagcaattt attgtcgtac tttatatcgt gttcattaac gatatcttgc 109560
aaaatagtaa tgattctatc ttccttcgat agatattctt cagagattat tgtcttatat 109620
tctttcttgt tatcagatat gaatttgata agactttgaa cattattgat acccgtctgt 109680
ttaatttttt ctacagatat tttagttttg gcagattcta tcgtatctgt caatagacat 109740
ccaacatcga cattcgacgt caattgtcta taaatcaacg tataaatttt agaaataaca 109800
ttagcgaatt gttgtgcatt gatgtcgtta ttctgaaaca gtatgatttt aggtagcatt 109860
ttcttaacaa agagaacgta tttattgtta ctcagttgaa cagatgatat atccagatta 109920
ctaacgcatc tgattccata taccaaactt tcagaagaaa tggtgtacaa ttgtttgtat 109980
tcattcaatg tctcttttc agaaattagt ttagagtcga atactgcaat aattttcaag 110040
agatagtttt catcagataa gattttattt agtgtagata tgataaaact attgttttgt 110100
tggagaactt gatacgccgc gttctctgta gtcgacgctc tcaaatggga aacaatctcc 110160
attatttttt tggaatcgga tacaatatct tcggtatctt gacgcaatct agtatacata 110220
gagttaagag aaattagagt ttgtacatta agcaacatgt ctctaaatgt ggctgcaaac 110280
ttttcctttt ccacatcatc tagtttatta tataccgatt tcacaacggc accagattta 110340
aggaaccaga atgaaaaact ctgataacta caatatttca tcatagttac gattttatca 110400
tcttctatag ttggtgtaat agcgcatacc tttttctcca agactggaac caacgtcata 110460
aaaatgttta aatcaaaatc catatcaaca tctgatgcgc taagaccagt ctcgcgttca 110520
agattatctt tactaatggt gacgaactca tcgtatagaa ctctaagttt gtccattatt 110580
tatttacaga tttagttgtt taatttattt gtgctcttcc agagttggga tagtattttt 110640
ctaacgtcgg tattatatta ttaggatcta cgttcatatg tatcataata ttaatcatcc 110700
acgttttgat aaatctatct ttagcttctg aaataacgta tttaaacaaa ggagaaaaat 110760
atttagctac ggcatcagac gcaataacat tttttgtaaa tgtaacgtat ttagacgaca 110820
gatcttcgtt aaaaagtttt ccatctatgt agaatccatc ggttgttaac accattcccg 110880
cgtcagattg aataggagtt tgaatagttt gttttggaaa tagatccttc aataacttat 110940
agttgggtgg gaaaaaatcg attttatcac tagactcttt ctttttttact atcattacct 111000

-continued catgaactat ttcttgaatg agtatatgta ttttctttcc tatatcggac gcgttcattg 111060
gaaaatatac catgtcgtta actataagaa tatttttatc ctcgtttaca aactgaataa 111120
tatcagatgt agttcgtaaa cgaactatat catcaccagc acaacatcta actatatgat 111180
atccactagt ttcctttagt cgtttattat cttgttccat attagcagtc attccatcat 111240
ttaagaaggc gtcaaagata atagggagaa atgacatttt ggattctgtt acaactttac 111300
caaaattaag gatatacgga cttactatct ttttctcaac gtcgatttga tgaacacacg 111360
atgaaaatgt acttcgatga gattgatcat gtagaaaaca acaagggata caatatttcc 111420
acatatcatg aaatatatta agaaatccca ccttattata tttccccaaa ggatccatgc 111480
atgtaaacat tatgccgtta tcattaataa agacttcttt ctcatcggat ctgtaaaagt 111540
tgttactgat tttttcatt ccaggatcta gataattaat aatgatgggt tttctattct 111600
tattctttgt attttggcat atcctagacc agtaaacagt ttccactttg gtaaaatcag 111660
cagacttttg aacgctatta aacatggcat taatggcaat aactaaaaat gtaaaatatt 111720
tttctatgtt aggaatatgg tttttcactt taatagatat atggtttttg gccaaaatga 111780
tagatatttt tttatccgag gatagtaaaa tattattagt cgccgtctct ataaaaatga 111840
agctagtctc gatatccaat tttattctag aattgatagg agtcgccaaa tgtaccttat 111900
acgttatatc tcccttgatg cgttccattt gtgtatctat atcggacaca agatctgtaa 111960
atagttttac gttattaatc atcacggtat cgccgtcgct agataacgct aatgtaccat 112020
ccaagtccca aatggagaga tttaactgtt catcgtttag aataaaatga ttaccggtca 112080
tattaataaa gtgttcatcg tatctagata acaacgactt ataattaatg tccaagtctt 112140
gaactcgctg aatgatcttt tttaacccag ttagttttag attggtacga aatatattgt 112200
taaactttga ttctacagta atgtccaaat ctagttgtgg aaatacttcc atcaacattg 112260
tttcaaactt gataatatta ttatctacat cttcatacga tccaaattcc ggaatagatg 112320
tatcgcacgc tctggccacc cagataacca aaaagtcaca cgctccagga tatacattgt 112380
ataaaaagct atcgtttttt agtagtgttt ttttctgagt atatacgaag ggattaaaaa 112440
tagtattatc aacgtaacta tattccaaat tattcttatg agaatagata ataatatcgt 112500
ccttaatatc taacaaattt cctaaatatc cctttaattg agtcattcga agcgtcaata 112560
gaatatgtct cttaactatt tccggctgtt gtatatttaa atgacttcgt aaaaaaataat 112620
atatgggcga cttctcatct atgtaatcat atggagtgag atatagggct cgttctacct 112680
cctgcccctt acccacctgt aataccaatt gcggacttac tatatatcgc atatttatat 112740
cgtggggtaa agtgaaaatc tactaccgat gatgtaagtc ttacaatgtt cgaaccagta 112800
ccagatctta atttggaggc ctccgtagaa ctaggggagg taaatataga tcaaacaaca 112860
cctatgataa aggaaaatag cggttttata tcccgtagta gacgtctatt cgcccataga 112920
tctaaggatg atgagagaaa actagcacta cgattctttt tacaaagact ttattttta 112980
gatcatagag agattcatta tttgttcaga tgcgttgacg ctgtaaaaga cgtcactatt 113040
accaaaaaaa ataacattat cgtggcgcct tatatagcac ttttaactat cgcatcaaaa 113100
ggatgcaaac ttacagaaac aatgattgaa gcattctttc cagaactata taatgaacat 113160
agtaagaaat ttaaattcaa ctctcaagta tccatcatcc aagaaaaact cggataccag 113220
tttggaaact atcacgttta tgattttgaa ccgtattact ctacagtagc tctggctatt 113280
cgagatgaac attcatctgg catttttaat atccgtcaag agagttatct ggtaagttca 113340
ttatctgaaa taacatatag attttatcta attaatctaa aatctgatct tgttcaatgg 113400

-continued agtgctagta cgggcgctgt aattaatcaa atggtaaata ctgtattgat tacagtgtat 113460
gaaaagttac aactggtcat agaaaatgat tcacaattta catgttcatt ggctgtggaa 113520
tcaaaacttc caataaaatt acttaaagat agaaatgaat tatttacaaa attcatcaac 113580
gagttaaaaa agaccagttc attcaagata agcaaacgcg ataaggatac gctactaaaa 113640
tattttactt aggactggag ttagaattta tagacgactc atttcgttta tcattattag 113700
tattcttctt gttatcttgt tcagaaatat acagcaatgc tatgcctaat actaaataca 113760
ttatcatgct tgcaatggct ctaacaacga cgaaccaaaa tgaatttggt cgtagctttt 113820
gttcacaaaa atacataaag aaatgtctac ataaatctat ggcgccattg gctacttgaa 113880
atagcgccag tcctcctaca gattttaata tagctgtata acatgacatt tattcatcat 113940
caaaagagac agagtcacca tctgtcatat ttagattttt tttcatgtgt tcaaagtatc 114000
ctctactcat ttcattataa tagtttatca tacttagaat tttaggacgg atcaatgagt 114060
aagacttgac tagatcgtca gtagtaattt gtgcatcgtc tattctgcat ccgcttcgtc 114120
gaataatgta tagcatcgct ttgagattct ccatagctat caagtcttta tacaatgaca 114180
tggaaatatc tgtgaatact ttatacttct ccaacatcga tgccttaaca tcatcgccta 114240
ctttagcatt gaaaatacgt tctattgtgt agatggatgt agcaagattt ttaaacaaca 114300
atgccatttt acacgatgat tgcctcaagt ctccaatcgt ttgtttagaa cgattagcta 114360
cagagtccaa tgcttggctg actagcatat tattatcttt agaaattgta ttcttcaatg 114420
aggcgtttat catatctgtg atttcgttag tcatattaca gtctgactgg gttgtaatgt 114480
tatccaacat atcacctatg gatacggtac acgtaccagc atttgtaata atcctatcta 114540
agatgttgta tggcattgcg cagaaaatat cttctcctgt aatatttcca ctctcgataa 114600
atctactcag attattctta aatgccttat tctctggaga aaagatatca gtgtccatca 114660
tttcattaat agtatacgca gaaaagatac cacgagtatc aattctatcc aagatactta 114720
tcggttccga gtcacagata atggtttcct ctccttcggg agatcctgca tagaaatatc 114780
taggacaata gtttctatac tgtctgtaac tctgataatc tctaaagtca ctaactgata 114840
ccatgaaatt gagaagatca aacgctgaag taattaattt ttctgcctcg tttttactac 114900
aactagtttt catcaatgta gtgacgatgt attgtttagt tactcttggt ctaatactga 114960
tgatagagat attattactt cccataatgg atcttctagt agtcacctta aagcccattg 115020
atgcaaatag cagatagata aagtcttggt atgactcctt tctaatatag tacggactac 115080
ctttgtcacc caactttata cccacataag ccataacaac ctctttaata gccgtttcat 115140
gaggtttatc agccatgagc ctgagtagtt ggaagaatct catgaatcct gtctcagaaa 115200
gtcctatatg catgatagat ttatctttcc tgggaaactc tcgtatagtc atagatgaaa 115260
tactcttcaa agtttctgaa ataagattag taacagtctt acctccgact actctaggta 115320
acaaacaaac tctaataggt gttttctctg cggagataat atcagaaagg atagagcaat 115380
aagtagtatt attgtgatta taaagaccga atacataaca ggtagaattt ataaacatca 115440
tgtcctgaag gtttttagac ttgtattcct cgtaatccat accgtcccaa aacatggatt 115500
tggtaacttt gatagccgta gatctttgtt ccttcgccaa caggttaaag aaattaataa 115560
agaatttgtg gtttctacct atgtctacaa attgcacgtt tggaagcgcc acggttacat 115620
tcactgcagc attttgagga tcgcgagtat gaagtacgat gttattgttt actggtatat 115680
ctggaaagaa ttctaccagt ctaggaataa gagattgata tcgcatagaa atacaaaagt 115740

-continued tcataatctc atcatctaag agcattttgt taccattgta ataaatatcc actctgtcat 115800
atgtataaat gaagtactgt tcaaacatga tgagatgttt atatgttggc atagtagtga 115860
gatctacgtt tggtaatggc aatgtattaa gattaactcc ataatgtcta gcagcatctg 115920
cgatgttata agcgttgtca aagcggggtc gatcttgtgc tgttatatat tgtctaacac 115980
ctataagatt atcaaaatct tgtctgctta atacaccgtt aacaattttt gccttgaatt 116040
cttttattgg tgcattaata acatccttat agaggatgtt aaacaaataa gtgttatcaa 116100
agttaagatc tggatatttc ttttctgcta gaacatccat tgagtcggag ccatctggtt 116160
taatataacc accgataaat ctagctctgt attctgtatc cgtcaatcta atattaagaa 116220
ggtgttgagt gaaaggtgga agatcgtaaa agctgtgagt attaatgata ggattagttt 116280
ccgaactaat gttaattggg gtattaataa tatctatatt tccagcgtta agtgtaacat 116340
taaacagttt taattcacgt gacgtggtat caattaaata attaatgccc aatttggata 116400
tagcagcctg aagctcatct tgtttagtta cggatcctaa tgagttatta agcaatatat 116460
cgaacggatg aacgaaggtt gttttaagtt ggtcacatac tttgtaatct agacatagat 116520
gcggaagaac ggtagaaact atacgaaata aatattcaga gtcctctaat tgatcaagag 116580
taactattga cttaataggc atcatttatt tagtattaaa tgacgaccgt accagtgacg 116640
gatatacaaa acgatttaat tacagagttt tcagaagata attatccatc taacaaaaat 116700
tatgaaataa ctcttcgtca aatgtctatt ctaactcacg ttaacaacgt ggtagataga 116760
gaacataatg ccgccgtagt gtcatctcca gaggaaatat cctcacaact taatgaagat 116820
ctatttccag atgatgattc tccggccact attatcgaac gagtacaacc tcatactact 116880
attattgacg atactccacc tcctacgttt cgtagagagt tattgatatc ggaacaacgt 116940
caacaacgag aaaaaagatt taatattaca gtatcgaaaa atgctgaagc aataatggaa 117000
tctagatcta tgatatcttc tatgccaaca caaacaccat ccttgggagt agtttatgat 117060
aaagataaaa gaattcagat gttggaggat gaagtggtta atcttagaaa tcaacgatct 117120
aatacaaaat catctgataa tttagataat tttaccagaa tactatttgg taagactccg 117180
tataaatcaa cagaagttaa taagcgtata gccatcgtta attatgcaaa tttgaacggg 117240
tctcccttat cagtcgagga cttggatgtt tgttcagagg atgaaataga tagaatctat 117300
aaaacgatta aacaatatca cgaaagtaga aaacgaaaaa ttatcgtcac taacgtgatt 117360
attattgtca taaatattat cgagcaagca ttgctaaaac tcggatttga agaaatcaaa 117420
ggactgagta ccgatatcac ttcagaaatt atcgatgtgg agatcggaga tgactgcgat 117480
gctgtagcat caaaactagg aatcggtaac agtccggttc ttaatattgt attgtttata 117540
ctcaagatat tcgttaaacg aattaaaatt atttaattta atacattccc atatccagac 117600
aacaatcgtc tggattaatc tgttcctgtc gtctcatacc ggacgacata ttaatctttt 117660
tattagtagg catcttttta gatggtttct ttttcccagc attaactgag tcgataccta 117720
gaagatcgtg attgatctct ccgaccattc cacgaacttc taattggccg tctctgacgg 117780
taccataaac tattttacca gcattagtaa cagcttggac aatctgacca tccatcgcat 117840
tgtacgatgt agtagtaact gttgttctac gtctaggagc accagaagta tttttggagc 117900
ccttggatgt tgatgtagaa gaagacgagg attttgattt tggtttacat gtaatacatt 117960
ttgtatcaca tgcgccggca gtcacatctg tttgagaatt aagattattg ttgcctcctt 118020
tgacggctgc atctccaccg atttgcgcta gtagattttt aagctgtggt gtaatcttat 118080
taactgtttc gatataatca tcgtaactgc ttctaacggc taaatttttt ttatccgcca 118140
tttagaagct aaaaatattt ttatttatgc agaagattta actagattat acaatgaact 118200
aatatgatcc ttttccagat tatttacaaa cttggtattt tttggttctg gaggaggcga 118260
atttaaattc ggacttggat ttggattttg tgggttcttg atcttattat acagcgcata 118320
taggatggcg acggtaactg ctacgcaaat accgatcaac aaaagaatac caatcattta 118380
ttgacaataa cttcactatt gatcaagtat gcaatatatc atcttttcac taaataagta 118440
gtaataatga ttcaacaatg tcgagatata tggacgataa taatttagtt catggaaata 118500
tcgctatgat tggtatgaat gactccgcta actctgtggg gcgcgcagtg ctttccccac 118560
atagaataaa ttagcattcc gactgtgata ataataccaa gtataaacgc cataatactc 118620
aatactttcc atgtacgagt gggactggta gacttactaa agtcaataaa ggcgaagata 118680
cacgaaagaa tcaaaagaat gattccagcg attagcacgc cggaaaaata atttccaatc 118740
ataagcatca tatccattta actaataaaa attttaaatc gccgaatgaa caaagtggaa 118800
tataaaccat ataaaaacaa tagtttgtac tgcaaaaata atatctattt ttgttttcga 118860
agatatggta aaattaaata gtagtacaca gcatgttata actaacagca gcaacggctc 118920
gtaattactt atcatttact agacgaaaag gtggtgggat attttcttgc tcaaataata 118980
cgaatatatc acccatccat tttatgcgat gtttatatac tctaatcttt aatagatcta 119040
tagacgacgg gtttaccaac aatatagatt ttatcgattc atctaattta aacccttcct 119100
taaacgtgaa tgatctatta tctggcataa cgatgactct acccgatgaa tcggacaatg 119160
tactgggcca tgtagaataa attatcaacg aattatcgtc tacgaacatt tatatcattt 119220
gttttaattt tagtacgcga ataaatagat ataaaataga aaataacaga tattacaacc 119280
aatgttatgg ccgcgcccaa ccaggtaggc agttttattt tatcttttac tacaggttct 119340
cctggatgta cgtcaccaac ggcggacgta gttctagtac aattagacgt aagttccgct 119400
tgggaatttt ttaacgctaa agagttaacg ttaatcgtgc acccaacgta tttacatcta 119460
gttctttgaa catcttgatt ataatataac cattttctat ctctagattc gtcggtgcac 119520
tcatgtaacc aacataccct aggtcctaaa tatttatctc cggaattaga ttttggataa 119580
ttcgcgcacc aacaatttct atttccttta tgatcgttac aaaagacgta taatgccgta 119640
tccccaaaag taaaataatc aggacgaata attctaataa actcagaaca atatctcgca 119700
tccatatgtt tggagcaaat atcggaataa gtagacatag ccggtttccg ttttgcacgt 119760
aaccattcta aacaattggg gtttccagga tcgtttctac aaaatccagt catgaaatca 119820
tcacaatgtt ctgtcttgta attattatta aatattttttg gacagtgttt ggtatttgtc 119880
ttagaacaac attttgccac gctatcacta tcgcccagga gataatcctt ttttataaaa 119940
tgacatcgtt gcccggatgc tatataatca gtagcgtgtt ttaaatcctt aatatattca 120000
ggagttacct cgttctgata atagattaat gatccaggac gaaatttgaa agaactacat 120060
ggttctccat gaattaatac atattgttta gcaaattcag gaactataaa actactacaa 120120
tgatctatcg acataccatc tatcaaacaa aacttgggtt taatttctcc cggagatgtt 120180
tcataatagt acgtataact ttcttctgca aacttaacag ctctattata ttcaggataa 120240
ttaaaaccta attccatata tttgtctcgt atatctgcta ttcctggtgc tattttgatt 120300
ctattaagag taacggctgc ccccattttt aataatcgtc agtatttaaa ctgttaaatg 120360
ttggtatatc aacatttacc ttatttcccg cagtataagg tttgttgcag gtatactgtt 120420
caggaatggt tacatttata ctttttctat agtcctgtct ttcgatgttc atcacatatg 120480

-continued caaagaacag aataaacaaa ataatgtaag aaataatatt aaatatctgt gaattcgtaa 120540
atacattgat tgccataata attacagcag ctacaataca tacaatagac attcccacag 120600
tgttgccatt acctccacga tacatttgag ttactaagca ataggtaata actaagctag 120660
taagaggcaa tagaaaagat gagataaata tcatcaatat agagattaga ggagggctat 120720
atagagccaa gacgaacaaa atcaaaccga gtaacgttct aacatcatta tttttgaaga 120780
ttcccaaata atcattcatt cctccataat cgttttgcat catacctcca tctttaggca 120840
taaacgattg ctgctgttcc tctgtaaata aatctttatc aagcactcca gcacccgcag 120900
agaagtcgtc aagcatattg taatatctta aataactcat ttatatatta aaaaatgtca 120960
ctattaaaga tggagtataa tctttatgcc gaactaaaaa aaatgacttg tggtcaaccc 121020
ctaagtcttt ttaacgaaga cggggatttc gtagaagttg aaccgggatc atcctttaag 121080
tttctgatac ctaagggatt ttacgcctct ccttccgtaa agacgagtct agtatttgaa 121140
acattaacaa cgaccgataa taaaattact agtatcaatc caacaaatgc gccaaagtta 121200
tatcctcttc aacgcaaagt cgtatctgaa gtagtttcta atatgaggaa aatgatcgaa 121260
tcaaaacgtc ctctatacat cactcttcac ttggcgtgtg gatttggtaa gactattacc 121320
acgtgttatc ttatggctac acacggtaga aaaaccgtca tttgcgtacc caataaaatg 121380
ttaatacatc aatggaagac acaggtagag gcagtcggat tggaacataa gatatccata 121440
gatggagtaa gtagtctatt aaaggaacta aagactcaaa gtccggatgt attaatagta 121500
gtcagtagac atctgacaaa cgatgccttt tgtaaatata tcaataagca ttatgatttg 121560
ttcatcttgg atgaatcaca tacgtataat ctgatgaaca atacagcagt tacaagattt 121620
ttagcgtatt atcctccgat gatgtgttat tttttaactg ctacacctag accatctaac 121680
agaatttatt gtaacagtat tattaatatt gccaagttat ccgatctaaa aaaaactatc 121740
tatgcagtag atagtttttt tgagccatat tccacagata atattagaca tatgataaaa 121800
cgattagatg gaccatctaa taaatatcat atatataccg agaagttatt atctgtagac 121860
gagcctagaa atcaacttat tcttaatacc ctggtagaag aattcaagtc aggaactatt 121920
aatcgcattt tagttattac taaactacgt gaacatatgg tattcttcta caaacgatta 121980
ttagattttt tcggatcaga ggttgtattt ataggagacg cccaaaatag acgtactcca 122040
gatatggtca aatcaatcaa ggaactaaat agatttatat tcgtatccac cttattttat 122100
tccggtactg gtttagatat tcctagtttg gattctttgt tcatttgctc ggcagtaatc 122160
aacaatatgc aaatagagca attactaggg agggtatgtc gagaaacaga actattagat 122220
aggacggtat atgtatttcc tagcacatcc atcaaagaaa taaagtacat gataggaaat 122280
ttcgttcaac gaattattag tctgtctgta gataaactag gatttaaaca aaaaagttat 122340
cggaaacatc aagaatccga tcccacttct gtatgtacaa catcctccag agaagaacgt 122400
gtattaaata gaatatttaa ctcgcaaaat cgttaagaag tttaagcgac gatccgcatg 122460
ctgcgcaggc cagtgtatta cccctcatag tattaatata atccaatgat acttttgtga 122520
tgtcggaaat cttaaccaat ttagactgac aggcagaaca cgtcatgcaa tcatcatcgt 122580
catcgataac tgtagtcttg ggcttctttt tgcggctctt cattccggaa cgcacattgg 122640
tgctatccat ttaggtagta aaaaataagt cagaatatgc cctatagcac gatcgtgcaa 122700
aacctggtat atcgtctcta tctttatcac aatatagtgt atcgacatct ttattattat 122760
tgacctcgtt tatcttggaa catggaatgg gaacattttt gttatcaacg gccacctttg 122820
ccttaattcc agatgttgta aaattataac taaacagtct atcatcgaca caaatgaaat 122880
tcttgtttag acgtttgtag tttacgtatg cggctcgttc gcgtctcatt ttttcagata 122940
ttgcaggtac tataatatta aaaataagaa tgaaataaca taggattaaa aataaagtta 123000
tcatgacttc tagcgctgat ttaactaact taaaagaatt acttagtctg tacaaaagtt 123060
tgaaattttc agattctgcg gctatagaaa agtataattc tttggtagaa tggggaacat 123120
ctacttactg gaaaataggc gtgcaaaagg tagctaatgt cgagacgtca atatctgatt 123180
attatgatga ggtaaaaaat aaaccgttta atattgatcc gggctattac attttcttac 123240
cggtatattt tgggagcgtc tttatttatt cgaagggtaa aaatatggta gaacttggat 123300
ctggaaactc ttttcaaata ccagatgata tgcgaagtgc gtgtaacaaa gtattagaca 123360
gcgataacgg aatagacttt ctgagatttg ttttgttaaa caatagatgg ataatggaag 123420
atgctatatc aaaatatcag tctccagtta atatatttaa actagctagt gagtacggat 123480
taaacatacc caaatattta gaaattgaaa tagaggaaga cacattattt gacgacgagt 123540
tatactctat tatagaacgc tctttcgatg ataaatttcc aaaaatatcc atatcgtata 123600
ttaagttggg agaacttagg cggcaagttg tagacttttt caaattctca ttcatgtata 123660
ttgagtccat caaggtagat cgtataggag ataatatttt tattcctagc gttataacaa 123720
aatcaggaaa aaagatatta gtaaaagatg tagaccattt aatacgatcc aaggttagag 123780
aacatacatt tgtaaaagta aaaaagaaaa acacattttc cattttatac gactatgatg 123840
gaaacggaac agaaactaga ggagaagtaa taaaacgaat tatagacact ataggacgag 123900
actattatgt taacggaaag tatttctcta aggttggtag tgcaggctta aagcaattga 123960
ctaataaatt agatattaat gagtgcgcaa ctgtcgatga gttagttgat gagattaata 124020
aatccggaac tgtaaaacga aaaataaaaa accaatcagc atttgattta agcagagaat 124080
gtttgggata tccagaagcg gattttataa cgttagttaa taacatgcgg ttcaaaatag 124140
aaaattgtaa ggttgtaaat ttcaatattg aaaatactaa ttgtttaaat aacccgagta 124200
ttgagactat atatggaaac tttaaccagt tcgtctcaat ctttaatatc gtcaccgatg 124260
tcaaaaaaag attattcgag tgaaataata tgcgcctttg atataggtgc aaaaaatcct 124320
gccagaactg ttttagaagt caaggataac tccgttaggg tattggatat atcaaaatta 124380
gactggagtt ctgattggga aaggcacata gctaaagatt tgtcacaata tgaatacact 124440
acagttcttc tagaacgtca gcctagaagg tcgccgtacg tcaaatttat ctattttatt 124500
aaaggctttt tatatcatac atcggctgcc aaagttattt gcgtctcgcc tgtcatgtct 124560
ggtaattcat atagagatcg aaaaaagaga tcggtcgaag catttcttga ttggatggac 124620
acattcggat tgcgagactc cgttccggat agacgcaaat tagacgatgt agcggatagt 124680
ttcaatttgg ctatgagata cgtattagat aaatggaata ctaattatac accttataat 124740
aggtgtaaat ctagaaatta cataaaaaaa atgtaataac gttagtaacg ccattatgga 124800
taatctattt acctttctac atgaaataga agatagatat gccagaacta tttttaactt 124860
tcatctaata agttgcgatg aaataggaga tatatatggt cttatgaaag aacgcatttc 124920
ctcagaggat atgtttgata atatagtgta taataaagat atacatcatg ccattaagaa 124980
actagtgtat tgcgacatcc aacttactaa acacattatt aatcagaata cgtatccggt 125040
atttaacgat tcttcacaag tgaaatgttg tcattatttc gatataaact cagataatag 125100
caatattagc tctcgtacag tagagatatt tgagagggaa aagtcatctc ttgtatcata 125160
tattaaaact accaataaga agagaaaggt caattatggg gaaataaaga aaactgtaca 125220

-continued tggaggcact aatgcaaatt acttttccgg taaaaagtct gatgagtatc tgagcactac 125280
agtcaggtcc aacattaatc aaccttggat caaaaccatt tctaagagaa tgagagtaga 125340
tatcattaat cactctatag taacgcgtgg aaaaagctct atattacaaa ctatagaaat 125400
tatttttact aatagaacat gtgtgaaaat attcaaggat tctactatgc acattattct 125460
atccaaggac aaggatgaaa aggggtgtat acacatgatt gacaaattat tctatgtcta 125520
ttataattta tttctgttgt tcgaggatat catccaaaac gagtacttta aagaagtagc 125580
taatgttgta aaccacgtac tcacggctac ggcattagat gagaaattat tcctaattaa 125640
gaaaatggct gaacacgatg tttatggagt tagcaatttc aaaataggga tgtttaacct 125700
gacatttatt aagtcgttgg atcataccgt tttcccctct ctgttagatg aggatagcaa 125760
aataaagttt tttaagggga aaaagctcaa tattgtagca ttacgatctc tggaggattg 125820
tataaattac gtgactaaat ccgagaatat gatagaaatg atgaaggaaa gatcgactat 125880
tttaaatagc atagatatag aaacggaatc ggtagatcgt ctaaaagaat tgcttctaaa 125940
atgaaaaaaa aacactaatt cagaaatgga tcaacgactc ggatataagt ttttggtgcc 126000
tgatcctaaa gccggagttt tttatagacc gttacatttc caatatgtat cgtattctaa 126060
ttttatattg catcgattgc atgaaatctt gaccgtcaag cggccactct tatcgtttaa 126120
gaataataca gaacgaatta tgatagaaat tagcaatgtt aaagtgactc ctccagatta 126180
ctcacctata atcgcgagta ttaaaggtaa gagttatgac gcattagcca cgttcactgt 126240
aaatatcttt aaagaggtaa tgaccaaaga gggtatatcc atcactaaaa taagtagtta 126300
tgagggaaaa gattctcatt tgataaaaat tccgctacta ataggatacg ggaataaaaa 126360
tccacttgat acagccaagt atcttgttcc taatgtcata ggtggagtct ttatcaataa 126420
acaatctgtc gaaaaagtag gaattaatct agtagaaaag attacaacat ggccaaaatt 126480
tagggttgtt aagccaaact cattcacttt ctcgttttcc tccgtatccc ctcctaatgt 126540
attaccgaca agatatcgcc attacaagat atctctggat atatcacaat tggaagcgtt 126600
gaatatatca tcgacaaaga catttataac ggtcaatatt gttttgctgt ctcaatattt 126660
atctagagtg agtctagaat tcattagacg tagtttatca tacgatatgc ctccagaagt 126720
tgtctatcta gtaaacgcga taatagatag tgctaaacga attactgaat ctattactga 126780
ctttaatatt gatacataca ttaatgacct ggtggaagct gaacacatta aacaaaaatc 126840
tcagttaacg atcaacgagt tcaaatatga aatgctgcat aactttttac ctcatatgaa 126900
ctatacaccc gatcaactaa agggatttta tatgatatct ttactaagaa agtttctcta 126960
ctgtatctac cacacttcta gatatccaga tagagattcg atggtttgtc atcgcatcct 127020
aacgtacggc aaatatttg agacgttggc acatgatgaa ttagagaatt acataggcaa 127080
catccgaaac gatatcatga acaatcacaa gaacagaggc acttacgcgg taaacattca 127140
tgtactaaca actcctggac ttaatcatgc attttctagt ctattgagtg gaaagttcaa 127200
aaagtcagac ggtagttatc gaacacatcc tcactattca tggatgcaga atatttctat 127260
tcctaggagt gttggatttt atccggatca agtaaagatt tcaaagatgt tttctgtcag 127320
aaaataccat ccaagtcaat atctttactt ttgttcatcg gacgttccgg aaagaggtcc 127380
tcaggtaggt ttagtatctc aattgtctgt cttgagttcc attacaaata tactaacgtc 127440
tgagtatttg gatttggaaa agaaaatttg tgagtatatc agatcatatt ataaagatga 127500
tataagttac tttgaaacag gatttccaat cactatagaa aatgctctag tcgcatctct 127560
taatccaaat atgatatgtg attttgtaac tgactttaga cgtagaaaac ggatgggatt 127620
cttcggtaac ttggaggtag gtattacttt agttagggat cacatgaatg aaattcgcat 127680
taatattgga gcgggaagat tagtcagacc attcttggtt gtggataacg gagagctcat 127740
gatggatgtg tgtccggagt tagaaagcag attagacgac atgacattct ctgacattca 127800
gaaagagttt ccgcatgtca tcgaaatggt agatatagaa caatttactt ttagtaacgt 127860
atgtgaatcg gttcaaaaat ttagaatgat gtcaaaggat gaaagaaagc aatacgattt 127920
atgtgacttt cctgccgaat ttagagatgg atatgtagca tcttcactag tgggaatcaa 127980
tcacaattct ggacccagag ctattcttgg atgtgctcaa gctaaacaag ctatctcttg 128040
tctgagctcg gatatacgaa ataaaataga caatggaatt catttgatgt atccagagag 128100
gccaatcgtg attagtaagg ctttagaaac ttcaaagatt gcggctaatt gcttcggcca 128160
acatgttact atagcattaa tgtcgtacaa aggtatcaat caagaggatg gaattatcat 128220
caaaaaacaa tttattcaga gaggcggtct cgatattgtt acagccaaga aacatcaagt 128280
agaaattccg ttggaaaact ttaataacaa agaaaagagat aggtctaacg cctattcaaa 128340
attagaaagt aatggattag ttagactgaa tgctttcttg gaatccggag acgctatagc 128400
acgaaatatc tcatcaagaa ctcttgaaga tgattttgct agagataatc agattagctt 128460
tgatgtttcc gaaaaatata ccgatatgta caaatctcgc gttgaacgag tacaagtaga 128520
acttactgac aaagttaagg tacgagtatt aaccatgaaa gaaagaagac ccattctagg 128580
agacaaattt accactagaa cgagtcaaaa gggaacagtc gcgtatatcg cggatgaaac 128640
ggaacttcca tacgatgaaa atggtatcac accagatgtc attattaatt ctacatccat 128700
cttctctaga aaaactatat ctatgttgat agaggttatt ttaacagccg catattctgc 128760
taagccgtac aacaataagg gagaaaaccg acctgtctgt tttcctagta gtaacgaaac 128820
atccatcgat acatatatgc aattcgctaa acaatgttat gagcattcaa atccgaaatt 128880
gtctgatgaa gaattatcgg ataaaatctt ttgtgaaaag attctctatg atcctgaaac 128940
ggataagcct tatgcatcca aagtattttt tggaccaatt tattacttgc gtctgaggca 129000
tttaactcag gacaaggcaa ccgttagatg tagaggtaaa aagacgaagc tcattagaca 129060
ggcgaatgag ggacgaaaac gtggaggagg tatcaagttc ggagaaatgg agagagactg 129120
tttaatagcg catggtgcag ccaatactat tacagaagtt ttgaaagatt cggaagaaga 129180
ttatcaagat gtgtatgttt gtgaaaattg tggagacata gcagcacaaa tcaagggtat 129240
taatacatgt cttagatgtt caaaacttaa tctctctcct ctcttaacaa aaattgatac 129300
cacgcacgta tctaaagtat ttcttactca aatgaacgcc agaggcgtaa aagttaaatt 129360
agatttcgaa cgaaggcctc cttcgtttta taaaccatta gataaagttg atctcaaacc 129420
gtcttttctg gtgtaatatt ctagtttggt agtagataca tatcaatatc atcaaattcg 129480
agatccgaat tataaaatgg gcgtggattg ttaactatag aatcggacgt ctgatattcg 129540
aaaatctgtg gagttttagg ttttggtgga ggtgtaactg ctacttggga tactgaagtc 129600
tgatattcag aaagctgggg gatgttctgg ttcgacatcc accgatggtg tcacatcact 129660
aatcggttcg gtaacgtctg tggacgatgg aggcaccact tctacaggtt ctggttcttt 129720
atcctcagtc atcaacggag ctacttcaat gcgaggaaat gtataatttg gtaatggttt 129780
ctcatgtgga tctgaagaag aggtaagata tctactagaa agataccgat cacgttctag 129840
ttctcttttg tagaacttaa ctttttcttt ctccgcatct agttgatatt ccaacctctt 129900
cacgttcgca tgggttacct ccgcagtttt tacgagcgat ttcacgttca gccttcatgc 129960
gtcttatagc atgaattcgc ttatcgttat cgggtttagc ttctgtcacc ttagcaattc 130020
ctttttttatt aaactctaca taatcatatc catttctatt gtttgttcta atataaacga 130080
gtatagcatc attgctaaat ttttcaatag tatcgaaaac agaatatcct aaaccatata 130140
atatatattc aggaacactc aaactaaatg tccaggattc tcctaaatac gtaaacttta 130200
atagtgcgaa atcattcaaa aatctaccac ttatagatag atagatagta cataaatgcg 130260
tatagtagtc tacctatctc tttattatga aaaccggcat tacgatcata tatgtcgtga 130320
tatacctgtg atccgtttac gttaaaccat aaatacatgg gtgatcctat aaacatgaat 130380
ttatttctaa ttctcagagc tatagttaat tgaccgtgta atatttgctt acatgcatac 130440
ttgatacgat cattaataag atttttatca ttgctcgtta tttcagaatc gtatatataa 130500
ggagtaccat cgtgattctt accagatatt atacaaaata ctatatataa aatatattga 130560
cccacgttag taatcatgta aatgtttaac gttttaaatt ttgtattcaa tgatccatta 130620
tcatacgcta gcatggtctt atgatattca ttctttaaaa tataatattg tgttagccat 130680
tgcattgggg ctcctaatgg agatttttta ttctcatcca ttttaggata ggctttcata 130740
aagtccctaa taacttcgtg aataatgttt ctatgttttc tactgatgca tgtatttgct 130800
tcgatttttt tatcccatgt ttcatctatc atagatttaa acgcagtaat gctcgcaaca 130860
ttaacatctt gaaccgttgg tacaattccg ttccataaat ttataatgtt cgccatttat 130920
ataactcatt ttttgaatat acttttaatt aacaaaagag ttaagttact catatggacg 130980
ccgtccagtc tgaacatcaa tctttttagc cagagatatc atagccgctc ttagagtttc 131040
agcgtgattt tccaacctaa atagaacttc atcgttgcgt ttacaacact tttctatttg 131100
ttcaaacttt gttgttacat tagtaatctt tttttccaaa ttagttagcc gttgtttgag 131160
agtttcctca ttgtcgtctt catcggcttt aacaattgct tcgcgtttag cctctggctt 131220
tttagcagcc gttgtagaaa aaaattcagt tgctggaatt gcaagatcgt catctccggg 131280
gaaaagagtt ccgtccattt aaagtacaga ttttagaaac tgacactctg cgttatttat 131340
atttggtaca acacatggat tataaatatt gatgttaata acatcagaaa atgtaaagtc 131400
tatacattgt tgcatcgtgt taaattttct aatggatcta gtattattgg gtccaacttc 131460
tgcctgaaat ccaaatatgg aagcggatac aaaaccgttt cctggataaa ccacacatct 131520
ccacttttgc tttacatcag aaattgtgtc gttgacatct tgaactctcc tatctaatgc 131580
cggtgttcca cctatagatt ttgaatattc gaatgctgca tgagtagcat taaattcctt 131640
aatattgcca taattttcat atattgagta accctggata aaaagtaaac acaccgcagc 131700
cgtagctacc acaataaaaa aaattgatag agagttcatt tataatctat tagaagctga 131760
caaaattttt ttacacgcat cagacaatgc tttaataaat agttcaacat ctacttttgt 131820
catatcgaac cgatggtatg attctaacct agaattacat ccgaaaaagt tgactatgtt 131880
catagtcatt aagtcattaa caaacaacat tccagactct ggattataag acgatactgt 131940
ttcgtcacaa ttacctacct taatcatgtg attatgaata ttggctatta gagcaccttc 132000
taagaaatct ataatatctt tgaaacacga tttaaaatca aaccacgaat atacttctac 132060
gaagaaagtt agtttaccca taggagaaat aactataaat ggagatctaa atacaaaatc 132120
cggatctatg atagttttaa cattattata ttctctatta aatacctcca catctaaaaa 132180
tgttaatttt gaaactatgt cttcgtttat taccgtacct gaactaaacg ctataagctc 132240
tattgtttga gaactcttta aacgatattc ttgaaataca tgtaacaaag tttcctttaa 132300
ctcggtcggt ttatctacca tagttacaga atttgtatcc ttatctataa tataataatc 132360
aaaatcgtat aaagttatat aattatcgcg ttcagattgg gatcttttca aatagactaa 132420
aaaccccatt tctctagtaa gtatcttatg tatatgtttg taaaatatct tcatggtggg 132480
aatatgctct accgcagtta gccattcctc attgacagcg gtagatgtat tagacaaaac 132540
tattccaatg tttaacaagg gccattttac gagattatta aatccttgtt tgataaatgt 132600
agccaatgag ggttcgagtt caacgacgat tgaattctct tcccgcggat gctgcatgat 132660
gaacgacggg atgttgttcg attgatttgg aattcttttt cgactttttg tttatattaa 132720
atattttaaa atttatagcg gatagcaatt catgtaccac ggataatgta gacgcgtatt 132780
gcgcatcgat atctttatta ttagataaat ttatcaataa atgtgagaag tttgcctcgt 132840
taaggtcttc catttaaata ttatataaac atttgtgttt gtatcttatt cgtcttttat 132900
ggaatagttt tttactagta aagctgcaat tacacacttt gtccgtaaaa cataaatata 132960
aacaccagct tttatcaatc gttccaaaaa gtcgacggcg gacattttta acatggcatc 133020
tattttaaat acacttaggt ttttggaaaa aacatcattt tataattgta acgattcaat 133080
aactaaagaa aagattaaga ttaaacataa gggaatgtca tttgtatttt ataagccaaa 133140
gcattctacc gttgttaaat acttgtctgg aggaggtata tatcatgatg atttggttgt 133200
attggggaag gtaacaatta atgatctaaa gatgatgcta ttttacatgg atttatcata 133260
tcatggagtg acaagtagtg gaacaattta caaattggga tcgtctatcg atagactttc 133320
tctaaatagg actattgtta caaaagttaa taattataat tatgatacat tttttgacga 133380
tgatgattga tcgctattgc acaattttgt ttttttactt tctaatatag cgtttagatt 133440
ctttttcatg tgcgaatatt gatttactaa aatatctatg tttaactttt gttctataac 133500
gtccttatcg gcggtatcgg tacatatacg taattcacct tcacaaaata cggagtcttc 133560
gataataata gccaatcgat tattggatct agctgtctgt atcatattca acatgtttaa 133620
tatatccttt cgtttcccct ttacaggcat cgatcgtagc atattttccg cgtctgagat 133680
ggaaatgtta aaactacaaa aatgcgtaat gttagcccgt cctaatattg gtacgtgtct 133740
ataagtttgg catagtagaa taatagacgt gtttaaatgc cttccaaagt ttaagaattc 133800
tattagagta ttgcattttg atagtttatc gcctacatca tcaaaaataa gtaaaaagtg 133860
tgctgatttt ttatgatttt gtgcgacagc aatacatttt tctatgttac ttttagttcg 133920
tatcagatta tattctagag attcctgact actaacgaaa ttaatatgat ttggccaaat 133980
gtatccatca taatctggat tataaacggg tgtaaacaag aatacatgtt tatatttttt 134040
aactagtgta gaaaacagag atagtaaata gatagttttt ccagatccag atcctcccgt 134100
taaaaccatt ctaaacggca tttttaataa attttctctt gaaaattgtt tttcttggaa 134160
acaattcata attatattta cagttactaa attaatttga taataaatca aaatatggaa 134220
aactaaggtc gttagtaggg aggagaacaa agaaggcaca tcgtgacata aataacattt 134280
attatcatga tgacaccaga aaacgacgaa gagcagacat ctgtgttctc cgctactgtt 134340
tacagagaca aaattcaggg aaagaataaa cgcaaacgcg tgattggtct atgtattaga 134400
atatctatgg ttatttcact actatctatg attaccatgt ccgcgtttct catagtgcgc 134460
ctaaatcaat gcatgtctgc taacgaggct gctattactg acgccgctgt tgccgttgct 134520
gctgcatcat ctactcatag aaaggttgcg tctagcacta cgcaatatga tcacaaagaa 134580
agctgtaatg gtttatatta ccagggttct tgttatatat tacattcaga ctaccagtta 134640
ttctcggatg ctaaagcaaa ttgcactgcg gaatcatcaa cactacccaa taaatccgat 134700

-continued gtcttgacta cctggctcat tgattatgtt aaggatacat ggggatctga tggtaatcca 134760
attacaaaaa ctacatccga ttatcaagat tctgatgtat cacaagaagt tagaaagtat 134820
ttttgtgtta aaacaatgaa ctaatattta tttttgtaca ttaataaatg aaatcgctta 134880
atagacaaac tgtaagtagg tttaagaagt tgtcggtgcc ggtcgctata atgatgatac 134940
tctcaaccat tattagtggc ataggaacat ttctgcatta caaagaagaa ctgatgccta 135000
gtgcttgcgc caatggatgg atacaatacg ataaacattg ttatttagat actaacatta 135060
aaatgtctac agataatgcg gtttatcagt gtcgtaaatt acgagccaga ttgcctagac 135120
cggatactag acatctgaga gtattgttta gtatttttta taaagattat tgggtaagtt 135180
taaaaaagac caatgataaa tggttagata ttaataatga taaagatata gatattagta 135240
aattaacaaa ttttaaacaa ctaaacagta cgacggatgc tgaagcgtgt tatatataca 135300
agtctggaaa actggttaaa acagtatgta aaagtactca atctgtacta tgtgttaaaa 135360
aattctacaa gtgacaacaa aaaatgaatt aataataagt cgttaacgta cgccgccatg 135420
gacgccgcgt ttgttattac tccaatgggt gtgttgacta taacagatac attgtatgat 135480
gatctcgata tctcaatcat ggactttata ggaccataca ttataggtaa cataaaaact 135540
gtccaaatag atgtacggga tataaaatat tccgacatgc aaaaatgcta ctttagctat 135600
aagggtaaaa tagttcctca ggattctaat gatttggcta gattcaacat ttatagcatt 135660
tgtgccgcat acagatcaaa aaataccatc atcatagcat gcgactatga tatcatgtta 135720
gatatagaag ataaacatca gccattttat ctattcccat ctattgatgt ttttaacgct 135780
acaatcatag aagcgtataa cctgtataca gctggagatt atcatctaat catcaatcct 135840
tcagataatc tgaaaatgaa attgtcgttt aattcttcat tctgcatatc agacggcaat 135900
ggatggatca taattgatgg gaaatgcaat agtaattttt tatcataaaa gttgtaaagt 135960
aaataataaa acaataaata ttgaactagt agtacgtata ttgagcaatc agaaatgatg 136020
ctggtacctc ttatcacggt gaccgtagtt gcgggaacaa tattagtatg ttatatatta 136080
tatatttgta ggaaaaagat acgtactgtc tataatgaca ataaaattat catgacaaaa 136140
ttaaaaaaga taaagagttc taattccagc aaatctagta aatcaactga tagcgaatca 136200
gactgggagg atcactgtag tgctatggaa caaaacaatg acgtagataa tatttctagg 136260
aatgagatat tggacgatga tagcttcgct ggtagtttaa tatgggataa cgaatccaat 136320
gttatggcgc ctagcacaga acacatttac gatagtgttg ctggaagcac gctgctaata 136380
aataatgatc gtaatgaaca gactatttat cagaacacta cagtagtact taatgaagat 136440
accaaacaga atcctaacta ttcatccaat cctttcgtaa attataataa aaccagtatt 136500
tgtagcaagt caaatccgtt cattacagaa ctcaacaata aatttagtga gaataatccg 136560
tttagacgag cacatagcga tgattatctt aataagcaag aacaagatca tgaacacgat 136620
gatatagaat cattggtgtg attagtttcc tttttataaa attgaagtaa tatttagtat 136680
tattgctgcc gtcacgttgt acaaatggag atattccctg tattcggcat ttctaaaatt 136740
agcaatttta ttgctaataa tgactgtaga tattatatag atacagaaca tcaaaaaatt 136800
atatctgatg agatcaatag acagatggat gaaacggtac ttcttaccaa catcttaagc 136860
gtagaagttg taaatgacaa tgagatgtac catcttattc ctcatagatt atcgacgatt 136920
atactctgta ttagttctgt cggaggatgt gttatctcta tagataatga cgtcaatggc 136980
aaaaatattc taacctttcc cattgatcat gctgtaatca tatccccact gagtaaatgt 137040
gtcgtagtta gcaagggtcc tacaaccata ttggttgtta aagcggatat acctagcaaa 137100
cgattggtaa catcgtttac aaacgacata ctgtatgtaa acaatctatc actgattaat 137160
tattcgccgt tgtctgtatt cattattaga cgagttaccg actatttgga tagacacata 137220
tgcgatcaga tatttgcgaa taataagtgg tattccatta taaccatcga caataagcag 137280
tttcctattc catcaaactg tataggtatg tcctctgcca agtacataaa ttctagcatc 137340
gagcaagata ctttaataca tgtttgtaac ctcgagcatc cattcgactt agtatacaaa 137400
aaaatgcagt cgtacaattc tgtacctatc aaggaacaaa tattgtacgg tagaattgat 137460
aatataaata tgagcattag tatttctgtg gattaataga tttctagtat ggggatcatt 137520
aatcatctct aatctctaaa tacctcataa aacgaaaaaa aagctattat caaatactgt 137580
acggaatgga ttcattctct tctcttttta tgaaactctg ttgtatatct actgataaaa 137640
ctggaagcaa aaaatctgat aaaaagaata agaataagat caaggattat tataaaataa 137700
caatagttcc tggttcctct tccacgtcta ctagctcgtg gtattataca catgcctagt 137760
aatagtctct ttgcgttgac ggaaagcaga ctagaaataa caggctaaaa tgttcagaca 137820
ccataatagt tcccaaccca gataataaca gagtaccatc aacacattcc tttaaactca 137880
atcccaaacc caaaaccgtt aaaatgtatc cggccaattg atagtagata atgaggtgta 137940
cagcgcatga tgatttacac agtaaccaaa atgaaaatac tttagtaatt ataagaaata 138000
tagatggtaa cgtcatcatc aacaatccaa taatatgccg gagagtaaac attgacggat 138060
aaaacaaaaa tgctccgcat aactctatca tggcaataac acaaccaaat acttgtaaga 138120
ttcctaaatt agtagaaaat acaacggata tcgatgtata agtgatctcg agaaataata 138180
agaataaagt aatgcccgta aagataaaca tcaacattgt ttggtaatca ttaaaccaat 138240
tagtatgaag ttgaactaat ttcacagtag attttattcc agtattatcc ccgcatgtat 138300
aagtacctgg taagatatct ttatattcca taatcaatga gacatcacta tctgataacg 138360
aatgaagtct agcactagta tgccatttac ttaatattgt cgtcttggaa gttttattat 138420
aagttaaaat atcatggtta tccaatttcc atctaatata ctttgtcgga ttatctatag 138480
tacacggaat aatgatggta tcattacatg ctgtatactc tatggtcttt gtagttgtta 138540
taacaaccaa cgtatagagg tatatcaacg atattctaac tcttgacatt ttttatttat 138600
ttaaaatgat acctttgtta tttattttat tctattttgc taacggtatt gaatggcata 138660
agtttgaaac gagtgaagaa ataatttcta cttacttatt agacgacgta ttatacacgg 138720
gtgttaatgg ggcggtatac acattttcaa ataataaact aaacaaaact ggtttaacta 138780
ataataatta tataacaaca tctataaaag tagaggatgc ggaaccaata acggaaatcc 138840
caaatgttgg aaaatagacg gttcagacga cccaaaacat agaggtagag gatacgctcc 138900
ttatcaaaat agcaaagtaa cgataatcag tcacaacgga tgtgtactat ctgacataaa 138960
catatcaaaa gaaggaatta aacgatggag aagatttgac ggaccatgtg gttatgattt 139020
atacacggcg gataacgtaa ttccaaaaga tggtttacga ggagcattcg tcgataaaga 139080
tggtacttat gacaaagttt acattctttt cactgatact atcggctcaa agagaattgt 139140
caaaattccg tatatagcac aaatgtgcct aaacgacgaa ggtggtccat catcattgtc 139200
tagtcataga tggtcgacgt ttctcaaagt cgaattagaa tgtgatatcg acggaagaag 139260
ttatagacaa attattcatt ctagaactat aaaaacagat aatgatacga tactatatgt 139320
attcttcgat agtccttatt ccaagtccgc attatgtacc tattctatga ataccattaa 139380
acaatctttt tctacgtcaa aattggaagg atatacaaag caattgccgt ctccagctcc 139440

-continued tggtatatgt ttaccagctg gaaaagttgt tccacatacc acgtttgaag tcatagaaaa 139500
atataatgta ctagatgata ttataaagcc tttatctaac caacctatct tcgaaggacc 139560
gtctggtgtt aaatggttcg atataaagga gaaggaaaat gaacatcggg aatatagaat 139620
atacttcata aaagaaaatt ctatatattc gttcgataca aaatctaaac aaactcgtag 139680
ctcgcaagtc gatgcgcgac tattttcagt aatggtaact tcgaaaccgt tatttatagc 139740
agatataggg ataggagtag gaatgccaca aatgaaaaaa atacttaaaa tgtaatctta 139800
atcgagtaca ccgcacgaca atgaacaaac ataagacaga ttatgctggt tatgcttgct 139860
gcgtaatatg cggtctaatt gttggaatta tttttacagc gacactatta aaagttgtag 139920
aacgtaaatt agttcataca ccatcaatag ataaaacgat aaaagatgca tatattagag 139980
aagattgtcc tactgactgg ataagctata ataataaatg tatccattta tctactgatc 140040
gaaaaacctg ggaggaagga cgtaatgcat gcaaagctct aaatccaaat tcggatctaa 140100
ttaagataga gactccaaac gagttaagtt ttttaagaag cattagacgc ggatattggg 140160
taggagaatc cgaaatatta aaccagacaa ccccatataa ttttatagct aaaaatgcca 140220
cgaagaatgg aactaaaaaa cggaaatata tttgtagtac aacgaatact cccaaactac 140280
atttttatca taccactact tcggttagat gttttagaaa aaaataaata tcgccgtacc 140340
gttcttgttt ttataaaaat aacaattaac aattatcaaa ttttttcttt aatattttac 140400
gtggttgacc attcttggtg gtaaaataat ctcttagtgt tggaatggaa tgctgtttaa 140460
tgtttccgca ctcatcgtat attttgacgt atgcagtcac atcgtttacg caatagtcag 140520
actgtagttc tatcatgctt cctacatcag aaggaggaac agttttaaag tctcttggtt 140580
ttaatctatt gccattagtt ttcatgaaat cctttgtttt atccacttca cattttaaat 140640
aaatgtccac tatacattct tctgttaatt ttactagatc gtcatgggtc atagaattta 140700
taggttccgt agtccatgga tccaaactag caaacttcgc gtatacggta tcgcgattag 140760
tgtatacacc aactgtatga aaattaagaa aacagtttaa taaatcaaca gaaatattta 140820
atcctccgtt tgatacagat gcgccatatt tatggatttc ggattcacac gttgtttgtc 140880
tgaggtgttc gtctagtgtt gcttctacgt aaacttcgat tcccatatat tctttattgt 140940
cagaatcgca taccgattta tcatcataca ctgtttgaaa actaaatggt atacacatca 141000
aaataataaa taataacgag tacattctgc aatattgtta tcgtaattgg aaaaatagtg 141060
ttcgagtgag ttggattatg tgagtattgg attgtatatt ttattttata ttttatattt 141120
tgtagtaaga atagaatgct aatgtcaagt ttattccaat agatgtctta ttaaaaaaca 141180
tatataataa ataacaatgg ctgaatggca taaaattatc gaggatatct caaaaaataa 141240
taagttcgag gatgccgcca tcgttgatta caagactaca aagaatgttc tagctgctat 141300
tcctaacaga acatttgcca agattaatcc tctcatcact aatcgtaata ttctaaaacc 141360
tcttattggt cagaaatatt gtattgtata tactaactct ctaatggatg agaacacgta 141420
tgctatggag ttgcttactg ggtacgcccc tgtatctccg atcgttatag cgagaactca 141480
taccgcactt atatttttga tgggtaagcc aacaacatcc agacgtgacg tgtatagaac 141540
gtgtagagat cacgctaccc gtgtacgtgc aactggtaat taaaataaaa agtaatattc 141600
atatgtagtg tcaattttaa atgatgatga tgaaatggat aatatccata ttgacgatgt 141660
caataatgcc ggtattggca tacagttcat cgatttttag atttcattca gaggatgtgg 141720
aattatgtta tgggcatttg tattttgata ggatctataa tgtagtaaat ataaaatata 141780
atccgcatat tccatataga tataatttta ttaatcgcac gttaaccgta gatgaactag 141840
acgataatgt ctttttttaca catggttatt ttttaaaaca caaatatggt tcacttaatc 141900
ctagtttgat tgtctcatta tcaggaaact taaaatataa tgatatacaa tgctcagtaa 141960
atgtatcgtg tctcattaaa aatttggcaa cgagtacatc tactatatta acatctaaac 142020
ataagactta ttctctacat cggtccacgt gtattactat aataggatac gattctatta 142080
tatggtataa agatataaat gacatctatg attttactgc aatatgtatg ctaatagcgt 142140
ctacattgat agtgaccata tacgtgttta aaaaaataaa aatgaactct taattatgct 142200
atgctattag aaatggataa aatcaaaatt acggttgatt caaaaattgg taatgttgtt 142260
accatatcgt ataacttgga aaagataact attgatgtca cacctaaaaa gaaaaaagaa 142320
aaggatgtat tattagcgca atcagttgct gtcgaagagg caaaagatgt caaggtagaa 142380
gaaaaaaata ttatcgatat tgaagatgac gatgatatgg atgtagaaag cgcataatac 142440
gatctataaa aataagtata taaatacttt ttatttactg tactcttact gtgtagtggt 142500
gataccctac tcgattattt ttttaaaaaa aaatacttat tctgattctt ctagccattt 142560
ccgtgttcgt tcgaatgcca catcgacgtt aaagataggg gagtagttga aatctagttc 142620
tgcattgttg gtacgcacct caaatgtagt gttggatatc ttcaacgtat agttgttgag 142680
tagtgatggt tttctaaata gaattctctt catatcattc ttgcacgcgt acatttttag 142740
catccatctt ggaatcctag atccttgttc tattcccaat ggtttcatca atagaagatt 142800
aaacatatcg tacgaacacg atggagagta atcgtagcaa aagtaagcat ttcctttaat 142860
ctcagatccc ggatactgga tatattttgc agccaacacg tgcatccatg cagcatttcc 142920
tacatatacc cggctatgta ccgcgttatc atcgactgta cgatacataa tgttaccgtg 142980
ttgcttacat tgctcgtaaa agactttcat caatttgtct ccttctccgt aaattccagt 143040
gggtcttagg caacaagtat acaattttgc tccattcatg attacggaat tattggcttt 143100
cataaccagt tgctcggcca tacgtttact ttttgcgtat acatgtcctg gtgatatatc 143160
ataaagggta tgctcatggc cgatgaatgg atcaccgtgt ttattgggtc ctattgcttc 143220
catgctacta gtatagatca aatacttgat tcctaggtcc acacaagctg ccaatatagt 143280
ctgtgttcca taatagttta ctttcatgat ttcattatcg gtgtattttc caaatacatc 143340
cactagagca gctgtatgaa taatcagatt taccccatct agcgcttctc ttaccttatc 143400
aaagtcgttt atatcacatt gtatatagtt tataacctta actttcgagg ttattggttg 143460
tggatcttct acaatatcta tgactctgat ttcttgaaca tcatctgcac taattaacag 143520
ttttactata tacctgccta gaaatccggc accaccagta accgcgtaca cggccattgc 143580
tgccactcat aatatcagac tacttattct attttactaa ataatggctg tttgtataat 143640
agaccacgat aatatcagag gagttattta ctttgaacca gtccatggaa aagataaagt 143700
tattggatta aaatccggaa cgtatagttt gataattcat cgttacggag atattagtca 143760
aggatgtgat tccataggca gtccagaaat atttatcggt aacatctttg taaacagata 143820
tggtgtagca tatgtttatt tagatacaga tgtaaatata tctacaatta ttggaaaggc 143880
gttatctatt tcaaaaaatg atcagagatt agcgtgtgga gttattggta tttcttacat 143940
aaatgaaaag ataatacatt ttcttacaat taacgagaat ggcgtttgat atatcagtta 144000
atgcgtctaa aacaataaat gcattagttt acttttctac tcagcaaaat aaattagtca 144060
tacgtaatga agttaatgat acacactaca ctgtcgaatt tgatagggac aaagtagttg 144120
acacgtttat ttcatataat agacataatg actccataga gataagaggg gtgcttccag 144180
aggaaactaa tattggttgc gcggttaata cgccggttag tatgacttac ttgtataata 144240
agtatagttt taaactgatt ttagcagaat atataagaca cagaaatact atatccggca 144300
atatttattc ggcattgatg acactagatg atttggctat taaacagtat ggagacattg 144360
atctattatt taatgagaaa cttaaagtag actccgattc gggactattt gactttgtca 144420
actttgtaaa ggatatgata tgttgtgatt ctagaatagt agtagctcta tctagtctag 144480
tatctaaaca ttgggaattg acaaataaaa aatataggtg tatggcatta gccgaacata 144540
tatctgatag tattccaata tctgagctat ctagactacg atacaatcta tgtaagtatc 144600
tacgcgggca cactgagagc atagaggatg aatttgatta ttttgaagac gatgattcgt 144660
ctacatgttc tgccgtaacc gacagggaaa cggatgtata attttttttta tagcgtgaag 144720
gatatgataa aaaatataat tgttgtattt atcccattcc aatcacctta tatgattctg 144780
taacacaatg aaggagtctt atagatgtat agaggtcaga tactggtttg ataaactgtt 144840
tattccacat aagtatgttt gactttatgg ttagacccgc atactttaac aaatcactga 144900
aaattggagt taggtattga cctctcagaa tcagttgccg ttctggaaca ttaaatgtat 144960
tttttatgat atactccaac gcatttatgt gggcatacaa caagtcatta ctaatggagt 145020
attccaagag aagagatttc aacagactgt ttatgaactc gaatgccgcc tcattgtcgc 145080
ttatattgat gatgtcgaat tctcccaata tcatcaccga tgagtagctc atcttgttat 145140
cgggatccaa gttttctaaa gatgtcatta aaccctcgat catgaatgga tttatcatca 145200
tcgtttttat gttggacatg agcttagtcc gtttgtccac atctatagac gacgatttct 145260
gaattatttc atatatccct ctctttaact ccaggaactt gtcaggatgg tctactttaa 145320
tatgttctcg tctaagagat gaaaatcttt ggatggttgc acgcgacttt tctctaaagg 145380
atcctctctt aaatgaatcc atcttatcct tggacaagat ggacagtcta ttttccttag 145440
atggtttaat atttttgtta cccatgatct ataaaggtag acctaatcgt ctcggatgac 145500
catatattta ttttcagttt tattatacgc ataaattgta aaaaatatgt taggtttaca 145560
aaaatgtctc gtggggcatt aatcgttttt gaaggattgg acaaatctgg aaaaacaaca 145620
caatgtatga acatcatgga atctataccg gcaaacacga taaaatatct taactttcct 145680
cagagatcca ctgtcactgg aaagatgata gatgactatc taactcgtaa aaaaacctat 145740
aatgatcata tagttaatct attattttgt gcaaatagat gggagtttgc atcttttata 145800
caagaacaac tagaacaggg aattacttta atagttgata gatacgcatt ctctggagta 145860
gcgtatgccg ccgctaaagg cgcgtcaatg actctcagta agagttatga atctggattg 145920
cctaaacccg acttagttat attcttggaa tctggtagca aagaaattaa tagaaacgtc 145980
ggcgaggaaa tttatgaaga tgttacattc caacaaaagg tattacaaga atataaaaaa 146040
atgattgaag aaggagatat tcattggcaa attatttctt ctgaattcga ggaagatgta 146100
aagaaggagt tgattaagaa tatagttata gaggctatac acacggttac tggaccagtg 146160
gggcaactgt ggatgtaata gtgaaattac atttttttata aatggatgaa gcatattact 146220
ctggcaactt ggaatcagta ctcggatacg tgtccgatat gcataccgaa ctcgcatcaa 146280
tatctcaatt agttattgcc aagatagaaa ctatagataa tgatatatta aacaaggaca 146340
ttgtaaattt tatcatgtgt agatcaaact tggataatcc atttatctct ttcctagata 146400
ctgtatatac tattatagat caagagatct atcagaccga attgattaat tcattagacg 146460
acaatgaaat tatcgattgt atagttaaca agtttatgag cttttataag gataacctag 146520
aaaatatagt agatgctatc attactctaa aatatataat gaataatcca gattttaaaa 146580

-continued ctacgtatgc cgaagtactc ggttccagaa tagcggatat agatattaaa caagtgatac 146640
gtgagaatat actacaattg tctaataata tccgcgaacg atatttgtga aaatattaaa 146700
aaaaaatact ttttttatta aatgacgtcg cttcgcgaat ttagaaaatt atgctgtgat 146760
atatatcacg catcaggata taaagaaaaa tctaaattaa ttagagactt tataacagat 146820
agggatgata aatatttgat cattaagcta ttgcttcccg gattagacga tagaatttat 146880
aacatgaacg ataaacaaat tataaaatta tatagtataa tatttaaaca atctcaggaa 146940
gatatgctac aagatttagg atacggatat ataggagaca ctattaggac tttcttcaaa 147000
gagaacacag aaatccgtcc acgagataaa agcattttaa ctttagaaga agtggatagt 147060
tttttaacta cgttatcatc cgtaactaaa gaatcgcatc aaataaaatt attgactgat 147120
atcgcatccg tttgtacatg taatgattta aaatgtgtag tcatgcttat tgataaagat 147180
ctaaaaatta aagcgggccc tcggtacgta cttaacgcta ttagtcctca tgcctatgat 147240
gtgtttagaa aatctaataa cttgaaagag ataatagaaa atgcatctaa acaaaatcta 147300
gactctatat ctatttctgt tatgactcca attaatccca tgttagcgga atcgtgtgat 147360
tctgtcaata aggcgtttaa aaaatttcca tcaggaatgt ttgcggaagt caaatacgat 147420
ggtgaaagag tacaagttca taaaaataat aacgagtttg ccttctttag tagaaacatg 147480
aaaccagtac tctctcataa agtggattat ctcaaagaat acataccgaa agcatttaaa 147540
aaagctacgt ctatcgtatt ggattctgaa attgttcttg tagacgaaca taatgtaccg 147600
ctcccgtttg gaagtttagg tatacacaaa aagaaagaat ataaaaactc taacatgtgt 147660
ttgttcgtgt ttgactgttt gtactttgat ggattcgata tgacggacat tccattgtac 147720
gaacgaagat cttttctcaa agatgttatg gttgaaatac ccaatagaat agtattctca 147780
gagttgacga atattagtaa cgagtctcag ttaactgacg tattggatga tgcactaacg 147840
agaaaattag aaggattggt cttaaaagat attaatggag tatacgaacc gggaaagaga 147900
agatggttaa aaataaagcg agactatttg aacgagggtt ccatggcaga ttctgccgat 147960
ttagtagtac taggtgctta ctatggtaaa ggagcaaagg gtggtatcat ggcagtcttt 148020
ctaatgggtt gttacgacga tgaatccggt aaatggaaga cggttaccaa gtgttcagga 148080
cacgatgata atacgttaag ggagttgcaa gaccaattaa agatgattaa aattaacaag 148140
gatcccaaaa aaattccaga gtggttagta gttaataaaa tctatattcc cgattttgta 148200
gtagaggatc caaaacaatc tcagatatgg gaaatttcag gagcagagtt tacatcttcc 148260
aagtcccata ccgcaaatgg aatatccatt agatttccta gatttactag gataagagag 148320
gataaaacgt ggaaagaatc tactcatcta aacgatttag taaacttgac taaatcttaa 148380
tagttacata caaattaaaa taacactatt tagttggtgg tcgccatgga tggtgttatt 148440
gtatactgtc taaacgcgtt agtaaaacat ggcgaggaaa taaatcatat aaaaaatgat 148500
ttcatgatta aaccatgttg tgaaaaagtc aagaacgttc acattggcgg acaatctaaa 148560
aacaatacag tgattgcaga tttgccatat atggataatg cggtatccga tgtatgcaat 148620
tcactgtata aaaagaatgt atcaagaata tccagatttg ctaatttgat aaagatagat 148680
gacgatgaca agactcctac tggtgtatat aattatttta aacctaaaga tgccattcct 148740
gttattatat ccataggaaa ggatagagat gtttgtgaac tattaatctc atctgataaa 148800
gcgtgtgcgt gtatagagtt aaattcatat aaagtagcca ttcttcccat ggatgtttcc 148860
tttttacca aaggaaatgc atcattgatt attctcctgt ttgatttctc tatcgatgcg 148920

-continued gcacctctct taagaagtgt aaccgataat aatgttatta tatctagaca ccagcgtcta 148980
catgacgagc ttccgagttc caattggttc aagttttaca taagtataaa gtccgactat 149040
tgttctatat tatatatggt tgttgatgga tctgtgatgc atgcaatagc tgataataga 149100
acttacgcaa atattagcaa aaatatatta gacaatacta caattaacga tgagtgtaga 149160
tgctgttatt ttgaaccaca gattaggatt cttgatagag atgagatgct caatggatca 149220
tcgtgtgata tgaacagaca ttgtattatg atgaatttac ctgatgtagg cgaatttgga 149280
tctagtatgt tggggaaata tgaacctgac atgattaaga ttgctctttc ggtggctggt 149340
atttggaaag ttttataggt agttgataga acaaaataca taattttgta aaaataaatc 149400
actttttata ctaatatgac acgattacca atacttttgt tactaatatc attagtatac 149460
gctacacctt ttcctcagac atctaaaaaa ataggtgatg atgcaacttt atcatgtaat 149520
cgaaataata caaatgacta cgttgttatg agtgcttggt ataaggagcc caattccatt 149580
attcttttag ctgctaaaag cgacgtcttg tattttgata attataccaa ggataaaata 149640
tcttacgact ctccatacga tgatctagtt acaactatca caattaaatc attgactgct 149700
agagatgccg gtacttatgt atgtgcattc tttatgacat cgcctacaaa tgacactgat 149760
aaagtagatt atgaagaata ctccacagag ttgattgtaa atacagatag tgaatcgact 149820
atagacataa tactatctgg atctacacat tcaccggaaa ctagttctga gaaacctgat 149880
tatatagata attctaattg ctcgtcggta ttcgaaatcg cgactccgga accaattact 149940
gataatgtag aagatcatac agacaccgtc acatacacta gtgatagcat taatacagta 150000
agtgcatcat ctggagaatc cacaacagac gagactccgg aaccaattac tgataaagaa 150060
gaagatcata cagttacaga cactgtctca tacactacag taagtacatc atctggaatt 150120
gtcactacta aatcaaccac cgatgatgcg gatctttatg atacgtacaa tgataatgat 150180
acagtaccat caactactgt aggcggtagt acaacctcta ttagcaatta taaaaccaag 150240
gactttgtag aaatatttgg tattaccgca ttaattatat tgtcggccgt ggcaatattc 150300
tgtattacat attatatata taataaacgt tcacgtaaat acaaaacaga gaacaaagtc 150360
tagatttttg acttacataa atgtctggga tagtaaaatc tatcatattg agcgggccat 150420
ctggtttagg aaagacagcc atagccaaaa gactatggga atatatttgg atttgtggtg 150480
tcccatacca ctagatttcc tcgtcctatg gaacgagaag gtgtcgatta ccattacgtt 150540
aacagagagg ccatctggaa gggaatagcc gccggaacat actgagtttt taggaaatat 150600
ttacggaact tctaaaactg ctgtgaatac agcggctatt aataatcgta tttgtgtgat 150660
ggatctaaac atcgacggtg ttagaagttt taaaaatact tacctaatgc cttactcggt 150720
gtatataaga cctacctctc ttaaaatggt tgagaccaag cttcgttgta gaaacactga 150780
agcggatgat gagattcatc gtcgtgtgat gttggcaaaa actgacatgg atgaggcagg 150840
tgaagccggt ctattcgaca ctattatcat tgaagatgat gtgaatttag catatagtaa 150900
gttaattcag atactacagg accgtattag aatgtatttt aacactaatt agagacttaa 150960
gacttaaaac ttgataatta ataatataac tcgtttttat atgtggctat ttcaacgtct 151020
aatgtattag ttaaatatta aaacttacca cgtaaaactt aaaatttaaa atgatatttc 151080
attgacagat agatcacaca ttatgaactt tcaaggactt gtgttaactg acaattgcaa 151140
aaatcaatgg gtcgttggac cattaatagg aaaaggtgga tttggtagta tttatactac 151200
taatgacaat aattatgtag taaaaataga gcccaaagct aacggatcat tatttaccga 151260
acaggcattt tatactagag tacttaaacc atccgttatc gaagaatgga aaaaatctca 151320
caatataaag cacgtaggtc ttatcacgtg caaggcattt ggtctataca aatccattaa 151380
tgtggaatat cgattcttgg taattaatag attaggtgca gatctagatg cggtgatcag 151440
agccaataat aatagattac caaaaaggtc ggtgatgttg atcggaatcg aaatcttaaa 151500
taccatacaa tttatgcacg agcaaggata ttctcacgga gatattaaag cgagtaatat 151560
agtcttggat caaatagata agaataaatt atatctagtg gattacggat tggtttctaa 151620
attcatgtct aatggcgaac atgttccatt tataagaaat ccaaataaaa tggataacgg 151680
tactctagaa tttacaccta tagattcgca taaaggatac gttgtatcta gacgtggaga 151740
tctagaaaca cttggatatt gtatgattag atggttggga ggtatcttgc catggactaa 151800
gatatctgaa acaaagaatt gtgcattagt aagtgccaca aaacagaaat atgttaacaa 151860
tactgcgact ttgttaatga ccagtttgca atatgcacct agagaattgc tgcaatatat 151920
taccatggta aactctttga catattttga ggaacccaat tacgacaagt ttcggcacat 151980
attaatgcag ggtgtatatt attaagtgtg gtgtttggtt gatgtaaaat ttttgtcgat 152040
aaaaattaaa aaataactta atttattatt gatctcgtgt gtacaaccga aatcatggcg 152100
atgttttacg cacacgctct cggtgggtac gacgagaatc ttcatgcctt tcctggaata 152160
tcatcgactg ttgccaatga tgtcagttta taataacaag tatgacattg taaaagacaa 152220
atatatgtgg tgttacagtc aggtgaacaa gagatatatt ggagcactgc tgcctatgtt 152280
tgagtgcaat gaatatctac aaattggaga tccgatccat gatcaagaag gaaatcacat 152340
atcgccacaa aaactactat gctctaagcg gaatcgggta cgagagtcta gacttgtgtt 152400
tggaaggagt agggattcat catcacgtac ttgaaacaga aaacgctgta tatggaaaag 152460
ttcaacatga ttattctact atcaaagaga aggccaaaga aatgaatgca ctcagttcag 152520
gacctatcat cgattaccac gtctggatag gagattgtat ctgtcaagtt actgctgtgg 152580
acgtacatgg aaaggaaatt atgagaatga gattcaaaaa gggtgcggtg cttccgatcc 152640
caaatctggt aaaagttaaa cttggggaga atgatacaga aaatctttct tctactatat 152700
cggcggcacc atcgaggtaa ccacctctct ggaagacagt gtgaatcatg tactcatgaa 152760
acgtttggaa tctatacgcc atatgtggtc tgttgtatat gatcattttg atattgtgaa 152820
tggtaaagaa tgctgttatg tgcatacgca tttgtctaat caaaatctta taccgagtac 152880
tgtaaaaaca aatttgtaca tgaagactat gggatcatgc attcaaatga gtatcttagc 152940
gaactgaagg aatcaggtgg atggagtccc agaccagaaa tgcaggaatt tgaatatcca 153000
gatggagtgg aagacactga atcaattgag agattggtag aggagttctt caatagatca 153060
gaacttcagg ctggtaaatc tattaatgtt aaacatacat ctgtttcagc taagcaacta 153120
agaacacgta tactctcatc ttttgccaac acagagggtg gatatttgtt cattggagtt 153180
gataataata cacacaaagt atttggattc acggtgggtt acgactacct cagactgata 153240
gagaatgata tagaaaagca tatcaaaaga ctttgtgttg tgtatttctg tgagaagaaa 153300
gaggacatca agtacacgtg tcgattcatc aaggtatata aacctgggga tgaggctacc 153360
tcgacatacg tgtgcgctat caaagtggaa agatgctgtt gtgctgtgtt tgcagattgg 153420
ccagaatcat ggtatcaaga agtattctcc agatgaatag gtgtcacata taaaatttta 153480
attaatgtaa ctatagagaa caaataatag gttgtaatat catatagaca ataactaaca 153540
attaattagt aactgttatc tctttttaac taactaacta tacctattaa tacatcgtaa 153600
ttatagttct taacatctat taatcattga ttcgcttctt taatttttta taaaccaaca 153660
ttgttaattg aaaagggata acatgttaca gaatataaat tatatatgga tttttttaa 153720 aaaggaaata cttgactgga gtgtatattt atctcttcat tatatagcac gcgtgttttc 153780
caatttttcc acatcccata taatacagga ttataatctc gttcgaacat acgagaaagt 153840
ggataaaaca atagttgatt ttttatctag gttgccaaat ttattccata ttttagaata 153900
tggggaaaat attctacata tttattctat ggatgatgct aatacgaata ttataatttt 153960
ttttctagat agagtattaa atattaataa gaacgggtca tttatacaca atctcaggtt 154020
atcatcatcc attaatataa aagaatatgt atatcaatta gttaataatg atcatccaga 154080
taataggata agactaatgc ttgaaaatgg acgtagaaca agacattttt tgtcctatat 154140
atcagataca gttaatatct atatatgtat tttatataga tgccgaagac agttacggtt 154200
gtacattatt acatagatgt atatatcact ataagaaatc agaatcagaa tcagaatcat 154260
acaatgaatt aattaagata ttgttaaata atggatcaga tgtagataaa aaagatacgt 154320
acggaaacac accttttatc ctattatgta aacacgatat caacaacgtg gaattgtttg 154380
agatatgttt agagaatgct aatatagact ctgtagactt taatagatat acacctcttc 154440
attatgtctc atgtcgtaat aaatatgatt ttgtaaagtt attaatttct aaaggagcaa 154500
atgttaatgc gcgtaataaa ttcggaacta ctccatttta ttgtggaatt atacacggta 154560
tctcgcttat aaaactatat ttggaatcag acacagagtt agaaatagat aatgaacata 154620
tagttcgtca tttaataatt tttgatgctg ttgaatcttt agattatcta ttatccagag 154680
gagttattga tattaactat cgtactattt acgacgctgt cagttataat gcgtataata 154740
cgttggtcta tctattaaac agaaatggtg attttgagac gattactact agtggatgta 154800
catgtatttc ggaagcagtc gcaaacaaca acaaaataat aatggaagta ctattgtcta 154860
aacgaccatc tttgaaaatt atgatacagt ctatgatagc aattactaaa cataaacagc 154920
ataatgcaga tttattgaaa atgtgtataa aatatactgc gtgtatgacc gattatgata 154980
ctcttataga tgtacaatca ctacagcaat ataaatggta tattttaaga tgtttcgatg 155040
aaatagatat catgaagaga tgttatataa aaaataaaac tgtattccaa ttagtttttt 155100
gtatcaaaga cattaatact ttaatgagat acggtaaaca tccttctttc gtgaagtgca 155160
ctagtctcga cgtatacgga agtcgtgtac gtaatatcat agcatctatt agatatcgtc 155220
agagattaat tagtctatta tccaagaagc tggatcctgg agataaatgg tcgtgttttc 155280
ctaacgaaat aaaatataac gataacgaac tgtccacata tctaaaaatc ttataaacac 155340
tattaaaata taaaatcaca ctacatcatt gtttcctttt agtgctcgac agtgtatact 155400
atttttaacg ctcataaata aaaatgaaaa cgatttccgt tgttacgttg ttatgcgtac 155460
tacctgctgt tgtttattca acatgtactg tacccactat gaataacgct aaattaacgt 155520
ctaccgaaac atcgtttaat aataaccaga aagttacgtt tacatgtgat cagggatatc 155580
attcttcgga tccaaatgct gtctgcgaaa cagataaatg gaaatacgaa aatccatgca 155640
aaaaaatgtg cacagtttct gattacatct ctgaactata taataaaccg ctatacgaag 155700
tgaattccac catgacacta agttgcaacg gcgaaacaaa atattttcgt tgcgaagaaa 155760
aaaatggaaa tacttcttgg aatgatactg ttacgtgtcc taatgcggaa tgtcaacctc 155820
ttcaattaga acacggatcg tgtcaaccag ttaaagaaaa atactcattt ggggaatata 155880
taactatcaa ctgtgatgtt ggatatgagg ttattggtgc ttcgtacata agttgtacag 155940
ctaattcttg gaatgttatt ccatcatgtc aacaaaaatg tgatataccg tctctatcta 156000
atggattaat ttccggatct acattttcta tcggtggcgt tatacatctt agttgtaaaa 156060
gtggttttat actaacggga tctccatcat ccacatgtat cgacggtaaa tggaatccca 156120
tactcccaac atgtgtacga tctaacgaaa aatttgatcc agtggatgat ggtcccgacg 156180
atgagacaga tttgagcaaa ctctcgaaag acgttgtaca atatgaacaa gaaatagaat 156240
cgttagaagc aacttatcat ataatcatag tggcgttaac aattatgggc gtcatatttt 156300
taatctccgt tatagtatta gtttgttcct gtgacaaaaa taatgaccaa tataagttcc 156360
ataaattgct accgtgaata taaatccgtt aaaataatga ataattaata attaataatt 156420
taataacaaa caagtatcaa aagattaaag acttatagct agaatcaatt gagatgtctt 156480
cttcagtgga tgttgatatc tacgatgccg ttagagcatt tttactcagg cactattata 156540
acaagagatt tattgtgtat ggaagaagta acgccatatt acataatata tacaggctat 156600
ttacaagatg cgccgttata ccgttcgatg atatagtacg tactatgcca aatgaatcac 156660
gtgttaaaca atgggtgatg gatacactta atggtataat gatgaatgaa cgcgatgttt 156720
ctgtaagcgt tggcaccgga atactattca tggaaatgtt tttcgattac aataaaaata 156780
gtatcaacaa tcaactaatg tatgatataa ttaatagcgt atctataatt ctagctaatg 156840
agagatatag aagcgctttt aacgacgatg gtatatacat ccgtagaaat atgattaaca 156900
agttgtacgg atacgcatct ctaactacta ttggcacgat cgctggaggt gtttgttatt 156960
atctgttgat gcatctagtt agtttgtata aataattatt tcaatatact agttaaaatt 157020
ttaagatttt aaatgtataa aaaactaata acgtttttat ttgtaatagg tgcattagca 157080
tcctattcga ataatgagta cactccgttt aataaactga gtgtaaaact ctatatagat 157140
ggagtagata atatagaaaa ttcatatact gatgataata atgaattggt gttaaatttt 157200
aaagagtaca caatttctat tattacagag tcatgcgacg tcggatttga ttccatagat 157260
atagatgtta taaacgacta taaaattatt gatatgtcta ctattcaacg cagaggtcac 157320
acgtgtagaa tatctaccaa attatcatgc cattatgata agtaccctta tattcacaaa 157380
tatgatggtg atgagcgaca atattctatt actgcagagg gaaaatgcta taaaggaata 157440
aaatatgaaa taagtatgat caacgatgat actctattga gaaaacatac tcttaaaatt 157500
ggatctactt atatatttga tcgtcatgga catagtaata catattattc aaaatatgat 157560
ttttaaaaat ttaaaatata ttatcacttc agtgacagta gtcaaataac aaacaacacc 157620
atgagatata ttataattct cgcagttttg ttcattaata gtatacacgc taaaataact 157680
agttataagt ttgaatccgt caattttgat tccaaaattg aatggactgg ggatggtcta 157740
tacaatatat cccttaaaaa ttatggcatc aagacgtggc aaacaatgta tacaaatgta 157800
ccagaaggaa catacgacat atccgcattt ccaaagaatg atttcgtatc tttctgggtt 157860
aaatttgaac aaggcgatta taaagtggaa gagtattgta cgggaccacc gactgtaaca 157920
ttaactgaat acgacgacca tccgtatgct actagaggta gcaaaaagat tcctatttac 157980
aaacgcggtg acatgtgtga tatctacttg ttgtatacgg ctaacttcac attcggagat 158040
tctaaagaac cagtaccata tgatatcgat gactacgatt gcacgtctac aggttgcagc 158100
atagactttg tcacaacaga aaaagtgtgc gtgacagcac agggagccac agaagggttt 158160
ctcgaaaaaa ttactccatg gagttcgaaa gtatgtctga cacctaaaaa gagtgtatat 158220
acatgcgcaa ttagatccaa agaagatgtt cccaatttca aggacaaaat ggccagagtt 158280
atcaagagaa aatttaacta aatttctcgg tagcacatca aatgatgtta ccacttttct 158340
tagcatgctt aacttgacta aatattcata actaattttt attaatgata caaaaacgaa 158400
ataaaactgc atattataca ctggttaacg cccttatagg ctctaaccat tttcaagatg 158460
aggtccctga ttatagtcct tctgttcccc tctatcatct actccatgtc tattagacga 158520
tgtgagaaga ctgaagagga aacatgggga ttgaaaatag ggttgtgtat aattgccaaa 158580
gatttctatc ccgaaagaac tgattgcagt gttcatctcc caactgcaag tgaaggcaat 158640
ggattcaggg atatacgaaa caccgataaa ttataaaaaa agcaatgtgt ccgctgtttc 158700
cgttaataat actattttcg taactggcgg attattcata aataactcta atagcacgat 158760
cgtggttaac aatatggaaa aacttgacat ttataaagac aaacaatggt cgattataga 158820
aatgcctatg gctagggtat atcacggcat cgactcgaca tttggaatgt tatattttgc 158880
cggaggtcta tccgttaccg aacaatatgg taatttagag aaaaacaacg agatatcttg 158940
ttacaatcct agaacgaata agtggtttga tatttcatat actatttata agatatccat 159000
atcatcattg tgtaaactaa ataacgtctt ctatgtattt agtaaggaca ttggatatgt 159060
ggaaaagtat gatggtctcc ccgctataaa ggcattatca acttctcctt attgattgaa 159120
aatgaaaata taaatagttt ttatgtatag cagtattacc ctatagtttt attgcttact 159180
actaacatgg atacagatac agatgttaca aatgtagaag atatcatgaa tgaaatagat 159240
agagagaaag aagaaatact aaaaaatgta gaaattgaaa ataataaaaa cattaacaag 159300
aatcatccca atgaatatat tagagaagca ctcgttatta atacaagtag taatagtgat 159360
tccattgata aagaagttat agaatgtatc agtcacgatg taggaatata gatcatatct 159420
actaattttt ataatcaata caaaacataa aaaacaactc gttattacat agcaggcatg 159480
gaatccttca agtattgttt tgataacgat ggcaagaaat ggattatcgg aaatacttta 159540
tattctggta attcaatact ctataaggtc agaaaaaatt tcactagttc gttctacaat 159600
tacgtaatga agatagatca caaatcacac aagccattgt tgtctgaaat acgattctat 159660
atatctgtat tggatccttt gactatcgac aactggacac gggaacgtgg tataaagtat 159720
ttggctattc cagatctgta tggaattgga gaaaccgatg attatatgtt cttcgttata 159780
aagaatttgg gaagagtatt cgccccaaag gatactgaat cagtcttcga agcatgcgtc 159840
actatgataa acacgttaga gtttatacac tctcgaggat ttacccatgg aaaaatagaa 159900
ccgaggaata tactgattag aaataaacgt ctttcactaa ttgactattc tagaactaac 159960
aaactataca agagtggaaa ctcacatata gattacaacg aggacatgat aacttcagga 160020
aatatcaatt atatgtgtgt agacaatcat cttggagcaa cagtttcaaa acgaggagat 160080
ttagaaatgt tgggatattg catgatagaa tggttcggtg gcaaacttcc atggaaaaac 160140
gaaagtagta taaaagtaat aaaacaaaaa aaagaatata aaaaatttat agctactttc 160200
tttgaggact gttttcctga aggaaatgaa cctctggaat tagttagata tatagaatta 160260
gtatacacgt tagattattc tcaaactcct aattatgaca gactacgtag actgtttata 160320
caagattgaa atattctttt tttatagagt gtggtagtgt tacggatatc taatattaat 160380
attagactat ctctatcgcg ctacacgacc aatatcgatt actatggata tcttctatga 160440
aaggagagaa tgtattcatt tctccagcgt caatctcgtc agtattgaca atactgtatt 160500
atggagctaa tggatccact gctgaacagc tatcaaaata tgtagaaaag gaggagaaca 160560
cggataaggt tagcgctcag aatatctcat tcaaatccat gaataaagta tatgggcgat 160620
attctgccgt gtttaaagat tcctttttga gaaaaattgg cgataagttt caaactgttg 160680
acttcactga ttgtcgcact atagatgcaa tcaacaagtg tgtagatatc tttactgagg 160740
ggaaaatcaa tccactattg gatgaacaat tgtctcctag caattagtgc cgtatacttt 160800
aaagcaaaat ggttgacgcc attcgaaaag gaatttacca gtgattatcc cttttacgta 160860
tcaccaacgg aaatggtaga cgtaagtatg atgtctatgt acggcgagct atttaatcac 160920
gcatctgtaa aagaatcatt cggtaacttt tcaatcatag aactgccata tgttggagat 160980
actagtatga tggtcattct tccagacaag attgatggat tagaatccat agaacaaaat 161040
ctaacagata caaattttaa gaaatggtgt aactctctgg aagctacgtt tatcgatgtt 161100
cacattccca agtttaaggt aacaggctcg tataatctgg tggatactct agtaaagtca 161160
ggactgacag aggtgttcgg ttcaactgga gattatagca atatgtgtaa tttagatgtg 161220
agtgtcgacg ctatgatcca caaaacgtat atagatgtca atgaagagta tacagaagca 161280
gctgcagcaa cttgtgcact ggtgtcagac tgtgcatcaa caattacaaa tgagttctgt 161340
gtagatcatc cgttcatcta tgtgattagg catgttgatg gaaaaatttt tttcgttggt 161400
agatattgct ctccgacaac taattgttaa ccattttttt taaaaaaata gaaaaaacat 161460
gtggtattag tgcaggtcgt tattcttcca attgcaattg gtaagatgac ggccaacttt 161520
agtacccacg tcttttcacc acagcactgt ggatgtgaca gactgaccag tattgatgac 161580
gtcaaacaat gtttgactga atatatttat tggtcgtcct atgcataccg caacaggcaa 161640
tgcgctggac aattgtattc cacactcctc tcttttagag atgatgcgga attagtgttc 161700
atcgacattc gcgagctggt aaaaaatatg ccgtgggatg atgtcaaaga ttgtgtagaa 161760
atcatccgtt gttatatacc ggatgagcaa aaaaccatca tcggactttg tgcatatgct 161820
gctacttact ggggaggtga agaccatccc actagtaaca gtctgaacgc attgtttgtg 161880
atgcttgaga tgctaaatta cgtggattat aacatcatat tccggcgtat gaattgatga 161940
gttgtacatc ttgacatttt cttctttctt ctcttctccc tttcccagaa acaaactttt 162000
tttacccact ataaaataaa atgagtatac tacctgttat atttctttct atattttttt 162060
attcttcatt cgttcagact tttaacgcgc ctgaatgtat cgacaaaggg caatattttg 162120
catcattcat ggagttagaa aacgagccag taatcttacc atgtcctcaa ataaatacgc 162180
tatcatccgg atataatata ttagatattt tatgggaaaa acgaggagcg gataatgata 162240
gaattatacc gatagataat ggtagcaata tgctaattct gaacccgaca caatcagact 162300
ctggtattta tatatgcatt accacgaacg aaacctactg tgacatgatg tcgttaaatt 162360
tgacaatcgt gtctgtctca gaatcaaata tagatcttat ctcgtatcca caaatagtaa 162420
atgagagatc tactggcgaa atggtatgtc ccaatattaa tgcatttatt gctagtaacg 162480
taaacgcaga tattatatgg agcgggcatc gacgccttag aaataagaga cttaaacaac 162540
ggacacctgg aattattacc atagaagatg ttagaaaaaa tgatgctggt tattatacat 162600
gtgttttaga atatatatac ggtggcaaaa catataacgt aaccagaatt gtaaaattag 162660
aggtacggga taaaataata ccttctacta tgcaattacc agaaggtgtt gtaacttcaa 162720
taggtagtaa tttgactatt gcgtgtagag tatcgttgag acctcccaca acggatgcag 162780
acgtcttttg gataagtaat ggtatgtatt acgaagaaga tgatggggac ggagacggta 162840
gaataagtgt agcaaataaa atctatatga ccgataagag acgtgttatt acatcccggt 162900
taaacattaa tcctgtcaag gaagaagatg ctacaacgtt tacgtgtatg gcgtttacta 162960
ttcctagcat cagcaaaaca gttactgtta gtataacgtg aatgtatgtt gttacatttc 163020
catgtcaatt gagtttataa gaatttttat acattatctt ccaacaaaca attgacgaac 163080
gtattgctat gattaactcc cacgatacta tgcatattat taatcattaa cttgcagact 163140

-continued atacctagtg ctattttgac atactcatgt tcttgtgtaa ttgcggtatc tatattatta 163200
aagtacgtaa atctagctat agttttatta tttaatttta gataatatac cgtctcctta 163260
tttttaaaaa ttgccacatc ctttattaaa tcatgaatgg gaatttctat gtcatcgtta 163320
atatattgtg aacaacaaga gcagatatct ataggaaagg gtggaatgcg atacattgat 163380
ctatgtagtt ttaaaacaca cgcgaacttt gaagaattta tataaatcat tccatcgata 163440
catccttcta tgttgacatg tatatatcca ggaattcttt tattaatgtc aggaaatgta 163500
taaactaaaa cattgcccga aagcggtgcc tctatctgcg ttatatccgt tcttaactta 163560
caaaatgtaa ccaatacctt tgcatgactt gttttgttcg gcaacgttag tttaaacttg 163620
acgaatggat taattacaat agcatgatcc gcgcatctat taagtttttt tactttaacg 163680
cccttgtatg tttttacaga gactttatct aaatttctag tgcttgtatg tgttataaat 163740
ataacgggat atagaactga atcacctacc ttagataccc aattacattt tatcagatcc 163800
agataataaa caaattttgt cgccctaact aattctatat tgttatatat tttacaattg 163860
gttatgatat catgtaataa cttggagtct aacgcgcatc gtcgtacgtt tatacaattg 163920
tgatttagtg tagtatatct acacatgtat ttttccgcac tatagtattc tggactagtg 163980
ataaaactat cgttatatct gtcttcaatg aactcatcga gatattgctc tctgtcatat 164040
tcatacacct gcataaactt tctagacatc ttacaatccg tgttatttta ggatcatatt 164100
tacatattta cgggtatatc aaagatgtta gattagttaa tgggaatcgt ctataataat 164160
gaatattaaa caattatatg aggactttta ccacaaagca tcataaaaat gagtcgtcgt 164220
ctgatttatg ttttaaatat caaccgcgaa tcaactcata aaatacaaga gaatgaaata 164280
tatacatatt ttagtcattg caatatagac catacttcta cagaacttga ttttgtagtt 164340
aaaaactatg atctaaacag acgacaacct gtaactgggt atactgcact acactgctat 164400
ttgtataata attactttac aaacgatgta ctgaagatat tattaaatca tggagtggat 164460
gtaacgatga aaaccagtag cggacgtatg cctgtttata tattgcttac tagatgttgt 164520
aatatttcac atgatgtagt gatagatatg atagacaaag ataaaaacca cttatcgcat 164580
agagactatt ccaacctact actagagtat ataaaatctc gttacatgtt attgaaggaa 164640
gaggatatcg atgagaacat agtatccact ttattagata agggaatcga tcctaacttt 164700
aaacaagacg gatatacagc gttacattat tattatttgt gtctcgcaca cgtttataaa 164760
ccaggtgagt gtagaaaacc gataacgata aaaaaggcca agcgaattat ttctttgttt 164820
atacaacatg gagctaatct aaacgcgtta gataattgtg gtaatacacc attccatttg 164880
tatcttagta ttgaaatgtg taataatatt catatgacta aaatgctgtt gacttttaat 164940
ccgaatttca aaatatgtaa taatcatgga ttaacgccta tactatgtta tataacttcc 165000
gactacatac aacacgatat tcttgttatg ttaatacatc actatgaaac aaatgttgga 165060
gaaatgccga tagatgagcg tcgtataatc gtattcgagt ttatcaaaac atattctaca 165120
cgtccggcag attcgataac ttatttgatg aataggttta aaaatataga tatttatacc 165180
cgctatgaag gaaagacatt attacacgta gcatgtgaat ataataatac acacgtaata 165240
gattatctta tacgtatcaa cggagatata aatgcgttaa ccgacaataa caaacacgct 165300
acacaactca ttatagataa caaagaaaat tccccatata ccattaattg tttactgtat 165360
atacttagat atattgtaga taagaatgtg ataagatcgt tggtggatca acttccatct 165420
ctacctatct tcgatataaa atcatttgag aaattcatat cctactgtat acttttagat 165480
gacacatttt acaatagaca cgttaggaat cgcaattcta aaacgtatcg atacgcattt 165540
tcaaaataca tgtcgtttga taaatacgat ggtataataa ctaaatgtca taaagaaaca 165600
atattgctca aactatccac tgttctagac actacactat atgcagtttt aagatgccat 165660
aattcgaaaa agttaagaag atacctcaac gagttaaaaa aatataataa cgataagtcc 165720
tttaaaatat attctaatat tatgaatgag agatacctta atgtatatta taaagatatg 165780
tacgtgtcaa aggtatatga taaactattt cctgttttca cagataaaaa ttgtctacta 165840
acattactac cttcagaaat tatatacgaa atattataca tgctgacaat taacgatctt 165900
tataatatat cgtatccacc taccaaagta tagttgtatt tttctcatgc gatgtgtgta 165960
aaaaaactga tattatataa atattttagt gccgtataat gaagatgacg atgaaaatga 166020
tggtacatat atatttcgta tcattattgt tattgctatt ccacagttac gccatagaca 166080
tcgaaaatga aatcacagaa ttcttcaata aaatgagaga tactctacca gctaaagact 166140
ctaaatggtt gaatccagca tgtatgttcg gaggcacaat gaatgatata gccgctctag 166200
gagagccatt cagcgcaaag tgtcctccta ttgaagacag tcttttatcg cacagatata 166260
aagactatgt ggttaaatgg gagaggctag aaaaaaatag acggcgacag gtttctaata 166320
aacgtgttaa acatggtgat ttatggatag ccaactatac atctaaattc agtaaccgta 166380
ggtatttgtg taccgtaact acaaagaatg gtgactgtgt tcagggtata gttagatctc 166440
atattaaaaa acctccttca tgcattccaa aaacatatga actaggtact catgataagt 166500
atggcataga cttatactgt ggaattcttt acgcaaaaca ttataataat ataacttggt 166560
ataaagataa taaggaaatt aatatcgacg atattaagta ttcacaaacg ggaaagaaat 166620
taattattca taatccagag ttagaagata gtggaagata caactgttac gttcattacg 166680
acgacgttag aatcaagatg taaaatactt acggttatac cgtcgcaaga ccacaggttt 166740
aaactaatac tagatccaaa aatcaacgta acgataggag aacctgccaa tataacatgc 166800
actgctgtgt caacgtcatt attgattgac gatgtactga ttgaatggga aaatccatcc 166860
ggatggctta taggattcga ttttgatgta tactctgttt taactagtag aggcggtatc 166920
accgaggcga ccttgtactt tgaaaatgtt actgaagaat atataggtaa tacatataaa 166980
tgtcgtggac acaactatta ttttgaaaaa acccttacaa ctacagtagt attggagtaa 167040
atacacaatg catttttata tacattactg aataattatt attattattt atatcgtatt 167100
tgtgctataa cgcgactatc taggtatttg tatctcaccg atagagaaca tataaatgta 167160
gactctatta aacagttgtg taaaatatca gatcctaata gatgtggatg tacggcttta 167220
gaaatgagtt cattaaaata tgtgatatca acggaacata tttatataat tatactattg 167280
ctgttagtat aattattgat tccacggaag aactaccaac agttactcca attacaacaa 167340
catataatta tactatcgat gatagcacta ctgaagaact acaagtgact cctcatatgg 167400
atctccatcg atgatacatg tattaaaata ctttccgaat aagtctttta aatattgtat 167460
taattatgaa aaactatgct atgcgagtat gatacgatac tagattttat ctctagcgag 167520
agatgtcgtt agaatcattt atcaacgaat atcgataaca tgtgtcattt atacgttaaa 167580
gtctgtccgt cttctctatt gtttagactg tttgtagaat gctgtgatat aaacaaacta 167640
gtagacacaa atatttaact catgatgaag ttgagaatga tatgctttag ctaatataaa 167700
aatatattaa tccactatat attctagact tgatttaaaa ccgataaact actactacgt 167760
actgtataag ttaggagcag accctaatta tgtagatgat agaggtaata cttctgcatc 167820
tatatgtcca cttatgagaa aacgtcattt aataagatgc atcgtgaaaa gaaatttatt 167880
aaagagttgg taaaatatga aaccgaaagt aaataatata ggaaatacac ctctacataa 167940
ctacgtatct caatatgata tcactctcat tcctcatcca caacccatta aaaaatggaa 168000
attaaagccc tctattagca taaacggcta caggtctacc tttacaatgg cctttccttg 168060
tgcccagttc agaccctgtc attgccacgc tactaaggac tccctgaata ccgtggccga 168120
cgtcagacat tgtctgactg aatacatcct gtgggtttct catagatgga cccatagaga 168180
aagcgcaggg tctctctaca ggcttctcat ctctttcaga actgatgcaa cggagctctt 168240
tggtggtgag ttgaaggatt cacttccgtg gagatcatta aatgactcca tgaaaaccgc 168300
cgaagaactt cgtgcaatca ttggactttg tactcaatca gctatcgtct ctggaagagt 168360
cttcaacgat aagtatatcg acatactact tatgctgcga aagattctga acgagaacga 168420
ctatctcacc ctcttggatc atatccgcac tgctaaatac taaatctcct tcatgctctc 168480
tcactacact ttttatcatc ttatgaggaa taattagcac cagaatagct atggattgca 168540
catgtattct atgtcgtcta ctggatgaag atgtgacgta caaaaaaata aaactagaaa 168600
ttgaaacgtg tcacaactta tcaaaacata tagatagacg aggaaacaat gcgctacatt 168660
gttacgtctc caataaatgc gatacagaca ttaagattgt tcgactgtta ctctctcgcg 168720
gagtcgagag actttgtaga aacaacgaag gattaactcc gctaggagca tacagtaagc 168780
atagatacgt aaaatctcag attgtgcatc tactgatatc cagctattcg aattcctcta 168840
acgaactcaa gtcgaatata aatgatttcg acttacgtct gctaaaatac ctaattgtgg 168900
ataaacggat acgtccgtcc aagaatacga attatgcaat caatggtctc ggattggtgg 168960
atatatacgt aacgacgcct aatccgagac cagaagtatt gctatggctt cttaaatcag 169020
aatgttacag caccggttac gtatttcgta cctgtatgta caacagtgat atgtgtaaga 169080
actctcttca ttactatata tcgtctcata gagaatctct atccaaggat gtaattaaat 169140
gtttgatcga taacaatgtt tccatccaat actactggtc ttgctcaacc atagatatag 169200
agattattaa taaaggatgt ggacacgtgt agagtatacg acgtcagccc tatattagag 169260
gcgtattatc taaacaagcg atttagagta accccatata atgtagacat ggaaatcgtt 169320
aatcttctta ttgagagacg tcatactctt gtcgacgtaa tgcgtagtat tacttcgtac 169380
gattccagag aatataacca ctacatcatc gataacattc taaagagatt tagacaacag 169440
gatgaatcca tcgtacaagc catactgata aactacttac attacggcga tatggtaagt 169500
atacctatca ttcaatgcat gttggataag acgacggaca acaactttgt taataataat 169560
ctcgtcgatg taaacgtcgt aaggtttatc gtggaaaata tggacacgcg gctgtaaatc 169620
acatatctaa caatggccgt ctatgtatgt acggtctgat attatcgaga tttaataatt 169680
gcgggtatca ctgttatgaa gatgtatttg atatactaag caagtacatg gatgatatag 169740
atatgatcga taactctact atattacgcg gtcgatgtca ataatataca atttgcaaag 169800
cggttattgg aatatggagc gagtgtcacg ctcgataatc aatacggcca tccagaaaag 169860
cagttaccaa agagaagcta gttgatttat tactgagtta ccatccccact ctagagacta 169920
tgattgacgc atttaataga gatatacgct atctatatcc tgaaccatta ttcgcctgta 169980
tcagatacgc cttaatccta gatgatgatt ttccttctaa agtaagtatg atatcgccgg 170040
tcgtcataag gaactaaagc gctatagagc agacattaat agaatgaaga atgcctacat 170100
atcaggcgtc tccatgtttg atatattatt taaacgaagc aaacgccaca gattgagata 170160
cgcaaagaac aatgagagga tcgactccat taaataattt atcatggagt gataatgtcc 170220
tgtttccatg gcatattaca aaatcgattc cgtccaagat gataaaaaca tttaccggca 170280
tcataaacac ggagtttatt ttatatgtct cgcataaaca ttactaaaaa aatatattgt 170340
tcggttttct ttcacatctt taattatgaa aaagtaaatc attatgagat ggacgcatcg 170400
ttcgcgacag tatgtggtac atacctaacg tatttatgga cgacggtaag aatgaaggtc 170460
acgtttctgt caacaatgtc gacgcgatcg tgtaacacga ctcacaatag aatctgtgaa 170520
tgctctcccg atcatggatg caaggcatgt gtttcccaaa caaaatgtgg aataggatac 170580
ggagtatccg gagacgtcat ctgttctccg tgtggtctcg gaacatattc tcacaccgtc 170640
tcttccgcag ataaatgcga acccgtaccc agaaatacct ttaactatat cgatgtggaa 170700
attaacctgt atccagttaa cgacacatcg tgtactcgga cgaccactac cggtctcagc 170760
gaatccatct caacgtcgga actaactatt actatgaatc ataaagactg cgatcccgtc 170820
ttcttaataa ggtagcgact tcaggtttct ttacaggaga aaggtgtgca ctctgaattt 170880
cgagattaaa tgcaataaca aagattcttc ctccaaacag ttaacgaaag caaagaatga 170940
tactatcatg ccgcattcgg agacagtaac tctagcgtcg acatctatat actatatagt 171000
aataccaata ctcaagacta cgaaactgat acaatctctt atcatgtggg taatgtagcc 171060
atatgcccgg tagttgcgat atacataaac tgatcactaa ttccaaaccc acccgctttt 171120
tatagtaagt ttttcaccca taaatacaat aattaatttc tcgtaaaagt agaaaatata 171180
ttctaattta ttgcacggta aggaagtaga atcataaaga acagtactca atcaatagca 171240
atcatgaaac aatatatcgt actggcatgc atgtgcctgc cagtcttcag caatcatcct 171300
catcgtgtac ggaagaagaa aacaaacatc atatgggaat cgatgttatt atcaaagtca 171360
caaagcaaga ccaaacaccg accgatgata agatttgcca atccgtaacg gaaattacag 171420
agtccgagtc agatccagat cccgaggtgg aatcagtcga ggatgtagat cctcctacca 171480
cttattactc catcatcggt ggaggtctga gaatgaactt tggattcacc aaatgtcctc 171540
agattaaatc catctcagaa tccgctgatg gaaagactgt gaggtgtcta tcgacatcag 171600
atgtagcgaa gaagagaaag acagcgacat caagacccat ccagtactcg ggtctaacat 171660
ctctcataag aaagtgagtt acgaagatat catcggttca acgatcgtcg atacaaaatg 171720
tgtcaagaat ctagagttta gcgttcgtat cggagacatg tgcaaggaat catctgaact 171780
tgaggtcaag tatgtcgacg gatcggcatc tgaaggtgca accgatgata cttcactcat 171840
cgattcaaca aaactcaaag cgtgtgtctg aatcgataac tctattcatc tgaaattgga 171900
tgagtagggt taatcgaacg attcaggcac accacgaatt aaaaaagtgt accggacact 171960
atattccggt ttgcaaaaca aaaagttacc tctcgcgact tcttcttttt ctgtctcaat 172020
agtgtgatac gattatgaca ctattcctat ttcctttcag ggtatcacaa aaatattaaa 172080
cctctttctg atggtctcat acaaaaatat ttttattctc tttctctctt tgatggtctc 172140
ataaaaaata tttttattct ctttctctct ttgatggtct cataaaatat ttttattctc 172200
tttctctctt tgatggtctc ataaaaaata tttttattct ctttctctct ttgatggtct 172260
cataaaatat ttttattctc tttctctctt tgatggtctc ataaaaaata tttttattct 172320
ctttctctct ttgatggtct cataaaaaat attaaacctc tttctgatgg tgtcactaaa 172380
atatttttat tctctttctc tcttcaatgg agtcataaaa tatttttatt ctctttctct 172440
cttcgatggt ctcacaaaaa tattaaacct ctttctgatg gtgtcactaa aatattttta 172500
ttctctttct ctcttcaatg gagtcataaa atatttttat tctctttctc tctttgatgg 172560
tctcacaaaa atatttttat tctctttctc tctttgatgg tctcacaaaa atatttttat 172620

-continued tctctttctc tctttgatgg tctcacaaaa atatttttat tctctttctc tctttgatgg 172680
tctcataaaa aaagttttac aaaaatattt ttattctctt tctctctttg atggtctcat 172740
aaaaaaagtt ttacaaaaat atttttattc tctttctctc tttgatggtc tcataaaaaa 172800
agttttacaa aaatattttt attctctttc tctctttgat ggtctcataa aaaatattaa 172860
acctctttct gatggtgtca ctaaaatatt tttattctca ttctctcttc aatggagtca 172920
taaaatattt ttattctctt tctctcttcg atggtctcac aaaaatatta aacctctttc 172980
tgatggtgtc actaaaatat ttttattctc attctctctt caatggagtc ataaaatatt 173040
tttattctct ttctctcttc gatggtctca caaaaatatt aaacctcttt ctgatggtgt 173100
cactaaaata tttttattct cattctctct tcaatggagt cataaaatat ttttattctc 173160
tttctctctt tgatggtctc ataaaaaaag ttttacaaaa atatttttat tctctttctc 173220
tctttgatgg tctcataaaa aatattaaac ctctttctga tggtgtcact aaaatatttt 173280
tattctcttt ctctcttcaa tggagtcata aaatattttt attctctttc tctcttcgat 173340
ggtctcacaa aaatattaaa cctctttctg atggtgtcac taaaatattt ttattctcat 173400
tctctcttca atggagtcat aaaatatttt tattctcttt ctctctttga tggtctcata 173460
aaaaaagttt tacaaaaata tttttattct ctttctctct ttgatggtct cataaaaaaa 173520
gttttacaaa aatattttta ttctctttct ctctttgatg gtctcataaa aaaagtttta 173580
caaaaatatt tttattctct ttctctcttt gatggtctca taaaaaaagt tttacaaaaa 173640
tatttttatt ctctttctct ctttgatggt ctcataaaaa atattaaacc tctttctgat 173700
ggtgtcacta aaatattttt attctcattc tctcttcaat ggagtcataa aatattttta 173760
ttctctttct ctcttcgatg gtctcacaaa aatattaaac ctctttctga tggtgtcact 173820
aaaatatttt tattctcatt ctctcttcaa tggagtcata aaatattttt attctctttc 173880
tctctttgat ggtctcataa aaaaagtttt acaaaaatat ttttattctc tttctctctt 173940
tgatggtctc ataaaaaaag ttttacaaaa atatttttat tctctttctc tctttgatgg 174000
tctcataaaa aaagttttac aaaaatattt ttattctctt tctctctttg atggtctcat 174060
aaaaaaagtt ttacaaaaat atttttattc tctttctctc tttgatggtc tcacaaaaat 174120
attaaacctc tttctgatgg agtcgtaaaa aagttttatc tctttctcct tcgatggtct 174180
cacaaaaata ttaaacctct ttctgatgga gtcgtaaaaa agttttatct ctttctctct 174240
tcgatggtct cacaaaaata ttaaacctct ttctgatgga gtcgtaaaaa agttttatct 174300
ctttctctct tcgatggtct cactaaaata tttttattc tctttctgat gcatcaacta 174360
tttcttaaac aataacgtcc aacaacatat actcgtcgag cttatcaaca tcccctatgc 174420
ccatctaggt taccagacaa ttgtatatca taaaataatg tttataattt ttacaaaaat 174480
atttttattc tctttctctc tttgatggtc tcataaaaaa agttttacaa aaatattttt 174540
attctctttc tctctttgat ggtctcataa aaaatattaa acctctttct gatggtgtca 174600
ctaaaatatt tttattctca ttctctcttc aatggagtca taaaatattt ttattctctt 174660
tctctcttcg atggtctcac aaaaatatta aacctctttc tgatggtgtc actaaaatat 174720
ttttattctc attctctctt caatggagtc ataaaatatt tttattctct ttctctcttt 174780
gatggtctca taaaaaaagt tttacaaaaa tatttttatt ctctttctct ctttgatggt 174840
ctcataaaaa aagttttaca aaaatatttt tattctcttt ctctctttga tggtctcata 174900
aaaaaagttt tacaaaaata tttttattct ctttctctct ttgatggtct cataaaaaaa 174960
gttttacaaa aatattttta ttctctttct ctctttgatg gtctcataaa aaaagtttta 175020
caaaaatatt tttattctct ttctctcttt gatggtctca taaaaaaagt tttacaaaaa 175080
tatttttatt ctctttctct ctttgatggt ctcataaaaa aagttttaca aaaatatttt 175140
tattctcttt ctctctttga tggtctcata aaaaatatta aacctctttc tgatggtgtc 175200
actaaaatat ttttattctc tttctctctt caatggagtc ataaaatatt tttattctct 175260
ttctctcttc gatggtctca caaaaatatt aaacctcttt ctgatggtgt cactaaaata 175320
tttttattct cattctctct tcaatggagt cataaaatat ttttattctc tttctctctt 175380
tgatggtctc ataaaaaaag ttttacaaaa atatttttat tctctttctc tctttgatgg 175440
tctcataaaa aaagttttac aaaaatattt ttattctctt tctctctttg atggtctcat 175500
aaaaaaagtt ttacaaaaat atttttattc tctttctctc tttgatggtc tcataaaaaa 175560
agttttacaa aaatattttt attctctttc tctctttgat ggtctcataa aaaaagtttt 175620
acaaaaatat ttttattctc tttctctctt tgatggtctc ataaaaaata ttaaacctct 175680
ttctgatggt gtcactaaaa tatttttatt ctctttctct cttcaatgga gtcataaaat 175740
atttttattc tctttctctc ttcgatggtc tcacaaaaat attaaacctc tttctgatgg 175800
tgtcactaaa atatttttat tctctttctc tcttcaatgg agtcataaaa tatttttatt 175860
ctctttctct ctttgatggt ctcataaaaa aagttttaca aaaatatttt tattctcttt 175920
ctctctttga tggtctcata aaaaaagttt tacaaaaata tttttattct ctttctctct 175980
ttgatggtct cataaaaaaa gttttacaaa aatattttta ttctctttct ctctttgatg 176040
gtctcataaa aaaagtttta caaaaatatt tttattctct ttctctcttt gatggtctca 176100
taaaaaaagt tttacaaaaa tatttttatt ctctttctct ctttgatggt ctcataaaaa 176160
aagttttaca aaaatatttt tattctcttt ctctctttga tggtctcata aaaaaagttt 176220
tacaaaaata tttttattct ctttctctct ttgatggtct cataaaaaat attaaacctc 176280
tttctgatgg tgtcactaaa atatttttat tctcatttc tctttctctc ttcaatggag 176340
tcataaaata tttttattct ctttctctct ttgatggtct cataaaaaat attaaacctc 176400
tttctgatgg tgtcactaaa atatttttat tctcattctc tcttcaatgg agtcataaaa 176460
aagttttatc tctttctctc ttcgatggtc tcacaaaaat attaaacctc tttctgatgg 176520
agtcgtaaaa aagttttatc tctttctctc ttcgatggtc tcacaaaaat attaaacctc 176580
tttctgatgc atcaactatt tcttaaacaa taacgtccaa caacatatac tcatccccta 176640
tgcccatcta ggttaccaga caattgtata tcataaaata atgtttataa tttacacgtt 176700
aaaatcatat aataaaacgt agatcgtata atattttttg gtatataaat gatctagtaa 176760
aatccatgta ggggatactg ctcacatttt ttctttggta caaaatttca cacaagtttt 176820
tatacagaca aattcttgtc catatatttt aaaacattga cttttgtact aagaaaaata 176880
tctagactaa ctatctcttt ctctttctct cttcgatggt ctttctgatg gagtcgtaaa 176940
aaagttttat ctctttctct cttcgatggt ctcacaaaaa tattaaacct ctttctgatg 177000
gagtcgtaaa aaagttttat ctctttctct cttcgatggt ctcacaaaaa tattaaacct 177060
ctttctgatg gagtcgtaaa aaagttttat ctctttctcc ttcgatggtc tcacaaaaat 177120
attaaacctc tttctgatgg agtcgtaaaa aagttttatc tctttctctc ttcgatggtc 177180
tcacaaaaat attaaacctc tttctgatgg tgtcactaaa atatttttat tctctttctc 177240
tcttcgatgg tctcacaaaa atattaaacc tctttctgat ggagtcgtaa aaaagtttta 177300
tctctttctc cttcgatggt ctcacaaaaa tattaaacct ctttctgatg gagtcgtaaa 177360
aaagttttat ctctttctct cttcgatggt ctcacaaaaa tattaaacct ctttctgatg 177420
gagtcgtaaa aaagttttat ctctttctcc ttcgatggtc tcacaaaaat attaaacctc 177480
tttctgatgg agtcgtaaaa aagttttatc tctttctcct tcgatggtct cacaaaaata 177540
ttaaacctct ttctgatgga gtcgtaaaaa agttttatct ctttctcctt cgatggtctc 177600
acaaaaatat taaacctctt tctgatggag tcgtaaaaaa gttttatctc tttctctctt 177660
cgatggtctc acaaaaatat taaacctctt tctgatggag tcgtaaaaaa gttttatctc 177720
tttctctctt cgatggtctc acaaaaatat taaacctctt tctgatggag tcgtaaaaaa 177780
gttttatctc tttctccttc gatggtctca caaaaatatt aaacctcttt ctgatggtct 177840
ctataaagcg attgattttt cttaccctct agagtttcct acggtcgttg gtcacacatt 177900
tttttctaga cactaaataa ata 177923

<210> SEQ ID NO 3
<211> LENGTH: 150
<212> TYPE: PRT
<213> ORGANISM: Vaccinia virus

<400> SEQUENCE: 3

Met Gly Ile Gln His Glu Phe Asp Ile Ile Ile Asn Gly Asp Ile Ala
1 5 10 15

Leu Arg Asn Leu Gln Leu His Lys Gly Asp Asn Tyr Gly Cys Lys Leu
20 25 30

Lys Ile Ile Ser Asn Asp Tyr Lys Lys Leu Lys Phe Arg Phe Ile Ile
35 40 45

Arg Pro Asp Trp Ser Glu Ile Asp Glu Val Lys Gly Leu Thr Val Phe
50 55 60

Ala Asn Asn Tyr Ala Val Lys Val Asn Lys Val Asp Asp Thr Phe Tyr
65 70 75 80

Tyr Val Ile Tyr Glu Ala Val Ile His Leu Tyr Asn Lys Lys Thr Glu
85 90 95

Ile Leu Ile Tyr Ser Asp Asp Glu Asn Glu Leu Phe Lys His Tyr Tyr
100 105 110

Pro Tyr Ile Ser Leu Asn Met Ile Ser Lys Lys Tyr Lys Val Lys Glu
115 120 125

Glu Asn Tyr Ser Ser Pro Tyr Ile Glu His Pro Leu Ile Pro Tyr Arg
130 135 140

Asp Tyr Glu Ser Met Asp
145 150

<210> SEQ ID NO 4
<211> LENGTH: 4445
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
gcggccgcct tcttgttgta ctgtaacttc tcgttttgtt agatgtttgc atcgtgcttt 60
aacatcaatg gtacaaattt tatcctcgct ttgtgtatca tattcgtccc tactataaaa 120
ttgtatattc agattatcat gagatgtgta tacgctaacg gtatcaataa acggagcaca 180
ccatttagtc ataaccgtaa tccaaaaatt tttaaagtat atcttaacga aagaagttgt 240
gtcattgtct acggtgtatg gtactagatc ctcataagtg tatatatcta cagtaatgtt 300

```
taatttatca aatggttgat aatatggatc ctcatgacaa tttccgaaga tggaaatgag    360
atatagacat gcaataaatc taattgcgga catggttact ccttaaaaaa atacgaataa    420
tcaccttggc tatttagtaa gtgtcattta acactatact catagcggcc gccgcgcgta    480
atacgactca ctatagggcg aattggagct ctttttatct gcgcggttaa ccgccttttt    540
atccatcagg tgatctgttt ttattgtgga gtctagaact agtggatccc ccgggctgca    600
ggaattcgat atcaagctca ggcctagatc tgtcgacttc gagcttattt atattccaaa    660
aaaaaaaaat aaaatttcaa tttttaagct ttcactaatt ccaaacccac ccgcttttta    720
tagtaagttt ttcacccata aataataaat acaataatta atttctcgta aaagtagaaa    780
atatattcta atttattgca cggtaaggaa gtagatcata actcgaggaa ttggggatct    840
ctataatctc gcgcaaccta ttttcccctc gaacactttt taagccgtag ataaacaggc    900
tgggacactt cacacgcgta tggtcagtaa aggtgaggag ctttttacag gagttgtgcc    960
aatacttgtg gagttagacg gagatgtaaa tggtcataag ttttctgttt cgggagaggg   1020
tgaaggtgac gcaacttatg gaaagttaac tttaaagttc atctgcacaa cgggtaaatt   1080
gccagttccc tggcctacat tagtaaccac gttgacttac ggagtccaat gcttttcacg   1140
ataccctgat cacatgaagc aacacgattt ctttaaatcg gcaatgcccg agggttacgt   1200
gcaggagaga acaatctttt ttaaggacga cggaaactat aaaacccgag ccgaagtaaa   1260
atttgaaggt gacacattag taaatcgaat tgaattgaaa ggtattgact ttaaagaaga   1320
tggtaacatt ttgggacaca agcttgagta caactacaac agtcacaacg tatatatcat   1380
ggccgataag cagaagaatg gaatcaaagt gaatttcaag atccgacata atatagaaga   1440
tggatcagtt caattagccg accactacca acagaacact cctattggag acggacccgt   1500
tttgttaccg gataatcact acctaagtac acagtccgct ttgagtaaag accccaacga   1560
gaaacgagac catatggtgc ttttggagtt cgttacggca gccggaatta cgttaggtat   1620
ggatgaatta tataagtaaa cgcgttcttt tcaacgcctg gcactgccgg gcgttgttct   1680
ttttaacttc aggcgggtta caatagtttc cagtaagtat tctggaggct gcatccatga   1740
cacaggcaaa cctgcggatc ccagcttttg ttccctttag tgagggttaa ttgcgcgcgc   1800
atgcactgaa tggatgaacg aataccgacg gcgttaatag taatttactt tttcatcttt   1860
acatattggg tactagtttt actatcataa gtttataaat tccacaagct actatggaat   1920
aagccaacca tcttagtata acacacatgt cttaaagttt attaattaat tacatgttgt   1980
tttatatatc gctacgaatt taaacagaga aatcagttta ggaaaaaaaa atatctatct   2040
acatcatcac gtctctgtat tctacgatag agtgctactt taagatgaga catatccgtg   2100
tcatcaaaaa tatactccat taaaatgatt attccggcag cgaacttgat attggatata   2160
tcacaacctt tgttaatatc tacgacaata gacagcagtc ccatggttcc ataaacagtg   2220
agtttatctt tctttgaaga gatattttgt agagatctta taaaactgtc gaatggcatg   2280
ctaggccgcg ttgctggcgt ttttccatag gctccgcccc cctgacgagc atcacaaaaa   2340
tcgacgctca agtcagaggt ggcgaaaccc gacaggacta taaagatacc aggcgtttcc   2400
ccctggaagc tccctcgtgc gctctcctgt tccgaccctg ccgcttaccg gatacctgtc   2460
cgcctttctc ccttcgggaa gcgtggcgct ttctcaatgc tcacgctgta ggtatctcag   2520
ttcggtgtag gtcgttcgct ccaagctggg ctgtgtgcac gaaccccccg ttcagcccga   2580
ccgctgcgcc ttatccggta actatcgtct tgagtccaac ccggtaagac acgacttatc   2640
gccactggca gcagccactg gtaacaggat tagcagagcg aggtatgtag gcggtgctac   2700
```

agagttcttg aagtggtggc ctaactacgg ctacactaga aggacagtat ttggtatctg 2760
cgctctgctg aagccagtta ccttcggaaa aagagttggt agctcttgat ccggcaaaca 2820
aaccaccgct ggtagcggtg gtttttttgt ttgcaagcag cagattacgc gcagaaaaaa 2880
aggatctcaa gaagatcctt tgatcttttc tacggggtct gacgctcagt ggaacgaaaa 2940
ctcacgttaa gggattttgg tcatgagatt atcaaaaagg atcttcacct agatcctttt 3000
aaattaaaaa tgaagtttta aatcaatcta aagtatatat gagtaaactt ggtctgacag 3060
ttaccaatgc ttaatcagtg aggcacctat ctcagcgatc tgtctatttc gttcatccat 3120
agttgcctga ctccccgtcg tgtagataac tacgatacgg gagggcttac catctggccc 3180
cagtgctgca atgataccgc gagacccacg ctcaccggct ccagatttat cagcaataaa 3240
ccagccagcc ggaagggccg agcgcagaag tggtcctgca actttatccg cctccatcca 3300
gtctattaat tgttgccggg aagctagagt aagtagttcg ccagttaata gtttgcgcaa 3360
cgttgttgcc attgctgcag gcatcgtggt gtcacgctcg tcgtttggta tggcttcatt 3420
cagctccggt tcccaacgat caaggcgagt tacatgatcc cccatgttgt gcaaaaaagc 3480
ggttagctcc ttcggtcctc cgatcgttgt cagaagtaag ttggccgcag tgttatcact 3540
catggttatg gcagcactgc ataattctct tactgtcatg ccatccgtaa gatgcttttc 3600
tgtgactggt gagtactcaa ccaagtcatt ctgagaatag tgtatgcggc gaccgagttg 3660
ctcttgcccg gcgtcaacac gggataatac cgcgccacat agcagaactt taaaagtgct 3720
catcattgga aaacgttctt cggggcgaaa actctcaagg atcttaccgc tgttgagatc 3780
cagttcgatg taacccactc gtgcacccaa ctgatcttca gcatctttta ctttcaccag 3840
cgtttctggg tgagcaaaaa caggaaggca aaatgccgca aaaaagggaa taagggcgac 3900
acggaaatgt tgaatactca tactcttcct ttttcaatat tattgaagca tttatcaggg 3960
ttattgtctc atgagcggat acatatttga atgtatttag aaaaataaac aaataggggt 4020
tccgcgcaca tttccccgaa aagtgccacc tgacgtctaa gaaaccatta ttatcatgac 4080
attaacctat aaaaataggc gtatcacgag gccctttcgt cttcgaataa atacctgtga 4140
cggaagatca cttcgcagaa taaataaatc ctggtgtccc tgttgatacc gggaagccct 4200
gggccaactt ttggcgaaaa tgagacgttg atcggcacgt aagaggttcc aactttcacc 4260
ataatgaaat aagatcacta ccgggcgtat tttttgagtt atcgagattt tcaggagcta 4320
aggaagctaa aatggagaaa aaaatcactg gatataccac cgttgatata tcccaatggc 4380
atcgtaaaga acattttgag gcatttcagt cagttgctca atgtacctat aaccagaccg 4440
ttcag 4445

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
atgggtatac agcacgaatt c 21

<210> SEQ ID NO 6
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 6

ttaatccatg gactcataat c                                              21
```

VACCINIA VIRUS MUTANTS USEFUL FOR CANCER IMMUNOTHERAPY

CROSS-REFERENCE TO RELATED APPLICATIONS

This application is a divisional of U.S. patent application Ser. No. 16/612,127, filed Nov. 8, 2019, which is a National Stage Application of PCT/US2018/032451, filed May 11, 2018, which claims the benefit of and priority to U.S. Provisional Application No. 62/505,713, filed May 12, 2017, each of which is incorporated herein by reference in its entirety.

STATEMENT OF FEDERALLY FUNDED RESEARCH

This invention was made with government support under AI073736, AI095692, AR068118, and CA008748 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 8, 2018, is named 115872-0781_SL.txt and is 492,760 bytes in size.

TECHNICAL FIELD

The technology of the present disclosure relates generally to the fields of oncology, virology, and immunotherapy. In particular, the present technology relates to the use of poxviruses, including a recombinant modified vaccinia Ankara (MVA) virus or vaccinia virus with deletion of vaccinia host range factor C7 (MVAΔC7L and VACVΔC7L, respectively), alone or in combination with immune checkpoint blocking agents, as an oncolytic and immunotherapeutic composition. In some embodiments, the technology of the present disclosure relates to an MVAΔC7L or VACVΔC7L virus further modified to express human Fms-like tyrosine kinase 3 ligand (hFlt3L).

BACKGROUND

The following description is provided to assist the understanding of the reader. None of the information provided or references cited is admitted to be prior art.

Malignant tumors such as melanoma are inherently resistant to conventional therapies and present significant therapeutic challenges. Immunotherapy is an evolving area of research and an additional option for the treatment of certain types of cancers. The immunotherapy approach rests on the rationale that the immune system may be stimulated to identify tumor cells, and target them for destruction. Despite presentation of antigens by cancer cells and the presence of immune cells that could potentially react against tumor cells, in many cases, the immune system is not activated or is affirmatively suppressed. Key to this phenomenon is the ability of tumors to protect themselves from immune response by coercing cells of the immune system to inhibit other cells of the immune system. Tumors develop a number of immunomodulatory mechanisms to evade antitumor immune responses. Thus, improved immunotherapeutic approaches are needed to enhance host antitumor immunity and target tumor cells for destruction.

SUMMARY

In one aspect, the present disclosure provides an engineered modified vaccinia Ankara (MVA) virus strain comprising a disruption of a C7L gene. In some embodiments, the disrupted C7L gene does not encode a full-length, wild-type gene product. In some embodiments, the disrupted C7L gene comprises an insertion of a heterologous nucleic acid sequence into the coding sequence of the C7L gene. In some embodiments, the disrupted C7L gene comprises an insertion of one or more gene cassettes. In some embodiments, the disrupted C7L gene comprises replacement of at least a portion of the gene with one or more gene cassettes. In some embodiments, the disrupted C7L gene comprises replacement of the entire C7L gene with one or more gene cassettes. In some embodiments, the one or more gene cassettes comprise a nucleotide sequence encoding a selectable marker. In some embodiments, the one or more gene cassettes comprise a nucleotide sequence encoding human Fms-like tyrosine kinase 3 ligand (hFlt3 L).

In one aspect, the present disclosure provides an engineered modified vaccinia Ankara (MVA) virus strain comprising a disruption of a C7L gene, wherein the MVA strain exhibits one or more of the following characteristics: (i) induction of increased levels of interferon beta (IFNB) expression in dendritic cells and THP-1 cells as compared to dendritic cells and THP-1 cells infected with the corresponding wild-type strain; (ii) induction of increased levels of TBK1 and IRF3 phosphorylation in dendritic cells as compared to dendritic cells infected with the corresponding wild-type strain; (iii) induction of increased levels of ISG expression in dendritic cells as compared to dendritic cells infected with the corresponding wild-type strain; (iv) induction of increased levels of at least one of IFNB, CCL4, CCL5, and CXCL10 in cancer cells as compared to cancer cells infected with the corresponding wild-type strain; and (v) reduction of tumor volume in tumors contacted with the engineered MVA strain as compared to tumors infected with the corresponding wild-type strain. In some embodiments, the cancer cells comprise melanoma cells. In some embodiments, the tumor comprises malignant melanoma.

In one aspect, the present disclosure provides an immunogenic composition comprising an engineered modified vaccinia Ankara (MVA) virus strain comprising a disruption of a C7L gene. In some embodiments, the immunogenic composition further comprises a pharmaceutically acceptable carrier. In some embodiments, the immunogenic composition further comprises a pharmaceutically acceptable adjuvant.

In one aspect, the present disclosure provides an engineered attenuated vaccinia virus (VACV) strain comprising a disruption of a C7L gene. In some embodiments, the disrupted C7L gene does not encode a full-length, wild-type gene product. In some embodiments, the disrupted C7L gene comprises an insertion of a heterologous nucleic acid sequence into the coding sequence of the C7L gene. In some embodiments, the disrupted C7L gene comprises an insertion of one or more gene cassettes. In some embodiments, the disrupted C7L gene comprises replacement of at least a portion of the gene with one or more gene cassettes. In some embodiments, the one or more gene cassettes comprise a nucleotide sequence encoding a selectable marker. In some embodiments, the one or more gene cassettes comprise a nucleotide sequence encoding human Fms-like tyrosine kinase 3 ligand (hFlt3L). In some embodiments, mice infected with the engineered attenuated VACV strain have in increased post-infection lifespan compared to mice infected with a corresponding wild-type strain.

In one aspect, the present disclosure provides an immunogenic composition comprising an engineered attenuated vaccinia virus (VACV) strain comprising a disruption of a C7L gene. In some embodiments, the immunogenic composition further comprises a pharmaceutically acceptable carrier. In some embodiments, the immunogenic composition further comprises a pharmaceutically acceptable adjuvant.

In one aspect, the present disclosure provides a recombinant vaccinia virus (VACV) nucleic acid sequence, wherein the nucleic acid sequence between position 15,716 and 16,168 of SEQ ID NO: 1 is replaced with a heterologous nucleic acid sequence comprising an open reading frame that encodes a selectable marker. In some embodiments, the open reading frame of the heterologous nucleic acid sequence is operably linked to a promoter that is capable of directing expression of the selectable marker. In some embodiments, the selectable marker is a bioluminescent protein, a fluorescent protein, a chemiluminescent protein, a xanthine-guanine phophoribosyl transferase gene (gpt), or any combination thereof. In some embodiments, the selectable marker is green fluorescent protein (GFP). In some embodiments, the heterologous nucleic acid sequence further comprises an open reading frame that encodes human Fms-like tyrosine kinase 3 ligand (hFlt3L).

In one aspect, the present disclosure provides a recombinant modified vaccinia Ankara (MVA) virus nucleic acid sequence, wherein the nucleic acid sequence between position 18,407 and 18,859 of SEQ ID NO: 2 is replaced with a heterologous nucleic acid sequence comprising an open reading frame that encodes a selectable marker. In some embodiments, the open reading frame of the heterologous nucleic acid sequence is operably linked to a promoter that is capable of directing expression of the selectable marker. In some embodiments, the selectable marker is a bioluminescent protein, a fluorescent protein, a chemiluminescent protein, a xanthine-guanine phophoribosyl transferase gene (gpt), or any combination thereof. In some embodiments, the selectable marker is green fluorescent protein (GFP). In some embodiments, the heterologous nucleic acid sequence further comprises an open reading frame that encodes human Fms-like tyrosine kinase 3 ligand (hFlt3L).

In one aspect, the present disclosure provides a method for treating a solid tumor in a subject in need thereof, the method comprising delivering to a tumor a composition comprising an effective amount of an engineered modified vaccinia Ankara (MVA) virus strain comprising a disruption of a C7L gene (MVAΔC7L) and/or a MVAΔC7L virus genetically engineered to express hFlt3L (MVAΔC7L-hFlt3L). In some embodiments, the disruption comprises a deletion of the C7L gene. In some embodiments, treatment comprises one or more of the following: inducing an immune response in the subject against the tumor or enhancing or promoting an ongoing immune response against the tumor in the subject, reducing the size of the tumor, eradicating the tumor, inhibiting growth of the tumor, inhibiting metastatic growth of the tumor, inducing apoptosis of tumor cells, or prolonging survival of the subject. In some embodiments, the induction, enhancement, or promotion of the immune response comprises one or more of the following: (i) increased levels of interferon beta (IFNB) expression in dendritic cells and THP-1 cells as compared to dendritic cells and THP-1 cells infected with the corresponding wild-type strain; (ii) increased levels of TBK1 and IRF3 phosphorylation in dendritic cells as compared to dendritic cells infected with the corresponding wild-type strain; (iii) increased levels of ISG expression in dendritic cells as compared to dendritic cells infected with the corresponding wild-type strain; and (iv) increased levels of at least one of IFNB, CCL4, CCL5, and CXCL10 in tumor cells as compared to tumor cells infected with the corresponding wild-type strain. In some embodiments, the composition is administered by intratumoral or intravenous injection or a simultaneous or sequential combination of intratumoral and intravenous injection. In some embodiments, the tumor is melanoma, colon, breast, or prostate carcinoma. In some embodiments, the composition further comprises one or more immune checkpoint blocking agents. In some embodiments, the immune checkpoint blocking agent is selected from the group consisting of: CTLA-4, CD80, CD86, PD-1, PDL1, PDL2, LAG3, B7-H3, B7-H4, TM/13, ICOS, II DLBCL inhibitors, BTLA, ipilimumab, nivolumab, pembrolizumab, pidilizumab, AMP-224, MPDL3280A, BMS-936559, MED14736, MSB 00107180, and any combination thereof.

In one aspect, the present disclosure provides a method for treating a solid tumor in a subject in need thereof, the method comprising delivering to a tumor a composition comprising an effective amount of an engineered vaccinia virus (VACV) strain comprising a disruption of a C7L gene VACVΔC7L) and/or a VACVΔC7L virus genetically engineered to express hFlt3L (VACVΔC7L-hFlt3L). In some embodiments, the disruption comprises a deletion of the C7L gene. In some embodiments, treatment comprises one or more of the following: inducing an immune response in the subject against the tumor or enhancing or promoting an ongoing immune response against the tumor in the subject, reducing the size of the tumor, eradicating the tumor, inhibiting growth of the tumor, inhibiting metastatic growth of the tumor, inducing apoptosis of tumor cells, or prolonging survival of the subject. In some embodiments, the induction, enhancement, or promotion of the immune response comprises one or more of the following: (i) increased levels of interferon beta (IFNB) expression in dendritic cells and THP-1 cells as compared to dendritic cells and THP-1 cells infected with the corresponding wild-type strain; (ii) increased levels of TBK1 and IRF3 phosphorylation in dendritic cells as compared to dendritic cells infected with the corresponding wild-type strain; (iii) increased levels of ISG expression in dendritic cells as compared to dendritic cells infected with the corresponding wild-type strain; and (iv) increased levels of at least one of IFNB, CCL4, CCL5, and CXCL10 in tumor cells as compared to tumor cells infected with the corresponding wild-type strain. In some embodiments, the composition is administered by intratumoral or intravenous injection or a simultaneous or sequential combination of intratumoral and intravenous injection. In some embodiments, the tumor is melanoma, colon, breast, or prostate carcinoma. In some embodiments, the composition further comprises one or more immune checkpoint blocking agents. In some embodiments, the immune checkpoint blocking agent is selected from the group consisting of: CTLA-4, CD80, CD86, PD-1, PDL1, PDL2, LAG3, B7-H3, B7-H4, TIM3, ICOS, II DLBCL inhibitors, BTLA, ipilimumab, nivolumab, pembrolizumab, pidilizumab, AMP-224, MPDL3280A, BMS-936559, MED14736, MSB 00107180, and any combination thereof.

In one aspect, the present disclosure provides a method of stimulating an immune response comprising administering to a subject an immunogenic composition comprising an engineered modified vaccinia Ankara (MVA) virus strain comprising a disruption of a C7L gene.

In one aspect, the present disclosure provides a method of stimulating an immune response comprising administering to a subject an immunogenic composition comprising an engineered attenuated vaccinia virus (VACV) strain comprising a disruption of a C7L gene.

BRIEF DESCRIPTION OF THE DRAWINGS

FIG. 1A: HEK293T-cells ($2\times10^5$) in 24-well plates were transfected with plasmids expressing IFNB-luc reporter, STING, C7L as indicated. Dual luciferase assays were performed at 24 h post transfection. The relative luciferase activity was expressed as arbitrary units by normalizing firefly luciferase activity under IFNB promoter to Renilla luciferase activity from a control plasmid pRL-TK. Fold induction was calculated by dividing relative luciferase activity by background level. Data are means±SEM (n=3). FIGS. 1B-1D: HEK293T-cells ($2\times10^5$) were transfected with plasmids expressing TBK1, IRF3, or IRF3-5D with or without increasing amounts of C7 (10, 50, or 250 ng). IRF3-5D is a phosphorylation active mutant IRF3. Data are means±SEM (n=3). (*P<0.05; P<0.01; *P<0.001, t test).

FIG. 1E: Whole cell lysates (WCL) were blotted with anti-Flag and anti-C7 antibody.

FIG. 2A: HEK293T-cells ($2\times10^5$) were transfected with plasmids expressing TLR3, IFN-β-luc reporter and increasing amount of C7 expression plasmid (10, 50, or 250 ng). After 24 h, cells were treated with poly IC (5 μg/ml). Luciferase activity was assayed 24 h post poly IC treatment. Data are means±SEM (n=3). FIG. 2B: HEK293T-cells ($2\times10^5$) were transfected with plasmids expressing TRIF, IFNB-luc reporter and increasing amount of C7 (10, 50, or 250 ng). Dual luciferase assays were performed at 24 h post transfection. Data are means±SEM (n=3). FIG. 2C: HEK293T-cells ($2\times10^5$) were transfected with plasmids expressing MAVS, IFNB-luc reporter and increasing amount of C7 (10, 50, or 250 ng). Dual luciferase assays were performed at 24 h post transfection. Data are means±SEM (n=3). (*P<0.05; P<0.01; *P<0.001, t test).

FIGS. 3C-3D: THP-1 stable cell lines expressing C7 or with empty vector ($2\times10^6$) were differentiated by (PMA; 20 ng/ml) for 3 days then were treated as in (FIGS. 3A-3B). Data are means±SEM (n=3). (P<0.01; *P<0.001, t test).

FIG. 5B: Same as in (FIG. 5A), BMDCs were infected with WT VACV, MVA or MVAΔC7L at a MOI of 10. Supernatants were collected at 22 h post infection. The concentrations of IFN-β were determined by ELISA. Data are means±SEM (n=3). FIG. 5D: BMDCs ($1\times10^6$) were infected with MVA or MVAΔC7L at a MOI of 10. Cells were collected at 2, 4, and 8 h post infection. Western blot analysis was performed using anti-phospho-TBK1, anti-TBK1, anti-phosphoserine-396 of IRF3, and anti-IRF3. β-actin was used as a loading control.

FIG. 6A: Screening of vaccinia ORFs (C1L-C10L) for their abilities to inhibit Type I IFN-induced interferon-stimulated response element (ISRE) activity. HEK293T-cells ($2\times10^5$) were transfected with plasmids expressing ISRE-luc reporter, which expresses firefly luciferase once ISRE is activated, and control plasmid pRL-TK, which expresses Renilla luciferase once it is activated and vaccinia ORFs (C1L-C10L) as indicated. 24 h post transfection, cells were treated with human IFN-β at a final concentration of 1000 U/ml. Dual luciferase assays were performed at 24 h post IFN-β treatment. The relative luciferase activity was expressed as arbitrary units by normalizing firefly luciferase activity to Renilla luciferase activity. Data are means±SEM (n=3). (P<0.01, t test). FIG. 6B: Conditions and analyses were performed as in FIG. 6A**, except that HEK293T cells were transfected with increasing amounts of plasmids containing C7L gene (10, 50, or 250 ng). Data are means±SEM (n=3). (*P<0.05; P<0.01; *P<0.001, t test).

FIG. 10A shows the western blot of whole cell lysates (WCL) using anti-FLAG and anti-HA antibodies demonstrating the expression of STAT1 or STAT2 and C7-HA in transfected cells. β-actin was used as a loading control. Following immunoprecipitation of whole cell lysates with an anti-HA antibody, the C7-HA protein-interacting proteins were then probed with anti-Flag antibody. FIG. 10B shows western blot of anti-HA immunoprecipitant using anti-Flag antibody, demonstrating that only Flag-tagged STAT2 was pulled down by anti-C7-HA from whole cell lysates.

FIG. 11A shows that C7 gene was deleted from VACV genome in VACVΔC7L virus. Western blot analysis was performed in HeLa cells infected with WT VACV or VACVΔC7L. FIG. 11B shows that vaccinia C7 protein was not expressed by the VACVΔC7L infected cells.

FIG. 12A shows plaque assay of WT VACV and VACVΔC7L on BSC40 cells (an African green monkey kidney cell line) pre-treated or mock-treated with human IFN-β at a final concentration of 1000 U/ml for 12 h prior to infection. The expected plaque forming units (pfu) in each well based on the viral titers were shown at the left upper corner. After the initial inoculation, the cells were either continued with or without human IFN-b at a final concentration of 1000 U/ml as indicated for 48 h before they were stained with crystal violet dye. FIG. 12B are the multistep growth curves of WT VACV and VACVΔC7L in the presence or absence of human IFN-β. BSC40 cells were pre-treated or mock-treated with human IFN-β at a final concentration of 1000 U/ml for 12 h. Cells were then infected with WT VACV or VACVΔC7L at a MOI of 0.05 in the presence or absence of IFN-β as indicated. The infected cells were collected at indicated times, and viral titers were determined by plaque assay on BSC40 cells.

FIG. 13A is a graph of % initial weight over days post intranasal infection with WT VACV at increasing doses, including $2\times10^3$, $2\times10^4$, $2\times10^5$, or $2\times10^6$ plaque forming units (PFU), in WT C57BL/6J mice. FIG. 13B is the Kaplan-Meier survival curve of mice infected with increasing doses of WT VACV. n=10 in each group. FIG. 13C is a graph of % initial weight over days post intranasal infection with VACVΔC7L at increasing doses, including $2\times10^5$, $2\times10^6$, or $2\times10^7$ PFU in WT C57BL/6J mice. FIG. 13D is the Kaplan-Meier survival curve of mice infected with increasing doses of VACVΔC7L. n=10 in each group.

FIG. 14A is a graph of % initial weight over days post intranasal infection with WT VACV at $2\times10^5$ PFU in $STING^{Gt/Gt}$ mice and WT age-matched C57BL/6J controls. FIG. 14B is the Kaplan-Meier survival curve of $STING^{Gt/Gt}$ and WT mice infected with WT VACV. n=6 in each group. FIG. 14C is a graph of % initial weight over days post intranasal infection with VACVΔC7L at $2\times10^5$ PFU in $STING^{Gt/Gt}$ mice and WT age-matched C57BL/6J controls. FIG. 14D is the Kaplan-Meier survival curve of $STING^{Gt/Gt}$ and WT mice infected with VACVΔC7L. n=10 in each group.

FIG. 15A is a graph of % initial weight over days post intranasal infection of $STING^{Gt/Gt}$ and WT mice survived infection with VACVΔC7L challenged with WT VACV at $2\times10^6$ PFU. Naïve mice that have never been infected with VACVΔC7L were also challenged with WT VACV at the same dose. FIG. 15B is the Kaplan-Meier survival curve of $STING^{Gt/Gt}$ and WT mice initially infected and survived VACVΔC7L infection and then challenged with WT VACV at $2\times10^6$ PFU.

FIG. 16A is a graph of % initial weight over days post intranasal infection with VACVΔC7L at $2\times10^7$ pfu in $STAT2^{-/-}$ $IFNAR1^{-/-}$, $MDA5^{-/-}$ mice and WT age-matched C57BL/6J controls. FIG. 16B is the Kaplan-Meier survival curve of $STAT2^{-/-}$, $IFNAR1^{-/-}$, $MDA5^{-/-}$ mice and WT control mice infected with VACVΔC7L virus. n=5 in each group. FIG. 16C is a graph of viral titers (Log pfu) per gram of tissue harvested at 4 h post infection. n=3 in each group. FIG. 16D is a graph of % initial weight over days post intranasal infection with VACVΔC7L at $2\times10^2$, $2\times10^3$, $2\times10^4$, or $2\times10^5$ pfu in $STAT2^{-/-}$ mice. FIG. 16E is the Kaplan-Meier survival curve of $STAT2^{-/-}$ infected with VACVΔC7L at $2\times10^2$, $2\times10^3$, $2\times10^4$, or $2\times10^5$ pfu virus. n=5 in each group. FIG. 16F is a graph of % initial weight over days post intranasal infection with VACVΔC7L at $2\times10^2$, $2\times10^3$, or $2\times10^5$ pfu in $IFNAR1^{-/-}$ mice. FIG. 16G is the Kaplan-Meier survival curve of $STAT2^{-/-}$ infected with VACVΔC7L at $2\times10^2$, $2\times10^3$, or $2\times10^5$ pfu virus. n=5 in each group.

FIG. 17A: % initial weight over days post intranasal infection with VACVΔC7L at $2\times10^7$ pfu in $STING^{Gt/Gt}$, $MDA5^{-/-}STING^{Gt/Gt}$ mice, and WT age-matched C57BL/6J controls. FIG. 17B: Kaplan-Meier survival curve of $STING^{Gt/Gt}$, $MDA5^{-/-}STING^{Gt/Gt}$ mice, and WT controls infected with VACVΔC7L virus. n=5 in each group.

FIG. 18A: Dot plots of Siglec $F^+CD11c^+$ alveolar macrophages in the bronchoalveolar lavage (BAL); FIG. 18B: Percentages of alveolar macrophages out of $CD45^+$ cells in the BAL; FIG. 18C: Absolute numbers of alveolar macrophages in the BAL. FIG. 18D: Dot plots of $CD11c^+$ $MHC\text{-}II^{hi}$ conventional dendritic cells (cDCs) in the BAL at day 3 and day 6 post infection; FIG. 18E: Percentages of cDCs out of $CD45^+$ cells in the BAL; FIG. 18F: Absolute numbers of cDCs in the BAL. FIG. 18G: Dot plots of $Ly6G^+Ly6C^+$ neutrophils in the BAL at day 3 and day 6 post infection; FIG. 18H: Percentages of $Ly6G^+Ly6C^+$ neutrophils out of $CD45^+$ cells in the BAL; FIG. 18I: Absolute numbers of $Ly6G^+Ly6C^+$ neutrophils in the BAL. FIG. 18J: Dot plots of $CD8^+$ T cells in the BAL at day 6 post infection; FIG. 18K: Percentages of $CD8^+$ T cells out of $CD45^+$ cells and absolute numbers of $CD8^+$ T cells in the BAL. FIG. 18L: Dot plots of $CD4^+$ T cells in the BAL at day 6 post infection; FIG. 18M: Percentages of $CD4^+$ T cells out of $CD45^+$ cells and absolute numbers of $CD4^+$ T cells in the BAL.

FIGS. 19A-9B are graphical representations of data showing that VACVΔC7L-induced $CD8^+$ T cell recruitment is reduced in $STAT2^{-/-}$ or $IFNAR1^{-/-}$ mice. FIG. 19A: Dot plots of $CD8^+$ T cells in the BAL at day 6 post mock infection with PBS, or infection in VACVΔC7L ($2\times10^5$ pfu) in WT, $STAT2^{-/-}$, or $IFNAR^{-/-}$ mice.

FIG. 20A: Dot plots of $CD8^+$ T cells in the lungs at day 6 post infection; Percentages of $CD8^+$ T cells out of $CD45^+$ cells in the lungs. FIG. 20B: Dot plots of $CD4^+$ T cells in the lungs at day 6 post infection; Percentages of $CD4^+$ T cells out of $CD45^+$ cells in the lungs.

FIG. 22A is a graph of % initial weight over days post intranasal infection with VACVΔC7L. FIG. 22B is the Kaplan-Meier survival curve of mice infected with VACVΔC7L. n=5 in each group.

FIG. 23A is the concentrations of IFN-β in BAL determined by ELISA. FIG. 23B is cytokines and chemokines profiles in BAL determined by Luminex analysis (Cytokine 20-Plex Mouse Panel, ThermoFisher).

FIG. 25A: Lineage-negative epithelial stem/progenitor cells (LNEPs) are defined as $CD45^-CD16^-$ $CD32^-CD31$"$EpCAM^{hi}CD104^+$ cells, which are FACS sorted for in vitro culture. FIG. 25B: Immunofluorescent staining for SPC (surfactant C) in differentiated primary lung type II alveolar epithelial cells (AECs) after culturing of LNEPs grown on matrigel coated plates in the presence of keratinocyte growth factor for 4 days. FIG. 25C: RT-PCR analysis of IFNB, CCL4 and CCL5 in primary lung type II AECs after WT VACV or VACVΔC7L infection (at a MOI of 10) for 12 h. FIG. 25D: ELISA analysis of IFN-β, CCL4 and CCL5 from supernatants of primary lung type II AECs after WT VACV or VACVΔC7L infection for 24 h.

FIG. 26A is a graph of % initial weight over days post intranasal infection with WT VACV. FIG. 26B is the Kaplan-Meier survival curve of mice infected with WT VACV. n=5 in each group.

FIG. 28A is a scheme of tumor implantation and treatment for a B16-F10 bilateral tumor implantation model. Briefly, B16-F10 melanoma cells were implanted intradermally to the left and right flanks of C57B/6J mice ($5\times10^5$ to the right flank and $1\times10^5$ to the left flank). 8 days post tumor implantation, we intratumorally injected $2\times10^7$ pfu of MVA or MVAΔC7L to the larger tumors on the right flank. The tumor sizes were measured and the tumors were injected twice a week. The survival of mice was monitored. FIG. 28B is a graph of the Kaplan-Meier survival curve of tumor-bearing mice treated with either PBS, MVA, or MVAΔC7L (n=10, *P<0.05; *P<0.001; Mantel-Cox test). FIGS. 28C and 28D are graphical representations of data showing volumes of injected (FIG. 28C) and non-injected (FIG. 28**D) tumors over days after PBS, MVA, or MVAΔC7L injections.

FIG. 29A are graphs of FACS analyses of tumor-infiltrating lymphocytes in injected tumors in mice treated with MVA, MVAΔC7L, or PBS. Percentages of Granzyme $CD8^+$ T cells, Granzyme $13^+$ $CD4^+$ T cells, the ratios of $CD8^+$/Treg within injected tumors in the mice treated with PBS (n=4) or MVA (n=4), or MVAΔC7L (n=5) were shown (*P<0.05; **P<0.0001, t test). FIG. 29**B are graphs of FACS analyses data showing the percentages of Granzyme $13^+$ $CD8^+$ T cells, Granzyme $B^+$ $CD4^+$ T cells, the ratios of $CD8^+$/Treg within non-injected tumors in the mice treated with PBS (n=4) or MVA (n=4), or MVAΔC7L (n=5) were shown (*P<0.05; P<0.01; *P<0.001; **P<0.0001, t test). FIG. 29C is a graph of FACS data showing tyrosinase-related protein 2 (TRP2) tetramer positive $CD8^+$ T cells in the TDLNs of the mice treated with PBS (n=4) or MVA (n=4), or MVAΔC7L (n=5). FIG. 29**D is a graph of FACS data showing TRP-2 tetramer positive $CD8^+$ T cells in the non-draining LNs of the mice treated with PBS (n=4) or MVA (n=4), or MVAΔC7L (n=5) (*P<0.05; P<0.01; *P<0.001).

FIG. 30A: schematic diagram showing the generation of MVAΔC7L-hFlt3L recombinant virus through homologous recombination at the C7 flanking sequences (C6L and C8L). Briefly, a single cassette with GFP under the control of vaccinia p7.5 promoter and hFlt3L gene under the vaccinia synthetic early and late promoter (PsE/L) flanked by C6 and C8 sequences were inserted to replace C7 gene in the MVA genome. FIG. 30B: primers used to amplify inserts and PCR verification of the recombinant virus. FIG. 30C: replication curves of MVAΔC7L-hFlt3L in CEFs and BHK21 cells. Cells were infected with MVAΔC7L-hFlt3L at a MOI of 0.05, and were collected at 1, 24, 36, 48, and 72 h post infection. Viral titers were determined by titration on BHK21 cells. Fold changes were calculated comparing viral titers at 72 h post infection with those at 1 h post infection.

DETAILED DESCRIPTION

Figure 1A:
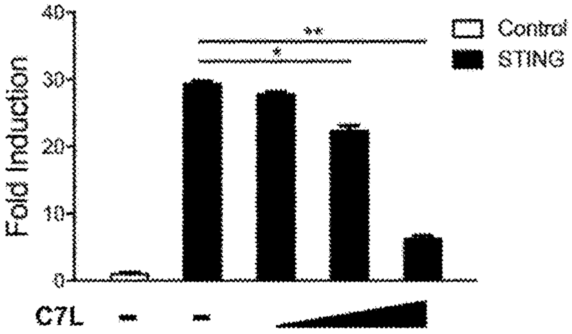
FIGS. 1A-1D are a series of graphical representations of data showing that vaccinia C7 inhibits STING, TBK1, or IRF3-mediated IFNB gene expression.

It is to be appreciated that certain aspects, modes, embodiments, variations, and features of the present technology are described below in various levels of detail in order to provide a substantial understanding of the present technology.

I. Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a," "an," and "the" include plural referents unless the content clearly dictates otherwise. For example, reference to "a cell" includes a combination of two or more cells, and the like.

As used herein, the term "about" encompasses the range of experimental error that may occur in a measurement and will be clear to the skilled artisan.

As used herein, "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus. This is in contrast to a killed or completely inactivated virus.

As used herein, "conjoint administration" refers to administration of a second therapeutic modality in combination with MVAΔC7L, MVAΔC7L-hFlt3L, VACVΔC7L, or VACVΔC7L-hFlt3L. For example, an immune checkpoint blocking agent administered in close temporal proximity with MVAΔC7L, MVAΔC7L-hFlt3L, VACVΔC7L, or VACVΔC7L-hFlt3L. For example, a PD-1/PDL-1 inhibitor and/or a CTLA4 inhibitor (in more specific embodiments, an antibody) can be administered simultaneously with MVAΔC7L, MVAΔC7L-hFlt3L, VACVΔC7L, or VACVΔC7L-hFlt3L (by intravenous or intratumoral injection when the MVAΔC7L, MVAΔC7L-hFlt3L, VACVΔC7L, or VACVΔC7L-hFlt3L is administered intratumorally or systemically as stated above) or before or after the MVAΔC7L, MVAΔC7L-hFlt3L, VACVΔC7L, or VACVΔC7L-hFlt3L administration. In some embodiments, if the MVAΔC7L, MVAΔC7L-hFlt3L, VACVΔC7L, or VACVΔC7L-hFlt3L administration and the immune checkpoint blocking agent are administered 1-7 days apart or even up to three weeks apart, this would still be within "close temporal proximity" as stated herein, therefore such administration will qualify as "conjoint."

The term "corresponding wild-type strain" is used herein to refer to the wild-type MVA or vaccinia virus (VACV) strain from which the engineered MVA or VACV strain was derived. As used herein, a wild-type MVA or VACV strain is a strain that has not been engineered to disrupt or delete (knock out) the C7 gene. The engineered MVA or VACV strain may have been modified to disrupt or delete (knock out) the C7 gene.

As used herein, the term "delivering" means depositing the MVAΔC7L, MVAΔC7L-hFlt3L, VACVΔC7L, or VACVΔC7L-hFlt3L of the present disclosure in the tumor microenvironment whether this is done by local administration to the tumor (intratumoral) or by, for example, intravenous route. The term focuses on MVAΔC7L, MVAΔC7L-hFlt3L, VACVΔC7L, or VACVΔC7L-hFlt3L that reaches the tumor itself. In some embodiments, "delivering" is synonymous with administering, but it is used with a particular administration locale in mind, e.g., intratumoral.

The terms "disruption" and "mutation" are used interchangeably herein to refer to a detectable and heritable change in the genetic material. Mutations may include insertions, deletions, substitutions (e.g., transitions, transversion), transpositions, inversions, knockouts and combinations thereof. Mutations may involve only a single nucleotide (e.g., a point mutation or a single nucleotide polymorphism) or multiple nucleotides. In some embodiments, mutations are silent, that is, no phenotypic effect of the mutation is detected. In other embodiments, the mutation causes a phenotypic change, for example, the expression level of the encoded product is altered, or the encoded product itself is altered. In some embodiments, a disruption or mutation may result in a disrupted gene with decreased levels of expression of a gene product (e.g., protein or RNA) as compared to the wild-type strain. In other embodiments, a disruption or mutation may result in an expressed protein with activity that is lower as compared to the activity of the expressed protein from the wild-type strain.

As used herein, an "effective amount" or "therapeutically effective amount" refers to a sufficient amount of an agent, which, when administered at one or more dosages and for a period of time, is sufficient to provide a desired biological result in alleviating, curing, or palliating a disease. In the present disclosure, an effective amount of MVAΔC7L, MVAΔC7L-hFlt3L, VACVΔC7L, or VACVΔC7L-hFlt3L is an amount that (when administered for a suitable period of time and at a suitable frequency) reduces the number of cancer cells; or reduces the tumor size or eradicates the tumor; or inhibits (i.e., slows down or stops) cancer cell infiltration into peripheral organs; inhibits (i.e., slows down or stops) metastatic growth; inhibits (stabilizes or arrests) tumor growth; allows for treatment of the tumor; and/or induces and promotes an immune response against the tumor. An appropriate therapeutic amount in any individual case may be determined by one of ordinary skill in the art using routine experimentation in light of the present disclosure. Such determination will begin with amounts found effective in vitro and amounts found effective in animals. The therapeutically effective amount will be initially determined based on the concentration or concentrations found to confer a benefit to cells in culture. Effective amounts can be extrapolated from data within the cell culture and can be adjusted up or down based on factors such as detailed herein. Effective amounts of the viral constructs are generally within the range of about $10^5$ to about $10^{10}$ plaque forming units (pfu), although a lower or higher dose may be administered. In some embodiments, the dosage is about $10^6$-$10^9$ pfu. In some embodiments, a unit dosage is administered in a volume within the range from 1 to 10 ml. The equivalence of pfu to virus particles can differ according to the specific pfu titration method used. Generally, pfu is equal to about 5 to 100 virus particles. A therapeutically effective amount the hFlt3L transgene bearing viruses can be administered in one or more divided doses for a prescribed period of time and at a prescribed frequency of administration. For example, a therapeutically effective amount of hFlt3L bearing viruses in accordance with the present disclosure may vary according to factors such as the disease state, age, sex, weight, and general condition of the subject, and the potency of the viral constructs to elicit a desired immunological response in the particular subject for the particular cancer.

With particular reference to the viral-based immunostimulatory agents disclosed herein, an "effective amount" or "therapeutically effective amount" refers to an amount of a composition comprising MVAΔC7L, MVAΔC7L-hFlt3L, VACVΔC7L, or VACVΔC7L-hFlt3L sufficient to reduce, inhibit, or abrogate tumor cell growth, thereby reducing or eradicating the tumor, or sufficient to inhibit, reduce or abrogate metastatic spread either in vitro, ex vivo, or in a subject or to elicit and promote an immune response against the tumor that will eventually result in one or more of metastatic spread reduction, inhibition, and/or abrogation as the case may be. The reduction, inhibition, or eradication of tumor cell growth may be the result of necrosis, apoptosis, or an immune response, or a combination of two or more of the foregoing (however, the precipitation of apoptosis, for example, may not be due to the same factors as observed with oncolytic viruses). The amount that is therapeutically effective may vary depending on such factors as the particular virus used in the composition, the age and condition of the subject being treated, the extent of tumor formation, the presence or absence of other therapeutic modalities, and the like. Similarly, the dosage of the composition to be administered and the frequency of its administration will depend on a variety of factors, such as the potency of the active ingredient, the duration of its activity once administered, the route of administration, the size, age, sex, and physical condition of the subject, the risk of adverse reactions and the judgment of the medical practitioner. The compositions are administered in a variety of dosage forms, such as injectable solutions.

With particular reference to combination therapy with an immune checkpoint inhibitor, an "effective amount" or "therapeutically effective amount" for an immune checkpoint blocking agent means an amount of an immune checkpoint blocking agent sufficient to reverse or reduce immune suppression in the tumor microenvironment and to activate or enhance host immunity in the subject being treated. Immune checkpoint blocking agents include, but are not limited to, inhibitory antibodies against CD28 inhibitor such as CTLA-4 (cytotoxic T lymphocyte antigen 4) (e.g., ipilimumab), anti-PD-1 (programmed Death 1) inhibitory antibodies (e.g., nivolumab, pembrolizumab, pidilizumab, lambrolizumab), and anti-PD-L1 (Programmed death ligand 1) inhibitory antibodies (MPDL3280A, BMS-936559, MEDI4736, MSB 00107180), as well as inhibitory antibodies against LAG-3 (lymphocyte activation gene 3), TIM3 (T-cell immunoglobulin and mucin-3), B7-H3, and TIGIT (T-cell immunoreceptor with Ig and ITIM domains). Dosage ranges of the foregoing are known or readily within the skill in the art as several dosing clinical trials have been completed, making extrapolation to other agents possible.

In some embodiments, the tumor expresses the particular checkpoint, but in the context of the present invention, this is not strictly necessary as immune checkpoint blocking agents block more generally immune suppressive mechanisms within the tumors, elicited by tumor cells, stromal cells, and tumor-infiltrating immune cells.

For example, the CTLA4 inhibitor ipilimumab, when administered as adjuvant therapy after surgery in melanoma, is administered at 1-2 mg/mL over 90 minutes for a total infusion amount of 3 mg/kg every three weeks for a total of 4 doses. This therapy is often accompanied by severe even life-threatening immune-mediated adverse reactions, which limits the tolerated dose as well as the cumulative amount that can be administered. It is anticipated that it will be possible to reduce the dose and/or cumulative amount of ipilimumab when it is administered conjointly with MVAΔC7L, MVAΔC7L-hFlt3L, VACVΔC7L, or VACVΔC7L-hFlt3L. In particular, in light of the experimental results set forth below, it is anticipated that it will be further possible to reduce the CTLA4 inhibitor's dose if it is administered directly to the tumor conjointly with one or both the foregoing MVA viruses. Accordingly, the amounts provided above for ipilimumab may be a starting point for determining the particular dosage and cumulative amount to be given to a patient in conjoint administration.

As another example, pembrolizumab is prescribed for administration as adjuvant therapy in melanoma diluted to 25 mg/mL. It is administered at a dosage of 2 mg/kg over 30 minutes every three weeks. This may be a starting point for determining dosage and administration in the conjoint administration of MVAΔC7L, MVAΔC7L-hFlt3L, VACVΔC7L, or VACVΔC7L-hFlt3L.

Nivolumab could also serve as a starting point in determining the dosage and administration regimen of checkpoint inhibitors administered in combination with MVAΔC7L, MVAΔC7L-hFlt3L, VACVΔC7L, or VACVΔC7L-hFlt3L. Nivolumab is prescribed for administration at 3 mg/kg as an intravenous infusion over 60 minutes every two weeks.

Immune stimulating agents such as agonist antibodies have also been explored as immunotherapy for cancers. For example, anti-ICOS antibody binds to the extracellular domain of ICOS leading to the activation of ICOS signaling and T-cell activation. Anti-OX40 antibody can bind to OX40 and potentiate T-cell receptor signaling leading to T-cell activation, proliferation and survival. Other examples include agonist antibodies against 4-1BB (CD137), GITR.

The immune stimulating agonist antibodies can be used systemically in combination with intratumoral injection of MVAΔC7L, MVAΔC7L-hFlt3L, VACVΔC7L, or VACVΔC7L-hFlt3L. Alternatively, the immune stimulating agonist antibodies can be used conjointly with MVAΔC7L, MVAΔC7L-hFlt3L, VACVΔC7L, or VACVΔC7L-hFlt3L via intratumoral delivery either simultaneously or sequentially.

The term "engineered" is used herein to refer to an organism that has been manipulated to be genetically altered, modified, or changed, e.g. by disruption of the genome. For example, an "engineered vaccinia virus strain" or "engineered modified vaccinia Anakara virus" refers to a vaccinia or modified vaccinia Ankara strain that has been manipulated to be genetically altered, modified, or changed.

The term "gene cassette" is used herein to refer to a DNA sequence encoding and capable of expressing one or more genes of interest (e.g., hFlt3L, a selectable marker, or a combination thereof) that can be inserted between one or more selected restriction sites of a DNA sequence. In some embodiments, insertion of a gene cassette results in a disrupted gene. In some embodiments, disruption of the gene involves replacement of at least a portion of the gene with a gene cassette, which includes a nucleotide sequence encoding a gene of interest (e.g., hFlt3L, a selectable marker, or a combination thereof).

As used herein, "immune checkpoint inhibitor" or "immune checkpoint blocking agent" or "immune checkpoint blockade inhibitor" refers to molecules that completely or partially reduce, inhibit, interfere with or modulate the activity of one or more checkpoint proteins. Checkpoint proteins regulate T-cell activation or function. Checkpoint proteins include, but are not limited to, CD28 receptor family members, CTLA-4 and its ligands CD80 and CD86; PD-1 and its ligands PD-L1 and PD-L2; LAG3, B7-H3, B7-H4, TIM3, ICOS, II DLBCL, BTLA or any combination of two or more of the foregoing. Non-limiting examples contemplated for use herein include ipilimumab, nivolumab, pembrolizumab, pidilizumab, AMP-224, MPDL3280A, BMS-936559, MEDI4736, MSB 00107180, or any combination thereof.

As used herein, "immune response" refers to the action of one or more of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc. An immune response may include a cellular response, such as a T-cell response that is an alteration (modulation, e.g., significant enhancement, stimulation, activation, impairment, or inhibition) of cellular, i.e., T-cell function. A T-cell response may include generation, proliferation or expansion, or stimulation of a particular type of T-cell, or subset of T-cells, for example, effector $CD4^+$, $CD4^+$ helper, effector $CD8^+$, $CD8^+$cytotoxic, or natural killer (NK) cells. Such T-cell subsets may be identified by detecting one or more cell receptors or cell surface molecules (e.g., CD or cluster of differentiation molecules). A T-cell response may also include altered expression (statistically significant increase or decrease) of a cellular factor, such as a soluble mediator (e.g., a cytokine, lymphokine, cytokine binding protein, or interleukin) that influences the differentiation or proliferation of other cells. For example, Type I interferon (INF-α/β) is a critical regulator of the innate immunity (Huber et al. *Immunology* 132(4):466-474 (2011)). Animal and human studies have shown a role for IFN-α/β in directly influencing the fate of both $CD4^+$ and $CD8^+$T-cells during the initial phases of antigen recognition and anti-tumor immune response. IFN Type I is induced in response to activation of dendritic cells, in turn a sentinel of the innate immune system. An immune response may also include humoral (antibody) response.

The term "immunogenic composition" is used herein to refer to a composition that will elicit an immune response in a mammal that has been exposed to the composition. In some embodiments, an immunogenic composition comprises MVAΔC7L, MVAΔC7L-hFlt3L, VACVΔC7L, and/or VACVΔC7L-hFlt3L, alone or in combination with immune checkpoint blockade inhibitors.

A "knocked out gene" or a "gene deletion" refers to a gene including a null mutation (e.g., the wild-type product encoded by the gene is not expressed, expressed at levels so low as to have no effect, or is non-functional). In some embodiments, the knocked out gene includes heterologous sequences or genetically engineered non-functional sequences of the gene itself, which renders the gene non-functional. In other embodiments, the knocked out gene is lacking a portion of the wild-type gene. For example, in some embodiments, at least about 10%, at least about 20%, at least about 30%, at least about 40% or at least about 60% of the wild-type gene sequence is deleted. In other embodiments, the knocked out gene is lacking at least about 70%, at least about 75%, at least about 80%, at least about 90%, at least about 95% or at least about 100% of the wild-type gene sequence. In other embodiments, the knocked out gene may include up to 100% of the wild-type gene sequence (e.g., some portion of the wild-type gene sequence may be deleted) but also include one or more heterologous and/or non-functional nucleic acid sequences inserted therein.

The term "MVAΔC7L," is used herein to refer to a modified vaccinia Ankara (MVA) mutant virus or a vaccine comprising the virus, in which the C7 gene is not expressed, expressed at levels so low as to have no effect, or the expressed protein is non-functional (e.g., is a null-mutation). As used herein, "MVAΔC7L" encompasses a recombinant MVA virus that does not express a functional C7 protein. In some embodiments, the ΔC7L mutant includes a heterologous nucleic acid sequence in place of all or a majority of the C7L gene sequence. For example, as used herein, "MVAΔC7L" encompasses a recombinant MVA nucleic acid sequence, wherein the nucleic acid sequence corresponding to the position of C7 in the MVA genome (e.g., position 18,407 to 18,859 of SEQ ID NO: 2) is replaced with a heterologous nucleic acid sequence comprising an open reading frame that encodes a specific gene of interest (SG), such as human Fms-like tyrosine kinase 3 ligand (hFlt3L) ("MVAΔC7L-hFlt3L"). In some embodiments, the heterologous nucleic acid sequence further comprises an open reading frame that encodes a selectable marker. In some embodiments, the selectable marker is a GFP protein. As used herein, "MVAΔC7L" means a deletion mutant of MVA which lacks a functional C7L gene and is infective but non replicative and it is further impaired in its ability to evade the host's immune system. The term "VACVΔC7L," is used herein to refer to a vaccinia mutant virus or vaccine comprising the virus in which the C7 gene is not expressed, expressed at levels so low as to have no effect, or the expressed protein is non-functional (e.g., is a null-mutation). As used herein, "VACVΔC7L" encompasses a recombinant vaccinia virus (VACV) that does not express a functional C7 protein. In some embodiments, the vaccinia virus is derived from the Western Reserve (WR) strain. In some embodiments, the ΔC7L mutant includes a heterologous sequence in place of all or a majority of the C7L gene sequence. For example, as used herein, "VACVΔC7L" encompasses a recombinant vaccinia virus nucleic acid sequence, wherein the nucleic acid sequence corresponding to the position of C7 in the VACV genome (e.g., position 15,716 to 16,168 of SEQ ID NO: 1) is replaced with a heterologous nucleic acid sequence comprising an open reading frame that encodes a specific gene of interest (SG), such as human Fms-like tyrosine kinase 3 ligand (hFlt3L) gene ("VACVΔC7L-hFlt3L"). In some embodiments, the heterologous nucleic acid sequence further comprises an open reading frame that encodes a selectable marker. In some embodiments, the selectable marker is a GFP protein.

As used herein, "metastasis" refers to the spread of cancer from its primary site to neighboring tissues or distal locations in the body. Cancer cells (including cancer stem cells) can break away from a primary tumor, penetrate lymphatic and blood vessels, circulate through the bloodstream, and grow in normal tissues elsewhere in the body. Metastasis is a sequential process, contingent on tumor cells (or cancer stem cells) breaking off from the primary tumor, traveling through the bloodstream or lymphatics, and stopping at a distant site. Once at another site, cancer cells re-penetrate through the blood vessels or lymphatic walls, continue to multiply, and eventually form a new tumor (metastatic tumor). In some embodiments, this new tumor is referred to as a metastatic (or secondary) tumor.

As used herein, "MVA" means "modified vaccinia Ankara" and refers to a highly attenuated strain of vaccinia derived from the Ankara strain and developed for use as a vaccine and vaccine adjuvant. The original MVA was isolated from the wild-type Ankara strain by successive passage through chicken embryonic cells. Treated thus, it lost about 15% of the genome of wild-type vaccinia including its ability to replicate efficiently in primate (including human) cells. (Mayr et al., *Zentralbl Bakteriol B* 167, 375-390 (1978)). The smallpox vaccination strain MVA: marker, genetic structure, experience gained with the parenteral vaccination and behavior in organisms with a debilitated defense mechanism. MVA is considered an appropriate candidate for development as a recombinant vector for gene or vaccination delivery against infectious diseases or tumors. (Verheust et al., *Vaccine* 30(16), 2623-2632 (2012)). MVA has a genome of 178 kb in length and a sequence first disclosed in Antoine et al., *Virol.* 244(2): 365-396 (1998). Sequences are also disclosed in Genbank U94848.1 (SEQ ID NO: 2). Clinical grade MVA is commercially and publicly available from Bavarian Nordic A/S Kvistgaard, Denmark. Additionally, MVA is available from ATCC, Rockville, MD and from CMCN (Institut Pasteur Collection Nationale des Microorganismes) Paris, France.

As used herein, "oncolytic virus" refers to a virus that preferentially infects cancer cells, replicates in such cells, and induces lysis of the cancer cells through its replication process. Nonlimiting examples of naturally occurring oncolytic viruses include vesicular stomatitis virus, reovirus, as well as viruses engineered to be oncoselective such as adenovirus, Newcastle disease virus and herpes simplex virus (See, e.g., Nemunaitis, *J. Invest New Drugs.* 17(4): 375-86 (1999); Kim, D H et al. *Nat Rev Cancer.* 9(1):64-71(2009); Kim et al. *Nat. Med.* 7:781 (2001); Coffey et al. *Science* 282:1332 (1998)). Vaccinia virus infects many types of cells but replicates preferentially in tumor cells due to the fact that tumor cells have a metabolism that favors replication, exhibit activation of certain pathways that also favor replication and create an environment that evades the innate immune system, which also favors viral replication.

As used herein, "parenteral," when used in the context of administration of a therapeutic substance or composition, includes any route of administration other than administration through the alimentary tract. Particularly relevant for the methods disclosed herein are intravenous (including, for example, through the hepatic portal vein for hepatic delivery), intratumoral, or intrathecal administration.

As used herein, "pharmaceutically acceptable carrier and/or diluent" or "pharmaceutically acceptable excipient" includes without limitation any and all solvents, dispersion media, coatings, antibacterial and antifungal agents, isotonic and absorption delaying agents, and the like. The use of such media and agents for biologically active substances is well known in the art. Further details of excipients are provided below. Supplementary active ingredients, such as antimicrobials, for example antifungal agents, can also be incorporated into the compositions.

As used herein, "pharmaceutically acceptable excipient" refers to substances and compositions that do not produce an adverse, allergic, or other untoward reaction when administered to an animal or a human. As used herein, the term includes all inert, non-toxic, liquid or solid fillers or diluents, as long as they do not react with the therapeutic substance of the invention in an inappropriate negative manner, solvents, dispersion media, coatings, antibacterial and antifungal agents, isotonic and absorption delaying agents, preservatives and the like, for example liquid pharmaceutical carriers e.g., sterile water, saline, sugar solutions, Tris buffer, ethanol and/or certain oils.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, "solid tumor" refers to all neoplastic cell growth and proliferation, and all pre-cancerous and cancerous cells and tissues, except for hematologic cancers such as lymphomas, leukemias, and multiple myeloma. Examples of solid tumors include, but are not limited to: soft tissue sarcoma, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor and other bone tumors (e.g., osteosarcoma, malignant fibrous histiocytoma), leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, brain/CNS tumors (e.g., astrocytoma, glioma, glioblastoma, childhood tumors, such as atypical teratoid/rhabdoid tumor, germ cell tumor, embryonal tumor, ependymoma) medulloblastoma, craniopharyngioma, ependymoma, pinealoma, hemangioblastoma, acoustic neuroma, oligodendroglioma, meningioma, melanoma, neuroblastoma, and retinoblastoma. Some of the most common solid tumors for which the compositions and methods of the present disclosure would be useful include: head-and-neck cancer, rectal adenocarcinoma, glioma, medulloblastoma, urothelial carcinoma, pancreatic adenocarcinoma, uterine (e.g., endometrial cancer, fallopian tube cancer) ovarian cancer, cervical cancer prostate adenocarcinoma, non-small cell lung cancer (squamous and adenocarcinoma), small cell lung cancer, melanoma, breast carcinoma, ductal carcinoma in situ, renal cell carcinoma, and hepatocellular carcinoma, adrenal tumors (e.g., adrenocortical carcinoma), esophageal, eye (e.g., melanoma, retinoblastoma), gallbladder, gastrointestinal, Wilms' tumor, heart, head and neck, laryngeal and hypopharyngeal, oral (e.g., lip, mouth, salivary gland), nasopharyngeal, neuroblastoma, peritoneal, pituitary, Kaposi's sarcoma, small intestine, stomach, testicular, thymus, thyroid, parathyroid, vaginal tumor, and the metastases of any of the foregoing.

As used herein, the terms "subject," "individual," or "patient" can be an individual organism, a vertebrate, a mammal, or a human. In some embodiments, "subject" means any animal (mammalian, human, or other) patient that can be afflicted with cancer and when thus afflicted is in need of treatment.

As used herein, a "synergistic therapeutic effect" refers to a greater-than-additive therapeutic effect which is produced by a combination of at least two agents, and which exceeds that which would otherwise result from the individual administration of the agents. For example, lower doses of one or more agents may be used in treating a disease or disorder, resulting in increased therapeutic efficacy and decreased side-effects.

"Treating," "treat," "treated," or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, "tumor immunity" refers to one or more processes by which tumors evade recognition and clearance by the immune system. Thus, as a therapeutic concept, tumor immunity is "treated" when such evasion is attenuated or eliminated, and the tumors are recognized and attacked by the immune system (the latter being termed herein "anti-tumor immunity"). An example of tumor recognition is tumor binding, and examples of tumor attack are tumor reduction (in number, size, or both) and tumor clearance.

As used herein, "T-cell" refers to a thymus derived lymphocyte that participates in a variety of cell-mediated adaptive immune reactions.

As used herein, "helper T-cell" refers to a $CD4^+$ T-cell; helper T-cells recognize antigen bound to MHC Class II molecules. There are at least two types of helper T-cells, Th1 and Th2, which produce different cytokines.

As used herein, "cytotoxic T-cell" refers to a T-cell that usually bears CD8 molecular markers on its surface ($CD8^+$) and that functions in cell-mediated immunity by destroying a targeT-cell having a specific antigenic molecule on its surface. Cytotoxic T-cells also release Granzyme, a serine protease that can enter targeT-cells via the perforin-formed pore and induce apoptosis (cell death). Granzyme serves as a marker of cytotoxic phenotype. Other names for cytotoxic T-cell include CTL, cytolytic T-cell, cytolytic T lymphocyte, killer T-cell, or killer T lymphocyte. Targets of cytotoxic T-cells may include virus-infected cells, cells infected with bacterial or protozoal parasites, or cancer cells. Most cytotoxic T-cells have the protein CD8 present on their cell surfaces. CD8 is attracted to portions of the Class I MHC molecule. Typically, a cytotoxic T-cell is a $CD8^+$ cell.

As used herein, "tumor-infiltrating leukocytes" refers to white blood cells of a subject afflicted with a cancer (such as melanoma), that are resident in or otherwise have left the circulation (blood or lymphatic fluid) and have migrated into a tumor.

As used herein, "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene. A non-limiting example of a pCB-C7L-GFP vector according to the present technology is set forth in SEQ ID NO: 4.

The term "virulence" as used herein to refer to the relative ability of a pathogen to cause disease. The term "attenuated virulence" or "reduced virulence" is used herein to refer to a reduced relative ability of a pathogen to cause disease.

II. Immune System and Cancer

Malignant tumors are inherently resistant to conventional therapies and present significant therapeutic challenges. Immunotherapy has become an evolving area of research and an additional option for the treatment of certain types of cancers. The immunotherapy approach rests on the rationale that the immune system may be stimulated to identify tumor cells, and target them for destruction.

Numerous studies support the importance of the differential presence of immune system components in cancer progression (Jochems et al., *Exp Biol Med,* 236(5): 567-579 (2011)). Clinical data suggest that high densities of tumor-infiltrating lymphocytes are linked to improved clinical outcome (Mlecnik et al., *Cancer Metastasis Rev.;* 30: 5-12, (2011)). The correlation between a robust lymphocyte infiltration and patient survival has been reported in various types of cancer, including melanoma, ovarian, head and neck, breast, urothelial, colorectal, lung, hepatocellular, gallbladder, and esophageal cancer (Angell et al., *Current Opinion in Immunology,* 25:1-7, (2013)). Tumor immune infiltrates include macrophages, dendritic cells (DC), monocytes, neutrophils, natural killer (NK) cells, naïve and memory lymphocytes, B cells and effector T-cells (T lymphocytes), primarily responsible for the recognition of antigens expressed by tumor cells and subsequent destruction of the tumor cells by cytotoxic T-cells.

Despite presentation of antigens by cancer cells and the presence of immune cells that could potentially react against tumor cells, in many cases the immune system does not get activated or is affirmatively suppressed. Key to this phenomenon is the ability of tumors to protect themselves from immune response by coercing cells of the immune system to inhibit other cells of the immune system. Tumors develop a number of immunomodulatory mechanisms to evade anti-tumor immune responses. For example, tumor cells secrete immune inhibitory cytokines (such as TGF-β) or induce immune cells, such as $CD4^+$ T regulatory cells and macrophages, in tumor lesions to secrete these cytokines. Tumors also have the ability to bias $CD4^+$ T-cells to express the regulatory phenotype. The overall result is impaired T-cell responses and impaired induction of apoptosis or reduced anti-tumor immune capacity of $CD8^+$ cytotoxic T-cells. Additionally, tumor-associated altered expression of MHC class I on the surface of tumor cells makes them "invisible" to the immune response (Garrido et al. *Cancer Immunol. Immunother.* 59(10), 1601-1606 (2010)). Inhibition of antigen-presenting functions and dendritic cell (DC) additionally contributes to the evasion of anti-tumor immunity (Gerlini et al. *Am. J. Pathol.* 165(6), 1853-1863 (2004)).

Moreover, the local immunosuppressive nature of the tumor microenvironment, along with immune editing, can lead to the escape of cancer cell subpopulations that do not express the target antigens. Thus, finding an approach that would promote the preservation and/or restoration of anti-tumor activities of the immune system would be of considerable therapeutic benefit.

Immune checkpoints have been implicated in the tumor-mediated downregulation of anti-tumor immunity and used as therapeutic targets. It has been demonstrated that T-cell dysfunction occurs concurrently with an induced expression of the inhibitory receptors, CTLA-4 and programmed death 1 polypeptide (PD-1), members of the CD28 family of receptors. PD-1 is an inhibitory member of the CD28 family of receptors that in addition to PD-1 includes CD28, CTLA-4, ICOS and BTLA. However, while promise regarding the use of immunotherapy in the treatment of melanoma has been underscored by the clinical use and even regulatory approval of anti-CTLA-4 (ipilimumab) and anti-PD-1 drugs (e.g., pembrolizumab and nivolumab), the response of patients to these immunotherapies has been limited. Clinical trials, focused on blocking these inhibitory signals in T-cells (e.g., CTLA-4, PD-1, and the ligand of PD-1 PD-L1), have shown that reversing T-cell suppression is critical for successful immunotherapy (Sharma et al., *Science* 348(6230), 56-61 (2015); Topalian et al., *Curr Opin Immunol.* 24(2), 202-217 (2012)). These observations highlight the need for development of novel therapeutic approaches for harnessing the immune system against cancer.

III. Poxviruses

Poxviruses, such as engineered vaccinia viruses, are in the forefront as oncolytic therapy for metastatic cancers (Kim et al., *Nature Review Cancer* 9, 64-71 (2009)). Vaccinia viruses are large DNA viruses, which have a rapid life cycle and efficient hematogenous spread to distant tissues (Moss, In Fields Virology (Lippincott Williams & Wilkins, 2007), pp. 2905-2946). Poxviruses are well-suited as vectors to express multiple transgenes in cancer cells and thus to enhance therapeutic efficacy (Breitbach et al., *Current pharmaceutical biotechnology* 13, 1768-1772 (2012)). Preclinical studies and clinical trials have demonstrated efficacy of using oncolytic vaccinia viruses and other poxviruses for treatment of advanced cancers refractory to conventional therapy (Park et al., *Lacent Oncol* 9, 533-542 (2008); Kirn et al., *PLoS Med* 4, e353 (2007); Thorne et al., *J Clin Invest* 117, 3350-3358 (2007)). Poxvirus-based oncolytic therapy has the advantage of killing cancer cells through a combination of cell lysis, apoptosis, and necrosis. It also triggers innate immune sensing pathway that facilitates the recruitment of immune cells to the tumors and the development of anti-tumor adaptive immune responses. The current oncolytic vaccinia strains in clinical trials (JX-594, for example) are replicative strains. They use wild-type vaccinia with deletion of thymidine kinase to enhance tumor selectivity, and with expression of transgenes such as granulocyte macrophage colony stimulating factor (GM-CSF) to stimulate immune responses (Breitbach et al., *Curr Pharm Biotechnol* 13, 1768-1772 (2012)). Many studies have shown, however, that wild-type vaccinia has immune suppressive effects on antigen presenting cells (APCs) (Engelmayer et al., *J Immunol* 163, 6762-6768 (1999); Jenne et al., *Gene therapy* 7, 1575-1583 (2000); P. Li et al., *J Immunol* 175, 6481-6488 (2005);

Deng et al., *J Virol* 80, 9977-9987 (2006)), and thus adds to the immunosuppressive and immunoevasive effects of tumors themselves.

The vaccinia virus (Western Reserve strain; WR) genome sequence is set forth in SEQ ID NO: 1, and is given by GenBank Accession No. AY243312.1.

IV. Modified Vaccinia Ankara (MVA)

Modified Vaccinia Ankara (MVA) virus is a member of the genera Orthopoxvirus in the family of Poxviridae. MVA was generated by approximately 570 serial passages on chicken embryo fibroblasts (CEF) of the Ankara strain of vaccinia virus (CVA) (Mayr et al., *Infection* 3, 6-14 (1975)). As a consequence of these long-term passages, the resulting MVA virus contains extensive genome deletions and is highly host cell restricted to avian cells (Meyer et al., *J. Gen. Virol.* 72, 1031-1038 (1991)). It was shown in a variety of animal models that the resulting MVA is significantly avirulent (Mayr et al., *Dev. Biol. Stand.* 41, 225-34 (1978)).

The safety and immunogenicity of MVA has been extensively tested and documented in clinical trials, particularly against the human smallpox disease. These studies included over 120,000 individuals and have demonstrated excellent efficacy and safety in humans. Moreover, compared to other vaccinia based vaccines, MVA has weakened virulence (infectiousness) while it triggers a good specific immune response. Thus, MVA has been established as a safe vaccine vector, with the ability to induce a specific immune response.

Due to the above mentioned characteristics, MVA became an attractive candidate for the development of engineered MVA vectors, used for recombinant gene expression and vaccines. As a vaccine vector, MVA has been investigated against numerous pathological conditions, including HIV, tuberculosis and malaria, as well as cancer (Sutter et al., *Curr Drug Targets Infect Disord* 3: 263-271(2003); Gomez et al., *Curr Gene Ther* 8: 97-120 (2008)).

It has been demonstrated that MVA infection of human monocyte-derived dendritic cells (DC) causes DC activation, characterized by the upregulation of co-stimulatory molecules and secretion of proinflammatory cytokines (Drillien et al., *J Gen Virol* 85: 2167-2175 (2004)). In this respect, MVA differs from standard wild type Vaccinia virus (WT-VAC), which fails to activate DCs. Dendritic cells can be classified into two main subtypes: conventional dendritic cells (cDCs) and plasmacytoid dendritic cells (pDCs). The former, especially the $CD103^+/CD8\alpha^+$ subtype, are particularly adapted to cross-presenting antigens to T-cells; the latter are strong producers of Type I IFN.

Viral infection of human cells results in activation of an innate immune response (the first line of defense) mediated by type I interferons, notably interferon-alpha (α). This normally leads to activation of an immunological "cascade," with recruitment and proliferation of activated T-cells (both CTL and helper) and eventually with antibody production. However, viruses express factors that dampen immune responses of the host. MVA is a better immunogen than WT-VAC and replicates poorly in mammalian cells. (See, e.g., Brandler et al., *J. Virol.* 84, 5314-5328 (2010)).

However, MVA is not entirely non-replicative and contains some residual immunosuppressive activity. Nevertheless, MVA has been shown to prolong survival of treated subjects.

The MVA genome sequence is set forth in SEQ ID NO: 2 and is given by GenBank Accession No. U94848.1.

V. Vaccinia Virus C7 Protein and MVA with Deletion of C7 (MVAΔC7L)

Vaccinia virus C7 protein is an important host range factor for vaccinia virus life cycle in mammalian cells. C7L homologs are present in almost all of the poxviruses that infect mammalian hosts. Deletion of both host range gene C7L and K1L renders the virus incapable of replication in human cells (Perkus et al., Virology, 1990). The mutant virus deficient of both K1L and C7L gains its ability to replicate in human HeLa cells when SAMD9 is knocked-out (Sivan et al., mbio, 2015). Both K1 and C7 have been found to interact with SAMD9 (Sivan et al., mbio, 2015). Overexpression of IRF1 leads to host restriction of C7L and K1L double deleted vaccinia virus (Meng et al. Journal of Virology, 2012). Both C7 and K1 interact with SAMD9 in vitro ((Sivan et al., mbio, 2015). Whether C7 directly modulates IFN production or signaling is unknown. Type I IFN plays an important role in host defense of viral infection, and yet, the role of C7 in immune modulation of the IFN pathway is unclear.

Without wishing to be bound by theory, it is thought that vaccinia C7 is an inhibitor of type I IFN induction and IFN signaling. TANK Binding Kinase 1 (TBK1) is a serine/threonine kinase that plays a critical role in the induction of innate immune responses to various pathogen-associated molecular patterns (PAMPs), including nucleic acids. On the one hand, RIG-I-like receptors such as RIG-I and MDA5, which detect 5' triphosphate RNA and dsRNA, respectively, interact with a mitochondrial protein IPS-1 or MAVS, leading to the activation and phosphorylation of TBK1. Endosomal dsRNA binds to Toll-like receptor 3 (TLR3), which results in the recruitment of TRIF and TRAF3 and activation of TBK1. On the other hand, cytosolic DNA can be detected by the cytosolic DNA sensor cyclic GMP-AMP synthase (cGAS), which leads to the production of cyclic GMP-AMP (cGAMP). cGAMP, in turn, binds to the endoplasmic reticulum (ER)-localized adaptor STING, leading to the recruitment and activation of TBK1. TBK1 phosphorylates transcription factor IRF3, which translocates to the nucleus to activate IFNB gene expression. Without wishing to be bound by theory, it is believed that C7 inhibits IFNB induction by various stimuli, including RNA virus, DNA virus, poly (I:C), immunostimulatory DNA (ISD). C7 may exert its inhibitory effect at the level of TBK1/IRF3 complex. Once secreted, type I IFN binds to IFNAR, which leads to the activation of the JAK/STAT signaling pathway. Phosphorylated STAT1 and STAT2 translocate to the nucleus, where together with IRF9, they activate the expression of IFN-stimulated genes (ISGs). Without wishing to be bound by theory, it is believed that in addition to its ability to inhibit IFNB induction, C7 can also block IFNAR signaling through its interaction of STAT2, thereby preventing IFN-β-induced STAT2 phosphorylation. Without wishing to be bound by theory, it is believed that vaccinia C7 has dual inhibitory role of type I IFN production and signaling. As described herein, deletion of C7L from WT vaccinia (VACVΔC7L) results in the attenuation of the virus and deletion of C7L from MVA (MVAΔC7L) leads to enhanced immunostimulatory functions compared with MVA.

In one aspect, the present disclosure demonstrates that ectopic C7 expression blocks STING, TBK1, or IRF3-induced IFNB and ISRE (interferon stimulated response element) promoter activation. In another aspect, the present disclosure shows that murine or human macrophage cell lines that overexpress C7 have blunted innate immune responses to DNA or RNA stimuli, or the infection of DNA or RNA viruses. In some embodiments, overexpression of C7 also attenuates ISG gene expression induced by IFN-β treatment. In some embodiments, MVA with deletion of C7L (MVAΔC7L) infection of cDCs induces higher levels of type I IFN than MVA. In some embodiments, C7 blocks IFN-β-induced Janus kinase/signal transducer and activator of transcription (JAK/STAT) signaling pathway via preventing Stat2 phosphorylation. By way of example, but not by way of limitation, C7 is shown to directly interact with Stat2 as demonstrated by co-immunoprecipitation studies.

An illustrative full-length vaccinia virus C7 host range protein, given by GenBank Accession No. AAB96405.1 (SEQ ID NO: 3) is provided below.

```
  1 mgiqhefdii ingdialrnl qlhkgdnygc klkiisndyk
    klkfrfiirp dwseidevkg

 61 ltvfannyav kvnkvddtfy yviyeavihl ynkkteiliy
    sddenelfkh yypyislnmi

121 skkykvkeen ysspyiehpl ipyrdyesmd
```

VI. Fms-Like Tyrosine Kinase 3 Ligand (Flt3L)

Human Flt3L (Fms-like tyrosine kinase 3 ligand), a type I transmembrane protein that stimulates the proliferation of bone marrow cells, was cloned in 1994 (Lyman et al., 1994). The use of hFlt3L has been explored in various preclinical and clinical settings including stem cell mobilization in preparation for bone marrow transplantation, cancer immunotherapy such as expansion of dendritic cells, as well as a vaccine adjuvant. Recombinant human Flt3L (rhuFlt3L) has been tested in more than 500 human subjects and is bioactive, safe, and well-tolerated (Fong et al., 1998; Maraskovsky et al., 2000; Shackleton et al., 2004; He et al., 2014; Anandasabapathy et al., 2015). Much progress has been made in understanding the critical role of the growth factor Flt3L in the development of DC subsets, including CD8α$^+$/CD103$^+$ DCs and pDCs (McKenna et al., 2000; Waskow et al., 2008; Liu et al., 2007; 2009; Naik et al., 2006; Ginhoux et al., 2009).

CD103$^+$/CD8α$^+$ DCs are required for spontaneous cross-priming of tumor antigen-specific CD8$^+$ T-cells (Hildner et al., 2008; Ginhoux et al., 2009, Zhang et al., 2015; Spranger et al., 2015). Broz et al. reported that CD103$^+$ DCs are sparsely present within the tumors and they compete for tumor antigens with abundant tumor-associated macrophages. CD103$^+$ DCs are uniquely capable of stimulating naïve as well as activated CD8$^+$ T-cells and are critical for the success of adoptive T-cell therapy (Broz, et al. Cancer Cell, 26(5):638-52, 2014). Spranger et al. reported that the activation of oncogenic signaling pathway WNT/β-catenin leads to reduction of CD103$^+$ DCs and anti-tumor T-cells within the tumors (Spranger et al., 2015). Intratumoral delivery of Flt3L-cultured bone marrow derived dendritic cells (BMDCs) leads to responsiveness to the combination of anti-CTLA-4 and anti-PD-L1 immunotherapy (Spranger et al., 2015). Systemic administration of Flt3L, a growth factor for CD103$^+$ DCs, and intratumor injection of poly I:C (TLR3 agonist) expanded and activated the CD103$^+$ DC populations within the tumors and overcame resistance or enhanced responsiveness to immunotherapy in a murine melanoma and MC38 colon cancer models (Salmon et al., 2016, Sanchez-Paulete et al., 2016).

The recent discovery of tumor neoantigens in various solid tumors indicates that solid tumors harbor unique neoantigens that usually differ from person to person (Castle et al., *Cancer Res* 72, 1081-1091 (2012); Schumacher et al., *Science* 348, 69-74 (2015)). The recombinant viruses disclosed herein do not exert their activity by expressing tumor antigens. Intratumoral delivery of the present recombinant MVA viruses allows efficient cross-presentation of tumor neoantigens and generation of anti-tumor adaptive immunity within the tumors (and also extending systemically), and therefore leads to "in situ cancer vaccination" utilizing tumor differentiation antigens and neoantigens expressed by the tumor cells in mounting an immune response against the tumor.

Despite the presence of neoantigens generated by somatic mutations within tumors, the functions of tumor antigen-specific T-cells are often held in check by multiple inhibitory mechanisms (Mellman et al., *Nature* 480, 480-489 (2011)). For example, the up-regulation of cytotoxic T lymphocyte antigen 4 (CTLA-4) on activated T-cells can compete with T-cell co-stimulator CD28 to interact with CD80 (B71)/CD86 (B7.2) on dendritic cells (DCs), and thereby inhibit T-cell activation and proliferation. CTLA-4 is also expressed on regulatory T (Treg) cells and plays an important role in mediating the inhibitory function of Tregs (Wing et al., *Science* 322, 271-275 (2008); Peggs, et al., *J Exp Med* 206, 1717-1725 (2009)). In addition, the expression of PD-L/PD-L2 on tumor cells can lead to the activation of the inhibitory receptor of the CD28 family, PD-1, leading to T-cell exhaustion. Immunotherapy utilizing antibodies against inhibitory receptors, such as CTLA-4 and programmed death 1 polypeptide (PD-1), have shown remarkable preclinical activities in animal studies and clinical responses in patients with metastatic cancers, and have been approved by the FDA for the treatment of metastatic melanoma, non-small cell lung cancer, as well as renal cell carcinoma (Leach et al., *Science* 271, 1734-1746 (1996); Hodi et al., *NEJM* 363, 711-723 (2010); Robert et al., *NEJM* 364, 2517-2526 (2011); Topalian et al., *Cancer Cell* 27, 450-461 (2012); Sharma et al., *Science* 348(6230), 56-61 (2015)).

VII. Melanoma

Melanoma, one of the deadliest cancers, is the fastest growing cancer in the U.S. and worldwide. In most cases, advanced melanoma is resistant to conventional therapies, including chemotherapy and radiation. As a result, people with metastatic melanoma have a very poor prognosis, with a life expectancy of only 6 to 10 months. The discovery that about 50% of melanomas have mutations in BRAF (a key tumor-promoting gene) opened the door for targeted therapy of this disease. Early clinical trials with BRAF inhibitors showed remarkable, but unfortunately not sustainable, responses in patients with melanomas with BRAF mutations. Therefore, alternative treatment strategies for these patients, as well as others with melanoma without BRAF mutations, are urgently needed.

Human pathological data indicate that the presence of T-cell infiltrates within melanoma lesions correlates positively with longer patient survival (Oble et al. *Cancer Immun.* 9, 3 (2009)). The importance of the immune system in protection against melanoma is further supported by partial success of immunotherapies, such as the immune activators IFN-α2b and IL-2 (Lacy et al. *Expert Rev Dermatol* 7(1):51-68 (2012)) as well as the unprecedented clinical responses of patients with metastatic melanoma to immune checkpoint therapy, including anti-CTLA-4 and anti-PD-1/PD-L1 either agent alone or in combination therapy (Sharma and Allison, Science 348(6230), 56-61 (2015); Hodi et al., NEJM 363(8), 711-723 (2010); Wolchok et al., Lancet Oncol. 11(6), 155-164 (2010); Topalian et al., NEJM 366(26), 2443-2454 (2012); Wolchok et al., NEJM 369(2), 122-133 (2013); Hamid et al., NEJM 369(2), 134-144 (2013); Tumeh et al., Nature 515(7528), 568-571 (2014)). However, many patients fail to respond to immune checkpoint blockade therapy alone.

VIII. Type I IFN and the Cytosolic DNA-Sensing Pathway in Tumor Immunity

Type I IFN plays important roles in host antitumor immunity (Fuertes et al., *Trends Immunol* 34, 67-73 (2013)). IFNAR1-deficent mice are more susceptible to developing tumors after implantation of tumor cells; spontaneous tumor-specific T-cell priming is also defective in IFNAR1-deficient mice (Diamond et al., *J Exp Med* 208, 1989-2003 (2011); Fuertes et al., *J Exp Med* 208, 2005-2016 (2011)). More recent studies have shown that the cytosolic DNA-sensing pathway is important in the innate immune sensing of tumor-derived DNA, which leads to the development of antitumor $CD8^+$ T-cell immunity (Woo et al., *Immunity* 41, 830-842 (2014)). This pathway also plays a role in radiation-induced antitumor immunity (Deng et al., *Immunity* 41, 843-852 (2014)). Although spontaneous anti-tumor T-cell responses can be detected in patients with cancers, cancers eventually overcome host antitumor immunity in most patients. Novel strategies to alter the tumor immune suppressive microenvironment would be beneficial for cancer therapy.

IX. Immune Response

In addition to induction of the immune response by up-regulation of particular immune system activities (such as antibody and/or cytokine production, or activation of cell mediated immunity), immune responses may also include suppression, attenuation, or any other downregulation of detectable immunity, so as to reestablish homeostasis and prevent excessive damage to the host's own organs and tissues. In some embodiments, an immune response that is induced according to the methods of the present disclosure generates effector $CD8^+$ (antitumor cytotoxic $CD8^+$) T-cells or activated T helper cells or both that can bring about directly or indirectly the death, or loss of the ability to propagate, of a tumor cell.

Induction of an immune response by the compositions and methods of the present disclosure may be determined by detecting any of a variety of well-known immunological parameters (Takaoka et al., *Cancer Sci.* 94:405-11 (2003); Nagorsen et al., *Crit. Rev. Immunol.* 22:449-62 (2002)). Induction of an immune response may therefore be established by any of a number of well-known assays, including immunological assays. Such assays include, but need not be limited to, in vivo, ex vivo, or in vitro determination of soluble immunoglobulins or antibodies; soluble mediators such as cytokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, altered intracellular cation gradient or concentration (such as calcium); phosphorylation or dephosphorylation of cellular polypeptides; induction of specialized activities such as specific gene expression or cytolytic behavior; cellular differentiation by cells of the immune system, including altered surface antigen expression profiles, or the onset of apoptosis (programmed cell death); or any other criterion by which the presence of an immune response may be detected. For example, cell surface markers that distinguish immune cell types may be detected by specific antibodies that bind to $CD4^+$, $CD8^+$, or NK cells. Other markers and cellular components that can be detected include but are not limited to interferon γ (IFN-γ), tumor necrosis factor (TNF), IFN-α, IFN-β (IFNB), IL-6, and CCL5. Common methods for detecting the immune response include, but are not limited to flow cytometry, ELISA, immunohistochemistry. Procedures for performing these and similar assays are widely known and may be found, for example in Letkovits (Immunology Methods Manual: The Comprehensive Sourcebook of Techniques, Current Protocols in Immunology, 1998).

X. Pharmaceutical Compositions and Preparations of the Present Technology

Disclosed herein are pharmaceutical compositions comprising MVAΔC7L, MVAΔC7L-hFlt3L, VACVΔC7L, or VACVΔC7L-hFlt3L that may contain a carrier or diluent, which can be a solvent or dispersion medium containing, for example, water, saline, Tris buffer, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be effected by various antibacterial and antifungal agents and preservatives, for example, parabens, chlorobutanol, phenol, sorbic acid, thimerosal, and the like. In some embodiments, isotonic agents, for example, sugars or sodium chloride, and buffering agents are included. Prolonged absorption of the injectable compositions can be brought about by the use in the compositions of agents delaying absorption, for example, aluminum monostearate and gelatin or carrier molecules. Other excipients may include wetting or emulsifying agents. In general, excipients suitable for injectable preparations can be included as apparent to those skilled in the art.

Pharmaceutical compositions and preparations comprising MVAΔC7L, MVAΔC7L-hFlt3L, VACVΔC7L, or VACVΔC7L-hFlt3L may be manufactured by means of conventional mixing, dissolving, granulating, emulsifying, encapsulating, entrapping or lyophilizing processes. Pharmaceutical viral compositions may be formulated in conventional manner using one or more physiologically acceptable carriers, diluents, excipients or auxiliaries that facilitate formulating virus preparations suitable for in vitro, in vivo, or ex vivo use. The compositions can be combined with one or more additional biologically active agents (for example parallel administration of GM-CSF) and may be formulated with a pharmaceutically acceptable carrier, diluent or excipient to generate pharmaceutical (including biologic) or veterinary compositions of the instant disclosure suitable for parenteral or intra-tumoral administration.

Many types of formulation are possible as is appreciated by those skilled in the art. The particular type chosen is dependent upon the route of administration chosen, as is well-recognized in the art. For example, systemic formulations will generally be designed for administration by injection, e.g., intravenous, as well as those designed for intratumoral delivery. In some embodiments, the systemic or intratumoral formulation is sterile.

Sterile injectable solutions are prepared by incorporating MVAΔC7L, MVAΔC7L-hFlt3L, VACVΔC7L, or VACVΔC7L-hFlt3L in the required amount of the appropriate solvent with various other ingredients enumerated herein, as required, followed by suitable sterilization means. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the virus plus any additional desired ingredient from a previously sterile-filtered solution thereof.

In some embodiments, the MVAΔC7L, MVAΔC7L-hFlt3L, VACVΔC7L, or VACVΔC7L-hFlt3L compositions of the present disclosure may be formulated in aqueous solutions, or in physiologically compatible solutions or buffers such as Hanks's solution, Ringer's solution, mannitol solutions or physiological saline buffer. In certain embodiments, any of the MVAΔC7L or MVAΔC7L-hFlt3L compositions may contain formulator agents, such as suspending, stabilizing, penetrating or dispersing agents, buffers, lyoprotectants or preservatives such as polyethylene glycol, polysorbate 80, 1-dodecylhexahydro-2H-azepin-2-one (laurocapran), oleic acid, sodium citrate, Tris HCl, dextrose, propylene glycol, mannitol, polysorbate polyethylenesorbitan monolaurate (Tween®-20), isopropyl myristate, benzyl alcohol, isopropyl alcohol, ethanol sucrose, trehalose and other such generally known in the art may be used in any of the compositions of the instant disclosure. (Pramanick et al., *Pharma Times* 45(3), 65-76 (2013)).

The biologic or pharmaceutical compositions of the present disclosure can be formulated to allow the virus contained therein to be available to infect tumor cells upon administration of the composition to a subject. The level of virus in serum, tumors, and if desired other tissues after administration can be monitored by various well-established techniques, such as antibody-based assays (e.g., ELISA, immunohistochemistry, etc.).

The recombinant viruses of the present invention can be stored at −80° C. with a titer of 3.5×$10^7$ PFU/ml formulated in about 10 mM Tris, 140 mM NaCl pH 7.7. For the preparation of vaccine shots, e.g., $10^2$-$10^8$ or $10^2$-$10^9$ viral particles can be lyophilized in 100 ml of phosphate-buffered saline (PBS) in the presence of 2% peptone and 1% human albumin in an ampoule, preferably a glass ampoule. Alternatively, the injectable preparations can be produced by stepwise freeze-drying of the recombinant virus in a formulation. This formulation can contain additional additives such as mannitol, dextran, sugar, glycine, lactose or polyvinylpyrrolidone or other additives such as antioxidants or inert gas, stabilizers or recombinant proteins (e.g., human serum albumin) suitable for in vivo administration. The glass ampoule is then sealed and can be stored between 4° C. and room temperature for several months. In some embodiments, the ampoule is stored at temperatures below −20° C.

For therapy, the lyophilisate can be dissolved in an aqueous solution, such as physiological saline or Tris buffer, and administered either systemically or intratumorally. The mode of administration, the dose, and the number of administrations can be optimized by those skilled in the art.

The pharmaceutical composition according to the present disclosure may comprise an additional adjuvant. As used herein, an "adjuvant" refers to a substance that enhances, augments or potentiates the host's immune response to tumor antigens. A typical adjuvant may be aluminum salts, such as aluminum hydroxide or aluminum phosphate, Quil A, bacterial cell wall peptidoglycans, virus-like particles, polysaccharides, toll-like receptors, nano-beads, etc. (Aguilar et al. (2007), Vaccine 25: 3752-3762).

XI. Kits Comprising Recombinant MVAΔC7L, MVAΔC7L-hFlt3L, VACVΔC7L, or VACVΔC7L-hFlt3L Viruses The present disclosure provides for kits comprising one or more compositions comprising one or more of the recombinant MVAΔC7L, MVAΔC7L-hFlt3L, VACVΔC7L, or VACVΔC7L-hFlt3L viruses described herein. The kit can comprise one or multiple containers or vials of the recombinant MVAΔC7L, MVAΔC7L-hFlt3L, VACVΔC7L, or VACVΔC7L-hFlt3L, together with instructions for the administration of the recombinant MVAΔC7L, MVAΔC7L-hFlt3L, VACVΔC7L, or VACVΔC7L-hFlt3L to a subject to be treated. The instructions may indicate a dosage regimen for administering the composition or compositions as provided below.

In some embodiments, the kit may also comprise an additional composition comprising a checkpoint inhibitor for conjoint administration with the recombinant MVAΔC7L, MVAΔC7L-hFlt3L, VACVΔC7L, or VACVΔC7L-hFlt3L composition.

XII. Effective Amount and Dosage of MVAΔC7L, MVAΔC7L-hFlt3L, VACVΔC7L, or VACVΔC7L-hFlt3L In general, the subject is administered a dosage MVAΔC7L, MVAΔC7L-hFlt3L, VACVΔC7L, or VACVΔC7L-hFlt3L in the range of about $10^6$ to about $10^{10}$ plaque forming units (pfu), although a lower or higher dose may be administered. In some embodiments, the dosage ranges from about $10^2$ to about $10^{10}$ pfu. In some embodiments, the dosage ranges from about $10^3$ to about $10^{10}$ pfu. In some embodiments, the dosage ranges from about $10^4$ to about $10^{10}$ pfu. In some embodiments, the dosage ranges from about $10^5$ to about $10^{10}$ pfu. In some embodiments, the dosage ranges from about $10^6$ to about $10^{10}$ pfu. In some embodiments, the dosage ranges from about $10^7$ to about $10^{10}$ pfu. In some embodiments, the dosage ranges from about $10^8$ to about $10^{10}$ pfu. In some embodiments, the dosage ranges from about $10^9$ to about $10^{10}$ pfu. In some embodiments, dosage is about $10^7$ to about $10^9$ pfu. The equivalence of pfu to virus particles can differ according to the specific pfu titration method used. Generally, a pfu is equal to about 5 to 100 virus particles and 0.69 PFU is about 1 TCID50. A therapeutically effective amount of M MVAΔC7L, MVAΔC7L-hFlt3L, VACVΔC7L, or VACVΔC7L-hFlt3L can be administered in one or more divided doses for a prescribed period of time and at a prescribed frequency of administration.

For example, as is apparent to those skilled in the art, a therapeutically effective amount of MVAΔC7L, MVAΔC7L-hFlt3L, VACVΔC7L, or VACVΔC7L-hFlt3L in accordance with the present disclosure may vary according to factors such as the disease state, age, sex, weight, and general condition of the subject, and the ability of MVAΔC7L, MVAΔC7L-hFlt3L, VACVΔC7L, or VACVΔC7L-hFlt3L to elicit a desired immunological response in the particular subject (the subject's response to therapy). In delivering MVAΔC7L, MVAΔC7L-hFlt3L, VACVΔC7L, or VACVΔC7L-hFlt3L to a subject, the dosage will also vary depending upon such factors as the general medical condition, previous medical history, disease type and progression, tumor burden, the presence or absence of tumor infiltrating immune cells in the tumor, and the like.

In some embodiments, it may be advantageous to formulate compositions of the present disclosure in dosage unit form for ease of administration and uniformity of dosage. "Dosage unit form as used herein" refers to physically discrete units suited as unitary dosages for the mammalian subjects to be treated; each unit containing a predetermined quantity of active material calculated to produce the desired therapeutic effect in association with the required pharmaceutically or veterinary acceptable carrier.

XIII. Administration and Therapeutic Regimen of MVAΔC7L, MVAΔC7L-hFlt3L, VACVΔC7L, or VACVΔC7L-hFlt3L Pharmaceutical compositions are typically formulated to be compatible with its intended route of administration. Administration of MVAΔC7L, MVAΔC7L-hFlt3L, VACVΔC7L, or VACVΔC7L-hFlt3L can be achieved using more than one route. Examples of routes of administration include, but are not limited to parenteral (e.g., intravenous, intramuscular, intraperitoneal, intradermal, subcutaneous), intratumoral, intrathecal, intranasal, systemic, transdermal, iontophoretic, intradermal, intraocular, or topical administration. In one embodiment, MVAΔC7L, MVAΔC7L-hFlt3L, VACVΔC7L, or VACVΔC7L-hFlt3L is administered directly into the tumor, e.g. by intratumoral injection, where a direct local reaction is desired. Additionally, administration routes of MVAΔC7L, MVAΔC7L-hFlt3L, VACVΔC7L, or VACVΔC7L-hFlt3L can vary, e.g., first administration using an intratumoral injection, and subsequent administration via an intravenous injection, or any combination thereof. A therapeutically effective amount of MVAΔC7L, MVAΔC7L-hFlt3L, VACVΔC7L, or VACVΔC7L-hFlt3L injection can be administered for a prescribed period of time and at a prescribed frequency of administration. In certain embodiments, MVAΔC7L, MVAΔC7L-hFlt3L, VACVΔC7L, or VACVΔC7L-hFlt3L can be used in conjunction with other therapeutic treatments. For example, MVAΔC7L, MVAΔC7L-hFlt3L, VACVΔC7L, or VACVΔC7L-hFlt3L can be administered in a neoadjuvant (preoperative) or adjuvant (postoperative) setting for subjects inflicted with bulky primary tumors. It is anticipated that such optimized therapeutic regimen will induce an immune response against the tumor, and reduce the tumor burden in a subject before or after primary therapy, such as surgery. Furthermore, MVAΔC7L, MVAΔC7L-hFlt3L, VACVΔC7L, or VACVΔC7L-hFlt3L can be administered in conjunction with other therapeutic treatments such as chemotherapy or radiation.

In certain embodiments, the MVAΔC7L, MVAΔC7L-hFlt3L, VACVΔC7L, or VACVΔC7L-hFlt3L virus is administered at least once weekly or monthly but can be administered more often if needed, such as two times weekly for several weeks, months, years or even indefinitely as long as benefits persist. More frequent administrations are contemplated if tolerated and if they result in sustained or increased benefits. Benefits of the present methods include but are not limited to the following: reduction of the number of cancer cells, reduction of the tumor size, eradication of tumor, inhibition of cancer cell infiltration into peripheral organs, inhibition or stabilization or eradication of metastatic growth, inhibition or stabilization of tumor growth, and stabilization or improvement of quality of life. Furthermore, the benefits may include induction of an immune response against the tumor, activation of effector $CD4^+$ T-cells, an increase of effector $CD8^+$ T-cells, or reduction of regulatory $CD4^+$ cells. For example, in the context of melanoma or, a benefit may be a lack of recurrences or metastasis within one, two, three, four, five or more years of the initial diagnosis of melanoma. Similar assessments can be made for colon cancer and other solid tumors.

In certain other embodiments, the tumor mass or tumor cells are treated with MVAΔC7L, MVAΔC7L-hFlt3L, VACVΔC7L, or VACVΔC7L-hFlt3L in vivo, ex vivo, or in vitro.

XIV. Vectors

In some embodiments, a pCB plasmid-based vector is used to insert a specific gene of interest (SG), such as murine GM-CSF (mGM-CSF) or human Flt3L (hFlt3L) under the control of the vaccinia synthetic early and late promoter (PsE/L). The methodology for constructing the vector has been described (See M. Puhlmann, C. K. Brown, M. Gnant, J. Huang, S. K. Libutti, H. R. Alexander, D. L. Bartlett, Vaccinia as a vector for tumor-directed gene therapy: Biodistribution of a thymidine kinase-deleted mutant. Cancer Gene Therapy, 7(1), 66-73 (2000)). An illustrative pCB-C7L-GFP vector nucleic acid sequence is set forth in SEQ ID NO: 4. A green fluorescent protein (GFP) under the control of vaccinia P7.5 promoter is used as a selectable marker. In some embodiments, these expression cassettes are flanked by a partial sequence of C7 gene on each side. In addition to the C7 locus, other suitable loci within the virus could be used. Homologous recombination that occurs at the C7 locus of the plasmid DNA and MVAΔC7L genomic DNA results in the insertion of SG and GFP expression cassettes into the MVAΔC7L genomic DNA C7 locus to generate MVAΔC7L-hFlt3L. In some embodiments, position 18,407 to 18,859 of the MVA genomic sequence (SEQ ID NO: 2) is replaced with a heterologous nucleic acid sequence comprising one or more open reading frames that encode for a selectable marker, such as GFP, and a gene of interest (SG), such as hFlt3L. Similarly, in some embodiments, homologous recombination that occurs at the C7 locus of the plasmid DNA and VACVΔC7L genomic DNA results in the insertion of SG and GFP expression cassettes into the VACVΔC7L genomic DNA C7 locus to generate VACVΔC7L-hFlt3L. In some embodiments, position 15,716 to 16,168 of the VACV genomic sequence (SEQ ID NO: 1) is replaced with a heterologous nucleic acid sequence comprising one or more open reading frames that encode for a selectable marker, such as GFP, and a gene of interest (SG), such as hFlt3L. The recombinant viruses are enriched by GFP selection and plaque-purified for 4-5 rounds until the appropriate recombinant viruses without contaminating MVAΔC7L or VACVΔC7L is obtained.

It will be appreciated, that any other expression vector suitable for integration into the MVAΔC7L or VACVΔC7L genome could be used as well as alternative promoters, regulatory elements, selectable markers, cleavage sites, non-essential insertion regions of MVA. In some embodiments, the selectable marker is a reporter protein, wherein the reporter protein is a bioluminescent protein, a fluorescent protein, or a chemiluminescent protein. In some embodiments, the reporter protein is green fluorescent protein (GFP). In some embodiments, the selectable marker is xanthine-guanine phophoribosyl transferase gene (gpt). MVA encodes many immune modulatory genes at the ends of the linear genome, including C11, C7, K3, F1, F2, F4, F6, F8, F9, F11, F14.5, J2, A46, C16. These genes can be deleted to potentially enhance immune activating properties of the virus, and allow insertion of transgenes.

EXPERIMENTAL EXAMPLES

The present technology is further illustrated by the following examples, which should not be construed as limiting in any way.

General Materials and Methods

Viruses and Cell lines. The Western Reserve (WR) strain of vaccinia virus (VACV) was propagated and virus titers were determined on BSC40 (African green monkey kidney cells) monolayers at 37° C. BSC40 cells were cultured in Dulbecco's modified Eagle's medium supplemented with 5% fetal bovine serum (FBS). MVA virus was kindly provided by Gerd Sutter (University of Munich), and propagated in BHK-21 (baby hamster kidney cell, ATCC CCL-10) cells. MVA is commercially and/or publicly available. The viruses were purified through a 36% sucrose cushion. BHK-21 were cultured in Eagle's Minimal Essential Medium (Eagle's MEM, can be purchased from Life Technologies, Cat #11095-080) containing 10% FBS, 0.1 mM nonessential amino acids (NEAA), and 50 mg/ml gentamycin. The murine melanoma cell line B16-F10 was originally obtained from I. Fidler (MD Anderson Cancer Center). B16-F10 cells were maintained in RPMI 1640 medium supplemented with 10% FBS, 100 Units/ml penicillin, 100 μg/ml streptomycin, 0.1 mM NEAA, 2 mM L-glutamine, 1 mM sodium pyruvate, and 10 mM HEPES buffer. All cells were grown at 37° C. in a 5% $CO_2$ incubator. Human embryonic kidney 293T cells were from American Type Culture Collection (ATCC). They were grown in DMEM supplemented with 10% FBS. RAW264.7 murine macrophage cell line were grown in DMEM supplemented with 10% FBS. THP-1 cells were grown in RPMI 1640 supplemented with 10% FBS. For THP-1 differentiation into macrophages, they were treated with PMA (10 ng/ml) for 48 h before subjecting them to experimental conditions.

Cells and cell lines used herein are commercially or publicly available unless otherwise indicated.

Multistep growth curve of WT VACV and VACVΔC7L. BSC40 cells were treated or mock-treated with IFN-0 at a final concentration of 1000 U/ml for 12 h. And the cells were then infected with WT VACV or VACVΔC7L at a MOI of 0.05. The cells were then scraped into the medium and collected at indicated times. After three cycles of freeze-thaw and subsequent sonication, viral titers in the collected samples were determined by plaque assay on BSC40 cells.

Construction of a C7 expression plasmid. IFN-β reporter plasmid (pIFN-β-luc) and ISRE reporter plasmid (p-ISRE-luc) were provided by Michaela Gack (University of Chicago). VACV C7L was amplified by PCR from VACV WR genome and subcloned into pcDNA3.1 and PQCXIP. For constructing flag tagged C7 expression plasmid, flag sequence was inserted into C-terminus of C7 and subcloned into pcDNA3.1.

Dual Luciferase Reporter assay. Luciferase activities were measured using the Dual Luciferase Reporter Assay system according to the manufacturer's instructions (Promega). Briefly, expression plasmids including a firefly luciferase reporter construct, a Renilla luciferase reporter construct, as well as other expression constructs were transfected into HEK293T cells. 24 h post transfection, cells were collected and lysed. 20 μl cell lysates were incubated with 50 μl of LARII to measure firefly luciferase activity and then were incubated with 50 μl of Stop & Glo Reagent to measure Renilla luciferase activity. The relative luciferase activity was expressed as arbitrary units by normalizing firefly luciferase activity under IFNB or ISRE promoter to Renilla luciferase activity from a control plasmid pRL-TK. Fold-induction was calculated by dividing relative luciferase activity under a certain test condition by that under background condition.

Generation of retrovirus expressing vaccinia C7. HEK293T cells were passaged into a 6-well plate. The next day, cells were transfected with three plasmids: VSVG (1 μg); gag/pol (2 μg); and PQCXIP-C7 (2 μg), with 10 μl lipofectamine 2000. After 2 days, cell supernatants were collected and filtered through a 0.45 μm filter and stored in −80° C.

Generation of HEK293T-cell line stably expressing vaccinia C7. HEK293 T cells were passaged into a 6-well plate. The next day, cells were infected with retrovirus expressing C7 at MOI 5. After 2 days, culture medium was replaced with fresh DMEM medium containing 1.2 μg/ml puromycin. After one week, survival cells are the cells stably expressing C7. The expression of C7 was verified by Western blot analysis using anti-C7 antibody.

Generation of RAW264.7 cell line stably expressing vaccinia C7. RAW264.7 cells were passaged into a 6-well plate. The next day, cells were infected with retrovirus expressing C7 at MOI 5. After 2 days, culture medium was replaced with fresh DMEM medium containing 5 μg/ml puromycin. After one week, survival cells are the cells stably expressing C7. The expression of C7 was verified by Western blot analysis using anti-C7 antibody.

Generation of THP-1 cell line stably expressing vaccinia C7. THP-1 cells were passaged into a 6-well plate. The next day, cells were infected with retrovirus expressing C7 at MOI 5. After 2 days, culture medium was replaced with fresh RPMI-1640 medium containing 5 μg/ml puromycin. After three weeks, survival cells are the cells stably expressing C7. The expression of C7 was verified by Western blot analysis using anti-C7 antibody.

Generation of recombinant VACVΔC7 virus. BSC40 cells were passaged into a 6-well plate. The next day, cells were infected with Vaccinia virus WR strain at MOI 0.2. After 1-2 h, cells were transfected with 0.75 μg pC7-GFP with 2 μl lipofectamine 2000. After 2 days, cells were collected and freeze/thaw three times. To select pure VACVΔC7, BSC40 cells were infected with virus mix above, then select plaques based on the GFP expression under microscope. After several rounds selection, all plaques were GFP positive. PCR was performed to confirm C7 absent.

Generation of recombinant MVAΔC7L virus. BHK21 cells were passaged into a 6-well plate. The next day, cells were infected with MVA at MOI 0.2. After 1-2 h, cells were transfected with 0.75 μg pC7-GFP with 2 μl lipofectamine 2000. After 2 days, cells were collected and freeze/thaw three times. To select pure MVAΔC7, BHK21 cells were infected with virus stock collected above, then select plaques based on the GFP expression under microscope. After 4-6 rounds of selection, all plaques were GFP positive. GFP-positive MVAΔC7L clones were amplified and the detection of C7L gene was confirmed by PCR analysis. The PCR primer sequences are as follows: forward primer 5'-ATGGGTATACAGCACGAATTC-3' (SEQ ID NO: 5) and reverse primer 5'-TTAATCCATGGACTCATAATC-3' (SEQ ID NO: 6).

Generation of bone marrow-derived dendritic cells (BMDCs). Bone marrow cells from the tibia and femur of mice were collected by first removing muscles from the bones, and then flushing the cells out using 0.5 cc U-100 insulin syringes (Becton Dickinson) with RPMI with 10% FCS. After centrifugation, cells were re-suspended in ACK Lysing Buffer (Lonza) for red blood cells lysis by incubating the cells on ice for 1-3 min. Cells were then collected, re-suspended in fresh medium, and filtered through a 40-μm cell strainer (BD Biosciences). The number of cells was counted. For the generation of GM-CSF-BMDCs, the bone marrow cells (5 million cells in each 15 cm cell culture dish) were cultured in CM in the presence of GM-CSF (30 ng/ml, produced by the Monoclonal Antibody Core facility at the Sloan Kettering Institute) for 10-12 days. CM is RPMI 1640 medium supplemented with 10% fetal bovine serum (FBS), 100 Units/ml penicillin, 100 μg/ml streptomycin, 0.1 mM essential and nonessential amino acids, 2 mM L-glutamine, 1 mM sodium pyruvate, and 10 mM HEPES buffer. Cells were fed every 2 days by replacing 50% of the old medium with fresh medium and re-plated every 3-4 days to remove adherent cells. Only non-adherent cells were used for experiments.

Western Blot Analysis. Bone marrow-derived dendritic cells (BMDCs) were generated according to the protocol (Dai et al., 2014). BMDCs ($1\times10^6$) from WT and KO mice were infected with MVA or MVAΔC7L at a MOI (multiplicity of infection) of 10. Whole-cell lysates were prepared. Equal amounts of proteins were subjected to sodium dodecyl sulfate-polyacrylamide gel electrophoresis and the polypeptides were transferred to a nitrocellulose membrane. Phosphorylation of TBK-1, TBK-1, phosphorylation of IRF3, IRF3, and STING levels were determined using respective antibodies (Cell Signaling). Anti-glyceraldehyde-3-phosphate dehydrogenase (GADPH) or anti-β-actin antibodies (Cell Signaling) were used as loading controls.

Co-immunoprecipitation. HEK293T cells were passaged into 10 cm plates. The next day, cells were transfected with flag-STAT1 or flag-STAT2 together with pcDNA3.1-C7-HA. After two days, cells were lysed in Pierce IP lysis buffer on ice for 30 min. For IFN treatment groups, cells were treated with 1000 U/ml IFNB for 45 min before cell lysis. HA antibody (Sigma H3663) was added into cell lysis to final concentration 1 μg/ml, and incubated at 4° C. overnight. The next day, protein A-agarose was added and incubate at 4° C. for 2 h. The agarose was washed with IP lysis buffer three times. Lastly, the proteins were denatured at 98° C. for 5 min.

Mice. Female C57BL/6J mice between 6 and 10 weeks of age were purchased from the Jackson Laboratory and were used for the preparation of bone marrow-derived dendritic cells and as control mice for in vivo experiments. These mice were maintained in the animal facility at the Sloan Kettering Institute. All procedures were performed in strict accordance with the recommendations in the Guide for the Care and Use of Laboratory Animals of the National Institute of Health. The protocol was approved by the Committee on the Ethics of Animal Experiments of Sloan-Kettering Cancer Institute. $STING^{Gt/Gt}$ mice were generated in the laboratory of Russell Vance (University of California, Berkeley).

Intranasal infection of WT VACV or VACVΔC7L in WT C57BL/6 mice and $STING^{Gt/Gt}$ mice. 10 WT mice in each group were anesthetized and infected intranasally with increasing doses of WT VACV at $2\times10^3$, $2\times10^4$, $2\times10^5$, or $2\times10^6$ pfu, and VACVΔC7L at $2\times10^5$, $2\times10^6$, or $2\times10^7$ pfu, inoculated to both nostrils in 10 μl each. Mice were monitored and weight daily. The $STING^{Gt/Gt}$ mice were infected with either WT VACV at $2\times10^4$ pfu or VACVΔC7L at $2\times10^5$ pfu. Mice that had lost 30% of initial weight were be euthanized. Kaplan-Meier survival curves were determined.

Bilateral tumor implantation model and intratumoral injection with recombinant MVAΔC7L or MVA. Briefly, B16-F10 melanoma cells were implanted intradermally to the left and right flanks of C57BL/6 mice ($5\times10^5$ to the right flank and $1\times10^5$ to the left flank). 9 days after tumor implantation, the larger tumors on the right flank were intratumorally injected with $2\times10^7$ pfu of MVA or MVAΔC7L. The tumor sizes were measured and the tumors were repeatedly injected twice a week. The survival of mice was monitored.

Generation of VACV C7 specific polycolnal antibodies. C7 cDNA was cloned into bacterial expression vector-pET28-N-His-SUMO. The C7 expression plasmids were transformed into *E. coli* BL21 (DE3) cells. Bacterial cultures (2-liter) amplified from a single transformant were grown at 37° C. in LB Broth containing 100 μg/ml ampicillin until the $A_{600}$ reached 0.8. The cultures were adjusted to 0.5 mM isopropyl-β-d-thiogalactopyranoside (IPTG), and then incubated for 20 h at 18° C. with constant shaking. Cells were harvested by centrifugation and re-suspended in buffer A (50 mM Tris-HCl, pH 7.5, 500 mM NaCl, 20 mM imidazole, 10% glycerol). The cells were lysed by sonication and the insoluble material was removed by centrifugation at 15000 rpm for 45 min. Supernatants were mixed for 1 h with 5 ml of Ni-NTA resin (Qiagen) that had been equilibrated with buffer A. The resins were poured into gravity-flow columns and then washed with 60 ml of buffer A. The adsorbed proteins were step-eluted with 300 mM imidazole in buffer A. The polypeptide compositions of the eluate fractions were monitored by SDS-PAGE and the peak fractions containing each recombinant protein were pooled. The eluates were dialyzed against buffer containing 50 mM Tris-HCl (pH 8), 200 mM NaCl, 2 mM DTT, 2 mM EDTA, 10% glycerol, and 0.1% Triton X-100 and then stored at −80° C. Rabbit immunization was performed in Pocono Rabbit Farm and Laboratory (PRF&L) to generate C7 specific rabbit antibodies. A rabbit was injected with 100 μg of purified C7 protein subcutaneous plus Mighty Quick Immune Stimulator in Incomplete Freund's Adjuvant (IFA) four times two weeks apart for two months. C7 antibodies were purified from rabbit serum using affinity purification.

Statistics. Two-tailed unpaired Student's t-test was used for comparisons of two groups in the studies. Survival data were analyzed by log-rank (Mantel-Cox) test. The p values deemed significant are indicated in the figures as follows: *, $p<0.05$; , $p<0.01$; *, $p<0.001$; ****, $p<0.0001$. The numbers of animals included in the study are discussed in each figure legend.

Figure 1B:
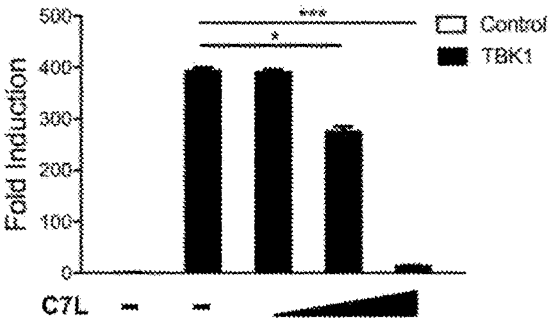
Figure 1C:
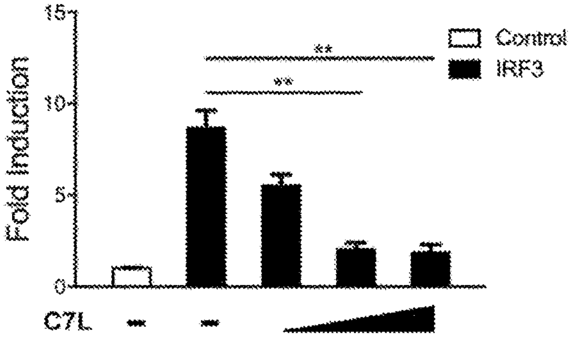
Figure 1D:
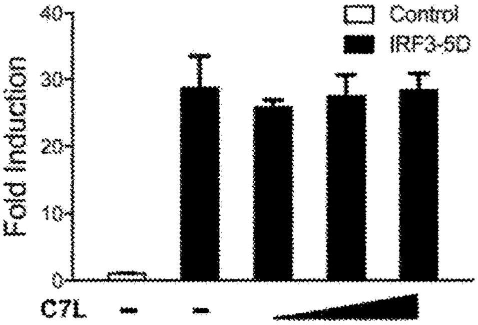
Figure 1E:
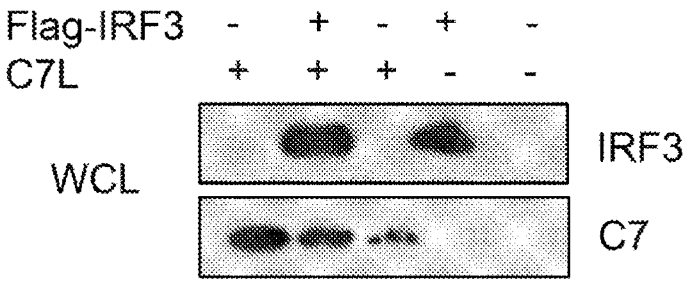
FIGS. 1E and IF are blots showing that vaccinia C7 interacts with transcription factor IRF3. HEK293T cells were co-transfected with Flag-tagged human IRF3 or C7L either alone or in combination.
Figure 1F:
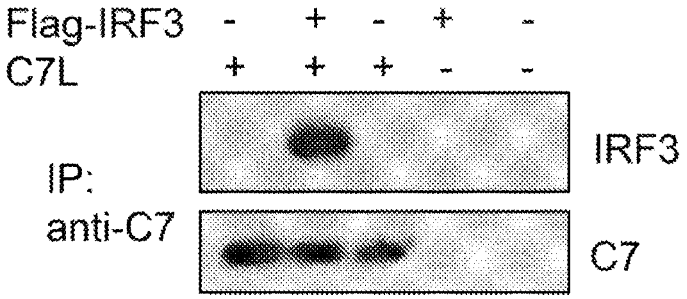
FIG. 1F: Whole cell lysates were immunoprecipitated with anti-C7 antibody (IP:anti-C7), and immunoblotted with anti-Flag antibody.

Example 1: Vaccinia C7 Inhibits STING, TBK1, and IRF3-Mediated IFN Gene Induction A dual-luciferase assay system was used to evaluate the role of vaccinia C7 in the regulation of STING, TBK1, or IRF3-induced IFNB promoter activation in HEK293T-cells, a human embryonic kidney cell line transformed with SV40 large T antigen. HEK293T-cells were transfected with plasmids expressing IFNB-firefly luciferase reporter, a control plasmid pRL-TK that expresses Renilla luciferase, STING, and vaccinia C7L as indicated. Dual luciferase assays were performed at 24 h post transfection. The relative luciferase activity was expressed as arbitrary units by normalizing firefly luciferase activity to Renilla luciferase activity. Over-expression of STING resulted in a 30-fold induction of IFNB promoter activity compared with that in the control sample without STING. Co-transfection of increasing amounts of C7L expression plasmid led to a significant reduction of STING-induced IFNB promoter activity (FIG. 1A). Similarly, over-expression of TBK1 resulted in a 400-fold induction of IFNB promoter activity compared with control. Co-transfection of increasing amounts of C7L expression plasmid (250 ng) led to over 90% reduction of TBK1-induced IFNB promoter activity (FIG. 1B). IRF3 is a member of the interferon regulatory transcription factor (IRF) family and it is an essential transcription factor for the IFNB promoter. Over-expression of C7 also caused 70% reduction of IRF3-induced IFNB promoter activity (FIG. 1C), whereas overexpression of C7 failed to reduce IRF3-5D-induced IFNB promoter activity (FIG. 1D). IRF3-5D is a phosphorylation active mutant of IRF3. FIGS. 1E and 1F show that vaccinia C7 interacts with transcription factor IRF3. These results indicate that C7 plays an inhibitory role in IRF3 phosphorylation and C7 is unable to block the activity of phosphorylated IRF3.

Figure 2A:
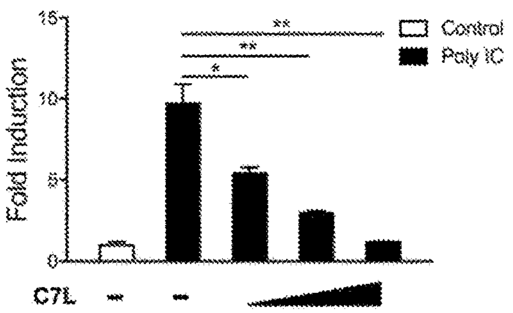
FIGS. 2A-2C are a series of graphical representations of data showing that vaccinia C7 inhibits poly IC/TLR3 and TRIF-mediated IFNB promoter activation.
Figure 2B:
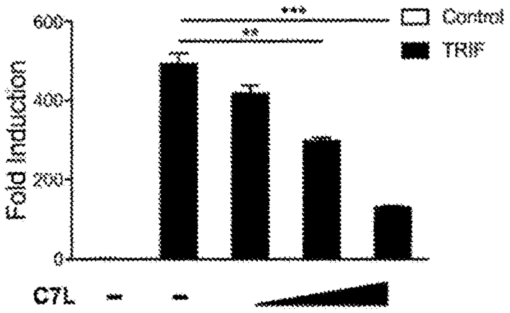
Figure 2C:
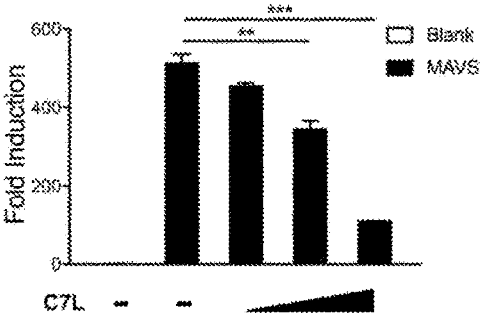

Example 2: Vaccinia C7 Inhibits Poly I:C (TLR3) or TRIF-Mediated IFN Gene Induction The TBK1-IRF3 axis is important for signal transduction from several sensing pathways, including cGAS-cGAMP- STING, RIG-I or MDA5-MAVS, TLR3-TRIF, and TLR4-TRIF. To test whether vaccinia C7 has an inhibitory role of TRIF signaling, the inventors transfected HEK293T-cells with TLR3 expression plasmid, IFN-β-luc reporter and increasing amount of C7 expression plasmid (10 ng, 50 ng, or 250 ng). After 24 h, cells were treated with poly I:C (5 μg/ml). Luciferase activity was assayed 24 h post poly I:C treatment. Transfection of TLR3 and treatment with poly I:C resulted in 9-fold induction of IFNB promoter activity compared with empty vector control (FIG. 2A). Overexpression of C7 resulted in the reduction of poly (I:C)/TLR3-induced IFNB promoter activity up to 90% (FIG. 2A). To test whether C7 also inhibits TRIF-induced IFNB promoter activity, HEK293T-cells were transfected with TRIF expression plasmid, which resulted in 500-fold induction of IFNB promoter activity compared with empty vector control (FIG. 2B). Overexpression of C7 resulted in the reduction of TRIF-induced IFNB promoter activity over 70% (FIG. 2B). RIG-I or MDA5-MAVS signaling is essential for RNA stimulated type I IFN production. MAVS overexpression induced high IFNB luciferase signal. It is about 500-fold induction compared with control. C7 also blocked MAVS induced luciferase signal by 70%. These results indicate that overexpression of C7 in HEK293T-cells exerts an inhibitory effect on STING, poly (I:C), TRIF, TBK1, and IRF3-induced IFNB promoter activity. By contrast, overexpression of C7 fails to inhibit a constitutively activated phosphorylated IR F3-5D. Since TBK1/IRF3 is a common node to these diverse DNA- and RNA-sensing pathways, it is possible that C7 targets the step that leads the activation of IRF3, resulting in the failure of IRF3 phosphorylation and nuclear translocation.

Figure 3A:
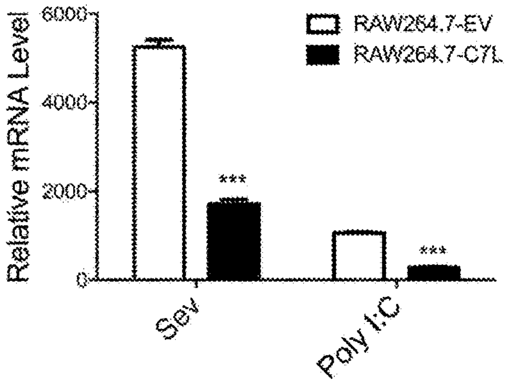
FIGS. 3A-3D are a series of graphical representations of data showing that over-expression of vaccinia C7 in macrophage cells inhibits IFNB gene expression induced by various stimuli. RAW264.7 stable cell lines expressing C7 or with empty vector (EV) ($2\times10^6$) were infected with Sendai virus (SeV) (10 HA units/ml), or transfected with poly IC (5 μg/ml) (FIG. 3A), or treated with Heat-inactivated MVA (H-MVA) (an equivalent of MOI of 10), or transfected with ISD (10 μg/ml) (FIG. 3B), respectively. After 24 h, IFNB gene expression level was measured by quantitative real-time PCR.
Figure 3B:
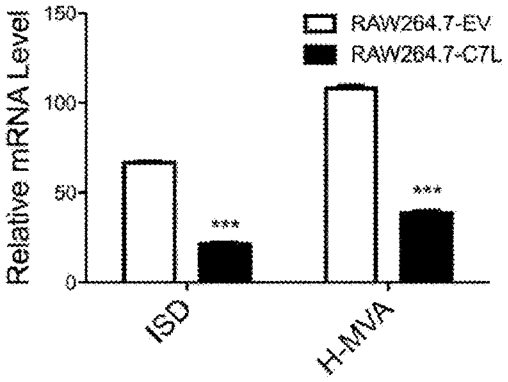
Figure 3C:
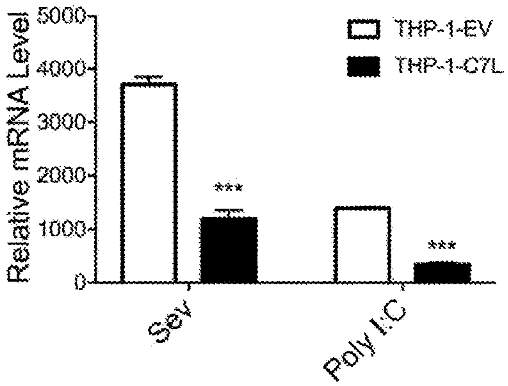
Figure 3D:
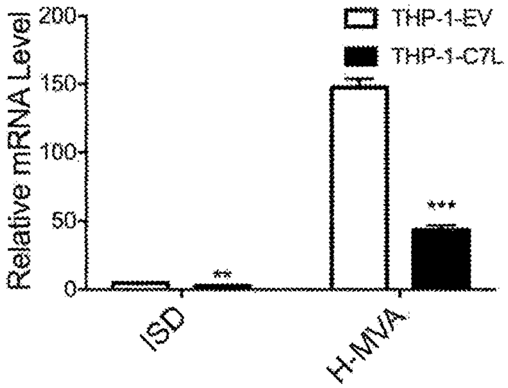

Example 3: Over-Expression of Vaccinia C7 in Immune Cells Inhibits IFNB Gene Induction To assess the effect of vaccinia C7 in IFNB gene induction in immune cells, we generated two cell lines stably expressing vaccinia C7, including murine macrophage RAW264.7 and human THP-1. THP-1 is a human monocytic leukemia cell line that has been used extensively to study human monocyte and macrophage function and immune regulation. Briefly, RAW264.7 and THP-1 were transduced with retrovirus containing the expression construct of vaccinia C7 under CMV promoter and puromycin selection marker. Empty vector with drug selection marker was also used to generate a control cell line. Drug resistant cells were obtained and used for the following experiments. THP-1 stable cell lines expressing C7 or with empty vector were differentiated by phorbol-12-myristate-13-acetate (PMA; 20 ng/ml) for 3 days before they were used for the experiments. Cells were either infected with Sendai virus (SeV), Heat-inactivated MVA (H-MVA), or incubated with poly I:C, or transfected with ISD (Invivogen). After 24 h, IFNB gene expression level was measured by quantitative real-time PCR. SeV infection induced highest level of IFNB gene expression in both RAW264.7 and THP-1 cells and overexpression of vaccinia C7 resulted in the reduction IFNB gene expression by 60% (FIGS. 3A and 3C). Vaccinia C7 also attenuated poly (I:C)-induced IFNB gene expression in RAW264.7 and THP-1 cells over 50%. Similarly, vaccinia C7 reduced Heat-iMVA-induced IFNB gene expression in RAW264.7 and THP-1 cells by 60%. SeV is a negative sense, single-stranded RNA virus belongs to the paramyxoviridae family. SeV can be sensed by the cytoplasmic RNA sensors retinoic-acid inducible gene-I (RIG-I) and melanoma differentiation-associated gene 5 (MDA-5) (Kato et al. 2005, Gitlin et al., 2010), which leads to the activation of the MAVS/TBK1/IRF3 axis. Poly (I:C) activates the endosomal dsRNA sensor, TLR3, which leads to activation of the TRIF/TBK1/IRF3 axis. H-MVA activates the cytosolic DNA-sensor cGAS, which leads to the generation of the second messenger, cyclic GMP-AMP (cGAMP), and the activation of STING/TBK1/IRF3 axis (Dai et al., Science immunology, in press). Taken together, these results indicate that vaccinia C7 inhibits multiple innate immune sensing pathways in macrophage cells.

Example 4: Generation of Recombinant MVAΔC7L Virus

Figure 4A:
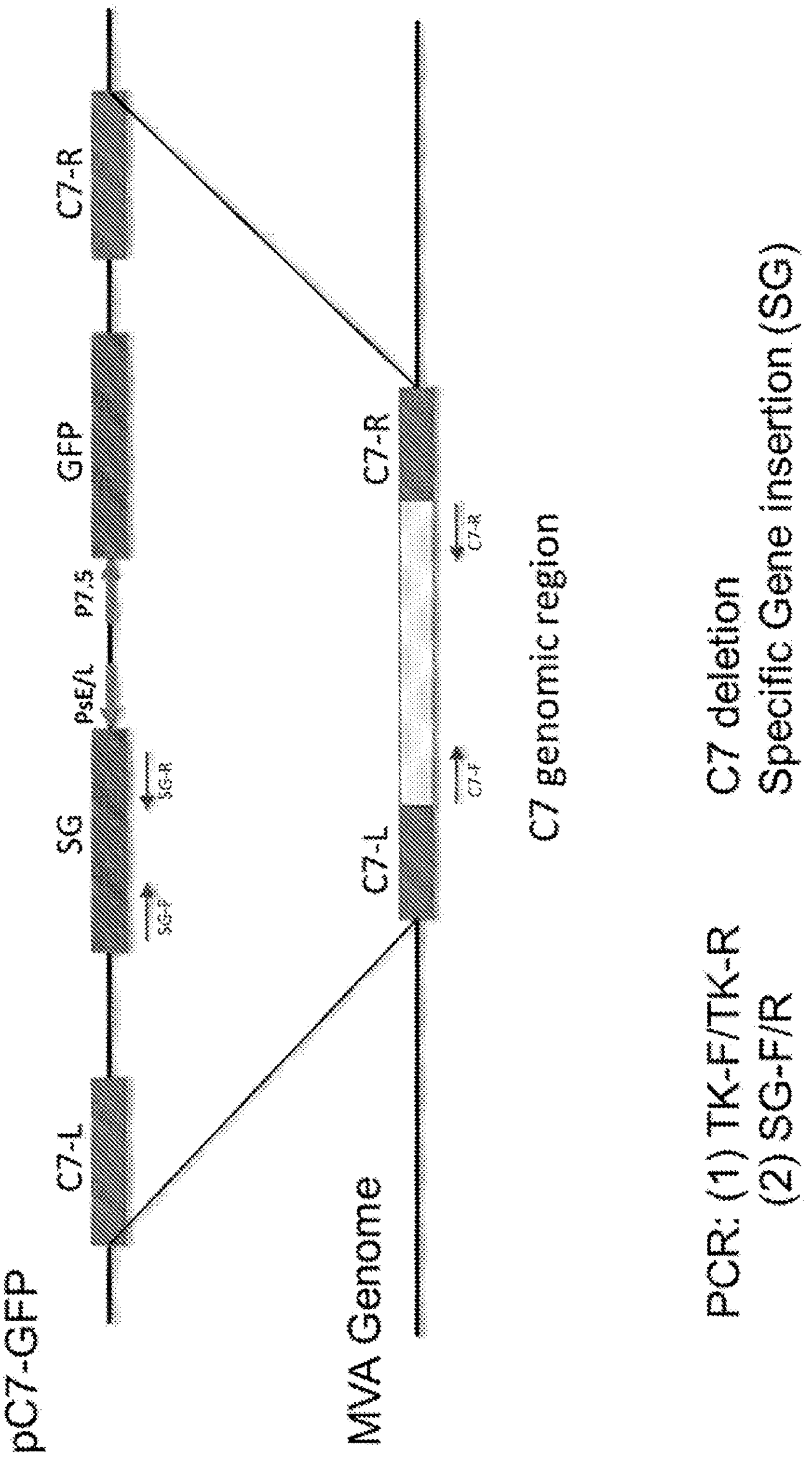
FIG. 4A is a schematic diagram of homologous recombination between plasmid DNA pC7L-GFP vector and MVA viral genomic DNA at the C7 gene locus. pC7L-GFP plasmid was used to insert specific gene of interest (SG), such as human Flt3L (hFlt3L), under the control of the vaccinia synthetic early and late promoter (PsE/L), into the C7L locus. In this case, GFP under the control of the vaccinia p7.5 promoter was used as a selection marker. The expression cassette was flanked by partial sequence of C7L gene flank regions (C7-L and C7-R) on each side.
Figure 4B:
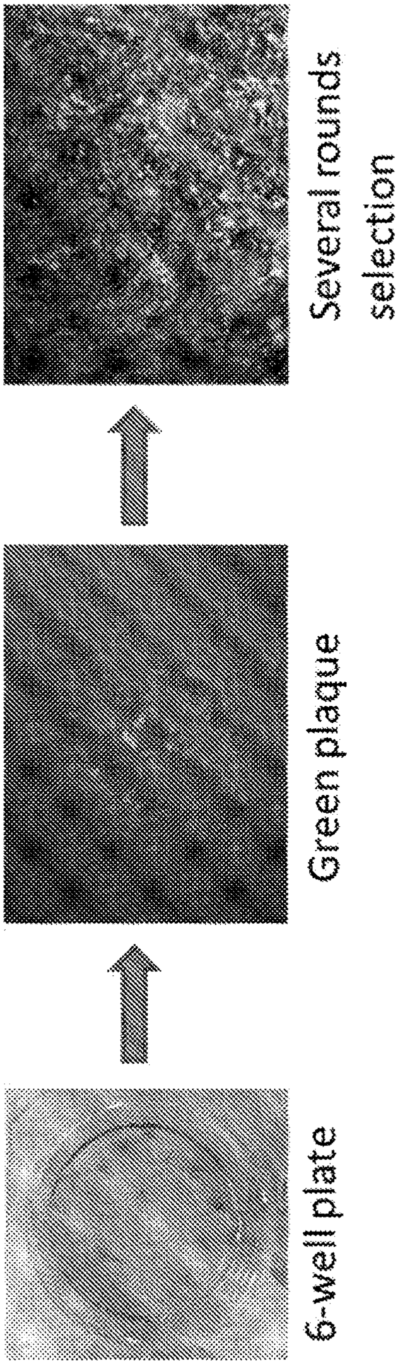
FIG. 4B shows plaque purification of MVAΔC7L virus expressing GFP. BHK21 cells ($1\times10^6$) were infected with MVA at a MOI of 0.2. After 1-2 h of infection, cells were transfected with pC7L-GFP with lipofectamine 2000. Homologous recombination that occurred at the C7L locus of the plasmid DNA and MVA genomic DNA results in the insertion of GFP expression cassette into the MVA genomic DNA C7 locus to delete the entire C7L gene from MVA genome and results in the generation of the recombinant virus MVAΔC7L. The recombinant virus was enriched based on the GFP expression, and $GFP^+$ plaques were purified for 4-5 rounds until the desired recombinant virus was obtained without contaminating MVA.
Figure 4C:
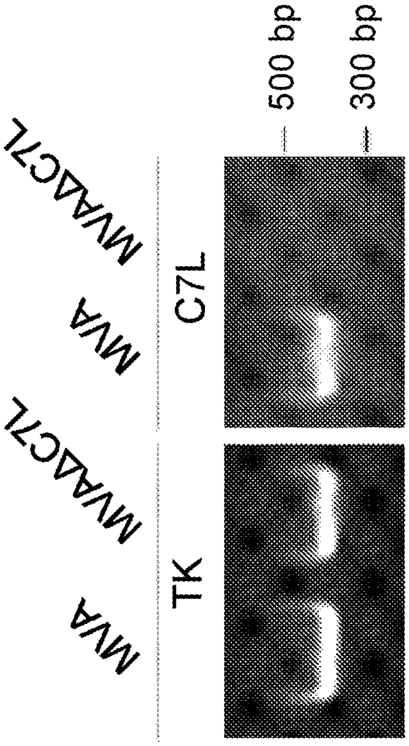
FIG. 4C provides the PCR verification of recombinant virus MVAΔC7L. PCR analysis of recombinant viruses demonstrated successful generation of MVAΔC7L. Viral genomic DNAs were analyzed by PCR to verify the deletion of C7L.

To further establish the role of C7 in immune modulation, a strategy to generate MVAΔC7L virus in which the C7L gene is deleted was designed. pC7LGFP vector (SEQ ID NO: 4) was constructed to insert specific gene of interest into the C7L locus of MVA. In this case, GFP under the control of the vaccinia P7.5 promoter was used as a selection marker. The expression cassette was flanked by partial sequence of C7 flank regions (C7-L and C7-R) on each side (FIG. 4A). BHK21 cells were infected with MVA virus expressing LacZ at a MOI of 0.05 for 1 h, and then were transfected with the plasmid DNA described above. The infected cells were collected at 48 h. Recombinant viruses were identified by their green fluorescence with the insertion of GFP into the C7 locus (FIG. 4B). The positive clones were plaque purified 4-5 times. PCR analysis was performed to confirm that recombinant virus MVAΔC7L has lost of the C7 gene (FIG. 4C).

Figure 5A:
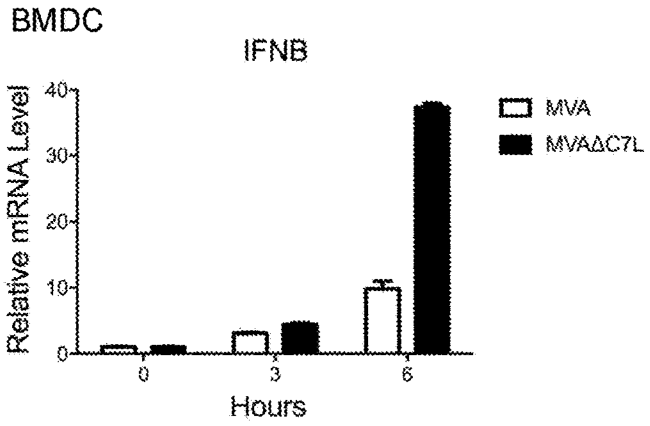
FIGS. 5A-5D are a series of graphical representations of data showing that MVAΔC7L induces stronger innate immune responses in bone marrow-derived dendritic cells (BMDC) and THP-1 cells compared with MVA. $1\times10^6$ BMDCs (FIG. 5A) or THP-1 (FIG. 5C) were infected with MVA or MVAΔC7L at a MOI of 10. At the indicated time points, quantitative real-time PCR analyses of IFNB mRNAs were performed. Data are means±SEM (n=3).
Figure 5B:
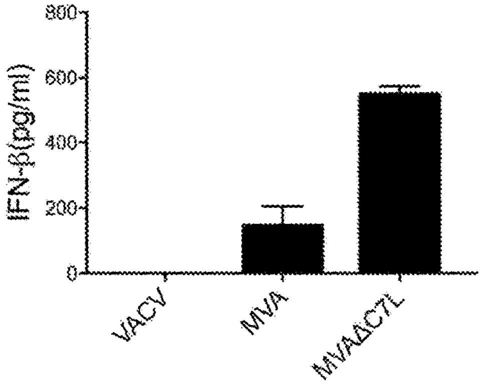
Figure 5C:
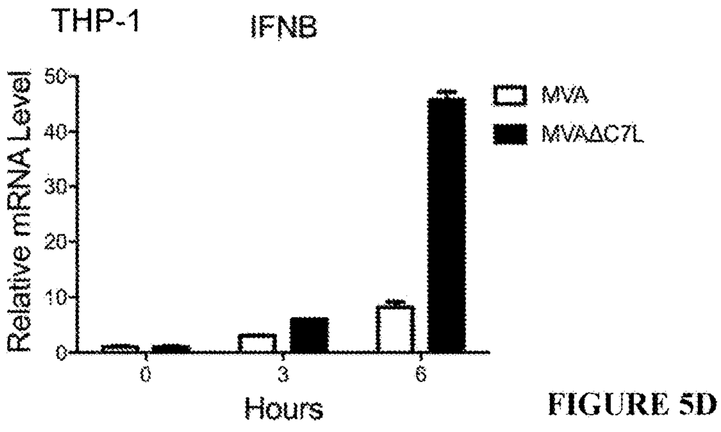
Figure 5D:
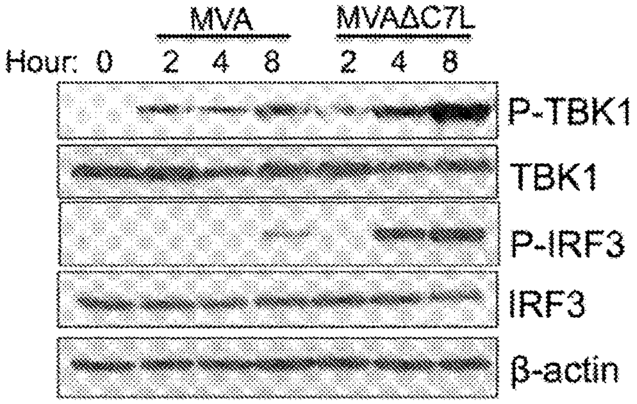

Example 5: MVAΔC7L Infection of Murine cDCs and Human THP-1 Cells Induces Higher Levels of IFNB Gene Expression and Phosphorylation of TBK1 and IRF3 than MVA MVA infection of conventional dendritic cells (cDCs) has been shown to induce type I IFN via a cGAS/STING/IRF3-dependent mechanism. To test whether C7 plays an inhibitory role in the induction of cytosolic DNA-sensing pathway, the innate immune responses of bone marrow-derived DCs (BMDCs) to MVAΔC7L vs. MVA were analyzed. BMDCs were infected with either MVAΔC7L or MVA at a MOI of 10. Cells were collected at 3 h and 6 h post infection. The IFNB gene expression levels were determined by quantitative PCR analyses. MVAΔC7L induced significantly higher levels of IFNB gene expression than MVA in cDCs at 3 h and 6 h post infection (FIG. 5A). The IFN-β protein level was also higher in the supernatants from MVAΔC7L-infected cDCs than other from MVA-infected cDCs (FIG. 5B). Western blot analyses demonstrated that MVAΔC7L infection induced higher levels of phosphorylation of TBK1 and IRF3 than MVA, which suggests that TBK1 might be the target of C7 (FIG. 5D). To test whether MVAΔC7L induces higher levels of IFNB gene activation in human immune cells, the widely used differentiated THP-1 cells were employed. THP-1 cells were infected with either MVAΔC7L or MVA at a MOI of 10, and they were collected at 3 h and 6 h post infection. MVAΔC7L infection induced higher levels of IFNB gene expression than MVA in THP-1 cells (FIG. 5C). These results indicate that C7 is an inhibitor that antagonizes the cytosolic DNA-sensing pathway, possibly at the level of TBK1. Accordingly, these results show that MVAΔC7L is useful in methods of inducing the innate immune response.

Example 6: Vaccinia C7 Attenuates Type I IFN-Induced JAK-STAT Signaling Pathway

Figure 6A:
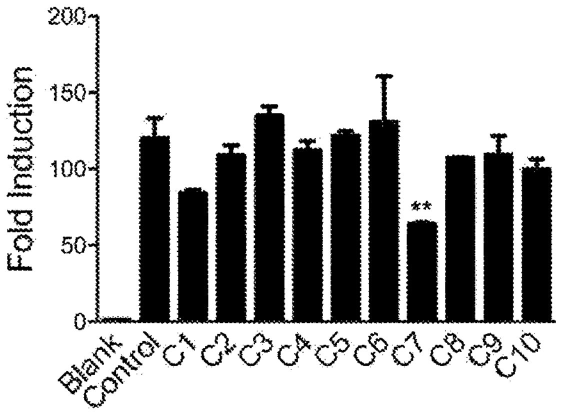
FIGS. 6A-6B are a series of graphical representations of data showing that vaccinia C7 attenuates Type I IFN-induced JAK-STAT signaling pathway.
Figure 6B:
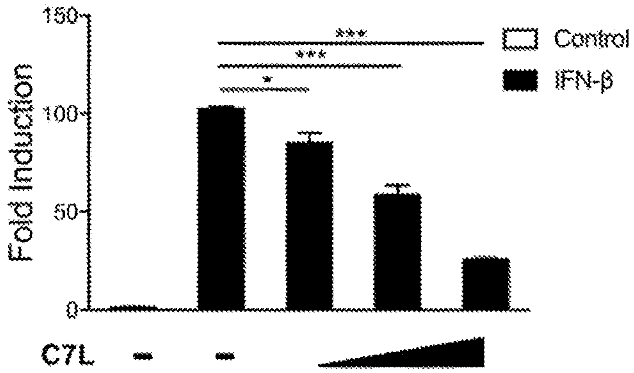

Whether C7 has any inhibitory effect on the IFN-β-induced interferon-stimulated gene (ISG) activation was analyzed. In this example, ISRE-luc reporter was used. Briefly, HEK293T-cells were transfected with ISRE-luc reporter, which expresses firefly luciferase once ISRE is activated, and control plasmid pRL-TK, which expresses Renilla luciferase once it is activated, as well as increasing amounts of plasmid expressing vaccinia C7. 24 h post transfection, the cells were treated with IFN-β for another 24 h. Cells were then collected and the relative levels of firefly luciferase over Renilla luciferase were determined. Fold change is defined as the relative levels. The over-expression of C7 resulted in the reduction of ISRE activation up to 75% (FIG. 6B).

Figure 7A:
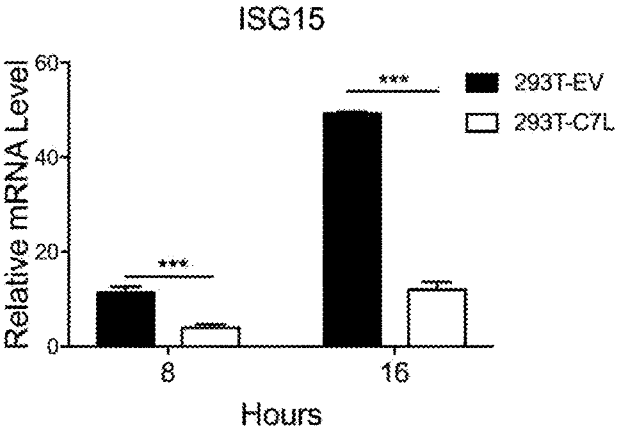
FIGS. 7A and 7B are a series of graphical representations of data showing that over-expression of vaccinia C7 in HEK293T and murine macrophage cells inhibits Type I IFN-induced ISG15 gene expression. HEK293T (FIG. 7A) or RAW264.7 (FIG. 7B) stable cell lines expressing C7 or with empty vector ($1\times10^6$) were treated with human (FIG. 7A) or murine (FIG. 7B) IFN-β at a final concentration of 1000 U/ml for 16 h. ISG15 mRNA levels were measured by quantitative real-time PCR. Data are means±SEM (n=3). (***P<0.001, t test).
Figure 7B:
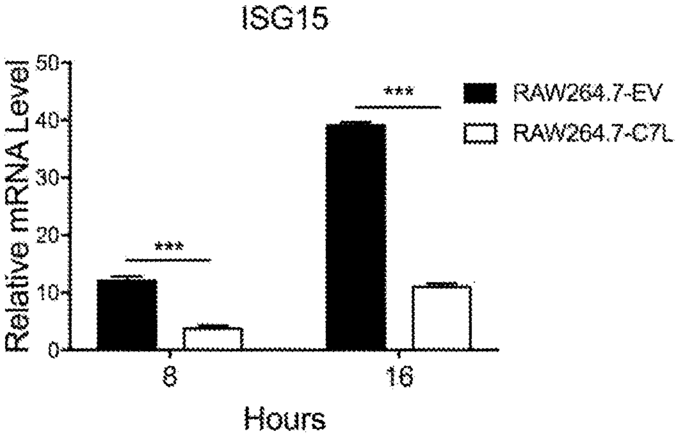

Example 7: Over-Expression of Vaccinia C7 Antagonizes IFN-β-Induced ISG Expression Whether over-expressing vaccinia C7 in HEK293T-cells (FIG. 7A) or RAW264.7 cells (FIG. 7B) would antagonize IFN-β-induced ISG gene expression was analyzed. RAW264.7 cells expressing vaccinia C7 have been described (Example 3). HEK293T-cells were transduced with retrovirus containing vaccinia C7L and a drug selection marker-puromycin. Stable HEK293T-cell line expressing vaccinia C7 was generated after several rounds of drug selection. Empty vector with drug selection marker was also used to generate a control cell line. The stable cell lines expressing C7 or with empty-vector were treated with IFN-β for 16 h. ISG15 mRNA levels were measured by quantitative real-time PCR. The ectopic expression of C7 resulted in the reduction of ISG15 gene expression compared with empty vector-control cell lines. These results further support that vaccinia C7 down-regulates IFN-β-induced ISG expression.

Figure 8A:
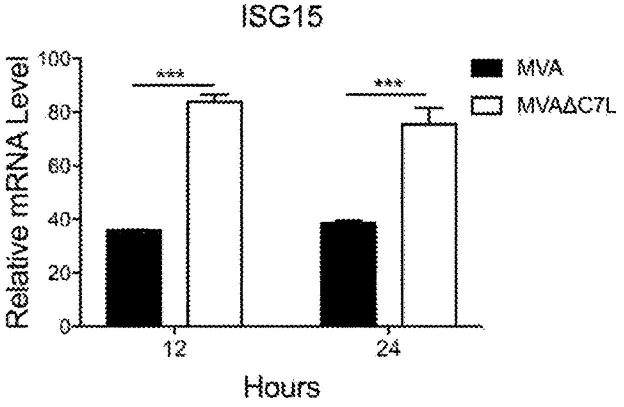
FIGS. 8A and 8B are a series of graphical representations of data showing that MVAΔC7L induces higher levels of interferon stimulatory gene (ISG) expression in BMDC compared with MVA. BMDCs ($1\times10^6$) were infected with MVA or MVAΔC7L at a MOI of 10. At 12 and 24 h post infection, cells were harvested and quantitative real-time PCR analysis of ISG15 (FIG. 8A) or Mx1 (FIG. 8B) mRNAs were performed. Data are means±SEM (n=3). (***P<0.001, t test).
Figure 8B:
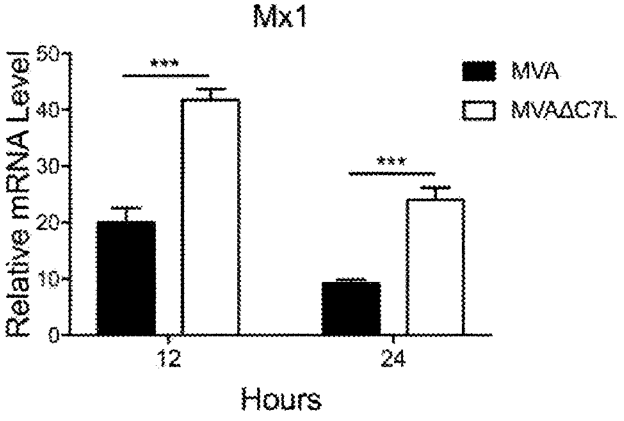

Example 8: MVAΔC7L Induces Higher Levels of ISG Expression in BMDC Compared with MVA Whether MVAΔC7L induces higher levels of interferon stimulated gene (ISG) expression than MVA was analyzed. BMDCs were infected with MVAΔC7L or MVA at a MOI of 10. Cells were collected at 12 and 24 h post infection. mRNAs were extracted and the expression levels of ISG15 and Mx1 were determined by quantitative real-time PCR. MVAΔC7L infection induced higher levels of ISG15 and Mx1 than MVA at 12 and 24 h post infection (FIGS. 8A and B). Accordingly, these results show that MVAΔC7L is useful in methods of inducing the innate immune response.

Figure 9A:
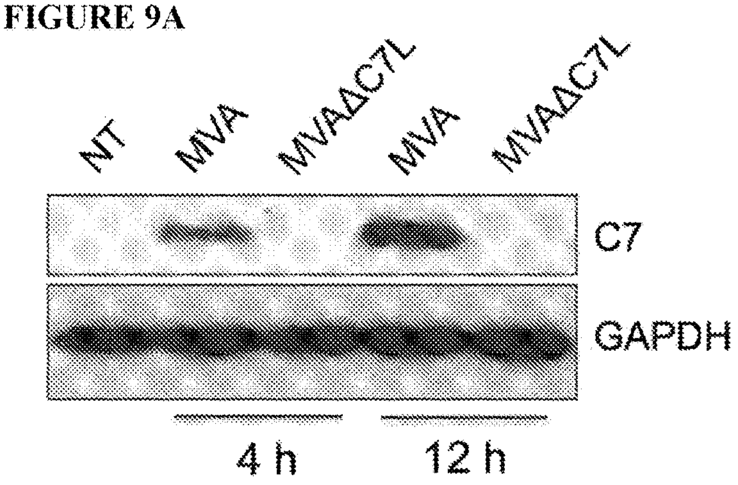
FIGS. 9A and 9B is a series of graphical representations of data showing that MVAΔC7L fails to express C7 protein and to inhibit IFN-β-induced STAT2 phosphorylation. (A) HeLa cells ($2\times10^5$) were infected with either MVA or MVAΔC7L at a MOI of 10. Cells were collected at 4 and 12 h post infection. Western blot analysis was performed using anti-C7 antibody. GAPDH was used as a loading control. (B) $TBK1^{-/-}$ MEFs were infected with either MVA or MVAΔC7L at a MOI of 10 for 6 h prior to treatment with murine IFN-β at a final concentration of 1000 U/ml for indicated times. Western blot analysis was performed using anti-pSTAT2 or anti-C7 antibodies. GAPDH was used as a loading control.

Example 9: MVAΔC7L Fails to Express C7 and to Inhibit IFN-β-Induced STAT2 Phosphorylation Vaccinia C7 protein was expressed and purified in the *E. coli* BL21 (DE3), and generated anti-C7 polyclonal rabbit antibodies by immunization in a rabbit. Anti-C7 antibody was purified through an affinity column. To verify the expression of C7 in MVA-infected cells and the loss of C7 expression in MVAΔC7L-infected cells, HeLa cells were infected with either MVA or MVAΔC7L at a MOI of 10. Cells were collected at 4 and 12 h post infection. Western blot analysis was performed. MVA infection resulted in the expression of C7 at 4 and 12 h post infection, whereas MVAΔC7L-infected cells did not have detectable C7 protein (FIG. 9A). This is consistent with the PCR results in FIG. 4C that C7L gene is deleted from MVAΔC7L.

Figure 9B:
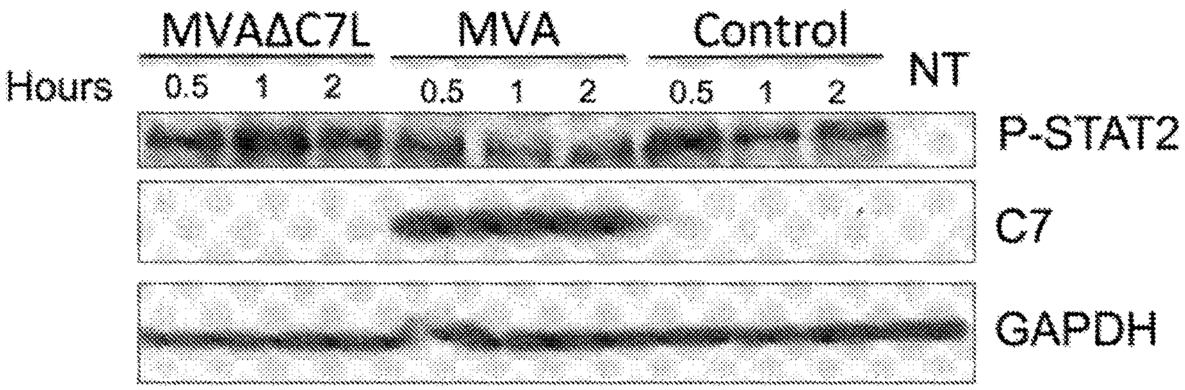

Upon binding of type I IFNs, IFNAR activates JAK/STAT pathway, leading to the phosphorylation and activation of Stat1 and Stat2 transcription factors, which in turn activates the expression of hundreds of ISGs leading to the establishment of an antiviral state. To test whether MVA infection inhibits IFN-0-induced JAK-STAT pathway activation, TBK1−/− MEF cells were used. MVA-induced IFNB gene induction in MEFs is dependent on TBK1. Therefore in TBK1−/− cells, the effect of MVA on IFNB gene induction is eliminated. TBK1−/− cells were infected with MVA or MVAΔC7L at a MOI of 10 for 6 h prior to treatment with murine IFN-β at a final concentration of 1000 U/ml for indicated times. IFN-β treatment resulted in rapid induction of phosphorylation of STAT2, which was reduced in MVA-infected cells, but was unaffected in MVAΔC7L-infected cells (FIG. 9B). Similar to what was observed in HeLa cells, C7 was detected in MVA-infected MEFs but not in MVAΔC7L-infected cells. These results indicate that C7 inhibits of the activation IFNAR-mediated JAK-STAT pathway by preventing STAT2 phosphorylation.

Example 10: Vaccinia C7 Protein Interacts with STAT2

Figure 10B:
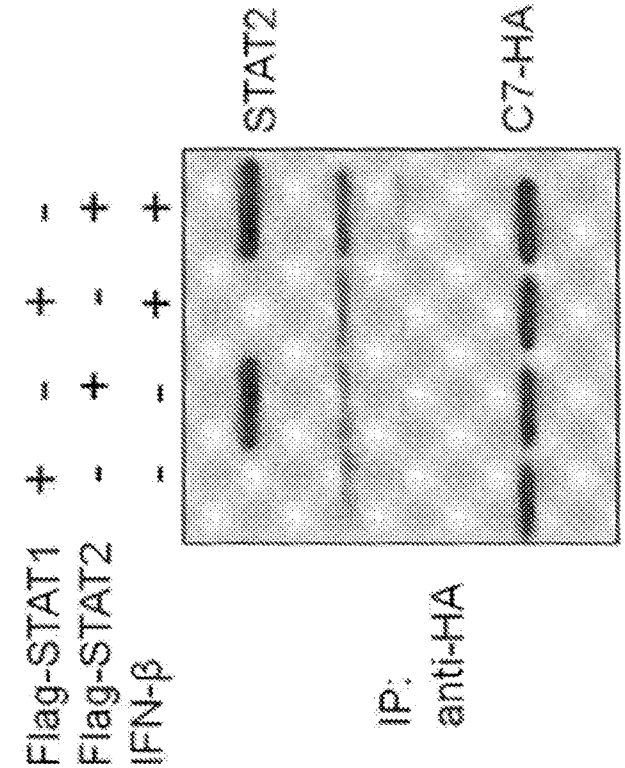
FIGS. 10A and 10B are a series of graphical representations of data showing that vaccinia C7 protein interacts with STAT2. HEK293T-cells ($1.5\times10^7$) were co-transfected with 2.5 μg of Flag-tagged human STAT1 or STAT2 with HA-tagged C7, and then treated or mock treated with human IFN-β at a final concentration of 1000 U/ml for 45 min.
Figure 10A:
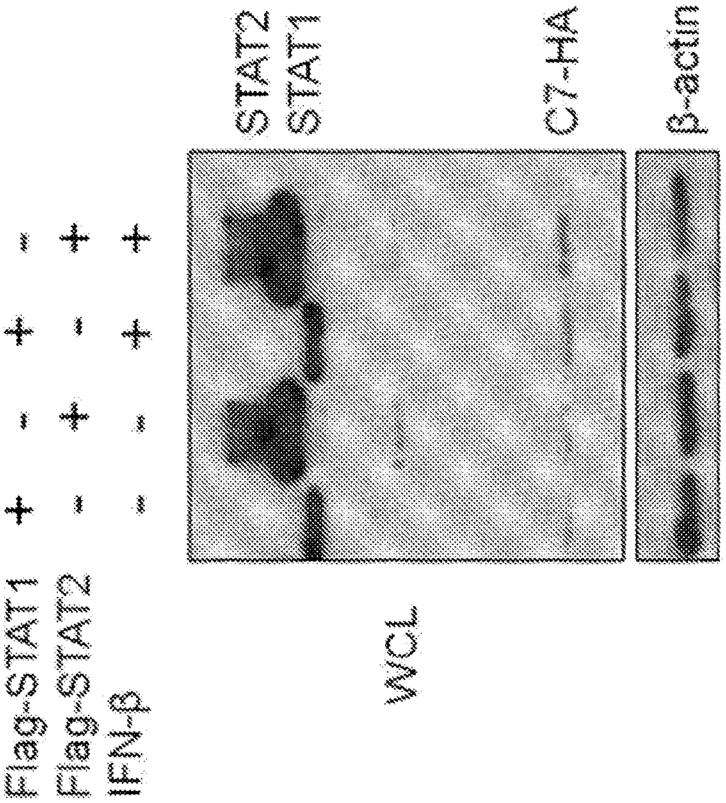

A co-immunoprecipitation assay was performed to determine whether vaccinia C7 down-regulates this pathway through interacting with either Stat1 or Stat2. Briefly, HEK293T-cells were co-transfected with Flag-tagged human STAT1 or STAT2 with HA-tagged C7, and then treated or mock treated with IFN-β for 45 min. The whole cell lysates (WCL) were prepared and blotted with anti-FLAG and anti-HA antibodies demonstrating the expression of STAT1 or STAT2 and C7-HA in transfected cells (FIG. 10A). Following immunoprecipitation of whole cell lysates with an anti-HA antibody, the C7-HA protein-interacting proteins were then probed with anti-Flag antibody. These results show that only Flag-tagged STAT2 was pulled down by anti-C7-HA from whole cell lysates (FIG. 10B).

Figures 11A, 11B:
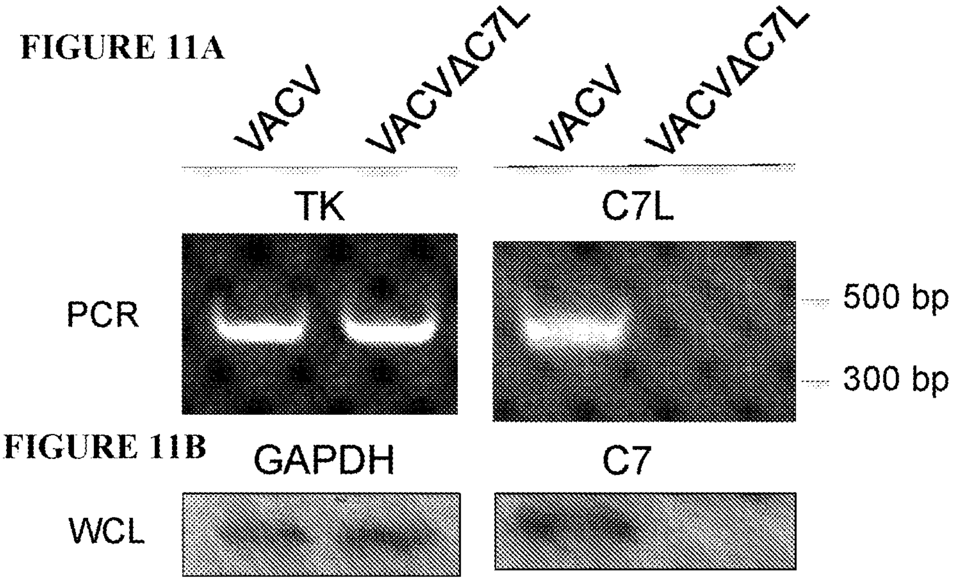
FIGS. 11A and 11B show PCR analyses of the recombinant virus VACVΔC7L demonstrating successful deletion of C7 gene from vaccinia genome. pC7L-GFP plasmid was used to insert specific gene of interest into the C7 locus. In this case, GFP under the control of the vaccinia p7.5 promoter was used as a selection marker (FIG. 4A). BSC40 cells ($1\times10^6$) were infected with MVA at a MOI of 0.2. After 1-2 h of infection, cells were transfected with pC7-GFP with lipofectamine 2000. Homologous recombination that occurred at the C7L locus of the plasmid DNA and VACV genomic DNA results in the insertion of GFP expression cassette into the VACV genomic DNA C7 locus to delete the entire C7L gene from VACV genome and result in the generation of the recombinant virus VACVΔC7L. Viral genomic DNAs were analyzed by PCR.

Example 11: Generation of Recombinant Vaccinia Virus with Deletion of C7L (VACVΔC7L)

pC7LGFP vector (SEQ ID NO: 4) was used to insert GFP under the control of the vaccinia P7.5 promoter into the C7L locus of MVA. The expression cassette was flanked by partial sequence of C7 flank regions (C7-L and C7-R) on each side. BSC40 cells were infected with WT vaccinia virus expressing at a MOI of 0.05 for 1 h, and then were transfected with the plasmid DNA described above. The infected cells were collected at 48 h. Recombinant viruses were identified by their green fluorescence with the insertion of GFP into the C7 locus. The positive clones were plaque purified 4-5 times on BSC40 cells. PCR analysis was performed to confirm that recombinant virus VACVΔC7L has loss of the C7 gene (FIGS. 11A and 11B).

Figure 12A:
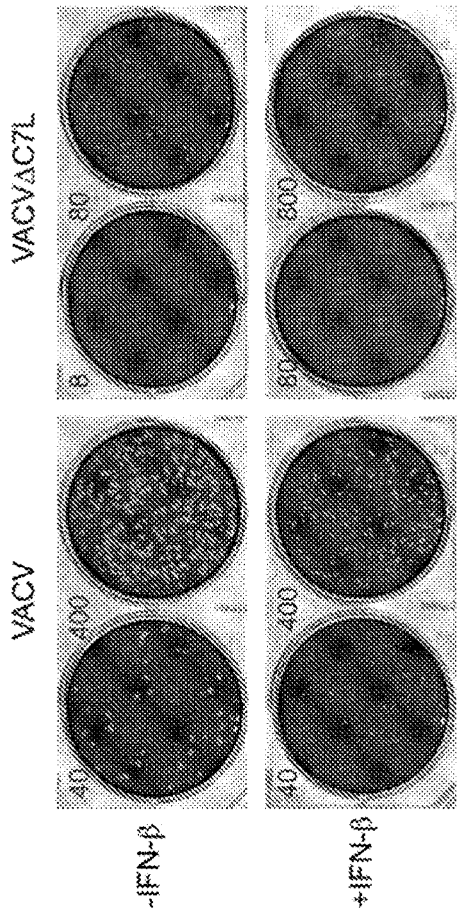
FIGS. 12A and 12B are images and graphical representations showing that VACVΔC7L has a smaller plaque size than WT VACV and is more sensitive to IFN inhibition.
Figure 12B:
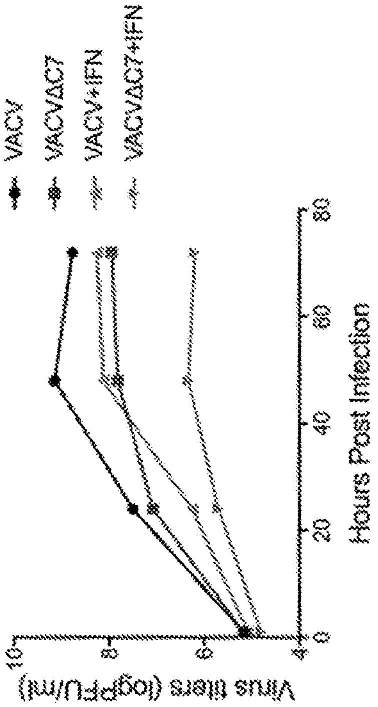

Example 12: VACVΔC7L has Smaller Plaque Size than WT VACV and is Sensitive to IFN Inhibition To investigate whether there is any phenotypical difference between WT VACV and VACVΔC7L and whether they are sensitive to IFN inhibition, BSC40 cells were either pre-treated or mock-treated with IFN-β (1000 U/ml) for 12 h prior to infection with the two viruses at indicated doses (PFU). In the absence of IFN-β pre-treatment, VACVΔC7L had a smaller plaque size than WT VACV. In the presence of IFN-β pre-treatment, there is some reduction of plaque size of WT VACV and the plaque size of VACVΔC7L was further reduced and was barely visible (FIG. 12A). The reduced plaque size of VACVΔC7L compared with WT VACV could be due to decreased replication capacity of VACVΔC7L or its reduced ability to spread to neighboring cells. To distinguish between these two possibilities, a multi-step growth experiment was performed in which BSC40 cells were either pre-treated or mock-treated with IFN-β (1000 U/ml) for 12 h prior to infection with the two viruses at a MOI of 0.05. Cells were collected at various times and viral titers were determined. In the absence of IFN-β pre-treatment, the titers of WT VACV increased from $1.5\times10^5$ to $7.0\times10^8$ (more than 1000-fold increase) during the 48 h of infection; whereas the titers of VACVΔC7L increased from $1.5\times10^5$ to $4.5\times10^7$ (about 300-fold increase) during the first 48 h of infection. In the presence of IFN-β pre-treatment, the titers of WT VACV increased from $1.2\times10^5$ to $9.0\times10^7$. (more than 700-fold increase) during the 48 h of infection; whereas the titers of VACVΔC7L increased from $6.0\times10^4$ to $8.0\times10^5$ (about 15-fold increase) during the first 48 h of infection (FIG. 12B). These results demonstrate that VACVΔC7L has reduced ability to replicate on BSC40 cells and is sensitive to IFN inhibition.

Figure 13A:
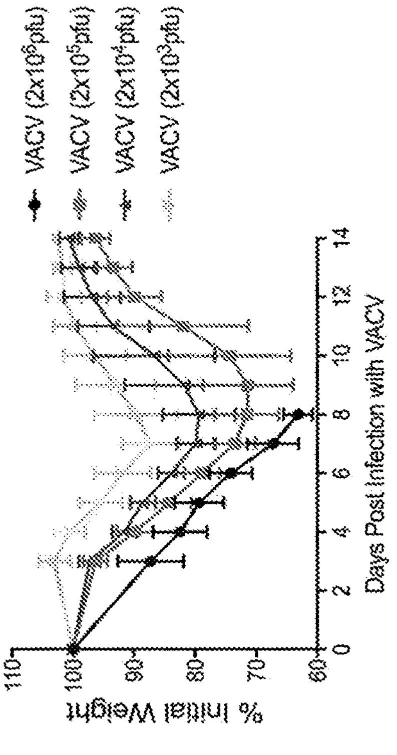
FIGS. 13A-13D is a series of graphical representations of data showing that VACVΔC7L is highly attenuated in a murine intranasal infection model.
Figure 13B:
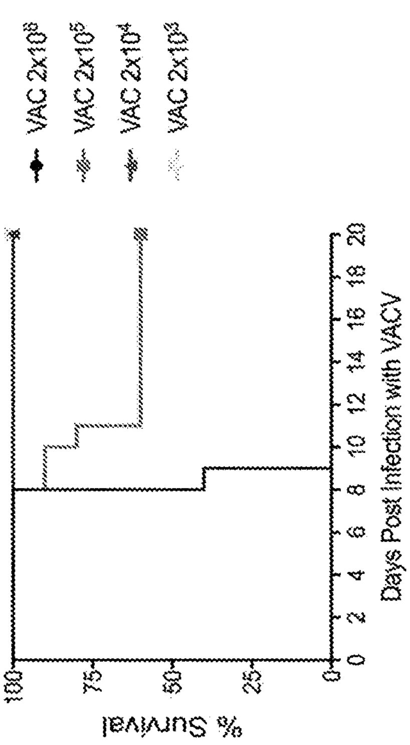
Figure 13C:
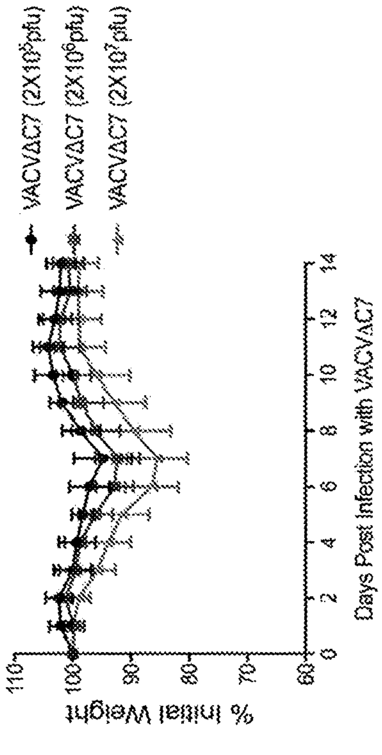
Figure 13D:
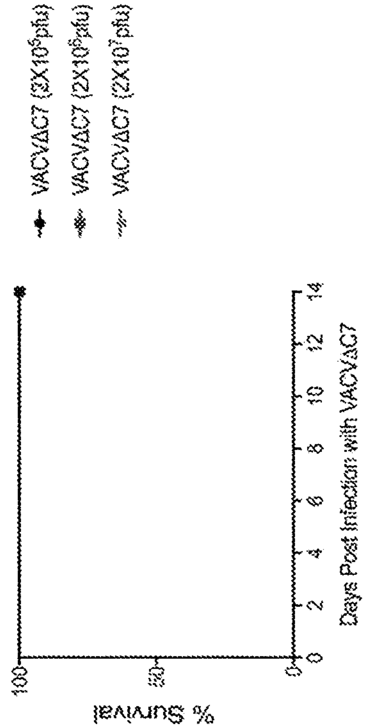

Example 13: VACVΔC7L is Highly Attenuated in a Murine Intranasal Infection Model Weight loss in C57BL/6J mice after intranasal infection with various doses of WT VACV was compared to that observed in C57BL/6J after infection with VACVΔC7L. WT VACV infection at $2\times10^3$ PFU per mouse caused over 10% weight loss at day 7 post infection and all of mice gained weight and recovered at day 14 post infection (FIGS. 13A and 13B). WT VACV infection at $2\times10^4$ PFU per mouse caused about 20% weight loss at day 7 and 8 post infection and all of mice gained weight and recovered at day 14 post infection (FIGS. 13A and 13B). WT VACV infection at $2\times10^5$ PFU per mouse caused about 30% weight loss at day 8 and 9 post infection and 6 out of 10 mice gained weight and slowly gained back most of their lost weight at day 14 post infection, whereas 4 out of 10 mice died (FIGS. 13A and 13B). WT VACV infection at $2\times10^5$ PFU per mouse caused 100% lethality (FIGS. 13A and 13B). By contrast, VACVΔC7L infection at the highest dose ($2\times10^7$ PFU) results in less than 20% weight loss and all of the mice recovered their weight at 11 to 12 days post infection (FIGS. 13C and 13D). These results indicate that C7 is a virulence factor and VACVΔC7L is highly attenuated in a murine intranasal infection model.

Figure 14A:
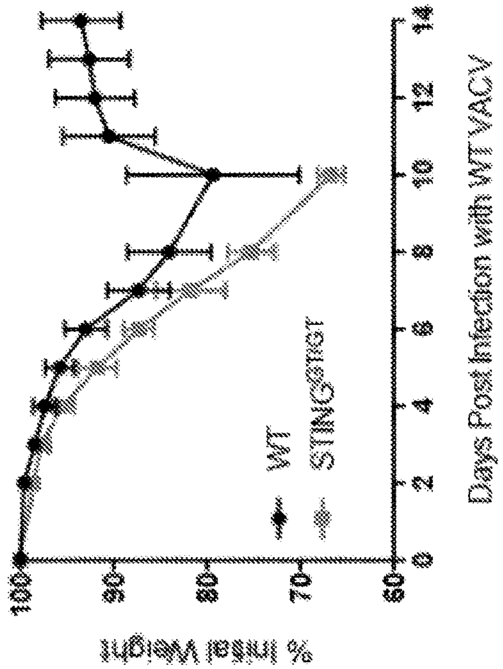
FIGS. 14A-14D are graphical representations of data showing that whereas WT VACV gained virulence in Sting-deficient ($STING^{Gt/Gt}$) mice, VACVΔC7L remained non-pathogenic in $STING^{Gt/Gt}$ mice in a murine intranasal infection model.
Figure 14B:
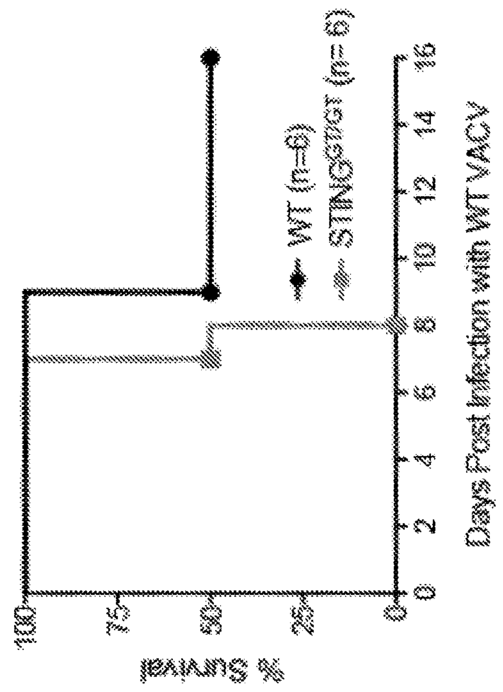
Figure 14C:
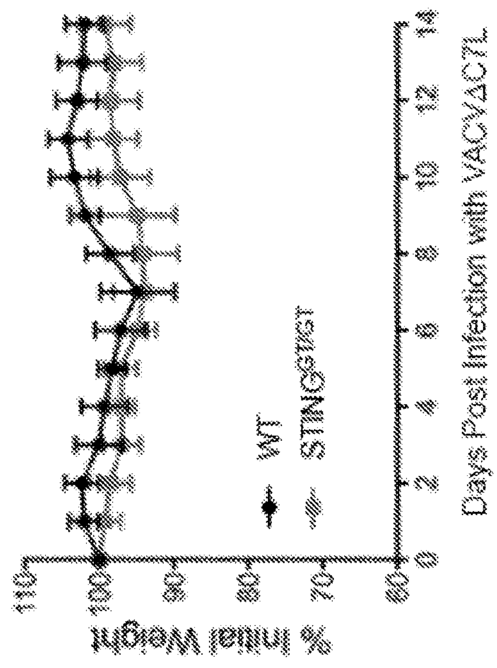
Figure 14D:
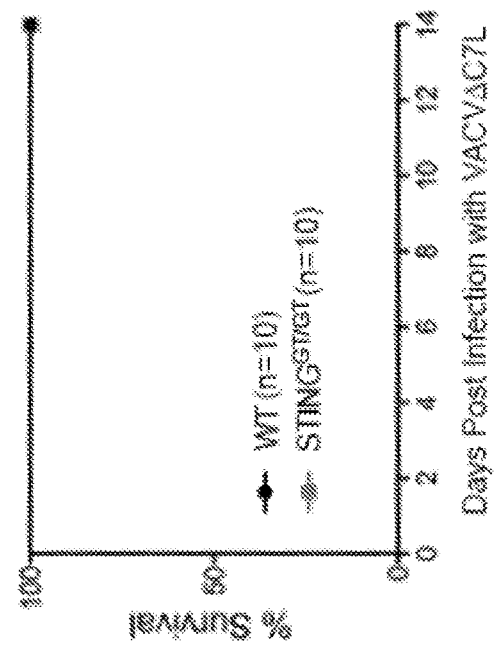

Example 14: VACVΔC7L Infection Did not Result in an Increase in Mortality in $STING^{Gt/Gt}$ Mice $STING^{Gt/Gt}$ mice were more susceptible to WT VACV infection. Infection with WT VACV at $2\times10^5$ PFU caused 50% lethality in WT C57BL/6J mice, whereas all of the $STING^{Gt/Gt}$ mice succumbed to WT VACV infection at this dose (FIGS. 14A and 14B). By contrast, VACVΔC7L infection at $2\times10^5$ PFU caused less than 5% weight loss in WT mice and slightly more weight loss in $STING^{Gt/Gt}$ mice compared with WT age-matched control mice. All of the mice survived the infection (FIGS. 14C and 14D). It is possible that VACVΔC7L infection is restricted to the infected lung tissues in the intranasal infection model because of its attenuation, and STING deficiency did not markedly influence the severity of the infection or its dissemination to the blood and distant organs.

Figure 15A:
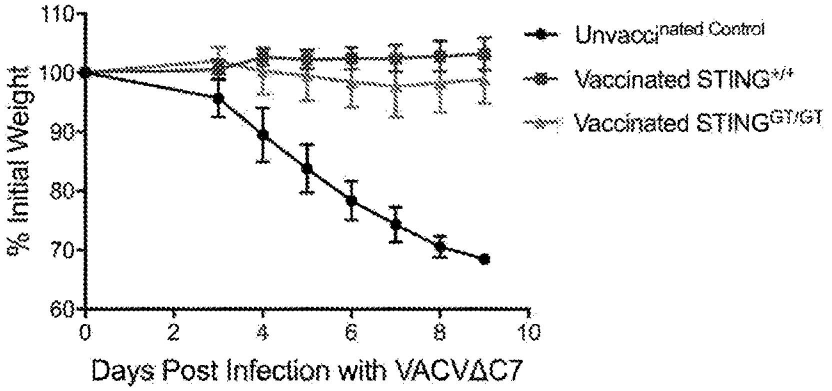
FIGS. 15A-15B are graphical representations of data showing both WT and $STING^{Gt/Gt}$ mice survived VACVΔC7L infection developed antiviral immunity protective against a lethal WT VACV infection.
Figure 15B:
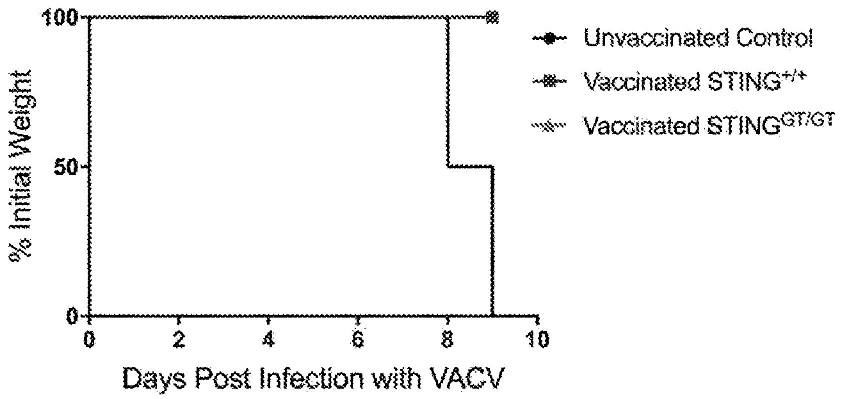

Example 15: VACVΔC7L-Infected Mice Developed Immunity Against Lethal WT VACV Challenge To test whether intranasal infection of VACVΔC7L in WT or $STING^{Gt/Gt}$ mice lead to the development of systemic antiviral immunity, survived mice (6 weeks after the initial infection) and naïve WT control mice were challenged with a lethal dose of WT VACV infection at $2\times10^6$ PFU. Whereas all of the naïve WT mice died at 8 or 9 days post infection, none of the previously infected WT or $STING^{Gt/Gt}$ mice lost more than 5% of the initial weight, and all of them survived the challenge (FIGS. 15A and 15B). These results indicate that prior infection with VACVΔC7L in either WT or STING-deficient mice lead to the development of systemic anti-viral immunity.

Figure 16A:
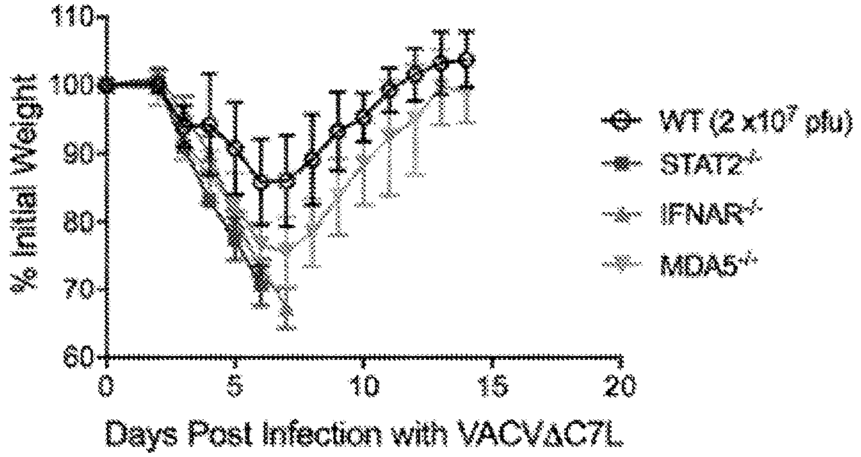
FIGS. 16A-16G are graphical representations of data showing that VACVΔC7L virus gained virulence in $STAT2^{-/-}$ or $IFNAR1^{-/-}$ mice in a murine intranasal infection model.
Figure 16B:
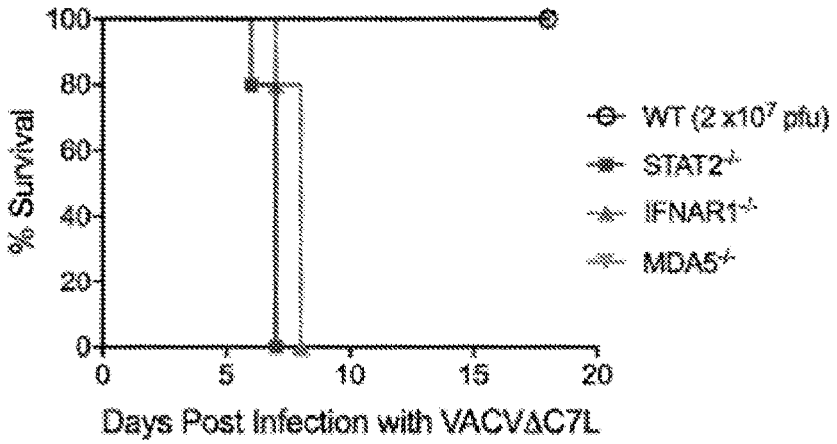
Figure 16C:
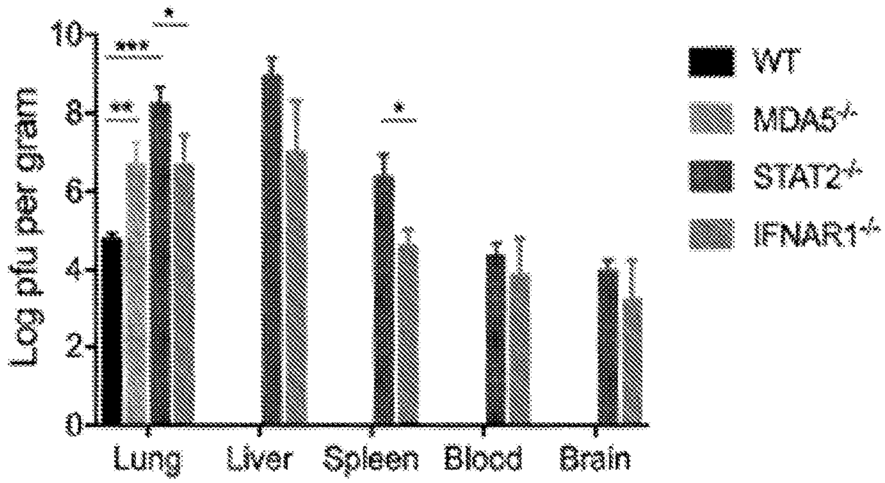
Figure 16D:
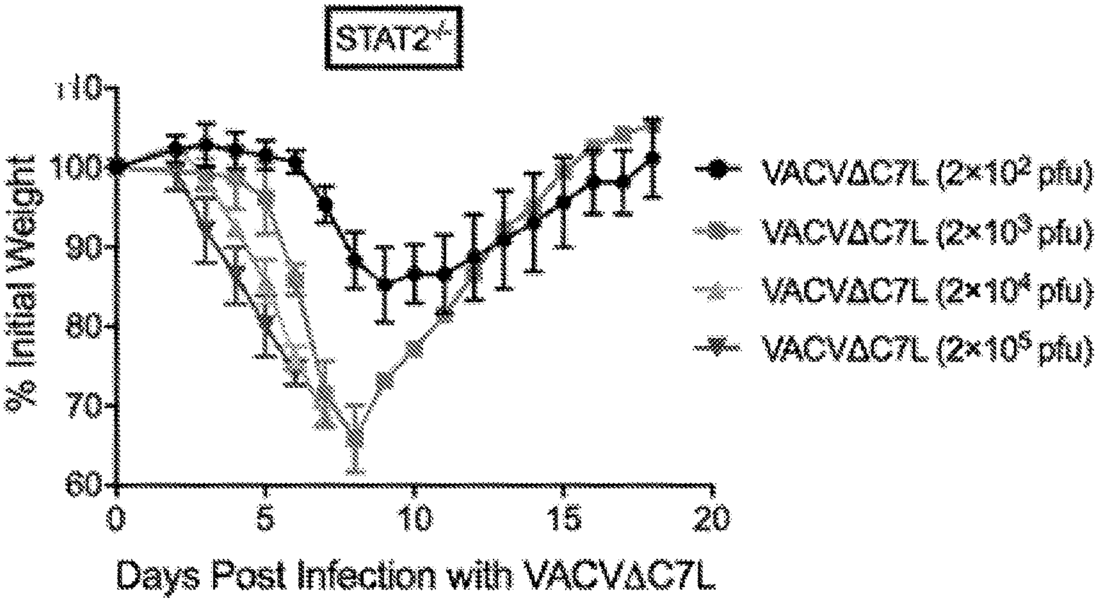
Figure 16E:
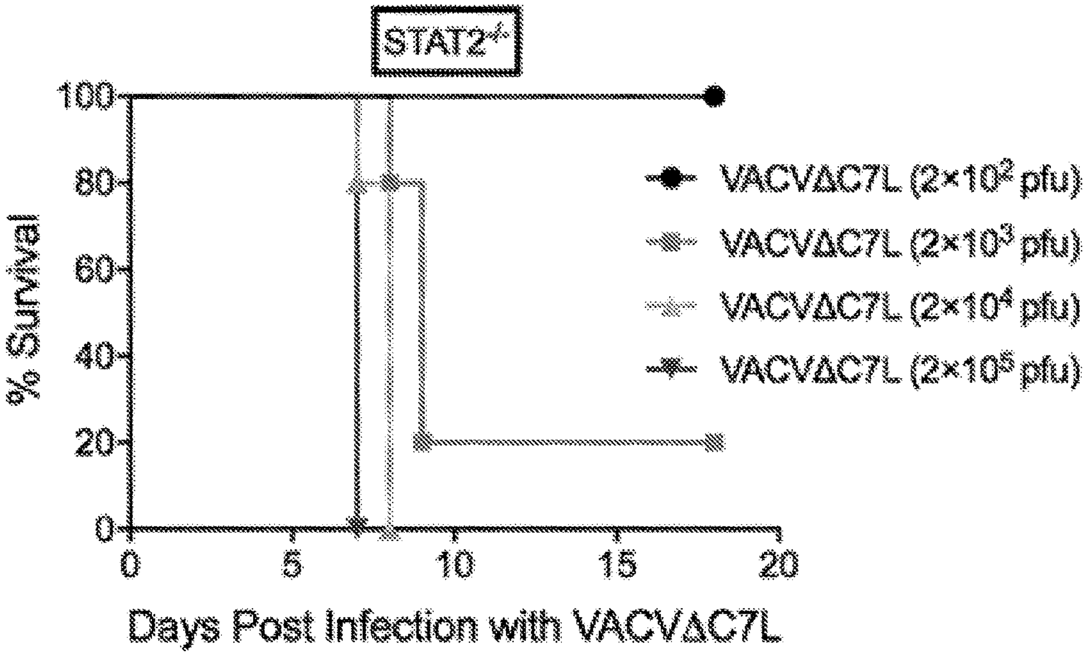
Figure 16F:
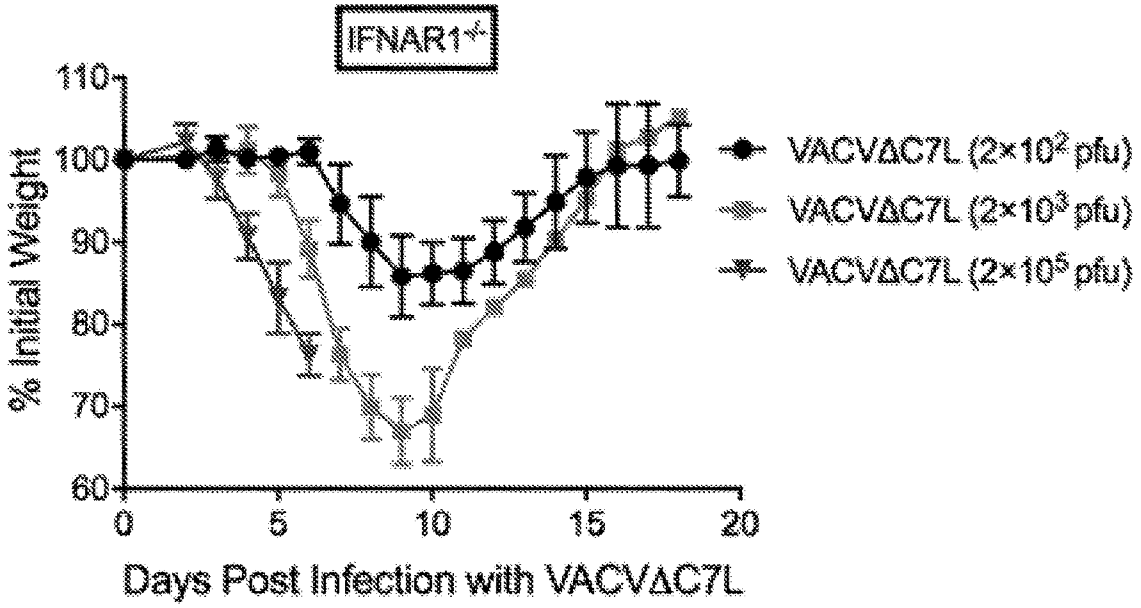
Figure 16G:
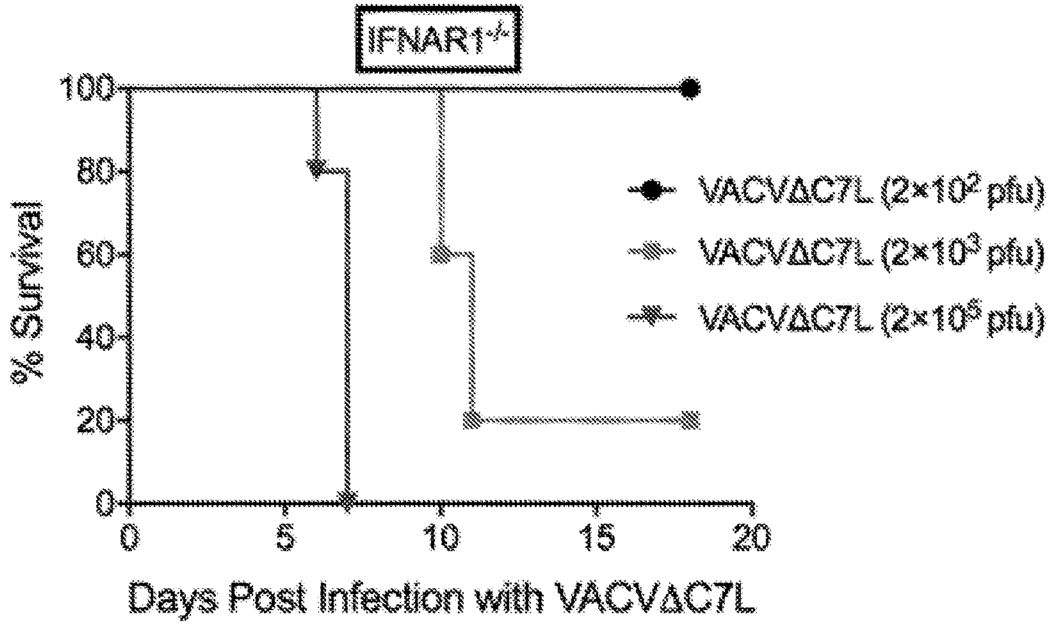

Example 16: VACVΔC7L Infection Gains Virulence in $STAT2^{-/-}$ and $IFNAR1^{-/-}$ Mice in an Intranasal Infection Model To test whether VACVΔC7L virus gains virulence in $STAT2^{-/-}$ or $IFNAR1^{-/-}$ mice, WT, $STAT2^{-/-}$, or $IFNAR1^{-/-}$ mice were intranasally infected with VACVΔC7L at a dose of $2\times10^7$ pfu and monitored for weight loss and survival over time. It was found that, in contrast to WT mice, the $STAT2^{-/-}$ and $IFNAR1^{-/-}$ mice were highly susceptible to VACVΔC7L infection, with rapid weight loss, severe illness and death (FIGS. 16A and 16B). The median survival time for $STAT2^{-/-}$ and $IFNAR1^{-/-}$ mice were 7 days and 8 days, respectively (FIG. 16B). This difference is statistically significant with P=0.0145 (n=5). The viral titers in various tissues from WT, $STAT2^{-/-}$, or $IFNAR1^{-/-}$ mice were compared at day 4 post infection with VACVΔC7L at $2\times10^7$ pfu. It was found that VACVΔC7L infection of WT mice caused localized infection in the lungs without dissemination of the virus or viremia. By contrast, in $STAT2^{-/-}$ or $IFNAR1^{-/-}$ mice, VACVΔC7L infection caused higher viral titers in the lungs. Viremia and dissemination of the virus to various distant organs including livers, spleens, and brains in $STAT2^{-/-}$ and $IFNAR1^{-/-}$ mice at day 4 post infection was also observed (FIG. 16C). VACVΔC7L virus infection of $MDA5^{-/-}$ mice caused more weight loss compared with WT mice, and the viral titers in the lungs of $MDA5^{-/-}$ mice at day 4 post infection were 100-fold higher than those in the lungs of the WT mice (FIGS. 16A and 16C). However, all of the $MDA5^{-/-}$ mice gradually gained weight and survived the infection (FIGS. 16A and 16B).

To determine the LD50 (the dose at which 50% of infected mice die from infection) of VACVΔC7L virus in $STAT2^{-/-}$ or $IFNAR1^{-/-}$ mice, these mice were intranasally infected with various doses of VACVΔC7L. It was found that at a dose of $2\times10^5$ pfu of VACVΔC7L, 5 out of 5 $STAT2^{-/-}$ and 5 out of 5 $IFNAR1^{-/-}$ mice lost weight quickly and died. At a dose of $2\times10^3$ pfu of VACVΔC7L, 1 out of 5 $STAT2^{-/-}$ and 1 out of 5 $IFNAR1^{-/-}$ mice died at a median survival time of 9 and 11 days, respectively. At a dose of $2\times10^2$ pfu of VACVΔC7L, 5 out of 5 $STAT2^{-/-}$ and 5 out of 5 $IFNAR1^{-/-}$ mice survived. It was estimated that the LD50 of VACVΔC7L in $STAT2^{-/-}$ and $IFNAR1^{-/-}$ mice is around 1000 pfu (FIGS. 16D-16G).

Figure 17A:
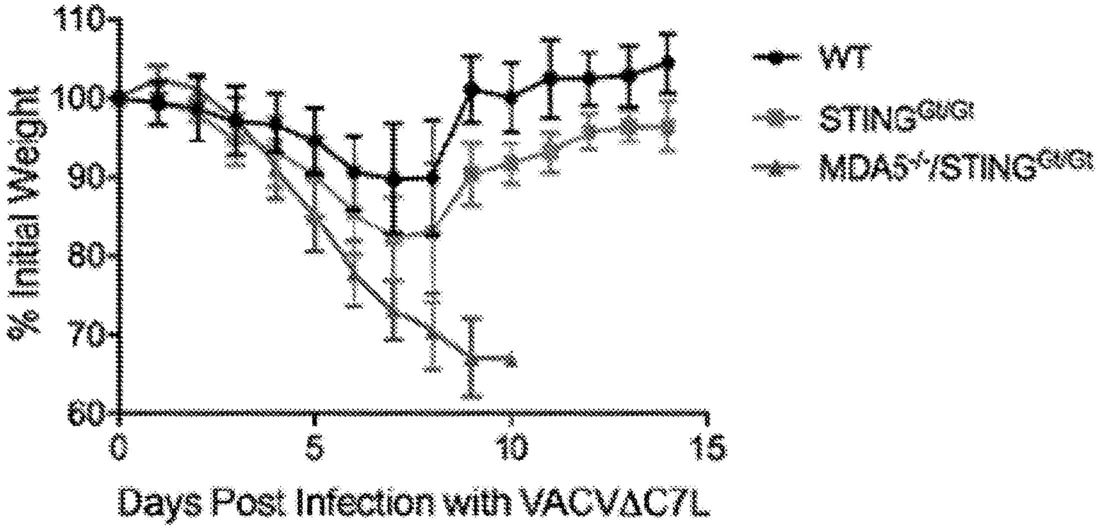
FIGS. 17A-17B are graphical representations of data showing that VACVΔC7L virus gained virulence in $MDA5^{-/-}STING^{Gt/Gt}$ mice in a murine intranasal infection model.
Figure 17B:
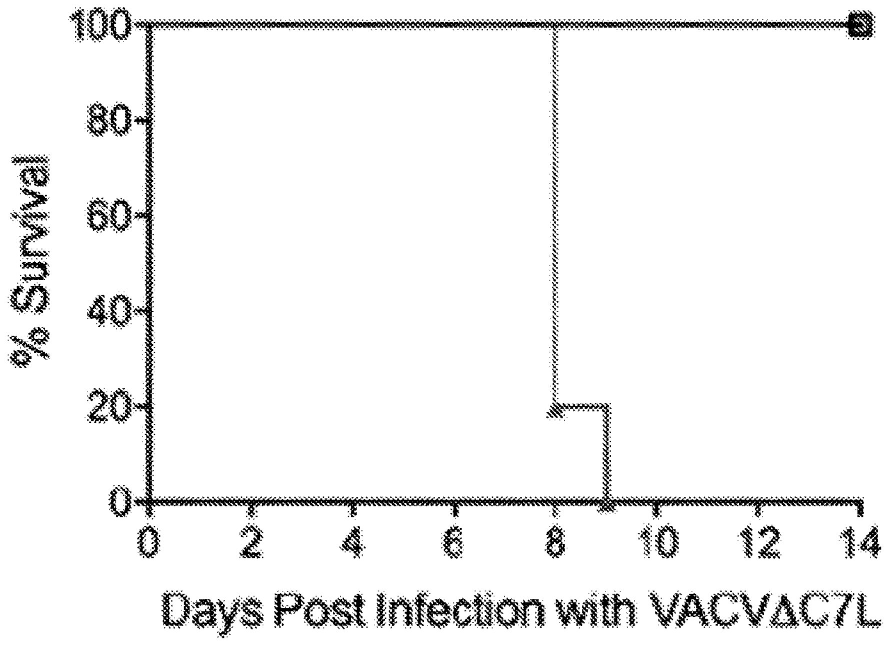

Example 17: VACVΔC7L Infection Gains Virulence in $MDA5^{-/-}STING^{Gt/Gt}$ Mice in an Intranasal Infection Model VACVΔC7L infection at $2\times10^7$ pfu caused more weight loss in $MDA5^{-/-}$ or $STING^{Gt/Gt}$ mice, compared with WT controls. To test whether VACVΔC7L virus gains virulence in MDA5$^{-/-}$STING$^{Gt/Gt}$ mice, MDA5$^{-/-}$STING$^{Gt/Gt}$, STING$^{Gt/Gt}$ or WT age-matched control mice were infected with VACVΔC7L virus at 2×10$^7$ pfu. It was observed that the MDA5$^{-/-}$ STING$^{Gt/Gt}$ lost more weight than STING$^{Gt/Gt}$ or WT mice (FIG. 17A), and five out of five mice died from VACVΔC7L infection (FIG. 17B). These results indicate that the cytosolic dsRNA-sensing pathway mediated by MDA5 and the cytosolic DNA-sensing pathway mediated by STING play synergistic roles in host defense against VACVΔC7L infection.

Figure 18A:
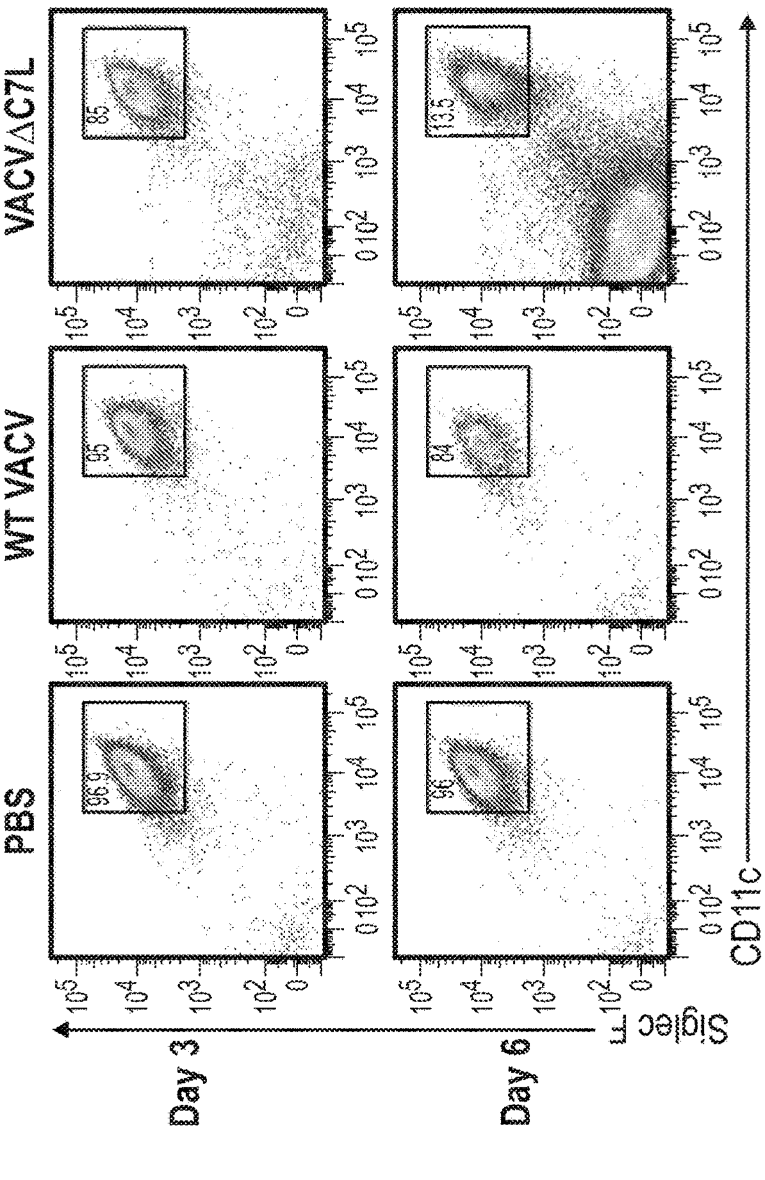
FIGS. 18A-18M are graphical representations of data showing that VACVΔC7L infection results in influx of dendritic cells (DCs), neutrophils, $CD8^+$ and $CD4^+$ T cells into the bronchoalveolar space of the infected lungs. C57BL/6J mice were intranasally infected with WT VACV at $2\times10^5$ pfu or VACVΔC7L at $2\times10^7$ pfu. BALF were collected at 3 and 6 days post infection. Cells were analyzed by FACS.
Figure 18B:
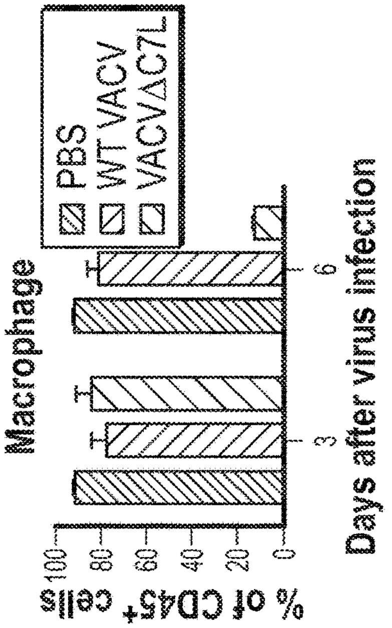
Figure 18C:
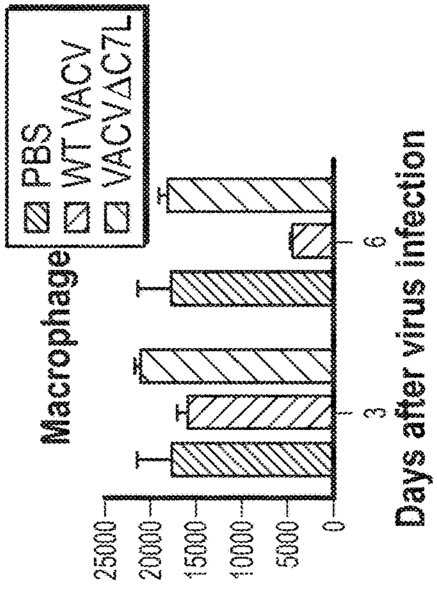
Figure 18D:
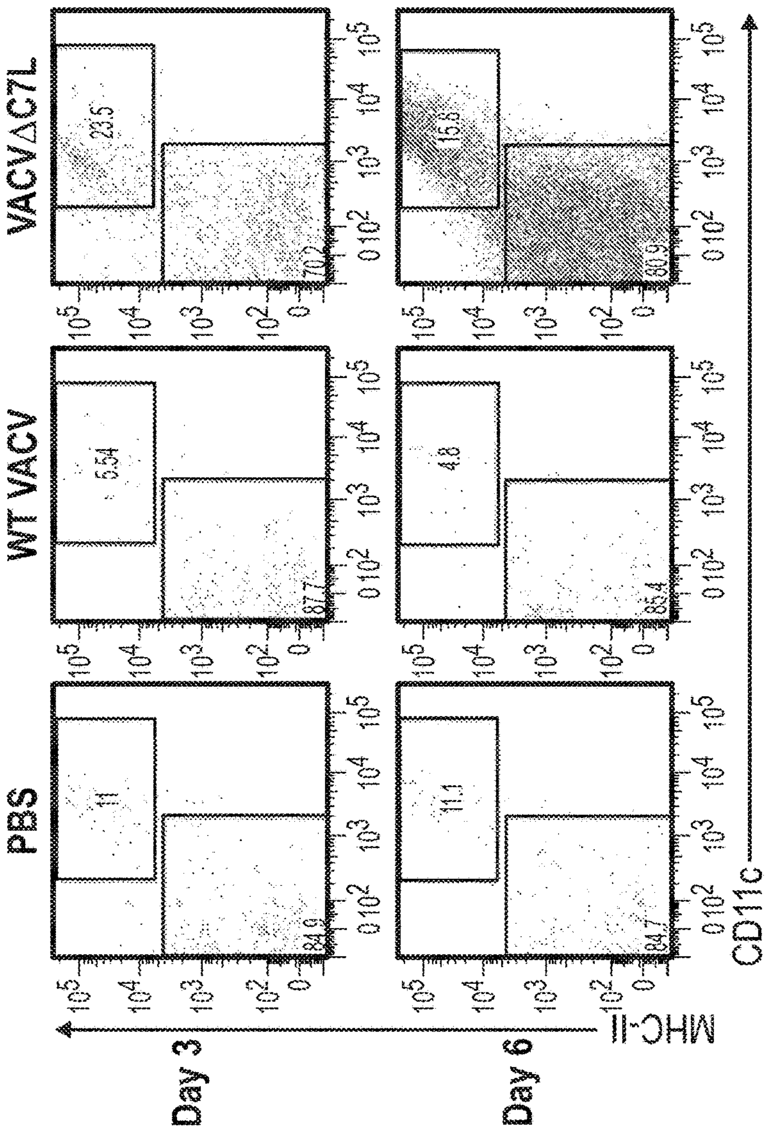
Figure 18E:
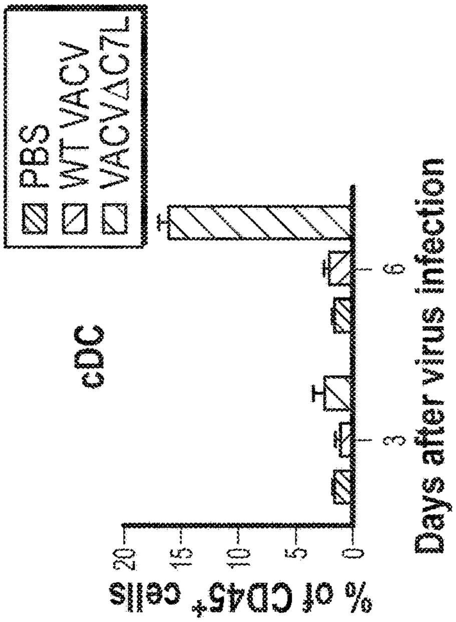
Figure 18F:
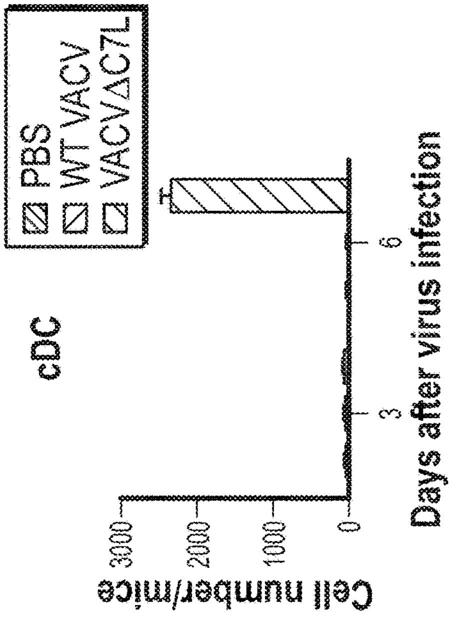
Figure 18G:
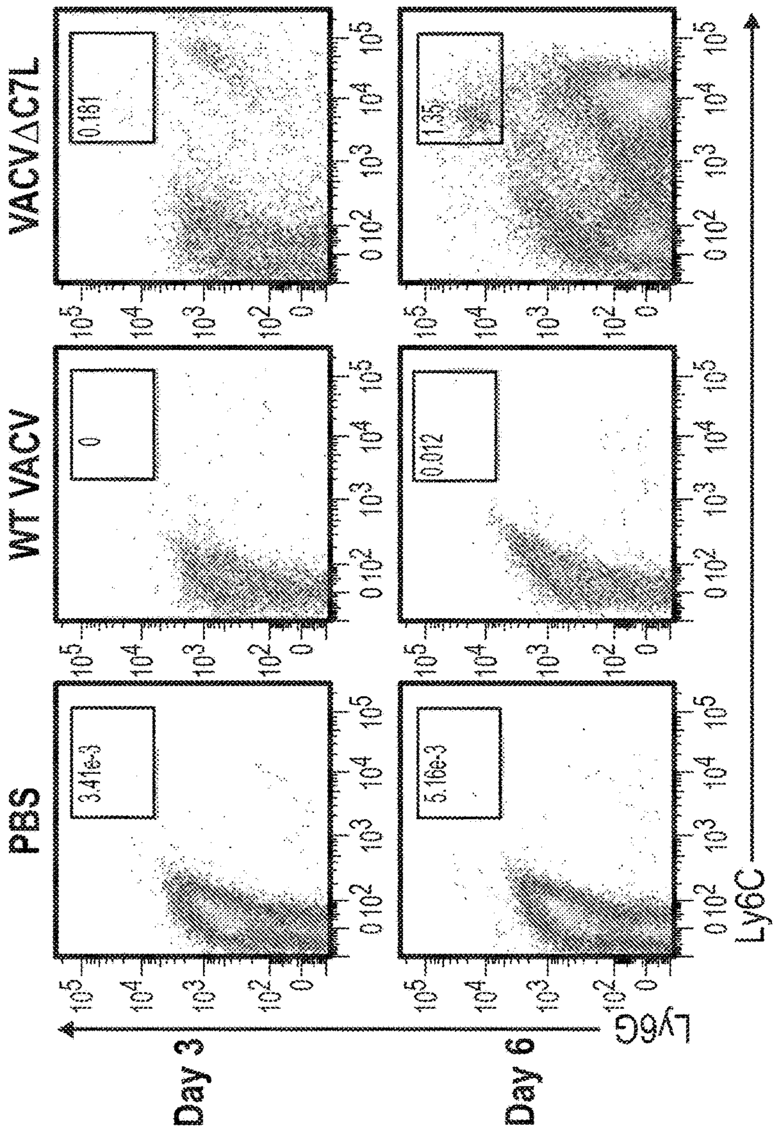
Figure 18H:
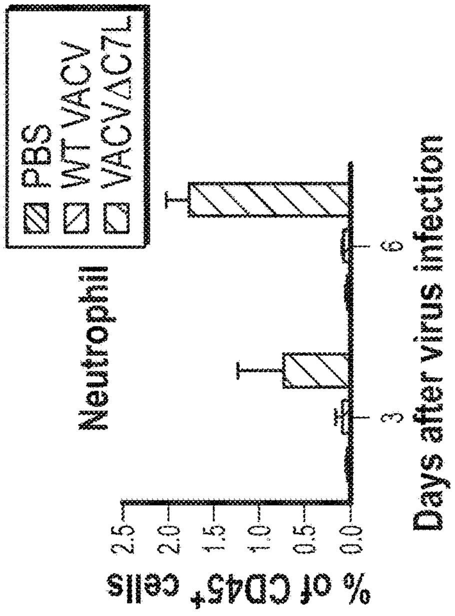
Figure 18I:
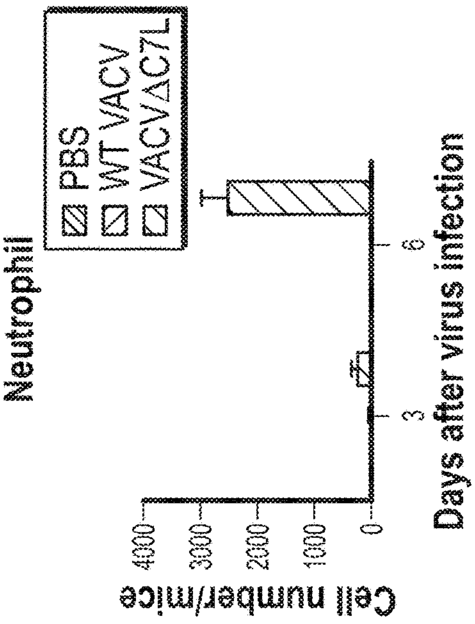
Figure 18J:
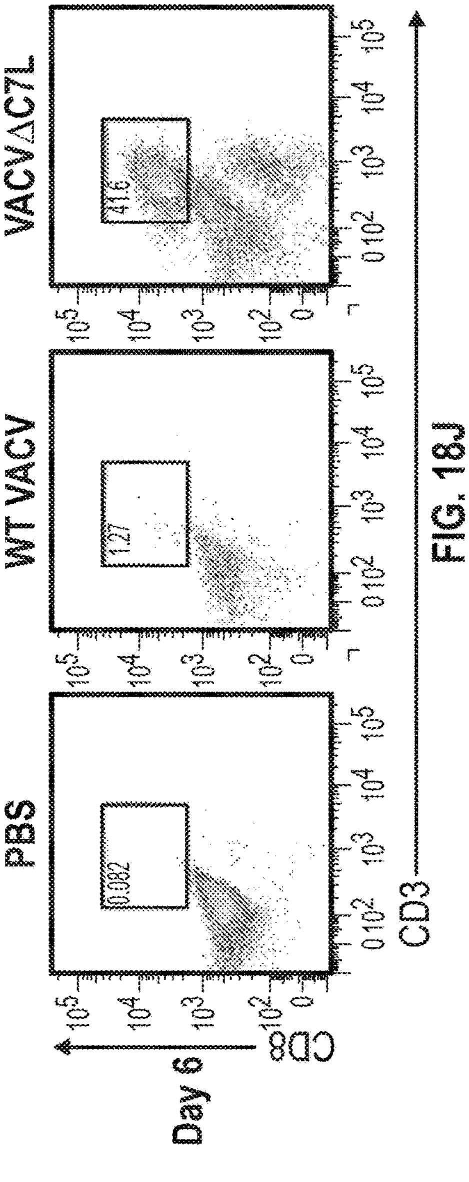
Figure 18K:
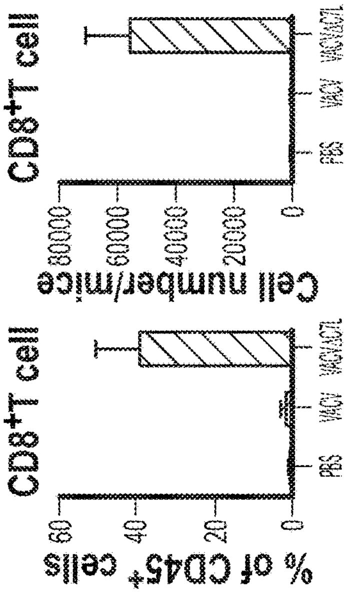
Figure 18L:
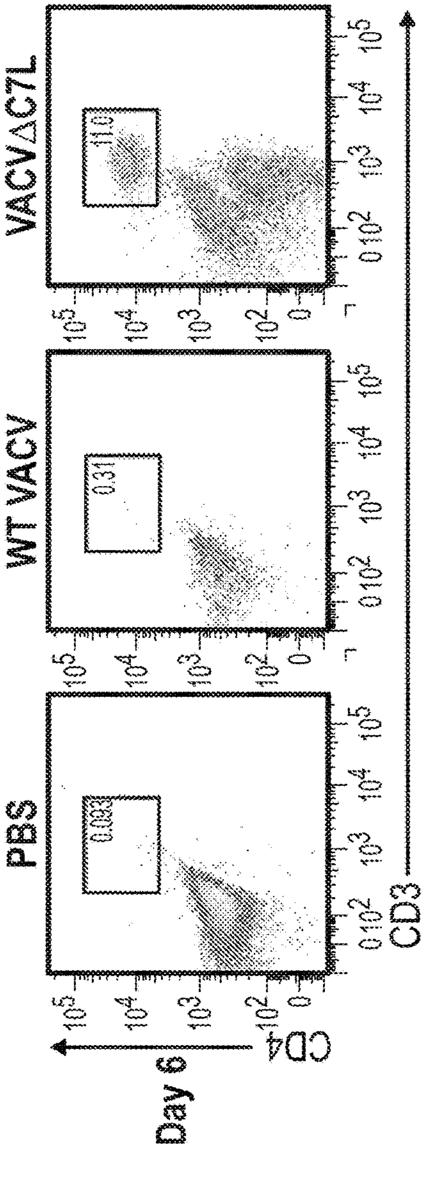
Figure 18M:
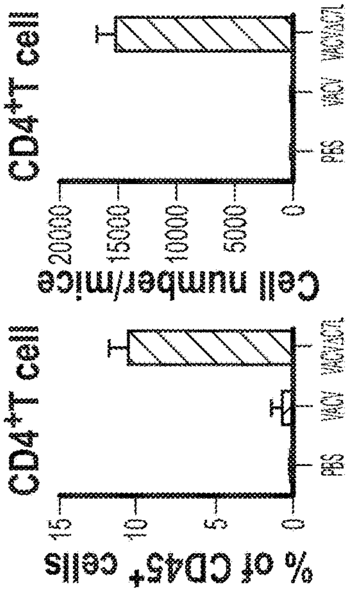

Example 18: Intranasal Infection of VACVΔC7L Results in Influx of Dendritic Cells (DCs), Neutrophils, CD8$^+$, and CD4$^+$ T Cells into Bronchoalveolar Space of the Infected Lungs To understand the dramatically reduced virulence of VACVΔC7L compared with WT VACV in the intranasal infection model, immune cell analyses of bronchoalveolar lavage fluid (BAL) of WT VACV- or VACVΔC7L-infected mice were performed. Mice were infected either with VACV at 2×10$^5$ pfu or with VACVΔC7L at 2×10$^7$ pfu, or mock-infected with PBS. BAL was collected at 3 and 6 days post infection or PBS treatment. It was observed that Siglec F$^+$CD11c$^+$ lung resident alveolar macrophages comprise majority of CD45$^+$ cells in the BAL in the PBS mock-infected mice. WT VACV infection resulted in the reduction of absolute number of Siglec F$^+$CD11c$^+$ macrophages at day 6 post infection, without affecting other myeloid cell populations in the BAL (FIGS. 18A-18C). By contrast, VACVΔC7L infection caused a large influx of CD45$^+$ myeloid cells into bronchoalveolar space at day 6 post infection. It was observed that cDCs and neutrophils were recruited into the bronchoalveolar space upon VACVΔC7L infection, but not with WT VACV infection (FIGS. 18D-18I). The percentage of cDCs were increased from 1.7% out of CD45$^+$ cells in BAL from PBS mock-treated mice to 16% out of CD45$^+$ cells in BAL from VACVΔC7L-infected mice at day 6 after infection (FIGS. 18D-18F). Other myeloid cells such as neutrophils were also increased in BAL of VACVΔC7L-infected lungs (FIGS. 18G-18I). DCs are important for presenting viral antigens to naïve T cells to generate antiviral T cells in the draining lymph nodes. The increased recruitment of DCs into the alveolar space positively correlates with the increased CD4$^+$ and CD8$^+$ T cells in the BAL at day 6 after VACVΔC7L infection. At day 6 after virus infection, the percentage of CD4$^+$ T cells out of CD45$^+$ cells were increased from 0.1% in BAL from PBS mock-treated mice to 11% in BAL from VACVΔC7L-infected mice (FIGS. 18L-18M). Most strikingly, VACVΔC7L infection led to the recruitment of higher percentages of CD8$^+$ T cells compared with WT VACV-infected mice (38% CD8$^+$ T cells out of CD45$^+$ cells in VACVΔC7L-infected mice vs. 2% CD8$^+$ T cells out of CD45$^+$ in WT VACV-infected mice) (FIGS. 18J-18K). Taken together, these results indicate that VACVΔC7L infection leads to the recruitment of dendritic cells, neutrophils, CD8$^+$, and CD4$^+$ T cells into the bronchoalveolar space of the infected lungs, whereas WT VACV infection does not.

Figure 19A:
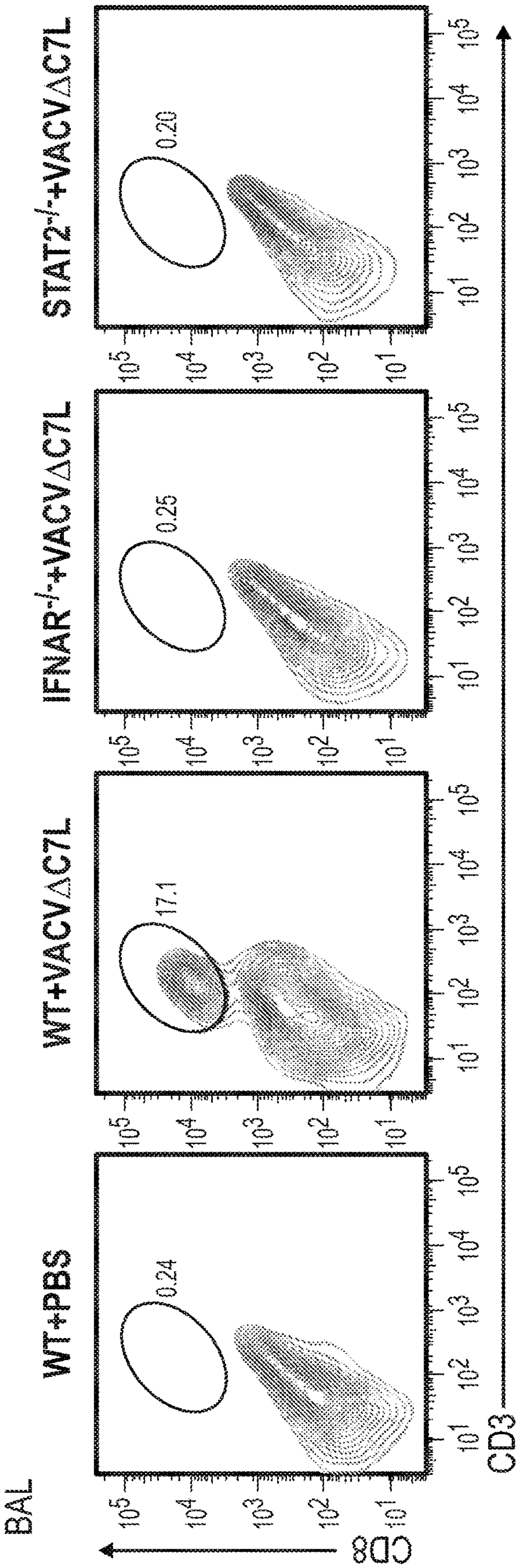
Figure 19B:
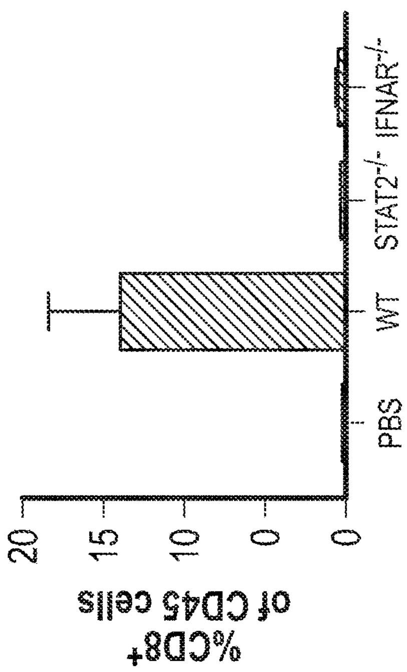
FIG. 19B: Percentages of $CD8^+$ T cells out of $CD45^+$ cells in the BAL at day 6 post infection.

Example 19: Type I IFN Signaling is Essential for CD8 T Cells Infiltration into Bronchoalveolar Space The CD8$^+$ T cell population in the BAL of WT, STAT2$^{-/-}$, or IFNAR1$^{-/-}$ mice at day 5 post infection with VACVΔC7L at 2×10$^5$ pfu was examined. It was found that although intranasal infection of VACVΔC7L virus induced recruitment of CD8$^+$ T cells into the BAL in WT mice, the numbers of CD8$^+$ T cells in STAT2$^{-/-}$ or IFNAR$^{-/-}$ mice were negligent, which indicates that Type I IFN signaling vis IFNAR1 and JAK/STAT pathway is crucial for the recruitment of CD8$^+$ T cells into the bronchoalveolar space (FIGS. 19A-19B).

Figure 20A:
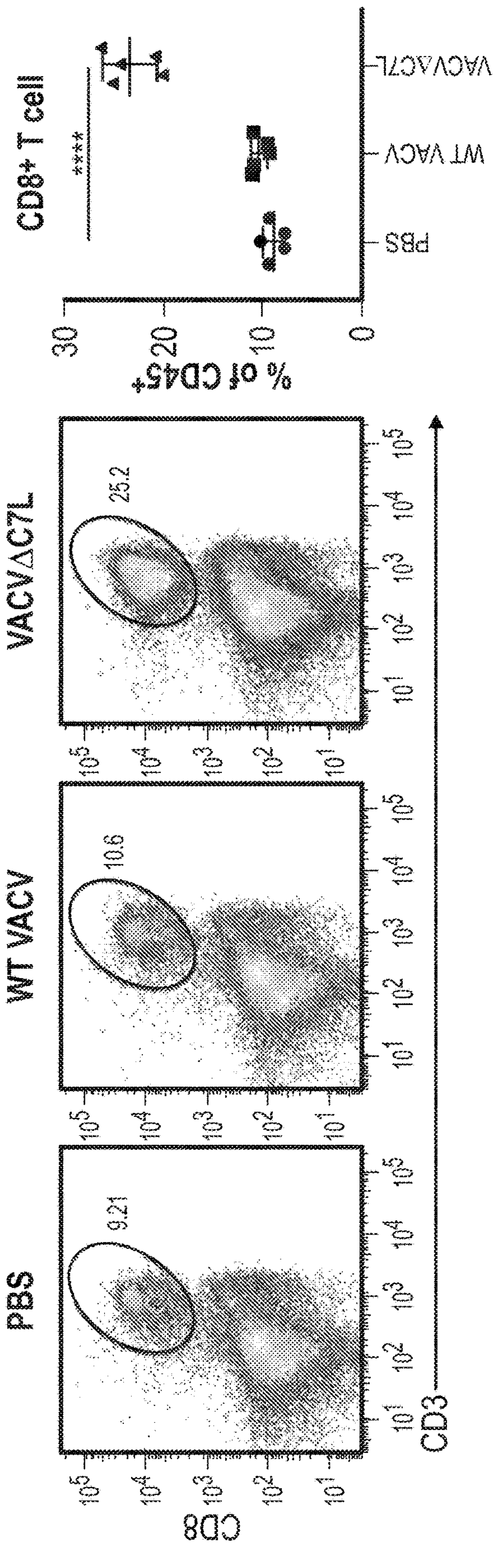
FIGS. 20A-20B are graphical representations of data showing that intranasal infection of VACVΔC7L leads to the recruitment of $CD8^+$ and $CD4^+$ T cells into the lung parenchyma. WT C57BL/6J mice were infected with either WT VACV or VACVΔC7L at $2\times10^5$ pfu. Lungs were collected and digested with Collagenase D at day 6 post infection. Single cell suspensions were stained with anti-CD45, -CD3, -CD4, and -CD8 antibodies and analyzed by FACS.
Figure 20B:
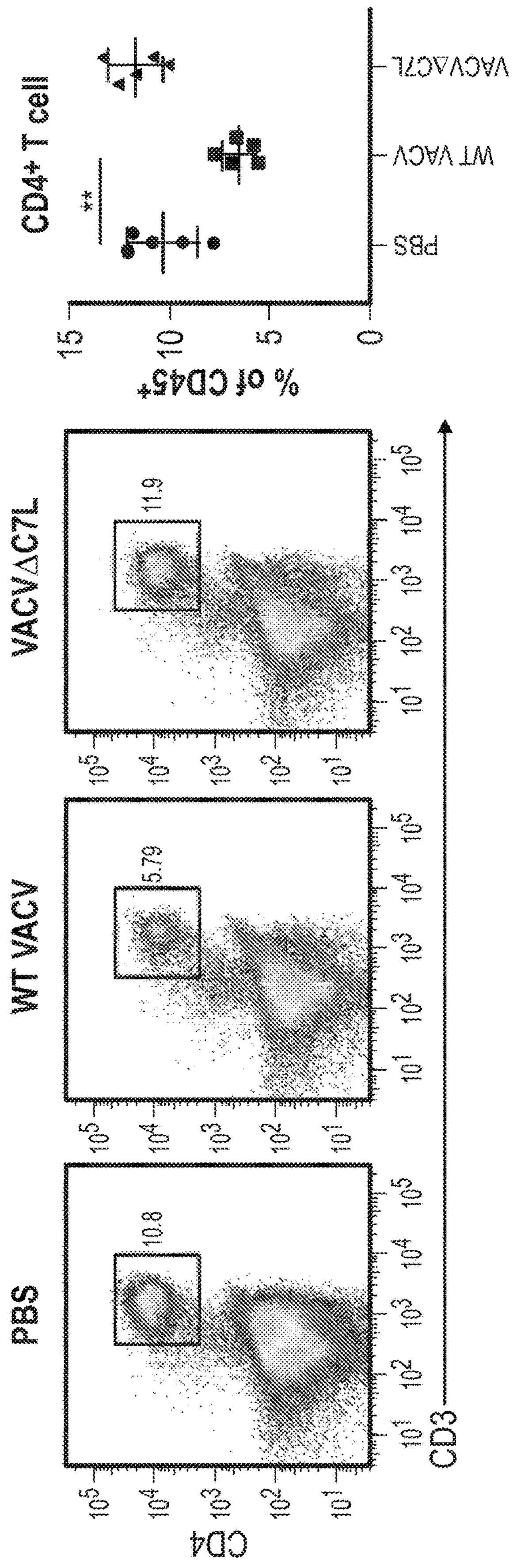

Example 20: Intranasal Infection of VACVΔC7L Leads to the Recruitment of CD8$^+$ and CD4$^+$ T Cells into the Lung Parenchyma To examine the effects of intranasal infection of WT VACV or VACVΔC7L on the CD8$^+$ and CD4$^+$ T cells in the lung parenchyma, WT C57BL6/J mice were infected with either WT VACV or VACVΔC7L at 2×10$^5$ pfu. Lungs were collected at 6 days post infection, and digested with collagenase D. Single cell suspensions were stained with anti-CD45, -CD3, -CD4, and -CD8 antibodies and FACS analysis showed that VACVΔC7L infection resulted in more than 2-fold increase of CD8$^+$ T cells in the lung parenchyma, whereas WT VACV infection resulted in very little change of the percentage of CD8$^+$ T cells out of CD45$^+$ T cells (FIG. 20A). VACVΔC7L infection resulted in a small increase of percentages of CD4$^+$ T cells out of CD45$^+$ T cells, whereas WT VACV infection caused a significant reduction of the percentages of CD4$^+$ T cells out of CD45$^+$ T cells in the lung parenchyma (FIG. 20B).

Figure 21A:
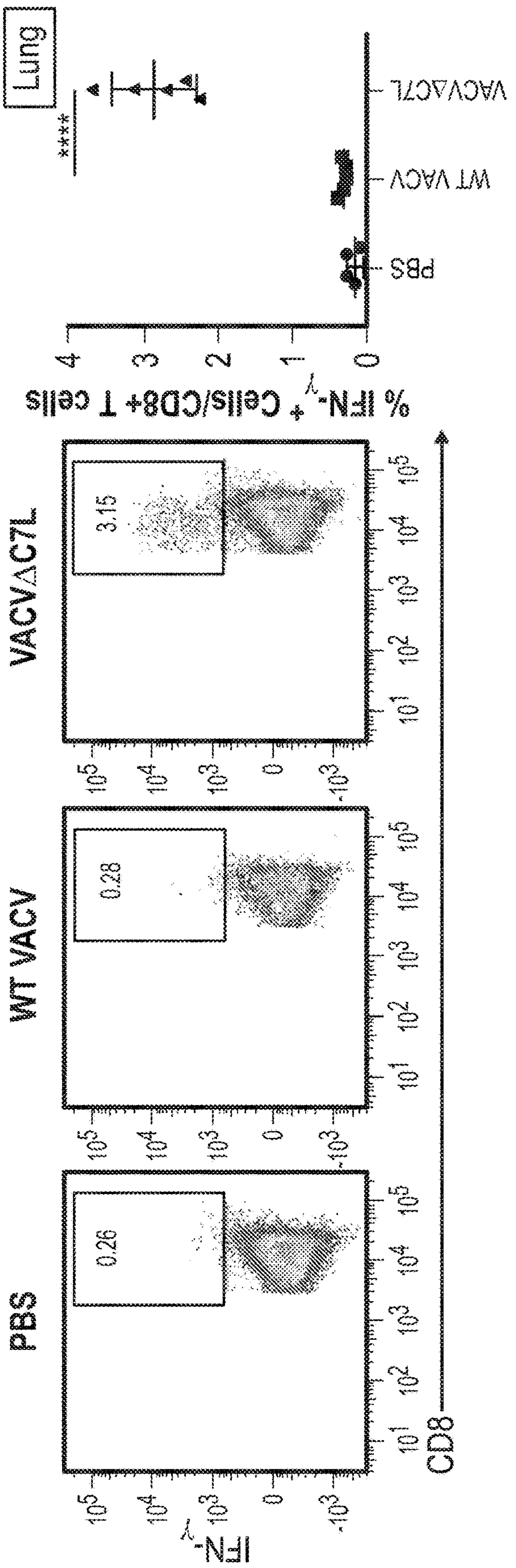
FIGS. 21A-21B are graphical representations of data showing that intranasal infection of VACVΔC7L results in the generation and recruitment of vaccinia virus B8R specific $CD8^+$ T cells into lungs and bronchoalveolar space. WT C57BL6/J mice were intranasally infected with either WT VACV or VACVΔC7L at $2\times10^5$ pfu. BAL and lungs were collected at 5 days post infection. Lungs were collected and digested with Collagenase D. Single cell suspensions were incubated with SIINFEKL (SEQ ID NO: 7) or TSYKFESV (SEQ ID NO: 8) peptide-pulsed BMDC for 6 h in the presence of brefeldin A (5 μg/ml), then stained with anti-CD45, -CD3, -CD8, and -IFN-γ antibodies and analyzed by FACS.
Figure 21B:
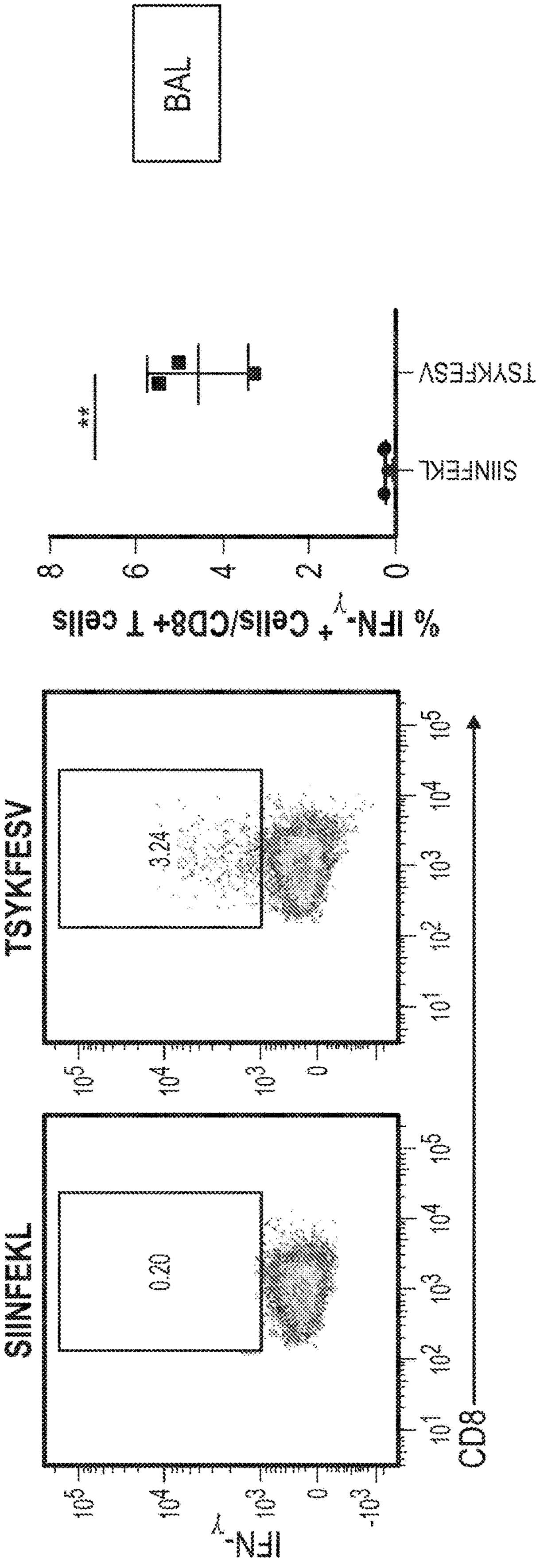

Example 21: Intranasal Infection of VACVΔC7L Results in the Generation and Recruitment of Vaccinia Virus B8R Specific CD8$^+$ T Cells into Lungs and Bronchoalveolar Space To test whether the CD8$^+$ T cells recruited to the BAL and lung parenchyma are viral specific, B8R$_{20-27}$ peptide TSYKFESV (SEQ ID NO: 8)-pulsed BMDCs were added to the single cell suspension of lungs from mice infected with either WT VACV at 2×10$^5$ pfu or VACVΔC7L at 2×10$^5$ pfu. They were incubated for 6 h in the presence of brefeldin A (5 μg/ml) before the cells were fixed and permeabilized and stained with anti-IFN-γ antibody. VACVΔC7L infection resulted in higher percentages of IFN-γ$^+$CD8$^+$ T cells in the lung parenchyma compared with WT VACV virus infection (FIG. 21A). BMDCs pulsed with either B8R$_{20-27}$ TSYKFESV (SEQ ID NO: 8) or with OVA$_{257-264}$ SIINFEKL (SEQ ID NO: 7) were incubated for 6 h with cells from BAL from VACVΔC7L-infected mice in the presence of brefeldin A (5 μg/ml) before the cells were fixed and permeabilized and stained with anti-IFN-γ antibody. FIG. 21B showed that the CD8$^+$ T cells in the BAL reacted to B8R$_{20-27}$ TSYKFESV (SEQ ID NO: 8), but not to an irrelevant peptide OVA$_{257-264}$ SIINFEKL (SEQ ID NO: 7). These results indicate that VACVΔC7L infection leads to the generation of viral-specific T cells and their recruitment into the lung parenchyma and BALs.

Figure 22A:
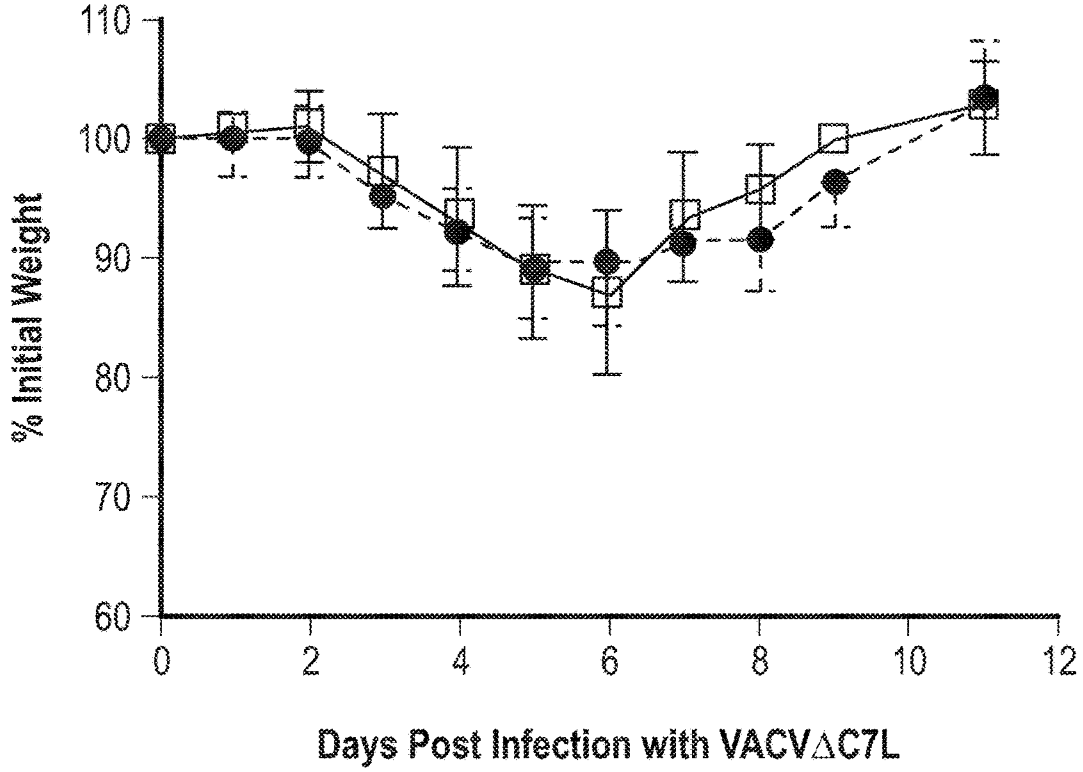
FIGS. 22A-22B are graphical representations of data showing that $CD8^+$ T cells are not required for host defense against acute intranasal infection of VACVΔC7L. WT C57BL6/J mice were intranasally infected with VACVΔC7L at $2\times10^7$ pfu. 200 μg anti-$CD8^+$ depleting antibodies (clone 2.43. BioXCell) was injected i.p 1 day prior virus infection and 1, 3, and 5 days post infection.
Figure 22B:
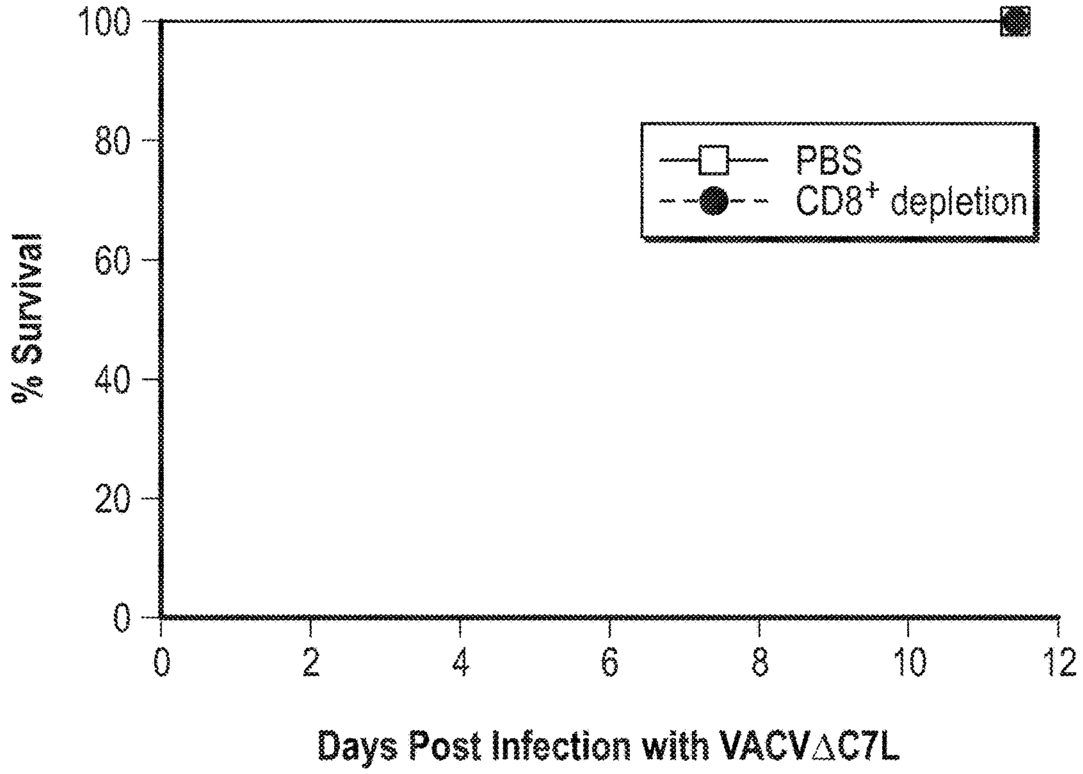

Example 22: CD8$^+$ T Cells are not Required for Host Defense Against Acute Intranasal Infection of VACVΔC7L To test whether CD8$^+$ T cells are required for host defense against acute VACVΔC7L infection, we depleted CD8$^+$ T cells by intraperitoneal delivery of anti-CD8 antibody (200 μg/mouse) at Day −1, +1, +3, and +5, and the mice were infected with VACVΔC7L virus at 2×10$^7$ pfu at Day 0. The efficiency of $CD8^+$ T cell depletion was verified by FACS analysis of peripheral blood of the $CD8^+$ T cell depleted or mock depleted mice. It was observed that $CD8^+$ T cell depletion did not affect weight loss or survival of the mice (FIGS. 22A and 22B), which indicate that $CD8^+$ T cells are not required for the protection against acute VACVΔC7L infection.

Figure 23A:
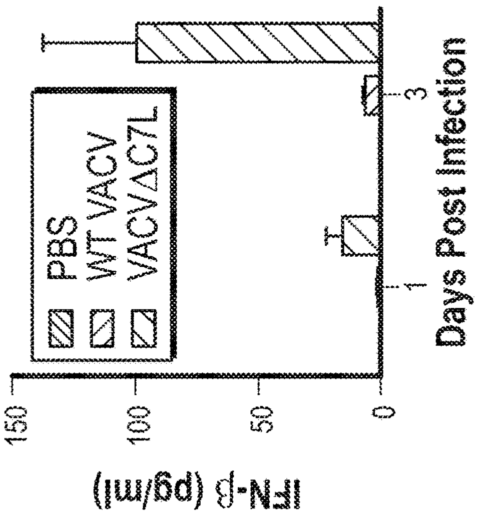
FIGS. 23A-23B are graphical representations of data showing that intranasal infection of VACVΔC7L results in the release of IFN-β, proinflammatory cytokines and chemokines into the bronchoalveolar space. C57BL/6J mice were intranasally infected with WT VACV at $2\times10^5$ pfu or VACVΔC7L at $2\times10^7$ pfu. BAL were collected at 1 and 3 days post infection.
Figure 23B:
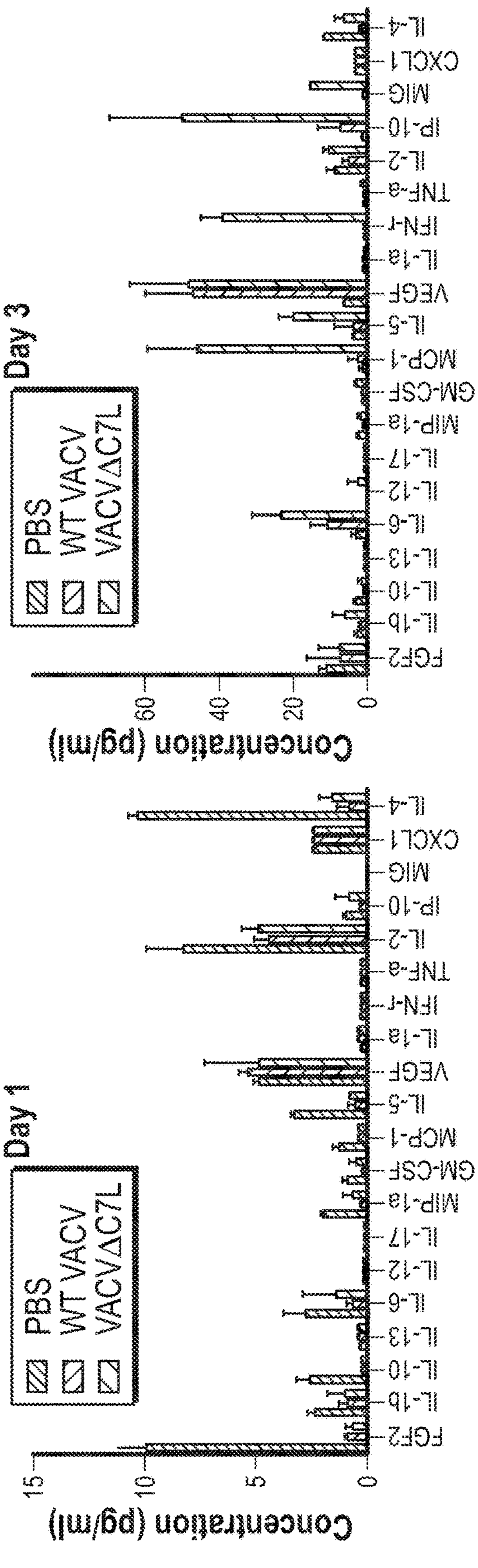

Example 23: Intranasal Infection of VACVΔC7L Results in the Release of IFN-β, Proinflammatory Cytokines and Chemokines into the Bronchoalveolar Space Given that T cell-mediated adaptive immunity may not play an important role in host protection against acute VACVΔC7L infection, the innate immune responses to either WT VACV or VACVΔC7L infection were analyzed. BAL were collected at 1 and 3 days post intranasal infection and tested for IFN-β concentration by ELISA as well as other cytokines and chemokine levels by Luminex Multiplex assay. VACVΔC7L infection increased the levels of IFN-β concentrations in the BAL collected at day 3 post infection compared those in the BAL collected at day 1 post infection, whereas WT VACV infection failed to induce (FIG. 23A). Luminex assay showed that VACVΔC7L infection also increased the concentrations of MCP-1 (CCL-2), IP-10 (CXCL10), MIG (CXCL9), and IFN-γ in the BAL collected at day 3 post infection compared those in the BAL collected at day 1 post infection (FIGS. 23B and 23C). These results indicate that VACVΔC7L infection caused release of IFN-0, and proinflammatory cytokines and chemokines into the BAL, whereas WT VACV infection did not.

Figure 24:
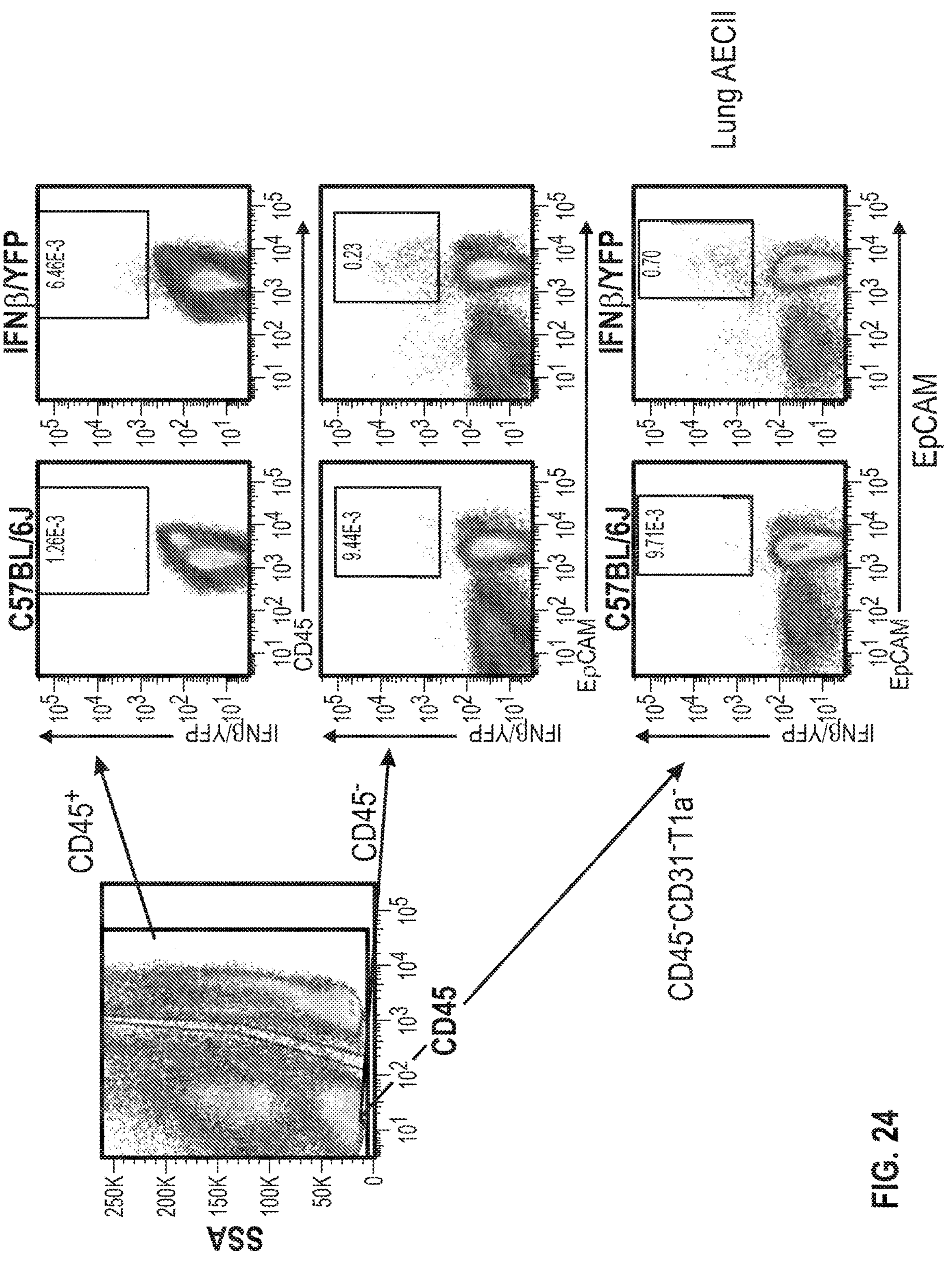
FIG. 24 provides graphical representations of data showing that VACVΔC7L infection induces IFN-β production from type II alveolar epithelial cells (AECII) in IFNβ/YFP reporter mice. IFNβ/YFP reporter mice or WT C57BL/6J WT controls were infected with VACVΔC7L intranasally ($2\times10^7$ pfu per mouse). After 48 h, lungs were collected and infused with dispase (1U per ml) in low-melting agarose (1%) at RT for 30 min before they were cut into pieces. Single cell suspensions were generated and analyzed by FACS. Shown on the upper right are $CD45^+$ cells from lungs in the WT and IFNβ/YFP reporter mice. Shown on the middle right are $CD45^-$ cells from lungs in the WT and IFNβ/YFP reporter mice. Shown on the lower right are $CD45^-$ $CD31^-T1a^-$ cells (excluding $CD31^+$ endothelial cells and $Tla^+$ type I AECs) from lungs in the WT and IFNβ/YFP reporter mice.

Example 24: VACVΔC7L Infection Induces IFN-β Production from Type II Alveolar Epithelial Cells (AECII) in IFNβ/YFP Reporter Mice To test which cell population is responsible for the production of IFN-β after intranasal infection with VACVΔC7L, WT mice and IFNB/yellow fluorescent protein (YFP) reporter mice were infected with VACVΔC7L at $2\times10^7$ pfu. The IFNB/YFP-knockin mouse, in which YFP is expressed from a bicistronic mRNA linked by an internal ribosomal entry site to the endogenous IFNbeta mRNA, was generated in Dr. Locksley's laboratory and it provides a tool to track IFN-0 producing cells at a single cell level (Scheu, et al., 2008). At 48 h post infection, lungs from the infected mice were collected and digested with Dispase in the presence of 1% low-melting agar for 30 min at room temperature (RT). Single cell suspensions were generated and FACS analysis was performed. It was observed that the majority of IFN-β/$YFP^+$ cells are in the $CD45^-$ cell population (FIG. 24). Among them, $EpCAM^+$ cell population has the highest percentages of IFN-β/$YFP^+$ cells. When $CD31^+$ cells (endothelial cells) and $Tla^+$ cells (type I lung alveolar epithelial cells; AECI) were excluded, it was observed that the type II lung alveolar epithelial cells (AECIIs) have the highest percentages of IFN-β/$YFP^+$ cells (FIG. 24). The results indicate that AECII are the most important cell type contributing to IFN-β production after intranasal infection of VACVΔC7L.

Figure 25B:
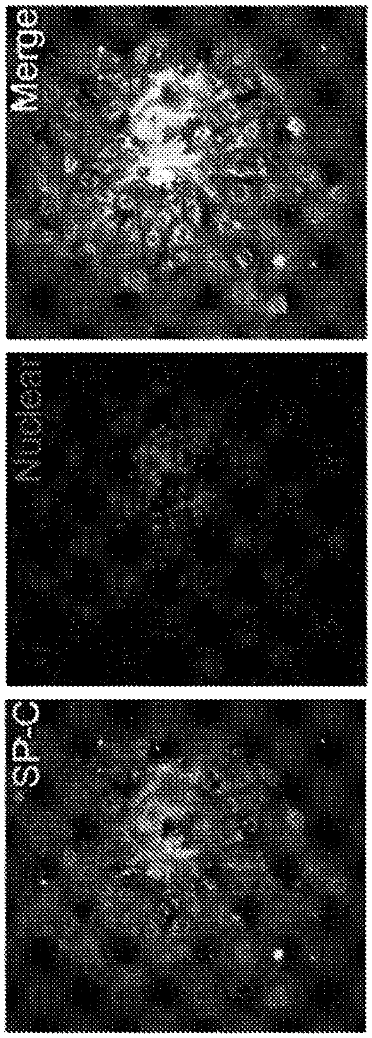
FIGS. 25A-25D are graphical representations of data showing that VACVΔC7L infection induces IFN-β, CCL4, and CCL5 production from lung type II alveolar epithelial cells (ACEII).
Figure 25A:
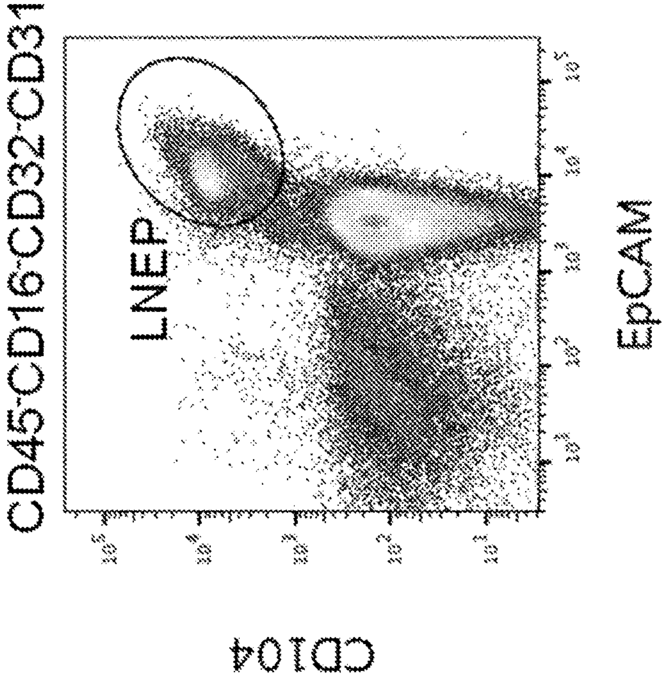
Figure 25C:
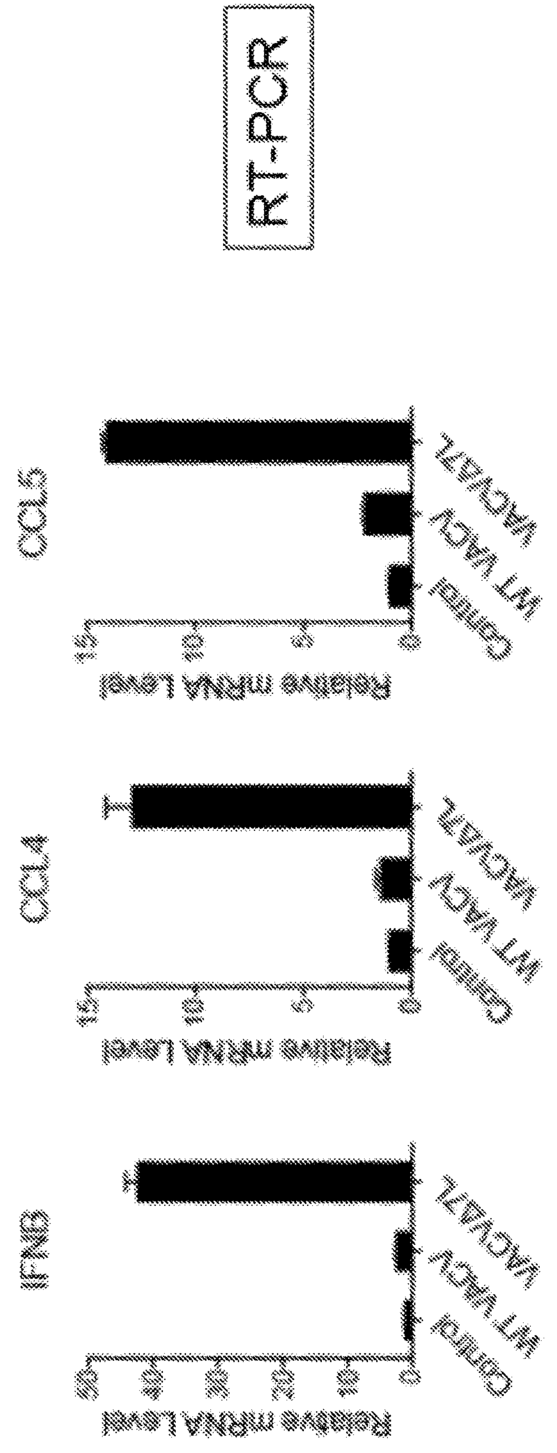
Figure 25D:
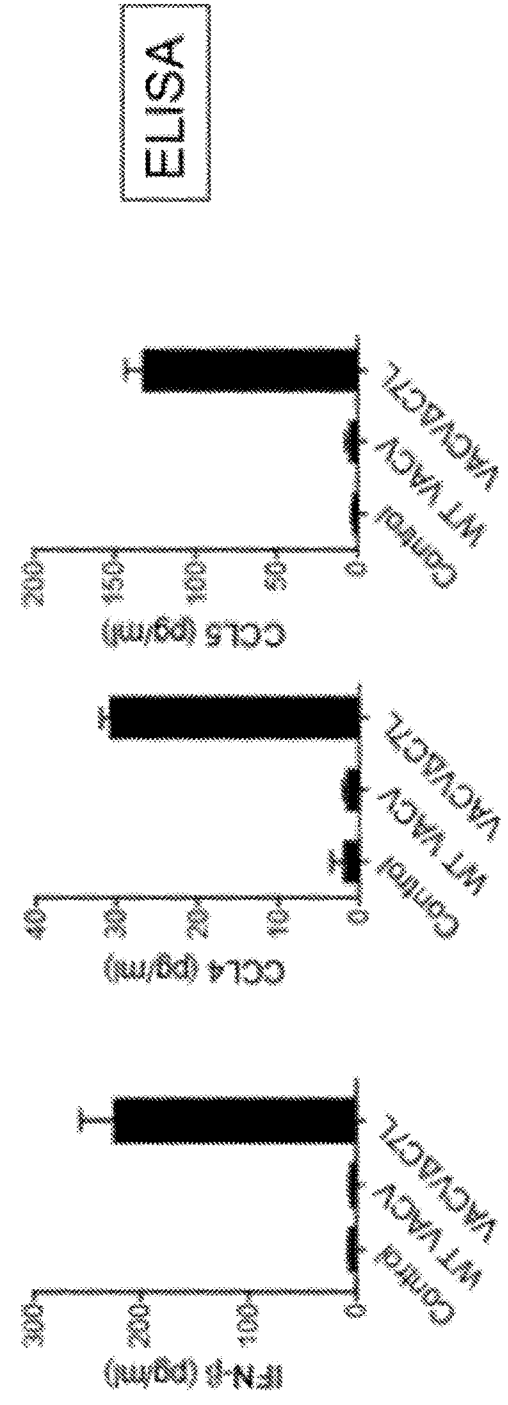
Figure 26A:
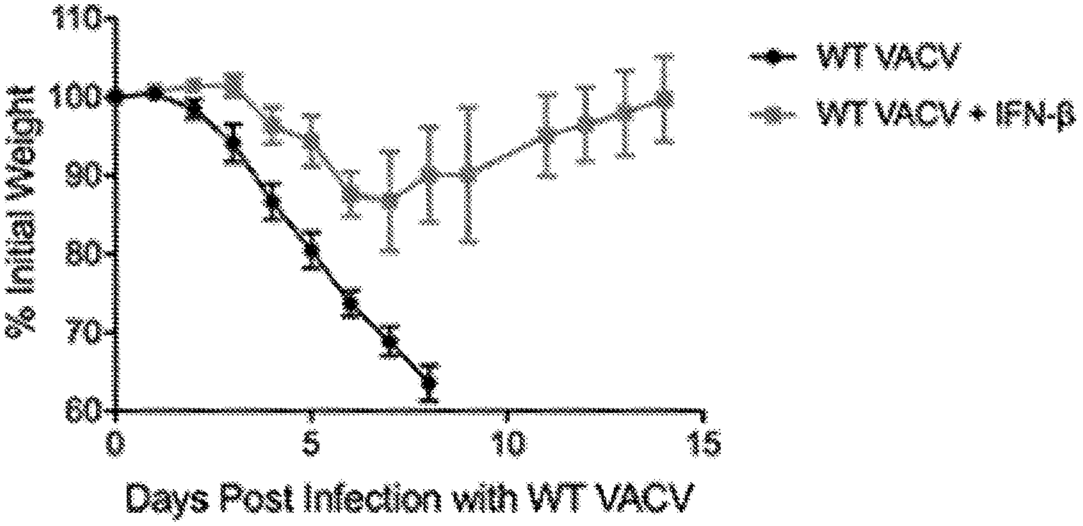
FIGS. 26A-26B are graphical representations of data showing that intranasal application of IFN-β rescues the mice from lethal VACV infection. WT C57BL6/J mice were intranasally infected with WT VACV at $2\times10^6$ pfu. After 12 h, mice were intranasally injected with 1 μg recombinant mouse IFN-β.
Figure 26B:
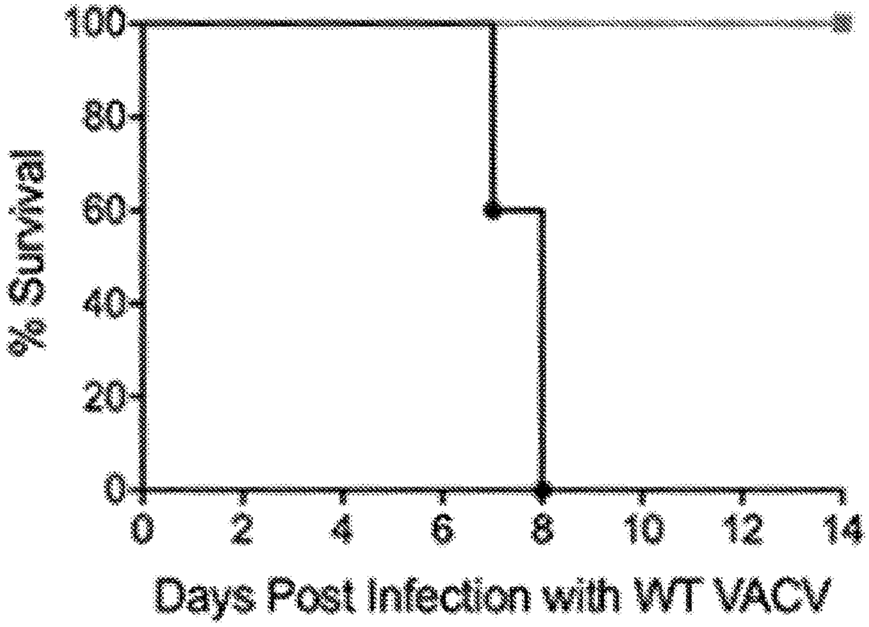
Figure 27A:
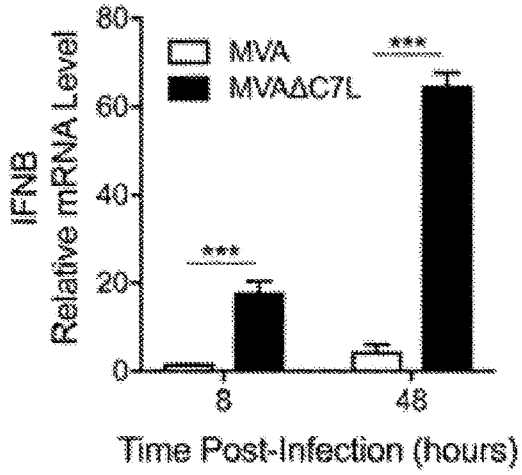
FIGS. 27A-D are graphical representations of data showing MVAΔC7L is a stronger inducer of innate immune responses than MVA in B16-F10 melanoma cells. B16-F10 cells were infected with MVA or MVAΔC7L at a MOI of 10, and the cells were collected at 8 and 48 h post infection. Quantitative real-time PCR analyses of Ifnb (FIG. 27A), Ccl4 (FIG. 27B), Ccl5 (FIG. 27C), Cxcl10 (FIG. 27D) gene expression are shown.
Figure 27B:
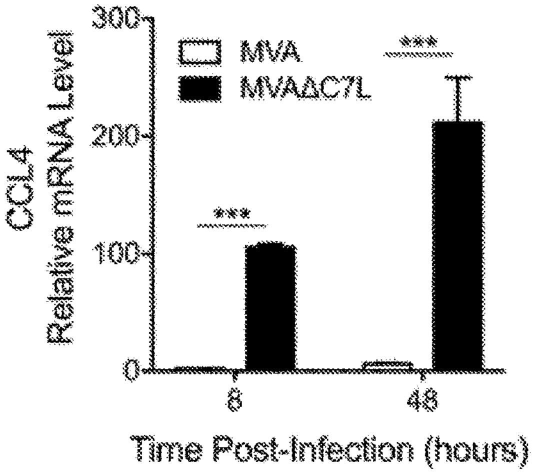
Figure 27C:
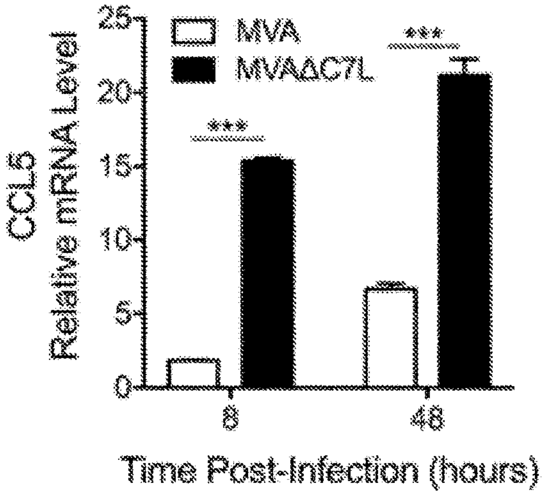
Figure 27D:
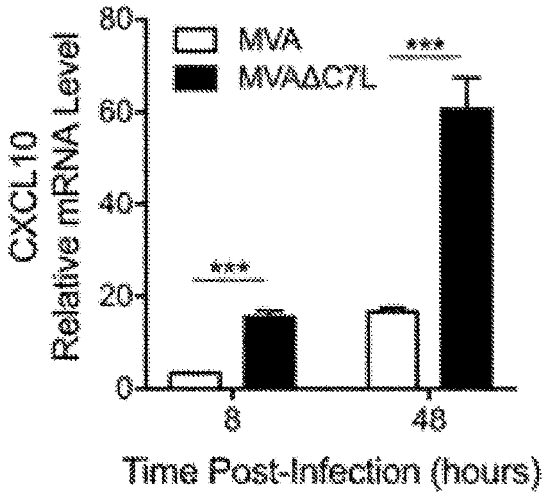

Example 25: VACVΔC7L Infection Induces IFN-β, CCL4, and CCL5 Production from Lung Type II Alveolar Epithelial Cells To test the innate immune responses of lung AECIIs to WT VACV vs. VACVΔC7L infection, lineage negative epithelial cell progenitors (LNEPs) were isolated by sorting $CD45^-$ $CD16^-CD32^-CD31^-EpCAM^{hi}CD104^+$ cells by FACS (FIG. 25A). These cells were cultured on Matrigel-coated 24-well plates in the presence of keratinocyte growth factor for 4 days. The differentiated cells express surfactant C, which is a marker for AECII (FIG. 25B). The cells were infected with either WT VACV or VACVΔC7L virus at a MOI of 10, and they were collected at 12 h for RNA extraction and quantitative real-time PCR analyses. VACVΔC7L infection induced higher levels Ifnb, Ccl4, Ccl5 gene expression compared with WT VACV (FIG. 25C). The supernatants of infected AECIIs were collected at 24 h post infection and were tested for the levels of IFN-β, CCL4, and CCL5. VACVΔC7L infection of AECII induced secretion of IFN-β, CCL4, and CCL5 into the supernatants, whereas WT VACV infection failed to induce (FIG. 25D). These results indicate that VACVΔC7L infection activates the innate immune-sensing mechanism of lung AECII, which leads to production of IFN-β, CCL4, and CCL5.

Example 26: Intranasal Application of IFN-β Rescues the Mice from Lethal VACV Infection To test whether IFN-β in the lung bronchalveolar space is sufficient to protect the mice from a lethal infection from WT VACV, WT C57BL/6J mice were intranasally infected with WT VACV at $2\times10^6$ pfu, then applied intranasally with 1 μg recombinant IFN-β per mouse or PBS. Mice were monitored for weight loss and survival. It was found that all of the WT VACV infected mice without IFN-β treatment died, whereas all of the IFN-β-treated mice only lost weight transiently and survived. These results indicate that IFN-β treatment is sufficient in restricting VACV from lethal challenge in the lung AECs.

Example 27: MVAΔC7L Elicits Stronger Innate Immune Responses in B16-F10 Murine Melanoma Cells than MVA To test whether MVAΔC7L induces stronger innate immune responses than MVA in murine B16-F10 melanoma cells, B16-F10 cells were infected with either MVAΔC7L or MVA at a MOI of 10. Cells were collected at 8 and 48 h post infection. Quantitative real-time PCR analyses showed that MVAΔC7L induced higher levels of Ifnb, Ccl4, Ccl5, and Cxc110 gene expression compared with MVA (FIGS. 27A-27D). These results indicate that MVAΔC7L is more immune stimulatory than MVA in tumor cells. As such, these results show that MVAΔC7L is useful in methods of inducing the innate immune response.

Figures 28A, 28B, 28C, 28D:
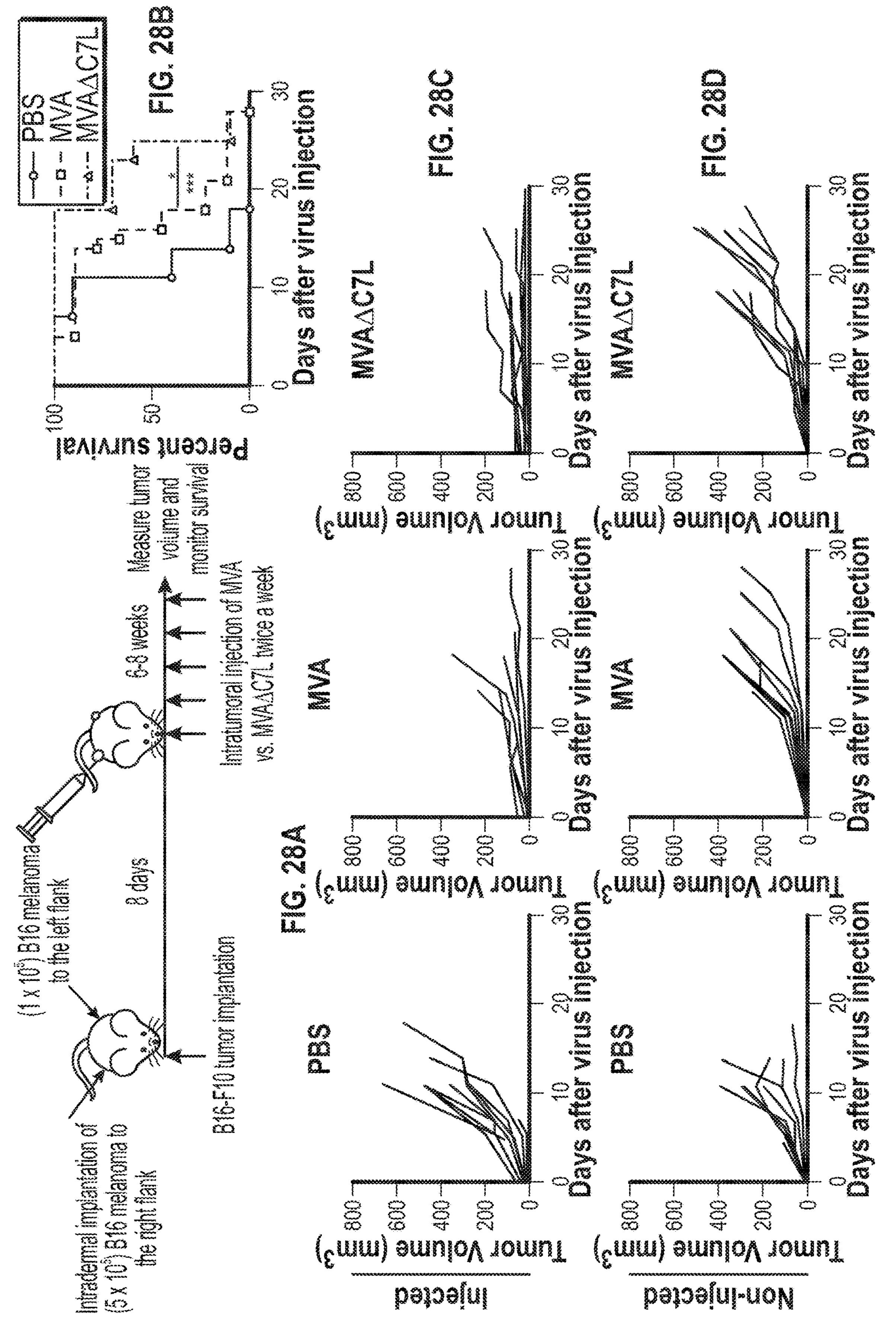
FIGS. 28A-D are graphical representations of data showing intratumoral injection of MVAΔC7L is more effective than MVA in a bilateral B16-F10 tumor implantation model.

Example 28: Intratumoral (IT) Injection of MVAΔC7L is More Effective than MVA in a Bilateral B16-F10 Tumor Implantation Model Based on the capacity of MVAΔC7L to induce higher levels of type I IFN, proinflammatory cytokines and chemokines relative to MVA, the capacity of MVAΔC7L to act as a stronger immunostimulatory agent than MVA was assessed in an in vivo murine tumor model. A murine bilateral B16-F10 tumor implantation model was used. Briefly, B16-F10 melanoma cells were implanted intradermally to the left and right flanks of C57B/6 mice ($5\times10^5$ to the right flank and $1\times10^5$ to the left flank). 9 days after tumor implantation, biweekly injections of $2\times10^7$ PFU of MVA or MVAΔC7L were made into the larger tumors on the right flank (FIG. 28A). The volumes of initial injected and non-injected tumors are shown in FIGS. 28C and 28D. In mice treated with PBS, tumors grew rapidly, which resulted in early death (FIG. 28B). Intratumoral injection of either MVAΔC7L or MVA resulted in delayed tumor growth and improved survival compared with PBS (FIG. 28B). Intratumoral injection of MVAΔC7L was more effective than MVA in eradicating injected tumors and delaying the growth of non-injected tumors at the contralateral side (FIGS. 28C and 28D), which resulted in improved survival in MVAΔC7L-treated mice compared with MVA-treated mice (FIG. 28B). Accordingly, these results show that MVAΔC7L is useful in methods of treating solid tumors.

Figures 29A, 29B:
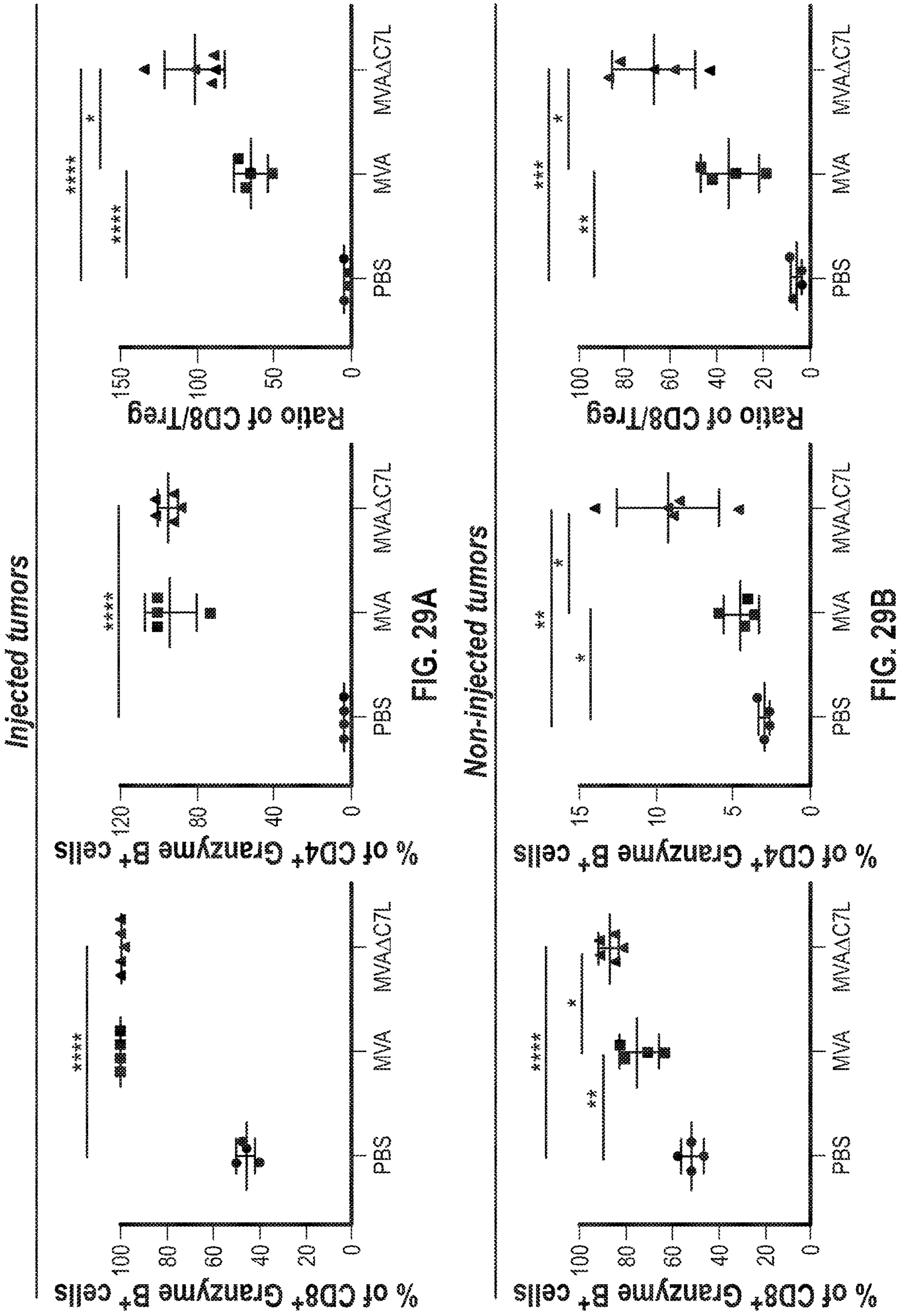
FIGS. 29A-D are graphical representations of data showing intratumoral injection of MVAΔC7L induces stronger $CD8^+$ and $CD4^+$ immune responses compared with MVA.
Figure 29C:
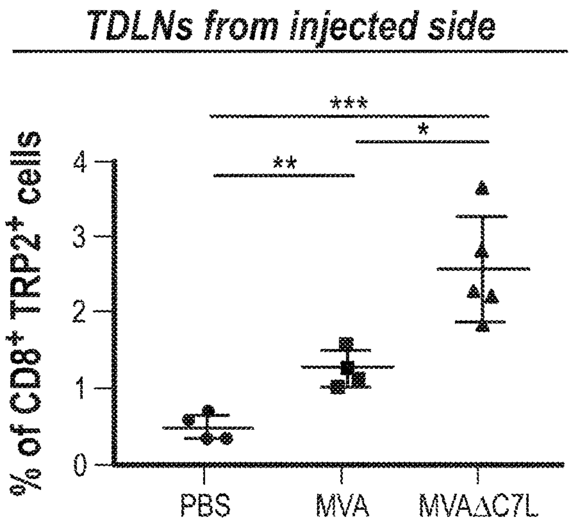
Figure 29D:
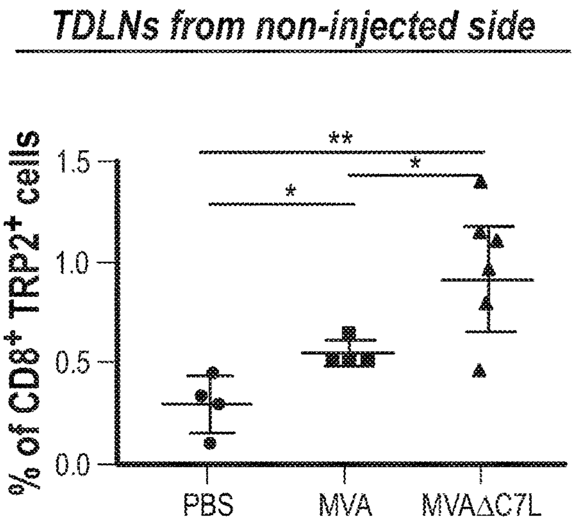

Example 29: Intratumoral Injection of MVAΔC7L Induces Stronger CD8+ and CD4+ Immune Responses Compared with MVA To test whether IT MVAΔC7L induces higher levels of activated CD8+ and CD4+ T cells in the injected and non-injected distant tumors compared with MVA, the inventors performed the following experiment in a bilateral B16-F10 melanoma implantation model. After tumor implantation, the larger tumors were injected with either MVA, or MVAΔC7L, or PBS twice, three days apart. Both the injected and non-injected distant tumors were harvested 2 days post the second injection. The live tumor infiltrating lymphocytes (TILs) were analyzed. Both IT MVA and MVAΔC7L induced high levels of activated Granzyme+ CD8+ and CD4+ T cells in the injected tumors (FIG. 29A). In addition, IT MVAΔC7L elicited higher percentages of TRP2+ CD8+ T cells in the draining lymph nodes of injected tumors compared with IT MVA-treated mice (FIG. 29C). In the non-injected tumors, IT MVAΔC7L induced higher levels of Granzyme+ CD8+ and CD4+ T cells compared with IT MVA (FIG. 29B). In the draining lymph nodes of non-injected tumors, there were also higher percentages of TRP2+ CD8+ T cells in MVAΔC7L-treated mice compared with MVA-treated mice (FIG. 29D). These results indicate that IT MVAΔC7L generated a stronger antitumor CD8+ and CD4+ T cell immune responses in both the injected and non-injected tumors and TDLNs compared with MVA.

Figure 30A:
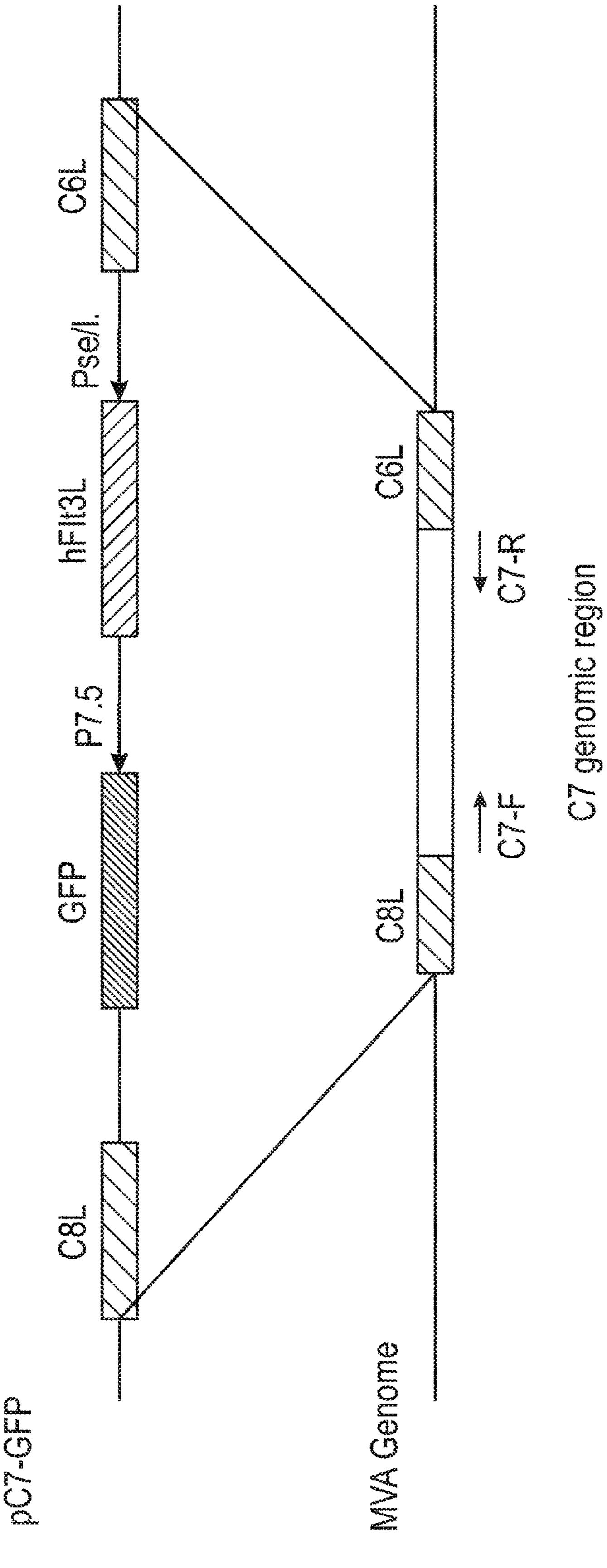
FIGS. 30A-C are graphical representations of data showing generation of recombinant MVAΔC7L-hFlt3L.
Figure 30B:
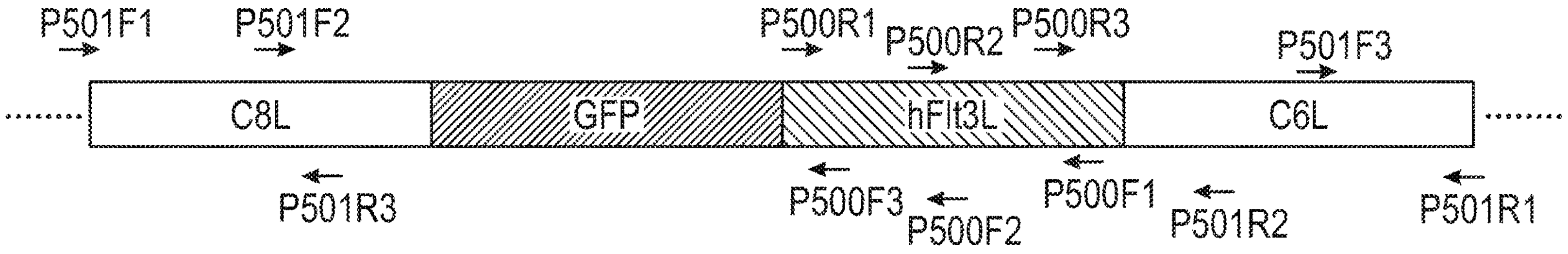
Figure 30B:
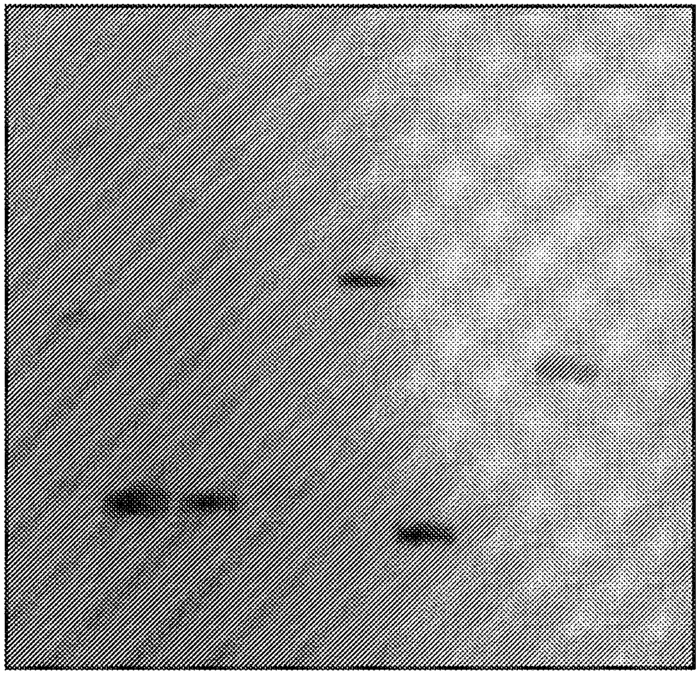

Example 30: Generation of MVAΔC7L-hFlt3L Recombinant Virus for Cancer Immunotherapy pC7LhFlt3L-GFP vector was used to insert an expression cassette with human Flt3L (hFlt3L) under the control of vaccinia synthetic early and late promoter (PsE/L) and GFP under the control of the vaccinia P7.5 promoter into the C7L locus of MVA. The expression cassette was flanked by C6R and C8R on each side. An exemplary expression cassette comprising hFlt3L under the control of vaccinia synthetic early and late promoter (PsE/L) and GFP under the control of the vaccinia P7.5 promoter flanked by C6R and C8R sequences is provided in Table 1. Chicken embryo fibroblasts (CEFs) were infected with MVA at a MOI of 0.05 for 1 h, and then were transfected with the plasmid DNA described above (FIG. 30A). The infected cells were collected at 48 h. Recombinant viruses were identified by their green fluorescence with the insertion of GFP into the C7 locus. The positive clones were plaque purified 4-5 times on CEFs. PCR analysis was performed to confirm that recombinant virus MVAΔC7L-hFlt3L had the insertion of GFP-hFlt3L cassette (FIG. 30B). The inserted plasmid DNA was PCR amplified and sequenced to verify the sequence of the insert.

Figure 30C:
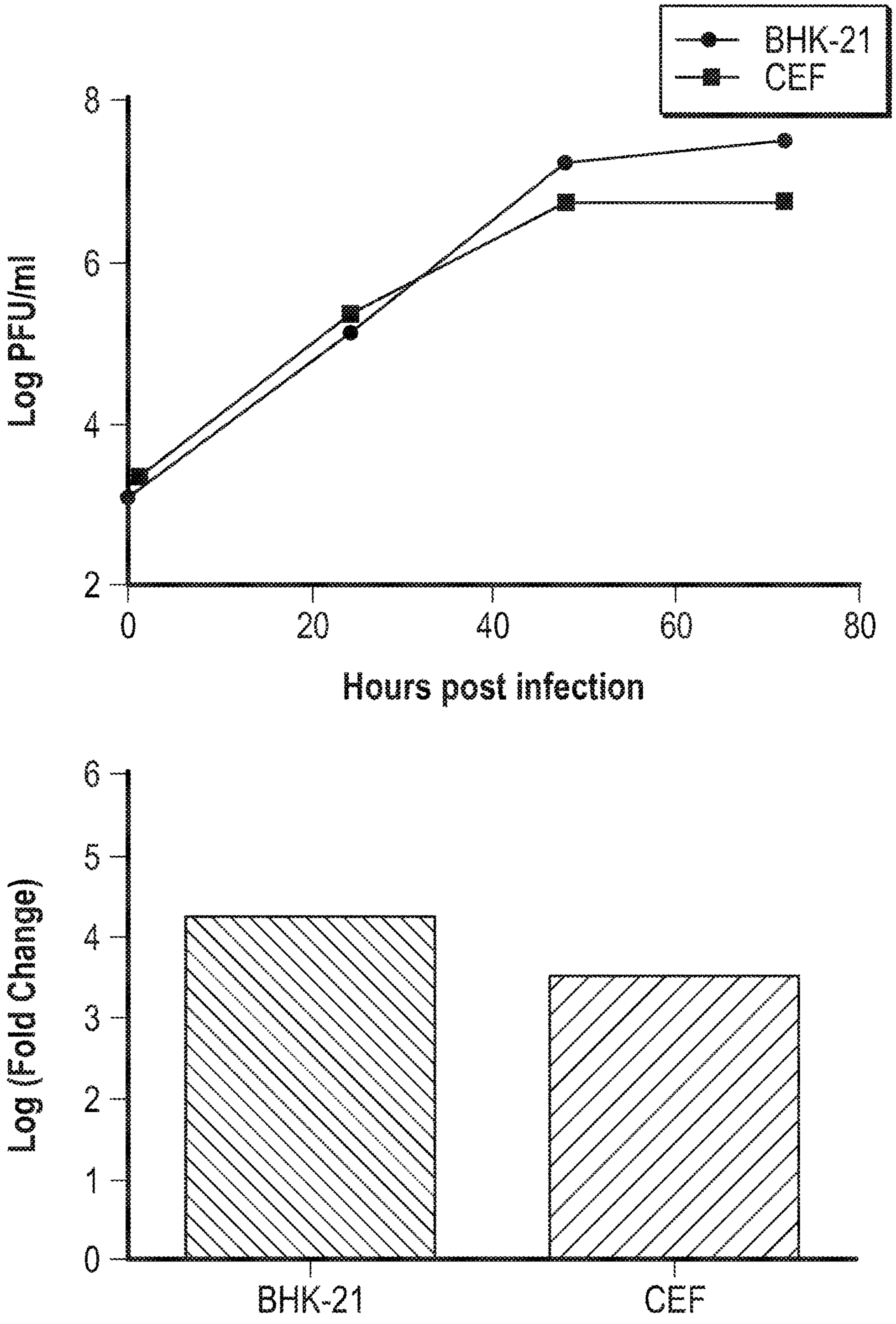

The replication capacities of the recombinant MVAΔC7L-hFlt3L virus in BHK21 cells and CEFs were tested using a multi-step growth assay. Briefly, BHK21 and CEFs were infected with MVAΔC7L-hFlt3L at a MOI of 0.05. Cells were collected at 1, 24, 48, and 72 h post infection. Viral titers were determined on BHK21 cells. MVAΔC7L-hFlt3L replicates robustly in both BHK21 and CEFs (FIG. 30C).

TABLE 1

Gene expression cassette comprising GFP under the control of vaccinia p7.5 promoter and hFlt3L gene under the vaccinia synthetic early and late promoter (PsE/L) flanked by C6 and C8 sequences that is inserted to replace C7 gene in the MVA genome (SEQ ID NO: 9).

```
  1 TATCTGTAGG CTTCTTGTTG TACTGTAACT TCTCGTTTTG TTAGATGTTT GCATCGTGCT

 61 TTAACATCAA TGGTACAAAT TTTATCCTCG CTTTGTGTAT CATATTCGTC CCTACTATAA

121 AATTGTATAT TCAGATTATC ATGAGATGTG TATACGCTAA CGGTATCAAT AAACGGAGCA

181 CACCATTTAG TCATAACCGT AATCCAAAAA TTTTTAAAGT ATATCTTAAC GAAAGAAGTT

241 GTGTCATTGT CTACGGTGTA TGGTACTAGA TCCTCATAAG TGTATATATC TAGAGTAATG

301 TTTAATTTAT CAAATGGTTG ATAATATGGA TCCTCATGAC AATTTCCGAA GATGGAAATG

361 AGATATAGAC ATGCAATAAA TCTAATTGCG GACATGGTTA CTCCTTAAAA AAATACGAAT

421 AATCACCTTG GCTATTTAGT AAGTGTCATT TAACACTATA CTCATACTCG AGTCAGTGCT

481 CCACAAGCAG CAGGTCCTGG GGACTGGGGA CGGGGGGCAC CTGCTCCCCA GGGCGGGGTG

541 TCCTCCGCCG CGTCCTCTGC CAGTGCAGGC ACCAGGCAGC GGCCAGCAGC AGGAGGCCCA

601 CGGGCAGCAG CAGTAGGAGG AGCAGAGGGG GCTGCGGGGC TGTCGGGGCT GTGGCCTCCA

661 GGGGCCGGGG ACTCCATGGG GGTGGCAGGG TTGAGGAGTC GGGCTGACAC TGCAGCTCCA

721 GGCACCGGGA GAAGTTCTGG CGAGTGATCC AGGGCTTCAG CGCCACCAGC TGCTCGGAGG

781 TCTCCTGCAG GAGGCGGGAG ATGTTGGTCT GGACGAAGCG AAGACAGCTG GGGGGGGGCT

841 GAAAGGCACA TTTGGTGACA AAGTGTATCT CCGTGTTCAC GCGCTCCAGC AAGCCTTGCA
```

TABLE 1-continued

| Gene expression cassette comprising GFP under the control of vaccinia p7.5 promoter and hFlt3L gene under the vaccinia synthetic early and late promoter (PsE/L) flanked by C6 and C8 sequences that is inserted to replace C7 gene in the MVA genome (SEQ ID NO: 9). |
|---|
| 901 TCTTGGACCC AGCGACAGTC TTGAGCCGCT CCATCCAGCG CTGTGCCAGG ACCAGCCGCC |
| 961 AGAGGCCCCC GGAGAGCTCC TCGTCCTGCA GGTTGGAGGC CACGGTGACT GGGTAATCTT |
| 1021 GAAGCAGGTA GTCAGACAGC TCACGGATTT TGACAGCGAA GTCGGAGGAG ATGGGGCTGT |
| 1081 GTTGGAAGGA GCAGTCCTGG GTCCCACTGA GTCCCGAGCT CAGCAGCAGC AGCAGGAGGA |
| 1141 GATAGGTTGT TGGGCTCCAG GCTGGCGCCA GCACTGTCAT GAATTCGTCG ACTTCGAGCT |
| 1201 TATTTATATT CCAAAAAAAA AAAATAAAAT TTCAATTTTT AAGCTTACTG AATGGATGAA |
| 1261 CGAATACCGA CGGCGTTAAT AGTAATTTAC TTTTTCATCT TTACATATTG GGTACTAGTT |
| 1321 TTACTATCAT AAGTTTATAA ATTCCACAAG CTACTATGGA ATAAGCCAAC CATCTTAGTA |
| 1381 TAACACACAT GTCTTAAAGT TTATTAATTA ATTACATGTT GTTTTATATA TCGCTACGAA |
| 1441 TTTAAACAGA GAAATCAGTT TAGGAAAAAA AAATATCTAT CTACATCATC ACGTCTCTGT |
| 1501 ATTCTACGAT AGAGTGCTAC TTTAAGATGA GACATATCCG TGTCATCAAA AATATACTCC |
| 1561 ATTAAAATGA TTATTCCGGC AGCGAACTTG ATATTGGATA TATCACAACC TTTGTTAATA |
| 1621 TCTACGACAA TAGACAGCAG TCCCATGGTT CCATAAACAG TGAGTTTATC TTTCTTTGAA |
| 1681 GAGATATTTT GTAGAGATCT TATAAAACTG TCGAATGACA TCGCATTTAT ATCTTTAGCT |
| 1741 AAATCGTATA TGTTACCATC GTAATAT |

Figure 31:
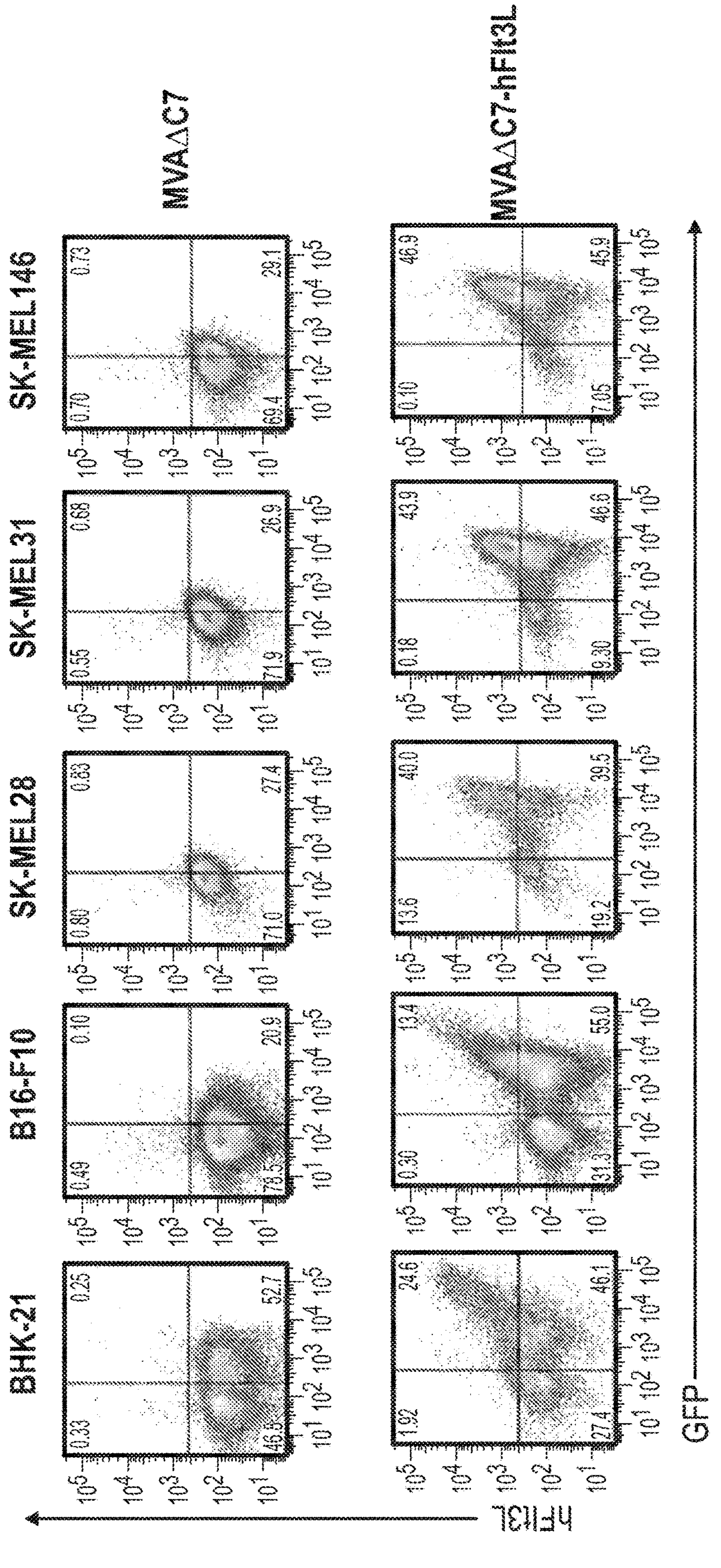
FIG. 31. Expression of hFlt3L by MVAΔC7L-hFlt3L-GFP infected cells. Cells were infected with either MVAΔC7L-GFP or MVAΔC7L-hFlt3L-GFP at a MOI of 10, and collected at 24 h post infection. hFlt3L expression was assessed by FACS analyses using anti-hFlt3L antibody.

Example 31: Expression of Transgenes Human Flt3L and GFP by Recombinant MVAΔC7L-hFlt3L Virus To test whether the recombinant virus MVAΔC7L-hFlt3L expresses the two transgenes, hFlt3L and GFP, BHK21, B16-F10 murine melanoma, SK-MEL28, SK-MEL31, and SK-MEL146 human melanoma cells were infected with either MVAΔC7L (expressing GFP) or MVAΔC7L-hFlt3L (expressing GFP) at a MOI of 10. Cells were collected at 24 h post infection and the expression of hFlt3L and GFP were analyzed by FACS. MVAΔC7L-hFlt3L infection induced higher levels of GFP and hFlt3L expression on infected cells (FIG. 31).

Example 32: MVAΔC7L, MVAΔC7L-hFlt3L, VACVΔC7L, and VACVΔC7L-hFlt3L Infection of MC38 Murine Colon Adenocarcinoma Cells Induces Type I IFN and Inflammatory Cytokines/Chemokines Production To determine whether MVAΔC7L, MVAΔC7L-hFlt3L, VACVΔC7L, and VACVΔC7L-hFlt3L trigger similar responses in other types of solid tumor cells, the capacity of MVAΔC7L, MVAΔC7L-hFlt3L, VACVΔC7L, and VACVΔC7L-hFlt3L to induce type I IFN pathway are tested in the MC38 colon adenocarcinoma cells. MC38 cells are infected with MVAΔC7L, MVAΔC7L-hFlt3L, VACVΔC7L, or VACVΔC7L-hFlt3L at a MOI of 10, or mock-infection control. Supernatants are collected at 22 h post infection. Using ELISA, levels of IFN-β, IL-6, CCL4, CCL5, and CXCL10 in MC38 cells are analyzed. Real-time PCR analysis will assess Ifnb, Il6, Ccl4, Ccl5, Cxcl10 gene expression levels in MC38 cells. Western blot analysis will assess levels of phosphorylation of IRF3 in MC38 cells at 22 h post infection. It is anticipated that these experiments will show that the efficacy of the present treatment is not confined to melanoma and the compositions of the present technology can be used as immunotherapeutic agents to treat solid tumors. Accordingly, this example will show that MVAΔC7L, MVAΔC7L-hFlt3L, VACVΔC7L, or VACVΔC7L-hFlt3L are useful in methods of inducing the innate immune response to treat solid tumors.

Example 33: MVAΔC7L, MVAΔC7L-hFlt3L, VACVΔC7L, and VACVΔC7L-hFlt3L Infection of MC38 Murine Colon Adenocarcinoma Cells Induces Apoptosis To investigate whether MVAΔC7L, MVAΔC7L-hFlt3L, VACVΔC7L, and VACVΔC7L-hFlt3L also trigger apoptosis in MC38 murine colon adenocarcinoma cells, MC38 cells are infected with MVAΔC7L, MVAΔC7L-hFlt3L, VACVΔC7L, and VACVΔC7L-hFlt3L at a MOI of 10, or mock-infection control. It is predicted that Western blot analysis will show that MVAΔC7L, MVAΔC7L-hFlt3L, VACVΔC7L, and VACVΔC7L-hFlt3L trigger cleavage of PARP from 116-kDa full-length protein to 89-kDa fragment. It is also predicted that MVAΔC7L, MVAΔC7L-hFlt3L, VACVΔC7L, and VACVΔC7L-hFlt3L will trigger apoptosis in different types of cancer cells. It is predicted that these experiments will indicate that the immune response elicited by the present viruses carries through to apoptosis, resulting in cancer cell death further establishing the presently disclosed treatments as a viable approach to therapy of melanoma, colon cancer, carcinomas in general, and solid tumors. Accordingly, this example will show that MVAΔC7L, MVAΔC7L-hFlt3L, VACVΔC7L, or VACVΔC7L-hFlt3L are useful in methods of treating solid tumors.

Example 34: MVAΔC7L, MVAΔC7L-hFlt3L, VACVΔC7L, and VACVΔC7L-hFlt3L Inhibit Tumorigenesis in Murine Model of Colon Carcinoma To test whether MVAΔC7L, MVAΔC7L-hFlt3L, VACVΔC7L, and VACVΔC7L-hFlt3L are capable of inhibiting tumor growth in other solid tumors, the anti-tumor effects of MVAΔC7L, MVAΔC7L-hFlt3L, VACVΔC7L, and VACVΔC7L-hFlt3L are tested in a murine colon carcinoma implantation model. Colon carcinoma is representative of a tumor not related to melanoma. $2\times10^5$ MC38 colon carcinoma cells are intradermally implanted into the right flank of C57B/6 mice. Tumors are allowed to form for 7 days, after which MVAΔC7L, MVAΔC7L-hFlt3L, VACVΔC7L, or VACVΔC7L-hFlt3L ($2\times10^7$) or PBS control are intratumorally injected into mice. Tumors are measured at prior to injection (day 0) and for up to 45 days post injection and tumor volume is calculated according the following formula: l (length)×w (width)×h (height)/2. It is anticipated that tumors treated with MVAΔC7L, MVAΔC7L-hFlt3L, VACVΔC7L, or VACVΔC7L-hFlt3L are significantly smaller than PBS-treated tumors. Furthermore, it is anticipated that mice treated with MVAΔC7L, MVAΔC7L-hFlt3L, VACVΔC7L, or VACVΔC7L-hFlt3L exhibit improved survival as demonstrated by the Kaplan-Meier survival curve of tumor-bearing mice injected with PBS or MVAΔC7L, MVAΔC7L-hFlt3L, VACVΔC7L, and VACVΔC7L-hFlt3L. Collectively, these results will show that in the context of colon cancer as well as melanoma, MVAΔC7L, MVAΔC7L-hFlt3L, VACVΔC7L, and VACVΔC7L-hFlt3L maintains the capacity to inhibit tumorigenesis and tumor growth. Accordingly, these results will demonstrate that MVAΔC7L, MVAΔC7L-hFlt3L, VACVΔC7L, and VACVΔC7L-hFlt3L are efficient in promoting anti-tumor effects in various solid tumors and that the applications of the present technology are not limited to melanoma but can be extrapolated to other solid tumors of diverse origins. Thus, this example will show that MVAΔC7L, MVAΔC7L-hFlt3L, VACVΔC7L, or VACVΔC7L-hFlt3L are useful in methods of treating solid tumors.

Example 35: The Combination of Intratumoral Injection of MVAΔC7L, MVAΔC7L-hFlt3L, VACVΔC7L, or VACVΔC7L-hFlt3L with Intraperitoneal Delivery of Immune Checkpoint Blockade Antibody in a Unilateral Melanoma Implantation Model Intratumoral injection of the present viruses will be used to enhance therapeutic effects of current immunotherapies, such as the blockade of immune checkpoints (for example, anti-CTLA-4 antibody), tumor-bearing mice will be treated with intratumoral injection of MVAΔC7L, MVAΔC7L-hFlt3L, VACVΔC7L, or VACVΔC7L-hFlt3L in combination with intraperitoneal delivery of anti-CTLA-4 antibody. Briefly, B16-F10 melanoma cells ($2\times10^5$) will be implanted intradermally into the right flank of WT C57B/6 mice. Ten days following tumor implantation, mice will be treated with the following combinations: PBS+isotype control, PBS+anti-CTLA-4 antibody, MVAΔC7L, MVAΔC7L-hFlt3L, VACVΔC7L, or VACVΔC7L-hFlt3L+isotype control, and MVAΔC7L-hFlt3L, VACVΔC7L, or VACVΔC7L-hFlt3L+anti-CTLA-4. It is anticipated that the treatment with MVAΔC7L-hFlt3L, VACVΔC7L, or VACVΔC7L-hFlt3L and anti-CTLA-4 antibody will lead to superior therapeutic efficacy compared to either immune checkpoint blockade alone or MVAΔC7L-hFlt3L, VACVΔC7L, or VACVΔC7L-hFlt3L treatment alone. Accordingly, this example will show that compositions comprising MVAΔC7L, MVAΔC7L-hFlt3L, VACVΔC7L, or VACVΔC7L-hFlt3L in combination with immune checkpoint blockade agents are useful in methods of treating solid tumors.

Example 36: The Combination of Intratumoral Injection of MVAΔC7L, MVAΔC7L-hFlt3L, VACVΔC7L, or VACVΔC7L-hFlt3L with Intraperitoneal Delivery of Immune Checkpoint Blockade in a Bilateral Melanoma Implantation Model The therapeutic effects of intratumorally injected MVAΔC7L, MVAΔC7L-hFlt3L, VACVΔC7L, or VACVΔC7L-hFlt3L and whether it enhances immune checkpoint blockade therapy, such as anti-CTLA-4, anti-PD-1, or anti-PD-L1 antibodies in a bilateral B16-F10 melanoma model, which also simulates an individual with metastatic disease, are analyzed. Briefly, B16-F10 melanoma cells will be implanted intradermally to the left and right flanks of C57B/6 mice ($5\times10^5$ to the right flank and $1\times10^5$ to the left flank). 8 days after tumor implantation, MVAΔC7L, MVAΔC7L-hFlt3L, VACVΔC7L, or VACVΔC7L-hFlt3L will be intratumorally injected ($2\times10^7$ pfu of MVAΔC7L, MVAΔC7L-hFlt3L, VACVΔC7L, or VACVΔC7L-hFlt3L) or PBS to the larger tumors on the right flank twice weekly. Four groups of mice are treated with MVAΔC7L, four groups of mice are treated with MVAΔC7L-hFlt3L, four groups of mice are treated with VACVΔC7L, and four groups of mice are treated with VACVΔC7L-hFlt3L, with each group receiving intraperitoneal delivery of either isotype control, or anti-CTLA-4, or anti-PD-1, or anti-PD-L1 antibodies.

It is anticipated that the combination of intratumoral injection of MVAΔC7L, MVAΔC7L-hFlt3L, VACVΔC7L, or VACVΔC7L-hFlt3L and systemic delivery of checkpoint inhibitors (represented by anti-CTLcomA-4, anti-PD-1 and anti-PD-L1 antibodies) will further delay growth or eradicate the non-injected tumors compared to intratumoral injection of either checkpoint inhibitor alone or MVAΔC7L, MVAΔC7L-hFlt3L, VACVΔC7L, or VACVΔC7L-hFlt3L alone.

It is anticipated that the results will show that intratumoral delivery of MVAΔC7L, MVAΔC7L-hFlt3L, VACVΔC7L, or VACVΔC7L-hFlt3L overcomes treatment resistance to immune checkpoint blockade in a metastatic B16 melanoma model which portends well for transferring this approach to human therapy with beneficial results. Accordingly, this example will show that compositions comprising MVAΔC7L, MVAΔC7L-hFlt3L, VACVΔC7L, or VACVΔC7L-hFlt3L in combination with immune checkpoint blockade agents are useful in methods of treating solid tumors.

Example 37: Combination of Intratumoral Injection of MVAΔC7L, MVAΔC7L-hFlt3L, VACVΔC7L, or VACVΔC7L-hFlt3L with Intraperitoneal Delivery of Immune Checkpoint Blockade in a Bilateral MC38 Colon Adenocarcinoma Implantation Model Experiments involving intratumoral injection of MVAΔC7L, MVAΔC7L-hFlt3L, VACVΔC7L, or VACVΔC7L-hFlt3L will show enhanced therapeutic effects of immune checkpoint blockade therapy such as anti-CTLA-4, anti- or anti-PD-L1 antibodies in another bilateral tumor implantation model, which simulates a subject with metastatic disease. Briefly, MC38 colon adenocarcinoma cells will be implanted intradermally to the left and right flanks of C57B/6 mice ($5\times10^5$ to the right flank and $1\times10^5$ to the left flank). 8 days after tumor implantation, MVAΔC7L, MVAΔC7L-hFlt3L, VACVΔC7L, or VACVΔC7L-hFlt3L will be intratumorally injected ($2\times10^7$ pfu of MVAΔC7L, MVAΔC7L-hFlt3L, VACVΔC7L, or VACVΔC7L-hFlt3L) or PBS to the larger tumors on the right flank twice weekly. Three groups of mice will be treated with PBS, with each group receiving intraperitoneal delivery of isotype control, or anti-CTLA-4, or anti-PD-L1 antibodies. For each of MVAΔC7L, MVAΔC7L-hFlt3L, VACVΔC7L, and VACVΔC7L-hFlt3L, there will be additional three groups of mice that will be treated with MVAΔC7L, MVAΔC7L-hFlt3L, VACVΔC7L, or VACVΔC7L-hFlt3L, with each group receiving intraperitoneal delivery of either isotype control, or anti-CTLA-4, or anti-PD-L1 antibodies. Each group will then be divided into a subgroup also treated with MVAΔC7L, MVAΔC7L-hFlt3L, VACVΔC7L, or VACVΔC7L-hFlt3L. Controls treated with virus alone will also be provided.

Tumor volumes of both injected and non-injected tumors of each group of mice will be monitored and evaluated. Additionally, the survival of each treatment group will be monitored.

It is anticipated that the combination of intratumoral delivery of MVAΔC7L, MVAΔC7L-hFlt3L, VACVΔC7L, or VACVΔC7L-hFlt3L with checkpoint blockade represented by intraperitoneal delivery of anti-CTLA-4 antibody or intratumoral delivery of MVAΔC7L, MVAΔC7L-hFlt3L, VACVΔC7L, or VACVΔC7L-hFlt3L with intraperitoneal delivery of anti-PD-1/PD-L1 will lead to eradication of non-injected distant tumors at a higher efficiency than MVAΔC7L, MVAΔC7L-hFlt3L, VACVΔC7L, or VACVΔC7L-hFlt3L. Thus, it is anticipated that these results show improvement to the treatment of metastatic solid tumors using a combination of MVAΔC7L, MVAΔC7L-hFlt3L, VACVΔC7L, or VACVΔC7L-hFlt3L and immune checkpoint blockade compared to either checkpoint blockade alone or virus alone. More specifically, it is anticipated that both injected and noninjected tumors will be reduced in size and even eradicated to a degree greater than that achieved with either type of monotherapy and that the results will persist for at least 45 days an longer, thereby validating the combination approach for primary and metastatic solid tumor treatment. Accordingly, this example will show that compositions comprising MVAΔC7L, MVAΔC7L-hFlt3L, VACVΔC7L, or VACVΔC7L-hFlt3L in combination with immune checkpoint blockade agents are useful in methods of treating solid tumors.

Example 38: Combination of Intratumoral Injection of MVAΔC7L, MVAΔC7L-hFlt3L, VACVΔC7L, or VACVΔC7L-hFlt3L with Intratumoral Delivery of Immune Checkpoint Blockade Anti-CTLA-4 Antibody in a Bilateral B16-F10 Implantation Model This Example will assess whether the co-administration of MVAΔC7L, MVAΔC7L-hFlt3L, VACVΔC7L, or VACVΔC7L-hFlt3L and checkpoint blockade represented by anti-CTLA-4 antibody (at 1/10 of dose used for intraperitoneal delivery) will achieve antitumor effects in a stringent bilateral tumor implantation model. Briefly, B16-F10 melanoma cells will be implanted intradermally to the left and right flanks of C57B/6 mice ($5\times10^5$ to the right flank and $1\times10^5$ to the left flank). 8 days after tumor implantation, MVAΔC7L, MVAΔC7L-hFlt3L, VACVΔC7L, or VACVΔC7L-hFlt3L will be intratumorally injected ($2\times10^7$ pfu of MVAΔC7L, MVAΔC7L-hFlt3L, VACVΔC7L, or VACVΔC7L-hFlt3L or PBS) into the larger tumors on the right flank twice weekly. Three groups of mice for each of MVAΔC7L, MVAΔC7L-hFlt3L, VACVΔC7L, and VACVΔC7L-hFlt3L will be treated with MVAΔC7L, MVAΔC7L-hFlt3L, VACVΔC7L, or VACVΔC7L-hFlt3L, with each group receiving: (i) intraperitoneal delivery of anti-CTLA-4 (100 μg/mouse) (ii) intratumoral delivery of isotype antibody (10 μg/mouse), or (iii) intratumoral delivery of anti-CTLA-4 antibody (10 μg/mouse).

Tumor volumes of both injected and non-injected tumors will be monitored and evaluated. The inventors anticipate that the intratumoral co-injection of MVAΔC7L, MVAΔC7L-hFlt3L, VACVΔC7L, or VACVΔC7L-hFlt3L and checkpoint blockade (anti-CTLA-4 antibody at 10 μg/mouse) will be comparable to the therapeutic effects of the combination of intratumoral injection of MVAΔC7L, MVAΔC7L-hFlt3L, VACVΔC7L, or VACVΔC7L-hFlt3L and intraperitoneal delivery of anti-CTLA-4 antibody (100 μg/mouse). It is anticipated that co-administration of MVAΔC7L, MVAΔC7L-hFlt3L, VACVΔC7L, or VACVΔC7L-hFlt3L and an immune checkpoint blockade at a substantially lower dose can achieve similar systemic antitumor effects to the combination of intratumoral delivery of MVAΔC7L, MVAΔC7L-hFlt3L, VACVΔC7L, or VACVΔC7L-hFlt3L with systemic delivery of anti-CTLA-4 antibody at a higher dose. Accordingly, this example will show that compositions comprising MVAΔC7L, MVAΔC7L-hFlt3L, VACVΔC7L, or VACVΔC7L-hFlt3L in combination with immune checkpoint blockade agents are useful in methods of treating solid tumors.

Example 39: Intratumoral Injections of MVAΔC7L, MVAΔC7L-hFlt3L, VACVΔC7L, and VACVΔC7L-hFlt3L are Effective in a Bilateral MC38 Tumor Implantation Model To analyze the antitumor efficacy of MVAΔC7L, MVAΔC7L-hFlt3L, VACVΔC7L, or VACVΔC7L-hFlt3L in a different solid tumor model, $5\times10^5$ MC38 colon cancer cells are intradermally implanted into the right flank and $1\times10^5$ cells into the left flank of C57B/6 mice. Tumors are allowed to grow for 7-8 days, after which MVAΔC7L or MVAΔC7L-hFlt3L ($2\times10^7$ pfu) or PBS control are injected into the larger tumors twice a week.

Intratumoral injection of MVAΔC7L, MVAΔC7L-hFlt3L, VACVΔC7L, or VACVΔC7L-hFlt3L is expected to extend the median survival. It is anticipated that MVAΔC7L-hFlt3L or VACVΔC7L-hFlt3L will be more efficacious than MVAΔC7L or VACVΔC7L in a bilateral MC38 tumor implantation model. As such, it is anticipated that compositions comprising MVAΔC7L, MVAΔC7L-hFlt3L, VACVΔC7L, or VACVΔC7L-hFlt3L will be useful in methods of treating solid tumors.

Example 40: Intratumoral Injections of MVAΔC7L, MVAΔC7L-hFlt3L, VACVΔC7L, or VACVΔC7L-hFlt3L are Also Effective in a Murine Triple-Negative Breast Cancer 4T1 Bilateral Implantation Model In addition to B16-F10 murine melanoma and MC38 colon adenocarcinoma models, whether intratumoral injection of MVAΔC7L, MVAΔC7L-hFlt3L, VACVΔC7L, or VACVΔC7L-hFlt3L has efficacy in the treatment of triple-negative breast cancer (TNBC) 4T1 bilateral tumor implantation model is also investigated. Briefly, 4T1 murine triple negative breast cancer (TNBC) cells are implanted intradermally to the left and right flanks of BALB/c mice ($2.5\times10^5$ to the right flank and $5\times10^4$ to the left flank). 5 days post tumor implantation, the larger tumors on the right flank are injected with MVAΔC7L, MVAΔC7L-hFlt3L, VACVΔC7L, or VACVΔC7L-hFlt3L ($2\times10^7$ pfu) twice weekly. Mice are monitored daily and tumor sizes are measured twice weekly. The survival of mice is monitored. It is anticipated that intratumoral injection of MVAΔC7L, MVAΔC7L-hFlt3L, VACVΔC7L, or VACVΔC7L-hFlt3L will lead to a decrease of tumor volumes of the injected tumors compared with PBS-treated tumors. These results will show that intratumoral injection of MVAΔC7L, MVAΔC7L-hFlt3L, VACVΔC7L, or VACVΔC7L-hFlt3L in a bilateral 4T1 breast cancer model is effective in delaying tumor growth and extending survival of the treated mice. Based on these results, it is anticipated that the combination of MVAΔC7L, MVAΔC7L-hFlt3L, VACVΔC7L, or VACVΔC7L-hFlt3L with immune checkpoint blockade such as anti-CTLA-4 or anti-PD-1/PD-L1 antibodies would also be more effective than virotherapy alone in this bilateral 4T1 implantation model.

Example 41: Intratumoral Injections of MVAΔC7L, MVAΔC7L-hFlt3L, VACVΔC7L, or VACVΔC7L-hFlt3L are Effective in a Murine Prostate Cancer TRAMP-C2 Unilateral Tumor Implantation Model, which Requires STING Whether intratumoral injection of MVAΔC7L, MVAΔC7L-hFlt3L, VACVΔC7L, or VACVΔC7L-hFlt3L has efficacy in the treatment of murine prostate adenocarcinoma TRAMP-C2 unilateral tumor implantation model is investigated. Briefly, TRAMP-C2 cells are implanted intradermally to the shaved right flank of $STING^{Gt/Gt}$ mice and age-matched WT C57B/6 controls ($1\times10^6$ cells in 50 μl of PBS per mouse). 17 days post tumor implantation, the tumors (around 3-4 mm in diameter) on the right flank are injected with either PBS or MVAΔC7L, MVAΔC7L-hFlt3L, VACVΔC7L, or VACVΔC7L-hFlt3L ($2\times10^7$ pfu) twice weekly. Mice are monitored daily and tumor sizes are measured twice weekly. The survival of mice is monitored. It is predicted that intratumoral injection of MVAΔC7L, MVAΔC7L-hFlt3L, VACVΔC7L, or VACVΔC7L-hFlt3L leads to a dramatic decrease of tumor volumes of the injected tumors in the WT mice compared with PBS-treated tumors, but that it is less effective in STING-deficient mice. It is anticipated that MVAΔC7L, MVAΔC7L-hFlt3L, VACVΔC7L, or VACVΔC7L-hFlt3L will have antitumor effects in both WT and $STING^{Gt/Gt}$ mice. As such, it is anticipated that compositions comprising MVAΔC7L, MVAΔC7L-hFlt3L, VACVΔC7L, or VACVΔC7L-hFlt3L will be useful in methods of treating solid tumors.

Example 42: Intratumoral Injection of MVAΔC7L, MVAΔC7L-hFlt3L, VACVΔC7L, or VACVΔC7L-hFlt3L is Also Effective in a Bilateral B16-F10 Melanoma Implantation Model To test whether intratumoral injection of MVAΔC7L, MVAΔC7L-hFlt3L, VACVΔC7L, or VACVΔC7L-hFlt3L exerts an antitumor effect in a bilateral B16-F10 implantation model, MVAΔC7L, MVAΔC7L-hFlt3L, VACVΔC7L, or VACVΔC7L-hFlt3L or PBS is injected into the larger tumors twice a week and tumor sizes and survival are monitored. It is anticipated that intratumoral injection of MVAΔC7L, MVAΔC7L-hFlt3L, VACVΔC7L, or VACVΔC7L-hFlt3L will eradicate or delay tumor growth in both injected and non-injected tumors and extend the median survival relative to the PBS group. These results will show that intratumoral injection of MVAΔC7L, MVAΔC7L-hFlt3L, VACVΔC7L, or VACVΔC7L-hFlt3L is also effective against tumors in a bilateral tumor implantation model. As such, it is anticipated that compositions comprising MVAΔC7L, MVAΔC7L-hFlt3L, VACVΔC7L, or VACVΔC7L-hFlt3L will be useful in methods of treating solid tumors.

Example 43: The Combination of Intratumoral Injection of MVAΔC7L, MVAΔC7L-hFlt3L, VACVΔC7L, or VACVΔC7L-hFlt3L and Systemic Delivery of Immune Checkpoint has Synergistic Antitumor Effects in a Bilateral B16-F10 Melanoma Implantation Model This Example will test whether the combination of intratumoral injection of MVAΔC7L, MVAΔC7L-hFlt3L, VACVΔC7L, or VACVΔC7L-hFlt3L and systemic delivery of immune checkpoint blockade will also result in better tumor killing and improved survival than virotherapy alone in a bilateral B16-F10 melanoma implantation model. 8 days after tumor implantation, MVAΔC7L, MVAΔC7L-hFlt3L, VACVΔC7L, or VACVΔC7L-hFlt3L virus is injected into the larger tumors on the right flank twice weekly. Four groups of mice were treated with MVAΔC7L, MVAΔC7L-hFlt3L, VACVΔC7L, or VACVΔC7L-hFlt3L, with each group receiving intraperitoneal delivery of either the isotype control, or anti-CTLA-4, or anti-PD-1, or anti-PD-L1 antibodies. It is anticipated that treatment with MVAΔC7L, MVAΔC7L-hFlt3L, VACVΔC7L, or VACVΔC7L-hFlt3L+isotype will significantly extend survival compared with the PBS group. The combination of intratumoral injection of MVAΔC7L, MVAΔC7L-hFlt3L, VACVΔC7L, or VACVΔC7L-hFlt3L and systemic delivery of anti-CTLA-4, anti-PD-1 and anti-PD-L1 antibodies is anticipated to have synergistic effects in eradicating or delaying the growth of both injected and non-injected tumors compared to intratumoral injection of MVAΔC7L, MVAΔC7L-hFlt3L, VACVΔC7L, or VACVΔC7L-hFlt3L alone. As such, it is anticipated that compositions comprising MVAΔC7L, MVAΔC7L-hFlt3L, VACVΔC7L, or VACVΔC7L-hFlt3L alone or in combination with immune checkpoint blockade agents will be useful in methods of treating solid tumors.

Example 44: Intratumoral Injection with MVAΔC7L, MVAΔC7L-hFlt3L, VACVΔC7L, or VACVΔC7L-hFlt3L Leads to the Generation of Antitumor $CD8^+$ T-Cell Immunity, which is Enhanced in the Presence of Anti-CTLA-4 Antibody Whether the surviving mice developed antitumor memory T-cell immunity against B16-F10 and MC3 8 colon cancers after treatment with intratumoral injection of MVAΔC7L, MVAΔC7L-hFlt3L, VACVΔC7L, or VACVΔC7L-hFlt3L alone or in the presence of intraperitoneal delivery of anti-CTLA-4 antibody by using Enzyme-linked ImmunoSpot (ELISpot) is examined. Briefly, $CD8^+$ T-cells are isolated from splenocytes and $1\times10^5$ cells are cultured overnight at 37° C. in anti-IFN-γ-coated BD ELISPOT plate microwells. $CD8^+$ T-cells are stimulated with either B16-F10 or MC38 cells irradiated with an γ-irradiator and cytokine secretion is detected with an anti-IFN-γ antibody. It is anticipated that the immunogenic MVAΔC7L, MVAΔC7L-hFlt3L, VACVΔC7L, or VACVΔC7L-hFlt3L vaccinia infection results in the efficient cross-presentation of tumor antigens that are present in both B16-F10 and MC38 cancer cells which leads to the development of cross-protection of heterologous tumors. As such, it is anticipated that compositions comprising MVAΔC7L, MVAΔC7L-hFlt3L, VACVΔC7L, or VACVΔC7L-hFlt3L alone or in combination with immune checkpoint blockade agents will be useful in methods of treating solid tumors.

REFERENCES

1. C. Jochems, J. Schlom, Tumor-infiltrating immune cells and prognosis: the potential link between conventional cancer therapy and immunity. *Exp Biol Med* (*Maywood*) 236, 567-579 (2011).
2. B. Mlecnik, G. Bindea, F. Pages, J. Galon, Tumor immunosurveillance in human cancers. *Cancer Metastasis Rev* 30, 5-12 (2011).
3. H. Angell, J. Galon, From the immune contexture to the Immunoscore: the role of prognostic and predictive immune markers in cancer. *Curr Opin Immunol* 25, 261-267 (2013).
4. F. Garrido, I. Algarra, A. M. Garcia-Lora, The escape of cancer from T lymphocytes: immunoselection of MHC class I loss variants harboring structural-irreversible "hard" lesions. *Cancer Immunol Immunother* 59, 1601-1606 (2010).
5. G. Gerlini et al., Metastatic melanoma secreted IL-10 down-regulates CD1 molecules on dendritic cells in metastatic tumor lesions. *Am J Pathol* 165, 1853-1863 (2004).
6. P. Sharma, J. P. Allison, The future of immune checkpoint therapy. *Science* 348, 56-61(2015).
7. S. L. Topalian, C. G. Drake, D. M. Pardoll, Targeting the PD-1/B7-H1(PD-L1) pathway to activate anti-tumor immunity. *Curr Opin Immunol* 24, 207-212 (2012).
8. D. H. Kim, S. H. Thorne, Targeted and armed oncolytic poxviruses: a novel multi-mechanistic therapeutic class for cancer. *Nature reviews. Cancer* 9, 64-71 (2009).
9. B. Moss, *Poxviridae: The viruses and their replication*. e. D. M. Knipe, Ed., In Fields Virology (Lippincott Williams & Wilkins, 2007), pp. pp. 2905-2946.
10. C. J. Breitbach, S. H. Thorne, J. C. Bell, D. H. Kim, Targeted and armed oncolytic poxviruses for cancer: the lead example of JX-594. *Current pharmaceutical biotechnology* 13, 1768-1772 (2012).
11. B. H. Park et al., Use of a targeted oncolytic poxvirus, JX-594, in patients with refractory primary or metastatic liver cancer: a phase I trial. *Lancet Oncol* 9, 533-542 (2008).
12. D. H. Kim, Y. Wang, F. Le Boeuf, J. Bell, S. H. Thorne, Targeting of interferon-beta to produce a specific, multi-mechanistic oncolytic vaccinia virus. *PLoS Med* 4, e353 (2007).
13. S. H. Thorne et al., Rational strain selection and engineering creates a broad-spectrum, systemically effective oncolytic poxvirus, JX-963. *J Clin Invest* 117, 3350-3358 (2007).
14. J. Engelmayer et al., Vaccinia virus inhibits the maturation of human dendritic cells: a novel mechanism of immune evasion. *J Immunol* 163, 6762-6768 (1999).
15. L. Jenne, C. Hauser, J. F. Arrighi, J. H. Saurat, A. W. Hugin, Poxvirus as a vector to transduce human dendritic cells for immunotherapy: abortive infection but reduced APC function. *Gene therapy* 7, 1575-1583 (2000).
16. P. Li et al., Disruption of MHC class II-restricted antigen presentation by vaccinia virus. *J Immunol* 175, 6481-6488 (2005).
17. L. Deng, P. Dai, W. Ding, R. D. Granstein, S. Shuman, Vaccinia virus infection attenuates innate immune responses and antigen presentation by epidermal dendritic cells. *J Virol* 80, 9977-9987 (2006).
18. R. Drillien, D. Spehner, D. Hanau, Modified vaccinia virus Ankara induces moderate activation of human dendritic cells. *J Gen Virol* 85, 2167-2175 (2004).
19. P. Dai et al., Modified vaccinia virus Ankara triggers type I IFN production in murine conventional dendritic cells via a cGAS/STING-mediated cytosolic DNA-sensing pathway. *PLoS Pathog* 10, e1003989 (2014).
20. G. Sutter, C. Staib, Vaccinia vectors as candidate vaccines: the development of modified vaccinia virus Ankara for antigen delivery. *Current drug targets. Infectious disorders* 3, 263-271 (2003).
21. C. E. Gomez, J. L. Najera, M. Krupa, M. Esteban, The poxvirus vectors MVA and NYVAC as gene delivery systems for vaccination against infectious diseases and cancer. *Curr Gene Ther* 8, 97-120 (2008).
22. C. E. Gomez, J. L. Najera, M. Krupa, B. Perdiguero, M. Esteban, MVA and NYVAC as vaccines against emergent infectious diseases and cancer. *Curr Gene Ther* 11, 189-217 (2011).
23. P. A. Goepfert et al., Phase 1 safety and immunogenicity testing of DNA and recombinant modified vaccinia Ankara vaccines expressing HIV-1 virus-like particles. *J Infect Dis* 203, 610-619 (2011).
24. L. S. Wyatt, I. M. Belyakov, P. L. Earl, J. A. Berzofsky, B. Moss, Enhanced cell surface expression, immunogenicity and genetic stability resulting from a spontaneous truncation of HIV Env expressed by a recombinant MVA. *Virology* 372, 260-272 (2008).
25. F. Garcia et al., Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVACO2). *Vaccine* 29, 8309-8316 (2011).
26. M. Tagliamonte, A. Petrizzo, M. L. Tornesello, F. M. Buonaguro, L. Buonaguro, Antigen-specific vaccines for cancer treatment. *Human vaccines & immunotherapeutics* 10, 3332-3346 (2014).
27. P. H. Verardi, A. Titong, C. J. Hagen, A vaccinia virus renaissance: new vaccine and immunotherapeutic uses after smallpox eradication. *Human vaccines & immunotherapeutics* 8, 961-970 (2012).
28. S. Hornemann et al., Replication of modified vaccinia virus Ankara in primary chicken embryo fibroblasts requires expression of the interferon resistance gene E3L. *J Virol* 77, 8394-8407 (2003).
29. H. Ludwig et al., Role of viral factor E3L in modified vaccinia virus ankara infection of human HeLa Cells: regulation of the virus life cycle and identification of differentially expressed host genes. *J Virol* 79, 2584-2596 (2005).
30. S. F. Fischer et al., Modified vaccinia virus Ankara protein F1L is a novel BH3-domain-binding protein and acts together with the early viral protein E3L to block virus-associated apoptosis. *Cell Death Differ* 13, 109-118 (2006).
31. J. C. Castle et al., Exploiting the mutanome for tumor vaccination. *Cancer Res* 72, 1081-1091 (2012).

32. T. N. Schumacher, R. D. Schreiber, Neoantigens in cancer immunotherapy. *Science* 348, 69-74 (2015).
33. I. Mellman, G. Coukos, G. Dranoff, Cancer immunotherapy comes of age. *Nature* 480, 480-489 (2011).
34. K. S. Peggs, S. A. Quezada, C. A. Chambers, A. J. Korman, J. P. Allison, Blockade of CTLA-4 on both effector and regulatory T-cell compartments contributes to the antitumor activity of anti-CTLA-4 antibodies. *J Exp Med* 206, 1717-1725 (2009).
35. K. Wing et al., CTLA-4 control over Foxp3+ regulatory T-cell function. *Science* 322, 271-275 (2008).
36. D. R. Leach, M. F. Krummel, J. P. Allison, Enhancement of antitumor immunity by CTLA-4 blockade. *Science* 271, 1734-1736 (1996).
37. F. S. Hodi et al., Improved survival with ipilimumab in patients with metastatic melanoma. *The New England journal of medicine* 363, 711-723 (2010).
38. C. Robert et al., Ipilimumab plus dacarbazine for previously untreated metastatic melanoma. *The New England journal of medicine* 364, 2517-2526 (2011).
39. S. L. Topalian, C. G. Drake, D. M. Pardoll, Immune checkpoint blockade: a common denominator approach to cancer therapy. *Cancer Cell* 27, 450-461 (2015).
40. D. A. Oble, R. Loewe, P. Yu, M. C. Mihm, Jr., Focus on TILs: prognostic significance of tumor infiltrating lymphocytes in human melanoma. *Cancer immunity* 9, 3 (2009).
41. K. E. Lacy, S. N. Karagiannis, and F. O. Nestle, Immunotherapy for Melanoma. *Expert Rev Dermatol* 7, 51-68 (2012).
42. J. D. Wolchok et al., Ipilimumab monotherapy in patients with pretreated advanced melanoma: a randomised, double-blind, multicentre, phase 2, dose-ranging study. *Lancet Oncol* 11, 155-164 (2010).
43. J. D. Wolchok et al., Nivolumab plus ipilimumab in advanced melanoma. *The New England journal of medicine* 369, 122-133 (2013).
44. O. Hamid et al., Safety and Tumor Responses with Lambrolizumab (Anti-PD-1) in Melanoma. *The New England journal of medicine*, (2013).
45. P. C. Tumeh et al., PD-1 blockade induces responses by inhibiting adaptive immune resistance. *Nature* 515, 568-571 (2014).
46. D. Zamarin et al., Localized oncolytic virotherapy overcomes systemic tumor resistance to immune checkpoint blockade immunotherapy. *Science translational medicine* 6, 226ra232 (2014).
47. M. B. Fuertes, S. R. Woo, B. Burnett, Y. X. Fu, T. F. Gajewski, Type I interferon response and innate immune sensing of cancer. *Trends Immunol* 34, 67-73 (2013).
48. M. S. Diamond et al., Type I interferon is selectively required by dendritic cells for immune rejection of tumors. *J Exp Med* 208, 1989-2003 (2011).
49. M. B. Fuertes et al., Host type I IFN signals are required for antitumor $CD8^+$ T-cell responses through CD8{alpha}$^+$ dendritic cells. *J Exp Med* 208, 2005-2016 (2011).
50. S. R. Woo et al., STING-dependent cytosolic DNA sensing mediates innate immune recognition of immunogenic tumors. *Immunity* 41, 830-842 (2014).
51. L. Deng et al., STING-Dependent Cytosolic DNA Sensing Promotes Radiation-Induced Type I Interferon-Dependent Antitumor Immunity in Immunogenic Tumors. *Immunity* 41, 843-852 (2014).
52. J. P. Huber, J. D. Farrar, Regulation of effector and memory T-cell functions by type I interferon. *Immunology* 132, 466-474 (2011).
53. D. M. Pardoll, The blockade of immune checkpoints in cancer immunotherapy. *Nature reviews. Cancer* 12, 252-264 (2012).
54. J. Nemunaitis, Oncolytic viruses. *Invest New Drugs* 17, 375-386 (1999).
55. D. Kirn, R. L. Martuza, J. Zwiebel, Replication-selective virotherapy for cancer: Biological principles, risk management and future directions. *Nat Med* 7, 781-787 (2001).
56. M. C. Coffey, J. E. Strong, P. A. Forsyth, P. W. Lee, Reovirus therapy of tumors with activated Ras pathway. *Science* 282, 1332-1334 (1998).
57. A. Mayr, H. Stickl, H. K. Muller, K. Danner, H. Singer, [The smallpox vaccination strain MVA: marker, genetic structure, experience gained with the parenteral vaccination and behavior in organisms with a debilitated defence mechanism (author's transl)]. *Zentralbl Bakteriol B* 167, 375-390 (1978).
58. C. Verheust, M. Goossens, K. Pauwels, D. Breyer, Biosafety aspects of modified vaccinia virus Ankara (MVA)-based vectors used for gene therapy or vaccination. *Vaccine* 30, 2623-2632 (2012).
59. G. Antoine, F. Scheiflinger, F. Dorner, F. G. Falkner, The complete genomic sequence of the modified vaccinia Ankara strain: comparison with other orthopoxviruses. *Virology* 244, 365-396 (1998).
60. A. Mayr, Hochstein-Mintzel V, Stickl H., Passage history, properties, and applicability of the attenuated vaccinia virus strain MVA [in German]. *Infection* 3, 6-14 (1975).
61. H. Meyer, G. Sutter, A. Mayr, Mapping of deletions in the genome of the highly attenuated vaccinia virus MVA and their influence on virulence. *J Gen Virol* 72 (Pt 5), 1031-1038 (1991).
62. S. Brandler et al., Preclinical studies of a modified vaccinia virus Ankara-based HIV candidate vaccine: antigen presentation and antiviral effect. *J Virol* 84, 5314-5328 (2010).
63. A. Takaoka, T. Taniguchi, New aspects of IFN-alpha/beta signalling in immunity, oncogenesis and bone metabolism. *Cancer Sci* 94, 405-411 (2003).
64. D. Nagorsen, E. Wang, F. M. Marincola, J. Even, Transcriptional analysis of tumor-specific T-cell responses in cancer patients. *Crit Rev Immunol* 22, 449-462 (2002).
65. S. Pramanick, Singodia, D., and Chandel, V., Excipient selection in parenteral formulation development. *Pharma Times* 45, 65-77 (2013).
66. J. R. Weaver et al., The identification and characterization of a monoclonal antibody to the vaccinia virus E3 protein. *Virus Res* 130, 269-274 (2007).
67. M. Sato et al., Distinct and essential roles of transcription factors IRF-3 and IRF-7 in response to viruses for IFN-alpha/beta gene induction. *Immunity* 13, 539-548 (2000).
68. H. Ishikawa, G. N. Barber, STING is an endoplasmic reticulum adaptor that facilitates innate immune signalling. *Nature* 455, 674-678 (2008).
69. G. N. Barber, Innate immune DNA sensing pathways: STING, AIMII and the regulation of interferon production and inflammatory responses. *Curr Opin Immunol* 23, 10-20 (2011).
70. J. D. Sauer et al., The N-ethyl-N-nitrosourea-induced Goldenticket mouse mutant reveals an essential function of Sting in the in vivo interferon response to Listeria monocytogenes and cyclic dinucleotides. *Infection and immunity* 79, 688-694 (2011).

71. L. Sun, J. Wu, F. Du, X. Chen, Z. J. Chen, Cyclic GMP-AMP synthase is a cytosolic DNA sensor that activates the type I interferon pathway. *Science* 339, 786-791 (2013).
72. X. D. Li et al., Pivotal roles of cGAS-cGAMP signaling in antiviral defense and immune adjuvant effects. *Science* 341, 1390-1394 (2013).
73. J. Wu et al., Cyclic GMP-AMP is an endogenous second messenger in innate immune signaling by cytosolic DNA. *Science* 339, 826-830 (2013).
74. P. Gao et al., Structure-function analysis of STING activation by c[G(2',5')pA(3',5')p] and targeting by antiviral DMXAA. *Cell* 154, 748-762 (2013).
75. K. V. Kibler et al., Double-stranded RNA is a trigger for apoptosis in vaccinia virus-infected cells. *J Virol* 71, 1992-2003 (1997).
76. S. B. Lee, M. Esteban, The interferon-induced double-stranded RNA-activated protein kinase induces apoptosis. *Virology* 199, 491-496 (1994).
77. D. Tormo et al., Targeted activation of innate immunity for therapeutic induction of autophagy and apoptosis in melanoma cells. Cancer Cell. 2009 Aug. 4; 16(2):103-14. doi: 10.1016/j.ccr.2009.07.004.
78. L. Gitlin et al., Essential role of mda-5 in type I IFN responses to polyriboinosinic:polyribocytidylic acid and encephalomyocarditis picornavirus. Proc Natl Acad Sci USA. 2006 May 30; 103(22):8459-64. Epub 2006 May 19.
79. M. E. Perkus, et al., Vaccinia virus host genes. *Virology* 179(1):276-286 (1990).
80. G. Sivan, et al., Identification of Restriction Factors by Human Genome-Wide RNA Interference Screening of Viral Host Range Mutants Exemplified by Discovery of SAMD9 and WDR6 as Inhibitors of the Vaccinia Virus K1L⁻ C7L⁻ Mutant. *mBio* 6(4):e01122-15 (July/August 2015).
81. X. Meng, et al., C7L Family of Poxvirus Host Range Genes Inhibits Antiviral Activities Induced by Type I Interferons and Interferon Regulatory Factor 1. *J. Virol.* 86(8):4538-4547 (2012).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. An engineered modified vaccinia Ankara (MVA) virus strain comprising a disruption of a C7L gene and a nucleotide sequence encoding human Fms-like tyrosine kinase 3 ligand (hFlt3L).

2. The engineered MVA virus strain of claim 1,
- wherein the disrupted C7L gene does not encode a full-length, wild-type gene product; or
- wherein the disrupted C7L gene comprises an insertion of a heterologous nucleic acid sequence into the coding sequence of the C7L gene; or
- wherein the disrupted C7L gene comprises replacement of at least a portion of the gene with one or more gene cassettes; or
- wherein the disrupted C7L gene comprises replacement of the entire C7L gene with one or more gene cassettes.

3. The engineered MVA virus strain of claim 1, wherein the disrupted C7L gene comprises an insertion of one or more gene cassettes.

4. The engineered MVA strain of claim 3,
- wherein the one or more gene cassettes comprise the nucleotide sequence encoding human Fms-like tyrosine kinase 3 ligand (hFlt3L); or
- wherein the one or more gene cassettes comprise a nucleotide sequence encoding a selectable marker.

5. The engineered MVA strain of claim 1, wherein the MVA strain exhibits one or more of the following characteristics:
- induction of increased levels of interferon beta (IFNB) expression in dendritic cells and THP-1 cells as compared to dendritic cells and THP-1 cells infected with the corresponding wild-type strain;
- induction of increased levels of TBK1 and IRF3 phosphorylation in dendritic cells as compared to dendritic cells infected with the corresponding wild-type strain;
- induction of increased levels of ISG expression in dendritic cells as compared to dendritic cells infected with the corresponding wild-type strain;
- induction of increased levels of at least one of IFNB, CCL4, CCL5, CXCL10 in cancer cells as compared to cancer cells infected with the corresponding wild-type strain; and
- reduction of tumor volume in tumors contacted with the engineered MVA strain as compared to tumors infected with the corresponding wild-type strain.

6. The engineered MVA strain of claim 5,
- wherein the cancer cells comprise melanoma cells; or
- wherein the tumor comprises malignant melanoma.

7. An immunogenic composition comprising the engineered modified vaccinia Ankara (MVA) virus strain of claim 1.

8. The immunogenic composition of claim 7, further comprising a pharmaceutically acceptable carrier.

9. The immunogenic composition of claim 7, further comprising a pharmaceutically acceptable adjuvant.

10. An engineered attenuated vaccinia virus (VACV) strain comprising a disruption of a C7L gene.

11. The engineered attenuated VACV strain of claim 10,
- wherein the disrupted C7L gene does not encode a full-length, wild-type gene product; or
- wherein the disrupted C7L gene comprises an insertion of a heterologous nucleic acid sequence into the coding sequence of the C7L gene; or
- wherein the disrupted C7L gene comprises an insertion of one or more gene cassettes; or
- wherein the disrupted C7L gene comprises replacement of at least a portion of the gene with one or more gene cassettes, and optionally wherein the one or more gene cassettes comprise a nucleotide sequence encoding human Fms-like tyrosine kinase 3 ligand (hFlt3L) or wherein the one or more gene cassettes comprise a nucleotide sequence encoding a selectable marker; or
- wherein mice infected with the engineered VACV strain have in increased post-infection lifespan compared to mice infected with a corresponding wild-type strain.

12. An immunogenic composition comprising the engineered vaccinia virus (VACV) strain of claim 10.

13. The immunogenic composition of claim 12, further comprising a pharmaceutically acceptable carrier.

14. The immunogenic composition of claim 12, further comprising a pharmaceutically acceptable adjuvant.

15. A recombinant vaccinia virus (VACV) nucleic acid sequence, wherein the nucleic acid sequence between position 15,716 and 16,168 of SEQ ID NO: 1 is replaced with a heterologous nucleic acid sequence comprising an open reading frame that encodes a selectable marker; or
- a recombinant modified vaccinia Ankara (MVA) virus nucleic acid sequence, wherein the nucleic acid sequence between position 18,407 and 18,859 of SEQ ID NO: 2 is replaced with a heterologous nucleic acid sequence comprising an open reading frame that encodes a selectable marker.

16. The recombinant VACV or MVA nucleic acid sequence of claim 15, wherein the open reading frame of the heterologous nucleic acid sequence is operably linked to a promoter that is capable of directing expression of the selectable marker; or
- wherein the selectable marker is a bioluminescent protein, a fluorescent protein, a chemiluminescent protein, a xanthine-guanine phosphoribosyl transferase gene (gpt), or any combination thereof; or
- wherein the selectable marker is green fluorescent protein (GFP); or
- wherein the heterologous nucleic acid sequence further comprises an open reading frame that encodes human Fms-like tyrosine kinase 3 ligand (hFlt3L).

* * * * *